(12) United States Patent
Chen et al.

(10) Patent No.: US 6,820,011 B2
(45) Date of Patent: Nov. 16, 2004

(54) THREE-DIMENSIONAL STRUCTURE OF COMPLEMENT RECEPTOR TYPE 2 AND USES THEREOF

(75) Inventors: Xiaojiang Chen, Denver, CO (US); Vernon Michael Holers, Denver, CO (US)

(73) Assignee: The Regents of the University of Colorado, Boulder, CO (US)

( * ) Notice: Subject to any disclaimer, the term of this patent is extended or adjusted under 35 U.S.C. 154(b) by 174 days.

(21) Appl. No.: 09/834,309

(22) Filed: Apr. 11, 2001

(65) Prior Publication Data

US 2004/0005538 A1 Jan. 8, 2004

(51) Int. Cl.[7] .......................... G01N 33/48; C12Q 1/68; A61K 38/00; C07K 1/00
(52) U.S. Cl. ............... 702/19; 702/19; 702/20; 435/6; 530/300; 530/350
(58) Field of Search ............... 702/19, 20, 27; 435/6; 530/300, 350

(56) References Cited

U.S. PATENT DOCUMENTS

| | | | |
|---|---|---|---|
| 6,291,239 B1 | 9/2001 | Prodinger et al. | 435/339.1 |
| 6,432,679 B1 * | 8/2002 | Mond et al. | 435/69.7 |

FOREIGN PATENT DOCUMENTS

WO     wo 98/07835 A2 *   2/1998   ............ C12N/9/00

OTHER PUBLICATIONS

Hampton Research, Crystal Screen User Guide, 27632 El Lazo Road, Laguna Niguel, California.*
Hampton Research, Catalog, 2001, pp. 5 and 7.*
Khurana et al., Crystal Structure of 2.5–diketo–p–gluconic acid reductase A complexed with NADPH at 2.1–A resolution, Proc. Natl. Acad. Sci., vol. 95, pp. 6768–6773, 1998.*
Molina et al., *J. Immunol.*, 154:5426–5435 (1995).
Prodinger et al., *J. Immunol.*, 161:4604–4610 (1998).

* cited by examiner

Primary Examiner—John S. Brusca
Assistant Examiner—Shubo Zhou
(74) Attorney, Agent, or Firm—Sheridan Ross P.C.

(57) ABSTRACT

Disclosed is a crystalline human CR2 protein in complex with C3d, and the three dimensional structure of the crystalline complex. Also disclosed are methods of use of the structure, particularly for structure-based identification of compounds that bind to CR2 and inhibit or enhance the binding of CR2 to a natural ligand, that bind to CR2 and agonize or antagonize the receptor, that bind to CR2 and inhibit or enhance CR2 dimerization, or that use the C3-binding ability of CR2 as a drug delivery vehicle. Also disclosed are therapeutic compounds obtained by such methods and uses for such compounds.

27 Claims, 7 Drawing Sheets

FIG. 5A              FIG. 5B

US 6,820,011 B2

THREE-DIMENSIONAL STRUCTURE OF COMPLEMENT RECEPTOR TYPE 2 AND USES THEREOF

GOVERNMENT SUPPORT

Figure 1A:
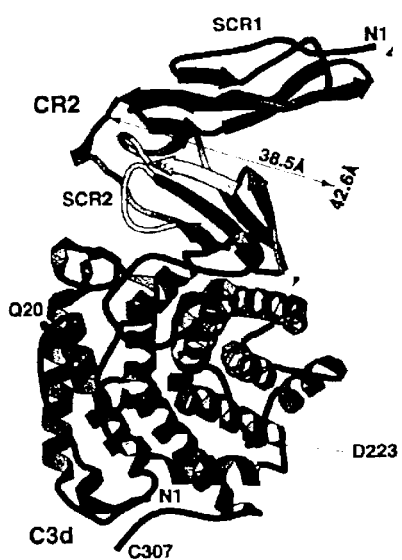

This invention was made in part with government support under Grant No. NIH R0-1CA53615 awarded by the National Institutes of Health. The government has certain rights to this invention.

FIELD OF THE INVENTION

This invention relates to the crystallization and resolution of the three-dimensional structure of the human complement receptor type 2 (CR2) protein, and to methods of using such structure, particularly for structure-based drug design of regulatory compounds.

BACKGROUND OF THE INVENTION

Complement receptor type 2 (CR2 or CD21) is a key interface between innate and adaptive immunity by serving as the receptor for complement component C3d, as well as for C3 and fragments of C3 that contain the C3d domain or a portion thereof, including but not limited to C3dg, iC3b and C3b (D. T. Fearon and R. H. Carter, *Annu Rev Immunol* 13, 127–49 (1995); D. T. Fearon, *Semin Immunol* 10, 355–61 (1998)). C3d and other CR2-binding C3 fragments that contain C3d or a portion thereof are covalently attached to foreign antigens (such as invading microorganisms) through the action of the classical, alternative or lectin complement pathways (S. K. A. Law and K. B. M. Reid, *Complement,*. D. Male, Ed., In Focus (Oxford, UK: IRL Press., ed. second edition, 1995)). C3d- or other CR2-binding C3 fragment-bound antigens then greatly amplify B cell responses by binding to CR2 through these C3 fragments at the same time as engaging the B cell receptor (BCR) via the bound antigen (R. H. Carter and D. T. Fearon, *Science* 256, 105–7 (1992); J. C. Cambier, *Biochem Soc Trans* 25, 441–5 (1997)). The cross-linking of CR2 to the BCR by C3d, C3, or other CR2-binding fragments of C3 that contain C3d or a portion thereof greatly amplifies a signal transduction cascade through the CR2/CD19/CD81 co-activation complex (D. T. Fearon, 1995 ibid.; D. T. Fearon, 1998, ibid.; J. C. Cambier, 1997, ibid.; A. K. Matsumoto, et al., *J Exp Med* 173, 55–64 (1991)).

Human CR2 is also the obligate receptor for the Epstein-Barr virus (EBV) through its interactions with the gp350/220 viral membrane protein (J. D. Fingeroth, et al., *Proc Natl Acad Sci USA* 81, 4510–4 (1984)). EBV causes infectious mononucleosis, and is associated with Burkitt's Lymphoma and several other lymphomas and non-lymphoid tumors (M. Okano, *Acta Paediatr* 87, 11–8 (1998)). In addition, human CR2 serves as a receptor for CD23 (J. P. Aubry et al., *Nature* 358, 505–7 (1992)) and is thus a receptor for at least three biologically important ligands. Using genetically manipulated mice and animal models, CR2 has been shown to be essential for the development of normal humoral immunity to T-dependent antigens (T. Hebell et al., *Science* 254, 102–5 (1991); J. M. Ahearn, et al., *Immunity* 4, 251–62 (1996); H. Molina, et al., *Proc Natl Acad Sci USA* 93, 3357–61 (1996)) as well as possibly play an important role in the maintenance of B cell self-tolerance and the development of autoimmunity (A. P. Prodeus, et al., *Immunity* 9, 721–31 (1998)). CR2 has also been shown to mediate the interaction of C3-bound HIV-1 as an immune complex with B cells in a fashion that promotes transfer of virus and infection of CD4 T cells (S. Moir, et al., *J Exp Med* 192, 637–46 (2000)). CR2 also mediates direct infection of CR2-expressing T cells or other CR2-expressing cell lineages that are bound by HIV-1 immune complexes containing C3, C3d or other CR2-binding C3 fragments (including, but not limited to, HIV-1 complexed with C3d).

Interactions with all three human CR2 ligands require the first two of 15 or 16 short consensus repeat (SCR) domains (C. A. Lowell, et al., *J Exp Med* 170, 1931–46 (1989); J. C. Carel et al., *J Biol Chem* 265, 12293–9(1990)). SCR domains, like Ig domains, are found in many proteins from both complement and non-complement families, and mediate diverse biological functions (A. P. Wiles, et al., *J Mol Biol* 272, 253–65 (1997)). Several of the SCR proteins also serve as receptors for important human pathogens. For example, in addition to CR2, CD46 is a Measles Virus receptor (R. E. Dorig et al., *Cell* 75, 295–305 (1993)), and CD55 is an echovirus receptor (T. Ward, et al., *EMBO J* 13, 5070–4 (1994); J. M. Bergelson, et al., *Proc Natl Acad Sci USA* 91, 6245–9 (1994)). Previously determined structures of SCR proteins containing two or four SCR domains have revealed a conserved core structure but variable orientations between domains mediated in part by relatively short 3–8 amino acid inter-SCR linker peptides (A. P. Wiles, et al., 1997, ibid.; P. N. Barlow, et al., *J Mol Biol* 232, 268–84 (1993); J. M. Casasnovas et al., *EMBO J* 18, 2911–22 (1999); R. Schwarzenbacher, et al., *EMBO J* 18, 6228–39 (1999)). As one of the major functions of SCR domains is to mediate protein-protein (such as receptor-ligand) interactions, and at least two SCRs have been found to be required for these interactions, the relative angle and orientation unique to each SCR-containing protein is likely to contribute to both biologic diversity as well as specificity. However, the lack of a high-resolution structure of a receptor-ligand complex in this family has hindered the understanding of the molecular recognition mechanisms of this class of proteins. With regard to the structure of CR2 and the molecular interactions with its ligands, C3d and EBVgp350/220, variable results have been obtained using mutagenesis, monoclonal antibody, and peptide strategies (C. A. Lowell, et al.,*J Exp Med* 170, 1931–46 (1989); D. R. Martin et al., *J Exp Med* 174, 1299–311 (1991); H. Molina, et al., *J Biol Chem* 266, 12173–9(1991); H. Molina et al., *J Immunol* 153, 789–95 (1994); D. R. Martin et al.,*J Virol* 68, 4716–26 (1994); H. Molina, et al., *J Immunol* 154, 5426–35 (1995)).

Therefore, there is a need in the art for a three dimensional structure of CR2 in order to better understand the molecular recognition mechanisms of the protein and to enable the identification and/or design of compounds that mimic, enhance, disrupt or compete with the interactions of CR2 with its ligands.

SUMMARY OF THE INVENTION

One embodiment of the present invention relates to a method of structure-based identification of compounds which potentially bind to complement receptor type 2 (CR2) proteins or to a complex of CR2 and its ligand. This method includes the steps of: (a) providing a three dimensional structure of a CR2 short consensus repeat (SCR) 1-2 region; and, (b) identifying a candidate compound for binding to the CR2 SCR 1-2 region by performing structure based drug design with the structure of (a). The three dimensional structure of a CR2 short consensus repeat (SCR) 1-2 region is selected from: (i) a structure defined by atomic coordinates of a three dimensional structure of a crystalline CR2 SCR1-2 region in complex with C3d; (ii) a structure defined by atomic coordinates selected from: (1) atomic coordinates represented in a table selected from the group consisting of Table 2 (CR2-C3d) and Table 3 (CR2 only); and, (2) atomic coordinates that define a three dimensional structure, wherein at least 50% of the structure has an average root-mean-square deviation (RMSD) from backbone atoms in secondary structure elements in at least one domain of a three dimensional structure represented by the atomic coordinates of (1) of equal to or less than about 1.0 Å; and (ii) a structure defined by atomic coordinates derived from CR2 protein molecules arranged in a crystalline manner in a space group R32 so as to form a unit cell of dimensions a=b=170.5 Å, c=173.8 Å.

In one aspect of this embodiment, the step of identifying comprises selecting candidate compounds that potentially bind to and activate CR2.

In another aspect of this embodiment, the method further includes the step of: (c) selecting candidate compounds of (b) that inhibit the binding of CR2 to its ligand. The step (c) of selecting can include: (i) contacting the candidate compound identified in step (b) with CR2 or a fragment thereof and a CR2 ligand or a fragment thereof under conditions in which a CR2-CR2 ligand complex can form in the absence of the candidate compound; and (ii) measuring the binding affinity of the CR2 or fragment thereof to the CR2 ligand or fragment thereof; wherein a candidate inhibitor compound is selected as a compound that inhibits the binding of CR2 to its ligand when there is a decrease in the binding affinity of the CR2 or fragment thereof for the CR2 ligand or fragment thereof, as compared to in the absence of the candidate inhibitor compound. The CR2 ligand can include, but is not limited to, C3d, C3, a CR2-binding fragment of C3 containing C3d, CD23, and Epstein Barr Virus (EBV) gp350/220, or CR2-binding fragments of any of the ligands. In one aspect, the CR2 protein or fragment thereof comprises an amino acid sequence selected from the group of SEQ ID NO:4 and SEQ ID NO:6.

In another aspect of this embodiment, the method further includes the step of: (c) selecting candidate compounds that stabilizes a complex of CR2 with its ligand. Step (c) can include: (i) contacting the candidate compound identified in step (b) with a CR2-CR2 ligand complex, wherein the CR2-CR2 ligand complex comprises CR2 or a fragment thereof and a CR2 ligand, or a fragment thereof; and (ii) measuring the stability of the CR2-CR2 ligand complex of (i), wherein a candidate stabilizer compound is selected as a compound that stabilizes the CR2-CR2 ligand complex when there is an increase in the stability of the complex as compared to in the absence of the candidate stabilizer compound. In this aspect, the ligand is preferably selected from C3d, C3, a CR2-binding fragment of C3 containing C3d, CD23, and CR2-binding fragments of any of the ligands. In this aspect, the CR2 protein or fragment thereof can comprise an amino acid sequence selected from the group of SEQ ID NO:4 and SEQ ID NO:6.

In the method of identifying a compound, the step (a) of identifying can include identifying candidate compounds for binding to the SCR2 domain of the CR2. In one aspect, the step of identifying includes identifying candidate compounds for binding to the interface between the SCR1 and SCR2 domains of CR2. In another aspect, the step of identifying includes identifying candidate compounds for binding to the dimer interface between two CR2 proteins. In yet another aspect, the step of identifying includes identifying candidate compounds for binding to the interface between CR2 and C3d, C3, a CR2-binding fragment of C3 containing C3d, or a fragment thereof. In one aspect, the step of identifying includes identifying candidate compounds for binding to the B strand and the B-C loop of CR2 SCR2 comprising the segment: G79-G80-Y81-K82-I83-R84-G85-S86-T87-P88-Y89. In another aspect, the step of identifying includes identifying candidate compounds for binding to a site on the B strand of CR2 SCR2 comprising position K100. In another aspect, the step of identifying includes identifying candidate compounds for binding to a segment of CR2 SCR2 comprising V130-F131-P132-L133. In yet another aspect, the step of identifying comprises identifying candidate compounds for binding to a segment of CR2 SCR2 comprising the fragment T101-N102-F103. In one aspect of the method of identifying, the step of identifying includes identifying candidate compounds for binding to amino acid residues at positions 84 and 86 of an amino acid sequence selected from the group consisting of SEQ ID NO:4 and SEQ ID NO:6.

When the ligand is C3d, C3, or a CR2-binding fragment of C3 containing C3d, the step of identifying can include identifying candidate compounds for binding to the loop between helix 2–3 of C3d comprising the segment Q68-P69-S70-S71. In another aspect, the step of identifying can include identifying candidate compounds for binding to Helix 5 of C3d comprising the segment S104-Q105-V106-L107-C108-G109-A110-V111-K112-W113-L114-I115-L116-E117-K118-Q119-K120-P121-D122. In another aspect, the step of identifying can include identifying candidate compounds for binding to Helix 7of C3d comprising the segment N170-S171-L172-P173-G 174-S175-I176-T177-K178-A179-G180-D181-F182-L183-E184-A185.

The step of identifying a compound in the method of the present invention can include any suitable method of drug design, drug screening or identification, including, but not limited to: directed drug design, random drug design, grid-based drug design, and/or computational screening of one or more databases of chemical compounds.

Yet another embodiment of the present invention relates to a method to identify a compound that inhibits the complement receptor type 2 (CR2)-dependent infection of a host cell by Epstein Barr Virus (EBV). This method includes the steps of: (a) providing a three dimensional structure of a CR2 short consensus repeat (SCR) 1-2 region as described in detail above; (b) identifying a candidate compound for binding to the CR2 SCR 1-2 region by performing structure based drug design with the structure of (a) to identify a compound structure that binds to the three dimensional structure of the CR2 SCR 1-2 region; (c) contacting the candidate compound identified in step (b) with a cell that expresses CR2 or a ligand binding fragment thereof and an Epstein Barr Virus (EBV) particle under conditions in which the EBV particle can bind to CR2 and infect the cell in the absence of the candidate compound; and (d) measuring the intracellular EBV titer of the cell; wherein a candidate inhibitor compound is selected as a compound that inhibits the EBV titer in the cell, as compared to in the absence of the candidate inhibitor compound.

Yet another embodiment of the present invention relates to a method to identify a compound that inhibits the binding of CD23 to complement receptor type 2 (CR2). This method includes the steps of: (a) providing a three dimensional structure of a CR2 short consensus repeat (SCR) 1-2 region as described in detail above; (b) identifying a candidate compound for binding to the CR2 SCR 1-2 region by performing structure based drug design with the structure of (a) to identify a compound structure that binds to the three dimensional structure of the CR2 SCR 1-2 region; (c) contacting the candidate compound identified in step (b) with a first cell expressing CR2 or a ligand binding fragment thereof and a second cell expressing a CD23 protein or fragment thereof under conditions in which the CD23 protein or fragment thereof and the CR2 or the ligand binding fragment thereof can bind in the absence of the candidate compound; and (d) measuring a biological activity induced by the interaction of CD23 and CR2 in the first or second cell; wherein a candidate inhibitor compound is selected as a compound that inhibits the biological activity as compared to in the absence of the candidate inhibitor compound. In a preferred embodiment, the biological activity is IgE isotype switching in the first cell.

Yet another embodiment of the present invention relates to a method to identify a compound that inhibits the binding of C3d, C3 or another CR2-binding fragment of C3 containing C3d or a portion thereof, to complement receptor type 2 (CR2). This method includes the steps of: (a) providing a three dimensional structure of a CR2 short consensus repeat (SCR) 1-2 region as described in detail above; (b) identifying a candidate compound for binding to the CR2 SCR 1-2 region by performing structure based drug design with the structure of (a) to identify a compound structure that binds to the three dimensional structure of the CR2 SCR 1-2 region; (c) contacting the candidate compound identified in step (b) with a cell expressing CR2 or a fragment thereof and C3d, C3, a CR2-binding fragment of C3 containing C3d, or a fragment thereof, under conditions in which the C3d, the C3, the CR2-binding fragment of C3 containing C3d, or a fragment thereof, can bind to CR2 or the fragment thereof and enhance cell activation in the absence of the candidate compound; and (d) measuring the activation of the cell; wherein a candidate inhibitor compound is selected as a compound that inhibits cell activation, as compared to in the absence of the candidate inhibitor compound. In this embodiment, the cell in (c) can include, but is not limited to: a B cell, a T cell, a thymocyte, an epithelial cell, and a mast cell. Activation can be measured by any suitable method including, but not limited to: measurement of cytokine production by the cell, measurement of calcium mobilization in the cell, measurement of lyn tyrosine kinase activity in the cell, measurement of phosphatidylinositol 3' kinase activity in the cell, measurement of activation of NF-κB, measurement of activation of MAP kinases, measurement of phosphorylation of CD19 in the cell, and measurement of activation of protein kinase C (PKC) in the cell.

Another embodiment of the present invention relates to a method to inhibit complement receptor type 2 (CR2)-dependent human immunodeficiency virus-1 (HIV-1) infection of cells in a patient. This method includes the steps of administering to a patient infected with HIV-1 an inhibitor compound that inhibits the binding of C3d, C3 or another CR2-binding fragment of C3 containing C3d or a portion thereof, -opsonized HIV-1 to B cells, follicular dendritic cells, T cells or macrophages in the patient. The inhibitor compound is selected by the steps of: (a) providing a three dimensional structure of a CR2 short consensus repeat (SCR) 1-2 region as described in detail above; (b) identifying a candidate compound for binding to the CR2 SCR 1-2 region by performing structure based drug design with the structure of (a) to identify a compound structure that binds to the three dimensional structure of the CR2 SCR 1-2 region; (c) contacting the candidate compound identified in step (b) with a B cell or follicular dendritic cell expressing CR2 or a fragment thereof and C3d, C3, a CR2-binding fragment of C3 containing C3d, or a fragment thereof, under conditions in which the C3d, the C3, the CR2-binding fragment of C3 containing C3d, or the fragment thereof, can bind to CR2 and enhance B cell activation or follicular dendritic cell activation in the absence of the candidate compound; and (d) measuring the activation of the B cell or the follicular dendritic cell, wherein a candidate inhibitor compound is selected as a compound that inhibits B cell activation or follicular dendritic cell activation, as compared to in the absence of the candidate inhibitor compound.

Yet another embodiment of the present invention relates to a method to prepare a vaccine. This method includes linking a compound that increases B cell activation to an antigen to form the vaccine, wherein the compound is selected by the steps of: (a) providing a three dimensional structure of a CR2 short consensus repeat (SCR) 1-2 region as described in detail above; (b) identifying a candidate compound for binding to the CR2 SCR 1-2 region by performing structure based drug design with the structure of (a) to identify a compound structure that binds to the three dimensional structure of the CR2 SCR 1-2 region; (c) contacting the candidate compound identified in step (b) with a B cell expressing CR2 or a fragment thereof and with C3d, C3, a CR2-binding fragment of C3 containing C3d, or a fragment thereof, under conditions in which the C3d, the C3, the CR2-binding fragment of C3 containing C3d, or the fragment thereof, can bind to and activate CR2 in the absence of the candidate compound; and (d) measuring the activation of the B cell; wherein a candidate compound for use in a vaccine is selected as a compound that increases B cell activation, as compared to in the absence of the candidate compound.

Yet another embodiment of the present invention relates to a drug delivery system, which includes: (a) a drug; and, (b) a portion of a CR2 protein selected from the group of: (i) positions on strand B and the B-C loop of SCR2 including: G79-G80-Y81-K82-I83-R84-G85-S86-T87-P88-Y89; (ii) position K100 on the B strand of CR2; and, (iii) positions: V130-F131-P132-L133; and (iv) combinations of (i)-(iii). The drug is linked to the portion of CR2.

Yet another embodiment of the present invention relates to an antibody that selectively binds to CR2. The antibody binds to a portion of CR2 selected from the group of: (a) the interface between the SCR1 and SCR2 domains of CR2; (b) the dimer interface between two CR2 proteins; and, (c) the interface between CR2 and C3d. Preferably, an antibody that binds to an interface between CR2 and C3d selectively binds to a site selected from: (i) the B strand and the B-C loop of CR2 SCR2 comprising the segment: G79-G80-Y81-K82-I83-R84-G85-S86-T87-P88-Y89; (ii) the B strand of CR2 SCR2 comprising position K100; (iii) a segment of CR2 SCR2 comprising V130-F131-P132-L133; and, (iv) a segment of CR2 SCR2 comprising T101-N102-F103.

Yet another embodiment of the present invention relates to a crystal comprising complement receptor type 2 (CR2) in complex with C3d. The CR2 consists of SEQ ID NO:4, and the C3d consists of SEQ ID NO:7. The crystal effectively diffracts X-rays for the determination of the atomic coordinates of the CR2 in complex with C3d to a resolution of greater than 2.0 Å, and the crystal has a space group R32 so as to form a unit cell of dimensions a=b=170.5 Å, c=173.8 Å.

Another embodiment of the present invention is a therapeutic composition that, when administered to an animal, enhances B cell responses in the animal. The therapeutic composition comprises a compound that stimulates the activity of a complement receptor type 2 (CR2). The compound is identified by the method that includes the steps of: (a) providing a three dimensional structure of a CR2 short consensus repeat (SCR) 1-2 region as described in detail herein; (b) identifying a candidate compound for binding to the CR2 SCR 1-2 region by performing structure based drug design with the structure of (a) to identify a compound structure that binds to the three dimensional structure of the CR2 SCR 1-2 region; (c) synthesizing the candidate compound; and (d) selecting candidate compounds that bind to and activate CR2.

Yet another embodiment relates to a therapeutic composition that, when administered to an animal, inhibits the biological activity of complement receptor type 2 (CR2) in the animal. The therapeutic composition includes a compound that inhibits the activity of a complement receptor type 2 (CR2). The compound is identified by the method that includes the steps of: (a) providing a three dimensional structure of a CR2 short consensus repeat (SCR) 1-2 region as described in detail above; (b) identifying a candidate compound for binding to the CR2 SCR 1-2 region by performing structure based drug design with the structure of (a) to identify a compound structure that binds to the three dimensional structure of the CR2 SCR 1-2 region; (c) synthesizing the candidate compound; and (d) selecting candidate compounds that inhibit the biological activity of CR2. Preferably, the compounds inhibit the formation of a complex between CR2 and a CR2 ligand. The ligand can include, C3d, C3, CR2-binding fragments of C3 containing C3d, CD23 and Epstein Barr Virus (EBV), and CR2-binding fragments any of the ligands. In one aspect, the compound inhibits the activation of CR2.

Yet another embodiment of the present invention relates to a method of preparing complement receptor type 2 (CR2) proteins having modified biological activity. This method includes the steps of: (a) providing a three dimensional structure of a CR2 short consensus repeat (SCR) 1-2 region as described in detail above; (b) analyzing the three dimensional structure to the three-dimensional structure of the CR2 SCR 1-2 region by performing structure based drug design with the structure of (a) to identify at least one site in the structure contributing to the biological activity of CR2; and (c) modifying the at least one site in a CR2 protein to alter the biological activity of the CR2 protein.

Yet another embodiment of the present invention relates to an isolated protein comprising a mutant C3d. The protein comprises an amino acid sequence that differs from SEQ ID NO:7 by an amino acid substitution selected from the group of: a non-asparagine amino acid residue at position 170, a non-isoleucine amino acid residue at position 115, and/or a non-leucine amino acid residue at position 116. The C3d mutant protein has reduced binding to complement receptor type 2 (CR2), as compared to a wild-type C3d protein. In one aspect, the mutant protein comprises an amino acid sequence selected from the group consisting of SEQ ID NO:8 and SEQ ID NO:9.

BRIEF DESCRIPTION OF THE DRAWINGS OF THE INVENTION

The patent or application file contains at least one drawing executed in color. Copies of this patent or patent application with color drawing will be provided by the Office upon request and payment of the necessary fee.

FIG. 1A shows an overall view of the structure of CR2 binding to C3d, showing only SCR2 contacting one portion of the edge of 3d.

FIG. 1B shows the overall structure showing a second CR2-C3d complex (colored in light blue and grey) that dimerizes with the first one in FIG. 1A.

FIG. 2 shows the structure of CR2: A is a ribbon representation of the CR2 SCR1 (in red) and SCR2 (in yellow) structures, showing the SCR fold and the packing of the two domains to form a V shape;

B is a representation of the structure and packing interaction at the interface of CR2 SCR1 and SCR2 domains;

C is a surface representation of the two-domain arrangement of CR2;

D is a representation of the dimerization of CR2 through interactions between SCR1 of each molecule: and E is a sequence alignment between human CR2 (hCR2) SCR1-2 domains (SEQ ID NO:4) and mouse CR2 (mCR2) SCR1-2 domains (SEQ ID NO:6).

FIG. 3 shows the structure at the CR2-C3d interface: A and B are representations of the surface features of the interface area on C3d (in cyan) and CR2 molecule (in yellow);

C shows the structure of the CR2 SCR2-C3d complex;

D and E show the detailed interactions between CR2 (in yellow) and C3d (in cyan) in two angles: and F shows the human C3d sequence (SEQ ID NO:7) with secondary structure assigned on top of the corresponding sequences.

FIG. 4A is a digitized image of a native gel shift assay of the binding between CR2 and C3d wild type (wt) or mutants (mt).

FIG. 4B is a graphical representation showing the intensity changes of the complex bands (measured by densitometry) as CR2 concentration increases from lanes 2 to 4 (wt), or lanes 6 to 8 (mt115), or lanes 10 to 12 (mt170) in FIG. 4A.

FIG. 4C is a graphical representation of a competitive ELISA demonstrating the relative abilities of wild type versus mutant forms of C3d to block CR2-wild type C3d interactions.

FIGS. 5A and 5B are two view with a 180 degree rotation to each other showing the localization of the epitopes of anti-CR2 monoclonal antibodies (mAb) on the CR2 surface.

FIG. 6A is a surface representation of the model containing a dimer of CR2 SCR1 and SCR2 that bind to C3d on each receptor.

FIG. 6B is a diagram of C3d-antigen cross-linking CR2 (as dimers) and BCR on the cell surface.

DETAILED DESCRIPTION OF THE INVENTION

The present invention relates to the discovery of the three-dimensional structure of complement receptor 2 (CR2/CD21), to crystalline CR2-C3d complexes, to models of such three-dimensional structures, to a method of structure based drug design using such structures, to the compounds identified by such methods and to the use of such compounds in therapeutic compositions and methods. Complement receptor 2 (CR2/CD21) is an important receptor bridging the innate and adaptive immune systems that greatly amplifies B lymphocyte activation. CR2 ligands include complement C3d, C3, a CR-2 binding fragment of C3 that contains C3d or a portion thereof, CD23 and Epstein-Barr virus gp350/220. The structural basis for ligand binding by short consensus repeat (SCR) containing proteins has been unknown, but CR2 interactions require the presence of a two SCR-containing domain. In an effort to understand how CR2 interacts with its cellular ligand C3d in the process of B cell activation, as well as its other natural ligands, the present inventors have determined the 2 Åcrystal structure of the CR2 SCR1 and SCR2 domain in complex with C3d. The present inventors describe herein the x-ray structure of this CR2 domain in complex with C3d, which reveals extensive main chain interactions of C3d with one SCR of CR2 and substantial SCR side-side packing. These results provide the first detailed understanding of receptor-ligand interactions in this protein family and reveal potential target sites for molecular drug design.

According to the present invention, the complement receptor 2 (CR2/CD21) is a protein that is characterized by the amino acid sequence represented by SEQ ID NO:1. SEQ ID NO:1 represents the full-length human CR2 protein sequence. The two short consensus repeat (SCR) domains of CR2 that are known to be required for CR2-ligand interactions, SCR1 and SCR2, are located, respectively, within the human CR2 amino acid sequence between positions Cys23 and Cys82 (i.e., between the first Cys and the fourth Cys residues) of SEQ ID NO:1 (SCR1, also represented herein by SEQ ID NO:2) and between positions Cys91 and Cys146 (i.e., between the fifth Cys and the eighth Cys residues) of SEQ ID NO:1 (SCR2, also represented herein by SEQ ID NO:3). The segment (fragment) of human CR2 represented in crystal structure herein contains both the SCR1 and the SCR2 domain (positions 20–153 of SEQ ID NO:1), and is represented herein by SEQ ID NO:4. SEQ ID NO:4 includes the 8 residue linker between SCR1 (SEQ ID NO:2) and SCR2 (SEQ ID NO:3). It also contains three residues at the N-terminus of SCR1 that match exactly positions Gly20-Ser22 of SEQ ID NO:1. At the C-terminus of SCR2, SEQ ID NO:4 contains seven residues that match exactly positions Val147-Glu153 of SEQ ID NO:1.

Figure 2:
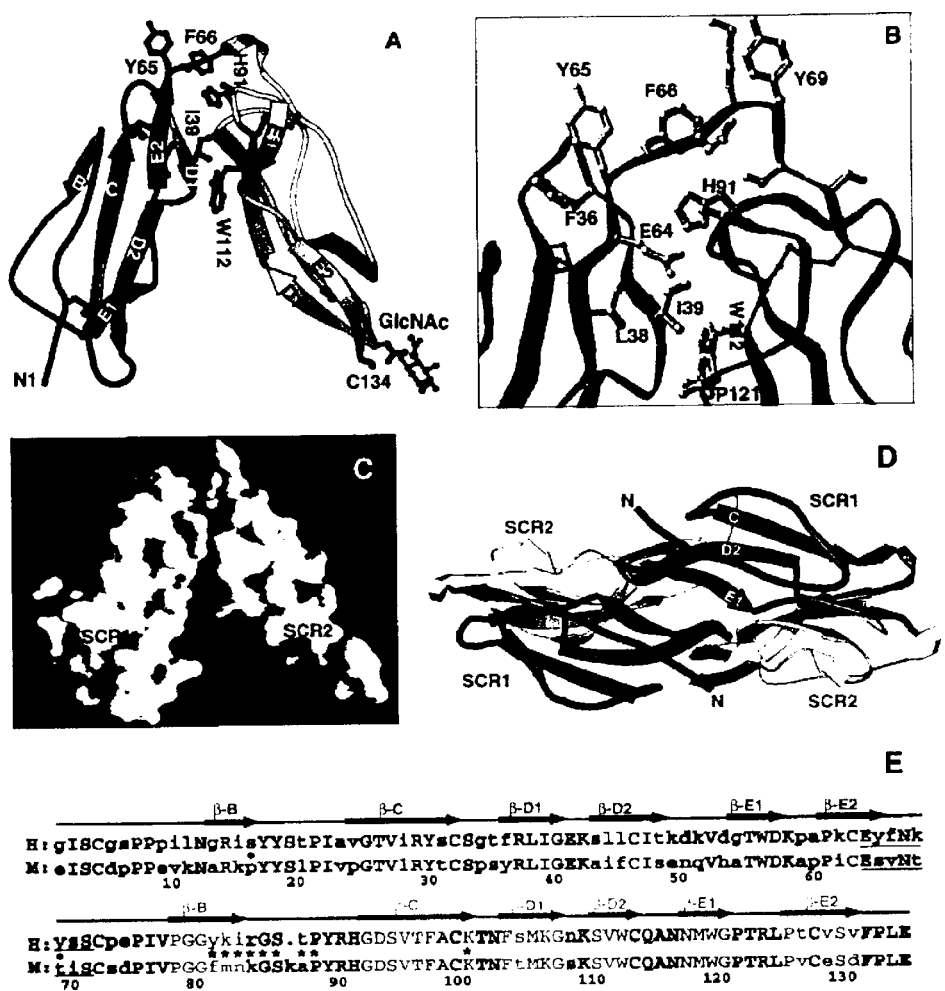

The full-length mouse CR2 protein sequence is represented herein by SEQ ID NO:5. The SCR1 and SCR2 domains of the mouse CR2 protein are located with the mouse CR2 amino sequence at positions 14–73 of SEQ ID NO:5 (SCR1) and positions 82–138 of SEQ ID NO:5 (SCR2). The segment (fragment) of mouse CR2 that contains both the SCR1 and SCR2 domains and the eight residue linker, and which is shown aligned with the human sequence in FIG. 2E, is located at positions 11–145 of SEQ ID NO:5 and is represented herein by SEQ ID NO:6. Human and mouse CR2 are approximately 66% identical over the full length amino acid sequences represented by SEQ ID NO:1 and SEQ ID NO:5 (using BLAST 2 pairwise alignment), and approximately 61% identical over the SCR1-SCR2 regions of SEQ ID NO:4 and SEQ ID NO:6 (using BLAST 2 pairwise alignment). It is noted that both mouse and human CR2 bind to C3 (in the C3d region).

According to the present invention, general reference to a complement receptor 2 (CR2/CD21) protein is a protein that, at a minimum, contains any portion of the SCR1 and SCR2 domains of a CR2 protein, and includes full-length CR2 proteins, soluble CR2 proteins, other biologically active fragments of CR2 proteins, CR2 proteins comprising SCR1 and SCR2, CR2 fusion proteins, or any homologue of a naturally occurring CR2, as described in detail below. A homologue of a CR2 protein includes proteins which differ from a naturally occurring CR2 in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). Preferably, a CR2 homologue has an amino acid sequence that is at least about 70% identical to the amino acid sequence of a naturally occurring CR2 (e.g., SEQ ID NO:1, or SEQ ID NO:5), and more preferably, at least about 75%, and more preferably, at least about 80%, and more preferably, at least about 85%, and more preferably, at least about 90%, and more preferably, at least about 95% identical to the amino acid sequence of a naturally occurring CR2. Preferred three-dimensional structural homologues of a CR2 are described in detail below. According to the present invention, a CR2 homologue preferably has, at a minimum, the ability to bind to a naturally occurring ligand of CR2 (e.g., C3d (including any C3 fragments with CR2-binding ability), CD23, EBV). Such homologues include fragments of a full length CR2 (e.g., the SCR2 region or the SCR1-SCR2 region) and can be referred to herein as a CR2 ligand-binding fragment. In one embodiment, a CR2 homologue has the biological activity of a naturally occurring CR2. Reference to a CR2 protein can also generally refer to CR2 in complex with a ligand.

In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein. As used herein, a protein that has "CR2 biological activity" or that is referred to as a CR2 refers to a protein that has an activity that can include any one, and preferably more than one, of the following characteristics: (a) binds to a natural ligand of CR2 (e.g., C3d, EBV, CD23, C3 or other CR2-binding C3 fragments); (b) mediates interactions between the natural ligands and other proteins; (c) responds to contact with a natural ligand or other agonist (i.e., stimulation) by activation of the signal transduction cascade through the CR2/CD19/CD81coactivation complex in a cell expressing such complex (D. T. Fearon, 1995 ibid.; D. T. Fearon, 1998, ibid.; J. C. Cambier, 1997, ibid.; A. K. Matsumoto, et al., *J Exp Med* 173, 55–64 (1991)), including activation of lyn tyrosine kinase, activations of phosphatidyl inositol 3' kinase, activation of NF-κB, activation of MAP kinases, phosphorylation of CD19, activation of PI3 kinase, and activation of protein kinase C (PKC). Such biological activities of (c) associated with the binding and activation of CR2 can be referred to as downstream biological activities, since they occur downstream of the binding of CR2 by its ligand.

An isolated protein (e.g., an isolated CR2 protein or an isolated C3d protein, an isolated C3 protein, or other CR2-binding C3 fragment), according to the present invention, is a protein that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein, and particularly, an isolated CR2 protein and/or an isolated C3d protein or other CR2-binding C3 fragment, is produced recombinantly. According to the present invention, a CR2-binding C3 fragment can include any portion of C3 that contains at least a portion of C3d sufficient to bind to CR2, and can include, but is not limited to, portions of C3 comprising C3dg, iC3b, and/or C3b, an isolated C3d segment or a portion thereof. The terms "fragment", "segment" and "portion" can be used interchangeably herein with regard to referencing a part of a protein.

Reference to a protein from a specific organism, such as a "human CR2", by way of example, refers to a CR2 (including a homologue of a naturally occurring CR2) from a human or a CR2 protein that has been otherwise produced from the knowledge of the primary structure (e.g., sequence) and/or the tertiary structure of a naturally occurring CR2 protein from a human. In other words, a human CR2 protein includes any CR2 protein that has the structure and function of a naturally occurring CR2 protein from a human or that has a structure and function that is sufficiently similar to a human CR2 protein such that the CR2 protein is a biologically active (i.e., has biological activity) homologue of a naturally occurring CR2 protein from a human. As such, a human CR2 protein can include purified, partially purified, recombinant, mutated/modified and synthetic proteins.

Proteins of the present invention are preferably retrieved, obtained, and/or used in "substantially pure" form. As used herein, "substantially pure" refers to a purity that allows for the effective use of the protein in vitro, ex vivo or in vivo according to the present invention. For a protein to be useful in an in vitro, ex vivo or in vivo method according to the present invention, it is substantially free of contaminants, other proteins and/or chemicals that might interfere or that would interfere with its use in a method disclosed by the present invention, or that at least would be undesirable for inclusion with the protein when it is used in a method disclosed by the present invention. For example, for a CR2 protein, such methods include crystallization of the protein, use of a portion of the protein as a drug delivery vehicle, antibody production, agonist/antagonist identification assays, and all other methods disclosed herein. Preferably, a "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition (e.g., the protein is about 80% of the protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition.

As used herein, a "structure" of a protein refers to the components and the manner of arrangement of the components to constitute the protein. The "three dimensional structure" or "tertiary structure" of the protein refers to the arrangement of the components of the protein in three dimensions. Such term is well known to those of skill in the art. It is also to be noted that the terms "tertiary" and "three dimensional" can be used interchangeably.

The present invention provides the atomic coordinates that define the three dimensional structure of a CR2 protein in complex with a C3d protein. A CR2-ligand complex, such as a CR2-C3d complex, refers to the complex (e.g., interaction, binding), that forms between CR2 and any of its ligands (e.g., C3d) in the absence of a compound that interferes with the interaction between the CR2 and its ligand(s). A complex is naturally formed between at least one full length CR2 and a full length ligand, but according to the present invention, a CR2-ligand can also include complexes that minimally contain: (1) a CR2 SCR1 and/or CR2 SCR2 domain; and (2) a CR2-contacting portion of a ligand of CR2.

One embodiment of the present invention includes a CR2 protein in crystalline form. The present invention specifically exemplifies a portion of CR2 comprising the SCR1 and SCR2 domains. As used herein, the terms "crystalline CR2" and "CR2 crystal" both refer to crystallized CR2 protein and are intended to be used interchangeably. Preferably, a crystalline CR2 is produced using the crystal formation method described herein, in particular according to the method disclosed in Example 1. A CR2 crystal of the present invention can comprise any crystal structure and preferably crystallizes as an orthorhombic crystal lattice. A suitable crystalline CR2 of the present invention includes a monomer or a dimer, or a multimer of CR2 protein. One preferred crystalline CR2 comprises between one and five CR2 proteins in an asymmetric unit. A more preferred crystalline CR2 comprises a dimer of CR2 proteins. Preferably, a composition of the present invention includes CR2 protein molecules arranged in a crystalline manner in a space group R3 or R32 so as to form a unit cell of dimensions a=b=170.5 Å, c=173.8 Å. A preferred crystal of the present invention provides X-ray diffraction data for determination of atomic coordinates of the CR2 protein to a resolution of about 4.0 Å, and preferably to about 3.0 Å, and more preferably to about 2.0 Å.

One embodiment of the present invention includes a method for producing crystals of CR2, alone or in complex with a CR2 ligand, comprising combining CR2 protein with a mother liquor and inducing crystal formation to produce the CR2 crystals. Although the production of crystals of CR2 in complex with C3d are specifically described herein, it is to be understood that such processes as are described herein can be adapted by those of skill in the art to produce crystals of CR2 in complex with other CR2 ligands, such as Epstein Barr Virus (EBV) or CD23.

By way of example, crystals of CR2 and C3d in complex are formed using a solution containing about 20 mg/ml of CR2-C3d complex in a mother liquor. A suitable mother liquor of the present invention comprises an acetate buffer or a sulfate buffer. A preferred acetate buffer of the present invention comprises zinc acetate or zinc sulfate. The concentration of ammonium acetate in the buffer prior to crystallization is preferably 0.2M. The pH of the acetate buffer (pH 7.36) is controlled using 0.1 M NaCacodylate. The acetate buffer also contains any polyethylene glycol (PEG), with PEG 2000 at a concentration of about 17% being more preferred. Supersaturated solutions of CR2-C3d complex can be induced to crystallize by several methods including, but not limited to, vapor diffusion, liquid diffusion, batch crystallization, constant temperature and temperature induction or a combination thereof. Preferably, supersaturated solutions of CR2-C3d complex are induced to crystallize by hanging drop vapor diffusion. In a vapor diffusion method, a CR2-C3d complex is combined with a mother liquor of the present invention that will cause the CR2-C3d complex solution to become supersaturated and form CR2-C3d complex crystals at a constant temperature. Vapor diffusion is preferably performed under a controlled temperature and, by way of example, can be performed at 4° C.

One embodiment of the present invention includes a representation, or model, of the three dimensional structure of a CR2 protein, such as a computer model. A computer model of the present invention can be produced using any suitable software program, including, but not limited to, MOLSCRIPT 2.0 (Avatar Software AB, Heleneborgsgatan 21C, SE-11731 Stockholm, Sweden), the graphical display program O (Jones et. al., *Acta Crystallography*, vol. A47, p. 110, 1991), the graphical display program GRASP, or the graphical display program INSIGHT. Suitable computer hardware useful for producing an image of the present invention are known to those of skill in the art (e.g., a Silicon Graphics Workstation).

A representation, or model, of the three dimensional structure of the CR2-C3d complex structure for which a crystal has been produced can also be determined using techniques which include molecular replacement or SIR/MIR (single/multiple isomorphous replacement). Methods of molecular replacement are generally known by those of skill in the art (generally described in Brunger, *Meth. Enzym.*, vol. 276, pp. 558–580, 1997; Navaza and Saludjian, *Meth. Enzym.*, vol. 276, pp. 581–594, 1997; Tong and Rossmann, *Meth. Enzym.*, vol. 276, pp. 594–611, 1997; and Bentley, *Meth. Enzym.*, vol. 276, pp. 611–619, 1997, each of which are incorporated by this reference herein in their entirety) and are performed in a software program including, for example, AmoRe (CCP4, *Acta Cryst.*D50, 760–763 (1994) or XPLOR. Briefly, X-ray diffraction data is collected from the crystal of a crystallized target structure. The X-ray diffraction data is transformed to calculate a Patterson function. The Patterson function of the crystallized target structure is compared with a Patterson function calculated from a known structure (referred to herein as a search structure). The Patterson function of the crystallized target structure is rotated on the search structure Patterson function to determine the correct orientation of the crystallized target structure in the crystal. The translation function is then calculated to determine the location of the target structure with respect to the crystal axes. Once the crystallized target structure has been correctly positioned in the unit cell, initial phases for the experimental data can be calculated. These phases are necessary for calculation of an electron density map from which structural differences can be observed and for refinement of the structure. Preferably, the structural features (e.g., amino acid sequence, conserved di-sulphide bonds, and β-strands or β-sheets) of the search molecule are related to the crystallized target structure.

As used herein, the term "model" refers to a representation in a tangible medium of the three dimensional structure of a protein, polypeptide or peptide. For example, a model can be a representation of the three dimensional structure in an electronic file, on a computer screen, on a piece of paper (i.e., on a two dimensional medium), and/or as a ball-and-stick figure. Physical three-dimensional models are tangible and include, but are not limited to, stick models and space-filling models. The phrase "imaging the model on a computer screen" refers to the ability to express (or represent) and manipulate the model on a computer screen using appropriate computer hardware and software technology known to those skilled in the art. Such technology is available from a variety of sources including, for example, Evans and Sutherland, Salt Lake City, Utah, and Biosym Technologies, San Diego, Calif. The phrase "providing a picture of the model" refers to the ability to generate a "hard copy" of the model. Hard copies include both motion and still pictures. Computer screen images and pictures of the model can be visualized in a number of formats including space-filling representations, α carbon traces, ribbon diagrams and electron density maps.

Preferably, a three dimensional structure of a CR2 protein provided by the present invention includes: (a) a structure defined by atomic coordinates of a three dimensional structure of a crystalline CR2 SCR1-2 region in complex with C3d; (b) a structure defined by atomic coordinates selected from the group consisting of: (i) atomic coordinates represented in a table selected from the group consisting of Table 2 (CR2-C3d) and Table 3 (CR2 only); and, (ii) atomic coordinates that define a three dimensional structure, wherein at least 50% of the structure has an average root-mean-square deviation (RMSD) from backbone atoms in secondary structure elements in at least one domain of a three dimensional structure represented by the atomic coordinates of (1) of equal to or less than about 1.0 Å; and/or (c) a structure defined by atomic coordinates derived from CR2 protein molecules arranged in a crystalline manner in a space group R3 or R32 so as to form a unit cell of dimensions a=b=170.5 Å, c=173.8 Å.

The present inventors have provided the atomic coordinates that define the three dimensional structure of a crystalline CR2 short consensus repeat (SCR) 1-2 region (CR2 SCR1-2 region) in complex with C3d. Using the guidance provided herein, one of skill in the art will be able to reproduce such a crystalline structure and define atomic coordinates of such a structure. Example 1 demonstrates the production of a CR2-C3d complex (CR2 SCR1-2 region in complex with C3d) arranged in a crystalline manner in a space group R3 or R32 so as to form a unit cell of dimensions a=b=170.5 Å, c=173.8 Å. The atomic coordinates determined from this crystal structure are represented in Table 2. Additionally, these atomic coordinates were deposited on Jan. 11, 2001, with the Protein Data Bank (PDB), operated by the Research Collaboratory for Structural Bioinfornatics (RCSB) (H. M. Berman, J. Westbrook, Z. Feng, G. Gilliland, T. N. Bhat, H. Weissig, I. N. Shindyalov, P. E. Bourne, *The Protein Data Bank; Nucleic Acids Research*, 28:235–242 (2000)), under PDB Deposit No. PDB id 1GHQ. The atomic coordinates in Table 3 are the coordinates that define the three dimensional structure of just the CR2 SCR1-SCR2 domains of the CR2-C3d complex (i.e., the coordinates defining the C3d portion have been removed).

In one embodiment, a three dimensional structure of a CR2 protein provided by the present invention includes a structure represented by atomic coordinates that define a three dimensional structure, wherein at least 50% of the structure has an average root-mean-square deviation (RMSD) from backbone atoms in secondary structure elements in at least one domain of a three dimensional structure represented by the atomic coordinates of Table 2 or Table 3 of equal to or less than about 1.0 Å. Such a structure can be referred to as a structural homologue of the CR2 structures defined by Tables 2 and 3. Preferably, at least 50% of the structure has an average root-mean-square deviation (RMSD) from backbone atoms in secondary structure elements in at least one domain of a three dimensional structure represented by the atomic coordinates of Table 2 or Table 3 of equal to or less than about 0.7 Å, equal to or less than about 0.5 Å, and most preferably, equal to or less than about 0.3 Å. In a more preferred embodiment, a three dimensional structure of a CR2 protein provided by the present invention includes a structure defined by atomic coordinates that define a three dimensional structure, wherein at least about 75% of such structure has the recited average root-mean-square deviation (RMSD) value, and more preferably, at least about 90% of such structure has the recited average root-mean-square deviation (RMSD) value, and most preferably, about 100% of such structure has the recited average root-mean-square deviation (RMSD) value.

In one embodiment, RMSD of a structural homologue of CR2 can be extended to include atoms of amino acid side chains. As used herein, the phrase "common amino acid side chains" refers to amino acid side chains that are common to both the structural homologue and to the structure that is actually represented by such atomic coordinates. Preferably, at least 50% of the structure has an average root-mean-square deviation (RMSD) from common amino acid side chains in at least one domain of a three dimensional structure represented by the atomic coordinates of Table 2 or Table 3 of equal to or less than about 1.0 Å equal to or less than about 0.7 Å, equal to or less than about 0.5 Å, and most preferably, equal to or less than about 0.3 Å. In a more preferred embodiment, a three dimensional structure of a CR2 protein provided by the present invention includes a structure defined by atomic coordinates that define a three dimensional structure, wherein at least about 75% of such structure has the recited average root-mean-square deviation (RMSD) value, and more preferably, at least about 90% of such structure has the recited average root-mean-square deviation (RMSD) value, and most preferably, about 100% of such structure has the recited average root-mean-square deviation (RMSD) value.

One embodiment of the present invention relates to a method of structure-based identification of compounds which potentially bind to complement receptor type 2 (CR2) proteins or to a complex of CR2 and its ligand, comprising: (a) providing a three dimensional structure of a CR2 short consensus repeat (SCR) 1-2region; and (b) identifying a candidate compound for binding to the CR2 SCR 1-2 region by performing structure based drug design with the structure of (a) to identify a compound structure that binds to the three dimensional structure of the CR2 SCR 1-2region. The three dimensional structure of the CR2 SCR 1-2region is selected from the group of:

(i) a structure defined by atomic coordinates of a three dimensional structure of a crystalline CR2 SCR1-2 region in complex with C3d;

(ii) a structure defined by atomic coordinates selected from the group consisting of:
  (1) atomic coordinates represented in a table selected from the group consisting of Table 2 (CR2-C3d) and Table 3 (CR2 only);
  (2) atomic coordinates that define a three dimensional structure, wherein at least 50% of the structure has an average root-mean-square deviation (RMSD) from backbone atoms in secondary structure elements in at least one domain of a three dimensional structure represented by the atomic coordinates of (1) of equal to or less than about 1.0 Å; and (iii) a structure defined by atomic coordinates derived from CR2 protein molecules arranged in a crystalline manner in a space group R3 or R32 so as to form a unit cell of dimensions a=b=170.5 Å, c=173.8 Å.

The structures used to perform the above-described method have been described in detail above and in the Examples section. According to the present invention, the phrase "providing a three dimensional structure of a CR2 short consensus repeat (SCR) 1-2 region" is defined as any means of providing, supplying, accessing, displaying, retrieving, or otherwise making available the three dimensional structure of the CR2 short consensus repeat (SCR) 1-2 region described herein. For example, the step of providing can include, but is not limited to, accessing the atomic coordinates for the structure from a database; importing the atomic coordinates for the structure into a computer or other database; displaying the atomic coordinates and/or a model of the structure in any manner, such as on a computer, on paper, etc.; and determining the three dimensional structure of a CR2 short consensus repeat (SCR) 1-2 region de novo using the guidance provided herein.

The second step of the method of structure based identification of compounds of the present invention includes identifying a candidate compound for binding to the CR2 SCR 1-2 region by performing structure based drug design with the structure of (a) to identify a compound structure that binds to the three dimensional structure of the CR2 SCR 1-2 region. CR2 is a receptor for at least three biologically important ligands, and has been shown to play a role in several aspects of the humoral immune response, EBV infection, and HIV-1 infection. Therefore, identification and/or design of compounds that mimic, enhance, disrupt or compete with the interactions of CR2 with its ligands are highly desirable. Such compounds can be designed using structure based drug design. Until the discovery of the three dimensional structure of the present invention, the only information available for the development of therapeutic compounds based on the CR2 protein was based on the primary sequence of the CR2 protein. Structure based drug design refers to the prediction of a conformation of a peptide, polypeptide, protein, or conformational interaction between a peptide or polypeptide, and a compound, using the three dimensional structure of the peptide, polypeptide or protein. Typically, structure based drug design is performed with a computer. For example, generally, for a protein to effectively interact with (e.g., bind to) a compound, it is necessary that the three dimensional structure of the compound assume a compatible conformation that allows the compound to bind to the protein in such a manner that a desired result is obtained upon binding. Knowledge of the three dimensional structure of the protein enables a skilled artisan to design a compound having such compatible conformation, or to select such a compound from available libraries of compounds. For example, knowledge of the three dimensional structure of the C3d binding site of CR2 enables one of skill in the art to design a compound that binds to CR2, is stable and results in, for example, inhibition of a biological response such as C3d binding to CR2, or cellular signal transduction through the CR2, upon such binding. In addition, for example, knowledge of the three dimensional structure of the C3d binding site of a CR2 enables a skilled artisan to design a substrate analog of CR2.

Suitable structures and models useful for structure based drug design are disclosed herein. Preferred target structures to use in a method of structure based drug design include any representations of structures produced by any modeling method disclosed herein, including molecular replacement and fold recognition related methods.

According to the present invention, the step of designing a compound for testing in a method of structure based identification of the present invention can include creating a new chemical compound or searching databases of libraries of known compounds (e.g., a compound listed in a computational screening database containing three dimensional structures of known compounds). Designing can also be performed by simulating chemical compounds having substitute moieties at certain structural features. The step of designing can include selecting a chemical compound based on a known function of the compound. A preferred step of designing comprises computational screening of one or more databases of compounds in which the three dimensional structure of the compound is known and is interacted (e.g., docked, aligned, matched, interfaced) with the three dimensional structure of a CR2 by computer (e.g. as described by Humblet and Dunbar, *Animal Reports in Medicinal Chemistry*, vol. 28, pp. 275–283, 1993, M Venuti, ed., Academic Press). Methods to synthesize suitable chemical compounds are known to those of skill in the art and depend upon the structure of the chemical being synthesized. Methods to evaluate the bioactivity of the synthesized compound depend upon the bioactivity of the compound (e.g., inhibitory or stimulatory) and are disclosed herein.

Various other methods of structure-based drug design are disclosed in Maulik et al., 1997, *Molecular Biotechnology: Therapeutic Applications and Strategies*, Wiley-Liss, Inc., which is incorporated herein by reference in its entirety. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

In the present method of structure based drug design, it is not necessary to align a candidate chemical compound (i.e., a chemical compound being analyzed in, for example, a computational screening method of the present invention) to each residue in a target site (target sites will be discussed in detail below). Suitable candidate chemical compounds can align to a subset of residues described for a target site. Preferably, a candidate chemical compound comprises a conformation that promotes the formation of covalent or noncovalent crosslinking between the target site and the candidate chemical compound. Preferably, a candidate chemical compound binds to a surface adjacent to a target site to provide an additional site of interaction in a complex. When designing an antagonist (i.e., a chemical compound that inhibits the binding of a ligand to CR2 by blocking a binding site or interface), for example, the antagonist should bind with sufficient affinity to the binding site or to substantially prohibit a ligand (i.e., a molecule that specifically binds to the target site) from binding to a target area. It will be appreciated by one of skill in the art that it is not necessary that the complementarity between a candidate chemical compound and a target site extend over all residues specified here in order to inhibit or promote binding of a ligand.

In general, the design of a chemical compound possessing stereochemical complementarity can be accomplished by techniques that optimize, chemically or geometrically, the "fit" between a chemical compound and a target site. Such techniques are disclosed by, for example, Sheridan and Venkataraghavan, *Acc. Chem Res.*, vol. 20, p. 322, 1987: Goodford, *J. Med. Chem.*, vol. 27, p. 557, 1984; Beddell, *Chem. Soc. Reviews*, vol. 279, 1985; Hol, *Angew. Chem.*, vol. 25, p. 767, 1986; and Verlinde and Hol, *Structure*, vol. 2, p. 577, 1994, each of which are incorporated by this reference herein in their entirety.

One embodiment of the present invention for structure based drug design comprises identifying a chemical compound that complements the shape of a CR2, including a portion of CR2, such as the SCR1-SCR2 region. Such method is referred to herein as a "geometric approach". In a geometric approach, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule, such as a ligand).

The geometric approach is described by Kuntz et al., *J. Mol. Biol.*, vol. 161, p. 269, 1982, which is incorporated by this reference herein in its entirety. The algorithm for chemical compound design can be implemented using the software program DOCK Package, Version 1.0 (available from the Regents of the University of California). Pursuant to the Kuntz algorithm, the shape of the cavity or groove on the surface of a structure (e.g., CR2) at a binding site or interface is defined as a series of overlapping spheres of different radii. One or more extant databases of crystallographic data (e.g., the Cambridge Structural Database System maintained by University Chemical Laboratory, Cambridge University, Lensfield Road, Cambridge CB2 1EW, U.K.) or the Protein Data Bank maintained by Brookhaven National Laboratory, is then searched for chemical compounds that approximate the shape thus defined.

Chemical compounds identified by the geometric approach can be modified to satisfy criteria associated with chemical complementarity, such as hydrogen bonding, ionic interactions or Van der Waals interactions.

Another embodiment of the present invention for structure based identification of compounds comprises determining the interaction of chemical groups ("probes") with an active site at sample positions within and around a binding site or interface, resulting in an array of energy values from which three dimensional contour surfaces at selected energy levels can be generated. This method is referred to herein as a "chemical-probe approach." The chemical-probe approach to the design of a chemical compound of the present invention is described by, for example, Goodford, *J. Med. Chem.*, vol. 28, p. 849, 1985, which is incorporated by this reference herein in its entirety, and is implemented using an appropriate software package, including for example, GRID (available from Molecular Discovery Ltd., Oxford OX2 9LL, U.K.). The chemical prerequisites for a site-complementing molecule can be identified at the outset, by probing the active site of a CR2, for example, (as represented by the atomic coordinates shown in Table 2 or Table 3) with different chemical probes, e.g., water, a methyl group, an amine nitrogen, a carboxyl oxygen and/or a hydroxyl. Preferred sites for interaction between an active site and a probe are determined. Putative complementary chemical compounds can be generated using the resulting three dimensional pattern of such sites.

According to the present invention, suitable candidate compounds to test using the method of the present invention include proteins, peptides or other organic molecules, and inorganic molecules. Suitable organic molecules include small organic molecules. Peptides refer to small molecular weight compounds yielding two or more amino acids upon hydrolysis. A polypeptide is comprised of two or more peptides. As used herein, a protein is comprised of one or more polypeptides. Preferred therapeutic compounds to design include peptides composed of "L" and/or "D" amino acids that are configured as normal or retroinverso peptides, peptidomimetic compounds, small organic molecules, or homo- or hetero-polymers thereof, in linear or branched configurations.

Preferably, a compound that is identified by the method of the present invention originates from a compound having chemical and/or stereochemical complementarity with CR2 and/or C3d. Such complementarity is characteristic of a compound that matches the surface of the receptor either in shape or in distribution of chemical groups and binds to CR2 to promote or inhibit CR2 ligand binding, or to induce cellular signal transduction in a cell expressing CR2 upon the binding of the compound to CR2. More preferably, a compound that binds to a ligand binding site of CR2 associates with an affinity of at least about $10^{-6}$ M, and more preferably with an affinity of at least about $10^{-7}$ M, and more preferably with an affinity of at least about $10^{-8}$ M.

Figure 6A:
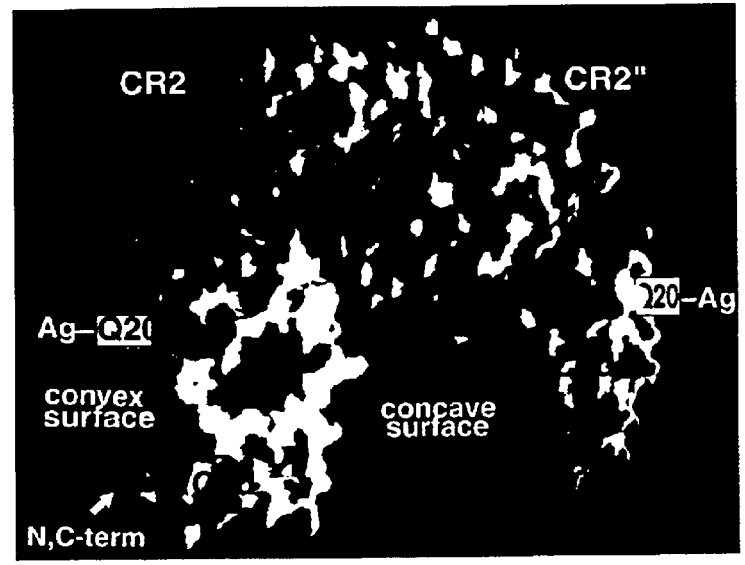

Preferably, three general sites of the CR2 are targets for structure based drug design (i.e., target sites), although other sites may become apparent to those of skill in the art. The three preferred sites include: (1) the interface between CR2 and C3d; (2) the interface between the SCR1 and SCR2 domains of CR2; and (3) the dimerization interface between two CR2 monomers. Combinations of any of these general sites are also suitable target sites. The interface between CR2 and C3d is depicted in FIG. 1A, and FIGS. 3A–3E. The interface between the SCR1 and SCR2 domains of CR2 is depicted in FIGS. 2A–2C. The dimer interface between CR2 monomeric proteins is depicted in FIGS. 1B, 2D and 6A. The following discussion provides specific detail on compound identification (e.g., drug design) using target sites of the CR2 based on its three-dimensional structure in complex with C3d. It is to be understood, however, that one of skill in the art, using the description of the CR2 structure provided herein, will be able to identify compounds that are potential candidates for inhibiting, stimulating or enhancing the interaction of CR2 with its other ligands.

Figure 3:
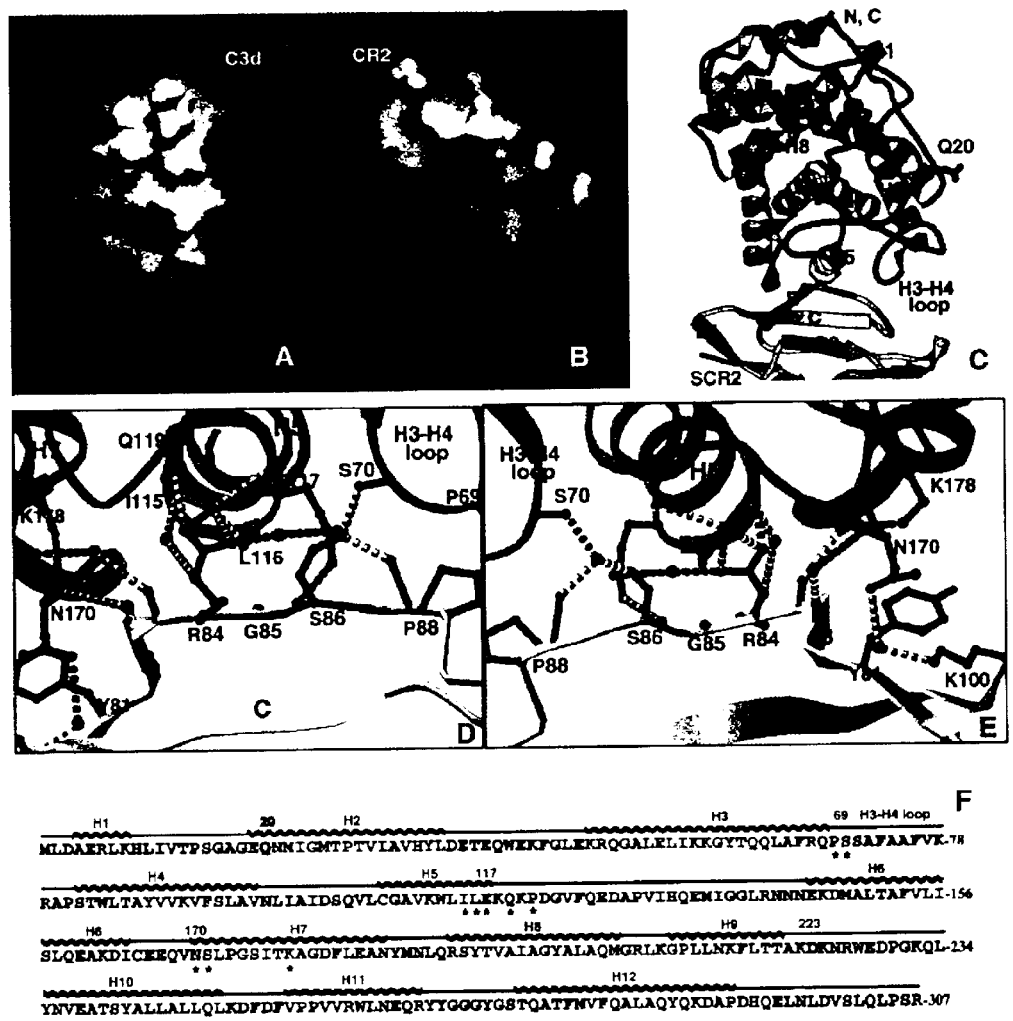

The C3d binding site (i.e., the interface between CR2 and C3d) is targeted to directly affect the binding of CR2 to C3d, other CR2-binding C3 fragments, or another ligand (i.e., inhibition or enhancement). In the CR2-C3d complex, no continuous stretch of residues on C3d participates in the interactions. Rather, residues that are separated in the linear sequence of C3d, but come together on the folded C3d, interact with CR2. Namely, the residues on the H3-H4 loop (the loop between helix 3 and 4), as well as H5, and H7 make contact with CR2 (FIG. 3C). On the CR2 part, however, a linear stretch of residues within SCR2 domain makes the contact with C3d. The B strand and B-C loop of SCR2 constitute the majority of the interactions with C3d. The nature of the contacts involves elegant networks of hydrogen bonds, plus some hydrophobic and van der Waals interactions (FIGS. 3D & 3E). The contact site is discussed in detail in the Examples. Preferred target sites in the C3d binding interface with CR2 include, but are not limited to: (1) a site on the B strand and the B-C loop of CR2 SCR2 comprising the segment: G79-G80-Y81-K82-I83-R84-G85-S86-T87-P88-Y89; (2) a site on the B strand of CR2 SCR2 comprising position K100; (3) a segment of CR2 SCR2 comprising V130-F131-P132-L133; and (4) a segment of CR2 SCR2 comprising the fragment T101-N102-F103. In the T101-N102-F103 site, the N102 residue is glycosylated. The N-acetylglucosamine residue attached to N102 forms a hydrogen bond with C3d. The present inventors have shown that amino acid residues at positions 84 and 86 of SEQ ID NO:4 are particularly important residues in the binding of C3d to CR2 and therefore, segments of CR2 including these residues are particularly desirable target sites. Alternatively, the CR2 contact points on C3d can be targeted for the identification of compounds that specifically modify the interaction between CR2 and C3d (and potentially the interaction of CR2 with its other ligands). Such sites include, but are not limited to: (1) the loop between helix 2-3 of C3d comprising the segment Q68-P69-S70-S71; (2) Helix 5 of C3d comprising the segment S104-Q105-V106-L107-C108-G109-A110-V111-K 112-W113-L114-I115-L116-E117-K118-Q119-K120-P121-D122; and (3) Helix 7of C3d comprising the segment N170-S171-L172-P173-G174-S175-I176-T177-K178-A179-G180-D181-F182-L183-E184-A185 (all positions are given with respect to SEQ ID NO:7).

The interface between the two monomers of CR2 can also be targeted to affect the binding of CR2 to a ligand. Two CR2 molecules dimerize through SCR1-SCR 1 contacts in the crystal structure (FIG. 2D). The contact is symmetrical, with the E1 strands from different molecules running antiparallel to each other. The C-terminus of the E1 strand also contacts the C-terminus of the D2 strand of another molecule. The nature of the interaction is hydrogen bonds. Without being bound by theory, the present inventors believe that a CR2 dimer, in contrast to a monomer, can allow a dramatic increase of cross-linked CR2/CD19/CD81 and B cell receptor molecules through binding to the antigen with two or more C3d attached, which can cause a 10,000-fold enhancement of the humoral immune response. Therefore, compounds that disrupt the dimer formation are expected to be primarily inhibitory compounds with regard to immune responses. Such compounds may also be beneficial, however, in inhibiting EBV or HIV infection mediated by CR2. Similarly, compounds that enhance or stabilize the dimer formation are expected to stimulate or enhance an immune response.

The interface between the SCR1 and SCR2 domains of CR2 is also targeted to affect the binding of CR2 to a ligand (i.e., inhibit or enhance). The packing of the two SCR domains in CR2 forms a V shape. Residues important for the tight packing between the two domains at the interface and the linker regions are shown in FIG. 2B. A very unique feature of the two domain CR2 structure is that the 8 amino acid linker makes a dramatic turn to allow the two SCR domains to pack against each other sideways (FIGS. 2A, 2B, 2C). Among the protein family containing SCR domains, the linkers connecting SCR domains are normally 3–5 amino acids in length, while an 8 amino acid linker is the longest known so far. The available structures of four SCR proteins containing two or 4 repeats (A. P. Wiles, et al.,(1997), supra;

P. N. Barlow, et al., (1993), supra; J. M. Casasnovas, et al.,(1999), supra; R. Schwarzenbacher et al., (1999), supra) all have end-end packing between consecutive SCRs, and CR2 is thus the first to demonstrate extensive side-side packing. In end-end packing, the adjacent domains could, in principle, adopt different rotations and bend angles relative to each other in different environments. Indeed, a commonly held concept is that SCRs are not absolutely fixed relative to each other but rather are allowed some freedom to move about this interface (P. N. Barlow, et al., (1993), ibid.; J. M. Casasnovas, et al.,(1999), ibid.). However, the side-side packing of the CR2 SCR1 and SCR2 would not give the two domains freedom to adopt different orientations, unless some active process is involved to first separate the two domains. The interface between the two domains is mainly hydrophobic (FIG. 2B). Trp112, which is unique to CR2 SCR2 sequence and located on strand D2, plays a critical role in the packing by interacting with Ile39 and the mainchain from SCR1. Trp112 would be unfavorably exposed to the solvent if the two domains do not pack against each other sideways in this manner. In addition to Trp112, several other residues also play a role in the packing, including Pro121, His91, Leu39, and the carbon side chain of Glu64. The 8 amino acid linker, which contains mainly hydrophobic residues such as Tyr65, Phe66, Tyr69, also participates in the hydrophobic packing outside the two-domain interface, further solidifying the interactions between SCR1 and SCR2 (FIG. 2B). The area of the interface of the two SCRs is very extensive, covering almost half of the length of one SCR domain (FIG. 2C). Since the above-mentioned previous studies of other SCR proteins were performed in the absence of their ligands, it is possible that this interface may change upon binding of CR2 to its ligand. In any event, it is predicted that the binding of a compound to this site will have an effect on the ligand-binding ability of CR2.

A candidate compound for binding to a CR2 protein, including to one of the preferred target sites described above, is identified by one or more of the methods of structure-based identification discussed above. As used herein, a "candidate compound" refers to a compound that is selected by a method of structure-based identification described herein as having a potential for binding to a CR2 protein (or its ligand) on the basis of a predicted conformational interaction between the candidate compound and the target site of the CR2 protein. The ability of the candidate compound to actually bind to a CR2 protein can be determined using techniques known in the art, as discussed in some detail below. A "putative compound" is a compound with an unknown regulatory activity, at least with respect to the ability of such a compound to bind to and/or regulate CR2 as described herein. Therefore, a library of putative compounds can be screened using structure based identification methods as discussed herein, and from the putative compounds, one or more candidate compounds for binding to CR2 can be identified. Alternatively, a candidate compound for binding to CR2 can be designed de novo using structure based drug design, also as discussed above. Candidate compounds can be selected based on their predicted ability to inhibit the binding of CR2 to its ligand, to stabilize (e.g., enhance) the binding of CR2 to its ligand, to bind to and activate CR2, to bind to and inhibit the activation of CR2, to bind to and activate a ligand of CR2, to bind to and inhibit the activation of a ligand of CR2, to disrupt the dimerization of CR2 monomers, or to stabilize the dimerization of CR2 monomers.

Accordingly, in one aspect of the present invention, the method of structure-based identification of compounds that potentially bind to complement receptor type 2 (CR2) proteins or to a complex of CR2 and its ligand further includes steps which confirm whether or not a candidate compound has the predicted properties with respect to its effect on CR2 (or a ligand of CR2). In one embodiment, the candidate compound is predicted to be an inhibitor of the binding of CR2 to its ligand, and the method further includes: (c) contacting the candidate compound identified in step (b) with CR2 or a fragment thereof and a CR2 ligand or a fragment thereof under conditions in which a CR2-CR2 ligand complex can form in the absence of the candidate compound; and (d) measuring the binding affinity of the CR2 or fragment thereof to the CR2 ligand or fragment thereof. A candidate inhibitor compound is selected as a compound that inhibits the binding of CR2 to its ligand when there is a decrease in the binding affinity of the CR2 or fragment thereof for the CR2 ligand or fragment thereof, as compared to in the absence of the candidate inhibitor compound.

In another embodiment, the candidate compound is predicted to be a stabilizer of the binding of CR2 to its ligand, and the method further comprises: (c) contacting the candidate compound identified in step (b) with a CR2-CR2 ligand complex, wherein the CR2-CR2 ligand complex comprises CR2 or a fragment thereof and a CR2 ligand, or a fragment thereof, (d) measuring the stability of the CR2-CR2 ligand complex of (i). A candidate stabilizer compound is selected as a compound that stabilizes the CR2-CR2 ligand complex when there is an increase in the stability of the complex as compared to in the absence of the candidate stabilizer compound.

In another embodiment, the candidate compound is predicted to bind to and activate CR2 (i.e., an agonist), and the method further comprises: (c) contacting the candidate compound identified in step (b) with CR2 or a ligand-binding fragment thereof, under conditions wherein in the absence of the compound, CR2 is not activated; and, (d) measuring the ability of the candidate compound to bind to CR2 to activate CR2. A candidate agonist compound is selected as a compound that binds to CR2 and activates CR2 as compared to in the absence of the candidate agonist compound. A similar embodiment includes the identification of candidate compounds that bind to target sites on the CR2 ligand which are now known as a result of the present inventors' work, and the determination of the ability of the candidate compound to bind to and activate the ligand of CR2 (e.g., by mimicking the structure of CR2).

In another embodiment, the candidate compound is predicted to bind to and inhibit CR2 (i.e., an antagonist), and the method further comprises: (c) contacting the candidate compound identified in step (b) with CR2 or a ligand-binding fragment thereof, wherein in the absence of the compound, CR2 is not activated; and, (d) measuring the ability of the candidate compound to bind to CR2 and activate CR2. A candidate antagonist compound is selected as a compound that binds to CR2 but does not activate and, in some embodiments, inhibits any constitutive activation, of the CR2. A similar embodiment includes the identification of candidate compounds that bind to target sites on the CR2 ligand which are now known as a result of the present inventors' work, and the determination of the ability of the candidate compound to bind to but not activate the ligand of CR2.

In another embodiment, the candidate compound is predicted to bind to CR2 and to disrupt the dimerization of CR2 monomers, and the method further comprises: (c) contacting the candidate compound identified in step (b) with at least two CR2 monomers or ligand-binding fragments thereof, in the presence and in the absence of a CR2 ligand or fragment thereof; and, (d) measuring the ability of the candidate compound to bind to CR2, the ability of the CR2 monomers to dimerize, and/or the ability of the CR2 ligand to activate CR2. A candidate compound for the disruption of CR2 dimerization is selected as a compound that binds to CR2 but inhibits the dimerization of CR2 and in some embodiments, inhibits the activation of CR2 by its ligand. Similarly, a candidate compound for stabilizing the dimerization of CR2 is a compound that binds to CR2, prolongs the dimerization of CR2 as compared to in the absence of the candidate compound, and in some embodiments, enhances or prolongs the activation of CR2 by its ligand.

In one embodiment, the conditions under which a CR2 according to the present invention is contacted with a candidate compound, such as by mixing, are conditions in which the receptor is not stimulated (activated) or bound to a natural ligand if essentially no candidate compound is present. For example, such conditions include normal culture conditions in the absence of a stimulatory compound (a stimulatory compound being, e.g., the natural ligand for the receptor (e.g., C3d, CD23, EBV), a stimulatory antibody, or other equivalent stimulus). In this embodiment, the candidate compound is then contacted with the CR2. In this embodiment, the step of detecting is designed to indicate whether the candidate compound binds to CR2, and in some embodiments, whether the candidate compound activates CR2.

In an alternate embodiment, the conditions under which a CR2 according to the present invention is contacted with a candidate compound, such as by mixing, are conditions in which the receptor is normally bound by a ligand or additionally stimulated (activated) if essentially no candidate compound is present. Such conditions can include, for example, contact of CR2 with a stimulator molecule (a stimulatory compound being, e.g., the natural ligand for the receptor, a stimulatory antibody, or other equivalent stimulus) which binds to the receptor and causes the receptor to become activated. In this embodiment, the candidate compound can be contacted with the receptor prior to the contact of the receptor with the stimulatory compound (e.g., to determine whether the candidate compound blocks or otherwise inhibits the binding and/or stimulation of CR2 by the stimulatory compound), or after contact of the receptor with the stimulatory compound (e.g., to determine whether the candidate compound downregulates, or reduces the activation of the receptor).

The present methods involve contacting CR2 with the candidate compound being tested for a sufficient time to allow for binding to, activation or inhibition of the receptor by the candidate compound. The period of contact with the candidate compound being tested can be varied depending on the result being measured, and can be determined by one of skill in the art. For example, for binding assays, a shorter time of contact with the candidate compound being tested is typically suitable, than when activation is assessed. As used herein, the term "contact period" refers to the time period during which the CR2 molecules are in contact with the compound being tested. The term "incubation period" refers to the entire time during which cells expressing CR2, for example, are allowed to grow prior to evaluation, and can be inclusive of the contact period. Thus, the incubation period includes all of the contact period and may include a further time period during which the compound being tested is not present but during which growth is continuing (in the case of a cell based assay) prior to scoring. The incubation time for growth of cells can vary but is sufficient to allow for the binding of CR2, activation of the receptor or signal transduction pathways associated with the receptor, and/or inhibition of the receptor. It will be recognized that shorter incubation times are preferable because compounds can be more rapidly screened. A preferred incubation time is between about 1 minute to about 48 hours.

In accordance with the present invention, a cell-based assay is conducted under conditions which are effective to screen for candidate compounds useful in the method of the present invention. Effective conditions include, but are not limited to, appropriate media, temperature, pH and oxygen conditions that permit the growth of the cell that expresses the receptor. An appropriate, or effective, medium refers to any medium in which a cell that naturally or recombinantly expresses a CR2, when cultured, is capable of cell growth and expression of CR2. Such a medium is typically a solid or liquid medium comprising growth factors and assimilable carbon, nitrogen and phosphate sources, as well as appropriate salts, minerals, metals and other nutrients, such as vitamins. Culturing is carried out at a temperature, pH and oxygen content appropriate for the cell. Such culturing conditions are within the expertise of one of ordinary skill in the art.

Cells that are useful in the cell-based assays of the present invention include any cell that expresses a CR2 and particularly, other proteins that are associated with CR2 signal transduction cascades (e.g., the CR2/CD19/CD81 co-activation complex (D. T. Fearon, 1995 ibid.; D. T. Fearon, 1998, ibid.; J. C. Cambier, 1997, ibid.; A. K. Matsumoto, et al., *J Exp Med* 173, 55–64 (1991))). Such cells include B lymphocytes, T lymphocytes, follicular dendritic cells, thymocytes, epithelial cells, and mast cells. Additionally, certain cells may be induced to express CR2, for example, some tumor cells. Therefore, cells that express CR2 can include cells that naturally express CR2, recombinantly express CR2, or which can be induced to express CR2. Cells useful in some embodiments can also include cells that express a natural ligand of CR2, such as CD23.

The assay of the present invention can also be a non-cell based assay. In this embodiment, the candidate compound can be directly contacted with an isolated CR2, or a receptor component (e.g., an isolated extracellular portion of the receptor, or soluble receptor), and the ability of the candidate compound to bind to the receptor or receptor component can be evaluated, such as by an immunoassay or other binding assay. The assay can, if desired, additionally include the step of further analyzing whether candidate compounds which bind to a portion of the receptor are capable of increasing or decreasing the activity of CR2. Such further steps can be performed by cell-based assay, as described above, or by non-cell-based assay. For example, isolated membranes may be used to identify compounds that interact with CR2. Membranes can be harvested from cells expressing CR2 by standard techniques and used in an in vitro binding assay. $^{125}$I-labeled (other labels can be used also) ligand (e.g., $^{125}$I-labeled C3d) is contacted with the membranes and assayed for specific activity; specific binding is determined by comparison with binding assays performed in the presence of excess unlabeled ligand. Membranes are typically incubated with labeled ligand in the presence or absence of test compound. Compounds that bind to the receptor and compete with labeled ligand for binding to the membranes reduced the signal compared to the vehicle control samples.

Alternatively, soluble CR2 may be recombinantly expressed and utilized in non-cell based assays to identify compounds that bind to CR2. Recombinantly expressed CR2 polypeptides or fusion proteins containing one or more extracellular domains of CR2, and preferably, at least SCR1 and SCR2, can be used in the non-cell based screening assays. Alternatively, peptides corresponding to the extracellular domain of CR2 or fusion proteins containing the extracellular domain of CR2 can be used in non-cell based assay systems to identify compounds that bind to the extracellular portion of CR2. In non-cell based assays the recombinantly expressed CR2 is attached to a solid substrate by means well known to those in the art. For example, CR2 and/or cell lysates containing such receptors can be immobilized on a substrate such as: artificial membranes, organic supports, biopolymer supports and inorganic supports. The protein can be immobilized on the solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports can be in any suitable form, including in a bead form, plate form, or well form. The test compounds are then assayed for their ability to bind to CR2.

In one embodiment, a BIAcore machine can be used to determine the binding constant of a complex between CR2 and a ligand (e.g., C3d) in the presence and absence of the candidate compound. For example, CR2 or a ligand binding fragment thereof can be immobilized on a substrate. A ligand, such as C3d, is contacted with the substrate to form a CR2-C3d complex. The dissociation constant for the complex can be determined by monitoring changes in the refractive index with respect to time as buffer is passed over the chip (O'Shannessy et al. Anal. Biochem. 212:457–468 (1993); Schuster et al., Nature 365:343–347 (1993)). Contacting a candidate compound at various concentrations with the CR2-ligand complex and monitoring the response function (e.g., the change in the refractive index with respect to time) allows the complex dissociation constant to be determined in the presence of the candidate compound and indicates whether the candidate compound is either an inhibitor or an agonist of the CR2-ligand complex. Alternatively, the candidate compound can be contacted with the immobilized CR2 at the same time as the ligand to see if the candidate compound inhibits or stabilizes the binding of the ligand to CR2.

Other suitable assays for measuring the binding of a candidate compound to a CR2 or CR2 ligand, and or for measuring the ability of such compound to affect the binding of a CR2 to its ligand include, for example, immunoassays such as enzyme linked immunoabsorbent assays (ELISA) and radioimmunoassays (RIA), as well as cell-based assays including, cytokine secretion assays, or intracellular signal transduction assays that determine, for example, protein or lipid phosphorylation, mediator release or intracellular $Ca^{++}$ mobilization upon CR2 binding to a cell signal transduction molecule or coreceptor.

As used herein, the phrase "agonist" refers to any compound that interacts with a CR2 and elicits an observable response. More particularly, a CR2 agonist can include, but is not limited to, a protein (including an antibody), a peptide, a nucleic acid or any suitable product of drug design (e.g., a mimetic) which is characterized by its ability to agonize (e.g., stimulate, induce, increase, enhance) the biological activity of a naturally occurring CR2 in a manner similar to a natural agonist (e.g., C3d, gp350/220, or CD23) (e.g., by interaction/binding with and/or direct or indirect activation of CR2, including by stabilizing the interaction of CR2 with a natural ligand). An "antagonist" refers to any compound which inhibits the effect of a CR2 agonist, as described above. More particularly, a CR2 antagonist is capable of associating with a CR2 such that the biological activity of the receptor is decreased (e.g., reduced, inhibited, blocked, reversed, altered) in a manner that is antagonistic (e.g., against, a reversal of, contrary to) to the action of a natural agonist on the receptor. It is noted that the three dimensional structures disclosed herein can be used to design or identify candidate compounds that agonize or antagonize the biological activity of the CR2 ligand. For example, a compound that enhances the interaction between CR2 and CD23 can also have a stimulatory effect on a cell that expresses CD23.

Preferred agonists (i.e., stimulatory compounds) to identify using the present method are compounds that exhibit improved binding to CR2 when compared with the ability of a natural CR2 ligand to bind to CR2, and also include compounds that enhance the binding of a natural ligand to CR2 or enhance signal transduction through CR2 coreceptor complexes. Preferred agonists of the present invention are identified by their ability to: (1) bind to, or otherwise interact with, CR2 at a higher level than, for example, a natural CR2 ligand; (2) enhance binding of CR2 to its ligand; (3) enhance dimer formation of CR2 by binding to CR2 or to the combination of CR2 bound to its ligand; and/or (4) enhance signal transduction through CR2. A preferred agonist of the present invention can also include a compound that binds to CR2 or a CR2 ligand, thereby enhancing the binding of CR2 to its ligand or improving cellular signal transduction during or after the binding of CR2 to its ligand, by, for example, modifying other regions of the CR2 by an allosteric interaction that modifies the ligand-binding site of CR2. Another suitable agonist compound of the present invention can include a compound that binds to CR2 in the absence of a natural ligand, in such a manner that CR2-mediated cellular signal transduction is stimulated.

Suitable antagonist (i.e., inhibitory) compounds to identify using the present method are compounds that interact directly with CR2, thereby inhibiting the binding of a natural ligand to CR2, by either blocking the ligand binding site of CR2 (referred to herein as substrate analogs) or by modifying other regions of CR2 (such as in the interface between the monomers of a CR2 dimer, or at the interface between the SCR1 and SCR2 regions of each monomer) such that the natural ligand cannot bind to CR2 (e.g., by allosteric interaction). A CR2 substrate analog refers to a compound that interacts with (e.g., binds to, associates with, modifies) the ligand binding site of a CR2 protein. A CR2 substrate analog can, for example, comprise a chemical compound that mimics the CR2 binding portion of a natural ligand, or that binds specifically to the ligand binding site of CR2 but does not mimic the CR2 binding portion of the natural ligand. An inhibitory compound of the present invention can also include a compound that essentially mimics at least a portion of CR2 that binds to a natural ligand (referred to herein as a peptidomimetic compound). Other suitable inhibitory compounds of the present invention include compounds that inhibit the binding of CR2 to a cell signal inducing molecule such as CD19.

Various specific embodiments of the present invention are described below. The description of the structure of CR2, and of structure based methods of identifying compounds that regulate CR2 are generally applicable to the methods described below, with particular modifications being noted in the specific description of the methods.

One embodiment of the present invention relates to a method to identify a compound that inhibits the complement receptor type 2 (CR2)-dependent infection of a host cell by Epstein Barr Virus (EBV). This method includes the steps of: (a) providing a three dimensional structure of a CR2 short consensus repeat (SCR) 1-2 region as previously described herein; (b) identifying a candidate compound for binding to the CR2 SCR 1-2 region by performing structure based drug design with the structure of (a) to identify a compound structure that binds to the three dimensional structure of the CR2 SCR 1-2 region; (c) contacting the candidate compound identified in step (b) with a cell that expresses CR2 or a ligand binding fragment thereof and an Epstein Barr Virus (EBV) particle under conditions in which the EBV particle can bind to CR2 and infect the cell in the absence of the candidate compound; and (d) measuring the intracellular EBV titer of the cell; wherein a candidate inhibitor compound is selected as a compound that inhibits the EBV titer in the cell, as compared to in the absence of the candidate inhibitor compound.

As discussed in the Background section, one of the naturally occurring ligand for human CR2 is Epstein-Barr virus (EBV). EBV interacts with CR2 via the gp350/220 viral membrane protein (J. D. Fingeroth, et al., *Proc Natl Acad Sci USA* 81, 4510–4 (1984)). EBV causes infectious mononucleosis, and is associated with Burkitt's Lymphoma and several other lymphomas and non-lymphoid tumors (M. Okano, *Acta Paediatr* 87, 11–8 (1998)). Therefore, the identification of compounds that inhibit the interaction between EBV and CR2 are desirable. Previous studies have suggested that two amino acid positions in CR2 Ser16 and Tyr68 to Tyr, FIG. 2E and green patch in FIGS. 5A and 5B) are likely to be involved in gp350/220 binding (D. R. Martin et al., *J Virol* 68, 4716–26(1994)). Given the three dimensional structure of the CR2 disclosed herein, one of skill in the art can now design or identify compounds that are predicted to bind to three dimensional face of CR2 including these residues.

In this embodiment, the steps of providing the CR2 structure and identifying a candidate compound are performed as described above generally for any candidate compound. The step of contacting the candidate can be performed under any suitable conditions for contacting a virus, or portion of the virus (e.g., gp350/220) with a receptor. Such a method preferably includes contacting (e.g., by mixing, adding, combining) EBV with a cell that expresses CR2 or a ligand binding fragment thereof (e.g., naturally, recombinantly or by induction) under conditions wherein, in the absence of the candidate compound, the EBV particle can bind to CR2 and infect the cell. The intracellular viral titer is measured in the presence and in the absence of the compound using methods well known to those of skill in the art. An inhibitor compound is selected as a compound that inhibits the EBV titer in the cell, as compared to in the absence of the candidate inhibitor compound.

Another embodiment of the present invention relates to a method to identify a compound that inhibits the binding of CD23 to complement receptor type 2 (CR2). This method includes the steps of: (a) providing a three dimensional structure of a CR2 short consensus repeat (SCR) 1-2 region as previously described herein; (b) identifying a candidate compound for binding to the CR2 SCR 1-2 region by performing structure based drug design with the structure of (a) to identify a compound structure that binds to the three dimensional structure of the CR2 SCR 1-2 region; (c) contacting the candidate compound identified in step (b) with a first cell expressing CR2 or a ligand binding fragment thereof and a second cell expressing a CD23 protein or fragment thereof under conditions in which the CD23 protein or fragment thereof and the CR2 or the ligand binding fragment thereof can bind in the absence of the candidate compound; and (d) measuring a biological activity induced by the interaction of CD23 and CR2 in the first or second cell; wherein a candidate inhibitor compound is selected as a compound that inhibits the biological activity as compared to in the absence of the candidate inhibitor compound.

CD23 is a molecule expressed on the follicular dendritic or other cell lineage surfaces which binds to B cells via CR2 (CR2/CD19/CD81 co-activation complex), thereby greatly potentiating signaling via the B cell antigen receptor. The identification of compounds that enhance the binding of CD23 to CR2 would be desirable under conditions when potentiation of the B cell antigen response is desired. However, CD23 is known to enhance IgE isotype switching in B cells. IgE is the prominent immunoglobulin isotype involved in allergic reactions. Inhibition of IgE production would reduce symptoms of allergic inflammation. Therefore, in one embodiment, it is desirable to inhibit the interaction between CR2 and CD23 to reduce IgE isotype switching in B cells.

In this embodiment, the step of contacting the candidate compound identified in step (b) with a first cell expressing CR2 or a ligand binding fragment thereof and a second cell expressing a CD23 protein or fragment thereof occurs under conditions in which the CD23 protein or fragment thereof and the CR2 or the ligand binding fragment thereof can bind in the absence of the candidate compound. Such conditions have been described above for cell-based assays. Preferably, the first cell is a B cell, although any CR2-expressing cell as described herein can be used. The CD23-expressing cell can include a follicular dendritic cell and a cell that recombinantly expresses CD23. Step (d) of measuring a biological activity induced by the interaction of CD23 and CR2 in the first or second cell can include the measurement of any suitable biological activity that is indicative of CR2 activation in the first cell and/or CD23 activation in the second cell. For example, biological activities associated with CR2 activation include, activation of lyn tyrosine kinase, activations of phosphatidyl inositol 3' kinase, phosphorylation of CD19, activation of PI3 kinase, and activation of protein kinase C (PKC). If the CR2-expressing cell is a B cell, isotype switching to IgE can be measured, for example, by comparing the amounts of expression of IgE between cells in the presence and absence of the compound. Biological activities associated with CD23 activation include, but are not limited to, increases in IgG synthesis, phosphatidylinositol hydrolysis, cAMP synthesis, Calcium flux, protein tyrosine kinase activation, increases in IL-6 and TNF-α synthesis, nitric oxide activation, increases in CD40 and HLA Class II expression, and NF-κB activation (J. Gordon, *Immunol. Today* 15, 411–417 (1994); B. Heyman, *Ann. Rev. Immunol.* 18, 709–737(2000); V. Fremeaux-Bacchi, et al, *Eur. J. Immunol.* 28, 4268–4274 (1998); R. M. Ten, et al, *J. Immunol.* 163, 3851–3857 (1999). Methods of measuring such biological activities of both CR2 and CD23 are known in the art and include immunoassays, kinase assays, flow cytometry, and phosphorylation assays. In this embodiment of the invention, an inhibitor compound is selected as a compound that inhibits the biological activity of CR2 or CD23 as compared to in the absence of the inhibitor compound.

Yet another embodiment of the present invention relates to a method to identify a compound that inhibits the binding of C3d, C3 or other CR2-binding fragments of C3 that contain C3d or a portion thereof, to complement receptor type 2 (CR2). This method includes the steps of: (a) providing a three dimensional structure of a CR2 short consensus repeat (SCR) 1-2 region as previously described herein; (b) identifying a candidate compound for binding to the CR2 SCR 1-2 region by performing structure based drug design with the structure of (a) to identify a compound structure that binds to the three dimensional structure of the CR2 SCR 1-2 region; (c) contacting the candidate compound identified in step (b) with a cell expressing CR2 or a fragment thereof and C3d or a fragment thereof, C3 or other CR2-binding fragments of C3 that contain C3d or a portion thereof, under conditions in which the C3d or fragment thereof, C3 or other CR2-binding fragments of C3 that contain C3d or a portion thereof, can bind to CR2 and enhance cell activation in the absence of the candidate compound; and (d) measuring the activation of the cell; wherein a candidate inhibitor compound is selected as a compound that inhibits cell activation, as compared to in the absence of the candidate inhibitor compound.

C3d-bound antigens, or antigens containing CR2-binding C3 fragments that contain C3d or a portion thereof, amplify B cell responses by binding to CR2 through C3d (or other CR2-binding C3 fragments that contain C3d or a portion thereof) at the same time as engaging the B cell antigen receptor (BCR) via the bound antigen (R. H. Carter and D. T. Fearon, *Science* 256, 105–7 (1992); J. C. Cambier, *Biochem Soc Trans* 25, 441–5 (1997)). The cross-linking of CR2 to the BCR by C3d greatly amplifies a signal transduction cascade through the CR2/CD19/CD81 co-activation complex (D. T. Fearon, 1995 ibid.; D. T. Fearon, 1998, ibid.; J. C. Cambier, 1997, ibid.; A. K. Matsumoto, et al., *J Exp Med* 173, 55–64 (1991)). Therefore, compounds that inhibit this interaction are useful for reducing an immune response and specifically, a humoral immune response (although effects on the cellular immune response may also be achieved). Compounds that enhance or mimic the interaction between CR2 and C3d are useful for potentiating such an immune response.

In this embodiment, the step of contacting the candidate compound identified in step (b) with a cell expressing CR2 or a fragment thereof and C3d or a fragment thereof, C3 or other CR2-binding fragments of C3 that contain C3d or a portion thereof, occurs under conditions in which the C3d or fragment thereof, C3 or other CR2-binding fragments of C3 that contain C3d or a portion thereof, can bind to CR2 and enhance cell activation in the absence of the candidate compound. Such cell-based methods of contacting have been described previously herein. Preferably, the cell expressing CR2 is selected from the group of a B cell, a T cell, a thymocyte, an epithelial cell, and a mast cell. The measurement of cell activation in (d) can be accomplished by any suitable method for detecting CR2 biological activity as previously described herein, and includes, but is not limited to: the measurement of: cytokine production by the cell, calcium mobilization in the cell, lyn tyrosine kinase activity in the cell, phosphatidyl inositol 3' kinase activity in the cell, phosphorylation of CD19 in the cell, and activation of protein kinase C (PKC) in the cell. An inhibitor compound is selected as a compound that inhibits cell activation, as compared to in the absence of the candidate inhibitor compound.

Another embodiment of the present invention relates to a method to inhibit complement receptor type 2 (CR2)-dependent human immunodeficiency virus-1 (HIV-1) infection of cells in a patient. This method includes the steps of administering to a patient infected with HIV-1 an inhibitor compound that inhibits the binding of C3d, C3 or another CR2-binding fragment of C3 containing C3d or a portion thereof, -opsonized HIV-1 to B cells, follicular dendritic cells, T cells or macrophages in the patient. The inhibitor compound is selected by the steps of: (a) providing a three dimensional structure of a CR2 short consensus repeat (SCR) 1-2 region as previously described herein; (b) identifying a candidate compound for binding to said CR2 SCR 1-2 region by performing structure based drug design with said structure of (a) to identify a compound structure that binds to said three dimensional structure of said CR2 SCR 1-2 region; (c) contacting said candidate compound identified in step (b) with a B cell, follicular dendritic cell, T cell or macrophage expressing CR2 or a fragment thereof and C3d or a fragment thereof, C3 or other CR2-binding fragments of C3 that contain C3d or a portion thereof, under conditions in which said C3d or fragment thereof, C3 or other CR2-binding fragments of C3 that contain C3d or a portion thereof, can bind to CR2 and enhance activation of the B cell, follicular dendritic cell, T cell or macrophage in the absence of said candidate compound; and (d) measuring the activation of the B cell, follicular dendritic cell, T cell or macrophage, wherein a candidate inhibitor compound is selected as a compound that inhibits activation of the B cell, follicular dendritic cell, T cell or macrophage, as compared to in the absence of said candidate inhibitor compound.

CR2 has been shown to mediate the interaction of C3d-bound HIV-1, or HIV-1 bound to other CR2-binding C3 fragments that contain C3d or a portion thereof, as an immune complex with B cells in a fashion that promotes transfer of virus and infection of CD4 T cells (S. Moir, et al., *J Exp Med* 192, 637–46 (2000)). Therefore, it would be desirable to design or identify compounds that inhibit the interaction of C3d, C3 or other CR2-binding fragments of C3 that contain C3d or a portion thereof with CR2 on B cells, follicular dendritic cells, T cells and macrophages to reduce the infection of CD4 T cells by HIV-1. In this embodiment, the step of contacting the candidate compound identified in step (b) with a B cell, follicular dendritic cell, T cell or macrophage, expressing CR2 or a fragment thereof and C3d or a fragment thereof, C3 or other CR2-binding fragments of C3 that contain C3d or a portion thereof, occurs under conditions in which the C3d or fragment thereof, C3 or other CR2-binding fragments of C3 that contain C3d or a portion thereof, can bind to CR2 and enhance activation of the B cell, follicular dendritic cell, T cell or macrophage in the absence of the candidate compound. Such conditions have been described in detail above. In addition, the step of measuring the activation of the B cell, follicular dendritic cell, T cell or macrophage expressing CR2 (i.e., by measuring a biological activity effected by CR2) have been described above.

Once a compound has been identified that inhibits the interaction between C3d and CR2 on B cells, follicular dendritic cells, T cells and/or macrophages, the compound is administered to a patient infected with HIV-1. A preferred patient to treat includes a patient with early-onset HIV infection. Such a patient can be defined herein as a patient that meets one or more of the following criteria: (1) the patient has a blood CD4$^+$ T cell count of at least about 100 cells/mm$^3$, and preferably, at least about 200 cells/mm$^3$, and more preferably, at least about 300 cells/mm$^3$, and even more preferably, at least about 400 cells/mm$^3$ as determined within 30 days of the time of employment of the present method; and (2) the patient has an HIV serum load of less than about 400 copies/ml, and preferably, less than about 300 copies/ml, and more preferably, less than about 200 copies/ml, and even more preferably, less than about 100 copies/ml, and most preferably undetectable viral load, as determined by plasma RNA PCT within 30 days of when the method is employed. In one embodiment, the patient is characterized as having a CD4$^+$ T cell count of at least about 100 cells/mm$^3$ when the method is employed and/or an HIV viral load of less than about 400 copies/ml when the method is employed.

A composition to be administered to a patient, such as in this embodiment, generally includes the compound identified by the structure based identification method and a carrier, and preferably, a pharmaceutically acceptable carrier. According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably at or near a cell that expresses a CR2, and most preferably, at or near a site of interest in the patient. Preferred pharmaceutically acceptable carriers are capable of maintaining a compound identified by the present methods in a form that, upon arrival of compound at the cell target in a culture or in patient, the compound is capable of interacting with its target (e.g., a CR2).

Suitable excipients of the present invention include excipients or formularies that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal,—or o-cresol, formalin and benzol alcohol. Compositions of the present invention can be sterilized by conventional methods and/or lyophilized.

One type of pharmaceutically acceptable carrier includes a controlled release formulation that is capable of slowly releasing a composition of the present invention into a patient or culture. As used herein, a controlled release formulation comprises a compound of the present invention (e.g., a protein (including homologues), a drug, an antibody, a nucleic acid molecule, or a mimetic) in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other carriers of the present invention include liquids that, upon administration to a patient, form a solid or a gel in situ. Preferred carriers are also biodegradable (i.e., bioerodible). When the compound is a recombinant nucleic acid molecule, suitable delivery vehicles include, but are not limited to liposomes, viral vectors or other delivery vehicles, including ribozymes. Natural lipid-containing delivery vehicles include cells and cellular membranes. Artificial lipid-containing delivery vehicles include liposomes and micelles. A delivery vehicle of the present invention can be modified to target to a particular site in a patient, thereby targeting and making use of a compound of the present invention at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

A pharmaceutically acceptable carrier which is capable of targeting is herein referred to as a "delivery vehicle." Delivery vehicles of the present invention are capable of delivering a composition of the present invention to a target site in a patient. A "target site" refers to a site in a patient to which one desires to deliver a composition. For example, a target site can be any cell which is targeted by direct injection or delivery using liposomes, viral vectors or other delivery vehicles, including ribozymes and antibodies. Examples of delivery vehicles include, but are not limited to, artificial and natural lipid-containing delivery vehicles, viral vectors, and ribozymes. Natural lipid-containing delivery vehicles include cells and cellular membranes. Artificial lipid-containing delivery vehicles include liposomes and micelles. A delivery vehicle of the present invention can be modified to target to a particular site in a subject, thereby targeting and making use of a compound of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics. In one embodiment, a targeting carrier can be a portion of a CR2 protein as described elsewhere herein, which is linked to the compound.

One preferred delivery vehicle of the present invention is a liposome. A liposome is capable of remaining stable in an animal for a sufficient amount of time to deliver a nucleic acid molecule or other compound to a preferred site in the animal. A liposome, according to the present invention, comprises a lipid composition that is capable of delivering a nucleic acid molecule or other compound to a particular, or selected, site in a patient. A liposome according to the present invention comprises a lipid composition that is capable of fusing with the plasma membrane of the targeted cell to deliver a nucleic acid molecule or other compound into a cell. Suitable liposomes for use with the present invention include any liposome. Preferred liposomes of the present invention include those liposomes commonly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule or other compound can be achieved using methods standard in the art.

A liposome delivery vehicle is preferably capable of remaining stable in a patient for a sufficient amount of time to deliver a nucleic acid molecule or other compound of the present invention to a preferred site in the patient (i.e., a target cell). A liposome delivery vehicle of the present invention is preferably stable in the patient into which it has been administered for at least about 30 minutes, more preferably for at least about 1 hour and even more preferably for at least about 24 hours. A preferred liposome delivery vehicle of the present invention is from about 0.01 microns to about 1 microns in size.

Another preferred delivery vehicle comprises a viral vector. A viral vector includes an isolated nucleic acid molecule useful in the present invention, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

A composition which includes an compound identified according to the present methods can be delivered to a cell culture or patient by any suitable method. Selection of such a method will vary with the type of compound being administered or delivered (i.e., protein, peptide, nucleic acid molecule, mimetic, or other type of compound), the mode of delivery (i.e., in vitro, in vivo, ex vivo) and the goal to be achieved by administration/delivery of the compound or composition. According to the present invention, an effective administration protocol (i.e., administering a composition in an effective manner) comprises suitable dose parameters and modes of administration that result in delivery of a composition to a desired site (i.e., to a desired cell) and/or in the desired regulatory event (e.g., inhibition of the binding of C3d-opsonized HIV-1 to B cells or follicular dendritic cells in the patient).

Administration routes include in vivo, in vitro and ex vivo routes. In vivo routes include, but are not limited to, oral, nasal, intratracheal injection, inhaled, transdermal, rectal, and parenteral routes. Preferred parenteral routes can include, but are not limited to, subcutaneous, intradermal, intravenous, intramuscular and intraperitoneal routes. Intravenous, intraperitoneal, intradermal, subcutaneous and intramuscular administrations can be performed using methods standard in the art. Aerosol (inhalation) delivery can also be performed using methods standard in the art (see, for example, Stribling et al., *Proc. Natl. Acad. Sci. USA* 189:11277–11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Direct injection techniques are particularly useful for suppressing graft rejection by, for example, injecting the composition into the transplanted tissue, or for site-specific administration of a compound, such as at the site of a tumor. Ex vivo refers to performing part of the regulatory step outside of the patient, such as by transfecting a population of cells removed from a patient with a recombinant molecule comprising a nucleic acid sequence encoding a protein according to the present invention under conditions such that the recombinant molecule is subsequently expressed by the transfected cell, and returning the transfected cells to the patient. In vitro and ex vivo routes of administration of a composition to a culture of host cells can be accomplished by a method including, but not limited to, transfection, transformation, electroporation, microinjection, lipofection, adsorption, protoplast fusion, use of protein carrying agents, use of ion carrying agents, use of detergents for cell permeabilization, and simply mixing (e.g., combining) a compound in culture with a target cell.

In this particular embodiment of the invention (i.e., the inhibition of HIV infection), it will be obvious to one of skill in the art that the number of doses administered to an immunodeficiency virus infected patient is dependent upon the extent of the infection and the response of an individual to the treatment. For example, in the case of HIV-infection, a patient having a high titer of HIV may require more doses than a patient having lower titers. In some cases, however, a patient having a high titer of HIV may require fewer doses than a patient having lower titers, if the patient with the high titer responds more favorably to the therapeutic composition than the patient with the lower titer. Thus, it is within the scope of the present invention that a suitable number of doses, as well as the time periods between administration, includes any number required to cause regression of a disease.

In another embodiment, this method is employed in conjunction with administration to the patient of one or more anti-retroviral therapeutic compounds. Such compounds include, but are not limited to, AZT, ddI, ddC, d4T, 3TC and/or protease inhibitors.

Another embodiment of the present invention relates to a method of preparing a vaccine, comprising linking a compound that increases B cell activation to an antigen to form the vaccine. The compound is selected by a method including the steps of: (a) providing a three dimensional structure of a CR2 short consensus repeat (SCR) 1-2 region as previously described herein; (b) identifying a candidate compound for binding to the CR2 SCR 1-2 region by performing structure based drug design with the structure of (a) to identify a compound structure that binds to the three dimensional structure of the CR2 SCR 1-2 region; (c) contacting the candidate compound identified in step (b) with a B cell expressing CR2 or a fragment thereof and with C3d or a fragment thereof, C3 or other CR2-binding fragments of C3 that contain C3d or a portion thereof, under conditions in which said C3d or fragment thereof, C3 or other CR2-binding fragments of C3 that contain C3d or a portion thereof, can bind to and activate CR2 in the absence of said candidate compound; and (d) measuring the activation of the B cell. A candidate compound for use in a vaccine is selected as a compound that increases B cell activation as compared to in the absence of the candidate compound.

Because CR2 plays a critical role as a coreceptor for B cells and is expressed on other cells as well, CR2 is a molecular target for adjuvants and can enhance the immune response to vaccines. Therefore, in this method, compounds are identified that bind to CR2 and that enhance B cell activation, either by enhancing the interaction between CR2 and a natural ligand (e.g., C3d), or by directly interacting with CR2 to enhance downstream biological activities of the receptor, as previously discussed herein. Methods for contacting a cell with the compound and measuring the activation events associated with CR2 activation have been previously described. In addition, to measure B cell activation, one can measure calcium mobilization, immunoglobulin class switching, cytokine production, activation of NF-κB, activation of MAP kinases, protein kinase activity and phosphorylation of proteins associated with B cell activation. In this embodiment, the conditions under which the B cell is contacted typically include the presence of an antigen that binds to the B cell antigen receptor, in addition to the other components. A compound for use in a vaccine, once identified, is typically associated with a protein (antigen or antigen-containing composition) or nucleic acid to be administered to a patient as part of the vaccine. The use of a compound identified by the present method will potentiate the immune response to the antigen.

Another embodiment of the present invention relates to a drug delivery system that will preferentially deliver compounds to sites of complement activation containing CR-2 binding fragments of C3 (e.g., C3 and portions thereof that contain C3d). Such a drug delivery system includes: (a) a drug; and, (b) a portion of a CR2 protein that includes one or more of: (i) a portion comprising positions on strand B and the B-C loop of SCR2 including: G79-G80-Y81-K82-I83-R84-G85-S86-T87-P88-Y89; (ii) a portion comprising position K100 on the B strand of CR2; and, (iii) a portion comprising positions: V130-F131-P132-L133 (positions given with reference to SEQ ID NO:4). In one embodiment, the portion of the CR2 protein can also contain positions T101-N102-F103 (reference again to SEQ ID NO:4). The drug is linked to the portion of CR2 by any suitable method, covalently or non-covalently, including by recombinant means or by chemical means. In this embodiment, the CR2 is not a full-length protein, or the soluble form of CR2, as it is known in the art (i.e., the natural soluble CR2 or the CR2 with the membrane portion removed), but rather, includes less of the amino acid sequence than the full-length or the soluble CR2, and preferably, just the portions of SCR1 and SCR2 that have been determined herein to be involved in the contact between CR2 and a natural ligand (e.g., C3d) and that are required to form a CR2 portion with the tertiary structure necessary to bind to C3d (or a fragment thereof). Therefore, the portion of CR2 used in the drug delivery system consists essentially of at least one or more of the above-recited segments of CR2, including a contiguous segment containing all of the segments (i.e., from positions 79–133 of SEQ ID NO:4), and has the three dimensional conformation of CR2 at the CR2-C3d interface, such that the portion will bind to C3d, C3 or other CR2-binding fragments of C3 that contain C3d or a portion thereof. Therefore, the portion of CR2 suitable for use in a drug delivery system includes the portions of CR2 that contact C3d, as well as the portions required to maintain the spatial positions of the contact residues, such that the tertiary structure of the C3d binding portion is conformationally similar to the tertiary structure of the C3d binding portion of the CR2 crystal described herein, using the parameters for structural homologues as described elsewhere herein for the structure of the CR2 complexed with C3d. According to the present invention, a CR2 fragment consisting essentially of the portions of SCR1 and SCP2 that have been determined herein to be involved in the contact between CR2 and C3d can have at least one, and up to about 20 (in whole number increments), additional heterologous amino acids flanking each of the C- and/or N-terminal end of the CR2 portion that contains the above-described segments and the sequence necessary to maintain the appropriate tertiary structure to bind to C3d (or a fragment thereof). According to the present invention, the heterologous amino acids are a sequence of amino acids that are not naturally found (i.e., not found in nature, in vivo) flanking the CR2 sequence that makes up the portion of CR2 or which would not be encoded by the nucleotides that flank the naturally occurring CR2 nucleic acid sequence as it occurs in the gene, if such nucleotides in the naturally occurring sequence were translated using standard codon usage for the organism from which the given CR2 portion is derived. Such heterologous amino acids can include a sequence that is less than about 75% similar to the natural sequence in the same positions. This embodiment also includes methods of identifying such portions of CR2.

Drugs that are desirable to deliver using the drug delivery system of the present invention include any drug that may have a beneficial effect on a subject when delivered to a site of complement activation wherein C3 and/or CR2-binding portions of C3 are present. The drugs can be protein-based, carbohydrate-based, lipid-based, nucleic acid-based, or any small molecule. Examples of such drugs include, but are not limited to, anti-inflammatory compounds, cytotoxic drugs, complement regulatory proteins, corticosteroids, and any compounds useful in ischemic, inflammatory autoimmune or vascular diseases, all of which have C3 fragments present.

In this embodiment, drug design strategies as specifically described above with regard to the identification of compounds that bind to CR2 and affect its interaction with various ligands can be similarly applied to the CR2 structure itself. CR2 proteins designed by this method can be used as drug delivery vehicles or to otherwise alter the biological activity of a CR2, such as by competing for a naturally occurring CR2 in vivo. One of ordinary skill in the art, using the art recognized modeling programs and drug design methods, many of which are described herein, to prepare portions of complement receptor type 2 (CR2) proteins that bind to their ligands, including CR2 homologues that retain ligand binding activity. In addition, one of skill in the art can produce CR2 proteins having modified biological activity. For example, such a method can include: (a) providing a three dimensional structure of a CR2 SCR1-2 domain as previously described herein; (b) analyzing the three dimensional structure to the three-dimensional structure of the CR2 SCR 1-2 region by performing structure based drug design with the structure of (a) to the sites in the structure contributing to ability of CR2 to bind to a ligand (e.g., C3d or other CR2-binding fragments of C3); and (c) producing a protein that is a portion of CR2 that includes such sites. In the method to produce a CR2 protein having modified biological activity, one can analyze the three dimensional structure of CR2 provided herein to identify at least one site that contributes to the biological activity of the protein, and then modify at least one such site to alter the biological activity of the CR2 protein. Methods to altered proteins for CR2 biological activity include testing the altered protein for any of the biological activities of CR2 previously described herein.

Another embodiment of the present invention relates to an antibody that selectively binds to CR2. The antibody binds to a portion of CR2 selected from the group consisting of: (a) the interface between the SCR1 and SCR2 domains of CR2; (b) the dimer interface between two CR2 proteins; and, (c) the interface between CR2 and C3d (where the C3d includes any CR2-binding fragments of C3 that contain C3d or a portion thereof). The portion of the CR2-C3d interface bound by the antibody preferably includes at site selected from: (a) the B strand and the B-C loop of CR2 SCR2 comprising the segment: G79-G80-Y81-K82-I83-R84-G85-S86-T87-P88-Y89; (b) the B strand of CR2 SCR2 comprising position K100; and (c) a segment of CR2 SCR2 comprising V130-F131-P132-L133. Prior to the present invention, the three dimensional structure of the CR2 interfaces set forth above were not known and therefore, it was not possible to design or identify an antibody by making use of such structural information. The present inventors have provided suitable target sites, including specific residues within such sites, for the design and identification of antibodies.

According to the present invention, the phrase "selectively binds to" refers to the ability of an antibody, antigen binding fragment or binding partner of the present invention to preferentially bind to specified proteins (e.g., the recited portions of a CR2 of the present invention). More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.

Limited digestion of an immunoglobulin with a protease may produce two fragments. An antigen binding fragment is referred to as an Fab, an Fab', or an F(ab')$_2$ fragment. A fragment lacking the ability to bind to antigen is referred to as an Fc fragment. An Fab fragment comprises one arm of an immunoglobulin molecule containing a L chain ($V_L$+$C_L$ domains) paired with the $V_H$ region and a portion of the $C_H$ region (CH1 domain). An Fab' fragment corresponds to an Fab fragment with part of the hinge region attached to the CH1 domain. An F(ab')$_2$ fragment corresponds to two Fab' fragments that are normally covalently linked to each other through a di-sulfide bond, typically in the hinge regions.

Functional aspects of an immunoglobulin molecule include the valency of an immunoglobulin molecule, the affinity of an immunoglobulin molecule, and the avidity of an immunoglobulin molecule. As used herein, affinity refers to the strength with which an immunoglobulin molecule binds to an antigen at a single site on an immunoglobulin molecule (i.e., a monovalent Fab fragment binding to a monovalent antigen). Affinity differs from avidity which refers to the sum total of the strength with which an immunoglobulin binds to an antigen. Immunoglobulin binding affinity can be measured using techniques standard in the art, such as competitive binding techniques, equilibrium dialysis or BIAcore methods. As used herein, valency refers to the number of different antigen binding sites per immunoglobulin molecule (i.e., the number of antigen binding sites per antibody molecule of antigen binding fragment). For example, a monovalent immunoglobulin molecule can only bind to one antigen at one time, whereas a bivalent immunoglobulin molecule can bind to two or more antigens at one time, and so forth. Both monovalent and bivalent antibodies that selectively bind to CR2 of the present invention are encompassed herein.

In one embodiment of the present invention, a monovalent antibody can be used as a regulatory compound. Such an antibody is not capable of aggregating receptors. Divalent antibodies can also be used in the present invention.

In one embodiment, the antibody is a bi- or multi-specific antibody. A bi-specific (or multi-specific) antibody is capable of binding two (or more) antigens, as with a divalent (or multivalent) antibody, but in this case, the antigens are different antigens (i.e., the antibody exhibits dual or greater specificity). A bi-specific antibody suitable for use in the present method includes an antibody having: (a) a first portion (e.g., a first antigen binding portion) which binds to CR2; and (b) a second portion which binds to a cell surface molecule expressed by a cell which expresses CR2. In this embodiment, the second portion can bind to any cell surface molecule. In a preferred embodiment, the second portion is capable of targeting the regulatory antibody to a specific target cell (i.e., the regulatory antibody binds to a target molecule).

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Genetically engineered antibodies of the invention include those produced by standard recombinant DNA techniques involving the manipulation and re-expression of DNA encoding antibody variable and/or constant regions. Particular examples include, chimeric antibodies, where the $V_H$ and/or $V_L$ domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source.

Construction of chimeric and CDR-grafted antibodies are described, for example, in European Patent Applications: EP-A 0194276, EP-A 0239400, EP-A 0451216 and EP-A 0460617.

Alternative methods, employing, for example, phage display technology (see for example U.S. Pat. No. 5,969,108, U.S. Pat. No. 5,565,332, U.S. Pat. No. 5,871,907, U.S. Pat. No. 5,858,657) or the selected lymphocyte antibody method of U.S. Pat. No. 5,627,052 may also be used for the production of antibodies and/or antigen fragments of the invention, as will be readily apparent to the skilled individual.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (*Nature* 256:495–497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

Another embodiment of the present invention relates to a therapeutic composition that, when administered to an animal, enhances B cell responses in the animal. The therapeutic composition includes a compound that stimulates the activity of a complement receptor type 2 (CR2), which has been identified by a method of structure based identification of compounds of the present invention, as described in detail above. Specifically, this method includes the steps of: (a) providing a three dimensional structure of a CR2 short consensus repeat (SCR) 1-2 region as described previously herein; (b) identifying a candidate compound for binding to the CR2 SCR 1-2 region by performing structure based drug design with the structure of (a) to identify a compound structure that binds to the three dimensional structure of the CR2 SCR 1-2 region; (c) synthesizing the candidate compound; and (d) selecting candidate compounds that bind to and activate CR2.

Another embodiment of the present invention relates to a therapeutic composition that, when administered to an animal, inhibits the biological activity of complement receptor type 2 (CR2) in the animal. The therapeutic composition comprises a compound that inhibits the activity of a complement receptor type 2 (CR2), the compound being identified by the method comprising: (a) providing a three dimensional structure of a CR2 short consensus repeat (SCR) 1-2 region as previously described herein; (b) identifying a candidate compound for binding to the CR2 SCR 1-2 region by performing structure based drug design with the structure of (a) to identify a compound structure that binds to the three dimensional structure of the CR2 SCR 1-2 region; (c) synthesizing the candidate compound; and (d) selecting candidate compounds that inhibit the biological activity of CR2. Preferably, the compounds inhibit the formation of a complex between CR2 and a CR2 ligand, such ligand including, but not limited to, C3d, CD23 and Epstein Barr Virus (EBV). In a more preferred embodiment, the compound inhibits the activation of CR2.

Methods of identifying candidate compounds and selecting compounds that bind to and activate or inhibit CR2 have been previously described herein. Candidate compounds can be synthesized using techniques known in the art, and depending on the type of compound. Synthesis techniques for the production of non-protein compounds, including organic and inorganic compounds are well known in the art.

For smaller peptides, chemical synthesis methods are preferred. For example, such methods include well known chemical procedures, such as solution or solid-phase peptide synthesis, or semi-synthesis in solution beginning with protein fragments coupled through conventional solution methods. Such methods are well known in the art and may be found in general texts and articles in the area such as: Merrifield, 1997, *Methods Enzymol.* 289:3–13; Wade et al., 1993,*Australas Biotechnol.* 3(6):332–336; Wong et al., 1991, *Experientia* 47(11–12):1123–1129; Carey et al., 1991, *Ciba Found Symp.* 158:187–203; Plaue et al., 1990, *Biologicals* 18(3):147–157; Bodanszky, 1985, *Int. J. Pept. Protein Res.* 25(5):449–474; or H. Dugas and C. Penney, BIOORGANIC CHEMISTRY, (1981) at pages 54–92, all of which are incorporated herein by reference in their entirety. For example, peptides may be synthesized by solid-phase methodology utilizing a commercially available peptide synthesizer and synthesis cycles supplied by the manufacturer. One skilled in the art recognizes that the solid phase synthesis could also be accomplished using the FMOC strategy and a TFA/scavenger cleavage mixture.

If larger quantities of a protein are desired, or if the protein is a larger polypeptide, the protein can be produced using recombinant DNA technology. A protein can be produced recombinantly by culturing a cell capable of expressing the protein (i.e., by expressing a recombinant nucleic acid molecule encoding the protein) under conditions effective to produce the protein, and recovering the protein. Effective culture conditions include, but are not limited to, effective media, bioreactor, temperature, pH and oxygen conditions that permit protein production. An effective medium refers to any medium in which a cell is cultured to produce the protein. Such medium typically comprises an aqueous medium having assimilable carbon, nitrogen and phosphate sources, and appropriate salts, minerals, metals and other nutrients, such as vitamins. Recombinant cells (i.e., cells expressing a nucleic acid molecule encoding the desired protein) can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Such techniques are well known in the art and are described, for example, in Sambrook et al., 1988, Molecular Cloning: A Laboratory Manual, Cold Spring Harbor Press, Cold Spring Harbor Laboratory, Cold Spring Harbor, N.Y. or Current Protocols in Molecular Biology (1989) and supplements.

As discussed above, a composition, and particularly a therapeutic composition, of the present invention generally includes the therapeutic compound (e.g., the compound identified by the structure based identification method) and a carrier, and preferably, a pharmaceutically acceptable carrier. Pharmaceutically acceptable carriers and preferred methods of administration of therapeutic compositions of the present invention have been described in detail above with regard to the administration of an inhibitor compound to a patient infected with HIV. Such carriers and administration protocols are applicable to this embodiment.

Yet another embodiment of the present invention relates to an isolated C3d mutant protein, C3 or other CR2-binding fragments of C3 that contain a mutant C3d or a portion thereof, comprising an amino acid substitution of an non-asparagine amino acid residue at position 170 wherein said C3d mutant protein, C3 or other CR2-binding fragments of C3 that contain the mutant C3d or a portion thereof, has reduced binding to complement receptor type 2 (CR2), as compared to a wild-type C3d protein (SEQ ID NO:7), or equivalent wild-type CR2-binding fragment of C3 that contain C3d or a portion thereof. Preferably, the mutant protein is at least about 50% identical to SEQ ID NO:7, and more preferably at least about 60% identical, and more preferably at least about 70% identical, and more preferably at least about 80% identical, and more preferably at least about 90% identical, and more preferably at least about 95% identical to SEQ ID NO:7. In a preferred embodiment, the mutant protein comprises SEQ ID NO:8 (mt170 or mut2) or SEQ ID NO:9 (mut4).

Another embodiment of the present invention relates to a computer for producing a three-dimensional model of a molecule or molecular structure, wherein the molecule or molecular structure comprises a three dimensional structure defined by atomic coordinates of a complement receptor type 2 (CR2) protein, according to Table 2 or Table 3, or a three-dimensional model of a homologue of the molecule or molecular structure, wherein the homologue comprises a three dimensional structure that has an average root-mean-square deviation (RMSD) of equal to or less than about 1.0 Å for the backbone atoms in secondary structure elements in the CR2 protein, wherein the computer comprises:

a. a computer-readable medium encoded with the atomic coordinates of the CR2 protein, according to Table 2 or Table 3, to create an electronic file;

b. a working memory for storing a graphical display software program for processing the electronic file;

c. a processor coupled to the working memory and to the computer-readable medium which is capable of representing the electronic file as the three dimensional model; and, d. a display coupled to the processor for visualizing the three dimensional model;

wherein the three dimensional structure of the CR2 protein is displayed on the computer.

The following examples are provided for the purpose of illustration and are not intended to limit the scope of the present invention.

EXAMPLES

Example 1

The following example describes the crystallization and structure determination of the complex of complement receptor type 2 (CR2) and C3d.

*Crystallization and Structure Determination of Structure*

The crystals of the complex of CR2-C3d were obtained by co-crystallization of CR2 and C3d, at a protein ratio where no free CR2 or C3d could be detected by native gel electrophoresis. The protein concentration of 20 mg/ml was used for crystallization by the method of hanging drop vapor diffusion. The crystallization buffer contained 17% PEG 2K, 0.2 M ZnAcetate, and 0.1 M NaCacodylate (pH 7.36). Crystals reached full size after 4–6 weeks at 4° C. Crystal was frozen under liquid nitrogen in the crystallization buffer containing 20% glycerol. Synchrotron data were collected at Brookhaven National Laboratory and was indexed, integrated and reduced using D*trek (licensed through MSC Inc., Table 1). The space group is R32, with unit cell a=b=170.5 Å, c=173.8 Å. AmoRe (CCP4, *Acta Cryst.* D50, 760–763 (1994)) was used to do molecular replacement that was carried out using C3d (Accession No. 1C3D from the Protein Data Bank (PDB)) as a search model. The final correlation function and R factor after rotation and translation search were 50% and 45%. Initial phase improvement was carried out using solvent flattening and two fold averaging by the program DM (CCP4, *Acta Cryst.* D50, 760–763 (1994)) in CCP4 suit. Stepwise model building and refinement were carried out using program "O" and CNS (P. D. A. A. T. Brunger, G. M. Clore, W. L. Delano, P. Gros, R. W. Grosse-Kunstleve, J.-S. Jiang, J. Kuszewski, N. S. P. M. Nilges, R. J. Read, L. M. Rice, T. Simonson, G. L. Warren, *Acta Cryst.* D54, 905–921 (1998)). The final complete model was refined using simulated annealing, positional refinement, and individual B factor refinement. Water molecules were added last using CNS (Table 1).

TABLE 1

Structure determination and refinement

| Data collection statistics | |
|---|---|
| Space group | R32 |
| Unit cell length (Å) | a = b = 170.5, c = 173.8 |
| Resolution (Å) | 25.0–2.04 |
| Completeness (last bin) | 94.1/83.6 |
| Total reflections | 255801 |
| Unique reflections | 63919 |
| [1] Rsym (last bin) % | 6.7/22.3 |
| I/δ (last bin) | 10.8/3.7 |
| Refinement statistics | |
| % of reflections for $R_{free}$ | 10 |
| $R_{work}/R_{free}$ | 20.8/23.9 |
| rmsd from ideality | |
| Bond length (Å) | 0.006 |
| Bond angle (°) | 1.10 |
| Dihedral angle (°) | 16.8 |
| Ramachandran plot (core, disallowed) | 92.3/0 |
| Average B factor | 33.98 |
| rmsd of B factor (Å$^2$) | 1.2 |
| Protein atoms in the model | 8878 |
| H$_2$O in the model | 580 |

[1] $Rsym = \Sigma_{ij} |I_i(j) - <I(j)>| / \Sigma_{ij} I_i(j)$, where $I_i(j)$ is the i-th measurement of reflection j and $<I(j)>$ is the overall weighted mean of j measurements.

The atomic coordinates representing the structure of the complex of CR2 and C3d were deposited on Jan. 11, 2001, with the Protein Data Bank (PDB), operated by the Research Collaboratory for Structural Bioinformatics (RCSB) (H. M. Berman, J. Westbrook, Z. Feng, G. Gilliland, T. N. Bhat, H. Weissig, I. N. Shindyalov, P. E. Bourne, *The Protein Data Bank; Nucleic Acids Research*, 28:235–242 (2000)), under PDB Deposit No. PDB id 1GHQ. These atomic coordinates are also represented herein as Table 2.

Description of the Overall Structure of the CR2-C3d Complex

Figure 1B:
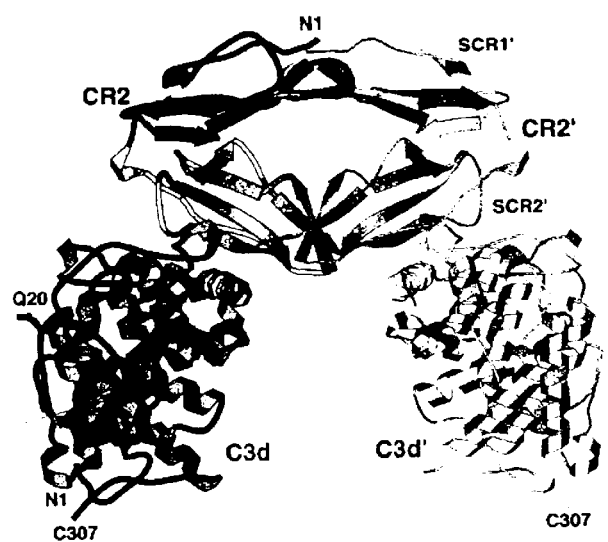

FIGS. 1A and 1B show the structure of the CR2-C3d complex. FIG. 1A is an overall view of the structure of CR2 binding to C3d, showing only SCR2 contacting one portion of the edge of C3d. CR2 SCR1 is colored in red and SCR2 in yellow, while C3d is in cyan. The side chain of residue Q20 of C3d that forms an ester-bond with antigen is drawn in pink and labeled. The position of residue D223 of C3d, which is the C3F form (fast migrating variant on agarose gel electrophoresis) that is associated with an increased incidence of certain diseases (M. C. Poznansky et al., *J Immunol* 143, 1254–8 (1989)), is also labeled. The other form of C3d, C3S (slow migration), has an N223 residue. The N and C termini of C3d (N1 and C307, respectively) are positioned next to each other. FIG. 1B shows the overall structure showing a second CR2-C3d complex (colored in light blue and grey) that dimerizes with the first one in FIG. 1A. The dimerization contact in the two-complex structure is through SCR1 of CR2 at the very top. (Prepared with the program MOLSCRIPT).

The complex contains a V-shaped CR2 receptor binding to a globular C3d ligand (FIG. 1A). The CR2 receptor portion contains two domains (SCR1 and SCR2) that pack against each other almost side to side, producing a drastic bend of 53 degrees between the two domains to give a V-shape. A well-structured linker of 8 amino acids (residues 64–71) connects the SCR1 and SCR2 domains. Both SCR1 and SCR2 domains consist of only beta-strands and coils, which is characteristic of the SCR fold that contains a beta-barrel core structure (A. P. Wiles, et al., *J Mol Biol* 272, 253–65 (1997); P. N. Barlow, et al., *J Mol Biol* 232, 268–84 (1993); J. M. Casasnovas, M. Larvie, T. Stehle, *EMBO J* 18, 2911-22 (1999); R. Schwarzenbacher, et al., *EMBO J* 18, 6228–39 (1999)). The V-shaped two-domain CR2 molecule has a span of 42.6 Å at the base of the molecule (from SCR1 to SCR2), and the height of "V" structure (from base to tip) measures 38.5 Å.

The C3d ligand, which has a dome-shaped structure that consists of mostly alpha helices (B. Nagar, R. G. Jones, R. J. Diefenbach, D. E. Isenman, J. M. Rini, *Science* 280, 1277–81 (1998)), interacts with the receptor using one portion of the edge of the dome. The CR2-contact edge of C3d is located on nearly the opposite side of the amino (N) and carboxyl (C) termini, which are physically proximate to each other (FIG. 1A). Binding to CR2 through this edge leaves the concave and convex surfaces free and the rest of the iC3b molecule (a form of C3 encompassing the C3d domain with which CR2 also interacts) likely oriented away from CR2 (FIG. 1A). The site of the ester-bond linkage to antigens (Q20) sits approximately half way between the receptor contact edge and the N and C termini of C3d (FIG. 1A). The site of mutation (N223 to D223, FIG. 1A) that defines an important disease-related allelic polymorphism, C3F (fast) versus C3S (slow) (M. C. Poznansky, P. M. Clissold, P. J. Lachmann, *J Immunol* 143, 1254–8 (1989)), is located away from the CR2 interaction site; therefore, this disease association is likely not directly related to CR2 binding but rather to other C3 functions.

Unexpectedly, a dimer of CR2 molecules is formed in the crystal through contacts between SCR1 domains (FIG. 1B). This CR2 dimer has a shape of two letter V's coming together head to head, with SCR1 facing SCR1 and SCR2 facing SCR2. No direct contacts occur between SCR2. This second CR2 is essentially a duplicate of the other CR2 molecule of the dimer that binds to C3d (FIG. 1B).

Description of the Structure of CR2

FIGS. 2A–2E show the structure of CR2. FIG. 2A is a ribbon representation of the CR2 SCR1 (in red) and SCR2 (in yellow) structures, showing the SCR fold and the packing of the two domains to form a V shape. The side chains of Cys residues that form intra-domain disulfide bonds are colored in cyan. Within each domain, the beta-strands B-E are labeled. A sugar residue GlcNAc (N-acetyl-glucosamine) is seen attached to N102 of SCR2. (Prepared using MOLSCRIPT). FIG. 2B shows the structure and packing interaction at the interface of CR2 SCR1 and SCR2 domains. Residues important for the tight packing between the two domains at the interface and the linker regions are shown. (Prepared with the program RIBBONS). FIG. 2C is a surface representation of the two-domain arrangement of CR2. (Prepared using GRASP). FIG. 2D shows the dimerization of CR2 through interactions between SCR1 of each molecule. Strand D2 and E1 of one CR2 molecule (red) packed against strand E1 and D2 of the second CR2 molecule in the dimer (blue). (Prepared using MOLSCRIPT). FIG. 2E shows a sequence alignment between human CR2 (SEQ ID NO:4) and mouse CR2 (mCR2) (SEQ ID NO:6). The first residue of CR2 (Gly) is changed to Ala in the structure due to PCR primer sequence. Secondary structure elements are shown above the corresponding aligned sequences. A black line represents coils and arrows represent beta-strands. The linker sequence between SCR1 and SCR2 is underlined. The residues whose side-chain or main-chain groups are involved in binding to C3 d are indicated by *. The symbol • indicates the two residues that, after mutating from mouse to human sequence, allow mCR2 to gain the ability to bind EBV gp350/220.

The CR2 structure described here contains residues 1–134 (SEQ ID NO:4; FIG. 2E, corresponding to residues 20–153 of the full length human CR2 (SEQ ID NO:1)) that fold into two SCR domains (FIG. 2A). Each domain shows a basic SCR fold: four anti-parallel beta-strands form a barrel-like beta-sheet. Strand D and E are separated into two segments, D1, D2 and E1, E2. In addition to the hydrogen bonds that hold together the antiparallel beta-strands, two intra-domain disulfide bonds cross-link the coiled N-terminus to strand D2, and strand C to strand E2 (FIG. 2A). A well ordered N-linked GlcNAc (N-acetyl-glucosamine) residue is linked to Asn102 that is located at the tip of SCR2. The rest of the sugar residues were digested away by EndoH.

A very unique feature of the two domain CR2 structure is that the 8 amino acid linker makes a dramatic turn to allow the two SCR domains to pack against each other sideways (FIGS. 2A, 2B, 2C). Among the protein family containing SCR domains, the linkers connecting SCR domains are normally 3–5 amino acids in length, while an 8 amino acid linker is the longest known so far. The available structures of four SCR proteins containing two or 4 repeats (A. P. Wiles, et al., (1997), supra; P. N. Barlow, et al., (1993), supra; J. M. Casasnovas, et al., (1999), supra; R. Schwarzenbacher et al., (1999), supra) all have end-end packing between consecutive SCRs, and CR2 is thus the first to demonstrate extensive side-side packing.

In end-end packing, the adjacent domains could, in principle, adopt different rotations and bend angles relative to each other in different environments. Indeed, a commonly held concept is that SCRs are not absolutely fixed relative to each other but rather are allowed some freedom to move about this interface (P. N. Barlow, et al., (1993), ibid.; J. M. Casasnovas, et al., (1999), ibid.). However, the side-side packing of the CR2 SCR1 and SCR2 would not give the two domains freedom to adopt different orientations, unless some active process is involved to first separate the two domains. The interface between the two domains is mainly hydrophobic (FIG. 2B). Trp112, which is unique to CR2 SCR2 sequence and located on strand D2, plays a critical role in the packing by interacting with Ile39 and the main-chain from SCR1. Trp112 would be unfavorably exposed to the solvent if the two domains do not pack against each other sideways in this manner. In addition to Trp112, several other residues also play a role in the packing, including Pro121, His91, Leu39, and the carbon side chain of Glu64. The 8 amino acid linker, which contains mainly hydrophobic residues such as Tyr65, Phe66, Tyr69, also participates in the hydrophobic packing outside the two-domain interface, further solidifying the interactions between SCR1 and SCR2 (FIG. 2B). The area of the interface of the two SCRs is very extensive, covering almost half of the length of one SCR domain (FIG. 2C). Because of the above mentioned observations of other SCR proteins studied in the absence of their ligands, it will be interesting to see if the packing of these two CR2 SCR domains remains the same in the unliganded crystal and solution states.

Two CR2 molecules dimerize through SCR1-SCR1 contacts in the crystal structure (FIG. 2D). The contact is symmetrical, with the E1 strands from different molecules running anti-parallel to each other. The C-terminus of the E1 strand also contacts the C-terminus of the D2 strand of another molecule. The nature of the interaction is hydrogen bonds. In solution, however, the present inventors have found that CR2 behaves like a monomer under physiological buffer condition as assayed by gel filtration chromatography, though this is a technique that can only detect strong protein-protein interaction. It is possible that the dimer interaction only occurs in the crystal packing and is not of relevance. Another possibility, though, is that the interaction plays biological roles under physiologic conditions, but it is too weak to be detected in solution. Considering that CR2 receptors are largely constrained in the cell membrane to only lateral movement, no strong interactions would be necessary to dimerize.

Description of the Structure of the CR2-C3d Interface

FIGS. 3A–3F show the structure at the CR2-C3d interface. FIGS. 3A and 3B show the surface features of the interface area on C3d (in cyan) and CR2 molecule (in yellow). The shape of the interface of one molecule complements that of the other. (Prepared using GRASP). FIG. 3C shows the structure of the CR2 SCR2-C3d complex. The strands of CR2 (yellow) and helices of C3d (cyan) near the interface are labeled to provide a sense of orientation. (Prepared using MOLSCRIPT). FIGS. 3D and 3E show the detailed interactions between CR2 (in yellow) and C3d (in cyan) in two angles. Dashed lines represent hydrogen bonds between carbonyl oxygen atoms (in red), nitrogen atoms (in blue) of amino acid side chains or main chain, and water molecules (in purple). (Prepared using RIBBONS). FIG. 3F shows the human C3d sequence (SEQ ID NO:7) with secondary structure assigned on top of the corresponding sequences. The residues involved in CR2 binding are indicated by *. The residue D223 in C3F from (vs. N223 in C3S) is in pink. The residue N170 shown to weaken C3d-CR2 interaction after being mutated to Arg (see FIG. 4) is colored in red. N170 is also the only residue among those involved in CR2 binding that has its side chain in close contact with and pointing toward CR2.

One particularly salient feature of the interface is the shape-matching between C3d and CR2 interacting surfaces, as the protrusions on one molecule exactly match the pits and cavities on the other (FIGS. 3A & 3B). The total of the buried area in the interface is 1400 $Å^2$. The contact interfaces between the receptor and C3d are neither hydrophobic nor particularly charged, but rather the well-fitted surface shapes from the two molecules come together to form the bonding contact in the complex. No major conformational difference is observed between the structures of free C3d and CR2-bound C3d, except for small movements (0.7–1.0 Å) of H3 (helix 3), H5, H7 and a few turns/loops on the surface.

In the CR2-C3d complex, no continuous stretch of residues on C3d participates in the interactions. Rather, residues that are separated in the linear sequence of C3d, but come together on the folded C3d, interact with CR2. Namely, the residues on the H3-H4 loop (the loop between helix 3 and 4), as well as H5, and H7 make contact with CR2 (FIG. 3C). On the CR2 part, however, a linear stretch of residues within SCR2 domain makes the contact with C3d. The B strand and B-C loop of SCR2 constitute the majority of the interactions with C3d. The nature of the contacts involves elegant networks of hydrogen bonds, plus some hydrophobic and van der Waals interactions (FIGS. 3D & 3E).

It is particularly intriguing that only SCR2 directly contacts C3d. Previous studies have shown that both SCR1 and SCR2 are required for binding of polymeric forms of C3d to CR2 on cell membranes (C. A. Lowell, et al., *J Exp Med* 170, 1931–46 (1989); J. C. Carel, et al., *J Biol Chem* 265, 12293–9 (1990); K. R. Kalli, et al., *J Immunol* 147, 590–4 (1991)). The requirement for both domains to bind C3d on the cell surface may be due to the necessity of inter-SCR packing for stabilization of the SCR2 site, or alternatively the dimerization of CR2 mediated by SCR1 plays a necessary role on cell membranes, as discussed later.

Specificity of CR2-C3d Interaction

A few features about the CR2-C3d interactions are very striking. The first of such is the extensive use of main-chain carbonyl oxygen and nitrogen atoms in forming hydrogen bonds (H-bonds) between CR2 and C3d. This is particularly true on the C3d side, where the majority of the H-bond contributors on C3d come from main-chain carbonyl groups (FIGS. 3D & 3E). No side chains other than Asn170 on the C3d side are involved in the direct interaction with CR2. This observation likely explains the difficulties in previous efforts to accurately identify the residues that directly interact with CR2 by site-directed mutagenesis of C3d or by using C3d-derived inhibitory peptides. This interaction mode of CR2-C3d is reminiscent of MHC-antigen peptide recognition where MHC interacts with the main-chain atoms of the antigen peptide in order to allow the limited number of MHC to bind the unlimited variations of antigens for antigen presentation to T cells (P. J. Bjorkman, et al., *Nature* 329, 512–8 (1987)). However, in distinct contrast to the MHC-antigen peptide interaction, the binding between CR2 and C3d through main-chain atoms here does not sacrifice the specificity of the CR2 receptor for C3d ligand due to an additional pronounced shape-fitting requirement, as further evident in later discussion.

Another important feature concerns one of the major sites for binding CR2 on C3d at the C-terminal end of H5. Here four carbonyl groups, one each from Ile115, Leu116, Glu117 and Gln119 of C3d, are positioned in such a way that, collectively, they form an anion hole at the C-terminus of H5 (FIG. 3D). In the complex structure, this anion hole is occupied by the positively charged Arg84 of CR2 that is located on the B-C loop of SCR2 domain. In this case, CR2 Arg84 acts as a capping residue in-trans to seal the alpha-helical dipole moment at the C-terminus of H5 of C3d. This is in contrast to the usual observation in other protein-ligand interactions that involve an alpha-helical dipole moment, in which usually a negatively charged group interacts with the other protein through the positively charged N-terminus of a helix, possibly because of the easily accessible nitrogen atoms on the main-chain (C. Branden, J. Tooze, *Introduction to Protein Structure*(Garland Publishing, ed. second edition, 1999) pp. 16). However, for CR2 to interact with the negatively charged C-terminus of C3d H5 that is shielded by the particular conformation at the end of H5 and its neighboring structure, it requires CR2 to have a well-matched surface around the positively charged capping residue, providing specificity to the interaction. The sequences and conformation of SCR2 around Arg84 of CR2 provides such a surface that is well-matched with the complimentary part on C3d, and that provides the necessary specificity for the interaction with C3d.

The conformation of the C3d-binding region, the B-C loop of SCR2 domain on CR2, is thus also important for the specific binding of C3d (FIGS. 3C, 3D, 3E). As one means to accomplish this conformation, the B-C loop is held and presented on the surface of CR2 by strand B and C of SCR2 in such a way that Arg84 readily fits into the anion hole at the end of the C3d H5. The residue after Arg84 is Gly85, which does not have a side chain that would interfere with the CR2 and C3d interface interaction. The side chain of Ser86 forms an H-bond with a carbonyl oxygen from the H3-H4 loop of C3d through a water molecule (FIG. 3E). Other residues around Arg84 have side chains pointing away from the interface and use either their main-chain carbonyl oxygen or nitrogen atoms to form H-bonds with C3d. This mode of interaction from the CR2 side predicts that the basic capping residue Arg84, as well as Ser86, are likely the most important residues on this interaction surface, as long as they are presented in a correct conformation.

In this regard, of importance also is a sequence comparison between human CR2 and mouse CR2 (mCR2), both of which bind C3d with similar affinity (D. R. Martin et al., *J Exp Med* 174, 1299–311 (1991); J. D. Fingeroth et al., *Proc Natl Acad Sci USA* 86, 242–6 (1989)). The SCR1-2 region of human CR2 is represented herein as SEQ ID NO:4 and is compared to the corresponding SCR1-2 region of mouse CR2 (SEQ ID NO:6). At the C3d-interacting interface the B-C loop of mCR2 SCR2 has a basic residue Lys in place of Arg84, while Gly85 and Ser86 are conserved (positions given relative to SEQ ID NO:4). Five other amino acids around Arg84 on the B-C loop are not highly conserved (FIG. 3F). The complex structure reveals, however, that the side chains of these five non-conserved residues do not participate in the CR2-C3d interaction. Importantly, Lys84 in mouse (SEQ ID NO:6) could replace Arg84 (SEQ ID NO:4) as the trans-capping residue for H5. Of interest, outside of the 5 amino acids around Lys84 (SEQ ID NO:6), there are stretches of amino acids that are the most highly conserved between human CR2 and mCR2 (FIG. 2E). These highly conserved segments likely play an important role in presenting the B-C loop in a correct conformation for specific C3d binding to mCR2.

Another feature of the complex structure is the participation of several water molecules in the interaction (FIGS. 3D & 3E). Well-ordered water molecules participate in the formation of some H-bonds between CR2 and C3d, acting as water "glue" between the two proteins. Extensive participation of water molecules in mediating receptor-ligand binding is also seen in the interaction between CAR receptor (coxsacki-adenovirus receptor) and adenovirus knob protein (M. C. Bewley et al., *Science* 286, 1579–83 (1999)).

A six-coordinated Zn atom is present on the edge of the interface between CR2 and C3d (FIG. 3D). Glu117 of C3d is the only amino acid side chain that participates in the coordination. The other four coordinates are mediated by water molecules, through which H-bond connections are formed with CR2 main-chain. The contribution of the Zn coordination to the CR2-C3 d binding is likely to be insignificant, because no obvious change in formation of the CR2-C3d complex can be detected in buffers with/without Zn ion, or when using a C3d mutant containing a Glu117 to Ala mutation (see next section). In addition, the binding of CR2 with C3d does not demonstrate a known cation dependence.

Example 2

The following example describes the construction of C3d mutants that affect CR2 binding.

Based on the complex structure, mutagenesis of C3d around the interface to disrupt CR2 binding was predicted to be difficult. This is because the interaction between CR2 and C3 d involves mostly main-chain H-bonding, and the side chain residues play relatively small roles in the binding. However, to confirm the accuracy of the CR2-C3d interaction seen in this co-crystal structure, two informative C3d mutants were constructed. In mutant 170 (mt170; SEQ ID NO:8), residue Asn170 was changed to Arg. Asn170 is located on H7 of C3d and is the only residue on C3d that more or less points directly toward CR2 in the interface (FIG. 3E). Asn170 also packs directly with Tyr81 of CR2 as well as forms an H-bond with CR2 (Lys100) through a water molecule (FIG. 3E). In solution, this mutant protein behaved very similarly like the wild type C3d and showed the same apparent molecular weight as the wild type in gel-filtration chromatography, suggesting correct folding. In the binding experiment assayed by native gel shift, however, the interaction between mt170 protein and CR2 was clearly less strong comparing with that between wild type C3d and CR2 (FIG. 4A, lanes 1–4 versus 9–12).

Figures 4A, 4B:
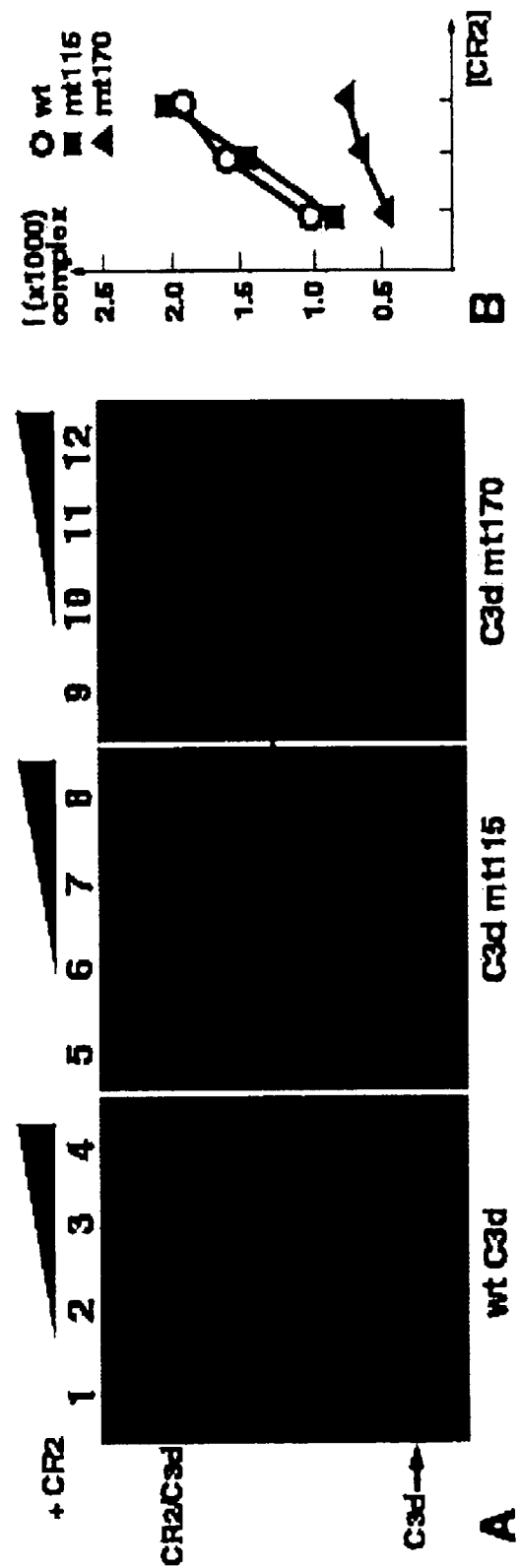

Briefly, FIGS. 4A and 4B show a native gel shift assay of the binding between CR2 and C3d wild type (wt) or mutants (mt). FIG. 4A shows a 6% native polyacrylamide gel of C3d alone (lanes 1, 5, and 9) or C3d plus increasing amount of CR2 (other lanes). mt170 C3d alone (lane 9) migrated slower than both wt (lane 1) and mt115 due to the introduction of a positively charged Arg residue at N170 (lane 5). CR2 alone does not enter the gel in this system. The C3d band will be shifted to the upper part of the gel when it forms a complex with CR2. The C3d concentration (for both wt and mt) is the same throughout lanes 1–12. The CR2 added to each corresponding lanes for wt and mt C3d was also the same, e.g. same amount of CR2 was added to the C3d samples in lane 2, 6 and 10, or in lanes 4, 8 and 12. In the lanes with the highest CR2 concentration (lanes 4, 8, 12), the bands of C3d wt and mt115 were completely shifted to the complex form (lane 4, 8), while mt170 (migrated slower than the wt or mt115) still contains an obvious C3d band (lane 12). These results indicate that the interaction between mt170 and CR2 is weaker than that between the wt or mt115 with CR2. The same conclusion can be drawn by comparing the intensity of the bands of the complexes containing the wt, mt115 and mt170. FIG. 4B is a graphical representation showing the intensity changes of the complex bands (measured by densitometry) as CR2 concentration increases from lanes 2 to 4 (wt), or lanes 6 to 8 (mt115), or lanes 10 to 12 (mt170). The result clearly shows that mt170 has less apparent affinity for CR2 than wt and mt115.

The result shown in this experiment is consistent with that predicted by the interaction interface seen in the complex structure. In another mutant of C3d (mt115), although three residues: Gln105, Leu116 and Glu117, were mutated to Ala, the mutant protein has no obvious effect on CR2 binding (FIG. 4A, lanes 1–4 versus 5–8). This is consistent with the complex structure in that all these three residues, even though located within the interface area, have their side chains pointing sideways and are not involved in the direct contact with CR2. The side chain of Glu117, however, participates in the Zn coordination. This mutant showed that Zn coordination by Glu117 does not contribute significantly to CR2-C3d binding. The coordinated Zn in the structure, therefore, could simply come from the crystallization buffer which contained ZnAcetate.

Figure 4C:
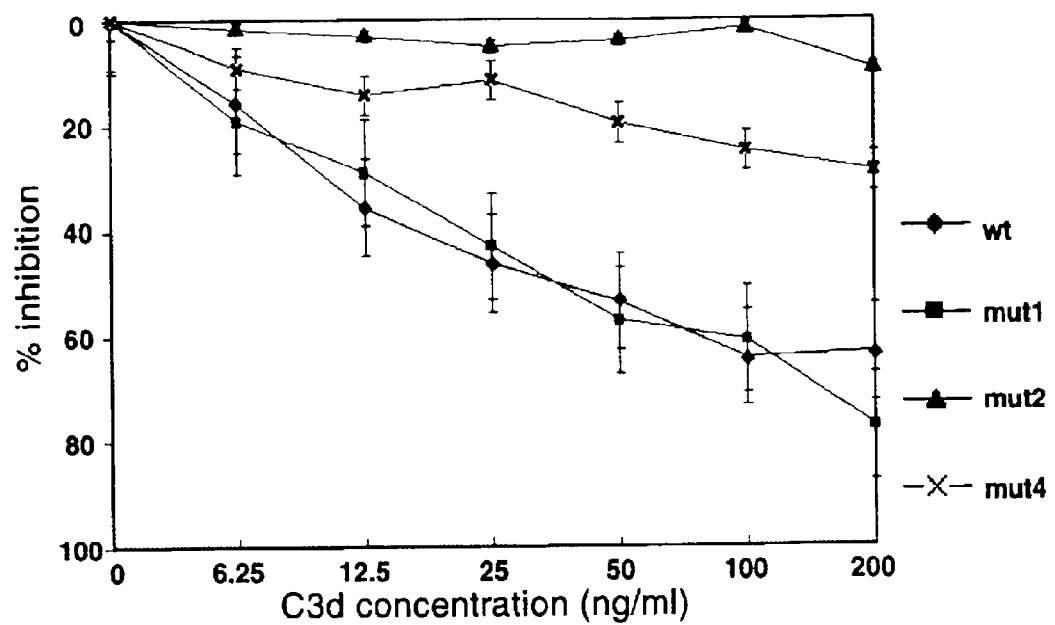

FIG. 4C demonstrates the results of a competitive ELISA analysis using informative C3d mutants. In this analysis, C3d mutant Gln105Ala, Leu116Ala, Glu117Ala (designated mt115 in FIGS. 4A and 4B and mut1 in FIG. 4C) manifests an equal ability as wild type C3d to block the binding of soluble full length CR2 to plate-bound wild type C3d. Therefore, mutations of these two residues which utilize only the main-chain atoms to interact with CR2 did not have an effect, which is predicted by the X-ray structure. Two other informative mutants, one Asn170Arg (designated mt170 in FIGS. 4A and 4B and mut2 in FIG. 4C, also represented herein as SEQ ID NO:8) and the other a new mutant Asn170Ala, Ile115Arg, Leu116Arg (designated mut4 in FIG. 4C, also represented herein as SEQ ID NO:9), are both unable to effectively block soluble CR2 binding to plate-bound wild type C3d. Therefore, we conclude that two mutations of C3d involving Asn170, whose side-chain interacts with CR2 directly, result in substantially decreased binding to CR2.

Of interest, the mode of interaction seen here is very different from that previously predicted by C3d mutants and C3d-derived peptides (J. D. Lambris et al., *Proc Natl Acad Sci USA* 82, 4235–9 (1985); R. J. Diefenbach et al., *J Immunol* 154, 2303–20 (1995); L. Clemenza et al., *J Immunol* 165, 3839–48 (2000)). Close examination of the complex structure, however, can explain some of the previous mutagenesis results. For example, residues Asp163, Ile164, and Glu166 of C3d, which affect CR2-binding after being mutated to Ala (Clemenza et al., 2000, ibid.), are located on H6 that is juxtaposed to H5 where the major CR2-recognizing anion hole is positioned (FIG. 3D). Based on the structure, it is obvious that mutations of some of the residues on H6 (such as Ile164) of C3d will affect the relative positions of H6 and H5, which may account for the reduced interaction with CR2. The other group of mutations on C3d (Asp36, Glu37, Glu39) reported to weaken CR2 binding (Clemenza et al., 2000, ibid.) are located right next to the N and C termini, and the present inventors' findings cannot account for those results. However, it is of note that this particular site would be juxtaposed to additional large peptides derived from iC3b, and these additional peptides in iC3b would present a steric hindrance for the interaction with CR2 if these residues were to be involved in CR2 binding. The present inventors' observation that CR2 contacts C3d on the opposite side from the N and C termini removes that concern and is more consistent with the observed high affinity binding of CR2 to iC3b.

Example 3

The following example describes the inhibition of CR2-C3d interaction by CR2-derived peptides.

Based on the structure of the CR2-C3d complex, the results from previously reported CR2 peptide inhibition and monoclonal antibody assays can now be explained. In the peptide inhibition tests using short synthetic peptides covering all of CR2 SCR1 and SCR2, peptides from two regions were shown to inhibit CR2-C3 binding (H. Molina, et al., *J Immunol* 154, 5426–35 (1995)). One of them contains sequences that are located right on the interaction interface of CR2 seen in the complex structure, namely the sequences from the B strand and B-C loop of SCR2 (FIGS. 3D & 3E). This independent result strongly supports the complex structure described by the present invention. However, the other peptide located on the B strand of SCR1 also showed a similar inhibition effect as the first one. Close examination of this fragment on CR2 structure within the SCR1 domain revealed a very similar 3-dimensional arrangement of these residues as the one on SCR2, but the sequence is in part reversed. Part of the C3d-binding sequences on the SCR2 B-C loop is 83-IRGSTP-88. The peptide from SCR1 that also has inhibitory effects has a sequence of 11-LNGRIS-16 (H. Molina et al., 1995, ibid). Similarities are apparent between these two peptides if one of the sequences is reversed. Specifically, at the 3-dimensional structure level, the conformation of -NGRI- of the SCR1 peptide looks like a reverse duplicate of -IRGS- on SCR2. However, in a folded CR2 molecule, the structure of the neighboring residues around the peptide on SCR1 restricts the accessibility of the sequences within the peptide, especially the Arg residue. Therefore, this part of CR2 should not be able to bind C3d unless some major conformational switch occurred to expose the segment in a fashion similar to it in a short peptide state.

Example 4

The following example describes the inhibition of CR2-C3d binding by anti-CR2 monoclonal antibodies.

Figures 5A, 5B:
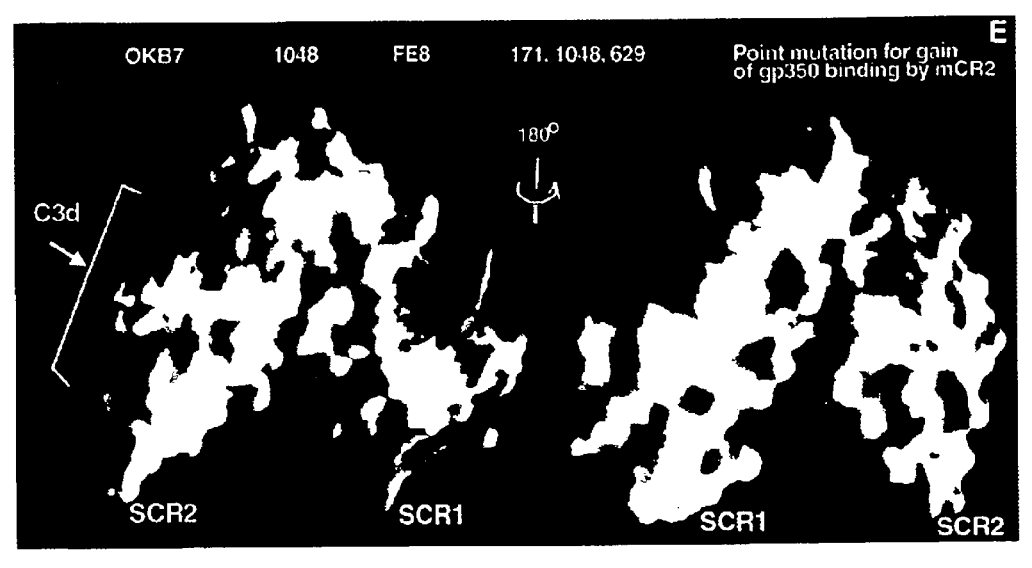

The previously mapped epitope positions on CR2 for inhibitory monoclonal antibodies also support the interaction sites seen in the CR2-C3d complex structure. Two inhibitory antibodies, OKB7 (P. E. Rao et al., *Cell Immunol* 93, 549–55 (1985)) and FE8 (W. M. Prodinger, et al., *J Immunol* 161, 4604–10 (1998)), have epitopes positioned right next to the C3d binding region (FIGS. 5A & 5B). The present inventors have also created three new monoclonal antibodies, denoted mAb171, mAb1048 and mAb629, that inhibit the specific binding of CR2 to C3d. All three have mapped epitopes on CR2 lying right within the C3d-interacting area (FIG. 5A, blue area).

FIGS. 5A and 5B show the localization of the epitopes of anti-CR2 monoclonal antibodies (mAb) on the CR2 surface. These figures are two views with a 180 degree rotation to each other. The C3d binding site is labeled. All of the mAbs inhibit the interactions between CR2 and C3d to some extent. mAb171, together with 1048 and 629 (colored in blue) have epitopes located within the C3d-binding area. OKB7 (Rao et al., 1985, ibid.) (colored in red) and FE8 (Prodinger et al., 1998, ibid.) (colored in pink) also have epitopes right next to the C3d-binding region. The green spots indicate the locations where mutations from mCR2 to hCR2 sequence allow mCR2 to gain the ability to bind EBV gp350/220. The surfaces around these two sites are likely located within the interface between CR2 and gp350/220.

Example 5

The following example describes a potential gp350/220 binding region in CR2.

Previous evidence suggests that CR2 binds to C3d and EBV gp350/220 with overlapping but distinct sites (D. R. Martin et al., *J Exp Med* 174, 1299–311 (1991); H. Molina et al., *J Biol Chem* 266, 12173–9 (1991); D. R. Martin et al., *J Virol* 68, 4716–26 (1994); H. Molina et al., *J Immunol* 154, 5426–35 (1995)). One instrumental result in this regard has been the ability to transform by point mutation mCR2 into a form capable of binding gp350/220. In this regard, mCR2 and CR2 both bind C3d, but mCR2 does not bind EBV or gp350/220. However, changing the sequence of mCR2 at two amino acids (Pro16 to Ser and Thr69 to Tyr, FIG. 2E) allowed mCR2 to gain the ability to bind EBV (D. R. Martin et al., *J Virol* 68, 4716–26 (1994)). Because of this, the locations of the two mutated residues are likely to be involved in gp350/220 binding. Of interest, these locations mapped on the CR2 surface (green patch on FIGS. 5A & 5B) are separated from the blue area that interacts with C3d in the complex structure of the present invention.

Example 6

The following example describes a structure model of CR2 in complex with C3d on the cell surface.

Figure 6B:
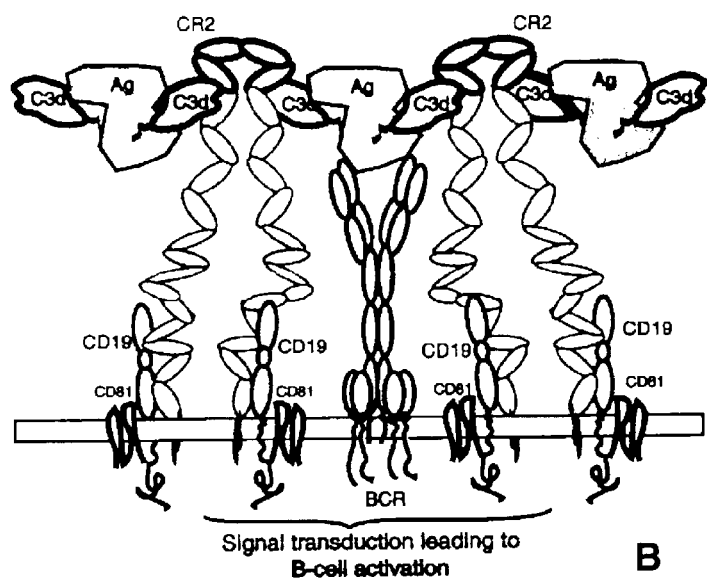

Based on the complex structure, the present inventors propose a model of CR2 binding to C3d or iC3b on the cell surface (FIG. 6). FIG. 6A is a surface representation of the model containing a dimer of CR2 SCR1 and SCR2 that bind to C3d on each receptor. The dimer contact is through SCR1 only, as seen in the crystal structure. FIG. 6B is a diagram of C3d-antigen cross-linking CR2 (as dimers) and BCR on the cell surface. The dimer form of CR2, as opposed to the monomer, in complex with CD19CD81 permits the cross-linking of multiple CR2 by C3d-antigen to greatly increase the local concentration of CR2/CD19/CD81.

In this model, CR2 in complex with C3d molecules exists as a dimer through SCR1-SCR1 contact (FIGS. 6A & 6B). C3d- or iC3b-bound antigen interacts with SCR2 in such a way that the site of ester-linkage with the antigen (residue Q20) is pointing in the lateral direction (FIG. 6A). This orientation allows CR2 maximum capabilities to interact with C3 bound to many shapes and sizes of antigens. In addition, though, there is also the opportunity for the antigen to cross-link a neighboring CR2 dimer with a second C3d/iC3b attached to it. Repeat of this interaction could cross-link many CR2/CD19/CD81 and BCR molecules, with the potential of greatly amplifying down-stream signal transduction. Of interest, previous reports of C3 d acting as a molecular adjuvant showed that two or three C3d attached to hen egg lysozyme (HEL) enhanced the IgG1 humoral response to HEL by 1,000 to 10,000 times, but one C3d had a suppressive effect (P. W. Dempsey et al., Science 271, 348–50 (1996)). The model in FIG. 6B provides one potential molecular explanation for this observation. Multiple CR2 dimers can be brought together by two (or more) C3d linked to an antigen, but only two (or three) CR2 monomers can be cross-linked together. Thus, the CR2 dimer model, in contrast to a monomer, allows a dramatic increase of cross-linked CR2/CD19/CD81 and BCR molecules through binding to the antigen with two or more C3d attached, which could account for the 10,000-fold enhancement of the observed immune response.

TABLE 2

| ATOM | 1 | CB | ALA | A | 1 | 113.978 | 74.531 | 51.463 | 1.00 | 24.47 | A |
| --- | --- | --- | --- | --- | --- | --- | --- | --- | --- | --- | --- |
| ATOM | 2 | C | ALA | A | 1 | 113.746 | 72.085 | 52.085 | 1.00 | 26.48 | A |
| ATOM | 3 | O | ALA | A | 1 | 112.896 | 72.106 | 52.942 | 1.00 | 30.12 | A |
| ATOM | 4 | N | ALA | A | 1 | 115.853 | 72.884 | 51.119 | 1.00 | 42.70 | A |
| ATOM | 5 | CA | ALA | A | 1 | 114.718 | 73.256 | 51.995 | 1.00 | 33.68 | A |
| ATOM | 6 | N | LEU | A | 2 | 113.868 | 71.065 | 51.232 | 1.00 | 24.18 | A |
| ATOM | 7 | CA | LEU | A | 2 | 112.952 | 69.905 | 51.320 | 1.00 | 27.55 | A |
| ATOM | 8 | CB | LEU | A | 2 | 112.148 | 69.728 | 50.001 | 1.00 | 23.79 | A |
| ATOM | 9 | CG | LEU | A | 2 | 110.907 | 68.774 | 50.002 | 1.00 | 26.21 | A |
| ATOM | 10 | CD1 | LEU | A | 2 | 109.785 | 69.339 | 50.877 | 1.00 | 20.38 | A |
| ATOM | 11 | CD2 | LEU | A | 2 | 110.365 | 68.568 | 48.562 | 1.00 | 22.09 | A |
| ATOM | 12 | C | LEU | A | 2 | 113.635 | 68.549 | 51.642 | 1.00 | 27.27 | A |
| ATOM | 13 | O | LEU | A | 2 | 114.746 | 68.266 | 51.172 | 1.00 | 22.30 | A |
| ATOM | 14 | N | ASP | A | 3 | 112.963 | 67.734 | 52.455 | 1.00 | 23.38 | A |
| ATOM | 15 | CA | ASP | A | 3 | 113.426 | 66.393 | 52.758 | 1.00 | 23.91 | A |
| ATOM | 16 | CB | ASP | A | 3 | 114.304 | 66.327 | 54.028 | 1.00 | 20.20 | A |
| ATOM | 17 | CG | ASP | A | 3 | 113.619 | 66.825 | 55.279 | 1.00 | 22.03 | A |
| ATOM | 18 | OD1 | ASP | A | 3 | 112.357 | 66.765 | 55.433 | 1.00 | 20.42 | A |
| ATOM | 19 | OD2 | ASP | A | 3 | 114.366 | 67.274 | 56.160 | 1.00 | 28.30 | A |
| ATOM | 20 | C | ASP | A | 3 | 112.201 | 65.488 | 52.875 | 1.00 | 23.39 | A |
| ATOM | 21 | O | ASP | A | 3 | 111.047 | 65.953 | 52.784 | 1.00 | 18.32 | A |
| ATOM | 22 | N | ALA | A | 4 | 112.438 | 64.194 | 53.060 | 1.00 | 24.33 | A |
| ATOM | 23 | CA | ALA | A | 4 | 111.330 | 63.243 | 53.164 | 1.00 | 23.20 | A |
| ATOM | 24 | CB | ALA | A | 4 | 111.854 | 61.819 | 53.288 | 1.00 | 17.28 | A |
| ATOM | 25 | C | ALA | A | 4 | 110.291 | 63.499 | 54.261 | 1.00 | 19.39 | A |
| ATOM | 26 | O | ALA | A | 4 | 109.113 | 63.369 | 53.958 | 1.00 | 16.69 | A |
| ATOM | 27 | N | GLU | A | 5 | 110.691 | 63.841 | 55.491 | 1.00 | 16.50 | A |
| ATOM | 28 | CA | GLU | A | 5 | 109.701 | 64.065 | 56.548 | 1.00 | 22.14 | A |
| ATOM | 29 | CB | GLU | A | 5 | 110.301 | 64.257 | 57.982 | 1.00 | 23.56 | A |
| ATOM | 30 | CG | GLU | A | 5 | 110.935 | 65.596 | 58.263 | 1.00 | 38.23 | A |
| ATOM | 31 | CD | GLU | A | 5 | 110.138 | 66.605 | 59.095 | 1.00 | 31.60 | A |
| ATOM | 32 | OE1 | GLU | A | 5 | 109.004 | 66.397 | 59.598 | 1.00 | 31.04 | A |
| ATOM | 33 | OE2 | GLU | A | 5 | 110.719 | 67.671 | 59.253 | 1.00 | 44.56 | A |
| ATOM | 34 | C | GLU | A | 5 | 108.853 | 65.262 | 56.208 | 1.00 | 20.89 | A |
| ATOM | 35 | O | GLU | A | 5 | 107.637 | 65.242 | 56.419 | 1.00 | 22.09 | A |
| ATOM | 36 | N | ARG | A | 6 | 109.470 | 66.300 | 55.662 | 1.00 | 17.73 | A |
| ATOM | 37 | CA | ARG | A | 6 | 108.703 | 67.491 | 55.302 | 1.00 | 23.39 | A |
| ATOM | 38 | CB | ARG | A | 6 | 109.618 | 68.614 | 54.815 | 1.00 | 25.00 | A |
| ATOM | 39 | CG | ARG | A | 6 | 110.433 | 69.194 | 55.948 | 1.00 | 24.66 | A |
| ATOM | 40 | CD | ARG | A | 6 | 111.430 | 70.240 | 55.488 | 1.00 | 30.21 | A |
| ATOM | 41 | NE | ARG | A | 6 | 112.143 | 70.710 | 56.662 | 1.00 | 31.75 | A |
| ATOM | 42 | CZ | ARG | A | 6 | 113.044 | 71.686 | 56.675 | 1.00 | 37.88 | A |
| ATOM | 43 | NH1 | ARG | A | 6 | 113.377 | 72.333 | 55.558 | 1.00 | 32.11 | A |
| ATOM | 44 | NH2 | ARG | A | 6 | 113.608 | 72.015 | 57.830 | 1.00 | 38.98 | A |
| ATOM | 45 | C | ARG | A | 6 | 107.696 | 67.156 | 54.219 | 1.00 | 25.83 | A |
| ATOM | 46 | O | ARG | A | 6 | 106.532 | 67.558 | 54.304 | 1.00 | 20.78 | A |
| ATOM | 47 | N | LEU | A | 7 | 108.122 | 66.409 | 53.205 | 1.00 | 19.13 | A |
| ATOM | 48 | CA | LEU | A | 7 | 107.179 | 66.068 | 52.143 | 1.00 | 17.13 | A |
| ATOM | 49 | CB | LEU | A | 7 | 107.916 | 65.488 | 50.945 | 1.00 | 16.82 | A |
| ATOM | 50 | CG | LEU | A | 7 | 106.984 | 65.041 | 49.805 | 1.00 | 23.63 | A |
| ATOM | 51 | CD1 | LEU | A | 7 | 106.086 | 66.207 | 49.303 | 1.00 | 18.87 | A |
| ATOM | 52 | CD2 | LEU | A | 7 | 107.870 | 64.538 | 48.676 | 1.00 | 25.78 | A |
| ATOM | 53 | C | LEU | A | 7 | 106.103 | 65.075 | 52.615 | 1.00 | 19.67 | A |
| ATOM | 54 | O | LEU | A | 7 | 104.935 | 65.191 | 52.246 | 1.00 | 20.24 | A |
| ATOM | 55 | N | LYS | A | 8 | 106.489 | 64.099 | 53.427 | 1.00 | 21.02 | A |
| ATOM | 56 | CA | LYS | A | 8 | 105.521 | 63.110 | 53.928 | 1.00 | 24.15 | A |
| ATOM | 57 | CB | LYS | A | 8 | 106.205 | 62.100 | 54.869 | 1.00 | 26.98 | A |
| ATOM | 58 | CG | LYS | A | 8 | 105.339 | 60.838 | 55.146 | 1.00 | 29.12 | A |
| ATOM | 59 | CD | LYS | A | 8 | 105.997 | 59.844 | 56.108 | 1.00 | 48.06 | A |
| ATOM | 60 | CE | LYS | A | 8 | 107.390 | 59.397 | 55.608 | 1.00 | 61.21 | A |
| ATOM | 61 | NZ | LYS | A | 8 | 108.117 | 58.353 | 56.469 | 1.00 | 69.61 | A |
| ATOM | 62 | C | LYS | A | 8 | 104.281 | 63.720 | 54.630 | 1.00 | 22.77 | A |
| ATOM | 63 | O | LYS | A | 8 | 103.163 | 63.203 | 54.499 | 1.00 | 16.94 | A |
| ATOM | 64 | N | HIS | A | 9 | 104.465 | 64.778 | 55.412 | 1.00 | 17.13 | A |

TABLE 2-continued

| | | | | | | | | | | |
|---|---|---|---|---|---|---|---|---|---|---|
| ATOM | 65 | CA | HIS | A | 9 | 103.303 | 65.454 | 56.034 | 1.00 | 23.94 | A |
| ATOM | 66 | CB | HIS | A | 9 | 103.759 | 66.675 | 56.838 | 1.00 | 15.51 | A |
| ATOM | 67 | CG | HIS | A | 9 | 104.457 | 66.331 | 58.109 | 1.00 | 25.05 | A |
| ATOM | 68 | CD2 | HIS | A | 9 | 105.755 | 66.445 | 58.478 | 1.00 | 22.49 | A |
| ATOM | 69 | ND1 | HIS | A | 9 | 103.792 | 65.831 | 59.209 | 1.00 | 24.32 | A |
| ATOM | 70 | CE1 | HIS | A | 9 | 104.649 | 65.654 | 60.200 | 1.00 | 26.37 | A |
| ATOM | 71 | NE2 | HIS | A | 9 | 105.851 | 66.015 | 59.786 | 1.00 | 31.51 | A |
| ATOM | 72 | C | HIS | A | 9 | 102.268 | 65.959 | 55.002 | 1.00 | 24.84 | A |
| ATOM | 73 | O | HIS | A | 9 | 101.161 | 66.278 | 55.375 | 1.00 | 23.11 | A |
| ATOM | 74 | N | LEU | A | 10 | 102.634 | 66.074 | 53.721 | 1.00 | 18.19 | A |
| ATOM | 75 | CA | LEU | A | 10 | 101.670 | 66.538 | 52.730 | 1.00 | 22.98 | A |
| ATOM | 76 | CB | LEU | A | 10 | 102.370 | 67.210 | 51.534 | 1.00 | 24.09 | A |
| ATOM | 77 | CG | LEU | A | 10 | 103.171 | 68.492 | 51.885 | 1.00 | 30.55 | A |
| ATOM | 78 | CD1 | LEU | A | 10 | 103.625 | 69.205 | 50.648 | 1.00 | 29.82 | A |
| ATOM | 79 | CD2 | LEU | A | 10 | 102.285 | 69.415 | 52.701 | 1.00 | 39.35 | A |
| ATOM | 80 | C | LEU | A | 10 | 100.789 | 65.391 | 52.237 | 1.00 | 30.17 | A |
| ATOM | 81 | O | LEU | A | 10 | 99.875 | 65.616 | 51.442 | 1.00 | 31.15 | A |
| ATOM | 82 | N | ILE | A | 11 | 101.065 | 64.159 | 52.663 | 1.00 | 20.98 | A |
| ATOM | 83 | CA | ILE | A | 11 | 100.194 | 63.053 | 52.229 | 1.00 | 22.19 | A |
| ATOM | 84 | CB | ILE | A | 11 | 101.002 | 61.747 | 52.060 | 1.00 | 27.01 | A |
| ATOM | 85 | CG2 | ILE | A | 11 | 100.044 | 60.547 | 51.788 | 1.00 | 29.34 | A |
| ATOM | 86 | CG1 | ILE | A | 11 | 101.984 | 61.940 | 50.863 | 1.00 | 21.97 | A |
| ATOM | 87 | CD1 | ILE | A | 11 | 103.039 | 60.904 | 50.736 | 1.00 | 31.22 | A |
| ATOM | 88 | C | ILE | A | 11 | 99.082 | 62.956 | 53.269 | 1.00 | 27.58 | A |
| ATOM | 89 | O | ILE | A | 11 | 99.300 | 62.542 | 54.411 | 1.00 | 26.44 | A |
| ATOM | 90 | N | VAL | A | 12 | 97.890 | 63.403 | 52.888 | 1.00 | 23.12 | A |
| ATOM | 91 | CA | VAL | A | 12 | 96.760 | 63.400 | 53.803 | 1.00 | 22.74 | A |
| ATOM | 92 | CB | VAL | A | 12 | 96.392 | 64.814 | 54.185 | 1.00 | 33.31 | A |
| ATOM | 93 | CG1 | VAL | A | 12 | 97.530 | 65.452 | 55.004 | 1.00 | 34.31 | A |
| ATOM | 94 | CG2 | VAL | A | 12 | 96.105 | 65.600 | 52.928 | 1.00 | 24.64 | A |
| ATOM | 95 | C | VAL | A | 12 | 95.487 | 62.726 | 53.265 | 1.00 | 28.78 | A |
| ATOM | 96 | O | VAL | A | 12 | 95.316 | 62.525 | 52.061 | 1.00 | 25.51 | A |
| ATOM | 97 | N | THR | A | 13 | 94.577 | 62.396 | 54.174 | 1.00 | 22.73 | A |
| ATOM | 98 | CA | THR | A | 13 | 93.348 | 61.747 | 53.787 | 1.00 | 24.33 | A |
| ATOM | 99 | CB | THR | A | 13 | 92.824 | 60.893 | 54.947 | 1.00 | 28.46 | A |
| ATOM | 100 | OG1 | THR | A | 13 | 93.834 | 59.921 | 55.298 | 1.00 | 37.06 | A |
| ATOM | 101 | CG2 | THR | A | 13 | 91.503 | 60.186 | 54.540 | 1.00 | 22.36 | A |
| ATOM | 102 | C | THR | A | 13 | 92.328 | 62.811 | 53.443 | 1.00 | 19.70 | A |
| ATOM | 103 | O | THR | A | 13 | 92.043 | 63.649 | 54.254 | 1.00 | 18.28 | A |
| ATOM | 104 | N | PRO | A | 14 | 91.760 | 62.781 | 52.239 | 1.00 | 23.16 | A |
| ATOM | 105 | CD | PRO | A | 14 | 92.057 | 61.889 | 51.100 | 1.00 | 27.40 | A |
| ATOM | 106 | CA | PRO | A | 14 | 90.765 | 63.803 | 51.883 | 1.00 | 23.69 | A |
| ATOM | 107 | CB | PRO | A | 14 | 90.675 | 63.699 | 50.355 | 1.00 | 20.22 | A |
| ATOM | 108 | CG | PRO | A | 14 | 90.959 | 62.232 | 50.106 | 1.00 | 26.75 | A |
| ATOM | 109 | C | PRO | A | 14 | 89.406 | 63.564 | 52.509 | 1.00 | 22.95 | A |
| ATOM | 110 | O | PRO | A | 14 | 89.009 | 62.415 | 52.725 | 1.00 | 20.64 | A |
| ATOM | 111 | N | SER | A | 15 | 88.719 | 64.651 | 52.845 | 1.00 | 19.26 | A |
| ATOM | 112 | CA | SER | A | 15 | 87.348 | 64.575 | 53.337 | 1.00 | 25.94 | A |
| ATOM | 113 | CB | SER | A | 15 | 87.295 | 64.124 | 54.797 | 1.00 | 25.47 | A |
| ATOM | 114 | OG | SER | A | 15 | 88.078 | 64.979 | 55.578 | 1.00 | 28.02 | A |
| ATOM | 115 | C | SER | A | 15 | 86.638 | 65.928 | 53.187 | 1.00 | 26.13 | A |
| ATOM | 116 | O | SER | A | 15 | 87.227 | 66.923 | 52.758 | 1.00 | 26.66 | A |
| ATOM | 117 | N | GLY | A | 16 | 85.364 | 65.948 | 53.556 | 1.00 | 28.55 | A |
| ATOM | 118 | CA | GLY | A | 16 | 84.593 | 67.167 | 53.481 | 1.00 | 25.28 | A |
| ATOM | 119 | C | GLY | A | 16 | 83.748 | 67.259 | 52.225 | 1.00 | 23.22 | A |
| ATOM | 120 | O | GLY | A | 16 | 83.667 | 66.314 | 51.428 | 1.00 | 20.49 | A |
| ATOM | 121 | N | ALA | A | 17 | 83.122 | 68.421 | 52.072 | 1.00 | 21.03 | A |
| ATOM | 122 | CA | ALA | A | 17 | 82.258 | 68.742 | 50.952 | 1.00 | 19.04 | A |
| ATOM | 123 | CB | ALA | A | 17 | 81.288 | 69.898 | 51.356 | 1.00 | 17.25 | A |
| ATOM | 124 | C | ALA | A | 17 | 83.051 | 69.097 | 49.692 | 1.00 | 19.33 | A |
| ATOM | 125 | O | ALA | A | 17 | 84.271 | 68.928 | 49.643 | 1.00 | 22.08 | A |
| ATOM | 126 | N | GLY | A | 18 | 82.356 | 69.566 | 48.668 | 1.00 | 17.15 | A |
| ATOM | 127 | CA | GLY | A | 18 | 82.983 | 69.869 | 47.376 | 1.00 | 17.27 | A |
| ATOM | 128 | C | GLY | A | 18 | 84.233 | 70.743 | 47.300 | 1.00 | 21.54 | A |
| ATOM | 129 | O | GLY | A | 18 | 84.993 | 70.629 | 46.350 | 1.00 | 16.56 | A |
| ATOM | 130 | N | GLU | A | 19 | 84.419 | 71.653 | 48.248 | 1.00 | 18.40 | A |
| ATOM | 131 | CA | GLU | A | 19 | 85.629 | 72.488 | 48.258 | 1.00 | 22.07 | A |
| ATOM | 132 | CB | GLU | A | 19 | 85.302 | 73.929 | 48.683 | 1.00 | 14.92 | A |
| ATOM | 133 | CG | GLU | A | 19 | 84.450 | 74.722 | 47.650 | 1.00 | 18.57 | A |
| ATOM | 134 | CD | GLU | A | 19 | 84.034 | 76.086 | 48.184 | 1.00 | 21.03 | A |
| ATOM | 135 | OE1 | GLU | A | 19 | 84.654 | 76.565 | 49.162 | 1.00 | 20.93 | A |
| ATOM | 136 | OE2 | GLU | A | 19 | 83.096 | 76.694 | 47.639 | 1.00 | 19.11 | A |
| ATOM | 137 | C | GLU | A | 19 | 86.679 | 71.889 | 49.203 | 1.00 | 18.24 | A |
| ATOM | 138 | O | GLU | A | 19 | 87.865 | 71.779 | 48.822 | 1.00 | 17.93 | A |
| ATOM | 139 | N | GLN | A | 20 | 86.235 | 71.519 | 50.415 | 1.00 | 15.20 | A |
| ATOM | 140 | CA | GLN | A | 20 | 87.084 | 70.923 | 51.502 | 1.00 | 23.25 | A |
| ATOM | 141 | CB | GLN | A | 20 | 86.217 | 70.526 | 52.751 | 1.00 | 23.39 | A |
| ATOM | 142 | CG | GLN | A | 20 | 85.294 | 71.692 | 53.342 | 1.00 | 43.73 | A |
| ATOM | 143 | CD | GLN | A | 20 | 84.079 | 71.273 | 54.296 | 1.00 | 42.22 | A |

TABLE 2-continued

| ATOM | 144 | OE1 | GLN | A | 20 | 83.301 | 70.366 | 53.989 | 1.00 | 38.04 | A |
|------|-----|-----|-----|---|----|--------|--------|--------|------|-------|---|
| ATOM | 145 | NE2 | GLN | A | 20 | 83.924 | 71.988 | 55.410 | 1.00 | 33.68 | A |
| ATOM | 146 | C | GLN | A | 20 | 87.816 | 69.660 | 50.976 | 1.00 | 24.37 | A |
| ATOM | 147 | O | GLN | A | 20 | 88.996 | 69.451 | 51.237 | 1.00 | 17.83 | A |
| ATOM | 148 | N | ASN | A | 21 | 87.100 | 68.832 | 50.225 | 1.00 | 15.50 | A |
| ATOM | 149 | CA | ASN | A | 21 | 87.677 | 67.616 | 49.677 | 1.00 | 18.10 | A |
| ATOM | 150 | CB | ASN | A | 21 | 86.601 | 66.790 | 48.967 | 1.00 | 13.23 | A |
| ATOM | 151 | CG | ASN | A | 21 | 87.145 | 65.457 | 48.485 | 1.00 | 23.30 | A |
| ATOM | 152 | OD1 | ASN | A | 21 | 87.490 | 64.598 | 49.294 | 1.00 | 17.88 | A |
| ATOM | 153 | ND2 | ASN | A | 21 | 87.251 | 65.294 | 47.168 | 1.00 | 17.44 | A |
| ATOM | 154 | C | ASN | A | 21 | 88.847 | 67.891 | 48.721 | 1.00 | 21.18 | A |
| ATOM | 155 | O | ASN | A | 21 | 89.789 | 67.088 | 48.658 | 1.00 | 21.46 | A |
| ATOM | 156 | N | MET | A | 22 | 88.787 | 69.004 | 47.971 | 1.00 | 14.28 | A |
| ATOM | 157 | CA | MET | A | 22 | 89.850 | 69.360 | 47.039 | 1.00 | 13.52 | A |
| ATOM | 158 | CB | MET | A | 22 | 89.330 | 70.305 | 45.939 | 1.00 | 19.05 | A |
| ATOM | 159 | CG | MET | A | 22 | 88.285 | 69.647 | 45.064 | 1.00 | 20.17 | A |
| ATOM | 160 | SD | MET | A | 22 | 88.876 | 68.159 | 44.293 | 1.00 | 28.63 | A |
| ATOM | 161 | CE | MET | A | 22 | 90.211 | 68.915 | 43.271 | 1.00 | 21.96 | A |
| ATOM | 162 | C | MET | A | 22 | 91.028 | 69.995 | 47.767 | 1.00 | 15.63 | A |
| ATOM | 163 | O | MET | A | 22 | 92.159 | 69.896 | 47.328 | 1.00 | 16.97 | A |
| ATOM | 164 | N | ILE | A | 23 | 90.743 | 70.644 | 48.886 | 1.00 | 11.88 | A |
| ATOM | 165 | CA | ILE | A | 23 | 91.784 | 71.242 | 49.714 | 1.00 | 19.19 | A |
| ATOM | 166 | CB | ILE | A | 23 | 91.126 | 72.029 | 50.870 | 1.00 | 13.50 | A |
| ATOM | 167 | CG2 | ILE | A | 23 | 92.159 | 72.357 | 51.971 | 1.00 | 13.80 | A |
| ATOM | 168 | CG1 | ILE | A | 23 | 90.476 | 73.296 | 50.297 | 1.00 | 16.98 | A |
| ATOM | 169 | CD1 | ILE | A | 23 | 89.807 | 74.203 | 51.351 | 1.00 | 17.93 | A |
| ATOM | 170 | C | ILE | A | 23 | 92.597 | 70.046 | 50.235 | 1.00 | 22.66 | A |
| ATOM | 171 | O | ILE | A | 23 | 93.843 | 70.053 | 50.257 | 1.00 | 18.47 | A |
| ATOM | 172 | N | GLY | A | 24 | 91.892 | 68.990 | 50.628 | 1.00 | 15.67 | A |
| ATOM | 173 | CA | GLY | A | 24 | 92.583 | 67.804 | 51.110 | 1.00 | 17.85 | A |
| ATOM | 174 | C | GLY | A | 24 | 93.291 | 67.056 | 50.000 | 1.00 | 21.53 | A |
| ATOM | 175 | O | GLY | A | 24 | 94.439 | 66.616 | 50.138 | 1.00 | 16.68 | A |
| ATOM | 176 | N | MET | A | 25 | 92.631 | 66.918 | 48.864 | 1.00 | 18.50 | A |
| ATOM | 177 | CA | MET | A | 25 | 93.234 | 66.170 | 47.767 | 1.00 | 15.73 | A |
| ATOM | 178 | CB | MET | A | 25 | 92.153 | 65.985 | 46.703 | 1.00 | 21.35 | A |
| ATOM | 179 | CG | MET | A | 25 | 92.469 | 65.151 | 45.529 | 1.00 | 26.92 | A |
| ATOM | 180 | SD | MET | A | 25 | 90.966 | 64.905 | 44.498 | 1.00 | 24.37 | A |
| ATOM | 181 | CE | MET | A | 25 | 91.718 | 63.617 | 43.360 | 1.00 | 17.81 | A |
| ATOM | 182 | C | MET | A | 25 | 94.511 | 66.832 | 47.185 | 1.00 | 23.64 | A |
| ATOM | 183 | O | MET | A | 25 | 95.432 | 66.146 | 46.757 | 1.00 | 17.81 | A |
| ATOM | 184 | N | THR | A | 26 | 94.577 | 68.164 | 47.180 | 1.00 | 17.90 | A |
| ATOM | 185 | CA | THR | A | 26 | 95.736 | 68.856 | 46.607 | 1.00 | 18.87 | A |
| ATOM | 186 | CB | THR | A | 26 | 95.629 | 70.395 | 46.847 | 1.00 | 17.83 | A |
| ATOM | 187 | OG1 | THR | A | 26 | 94.436 | 70.869 | 46.218 | 1.00 | 17.41 | A |
| ATOM | 188 | CG2 | THR | A | 26 | 96.851 | 71.139 | 46.262 | 1.00 | 16.75 | A |
| ATOM | 189 | C | THR | A | 26 | 97.149 | 68.423 | 47.052 | 1.00 | 11.10 | A |
| ATOM | 190 | O | THR | A | 26 | 97.990 | 68.069 | 46.229 | 1.00 | 17.69 | A |
| ATOM | 191 | N | PRO | A | 27 | 97.418 | 68.448 | 48.353 | 1.00 | 13.60 | A |
| ATOM | 192 | CD | PRO | A | 27 | 96.664 | 68.937 | 49.532 | 1.00 | 11.14 | A |
| ATOM | 193 | CA | PRO | A | 27 | 98.788 | 68.049 | 48.696 | 1.00 | 17.00 | A |
| ATOM | 194 | CB | PRO | A | 27 | 98.861 | 68.267 | 50.218 | 1.00 | 12.53 | A |
| ATOM | 195 | CG | PRO | A | 27 | 97.406 | 68.312 | 50.676 | 1.00 | 15.76 | A |
| ATOM | 196 | C | PRO | A | 27 | 99.193 | 66.662 | 48.277 | 1.00 | 21.64 | A |
| ATOM | 197 | O | PRO | A | 27 | 100.324 | 66.455 | 47.840 | 1.00 | 19.29 | A |
| ATOM | 198 | N | THR | A | 28 | 98.273 | 65.709 | 48.393 | 1.00 | 16.44 | A |
| ATOM | 199 | CA | THR | A | 28 | 98.607 | 64.333 | 48.046 | 1.00 | 17.14 | A |
| ATOM | 200 | CB | THR | A | 28 | 97.488 | 63.396 | 48.522 | 1.00 | 18.78 | A |
| ATOM | 201 | OG1 | THR | A | 28 | 97.290 | 63.620 | 49.926 | 1.00 | 16.04 | A |
| ATOM | 202 | CG2 | THR | A | 28 | 97.822 | 61.967 | 48.263 | 1.00 | 20.93 | A |
| ATOM | 203 | C | THR | A | 28 | 98.827 | 64.211 | 46.567 | 1.00 | 19.51 | A |
| ATOM | 204 | O | THR | A | 28 | 99.799 | 63.572 | 46.116 | 1.00 | 17.24 | A |
| ATOM | 205 | N | VAL | A | 29 | 97.957 | 64.844 | 45.781 | 1.00 | 16.43 | A |
| ATOM | 206 | CA | VAL | A | 29 | 98.164 | 64.762 | 44.346 | 1.00 | 16.98 | A |
| ATOM | 207 | CB | VAL | A | 29 | 97.035 | 65.430 | 43.524 | 1.00 | 21.71 | A |
| ATOM | 208 | CG1 | VAL | A | 29 | 97.421 | 65.427 | 41.999 | 1.00 | 14.09 | A |
| ATOM | 209 | CG2 | VAL | A | 29 | 95.731 | 64.619 | 43.708 | 1.00 | 22.05 | A |
| ATOM | 210 | C | VAL | A | 29 | 99.474 | 65.393 | 43.939 | 1.00 | 24.43 | A |
| ATOM | 211 | O | VAL | A | 29 | 100.260 | 64.768 | 43.179 | 1.00 | 19.52 | A |
| ATOM | 212 | N | ILE | A | 30 | 99.767 | 66.608 | 44.420 | 1.00 | 21.18 | A |
| ATOM | 213 | CA | ILE | A | 30 | 101.022 | 67.194 | 43.950 | 1.00 | 21.90 | A |
| ATOM | 214 | CB | ILE | A | 30 | 101.165 | 68.700 | 44.228 | 1.00 | 25.58 | A |
| ATOM | 215 | CG2 | ILE | A | 30 | 100.124 | 69.422 | 43.519 | 1.00 | 45.44 | A |
| ATOM | 216 | CG1 | ILE | A | 30 | 101.109 | 68.995 | 45.713 | 1.00 | 20.88 | A |
| ATOM | 217 | CD1 | ILE | A | 30 | 102.385 | 68.792 | 46.400 | 1.00 | 43.61 | A |
| ATOM | 218 | C | ILE | A | 30 | 102.227 | 66.495 | 44.510 | 1.00 | 8.84 | A |
| ATOM | 219 | O | ILE | A | 30 | 103.227 | 66.413 | 43.837 | 1.00 | 20.78 | A |
| ATOM | 220 | N | ALA | A | 31 | 102.137 | 65.986 | 45.730 | 1.00 | 11.98 | A |
| ATOM | 221 | CA | ALA | A | 31 | 103.289 | 65.247 | 46.282 | 1.00 | 16.32 | A |
| ATOM | 222 | CB | ALA | A | 31 | 102.982 | 64.774 | 47.668 | 1.00 | 11.90 | A |

TABLE 2-continued

| | | | | | | | | | | |
|---|---|---|---|---|---|---|---|---|---|---|
| ATOM | 223 | C | ALA | A | 31 | 103.613 | 64.026 | 45.381 | 1.00 | 20.08 | A |
| ATOM | 224 | O | ALA | A | 31 | 104.779 | 63.774 | 45.047 | 1.00 | 18.22 | A |
| ATOM | 225 | N | VAL | A | 32 | 102.594 | 63.254 | 45.005 | 1.00 | 16.38 | A |
| ATOM | 226 | CA | VAL | A | 32 | 102.852 | 62.078 | 44.161 | 1.00 | 18.95 | A |
| ATOM | 227 | CB | VAL | A | 32 | 101.597 | 61.176 | 44.042 | 1.00 | 22.56 | A |
| ATOM | 228 | CG1 | VAL | A | 32 | 101.803 | 60.122 | 42.937 | 1.00 | 22.34 | A |
| ATOM | 229 | CG2 | VAL | A | 32 | 101.348 | 60.477 | 45.364 | 1.00 | 13.55 | A |
| ATOM | 230 | C | VAL | A | 32 | 103.328 | 62.569 | 42.778 | 1.00 | 22.75 | A |
| ATOM | 231 | O | VAL | A | 32 | 104.310 | 62.061 | 42.211 | 1.00 | 22.15 | A |
| ATOM | 232 | N | HIS | A | 33 | 102.662 | 63.581 | 42.234 | 1.00 | 17.13 | A |
| ATOM | 233 | CA | HIS | A | 33 | 103.113 | 64.112 | 40.945 | 1.00 | 15.67 | A |
| ATOM | 234 | CB | HIS | A | 33 | 102.301 | 65.335 | 40.554 | 1.00 | 19.93 | A |
| ATOM | 235 | CG | HIS | A | 33 | 102.849 | 66.078 | 39.380 | 1.00 | 19.22 | A |
| ATOM | 236 | CD2 | HIS | A | 33 | 103.579 | 67.220 | 39.317 | 1.00 | 25.53 | A |
| ATOM | 237 | ND1 | HIS | A | 33 | 102.541 | 65.747 | 38.076 | 1.00 | 24.42 | A |
| ATOM | 238 | CE1 | HIS | A | 33 | 103.042 | 66.661 | 37.262 | 1.00 | 21.19 | A |
| ATOM | 239 | NE2 | HIS | A | 33 | 103.674 | 67.567 | 37.992 | 1.00 | 27.74 | A |
| ATOM | 240 | C | HIS | A | 33 | 104.580 | 64.549 | 41.036 | 1.00 | 15.68 | A |
| ATOM | 241 | O | HIS | A | 33 | 105.364 | 64.348 | 40.108 | 1.00 | 20.03 | A |
| ATOM | 242 | N | TYR | A | 34 | 104.944 | 65.179 | 42.144 | 1.00 | 16.97 | A |
| ATOM | 243 | CA | TYR | A | 34 | 106.317 | 65.646 | 42.304 | 1.00 | 20.05 | A |
| ATOM | 244 | CB | TYR | A | 34 | 106.420 | 66.500 | 43.571 | 1.00 | 19.93 | A |
| ATOM | 245 | CG | TYR | A | 34 | 107.826 | 66.882 | 43.969 | 1.00 | 14.48 | A |
| ATOM | 246 | CD1 | TYR | A | 34 | 108.374 | 68.143 | 43.629 | 1.00 | 19.63 | A |
| ATOM | 247 | CE1 | TYR | A | 34 | 109.672 | 68.522 | 44.095 | 1.00 | 15.16 | A |
| ATOM | 248 | CD2 | TYR | A | 34 | 108.597 | 66.021 | 44.746 | 1.00 | 21.63 | A |
| ATOM | 249 | CE2 | TYR | A | 34 | 109.889 | 66.380 | 45.183 | 1.00 | 17.33 | A |
| ATOM | 250 | CZ | TYR | A | 34 | 110.419 | 67.633 | 44.861 | 1.00 | 21.32 | A |
| ATOM | 251 | OH | TYR | A | 34 | 111.695 | 67.974 | 45.318 | 1.00 | 20.25 | A |
| ATOM | 252 | C | TYR | A | 34 | 107.326 | 64.471 | 42.392 | 1.00 | 21.84 | A |
| ATOM | 253 | O | TYR | A | 34 | 108.389 | 64.514 | 41.770 | 1.00 | 20.07 | A |
| ATOM | 254 | N | LEU | A | 35 | 107.010 | 63.454 | 43.197 | 1.00 | 19.69 | A |
| ATOM | 255 | CA | LEU | A | 35 | 107.924 | 62.333 | 43.345 | 1.00 | 19.40 | A |
| ATOM | 256 | CB | LEU | A | 35 | 107.451 | 61.435 | 44.478 | 1.00 | 17.56 | A |
| ATOM | 257 | CG | LEU | A | 35 | 107.627 | 62.047 | 45.884 | 1.00 | 16.05 | A |
| ATOM | 258 | CD1 | LEU | A | 35 | 106.927 | 61.165 | 46.915 | 1.00 | 19.26 | A |
| ATOM | 259 | CD2 | LEU | A | 35 | 109.123 | 62.096 | 46.253 | 1.00 | 15.28 | A |
| ATOM | 260 | C | LEU | A | 35 | 108.066 | 61.564 | 42.015 | 1.00 | 23.12 | A |
| ATOM | 261 | O | LEU | A | 35 | 109.187 | 61.215 | 41.608 | 1.00 | 17.85 | A |
| ATOM | 262 | N | ASP | A | 36 | 106.954 | 61.305 | 41.329 | 1.00 | 16.70 | A |
| ATOM | 263 | CA | ASP | A | 36 | 107.009 | 60.614 | 40.024 | 1.00 | 21.87 | A |
| ATOM | 264 | CB | ASP | A | 36 | 105.620 | 60.458 | 39.375 | 1.00 | 23.42 | A |
| ATOM | 265 | CG | ASP | A | 36 | 104.722 | 59.442 | 40.071 | 1.00 | 19.96 | A |
| ATOM | 266 | OD1 | ASP | A | 36 | 105.160 | 58.736 | 41.003 | 1.00 | 23.17 | A |
| ATOM | 267 | OD2 | ASP | A | 36 | 103.556 | 59.366 | 39.646 | 1.00 | 26.39 | A |
| ATOM | 268 | C | ASP | A | 36 | 107.830 | 61.430 | 39.021 | 1.00 | 26.32 | A |
| ATOM | 269 | O | ASP | A | 36 | 108.750 | 60.927 | 38.360 | 1.00 | 22.51 | A |
| ATOM | 270 | N | GLU | A | 37 | 107.505 | 62.709 | 38.909 | 1.00 | 19.41 | A |
| ATOM | 271 | CA | GLU | A | 37 | 108.180 | 63.550 | 37.919 | 1.00 | 23.12 | A |
| ATOM | 272 | CB | GLU | A | 37 | 107.476 | 64.916 | 37.874 | 1.00 | 31.20 | A |
| ATOM | 273 | CG | GLU | A | 37 | 107.620 | 65.640 | 36.601 | 1.00 | 42.72 | A |
| ATOM | 274 | CD | GLU | A | 37 | 106.461 | 65.412 | 35.676 | 1.00 | 49.79 | A |
| ATOM | 275 | OE1 | GLU | A | 37 | 106.263 | 64.269 | 35.210 | 1.00 | 51.12 | A |
| ATOM | 276 | OE2 | GLU | A | 37 | 105.728 | 66.387 | 35.415 | 1.00 | 58.13 | A |
| ATOM | 277 | C | GLU | A | 37 | 109.679 | 63.735 | 38.197 | 1.00 | 28.37 | A |
| ATOM | 278 | O | GLU | A | 37 | 110.506 | 63.788 | 37.269 | 1.00 | 19.17 | A |
| ATOM | 279 | N | THR | A | 38 | 110.044 | 63.821 | 39.469 | 1.00 | 19.70 | A |
| ATOM | 280 | CA | THR | A | 38 | 111.446 | 64.046 | 39.777 | 1.00 | 18.16 | A |
| ATOM | 281 | CB | THR | A | 38 | 111.615 | 64.951 | 41.051 | 1.00 | 24.32 | A |
| ATOM | 282 | OG1 | THR | A | 38 | 111.062 | 64.292 | 42.206 | 1.00 | 17.55 | A |
| ATOM | 283 | CG2 | THR | A | 38 | 110.872 | 66.295 | 40.874 | 1.00 | 17.35 | A |
| ATOM | 284 | C | THR | A | 38 | 112.173 | 62.725 | 39.992 | 1.00 | 23.12 | A |
| ATOM | 285 | O | THR | A | 38 | 113.384 | 62.708 | 40.176 | 1.00 | 20.01 | A |
| ATOM | 286 | N | GLU | A | 39 | 111.423 | 61.626 | 39.973 | 1.00 | 19.41 | A |
| ATOM | 287 | CA | GLU | A | 39 | 111.997 | 60.298 | 40.178 | 1.00 | 24.05 | A |
| ATOM | 288 | CB | GLU | A | 39 | 112.918 | 59.965 | 38.997 | 1.00 | 26.82 | A |
| ATOM | 289 | CG | GLU | A | 39 | 112.089 | 59.751 | 37.704 | 1.00 | 27.56 | A |
| ATOM | 290 | CD | GLU | A | 39 | 112.915 | 59.531 | 36.414 | 1.00 | 40.15 | A |
| ATOM | 291 | OE1 | GLU | A | 39 | 113.910 | 58.776 | 36.430 | 1.00 | 32.93 | A |
| ATOM | 292 | OE2 | GLU | A | 39 | 112.555 | 60.113 | 35.358 | 1.00 | 42.52 | A |
| ATOM | 293 | C | GLU | A | 39 | 112.740 | 60.228 | 41.519 | 1.00 | 25.56 | A |
| ATOM | 294 | O | GLU | A | 39 | 113.898 | 59.818 | 41.597 | 1.00 | 23.18 | A |
| ATOM | 295 | N | GLN | A | 40 | 112.059 | 60.614 | 42.601 | 1.00 | 24.46 | A |
| ATOM | 296 | CA | GLN | A | 40 | 112.707 | 60.592 | 43.899 | 1.00 | 18.16 | A |
| ATOM | 297 | CB | GLN | A | 40 | 112.682 | 62.002 | 44.489 | 1.00 | 24.56 | A |
| ATOM | 298 | CG | GLN | A | 40 | 113.517 | 63.012 | 43.708 | 1.00 | 10.67 | A |
| ATOM | 299 | CD | GLN | A | 40 | 113.705 | 64.283 | 44.507 | 1.00 | 19.34 | A |
| ATOM | 300 | OE1 | GLN | A | 40 | 114.594 | 64.350 | 45.334 | 1.00 | 17.51 | A |
| ATOM | 301 | NE2 | GLN | A | 40 | 112.845 | 65.298 | 44.275 | 1.00 | 17.15 | A |

TABLE 2-continued

| | | | | | | | | | | |
|---|---|---|---|---|---|---|---|---|---|---|
| ATOM | 302 | C | GLN | A | 40 | 112.118 | 59.603 | 44.894 | 1.00 | 19.24 | A |
| ATOM | 303 | O | GLN | A | 40 | 112.350 | 59.725 | 46.100 | 1.00 | 23.09 | A |
| ATOM | 304 | N | TRP | A | 41 | 111.345 | 58.635 | 44.403 | 1.00 | 18.32 | A |
| ATOM | 305 | CA | TRP | A | 41 | 110.700 | 57.670 | 45.311 | 1.00 | 18.31 | A |
| ATOM | 306 | CB | TRP | A | 41 | 109.808 | 56.715 | 44.511 | 1.00 | 18.08 | A |
| ATOM | 307 | CG | TRP | A | 41 | 108.504 | 57.334 | 44.147 | 1.00 | 16.18 | A |
| ATOM | 308 | CD2 | TRP | A | 41 | 107.382 | 57.574 | 45.024 | 1.00 | 18.90 | A |
| ATOM | 309 | CE2 | TRP | A | 41 | 106.376 | 58.204 | 44.257 | 1.00 | 16.03 | A |
| ATOM | 310 | CE3 | TRP | A | 41 | 107.134 | 57.322 | 46.379 | 1.00 | 16.13 | A |
| ATOM | 311 | CD1 | TRP | A | 41 | 108.139 | 57.816 | 42.926 | 1.00 | 20.37 | A |
| ATOM | 312 | NE1 | TRP | A | 41 | 106.860 | 58.344 | 42.977 | 1.00 | 19.88 | A |
| ATOM | 313 | CZ2 | TRP | A | 41 | 105.136 | 58.583 | 44.800 | 1.00 | 15.32 | A |
| ATOM | 314 | CZ3 | TRP | A | 41 | 105.893 | 57.703 | 46.929 | 1.00 | 19.86 | A |
| ATOM | 315 | CH2 | TRP | A | 41 | 104.908 | 58.330 | 46.127 | 1.00 | 17.50 | A |
| ATOM | 316 | C | TRP | A | 41 | 111.717 | 56.895 | 46.152 | 1.00 | 23.10 | A |
| ATOM | 317 | O | TRP | A | 41 | 111.457 | 56.555 | 47.312 | 1.00 | 24.58 | A |
| ATOM | 318 | N | GLU | A | 42 | 112.886 | 56.633 | 45.587 | 1.00 | 22.30 | A |
| ATOM | 319 | CA | GLU | A | 42 | 113.937 | 55.916 | 46.322 | 1.00 | 30.40 | A |
| ATOM | 320 | CB | GLU | A | 42 | 115.163 | 55.750 | 45.427 | 1.00 | 36.58 | A |
| ATOM | 321 | CG | GLU | A | 42 | 116.448 | 55.477 | 46.147 | 1.00 | 53.35 | A |
| ATOM | 322 | CD | GLU | A | 42 | 116.751 | 54.016 | 46.210 | 1.00 | 62.20 | A |
| ATOM | 323 | OE1 | GLU | A | 42 | 117.946 | 53.652 | 46.164 | 1.00 | 67.07 | A |
| ATOM | 324 | OE2 | GLU | A | 42 | 115.790 | 53.227 | 46.306 | 1.00 | 71.58 | A |
| ATOM | 325 | C | GLU | A | 42 | 114.292 | 56.689 | 47.595 | 1.00 | 26.77 | A |
| ATOM | 326 | O | GLU | A | 42 | 114.483 | 56.112 | 48.658 | 1.00 | 25.14 | A |
| ATOM | 327 | N | LYS | A | 43 | 114.352 | 58.005 | 47.515 | 1.00 | 24.54 | A |
| ATOM | 328 | CA | LYS | A | 43 | 114.639 | 58.771 | 48.717 | 1.00 | 25.18 | A |
| ATOM | 329 | CB | LYS | A | 43 | 115.106 | 60.173 | 48.344 | 1.00 | 33.24 | A |
| ATOM | 330 | CG | LYS | A | 43 | 116.398 | 60.152 | 47.566 | 1.00 | 36.94 | A |
| ATOM | 331 | CD | LYS | A | 43 | 117.068 | 61.498 | 47.549 | 1.00 | 39.52 | A |
| ATOM | 332 | CE | LYS | A | 43 | 116.841 | 62.204 | 46.242 | 1.00 | 39.10 | A |
| ATOM | 333 | NZ | LYS | A | 43 | 117.597 | 63.486 | 46.197 | 1.00 | 37.63 | A |
| ATOM | 334 | C | LYS | A | 43 | 113.437 | 58.885 | 49.640 | 1.00 | 30.60 | A |
| ATOM | 335 | O | LYS | A | 43 | 113.583 | 59.064 | 50.854 | 1.00 | 28.31 | A |
| ATOM | 336 | N | PHE | A | 44 | 112.232 | 58.754 | 49.089 | 1.00 | 23.22 | A |
| ATOM | 337 | CA | PHE | A | 44 | 111.061 | 58.940 | 49.924 | 1.00 | 22.11 | A |
| ATOM | 338 | CB | PHE | A | 44 | 109.995 | 59.654 | 49.078 | 1.00 | 19.24 | A |
| ATOM | 339 | CG | PHE | A | 44 | 108.732 | 59.989 | 49.809 | 1.00 | 21.27 | A |
| ATOM | 340 | CD1 | PHE | A | 44 | 108.627 | 61.162 | 50.555 | 1.00 | 23.33 | A |
| ATOM | 341 | CD2 | PHE | A | 44 | 107.624 | 59.154 | 49.710 | 1.00 | 22.69 | A |
| ATOM | 342 | CE1 | PHE | A | 44 | 107.424 | 61.514 | 51.193 | 1.00 | 22.52 | A |
| ATOM | 343 | CE2 | PHE | A | 44 | 106.405 | 59.486 | 50.344 | 1.00 | 27.02 | A |
| ATOM | 344 | CZ | PHE | A | 44 | 106.306 | 60.674 | 51.083 | 1.00 | 27.40 | A |
| ATOM | 345 | C | PHE | A | 44 | 110.533 | 57.628 | 50.510 | 1.00 | 24.45 | A |
| ATOM | 346 | O | PHE | A | 44 | 110.059 | 57.605 | 51.647 | 1.00 | 18.55 | A |
| ATOM | 347 | N | GLY | A | 45 | 110.636 | 56.550 | 49.730 | 1.00 | 20.97 | A |
| ATOM | 348 | CA | GLY | A | 45 | 110.142 | 55.236 | 50.131 | 1.00 | 20.25 | A |
| ATOM | 349 | C | GLY | A | 45 | 109.064 | 54.826 | 49.136 | 1.00 | 23.29 | A |
| ATOM | 350 | O | GLY | A | 45 | 107.871 | 55.185 | 49.279 | 1.00 | 17.57 | A |
| ATOM | 351 | N | LEU | A | 46 | 109.465 | 54.095 | 48.104 | 1.00 | 20.22 | A |
| ATOM | 352 | CA | LEU | A | 46 | 108.525 | 53.666 | 47.089 | 1.00 | 18.57 | A |
| ATOM | 353 | CB | LEU | A | 46 | 109.243 | 52.881 | 45.977 | 1.00 | 27.58 | A |
| ATOM | 354 | CG | LEU | A | 46 | 108.444 | 52.315 | 44.770 | 1.00 | 35.06 | A |
| ATOM | 355 | CD1 | LEU | A | 46 | 107.661 | 53.396 | 44.022 | 1.00 | 27.92 | A |
| ATOM | 356 | CD2 | LEU | A | 46 | 109.443 | 51.614 | 43.809 | 1.00 | 32.82 | A |
| ATOM | 357 | C | LEU | A | 46 | 107.322 | 52.884 | 47.611 | 1.00 | 23.74 | A |
| ATOM | 358 | O | LEU | A | 46 | 106.255 | 52.927 | 46.995 | 1.00 | 19.46 | A |
| ATOM | 359 | N | GLU | A | 47 | 107.450 | 52.190 | 48.738 | 1.00 | 19.11 | A |
| ATOM | 360 | CA | GLU | A | 47 | 106.292 | 51.453 | 49.220 | 1.00 | 29.84 | A |
| ATOM | 361 | CB | GLU | A | 47 | 106.629 | 50.448 | 50.332 | 1.00 | 30.68 | A |
| ATOM | 362 | CG | GLU | A | 47 | 107.600 | 50.871 | 51.370 | 1.00 | 45.90 | A |
| ATOM | 363 | CD | GLU | A | 47 | 107.135 | 52.019 | 52.226 | 1.00 | 52.96 | A |
| ATOM | 364 | OE1 | GLU | A | 47 | 105.927 | 52.017 | 52.597 | 1.00 | 60.58 | A |
| ATOM | 365 | OE2 | GLU | A | 47 | 107.991 | 52.901 | 52.541 | 1.00 | 47.47 | A |
| ATOM | 366 | C | GLU | A | 47 | 105.151 | 52.350 | 49.678 | 1.00 | 27.56 | A |
| ATOM | 367 | O | GLU | A | 47 | 104.061 | 51.855 | 49.854 | 1.00 | 24.22 | A |
| ATOM | 368 | N | LYS | A | 48 | 105.403 | 53.655 | 49.861 | 1.00 | 26.01 | A |
| ATOM | 369 | CA | LYS | A | 48 | 104.340 | 54.594 | 50.262 | 1.00 | 20.77 | A |
| ATOM | 370 | CB | LYS | A | 48 | 104.924 | 55.863 | 50.888 | 1.00 | 20.15 | A |
| ATOM | 371 | CG | LYS | A | 48 | 105.694 | 55.636 | 52.167 | 1.00 | 19.21 | A |
| ATOM | 372 | CD | LYS | A | 48 | 106.344 | 56.939 | 52.656 | 1.00 | 20.50 | A |
| ATOM | 373 | CE | LYS | A | 48 | 107.190 | 56.673 | 53.891 | 1.00 | 30.14 | A |
| ATOM | 374 | NZ | LYS | A | 48 | 108.457 | 55.962 | 53.556 | 1.00 | 23.91 | A |
| ATOM | 375 | C | LYS | A | 48 | 103.512 | 55.013 | 49.059 | 1.00 | 19.66 | A |
| ATOM | 376 | O | LYS | A | 48 | 102.415 | 55.567 | 49.217 | 1.00 | 23.92 | A |
| ATOM | 377 | N | ARG | A | 49 | 104.005 | 54.750 | 47.850 | 1.00 | 17.52 | A |
| ATOM | 378 | CA | ARG | A | 49 | 103.257 | 55.178 | 46.655 | 1.00 | 21.83 | A |
| ATOM | 379 | CB | ARG | A | 49 | 104.048 | 54.879 | 45.360 | 1.00 | 16.40 | A |
| ATOM | 380 | CG | ARG | A | 49 | 103.443 | 55.612 | 44.111 | 1.00 | 14.73 | A |

TABLE 2-continued

| | | | | | | | | | | |
|---|---|---|---|---|---|---|---|---|---|---|
| ATOM | 381 | CD | ARG | A | 49 | 104.410 | 55.661 | 42.916 | 1.00 | 21.52 | A |
| ATOM | 382 | NE | ARG | A | 49 | 103.924 | 56.478 | 41.815 | 1.00 | 16.66 | A |
| ATOM | 383 | CZ | ARG | A | 49 | 103.062 | 56.056 | 40.889 | 1.00 | 31.21 | A |
| ATOM | 384 | NH1 | ARG | A | 49 | 102.592 | 54.803 | 40.922 | 1.00 | 20.87 | A |
| ATOM | 385 | NH2 | ARG | A | 49 | 102.657 | 56.894 | 39.938 | 1.00 | 21.02 | A |
| ATOM | 386 | C | ARG | A | 49 | 101.826 | 54.612 | 46.536 | 1.00 | 24.68 | A |
| ATOM | 387 | O | ARG | A | 49 | 100.872 | 55.334 | 46.224 | 1.00 | 20.52 | A |
| ATOM | 388 | N | GLN | A | 50 | 101.681 | 53.313 | 46.785 | 1.00 | 31.61 | A |
| ATOM | 389 | CA | GLN | A | 50 | 100.398 | 52.629 | 46.691 | 1.00 | 24.84 | A |
| ATOM | 390 | CB | GLN | A | 50 | 100.531 | 51.187 | 47.168 | 1.00 | 33.17 | A |
| ATOM | 391 | CG | GLN | A | 50 | 100.197 | 50.169 | 46.142 | 1.00 | 46.59 | A |
| ATOM | 392 | CD | GLN | A | 50 | 98.794 | 50.305 | 45.608 | 1.00 | 42.68 | A |
| ATOM | 393 | OE1 | GLN | A | 50 | 97.825 | 50.200 | 46.346 | 1.00 | 40.26 | A |
| ATOM | 394 | NE2 | GLN | A | 50 | 98.684 | 50.542 | 44.308 | 1.00 | 47.02 | A |
| ATOM | 395 | C | GLN | A | 50 | 99.381 | 53.289 | 47.577 | 1.00 | 27.71 | A |
| ATOM | 396 | O | GLN | A | 50 | 98.257 | 53.562 | 47.157 | 1.00 | 18.05 | A |
| ATOM | 397 | N | GLY | A | 51 | 99.795 | 53.504 | 48.822 | 1.00 | 19.41 | A |
| ATOM | 398 | CA | GLY | A | 51 | 98.944 | 54.124 | 49.820 | 1.00 | 24.54 | A |
| ATOM | 399 | C | GLY | A | 51 | 98.517 | 55.489 | 49.329 | 1.00 | 27.23 | A |
| ATOM | 400 | O | GLY | A | 51 | 97.347 | 55.861 | 49.470 | 1.00 | 27.21 | A |
| ATOM | 401 | N | ALA | A | 52 | 99.444 | 56.233 | 48.723 | 1.00 | 21.82 | A |
| ATOM | 402 | CA | ALA | A | 52 | 99.089 | 57.561 | 48.220 | 1.00 | 21.64 | A |
| ATOM | 403 | CB | ALA | A | 52 | 100.343 | 58.319 | 47.777 | 1.00 | 20.17 | A |
| ATOM | 404 | C | ALA | A | 52 | 98.117 | 57.446 | 47.065 | 1.00 | 18.79 | A |
| ATOM | 405 | O | ALA | A | 52 | 97.209 | 58.265 | 46.947 | 1.00 | 21.57 | A |
| ATOM | 406 | N | LEU | A | 53 | 98.296 | 56.436 | 46.206 | 1.00 | 16.94 | A |
| ATOM | 407 | CA | LEU | A | 53 | 97.379 | 56.279 | 45.079 | 1.00 | 20.49 | A |
| ATOM | 408 | CB | LEU | A | 53 | 97.816 | 55.148 | 44.151 | 1.00 | 22.88 | A |
| ATOM | 409 | CG | LEU | A | 53 | 99.197 | 55.310 | 43.509 | 1.00 | 27.56 | A |
| ATOM | 410 | CD1 | LEU | A | 53 | 99.526 | 54.081 | 42.643 | 1.00 | 28.51 | A |
| ATOM | 411 | CD2 | LEU | A | 53 | 99.207 | 56.557 | 42.665 | 1.00 | 19.40 | A |
| ATOM | 412 | C | LEU | A | 53 | 95.966 | 56.027 | 45.571 | 1.00 | 22.20 | A |
| ATOM | 413 | O | LEU | A | 53 | 95.014 | 56.559 | 44.996 | 1.00 | 22.74 | A |
| ATOM | 414 | N | GLU | A | 54 | 95.838 | 55.241 | 46.643 | 1.00 | 20.38 | A |
| ATOM | 415 | CA | GLU | A | 54 | 94.542 | 54.937 | 47.247 | 1.00 | 22.21 | A |
| ATOM | 416 | CB | GLU | A | 54 | 94.705 | 53.920 | 48.404 | 1.00 | 22.94 | A |
| ATOM | 417 | CG | GLU | A | 54 | 95.023 | 52.489 | 47.951 | 1.00 | 41.26 | A |
| ATOM | 418 | CD | GLU | A | 54 | 95.587 | 51.579 | 49.071 | 1.00 | 48.52 | A |
| ATOM | 419 | OE1 | GLU | A | 54 | 95.476 | 51.903 | 50.286 | 1.00 | 50.15 | A |
| ATOM | 420 | OE2 | GLU | A | 54 | 96.141 | 50.514 | 48.717 | 1.00 | 50.86 | A |
| ATOM | 421 | C | GLU | A | 54 | 93.870 | 56.214 | 47.801 | 1.00 | 24.94 | A |
| ATOM | 422 | O | GLU | A | 54 | 92.644 | 56.351 | 47.710 | 1.00 | 21.97 | A |
| ATOM | 423 | N | LEU | A | 55 | 94.656 | 57.126 | 48.392 | 1.00 | 18.88 | A |
| ATOM | 424 | CA | LEU | A | 55 | 94.085 | 58.351 | 48.948 | 1.00 | 21.65 | A |
| ATOM | 425 | CB | LEU | A | 55 | 95.099 | 59.091 | 49.809 | 1.00 | 17.30 | A |
| ATOM | 426 | CG | LEU | A | 55 | 95.464 | 58.303 | 51.072 | 1.00 | 26.70 | A |
| ATOM | 427 | CD1 | LEU | A | 55 | 96.576 | 59.072 | 51.841 | 1.00 | 25.33 | A |
| ATOM | 428 | CD2 | LEU | A | 55 | 94.196 | 58.153 | 51.981 | 1.00 | 20.15 | A |
| ATOM | 429 | C | LEU | A | 55 | 93.646 | 59.229 | 47.802 | 1.00 | 18.82 | A |
| ATOM | 430 | O | LEU | A | 55 | 92.613 | 59.897 | 47.902 | 1.00 | 16.55 | A |
| ATOM | 431 | N | ILE | A | 56 | 94.413 | 59.218 | 46.712 | 1.00 | 15.84 | A |
| ATOM | 432 | CA | ILE | A | 56 | 94.065 | 60.024 | 45.513 | 1.00 | 16.74 | A |
| ATOM | 433 | CB | ILE | A | 56 | 95.151 | 59.930 | 44.390 | 1.00 | 21.15 | A |
| ATOM | 434 | CG2 | ILE | A | 56 | 94.710 | 60.691 | 43.120 | 1.00 | 25.29 | A |
| ATOM | 435 | CG1 | ILE | A | 56 | 96.461 | 60.644 | 44.806 | 1.00 | 20.28 | A |
| ATOM | 436 | CD1 | ILE | A | 56 | 96.234 | 61.948 | 45.382 | 1.00 | 40.37 | A |
| ATOM | 437 | C | ILE | A | 56 | 92.723 | 59.508 | 44.945 | 1.00 | 25.52 | A |
| ATOM | 438 | O | ILE | A | 56 | 91.816 | 60.297 | 44.615 | 1.00 | 18.85 | A |
| ATOM | 439 | N | LYS | A | 57 | 92.589 | 58.183 | 44.822 | 1.00 | 20.21 | A |
| ATOM | 440 | CA | LYS | A | 57 | 91.354 | 57.595 | 44.308 | 1.00 | 19.21 | A |
| ATOM | 441 | CB | LYS | A | 57 | 91.496 | 56.088 | 44.221 | 1.00 | 26.24 | A |
| ATOM | 442 | CG | LYS | A | 57 | 90.244 | 55.363 | 43.763 | 1.00 | 37.40 | A |
| ATOM | 443 | CD | LYS | A | 57 | 90.531 | 53.831 | 43.577 | 1.00 | 39.50 | A |
| ATOM | 444 | CE | LYS | A | 57 | 89.290 | 53.088 | 43.091 | 1.00 | 45.08 | A |
| ATOM | 445 | NZ | LYS | A | 57 | 89.516 | 51.637 | 42.936 | 1.00 | 50.42 | A |
| ATOM | 446 | C | LYS | A | 57 | 90.192 | 57.952 | 45.242 | 1.00 | 23.30 | A |
| ATOM | 447 | O | LYS | A | 57 | 89.082 | 58.273 | 44.789 | 1.00 | 20.92 | A |
| ATOM | 448 | N | LYS | A | 58 | 90.445 | 57.902 | 46.550 | 1.00 | 16.98 | A |
| ATOM | 449 | CA | LYS | A | 58 | 89.421 | 58.260 | 47.513 | 1.00 | 17.12 | A |
| ATOM | 450 | CB | LYS | A | 58 | 89.971 | 58.041 | 48.937 | 1.00 | 18.85 | A |
| ATOM | 451 | CG | LYS | A | 58 | 88.973 | 58.307 | 50.047 | 1.00 | 25.94 | A |
| ATOM | 452 | CD | LYS | A | 58 | 89.491 | 57.947 | 51.437 | 1.00 | 35.63 | A |
| ATOM | 453 | CE | LYS | A | 58 | 88.639 | 58.677 | 52.501 | 1.00 | 42.54 | A |
| ATOM | 454 | NZ | LYS | A | 58 | 88.728 | 58.038 | 53.858 | 1.00 | 50.94 | A |
| ATOM | 455 | C | LYS | A | 58 | 89.011 | 59.749 | 47.300 | 1.00 | 25.76 | A |
| ATOM | 456 | O | LYS | A | 58 | 87.808 | 60.095 | 47.288 | 1.00 | 22.91 | A |
| ATOM | 457 | N | GLY | A | 59 | 89.999 | 60.629 | 47.099 | 1.00 | 21.23 | A |
| ATOM | 458 | CA | GLY | A | 59 | 89.691 | 62.041 | 46.894 | 1.00 | 23.41 | A |
| ATOM | 459 | C | GLY | A | 59 | 88.819 | 62.247 | 45.664 | 1.00 | 25.51 | A |

TABLE 2-continued

| | | | | | | | | | | |
|---|---|---|---|---|---|---|---|---|---|---|
| ATOM | 460 | O | GLY | A | 59 | 87.820 | 62.978 | 45.683 | 1.00 | 21.04 | A |
| ATOM | 461 | N | TYR | A | 60 | 89.213 | 61.576 | 44.588 | 1.00 | 21.05 | A |
| ATOM | 462 | CA | TYR | A | 60 | 88.517 | 61.642 | 43.312 | 1.00 | 23.66 | A |
| ATOM | 463 | CB | TYR | A | 60 | 89.244 | 60.776 | 42.296 | 1.00 | 13.71 | A |
| ATOM | 464 | CG | TYR | A | 60 | 88.456 | 60.499 | 41.039 | 1.00 | 25.98 | A |
| ATOM | 465 | CD1 | TYR | A | 60 | 88.276 | 61.495 | 40.082 | 1.00 | 22.56 | A |
| ATOM | 466 | CE1 | TYR | A | 60 | 87.570 | 61.250 | 38.915 | 1.00 | 26.16 | A |
| ATOM | 467 | CD2 | TYR | A | 60 | 87.893 | 59.223 | 40.792 | 1.00 | 27.02 | A |
| ATOM | 468 | CE2 | TYR | A | 60 | 87.180 | 58.966 | 39.610 | 1.00 | 23.07 | A |
| ATOM | 469 | CZ | TYR | A | 60 | 87.027 | 59.994 | 38.677 | 1.00 | 27.86 | A |
| ATOM | 470 | OH | TYR | A | 60 | 86.347 | 59.798 | 37.490 | 1.00 | 19.73 | A |
| ATOM | 471 | C | TYR | A | 60 | 87.089 | 61.131 | 43.448 | 1.00 | 23.97 | A |
| ATOM | 472 | O | TYR | A | 60 | 86.129 | 61.776 | 43.024 | 1.00 | 16.61 | A |
| ATOM | 473 | N | THR | A | 61 | 86.947 | 59.954 | 44.029 | 1.00 | 22.77 | A |
| ATOM | 474 | CA | THR | A | 61 | 85.615 | 59.365 | 44.185 | 1.00 | 22.30 | A |
| ATOM | 475 | CB | THR | A | 61 | 85.739 | 58.003 | 44.849 | 1.00 | 30.49 | A |
| ATOM | 476 | OG1 | THR | A | 61 | 86.448 | 57.145 | 43.960 | 1.00 | 31.94 | A |
| ATOM | 477 | CG2 | THR | A | 61 | 84.371 | 57.401 | 45.164 | 1.00 | 42.36 | A |
| ATOM | 478 | C | THR | A | 61 | 84.724 | 60.246 | 45.008 | 1.00 | 23.97 | A |
| ATOM | 479 | O | THR | A | 61 | 83.554 | 60.480 | 44.668 | 1.00 | 22.40 | A |
| ATOM | 480 | N | GLN | A | 62 | 85.267 | 60.743 | 46.108 | 1.00 | 20.42 | A |
| ATOM | 481 | CA | GLN | A | 62 | 84.476 | 61.619 | 46.958 | 1.00 | 23.93 | A |
| ATOM | 482 | CB | GLN | A | 62 | 85.255 | 61.966 | 48.242 | 1.00 | 24.47 | A |
| ATOM | 483 | CG | GLN | A | 62 | 85.293 | 60.776 | 49.207 | 1.00 | 26.29 | A |
| ATOM | 484 | CD | GLN | A | 62 | 86.265 | 60.940 | 50.385 | 1.00 | 27.78 | A |
| ATOM | 485 | OE1 | GLN | A | 62 | 86.263 | 60.126 | 51.289 | 1.00 | 27.57 | A |
| ATOM | 486 | NE2 | GLN | A | 62 | 87.098 | 61.980 | 50.362 | 1.00 | 22.36 | A |
| ATOM | 487 | C | GLN | A | 62 | 84.037 | 62.885 | 46.215 | 1.00 | 19.82 | A |
| ATOM | 488 | O | GLN | A | 62 | 82.903 | 63.334 | 46.374 | 1.00 | 21.86 | A |
| ATOM | 489 | N | GLN | A | 63 | 84.910 | 63.441 | 45.382 | 1.00 | 20.60 | A |
| ATOM | 490 | CA | GLN | A | 63 | 84.569 | 64.669 | 44.667 | 1.00 | 23.75 | A |
| ATOM | 491 | CB | GLN | A | 63 | 85.772 | 65.168 | 43.862 | 1.00 | 17.42 | A |
| ATOM | 492 | CG | GLN | A | 63 | 85.669 | 66.602 | 43.360 | 1.00 | 15.84 | A |
| ATOM | 493 | CD | GLN | A | 63 | 85.470 | 67.642 | 44.449 | 1.00 | 18.31 | A |
| ATOM | 494 | OE1 | GLN | A | 63 | 85.851 | 67.455 | 45.610 | 1.00 | 15.34 | A |
| ATOM | 495 | NE2 | GLN | A | 63 | 84.900 | 68.779 | 44.062 | 1.00 | 17.92 | A |
| ATOM | 496 | C | GLN | A | 63 | 83.371 | 64.460 | 43.721 | 1.00 | 27.22 | A |
| ATOM | 497 | O | GLN | A | 63 | 82.590 | 65.388 | 43.471 | 1.00 | 16.84 | A |
| ATOM | 498 | N | LEU | A | 64 | 83.223 | 63.249 | 43.201 | 1.00 | 18.15 | A |
| ATOM | 499 | CA | LEU | A | 64 | 82.113 | 62.984 | 42.289 | 1.00 | 20.34 | A |
| ATOM | 500 | CB | LEU | A | 64 | 82.194 | 61.562 | 41.738 | 1.00 | 20.67 | A |
| ATOM | 501 | CG | LEU | A | 64 | 83.460 | 61.266 | 40.904 | 1.00 | 29.97 | A |
| ATOM | 502 | CD1 | LEU | A | 64 | 83.341 | 59.848 | 40.328 | 1.00 | 28.53 | A |
| ATOM | 503 | CD2 | LEU | A | 64 | 83.645 | 62.308 | 39.769 | 1.00 | 25.04 | A |
| ATOM | 504 | C | LEU | A | 64 | 80.781 | 63.214 | 42.971 | 1.00 | 20.30 | A |
| ATOM | 505 | O | LEU | A | 64 | 79.818 | 63.568 | 42.314 | 1.00 | 23.21 | A |
| ATOM | 506 | N | ALA | A | 65 | 80.708 | 63.015 | 44.288 | 1.00 | 15.07 | A |
| ATOM | 507 | CA | ALA | A | 65 | 79.459 | 63.267 | 44.975 | 1.00 | 19.06 | A |
| ATOM | 508 | CB | ALA | A | 65 | 79.595 | 62.955 | 46.447 | 1.00 | 19.25 | A |
| ATOM | 509 | C | ALA | A | 65 | 79.010 | 64.717 | 44.790 | 1.00 | 19.22 | A |
| ATOM | 510 | O | ALA | A | 65 | 77.864 | 65.042 | 45.087 | 1.00 | 24.93 | A |
| ATOM | 511 | N | PHE | A | 66 | 79.895 | 65.592 | 44.314 | 1.00 | 22.94 | A |
| ATOM | 512 | CA | PHE | A | 66 | 79.533 | 67.015 | 44.134 | 1.00 | 22.02 | A |
| ATOM | 513 | CB | PHE | A | 66 | 80.481 | 67.908 | 44.943 | 1.00 | 21.43 | A |
| ATOM | 514 | CG | PHE | A | 66 | 80.548 | 67.511 | 46.386 | 1.00 | 24.76 | A |
| ATOM | 515 | CD1 | PHE | A | 66 | 79.542 | 67.914 | 47.287 | 1.00 | 21.43 | A |
| ATOM | 516 | CD2 | PHE | A | 66 | 81.573 | 66.657 | 46.840 | 1.00 | 20.02 | A |
| ATOM | 517 | CE1 | PHE | A | 66 | 79.555 | 67.467 | 48.605 | 1.00 | 22.96 | A |
| ATOM | 518 | CE2 | PHE | A | 66 | 81.594 | 66.203 | 48.162 | 1.00 | 18.70 | A |
| ATOM | 519 | CZ | PHE | A | 66 | 80.584 | 66.611 | 49.049 | 1.00 | 21.49 | A |
| ATOM | 520 | C | PHE | A | 66 | 79.511 | 67.461 | 42.693 | 1.00 | 17.64 | A |
| ATOM | 521 | O | PHE | A | 66 | 79.405 | 68.673 | 42.389 | 1.00 | 18.14 | A |
| ATOM | 522 | N | ARG | A | 67 | 79.606 | 66.481 | 41.796 | 1.00 | 21.16 | A |
| ATOM | 523 | CA | ARG | A | 67 | 79.541 | 66.745 | 40.354 | 1.00 | 23.23 | A |
| ATOM | 524 | CB | ARG | A | 67 | 79.971 | 65.496 | 39.598 | 1.00 | 18.11 | A |
| ATOM | 525 | CG | ARG | A | 67 | 79.896 | 65.665 | 38.107 | 1.00 | 28.17 | A |
| ATOM | 526 | CD | ARG | A | 67 | 80.315 | 64.386 | 37.363 | 1.00 | 25.25 | A |
| ATOM | 527 | NE | ARG | A | 67 | 80.344 | 64.619 | 35.923 | 1.00 | 25.71 | A |
| ATOM | 528 | CZ | ARG | A | 67 | 80.004 | 63.715 | 35.012 | 1.00 | 26.53 | A |
| ATOM | 529 | NH1 | ARG | A | 67 | 79.601 | 62.496 | 35.388 | 1.00 | 23.05 | A |
| ATOM | 530 | NH2 | ARG | A | 67 | 80.089 | 64.028 | 33.724 | 1.00 | 16.97 | A |
| ATOM | 531 | C | ARG | A | 67 | 78.055 | 67.034 | 40.044 | 1.00 | 25.46 | A |
| ATOM | 532 | O | ARG | A | 67 | 77.223 | 66.244 | 40.427 | 1.00 | 18.92 | A |
| ATOM | 533 | N | GLN | A | 68 | 77.716 | 68.150 | 39.395 | 1.00 | 21.57 | A |
| ATOM | 534 | CA | GLN | A | 68 | 76.305 | 68.440 | 39.084 | 1.00 | 20.68 | A |
| ATOM | 535 | CB | GLN | A | 68 | 76.073 | 69.964 | 39.186 | 1.00 | 23.31 | A |
| ATOM | 536 | CG | GLN | A | 68 | 76.532 | 70.448 | 40.570 | 1.00 | 17.98 | A |
| ATOM | 537 | CD | GLN | A | 68 | 75.990 | 71.790 | 40.937 | 1.00 | 25.72 | A |
| ATOM | 538 | OE1 | GLN | A | 68 | 75.464 | 72.528 | 40.084 | 1.00 | 23.05 | A |

TABLE 2-continued

| | | | | | | | | | | |
|---|---|---|---|---|---|---|---|---|---|---|
| ATOM | 539 | NE2 | GLN | A | 68 | 76.132 | 72.140 | 42.206 | 1.00 | 15.43 | A |
| ATOM | 540 | C | GLN | A | 68 | 75.871 | 67.887 | 37.722 | 1.00 | 16.68 | A |
| ATOM | 541 | O | GLN | A | 68 | 76.704 | 67.367 | 36.998 | 1.00 | 19.76 | A |
| ATOM | 542 | N | PRO | A | 69 | 74.563 | 67.945 | 37.368 | 1.00 | 22.91 | A |
| ATOM | 543 | CD | PRO | A | 69 | 73.385 | 68.286 | 38.198 | 1.00 | 21.74 | A |
| ATOM | 544 | CA | PRO | A | 69 | 74.144 | 67.408 | 36.046 | 1.00 | 20.68 | A |
| ATOM | 545 | CB | PRO | A | 69 | 72.628 | 67.698 | 35.995 | 1.00 | 17.83 | A |
| ATOM | 546 | CG | PRO | A | 69 | 72.208 | 67.532 | 37.454 | 1.00 | 16.18 | A |
| ATOM | 547 | C | PRO | A | 69 | 74.886 | 68.078 | 34.892 | 1.00 | 23.73 | A |
| ATOM | 548 | O | PRO | A | 69 | 75.152 | 67.467 | 33.875 | 1.00 | 23.28 | A |
| ATOM | 549 | N | SER | A | 70 | 75.246 | 69.340 | 35.086 | 1.00 | 24.11 | A |
| ATOM | 550 | CA | SER | A | 70 | 75.975 | 70.114 | 34.092 | 1.00 | 23.11 | A |
| ATOM | 551 | CB | SER | A | 70 | 76.000 | 71.580 | 34.528 | 1.00 | 20.68 | A |
| ATOM | 552 | OG | SER | A | 70 | 76.662 | 71.709 | 35.793 | 1.00 | 27.57 | A |
| ATOM | 553 | C | SER | A | 70 | 77.436 | 69.654 | 33.942 | 1.00 | 27.84 | A |
| ATOM | 554 | O | SER | A | 70 | 78.127 | 70.080 | 33.021 | 1.00 | 24.67 | A |
| ATOM | 555 | N | SER | A | 71 | 77.885 | 68.805 | 34.868 | 1.00 | 19.80 | A |
| ATOM | 556 | CA | SER | A | 71 | 79.288 | 68.333 | 34.971 | 1.00 | 20.11 | A |
| ATOM | 557 | CB | SER | A | 71 | 79.953 | 68.052 | 33.613 | 1.00 | 22.15 | A |
| ATOM | 558 | OG | SER | A | 71 | 79.498 | 66.853 | 33.011 | 1.00 | 21.54 | A |
| ATOM | 559 | C | SER | A | 71 | 80.131 | 69.401 | 35.702 | 1.00 | 20.52 | A |
| ATOM | 560 | O | SER | A | 71 | 81.329 | 69.262 | 35.782 | 1.00 | 19.50 | A |
| ATOM | 561 | N | ALA | A | 72 | 79.522 | 70.477 | 36.199 | 1.00 | 19.13 | A |
| ATOM | 562 | CA | ALA | A | 72 | 80.273 | 71.479 | 36.973 | 1.00 | 21.30 | A |
| ATOM | 563 | CB | ALA | A | 72 | 79.665 | 72.897 | 36.823 | 1.00 | 16.76 | A |
| ATOM | 564 | C | ALA | A | 72 | 80.250 | 71.064 | 38.447 | 1.00 | 24.51 | A |
| ATOM | 565 | O | ALA | A | 72 | 79.540 | 70.122 | 38.840 | 1.00 | 20.95 | A |
| ATOM | 566 | N | PHE | A | 73 | 81.026 | 71.773 | 39.266 | 1.00 | 22.89 | A |
| ATOM | 567 | CA | PHE | A | 73 | 81.113 | 71.484 | 40.695 | 1.00 | 19.84 | A |
| ATOM | 568 | CB | PHE | A | 73 | 82.541 | 70.958 | 41.056 | 1.00 | 16.24 | A |
| ATOM | 569 | CG | PHE | A | 73 | 82.890 | 69.625 | 40.409 | 1.00 | 17.75 | A |
| ATOM | 570 | CD1 | PHE | A | 73 | 83.265 | 69.554 | 39.067 | 1.00 | 14.21 | A |
| ATOM | 571 | CD2 | PHE | A | 73 | 82.791 | 68.439 | 41.140 | 1.00 | 21.80 | A |
| ATOM | 572 | CE1 | PHE | A | 73 | 83.527 | 68.310 | 38.447 | 1.00 | 18.43 | A |
| ATOM | 573 | CE2 | PHE | A | 73 | 83.048 | 67.196 | 40.546 | 1.00 | 20.67 | A |
| ATOM | 574 | CZ | PHE | A | 73 | 83.418 | 67.115 | 39.190 | 1.00 | 17.64 | A |
| ATOM | 575 | C | PHE | A | 73 | 80.846 | 72.708 | 41.561 | 1.00 | 15.55 | A |
| ATOM | 576 | O | PHE | A | 73 | 81.079 | 73.846 | 41.134 | 1.00 | 17.42 | A |
| ATOM | 577 | N | ALA | A | 74 | 80.392 | 72.437 | 42.787 | 1.00 | 18.86 | A |
| ATOM | 578 | CA | ALA | A | 74 | 80.196 | 73.440 | 43.842 | 1.00 | 21.20 | A |
| ATOM | 579 | CB | ALA | A | 74 | 78.774 | 74.076 | 43.782 | 1.00 | 14.22 | A |
| ATOM | 580 | C | ALA | A | 74 | 80.381 | 72.705 | 45.171 | 1.00 | 19.11 | A |
| ATOM | 581 | O | ALA | A | 74 | 80.364 | 71.471 | 45.211 | 1.00 | 23.95 | A |
| ATOM | 582 | N | ALA | A | 75 | 80.579 | 73.456 | 46.259 | 1.00 | 17.13 | A |
| ATOM | 583 | CA | ALA | A | 75 | 80.738 | 72.883 | 47.584 | 1.00 | 21.11 | A |
| ATOM | 584 | CB | ALA | A | 75 | 80.813 | 73.959 | 48.592 | 1.00 | 12.54 | A |
| ATOM | 585 | C | ALA | A | 75 | 79.600 | 71.944 | 47.961 | 1.00 | 19.04 | A |
| ATOM | 586 | O | ALA | A | 75 | 79.821 | 70.901 | 48.589 | 1.00 | 18.22 | A |
| ATOM | 587 | N | PHE | A | 76 | 78.386 | 72.317 | 47.591 | 1.00 | 20.53 | A |
| ATOM | 588 | CA | PHE | A | 76 | 77.202 | 71.519 | 47.920 | 1.00 | 15.82 | A |
| ATOM | 589 | CB | PHE | A | 76 | 76.420 | 72.195 | 49.053 | 1.00 | 17.12 | A |
| ATOM | 590 | CG | PHE | A | 76 | 77.249 | 72.514 | 50.258 | 1.00 | 26.60 | A |
| ATOM | 591 | CD1 | PHE | A | 76 | 77.723 | 71.505 | 51.098 | 1.00 | 27.70 | A |
| ATOM | 592 | CD2 | PHE | A | 76 | 77.576 | 73.824 | 50.551 | 1.00 | 22.87 | A |
| ATOM | 593 | CE1 | PHE | A | 76 | 78.512 | 71.807 | 52.212 | 1.00 | 22.16 | A |
| ATOM | 594 | CE2 | PHE | A | 76 | 78.367 | 74.125 | 51.667 | 1.00 | 28.08 | A |
| ATOM | 595 | CZ | PHE | A | 76 | 78.832 | 73.124 | 52.490 | 1.00 | 23.72 | A |
| ATOM | 596 | C | PHE | A | 76 | 76.343 | 71.444 | 46.654 | 1.00 | 23.48 | A |
| ATOM | 597 | O | PHE | A | 76 | 76.308 | 72.404 | 45.866 | 1.00 | 15.81 | A |
| ATOM | 598 | N | VAL | A | 77 | 75.639 | 70.327 | 46.465 | 1.00 | 19.15 | A |
| ATOM | 599 | CA | VAL | A | 77 | 74.845 | 70.141 | 45.255 | 1.00 | 23.84 | A |
| ATOM | 600 | CB | VAL | A | 77 | 74.279 | 68.688 | 45.144 | 1.00 | 24.38 | A |
| ATOM | 601 | CG1 | VAL | A | 77 | 75.456 | 67.682 | 44.930 | 1.00 | 20.82 | A |
| ATOM | 602 | CG2 | VAL | A | 77 | 73.465 | 68.349 | 46.390 | 1.00 | 19.64 | A |
| ATOM | 603 | C | VAL | A | 77 | 73.701 | 71.122 | 45.082 | 1.00 | 20.75 | A |
| ATOM | 604 | O | VAL | A | 77 | 73.201 | 71.320 | 43.973 | 1.00 | 24.71 | A |
| ATOM | 605 | N | LYS | A | 78 | 73.302 | 71.723 | 46.184 | 1.00 | 15.92 | A |
| ATOM | 606 | CA | LYS | A | 78 | 72.245 | 72.712 | 46.200 | 1.00 | 28.31 | A |
| ATOM | 607 | CB | LYS | A | 78 | 71.642 | 72.818 | 47.590 | 1.00 | 31.59 | A |
| ATOM | 608 | CG | LYS | A | 78 | 70.888 | 71.559 | 47.898 | 1.00 | 52.94 | A |
| ATOM | 609 | CD | LYS | A | 78 | 69.877 | 71.719 | 48.992 | 1.00 | 60.83 | A |
| ATOM | 610 | CE | LYS | A | 78 | 68.914 | 70.543 | 48.967 | 1.00 | 61.05 | A |
| ATOM | 611 | NZ | LYS | A | 78 | 68.246 | 70.353 | 47.672 | 1.00 | 30.69 | A |
| ATOM | 612 | C | LYS | A | 78 | 72.755 | 74.071 | 45.823 | 1.00 | 26.47 | A |
| ATOM | 613 | O | LYS | A | 78 | 71.956 | 74.971 | 45.569 | 1.00 | 24.70 | A |
| ATOM | 614 | N | ARG | A | 79 | 74.080 | 74.223 | 45.818 | 1.00 | 20.39 | A |
| ATOM | 615 | CA | ARG | A | 79 | 74.723 | 75.499 | 45.514 | 1.00 | 21.78 | A |
| ATOM | 616 | CB | ARG | A | 79 | 76.013 | 75.592 | 46.349 | 1.00 | 19.49 | A |
| ATOM | 617 | CG | ARG | A | 79 | 76.859 | 76.847 | 46.120 | 1.00 | 23.95 | A |

TABLE 2-continued

| | | | | | | | | | | |
|---|---|---|---|---|---|---|---|---|---|---|
| ATOM | 618 | CD | ARG | A | 79 | 78.098 | 76.897 | 47.058 | 1.00 | 20.40 | A |
| ATOM | 619 | NE | ARG | A | 79 | 78.758 | 78.204 | 47.005 | 1.00 | 25.41 | A |
| ATOM | 620 | CZ | ARG | A | 79 | 78.559 | 79.167 | 47.899 | 1.00 | 30.60 | A |
| ATOM | 621 | NH1 | ARG | A | 79 | 77.724 | 78.956 | 48.915 | 1.00 | 29.61 | A |
| ATOM | 622 | NH2 | ARG | A | 79 | 79.177 | 80.338 | 47.780 | 1.00 | 23.38 | A |
| ATOM | 623 | C | ARG | A | 79 | 75.036 | 75.716 | 44.030 | 1.00 | 21.79 | A |
| ATOM | 624 | O | ARG | A | 79 | 75.417 | 74.764 | 43.332 | 1.00 | 19.63 | A |
| ATOM | 625 | N | ALA | A | 80 | 74.877 | 76.967 | 43.553 | 1.00 | 21.57 | A |
| ATOM | 626 | CA | ALA | A | 80 | 75.180 | 77.331 | 42.159 | 1.00 | 26.40 | A |
| ATOM | 627 | CB | ALA | A | 80 | 74.960 | 78.868 | 41.923 | 1.00 | 22.62 | A |
| ATOM | 628 | C | ALA | A | 80 | 76.659 | 76.953 | 41.914 | 1.00 | 20.22 | A |
| ATOM | 629 | O | ALA | A | 80 | 77.519 | 77.179 | 42.780 | 1.00 | 23.83 | A |
| ATOM | 630 | N | PRO | A | 81 | 76.959 | 76.365 | 40.744 | 1.00 | 23.02 | A |
| ATOM | 631 | CD | PRO | A | 81 | 75.984 | 76.235 | 39.641 | 1.00 | 22.02 | A |
| ATOM | 632 | CA | PRO | A | 81 | 78.301 | 75.909 | 40.337 | 1.00 | 20.18 | A |
| ATOM | 633 | CB | PRO | A | 81 | 78.046 | 75.207 | 38.995 | 1.00 | 23.34 | A |
| ATOM | 634 | CG | PRO | A | 81 | 76.879 | 75.999 | 38.416 | 1.00 | 25.62 | A |
| ATOM | 635 | C | PRO | A | 81 | 79.370 | 76.990 | 40.238 | 1.00 | 24.53 | A |
| ATOM | 636 | O | PRO | A | 81 | 79.132 | 78.085 | 39.736 | 1.00 | 18.24 | A |
| ATOM | 637 | N | SER | A | 82 | 80.560 | 76.677 | 40.736 | 1.00 | 18.76 | A |
| ATOM | 638 | CA | SER | A | 82 | 81.648 | 77.630 | 40.669 | 1.00 | 15.88 | A |
| ATOM | 639 | CB | SER | A | 82 | 82.494 | 77.549 | 41.942 | 1.00 | 19.09 | A |
| ATOM | 640 | OG | SER | A | 82 | 83.781 | 78.102 | 41.725 | 1.00 | 15.72 | A |
| ATOM | 641 | C | SER | A | 82 | 82.529 | 77.411 | 39.437 | 1.00 | 18.93 | A |
| ATOM | 642 | O | SER | A | 82 | 82.981 | 76.286 | 39.114 | 1.00 | 17.23 | A |
| ATOM | 643 | N | THR | A | 83 | 82.762 | 78.494 | 38.725 | 1.00 | 17.20 | A |
| ATOM | 644 | CA | THR | A | 83 | 83.628 | 78.442 | 37.544 | 1.00 | 16.78 | A |
| ATOM | 645 | CB | THR | A | 83 | 83.692 | 79.829 | 36.868 | 1.00 | 19.03 | A |
| ATOM | 646 | OG1 | THR | A | 83 | 82.397 | 80.168 | 36.392 | 1.00 | 20.73 | A |
| ATOM | 647 | CG2 | THR | A | 83 | 84.666 | 79.840 | 35.692 | 1.00 | 17.21 | A |
| ATOM | 648 | C | THR | A | 83 | 85.060 | 78.069 | 38.027 | 1.00 | 20.11 | A |
| ATOM | 649 | O | THR | A | 83 | 85.740 | 77.214 | 37.446 | 1.00 | 15.09 | A |
| ATOM | 650 | N | TRP | A | 84 | 85.514 | 78.745 | 39.084 | 1.00 | 16.86 | A |
| ATOM | 651 | CA | TRP | A | 84 | 86.839 | 78.483 | 39.627 | 1.00 | 24.71 | A |
| ATOM | 652 | CB | TRP | A | 84 | 87.171 | 79.427 | 40.780 | 1.00 | 16.82 | A |
| ATOM | 653 | CG | TRP | A | 84 | 88.624 | 79.255 | 41.247 | 1.00 | 17.86 | A |
| ATOM | 654 | CD2 | TRP | A | 84 | 89.106 | 78.315 | 42.218 | 1.00 | 16.17 | A |
| ATOM | 655 | CE2 | TRP | A | 84 | 90.510 | 78.464 | 42.284 | 1.00 | 22.04 | A |
| ATOM | 656 | CE3 | TRP | A | 84 | 88.486 | 77.366 | 43.035 | 1.00 | 17.61 | A |
| ATOM | 657 | CD1 | TRP | A | 84 | 89.727 | 79.915 | 40.783 | 1.00 | 23.03 | A |
| ATOM | 658 | NE1 | TRP | A | 84 | 90.859 | 79.447 | 41.405 | 1.00 | 16.07 | A |
| ATOM | 659 | CZ2 | TRP | A | 84 | 91.308 | 77.686 | 43.141 | 1.00 | 21.59 | A |
| ATOM | 660 | CZ3 | TRP | A | 84 | 89.279 | 76.595 | 43.892 | 1.00 | 21.38 | A |
| ATOM | 661 | CH2 | TRP | A | 84 | 90.670 | 76.759 | 43.936 | 1.00 | 17.83 | A |
| ATOM | 662 | C | TRP | A | 84 | 87.001 | 77.049 | 40.136 | 1.00 | 22.89 | A |
| ATOM | 663 | O | TRP | A | 84 | 87.973 | 76.398 | 39.800 | 1.00 | 18.84 | A |
| ATOM | 664 | N | LEU | A | 85 | 86.065 | 76.561 | 40.949 | 1.00 | 23.94 | A |
| ATOM | 665 | CA | LEU | A | 85 | 86.175 | 75.193 | 41.495 | 1.00 | 19.54 | A |
| ATOM | 666 | CB | LEU | A | 85 | 85.011 | 74.891 | 42.475 | 1.00 | 14.42 | A |
| ATOM | 667 | CG | LEU | A | 85 | 85.115 | 73.580 | 43.258 | 1.00 | 19.45 | A |
| ATOM | 668 | CD1 | LEU | A | 85 | 86.371 | 73.566 | 44.197 | 1.00 | 11.14 | A |
| ATOM | 669 | CD2 | LEU | A | 85 | 83.825 | 73.422 | 44.060 | 1.00 | 18.37 | A |
| ATOM | 670 | C | LEU | A | 85 | 86.175 | 74.195 | 40.356 | 1.00 | 24.50 | A |
| ATOM | 671 | O | LEU | A | 85 | 86.994 | 73.257 | 40.330 | 1.00 | 19.38 | A |
| ATOM | 672 | N | THR | A | 86 | 85.285 | 74.413 | 39.383 | 1.00 | 16.67 | A |
| ATOM | 673 | CA | THR | A | 86 | 85.226 | 73.494 | 38.279 | 1.00 | 18.11 | A |
| ATOM | 674 | CB | THR | A | 86 | 84.068 | 73.818 | 37.357 | 1.00 | 17.96 | A |
| ATOM | 675 | OG1 | THR | A | 86 | 82.871 | 73.696 | 38.127 | 1.00 | 12.56 | A |
| ATOM | 676 | CG2 | THR | A | 86 | 84.007 | 72.851 | 36.202 | 1.00 | 14.63 | A |
| ATOM | 677 | C | THR | A | 86 | 86.534 | 73.480 | 37.569 | 1.00 | 18.80 | A |
| ATOM | 678 | O | THR | A | 86 | 87.057 | 72.395 | 37.283 | 1.00 | 15.97 | A |
| ATOM | 679 | N | ALA | A | 87 | 87.111 | 74.657 | 37.315 | 1.00 | 15.61 | A |
| ATOM | 680 | CA | ALA | A | 87 | 88.422 | 74.679 | 36.645 | 1.00 | 21.28 | A |
| ATOM | 681 | CB | ALA | A | 87 | 88.812 | 76.132 | 36.265 | 1.00 | 17.13 | A |
| ATOM | 682 | C | ALA | A | 87 | 89.532 | 74.068 | 37.535 | 1.00 | 21.82 | A |
| ATOM | 683 | O | ALA | A | 87 | 90.531 | 73.527 | 37.036 | 1.00 | 18.47 | A |
| ATOM | 684 | N | TYR | A | 88 | 89.400 | 74.203 | 38.845 | 1.00 | 16.96 | A |
| ATOM | 685 | CA | TYR | A | 88 | 90.439 | 73.637 | 39.708 | 1.00 | 19.62 | A |
| ATOM | 686 | CB | TYR | A | 88 | 90.324 | 74.155 | 41.140 | 1.00 | 17.51 | A |
| ATOM | 687 | CG | TYR | A | 88 | 91.533 | 73.749 | 41.989 | 1.00 | 17.09 | A |
| ATOM | 688 | CD1 | TYR | A | 88 | 92.843 | 73.975 | 41.528 | 1.00 | 17.38 | A |
| ATOM | 689 | CE1 | TYR | A | 88 | 93.947 | 73.554 | 42.259 | 1.00 | 18.76 | A |
| ATOM | 690 | CD2 | TYR | A | 88 | 91.366 | 73.093 | 43.214 | 1.00 | 20.06 | A |
| ATOM | 691 | CE2 | TYR | A | 88 | 92.475 | 72.663 | 43.971 | 1.00 | 20.12 | A |
| ATOM | 692 | CZ | TYR | A | 88 | 93.746 | 72.903 | 43.488 | 1.00 | 20.21 | A |
| ATOM | 693 | OH | TYR | A | 88 | 94.817 | 72.537 | 44.255 | 1.00 | 13.27 | A |
| ATOM | 694 | C | TYR | A | 88 | 90.318 | 72.119 | 39.706 | 1.00 | 21.43 | A |
| ATOM | 695 | O | TYR | A | 88 | 91.316 | 71.390 | 39.776 | 1.00 | 16.93 | A |
| ATOM | 696 | N | VAL | A | 89 | 89.092 | 71.625 | 39.636 | 1.00 | 19.57 | A |

TABLE 2-continued

| | | | | | | | | | | |
|---|---|---|---|---|---|---|---|---|---|---|
| ATOM | 697 | CA | VAL | A | 89 | 88.949 | 70.192 | 39.599 | 1.00 | 19.82 | A |
| ATOM | 698 | CB | VAL | A | 89 | 87.486 | 69.796 | 39.599 | 1.00 | 18.50 | A |
| ATOM | 699 | CG1 | VAL | A | 89 | 87.331 | 68.263 | 39.251 | 1.00 | 15.01 | A |
| ATOM | 700 | CG2 | VAL | A | 89 | 86.918 | 70.101 | 40.995 | 1.00 | 13.83 | A |
| ATOM | 701 | C | VAL | A | 89 | 89.659 | 69.678 | 38.349 | 1.00 | 23.95 | A |
| ATOM | 702 | O | VAL | A | 89 | 90.348 | 68.656 | 38.395 | 1.00 | 18.30 | A |
| ATOM | 703 | N | VAL | A | 90 | 89.491 | 70.382 | 37.232 | 1.00 | 17.40 | A |
| ATOM | 704 | CA | VAL | A | 90 | 90.160 | 69.981 | 35.990 | 1.00 | 18.85 | A |
| ATOM | 705 | CB | VAL | A | 90 | 89.724 | 70.929 | 34.791 | 1.00 | 19.41 | A |
| ATOM | 706 | CG1 | VAL | A | 90 | 90.600 | 70.715 | 33.553 | 1.00 | 13.53 | A |
| ATOM | 707 | CG2 | VAL | A | 90 | 88.248 | 70.648 | 34.399 | 1.00 | 17.29 | A |
| ATOM | 708 | C | VAL | A | 90 | 91.703 | 70.043 | 36.175 | 1.00 | 19.91 | A |
| ATOM | 709 | O | VAL | A | 90 | 92.452 | 69.188 | 35.696 | 1.00 | 20.47 | A |
| ATOM | 710 | N | LYS | A | 91 | 92.181 | 71.075 | 36.858 | 1.00 | 20.83 | A |
| ATOM | 711 | CA | LYS | A | 91 | 93.614 | 71.240 | 37.046 | 1.00 | 23.83 | A |
| ATOM | 712 | CB | LYS | A | 91 | 93.861 | 72.579 | 37.741 | 1.00 | 21.45 | A |
| ATOM | 713 | CG | LYS | A | 91 | 95.232 | 73.277 | 37.527 | 1.00 | 24.31 | A |
| ATOM | 714 | CD | LYS | A | 91 | 95.603 | 73.978 | 38.817 | 1.00 | 28.86 | A |
| ATOM | 715 | CE | LYS | A | 91 | 96.264 | 75.359 | 38.681 | 1.00 | 41.38 | A |
| ATOM | 716 | NZ | LYS | A | 91 | 97.276 | 75.477 | 37.603 | 1.00 | 23.09 | A |
| ATOM | 717 | C | LYS | A | 91 | 94.176 | 70.090 | 37.904 | 1.00 | 22.83 | A |
| ATOM | 718 | O | LYS | A | 91 | 95.288 | 69.615 | 37.659 | 1.00 | 28.75 | A |
| ATOM | 719 | N | VAL | A | 92 | 93.422 | 69.641 | 38.908 | 1.00 | 16.52 | A |
| ATOM | 720 | CA | VAL | A | 92 | 93.938 | 68.571 | 39.767 | 1.00 | 15.54 | A |
| ATOM | 721 | CB | VAL | A | 92 | 93.220 | 68.564 | 41.134 | 1.00 | 14.74 | A |
| ATOM | 722 | CG1 | VAL | A | 92 | 93.669 | 67.333 | 41.957 | 1.00 | 12.97 | A |
| ATOM | 723 | CG2 | VAL | A | 92 | 93.531 | 69.882 | 41.912 | 1.00 | 15.57 | A |
| ATOM | 724 | C | VAL | A | 92 | 93.780 | 67.195 | 39.100 | 1.00 | 22.13 | A |
| ATOM | 725 | O | VAL | A | 92 | 94.735 | 66.398 | 39.027 | 1.00 | 19.97 | A |
| ATOM | 726 | N | PHE | A | 93 | 92.575 | 66.936 | 38.599 | 1.00 | 15.35 | A |
| ATOM | 727 | CA | PHE | A | 93 | 92.262 | 65.649 | 37.986 | 1.00 | 21.59 | A |
| ATOM | 728 | CB | PHE | A | 93 | 90.780 | 65.619 | 37.538 | 1.00 | 20.43 | A |
| ATOM | 729 | CG | PHE | A | 93 | 89.762 | 65.399 | 38.658 | 1.00 | 21.63 | A |
| ATOM | 730 | CD1 | PHE | A | 93 | 90.101 | 65.531 | 40.003 | 1.00 | 22.34 | A |
| ATOM | 731 | CD2 | PHE | A | 93 | 88.435 | 65.083 | 38.327 | 1.00 | 25.57 | A |
| ATOM | 732 | CE1 | PHE | A | 93 | 89.146 | 65.347 | 41.015 | 1.00 | 18.59 | A |
| ATOM | 733 | CE2 | PHE | A | 93 | 87.474 | 64.900 | 39.309 | 1.00 | 16.00 | A |
| ATOM | 734 | CZ | PHE | A | 93 | 87.827 | 65.034 | 40.660 | 1.00 | 18.70 | A |
| ATOM | 735 | C | PHE | A | 93 | 93.183 | 65.348 | 36.778 | 1.00 | 20.69 | A |
| ATOM | 736 | O | PHE | A | 93 | 93.572 | 64.201 | 36.582 | 1.00 | 22.65 | A |
| ATOM | 737 | N | SER | A | 94 | 93.516 | 66.364 | 35.975 | 1.00 | 19.95 | A |
| ATOM | 738 | CA | SER | A | 94 | 94.382 | 66.192 | 34.795 | 1.00 | 23.79 | A |
| ATOM | 739 | CB | SER | A | 94 | 94.563 | 67.526 | 34.040 | 1.00 | 23.74 | A |
| ATOM | 740 | OG | SER | A | 94 | 93.351 | 67.930 | 33.393 | 1.00 | 23.03 | A |
| ATOM | 741 | C | SER | A | 94 | 95.759 | 65.623 | 35.169 | 1.00 | 29.47 | A |
| ATOM | 742 | O | SER | A | 94 | 96.379 | 64.867 | 34.406 | 1.00 | 24.55 | A |
| ATOM | 743 | N | LEU | A | 95 | 96.230 | 65.998 | 36.346 | 1.00 | 25.17 | A |
| ATOM | 744 | CA | LEU | A | 95 | 97.500 | 65.515 | 36.858 | 1.00 | 29.40 | A |
| ATOM | 745 | CB | LEU | A | 95 | 97.953 | 66.430 | 37.992 | 1.00 | 32.98 | A |
| ATOM | 746 | CG | LEU | A | 95 | 99.047 | 67.438 | 37.643 | 1.00 | 41.49 | A |
| ATOM | 747 | CD1 | LEU | A | 95 | 98.732 | 68.151 | 36.358 | 1.00 | 36.09 | A |
| ATOM | 748 | CD2 | LEU | A | 95 | 99.244 | 68.378 | 38.800 | 1.00 | 40.51 | A |
| ATOM | 749 | C | LEU | A | 95 | 97.413 | 64.064 | 37.368 | 1.00 | 31.25 | A |
| ATOM | 750 | O | LEU | A | 95 | 98.433 | 63.376 | 37.493 | 1.00 | 24.33 | A |
| ATOM | 751 | N | ALA | A | 96 | 96.203 | 63.614 | 37.685 | 1.00 | 28.03 | A |
| ATOM | 752 | CA | ALA | A | 96 | 95.991 | 62.260 | 38.208 | 1.00 | 27.75 | A |
| ATOM | 753 | CB | ALA | A | 96 | 94.901 | 62.301 | 39.286 | 1.00 | 26.88 | A |
| ATOM | 754 | C | ALA | A | 96 | 95.629 | 61.204 | 37.157 | 1.00 | 29.48 | A |
| ATOM | 755 | O | ALA | A | 96 | 95.529 | 60.013 | 37.479 | 1.00 | 25.41 | A |
| ATOM | 756 | N | VAL | A | 97 | 95.447 | 61.639 | 35.910 | 1.00 | 25.39 | A |
| ATOM | 757 | CA | VAL | A | 97 | 95.035 | 60.759 | 34.802 | 1.00 | 29.11 | A |
| ATOM | 758 | CB | VAL | A | 97 | 95.034 | 61.571 | 33.480 | 1.00 | 28.78 | A |
| ATOM | 759 | CG1 | VAL | A | 97 | 95.057 | 60.663 | 32.321 | 1.00 | 38.20 | A |
| ATOM | 760 | CG2 | VAL | A | 97 | 93.748 | 62.496 | 33.422 | 1.00 | 24.13 | A |
| ATOM | 761 | C | VAL | A | 97 | 95.813 | 59.424 | 34.636 | 1.00 | 33.92 | A |
| ATOM | 762 | O | VAL | A | 97 | 95.222 | 58.381 | 34.289 | 1.00 | 31.47 | A |
| ATOM | 763 | N | ASN | A | 98 | 97.124 | 59.457 | 34.848 | 1.00 | 21.59 | A |
| ATOM | 764 | CA | ASN | A | 98 | 97.923 | 58.240 | 34.770 | 1.00 | 36.51 | A |
| ATOM | 765 | CB | ASN | A | 98 | 99.222 | 58.471 | 33.983 | 1.00 | 36.15 | A |
| ATOM | 766 | CG | ASN | A | 98 | 98.971 | 58.837 | 32.510 | 1.00 | 36.17 | A |
| ATOM | 767 | OD1 | ASN | A | 98 | 98.119 | 58.252 | 31.844 | 1.00 | 38.38 | A |
| ATOM | 768 | ND2 | ASN | A | 98 | 99.730 | 59.805 | 32.007 | 1.00 | 40.71 | A |
| ATOM | 769 | C | ASN | A | 98 | 98.260 | 57.700 | 36.178 | 1.00 | 37.38 | A |
| ATOM | 770 | O | ASN | A | 98 | 99.138 | 56.844 | 36.316 | 1.00 | 31.38 | A |
| ATOM | 771 | N | LEU | A | 99 | 97.562 | 58.205 | 37.205 | 1.00 | 25.80 | A |
| ATOM | 772 | CA | LEU | A | 99 | 97.763 | 57.760 | 38.592 | 1.00 | 34.00 | A |
| ATOM | 773 | CB | LEU | A | 99 | 97.747 | 58.936 | 39.580 | 1.00 | 23.10 | A |
| ATOM | 774 | CG | LEU | A | 99 | 98.867 | 59.966 | 39.407 | 1.00 | 26.85 | A |
| ATOM | 775 | CD1 | LEU | A | 99 | 98.812 | 61.017 | 40.508 | 1.00 | 25.56 | A |

TABLE 2-continued

| | | | | | | | | | | |
|---|---|---|---|---|---|---|---|---|---|---|
| ATOM | 776 | CD2 | LEU | A | 99 | 100.191 | 59.231 | 39.390 | 1.00 | 29.12 | A |
| ATOM | 777 | C | LEU | A | 99 | 96.656 | 56.804 | 38.994 | 1.00 | 34.25 | A |
| ATOM | 778 | O | LEU | A | 99 | 96.911 | 55.782 | 39.629 | 1.00 | 29.94 | A |
| ATOM | 779 | N | ILE | A | 100 | 95.431 | 57.169 | 38.623 | 1.00 | 24.08 | A |
| ATOM | 780 | CA | ILE | A | 100 | 94.232 | 56.407 | 38.913 | 1.00 | 28.23 | A |
| ATOM | 781 | CB | ILE | A | 100 | 93.446 | 57.007 | 40.119 | 1.00 | 26.92 | A |
| ATOM | 782 | CG2 | ILE | A | 100 | 94.300 | 56.986 | 41.388 | 1.00 | 21.39 | A |
| ATOM | 783 | CG1 | ILE | A | 100 | 93.022 | 58.457 | 39.786 | 1.00 | 22.04 | A |
| ATOM | 784 | CD1 | ILE | A | 100 | 91.965 | 59.043 | 40.791 | 1.00 | 21.31 | A |
| ATOM | 785 | C | ILE | A | 100 | 93.340 | 56.511 | 37.684 | 1.00 | 28.89 | A |
| ATOM | 786 | O | ILE | A | 100 | 93.676 | 57.218 | 36.738 | 1.00 | 25.36 | A |
| ATOM | 787 | N | ALA | A | 101 | 92.195 | 55.834 | 37.701 | 1.00 | 21.87 | A |
| ATOM | 788 | CA | ALA | A | 101 | 91.278 | 55.891 | 36.563 | 1.00 | 25.41 | A |
| ATOM | 789 | CB | ALA | A | 101 | 90.323 | 54.656 | 36.557 | 1.00 | 29.20 | A |
| ATOM | 790 | C | ALA | A | 101 | 90.426 | 57.148 | 36.639 | 1.00 | 27.34 | A |
| ATOM | 791 | O | ALA | A | 101 | 89.546 | 57.235 | 37.493 | 1.00 | 27.43 | A |
| ATOM | 792 | N | ILE | A | 102 | 90.676 | 58.121 | 35.774 | 1.00 | 25.35 | A |
| ATOM | 793 | CA | ILE | A | 102 | 89.837 | 59.308 | 35.794 | 1.00 | 26.53 | A |
| ATOM | 794 | CB | ILE | A | 102 | 90.666 | 60.596 | 35.788 | 1.00 | 30.43 | A |
| ATOM | 795 | CG2 | ILE | A | 102 | 89.775 | 61.805 | 35.343 | 1.00 | 26.72 | A |
| ATOM | 796 | CG1 | ILE | A | 102 | 91.165 | 60.849 | 37.221 | 1.00 | 33.11 | A |
| ATOM | 797 | CD1 | ILE | A | 102 | 92.470 | 61.458 | 37.221 | 1.00 | 45.56 | A |
| ATOM | 798 | C | ILE | A | 102 | 88.919 | 59.248 | 34.585 | 1.00 | 22.33 | A |
| ATOM | 799 | O | ILE | A | 102 | 89.378 | 59.106 | 33.461 | 1.00 | 26.71 | A |
| ATOM | 800 | N | ASP | A | 103 | 87.621 | 59.318 | 34.836 | 1.00 | 26.27 | A |
| ATOM | 801 | CA | ASP | A | 103 | 86.616 | 59.227 | 33.776 | 1.00 | 25.84 | A |
| ATOM | 802 | CB | ASP | A | 103 | 85.231 | 59.056 | 34.425 | 1.00 | 25.81 | A |
| ATOM | 803 | CG | ASP | A | 103 | 84.114 | 58.863 | 33.403 | 1.00 | 34.26 | A |
| ATOM | 804 | OD1 | ASP | A | 103 | 84.361 | 59.023 | 32.187 | 1.00 | 25.53 | A |
| ATOM | 805 | OD2 | ASP | A | 103 | 82.979 | 58.551 | 33.828 | 1.00 | 39.65 | A |
| ATOM | 806 | C | ASP | A | 103 | 86.642 | 60.484 | 32.900 | 1.00 | 24.26 | A |
| ATOM | 807 | O | ASP | A | 103 | 86.385 | 61.577 | 33.381 | 1.00 | 26.29 | A |
| ATOM | 808 | N | SER | A | 104 | 86.972 | 60.331 | 31.627 | 1.00 | 24.09 | A |
| ATOM | 809 | CA | SER | A | 104 | 87.010 | 61.465 | 30.700 | 1.00 | 30.37 | A |
| ATOM | 810 | CB | SER | A | 104 | 87.490 | 60.999 | 29.333 | 1.00 | 35.62 | A |
| ATOM | 811 | OG | SER | A | 104 | 88.890 | 60.808 | 29.371 | 1.00 | 42.20 | A |
| ATOM | 812 | C | SER | A | 104 | 85.689 | 62.219 | 30.544 | 1.00 | 27.77 | A |
| ATOM | 813 | O | SER | A | 104 | 85.679 | 63.399 | 30.237 | 1.00 | 26.73 | A |
| ATOM | 814 | N | GLN | A | 105 | 84.576 | 61.534 | 30.741 | 1.00 | 26.58 | A |
| ATOM | 815 | CA | GLN | A | 105 | 83.264 | 62.158 | 30.673 | 1.00 | 31.05 | A |
| ATOM | 816 | CB | GLN | A | 105 | 82.162 | 61.141 | 30.991 | 1.00 | 33.79 | A |
| ATOM | 817 | CG | GLN | A | 105 | 81.964 | 60.052 | 29.984 | 1.00 | 45.91 | A |
| ATOM | 818 | CD | GLN | A | 105 | 81.570 | 60.627 | 28.655 | 1.00 | 53.89 | A |
| ATOM | 819 | OE1 | GLN | A | 105 | 82.400 | 61.212 | 27.938 | 1.00 | 55.25 | A |
| ATOM | 820 | NE2 | GLN | A | 105 | 80.286 | 60.499 | 28.320 | 1.00 | 55.15 | A |
| ATOM | 821 | C | GLN | A | 105 | 83.227 | 63.209 | 31.778 | 1.00 | 30.55 | A |
| ATOM | 822 | O | GLN | A | 105 | 82.602 | 64.258 | 31.644 | 1.00 | 26.07 | A |
| ATOM | 823 | N | VAL | A | 106 | 83.867 | 62.889 | 32.897 | 1.00 | 26.33 | A |
| ATOM | 824 | CA | VAL | A | 106 | 83.888 | 63.790 | 34.056 | 1.00 | 25.39 | A |
| ATOM | 825 | CB | VAL | A | 106 | 84.395 | 63.046 | 35.315 | 1.00 | 24.50 | A |
| ATOM | 826 | CG1 | VAL | A | 106 | 84.635 | 64.032 | 36.470 | 1.00 | 21.15 | A |
| ATOM | 827 | CG2 | VAL | A | 106 | 83.369 | 61.966 | 35.738 | 1.00 | 18.61 | A |
| ATOM | 828 | C | VAL | A | 106 | 84.829 | 64.931 | 33.742 | 1.00 | 22.14 | A |
| ATOM | 829 | O | VAL | A | 106 | 84.446 | 66.083 | 33.719 | 1.00 | 25.05 | A |
| ATOM | 830 | N | LEU | A | 107 | 86.076 | 64.589 | 33.498 | 1.00 | 20.26 | A |
| ATOM | 831 | CA | LEU | A | 107 | 87.076 | 65.582 | 33.195 | 1.00 | 22.29 | A |
| ATOM | 832 | CB | LEU | A | 107 | 88.416 | 64.907 | 32.888 | 1.00 | 19.77 | A |
| ATOM | 833 | CG | LEU | A | 107 | 89.520 | 65.924 | 32.603 | 1.00 | 28.38 | A |
| ATOM | 834 | CD1 | LEU | A | 107 | 89.898 | 66.617 | 33.883 | 1.00 | 29.44 | A |
| ATOM | 835 | CD2 | LEU | A | 107 | 90.737 | 65.230 | 32.030 | 1.00 | 37.22 | A |
| ATOM | 836 | C | LEU | A | 107 | 86.652 | 66.472 | 32.017 | 1.00 | 25.15 | A |
| ATOM | 837 | O | LEU | A | 107 | 86.572 | 67.690 | 32.153 | 1.00 | 24.72 | A |
| ATOM | 838 | N | CYS | A | 108 | 86.334 | 65.874 | 30.877 | 1.00 | 23.13 | A |
| ATOM | 839 | CA | CYS | A | 108 | 85.959 | 66.654 | 29.711 | 1.00 | 20.45 | A |
| ATOM | 840 | C | CYS | A | 108 | 84.576 | 67.314 | 29.811 | 1.00 | 27.92 | A |
| ATOM | 841 | O | CYS | A | 108 | 84.319 | 68.330 | 29.156 | 1.00 | 25.68 | A |
| ATOM | 842 | CB | CYS | A | 108 | 86.043 | 65.787 | 28.446 | 1.00 | 27.49 | A |
| ATOM | 843 | SG | CYS | A | 108 | 87.690 | 65.037 | 28.227 | 1.00 | 28.60 | A |
| ATOM | 844 | N | GLY | A | 109 | 83.684 | 66.748 | 30.613 | 1.00 | 29.41 | A |
| ATOM | 845 | CA | GLY | A | 109 | 82.370 | 67.355 | 30.765 | 1.00 | 21.87 | A |
| ATOM | 846 | C | GLY | A | 109 | 82.542 | 68.681 | 31.483 | 1.00 | 26.48 | A |
| ATOM | 847 | O | GLY | A | 109 | 81.879 | 69.660 | 31.155 | 1.00 | 24.15 | A |
| ATOM | 848 | N | ALA | A | 110 | 83.475 | 68.737 | 32.440 | 1.00 | 19.49 | A |
| ATOM | 849 | CA | ALA | A | 110 | 83.684 | 69.970 | 33.184 | 1.00 | 17.06 | A |
| ATOM | 850 | CB | ALA | A | 110 | 84.578 | 69.736 | 34.402 | 1.00 | 18.01 | A |
| ATOM | 851 | C | ALA | A | 110 | 84.318 | 70.995 | 32.258 | 1.00 | 18.22 | A |
| ATOM | 852 | O | ALA | A | 110 | 83.970 | 72.180 | 32.307 | 1.00 | 19.57 | A |
| ATOM | 853 | N | VAL | A | 111 | 85.268 | 70.552 | 31.450 | 1.00 | 21.00 | A |
| ATOM | 854 | CA | VAL | A | 111 | 85.947 | 71.421 | 30.492 | 1.00 | 19.95 | A |

TABLE 2-continued

| | | | | | | | | | | | |
|---|---|---|---|---|---|---|---|---|---|---|---|
| ATOM | 855 | CB | VAL | A | 111 | 87.013 | 70.609 | 29.645 | 1.00 | 26.47 | A |
| ATOM | 856 | CG1 | VAL | A | 111 | 87.331 | 71.346 | 28.314 | 1.00 | 19.61 | A |
| ATOM | 857 | CG2 | VAL | A | 111 | 88.307 | 70.414 | 30.463 | 1.00 | 20.68 | A |
| ATOM | 858 | C | VAL | A | 111 | 84.883 | 72.006 | 29.549 | 1.00 | 25.73 | A |
| ATOM | 859 | O | VAL | A | 111 | 84.835 | 73.210 | 29.305 | 1.00 | 24.22 | A |
| ATOM | 860 | N | LYS | A | 112 | 84.016 | 71.143 | 29.034 | 1.00 | 24.78 | A |
| ATOM | 861 | CA | LYS | A | 112 | 82.996 | 71.589 | 28.096 | 1.00 | 29.18 | A |
| ATOM | 862 | CB | LYS | A | 112 | 82.162 | 70.391 | 27.599 | 1.00 | 29.48 | A |
| ATOM | 863 | CG | LYS | A | 112 | 81.141 | 70.772 | 26.507 | 1.00 | 35.04 | A |
| ATOM | 864 | CD | LYS | A | 112 | 80.441 | 69.565 | 25.878 | 1.00 | 35.71 | A |
| ATOM | 865 | CE | LYS | A | 112 | 81.420 | 68.677 | 25.104 | 1.00 | 41.21 | A |
| ATOM | 866 | NZ | LYS | A | 112 | 80.780 | 67.431 | 24.529 | 1.00 | 43.02 | A |
| ATOM | 867 | C | LYS | A | 112 | 82.088 | 72.660 | 28.688 | 1.00 | 24.46 | A |
| ATOM | 868 | O | LYS | A | 112 | 81.776 | 73.643 | 28.024 | 1.00 | 26.79 | A |
| ATOM | 869 | N | TRP | A | 113 | 81.672 | 72.470 | 29.939 | 1.00 | 23.58 | A |
| ATOM | 870 | CA | TRP | A | 113 | 80.810 | 73.415 | 30.626 | 1.00 | 20.72 | A |
| ATOM | 871 | CB | TRP | A | 113 | 80.459 | 72.878 | 32.014 | 1.00 | 25.99 | A |
| ATOM | 872 | CG | TRP | A | 113 | 79.627 | 73.817 | 32.856 | 1.00 | 22.08 | A |
| ATOM | 873 | CD2 | TRP | A | 113 | 80.101 | 74.659 | 33.909 | 1.00 | 24.19 | A |
| ATOM | 874 | CE2 | TRP | A | 113 | 78.961 | 75.282 | 34.494 | 1.00 | 24.99 | A |
| ATOM | 875 | CE3 | TRP | A | 113 | 81.379 | 74.945 | 34.426 | 1.00 | 19.23 | A |
| ATOM | 876 | CD1 | TRP | A | 113 | 78.251 | 73.971 | 32.828 | 1.00 | 19.34 | A |
| ATOM | 877 | NE1 | TRP | A | 113 | 77.856 | 74.845 | 33.820 | 1.00 | 20.42 | A |
| ATOM | 878 | CZ2 | TRP | A | 113 | 79.060 | 76.153 | 35.557 | 1.00 | 22.43 | A |
| ATOM | 879 | CZ3 | TRP | A | 113 | 81.484 | 75.808 | 35.491 | 1.00 | 26.60 | A |
| ATOM | 880 | CH2 | TRP | A | 113 | 80.324 | 76.408 | 36.056 | 1.00 | 30.42 | A |
| ATOM | 881 | C | TRP | A | 113 | 81.475 | 74.775 | 30.793 | 1.00 | 23.72 | A |
| ATOM | 882 | O | TRP | A | 113 | 80.848 | 75.815 | 30.600 | 1.00 | 21.74 | A |
| ATOM | 883 | N | LEU | A | 114 | 82.750 | 74.756 | 31.182 | 1.00 | 23.73 | A |
| ATOM | 884 | CA | LEU | A | 114 | 83.508 | 75.976 | 31.396 | 1.00 | 19.99 | A |
| ATOM | 885 | CB | LEU | A | 114 | 84.971 | 75.624 | 31.687 | 1.00 | 16.92 | A |
| ATOM | 886 | CG | LEU | A | 114 | 85.231 | 75.166 | 33.138 | 1.00 | 17.13 | A |
| ATOM | 887 | CD1 | LEU | A | 114 | 86.620 | 74.621 | 33.322 | 1.00 | 14.89 | A |
| ATOM | 888 | CD2 | LEU | A | 114 | 85.050 | 76.365 | 34.046 | 1.00 | 17.43 | A |
| ATOM | 889 | C | LEU | A | 114 | 83.413 | 76.839 | 30.143 | 1.00 | 24.77 | A |
| ATOM | 890 | O | LEU | A | 114 | 83.101 | 78.042 | 30.204 | 1.00 | 20.50 | A |
| ATOM | 891 | N | ILE | A | 115 | 83.676 | 76.197 | 29.008 | 1.00 | 23.02 | A |
| ATOM | 892 | CA | ILE | A | 115 | 83.670 | 76.848 | 27.702 | 1.00 | 26.10 | A |
| ATOM | 893 | CB | ILE | A | 115 | 84.191 | 75.920 | 26.552 | 1.00 | 24.85 | A |
| ATOM | 894 | CG2 | ILE | A | 115 | 84.215 | 76.694 | 25.249 | 1.00 | 27.04 | A |
| ATOM | 895 | CG1 | ILE | A | 115 | 85.585 | 75.368 | 26.851 | 1.00 | 32.98 | A |
| ATOM | 896 | CD1 | ILE | A | 115 | 86.479 | 76.372 | 27.492 | 1.00 | 52.20 | A |
| ATOM | 897 | C | ILE | A | 115 | 82.287 | 77.278 | 27.240 | 1.00 | 23.55 | A |
| ATOM | 898 | O | ILE | A | 115 | 82.087 | 78.433 | 26.884 | 1.00 | 21.22 | A |
| ATOM | 899 | N | LEU | A | 116 | 81.356 | 76.330 | 27.222 | 1.00 | 15.47 | A |
| ATOM | 900 | CA | LEU | A | 116 | 80.009 | 76.584 | 26.722 | 1.00 | 23.51 | A |
| ATOM | 901 | CB | LEU | A | 116 | 79.298 | 75.260 | 26.459 | 1.00 | 23.69 | A |
| ATOM | 902 | CG | LEU | A | 116 | 79.986 | 74.298 | 25.494 | 1.00 | 29.79 | A |
| ATOM | 903 | CD1 | LEU | A | 116 | 78.985 | 73.211 | 25.148 | 1.00 | 24.68 | A |
| ATOM | 904 | CD2 | LEU | A | 116 | 80.479 | 75.022 | 24.250 | 1.00 | 26.74 | A |
| ATOM | 905 | C | LEU | A | 116 | 79.126 | 77.454 | 27.598 | 1.00 | 22.96 | A |
| ATOM | 906 | O | LEU | A | 116 | 78.214 | 78.095 | 27.100 | 1.00 | 23.54 | A |
| ATOM | 907 | N | GLU | A | 117 | 79.386 | 77.479 | 28.902 | 1.00 | 26.63 | A |
| ATOM | 908 | CA | GLU | A | 117 | 78.567 | 78.272 | 29.813 | 1.00 | 24.27 | A |
| ATOM | 909 | CB | GLU | A | 117 | 78.033 | 77.403 | 30.936 | 1.00 | 21.64 | A |
| ATOM | 910 | CG | GLU | A | 117 | 77.035 | 76.355 | 30.526 | 1.00 | 27.37 | A |
| ATOM | 911 | CD | GLU | A | 117 | 75.767 | 76.959 | 29.969 | 1.00 | 26.27 | A |
| ATOM | 912 | OE1 | GLU | A | 117 | 75.449 | 78.124 | 30.316 | 1.00 | 25.92 | A |
| ATOM | 913 | OE2 | GLU | A | 117 | 75.090 | 76.260 | 29.191 | 1.00 | 30.37 | A |
| ATOM | 914 | C | GLU | A | 117 | 79.257 | 79.457 | 30.470 | 1.00 | 24.39 | A |
| ATOM | 915 | O | GLU | A | 117 | 78.611 | 80.460 | 30.753 | 1.00 | 25.44 | A |
| ATOM | 916 | N | LYS | A | 118 | 80.561 | 79.373 | 30.706 | 1.00 | 18.78 | A |
| ATOM | 917 | CA | LYS | A | 118 | 81.189 | 80.460 | 31.440 | 1.00 | 19.49 | A |
| ATOM | 918 | CB | LYS | A | 118 | 81.782 | 79.887 | 32.748 | 1.00 | 25.65 | A |
| ATOM | 919 | CG | LYS | A | 118 | 80.761 | 79.090 | 33.606 | 1.00 | 17.16 | A |
| ATOM | 920 | CD | LYS | A | 118 | 79.665 | 80.070 | 34.058 | 1.00 | 21.32 | A |
| ATOM | 921 | CE | LYS | A | 118 | 78.463 | 79.410 | 34.663 | 1.00 | 23.09 | A |
| ATOM | 922 | NZ | LYS | A | 118 | 77.522 | 80.476 | 35.101 | 1.00 | 23.88 | A |
| ATOM | 923 | C | LYS | A | 118 | 82.213 | 81.332 | 30.744 | 1.00 | 22.37 | A |
| ATOM | 924 | O | LYS | A | 118 | 82.898 | 82.122 | 31.400 | 1.00 | 20.49 | A |
| ATOM | 925 | N | GLN | A | 119 | 82.360 | 81.202 | 29.431 | 1.00 | 20.57 | A |
| ATOM | 926 | CA | GLN | A | 119 | 83.332 | 82.060 | 28.748 | 1.00 | 32.06 | A |
| ATOM | 927 | CB | GLN | A | 119 | 84.242 | 81.238 | 27.801 | 1.00 | 20.00 | A |
| ATOM | 928 | CG | GLN | A | 119 | 85.382 | 82.091 | 27.173 | 1.00 | 20.89 | A |
| ATOM | 929 | CD | GLN | A | 119 | 86.339 | 81.257 | 26.337 | 1.00 | 23.85 | A |
| ATOM | 930 | OE1 | GLN | A | 119 | 85.940 | 80.270 | 25.734 | 1.00 | 18.93 | A |
| ATOM | 931 | NE2 | GLN | A | 119 | 87.602 | 81.661 | 26.285 | 1.00 | 15.38 | A |
| ATOM | 932 | C | GLN | A | 119 | 82.543 | 83.095 | 27.929 | 1.00 | 24.21 | A |
| ATOM | 933 | O | GLN | A | 119 | 81.649 | 82.725 | 27.195 | 1.00 | 21.97 | A |

TABLE 2-continued

| ATOM | 934 | N | LYS | A | 120 | 82.880 | 84.367 | 28.048 | 1.00 | 28.47 | A |
|---|---|---|---|---|---|---|---|---|---|---|---|
| ATOM | 935 | CA | LYS | A | 120 | 82.193 | 85.403 | 27.288 | 1.00 | 33.91 | A |
| ATOM | 936 | CB | LYS | A | 120 | 82.448 | 86.774 | 27.918 | 1.00 | 29.00 | A |
| ATOM | 937 | CG | LYS | A | 120 | 81.948 | 86.897 | 29.337 | 1.00 | 38.95 | A |
| ATOM | 938 | CD | LYS | A | 120 | 82.173 | 88.303 | 29.892 | 1.00 | 47.54 | A |
| ATOM | 939 | CE | LYS | A | 120 | 81.955 | 88.332 | 31.396 | 1.00 | 56.75 | A |
| ATOM | 940 | NZ | LYS | A | 120 | 80.623 | 87.776 | 31.790 | 1.00 | 65.69 | A |
| ATOM | 941 | C | LYS | A | 120 | 82.673 | 85.434 | 25.818 | 1.00 | 36.89 | A |
| ATOM | 942 | O | LYS | A | 120 | 83.700 | 84.864 | 25.460 | 1.00 | 30.22 | A |
| ATOM | 943 | N | PRO | A | 121 | 81.926 | 86.120 | 24.949 | 1.00 | 37.55 | A |
| ATOM | 944 | CD | PRO | A | 121 | 80.622 | 86.771 | 25.165 | 1.00 | 41.75 | A |
| ATOM | 945 | CA | PRO | A | 121 | 82.327 | 86.197 | 23.548 | 1.00 | 31.55 | A |
| ATOM | 946 | CB | PRO | A | 121 | 81.271 | 87.114 | 22.940 | 1.00 | 39.82 | A |
| ATOM | 947 | CG | PRO | A | 121 | 80.041 | 86.762 | 23.756 | 1.00 | 44.17 | A |
| ATOM | 948 | C | PRO | A | 121 | 83.724 | 86.780 | 23.443 | 1.00 | 31.58 | A |
| ATOM | 949 | O | PRO | A | 121 | 84.489 | 86.388 | 22.568 | 1.00 | 29.41 | A |
| ATOM | 950 | N | ASP | A | 122 | 84.076 | 87.693 | 24.342 | 1.00 | 27.25 | A |
| ATOM | 951 | CA | ASP | A | 122 | 85.401 | 88.285 | 24.268 | 1.00 | 29.04 | A |
| ATOM | 952 | CB | ASP | A | 122 | 85.435 | 89.636 | 24.985 | 1.00 | 28.38 | A |
| ATOM | 953 | CG | ASP | A | 122 | 85.281 | 89.525 | 26.494 | 1.00 | 38.36 | A |
| ATOM | 954 | OD1 | ASP | A | 122 | 84.964 | 88.438 | 27.033 | 1.00 | 39.09 | A |
| ATOM | 955 | OD2 | ASP | A | 122 | 85.477 | 90.558 | 27.156 | 1.00 | 38.98 | A |
| ATOM | 956 | C | ASP | A | 122 | 86.531 | 87.363 | 24.783 | 1.00 | 32.13 | A |
| ATOM | 957 | O | ASP | A | 122 | 87.693 | 87.759 | 24.780 | 1.00 | 26.62 | A |
| ATOM | 958 | N | GLY | A | 123 | 86.186 | 86.145 | 25.214 | 1.00 | 30.31 | A |
| ATOM | 959 | CA | GLY | A | 123 | 87.203 | 85.196 | 25.678 | 1.00 | 30.38 | A |
| ATOM | 960 | C | GLY | A | 123 | 87.422 | 85.098 | 27.188 | 1.00 | 30.19 | A |
| ATOM | 961 | O | GLY | A | 123 | 88.039 | 84.144 | 27.654 | 1.00 | 29.94 | A |
| ATOM | 962 | N | VAL | A | 124 | 86.930 | 86.077 | 27.940 | 1.00 | 24.05 | A |
| ATOM | 963 | CA | VAL | A | 124 | 87.055 | 86.116 | 29.403 | 1.00 | 23.87 | A |
| ATOM | 964 | CB | VAL | A | 124 | 86.546 | 87.473 | 29.951 | 1.00 | 23.70 | A |
| ATOM | 965 | CG1 | VAL | A | 124 | 86.353 | 87.413 | 31.459 | 1.00 | 27.05 | A |
| ATOM | 966 | CG2 | VAL | A | 124 | 87.522 | 88.581 | 29.581 | 1.00 | 24.79 | A |
| ATOM | 967 | C | VAL | A | 124 | 86.240 | 85.041 | 30.106 | 1.00 | 29.58 | A |
| ATOM | 968 | O | VAL | A | 124 | 85.071 | 84.813 | 29.733 | 1.00 | 26.81 | A |
| ATOM | 969 | N | PHE | A | 125 | 86.824 | 84.383 | 31.126 | 1.00 | 24.92 | A |
| ATOM | 970 | CA | PHE | A | 125 | 86.040 | 83.394 | 31.891 | 1.00 | 25.88 | A |
| ATOM | 971 | CB | PHE | A | 125 | 86.893 | 82.228 | 32.352 | 1.00 | 24.21 | A |
| ATOM | 972 | CG | PHE | A | 125 | 87.069 | 81.189 | 31.312 | 1.00 | 25.00 | A |
| ATOM | 973 | CD1 | PHE | A | 125 | 86.059 | 80.277 | 31.059 | 1.00 | 23.52 | A |
| ATOM | 974 | CD2 | PHE | A | 125 | 88.224 | 81.146 | 30.534 | 1.00 | 22.60 | A |
| ATOM | 975 | CE1 | PHE | A | 125 | 86.186 | 79.345 | 30.063 | 1.00 | 23.68 | A |
| ATOM | 976 | CE2 | PHE | A | 125 | 88.354 | 80.202 | 29.517 | 1.00 | 16.73 | A |
| ATOM | 977 | CZ | PHE | A | 125 | 87.338 | 79.306 | 29.282 | 1.00 | 20.14 | A |
| ATOM | 978 | C | PHE | A | 125 | 85.479 | 84.135 | 33.090 | 1.00 | 24.56 | A |
| ATOM | 979 | O | PHE | A | 125 | 86.175 | 84.941 | 33.710 | 1.00 | 21.73 | A |
| ATOM | 980 | N | GLN | A | 126 | 84.214 | 83.866 | 33.414 | 1.00 | 21.30 | A |
| ATOM | 981 | CA | GLN | A | 126 | 83.558 | 84.549 | 34.530 | 1.00 | 22.03 | A |
| ATOM | 982 | CB | GLN | A | 126 | 82.348 | 85.333 | 34.003 | 1.00 | 33.53 | A |
| ATOM | 983 | CG | GLN | A | 126 | 81.694 | 86.233 | 35.019 | 1.00 | 46.06 | A |
| ATOM | 984 | CD | GLN | A | 126 | 80.588 | 87.096 | 34.409 | 1.00 | 54.63 | A |
| ATOM | 985 | OE1 | GLN | A | 126 | 79.474 | 86.612 | 34.131 | 1.00 | 56.00 | A |
| ATOM | 986 | NE2 | GLN | A | 126 | 80.897 | 88.383 | 34.188 | 1.00 | 55.55 | A |
| ATOM | 987 | C | GLN | A | 126 | 83.085 | 83.607 | 35.634 | 1.00 | 18.80 | A |
| ATOM | 988 | O | GLN | A | 126 | 82.611 | 82.489 | 35.360 | 1.00 | 18.84 | A |
| ATOM | 989 | N | GLU | A | 127 | 83.202 | 84.068 | 36.871 | 1.00 | 19.63 | A |
| ATOM | 990 | CA | GLU | A | 127 | 82.770 | 83.301 | 38.050 | 1.00 | 18.00 | A |
| ATOM | 991 | CB | GLU | A | 127 | 83.708 | 83.576 | 39.232 | 1.00 | 17.47 | A |
| ATOM | 992 | CG | GLU | A | 127 | 83.190 | 82.969 | 40.556 | 1.00 | 21.51 | A |
| ATOM | 993 | CD | GLU | A | 127 | 83.051 | 81.442 | 40.446 | 1.00 | 23.16 | A |
| ATOM | 994 | OE1 | GLU | A | 127 | 82.025 | 80.930 | 39.942 | 1.00 | 17.83 | A |
| ATOM | 995 | OE2 | GLU | A | 127 | 84.008 | 80.754 | 40.848 | 1.00 | 21.73 | A |
| ATOM | 996 | C | GLU | A | 127 | 81.374 | 83.823 | 38.419 | 1.00 | 26.19 | A |
| ATOM | 997 | O | GLU | A | 127 | 81.232 | 85.016 | 38.663 | 1.00 | 21.32 | A |
| ATOM | 998 | N | ASP | A | 128 | 80.339 | 82.981 | 38.438 | 1.00 | 24.79 | A |
| ATOM | 999 | CA | ASP | A | 128 | 79.015 | 83.486 | 38.837 | 1.00 | 23.86 | A |
| ATOM | 1000 | CB | ASP | A | 128 | 77.909 | 83.020 | 37.876 | 1.00 | 28.03 | A |
| ATOM | 1001 | CG | ASP | A | 128 | 77.970 | 83.709 | 36.523 | 1.00 | 31.99 | A |
| ATOM | 1002 | OD1 | ASP | A | 128 | 78.166 | 84.944 | 36.495 | 1.00 | 35.60 | A |
| ATOM | 1003 | OD2 | ASP | A | 128 | 77.807 | 83.018 | 35.492 | 1.00 | 29.56 | A |
| ATOM | 1004 | C | ASP | A | 128 | 78.659 | 83.006 | 40.253 | 1.00 | 22.48 | A |
| ATOM | 1005 | O | ASP | A | 128 | 77.629 | 83.368 | 40.796 | 1.00 | 23.11 | A |
| ATOM | 1006 | N | ALA | A | 129 | 79.498 | 82.172 | 40.849 | 1.00 | 20.40 | A |
| ATOM | 1007 | CA | ALA | A | 129 | 79.215 | 81.676 | 42.210 | 1.00 | 25.25 | A |
| ATOM | 1008 | CB | ALA | A | 129 | 78.336 | 80.383 | 42.153 | 1.00 | 24.60 | A |
| ATOM | 1009 | C | ALA | A | 129 | 80.531 | 81.385 | 42.926 | 1.00 | 21.47 | A |
| ATOM | 1010 | O | ALA | A | 129 | 81.012 | 80.267 | 42.901 | 1.00 | 20.12 | A |
| ATOM | 1011 | N | PRO | A | 130 | 81.142 | 82.412 | 43.535 | 1.00 | 22.93 | A |
| ATOM | 1012 | CD | PRO | A | 130 | 80.707 | 83.830 | 43.484 | 1.00 | 18.89 | A |

TABLE 2-continued

| | | | | | | | | | | |
|---|---|---|---|---|---|---|---|---|---|---|
| ATOM | 1013 | CA | PRO | A | 130 | 82.406 | 82.269 | 44.248 | 1.00 | 20.89 | A |
| ATOM | 1014 | CB | PRO | A | 130 | 82.610 | 83.637 | 44.868 | 1.00 | 24.77 | A |
| ATOM | 1015 | CG | PRO | A | 130 | 81.951 | 84.575 | 43.823 | 1.00 | 29.40 | A |
| ATOM | 1016 | C | PRO | A | 130 | 82.417 | 81.168 | 45.314 | 1.00 | 25.72 | A |
| ATOM | 1017 | O | PRO | A | 130 | 81.421 | 80.932 | 46.010 | 1.00 | 20.76 | A |
| ATOM | 1018 | N | VAL | A | 131 | 83.557 | 80.497 | 45.431 | 1.00 | 18.66 | A |
| ATOM | 1019 | CA | VAL | A | 131 | 83.709 | 79.442 | 46.421 | 1.00 | 25.11 | A |
| ATOM | 1020 | CB | VAL | A | 131 | 85.057 | 78.722 | 46.307 | 1.00 | 15.74 | A |
| ATOM | 1021 | CG1 | VAL | A | 131 | 85.116 | 77.946 | 44.960 | 1.00 | 15.94 | A |
| ATOM | 1022 | CG2 | VAL | A | 131 | 86.188 | 79.725 | 46.459 | 1.00 | 19.54 | A |
| ATOM | 1023 | C | VAL | A | 131 | 83.618 | 80.030 | 47.806 | 1.00 | 19.19 | A |
| ATOM | 1024 | O | VAL | A | 131 | 83.848 | 81.225 | 48.014 | 1.00 | 21.17 | A |
| ATOM | 1025 | N | ILE | A | 132 | 83.251 | 79.169 | 48.747 | 1.00 | 18.82 | A |
| ATOM | 1026 | CA | ILE | A | 132 | 83.149 | 79.556 | 50.154 | 1.00 | 23.91 | A |
| ATOM | 1027 | CB | ILE | A | 132 | 82.332 | 78.512 | 50.929 | 1.00 | 24.37 | A |
| ATOM | 1028 | CG2 | ILE | A | 132 | 82.271 | 78.876 | 52.417 | 1.00 | 20.00 | A |
| ATOM | 1029 | CG1 | ILE | A | 132 | 80.941 | 78.425 | 50.306 | 1.00 | 21.42 | A |
| ATOM | 1030 | CD1 | ILE | A | 132 | 80.142 | 77.180 | 50.747 | 1.00 | 24.98 | A |
| ATOM | 1031 | C | ILE | A | 132 | 84.541 | 79.688 | 50.790 | 1.00 | 19.79 | A |
| ATOM | 1032 | O | ILE | A | 132 | 84.781 | 80.623 | 51.520 | 1.00 | 17.40 | A |
| ATOM | 1033 | N | HIS | A | 133 | 85.467 | 78.766 | 50.504 | 1.00 | 18.82 | A |
| ATOM | 1034 | CA | HIS | A | 133 | 86.827 | 78.851 | 51.100 | 1.00 | 17.96 | A |
| ATOM | 1035 | CB | HIS | A | 133 | 87.434 | 77.437 | 51.218 | 1.00 | 18.01 | A |
| ATOM | 1036 | CG | HIS | A | 133 | 86.691 | 76.548 | 52.180 | 1.00 | 22.75 | A |
| ATOM | 1037 | CD2 | HIS | A | 133 | 85.617 | 75.738 | 51.996 | 1.00 | 18.28 | A |
| ATOM | 1038 | ND1 | HIS | A | 133 | 86.992 | 76.499 | 53.531 | 1.00 | 25.58 | A |
| ATOM | 1039 | CE1 | HIS | A | 133 | 86.128 | 75.693 | 54.137 | 1.00 | 21.42 | A |
| ATOM | 1040 | NE2 | HIS | A | 133 | 85.289 | 75.222 | 53.231 | 1.00 | 27.04 | A |
| ATOM | 1041 | C | HIS | A | 133 | 87.711 | 79.735 | 50.221 | 1.00 | 14.42 | A |
| ATOM | 1042 | O | HIS | A | 133 | 88.525 | 79.250 | 49.431 | 1.00 | 17.65 | A |
| ATOM | 1043 | N | GLN | A | 134 | 87.517 | 81.039 | 50.373 | 1.00 | 11.52 | A |
| ATOM | 1044 | CA | GLN | A | 134 | 88.238 | 82.045 | 49.608 | 1.00 | 21.65 | A |
| ATOM | 1045 | CB | GLN | A | 134 | 87.689 | 83.424 | 50.025 | 1.00 | 17.09 | A |
| ATOM | 1046 | CG | GLN | A | 134 | 86.298 | 83.729 | 49.418 | 1.00 | 22.43 | A |
| ATOM | 1047 | CD | GLN | A | 134 | 86.376 | 84.059 | 47.908 | 1.00 | 21.78 | A |
| ATOM | 1048 | OE1 | GLN | A | 134 | 87.129 | 84.944 | 47.522 | 1.00 | 28.45 | A |
| ATOM | 1049 | NE2 | GLN | A | 134 | 85.604 | 83.340 | 47.061 | 1.00 | 22.37 | A |
| ATOM | 1050 | C | GLN | A | 134 | 89.759 | 81.873 | 49.837 | 1.00 | 20.34 | A |
| ATOM | 1051 | O | GLN | A | 134 | 90.565 | 82.314 | 49.052 | 1.00 | 26.33 | A |
| ATOM | 1052 | N | GLU | A | 135 | 90.079 | 81.179 | 50.928 | 1.00 | 19.09 | A |
| ATOM | 1053 | CA | GLU | A | 135 | 91.407 | 80.777 | 51.431 | 1.00 | 24.48 | A |
| ATOM | 1054 | CB | GLU | A | 135 | 91.169 | 79.850 | 52.767 | 1.00 | 24.93 | A |
| ATOM | 1055 | CG | GLU | A | 135 | 89.522 | 79.250 | 53.099 | 1.00 | 4.96 | A |
| ATOM | 1056 | CD | GLU | A | 135 | 89.446 | 77.808 | 53.925 | 1.00 | 27.66 | A |
| ATOM | 1057 | OE1 | GLU | A | 135 | 90.527 | 77.338 | 53.831 | 1.00 | 37.42 | A |
| ATOM | 1058 | OE2 | GLU | A | 135 | 88.528 | 77.190 | 54.620 | 1.00 | 1.00 | A |
| ATOM | 1059 | C | GLU | A | 135 | 92.140 | 79.938 | 50.318 | 1.00 | 20.82 | A |
| ATOM | 1060 | O | GLU | A | 135 | 93.362 | 80.014 | 50.119 | 1.00 | 15.84 | A |
| ATOM | 1061 | N | MET | A | 136 | 91.377 | 79.109 | 49.602 | 1.00 | 18.40 | A |
| ATOM | 1062 | CA | MET | A | 136 | 91.967 | 78.147 | 48.626 | 1.00 | 17.42 | A |
| ATOM | 1063 | CB | MET | A | 136 | 91.123 | 76.853 | 48.571 | 1.00 | 15.67 | A |
| ATOM | 1064 | CG | MET | A | 136 | 89.868 | 76.961 | 47.675 | 1.00 | 17.99 | A |
| ATOM | 1065 | SD | MET | A | 136 | 88.703 | 75.563 | 47.631 | 1.00 | 29.44 | A |
| ATOM | 1066 | CE | MET | A | 136 | 89.744 | 74.260 | 47.009 | 1.00 | 11.97 | A |
| ATOM | 1067 | C | MET | A | 136 | 92.269 | 78.546 | 47.203 | 1.00 | 15.51 | A |
| ATOM | 1068 | O | MET | A | 136 | 92.791 | 77.747 | 46.443 | 1.00 | 14.46 | A |
| ATOM | 1069 | N | ILE | A | 137 | 91.988 | 79.787 | 46.831 | 1.00 | 16.94 | A |
| ATOM | 1070 | CA | ILE | A | 137 | 92.217 | 80.213 | 45.449 | 1.00 | 15.24 | A |
| ATOM | 1071 | CB | ILE | A | 137 | 90.980 | 80.959 | 44.955 | 1.00 | 20.19 | A |
| ATOM | 1072 | CG2 | ILE | A | 137 | 89.724 | 80.121 | 45.254 | 1.00 | 14.68 | A |
| ATOM | 1073 | CG1 | ILE | A | 137 | 90.847 | 82.300 | 45.723 | 1.00 | 11.83 | A |
| ATOM | 1074 | CD1 | ILE | A | 137 | 89.473 | 82.985 | 45.435 | 1.00 | 23.22 | A |
| ATOM | 1075 | C | ILE | A | 137 | 93.446 | 81.121 | 45.287 | 1.00 | 19.40 | A |
| ATOM | 1076 | O | ILE | A | 137 | 93.658 | 81.729 | 44.228 | 1.00 | 18.10 | A |
| ATOM | 1077 | N | GLY | A | 138 | 94.222 | 81.215 | 46.361 | 1.00 | 15.44 | A |
| ATOM | 1078 | CA | GLY | A | 138 | 95.438 | 82.007 | 46.314 | 1.00 | 18.65 | A |
| ATOM | 1079 | C | GLY | A | 138 | 95.197 | 83.450 | 45.897 | 1.00 | 23.13 | A |
| ATOM | 1080 | O | GLY | A | 138 | 94.182 | 84.061 | 46.313 | 1.00 | 15.00 | A |
| ATOM | 1081 | N | GLY | A | 139 | 96.097 | 83.962 | 45.044 | 1.00 | 20.15 | A |
| ATOM | 1082 | CA | GLY | A | 139 | 96.054 | 85.338 | 44.585 | 1.00 | 17.13 | A |
| ATOM | 1083 | C | GLY | A | 139 | 94.767 | 85.808 | 43.967 | 1.00 | 29.17 | A |
| ATOM | 1084 | O | GLY | A | 139 | 94.568 | 87.013 | 43.807 | 1.00 | 33.25 | A |
| ATOM | 1085 | N | LEU | A | 140 | 93.875 | 84.890 | 43.618 | 1.00 | 23.37 | A |
| ATOM | 1086 | CA | LEU | A | 140 | 92.621 | 85.317 | 43.023 | 1.00 | 24.08 | A |
| ATOM | 1087 | CB | LEU | A | 140 | 91.930 | 84.142 | 42.322 | 1.00 | 22.29 | A |
| ATOM | 1088 | CG | LEU | A | 140 | 92.000 | 84.065 | 40.800 | 1.00 | 36.28 | A |
| ATOM | 1089 | CD1 | LEU | A | 140 | 93.365 | 84.425 | 40.297 | 1.00 | 39.55 | A |
| ATOM | 1090 | CD2 | LEU | A | 140 | 91.640 | 82.663 | 40.376 | 1.00 | 31.19 | A |
| ATOM | 1091 | C | LEU | A | 140 | 91.682 | 85.918 | 44.065 | 1.00 | 30.45 | A |

TABLE 2-continued

| | | | | | | | | | | |
|---|---|---|---|---|---|---|---|---|---|---|
| ATOM | 1092 | O | LEU | A | 140 | 90.698 | 86.572 | 43.697 | 1.00 | 29.82 | A |
| ATOM | 1093 | N | ARG | A | 141 | 91.977 | 85.715 | 45.353 | 1.00 | 23.95 | A |
| ATOM | 1094 | CA | ARG | A | 141 | 91.105 | 86.235 | 46.411 | 1.00 | 26.90 | A |
| ATOM | 1095 | CB | ARG | A | 141 | 91.577 | 85.782 | 47.790 | 1.00 | 23.51 | A |
| ATOM | 1096 | CG | ARG | A | 141 | 90.622 | 86.183 | 48.883 | 1.00 | 31.94 | A |
| ATOM | 1097 | CD | ARG | A | 141 | 91.045 | 85.655 | 50.222 | 1.00 | 41.48 | A |
| ATOM | 1098 | NE | ARG | A | 141 | 90.058 | 85.983 | 51.254 | 1.00 | 56.61 | A |
| ATOM | 1099 | CZ | ARG | A | 141 | 89.989 | 85.390 | 52.451 | 1.00 | 62.59 | A |
| ATOM | 1100 | NH1 | ARG | A | 141 | 90.853 | 84.427 | 52.773 | 1.00 | 61.70 | A |
| ATOM | 1101 | NH2 | ARG | A | 141 | 89.055 | 85.761 | 53.330 | 1.00 | 64.29 | A |
| ATOM | 1102 | C | ARG | A | 141 | 91.103 | 87.771 | 46.308 | 1.00 | 31.97 | A |
| ATOM | 1103 | O | ARG | A | 141 | 90.112 | 88.440 | 46.571 | 1.00 | 35.29 | A |
| ATOM | 1104 | N | ASN | A | 142 | 92.233 | 88.327 | 45.932 | 1.00 | 35.39 | A |
| ATOM | 1105 | CA | ASN | A | 142 | 92.292 | 89.759 | 45.708 | 1.00 | 47.29 | A |
| ATOM | 1106 | CB | ASN | A | 142 | 93.755 | 90.199 | 45.620 | 1.00 | 44.19 | A |
| ATOM | 1107 | CG | ASN | A | 142 | 93.903 | 91.672 | 45.316 | 1.00 | 50.84 | A |
| ATOM | 1108 | OD1 | ASN | A | 142 | 93.081 | 92.260 | 44.606 | 1.00 | 50.20 | A |
| ATOM | 1109 | ND2 | ASN | A | 142 | 94.968 | 92.273 | 45.829 | 1.00 | 52.23 | A |
| ATOM | 1110 | C | ASN | A | 142 | 91.588 | 89.889 | 44.342 | 1.00 | 43.41 | A |
| ATOM | 1111 | O | ASN | A | 142 | 92.160 | 89.542 | 43.302 | 1.00 | 41.71 | A |
| ATOM | 1112 | N | ASN | A | 143 | 90.343 | 90.361 | 44.363 | 1.00 | 49.05 | A |
| ATOM | 1113 | CA | ASN | A | 143 | 89.511 | 90.522 | 43.151 | 1.00 | 54.92 | A |
| ATOM | 1114 | CB | ASN | A | 143 | 88.071 | 90.941 | 43.523 | 1.00 | 58.67 | A |
| ATOM | 1115 | CG | ASN | A | 143 | 87.097 | 89.762 | 43.556 | 1.00 | 67.74 | A |
| ATOM | 1116 | OD1 | ASN | A | 143 | 87.173 | 88.843 | 42.721 | 1.00 | 72.16 | A |
| ATOM | 1117 | ND2 | ASN | A | 143 | 86.159 | 89.795 | 44.510 | 1.00 | 73.35 | A |
| ATOM | 1118 | C | ASN | A | 143 | 90.024 | 91.509 | 42.102 | 1.00 | 51.69 | A |
| ATOM | 1119 | O | ASN | A | 143 | 89.457 | 91.625 | 41.012 | 1.00 | 52.71 | A |
| ATOM | 1120 | N | ASN | A | 144 | 91.067 | 92.245 | 42.432 | 1.00 | 47.25 | A |
| ATOM | 1121 | CA | ASN | A | 144 | 91.597 | 93.191 | 41.479 | 1.00 | 47.83 | A |
| ATOM | 1122 | CB | ASN | A | 144 | 92.706 | 93.993 | 42.126 | 1.00 | 58.20 | A |
| ATOM | 1123 | CG | ASN | A | 144 | 92.406 | 95.451 | 42.142 | 1.00 | 67.49 | A |
| ATOM | 1124 | OD1 | ASN | A | 144 | 92.353 | 96.070 | 43.210 | 1.00 | 75.34 | A |
| ATOM | 1125 | ND2 | ASN | A | 144 | 92.194 | 96.027 | 40.954 | 1.00 | 70.42 | A |
| ATOM | 1126 | C | ASN | A | 144 | 92.157 | 92.456 | 40.274 | 1.00 | 42.44 | A |
| ATOM | 1127 | O | ASN | A | 144 | 92.967 | 91.540 | 40.432 | 1.00 | 43.00 | A |
| ATOM | 1128 | N | GLU | A | 145 | 91.740 | 92.866 | 39.081 | 1.00 | 35.72 | A |
| ATOM | 1129 | CA | GLU | A | 145 | 92.207 | 92.277 | 37.832 | 1.00 | 30.80 | A |
| ATOM | 1130 | CB | GLU | A | 145 | 93.751 | 92.269 | 37.777 | 1.00 | 29.82 | A |
| ATOM | 1131 | CG | GLU | A | 145 | 94.342 | 93.705 | 37.873 | 1.00 | 34.98 | A |
| ATOM | 1132 | CD | GLU | A | 145 | 95.866 | 93.839 | 37.711 | 1.00 | 33.90 | A |
| ATOM | 1133 | OE1 | GLU | A | 145 | 96.311 | 94.948 | 37.366 | 1.00 | 37.12 | A |
| ATOM | 1134 | OE2 | GLU | A | 145 | 96.641 | 92.890 | 37.938 | 1.00 | 36.12 | A |
| ATOM | 1135 | C | GLU | A | 145 | 91.639 | 90.883 | 37.705 | 1.00 | 32.53 | A |
| ATOM | 1136 | O | GLU | A | 145 | 92.261 | 89.979 | 37.134 | 1.00 | 29.47 | A |
| ATOM | 1137 | N | LYS | A | 146 | 90.410 | 90.715 | 38.179 | 1.00 | 33.08 | A |
| ATOM | 1138 | CA | LYS | A | 146 | 89.829 | 89.386 | 38.144 | 1.00 | 34.99 | A |
| ATOM | 1139 | CB | LYS | A | 146 | 88.545 | 89.324 | 38.969 | 1.00 | 38.84 | A |
| ATOM | 1140 | CG | LYS | A | 146 | 87.328 | 89.843 | 38.309 | 1.00 | 46.43 | A |
| ATOM | 1141 | CD | LYS | A | 146 | 86.173 | 89.733 | 39.312 | 1.00 | 53.97 | A |
| ATOM | 1142 | CE | LYS | A | 146 | 84.799 | 89.902 | 38.655 | 1.00 | 56.22 | A |
| ATOM | 1143 | NZ | LYS | A | 146 | 84.630 | 91.185 | 37.909 | 1.00 | 58.13 | A |
| ATOM | 1144 | C | LYS | A | 146 | 89.597 | 88.782 | 36.778 | 1.00 | 29.69 | A |
| ATOM | 1145 | O | LYS | A | 146 | 89.864 | 87.593 | 36.608 | 1.00 | 22.87 | A |
| ATOM | 1146 | N | ASP | A | 147 | 89.125 | 89.558 | 35.800 | 1.00 | 26.03 | A |
| ATOM | 1147 | CA | ASP | A | 147 | 88.883 | 88.989 | 34.459 | 1.00 | 24.17 | A |
| ATOM | 1148 | CB | ASP | A | 147 | 88.363 | 90.051 | 33.483 | 1.00 | 26.31 | A |
| ATOM | 1149 | CG | ASP | A | 147 | 86.884 | 90.374 | 33.687 | 1.00 | 33.37 | A |
| ATOM | 1150 | OD1 | ASP | A | 147 | 86.419 | 91.396 | 33.148 | 1.00 | 41.72 | A |
| ATOM | 1151 | OD2 | ASP | A | 147 | 86.160 | 89.619 | 34.369 | 1.00 | 28.33 | A |
| ATOM | 1152 | C | ASP | A | 147 | 90.175 | 88.402 | 33.894 | 1.00 | 29.67 | A |
| ATOM | 1153 | O | ASP | A | 147 | 90.177 | 87.328 | 33.291 | 1.00 | 30.44 | A |
| ATOM | 1154 | N | MET | A | 148 | 91.277 | 89.112 | 34.087 | 1.00 | 21.79 | A |
| ATOM | 1155 | CA | MET | A | 148 | 92.562 | 88.631 | 33.567 | 1.00 | 27.79 | A |
| ATOM | 1156 | CB | MET | A | 148 | 93.591 | 89.770 | 33.532 | 1.00 | 21.45 | A |
| ATOM | 1157 | CG | MET | A | 148 | 93.406 | 90.794 | 32.411 | 1.00 | 16.88 | A |
| ATOM | 1158 | SD | MET | A | 148 | 94.007 | 90.171 | 30.836 | 1.00 | 26.17 | A |
| ATOM | 1159 | CE | MET | A | 148 | 95.843 | 90.114 | 31.224 | 1.00 | 25.36 | A |
| ATOM | 1160 | C | MET | A | 148 | 93.097 | 87.466 | 34.431 | 1.00 | 23.06 | A |
| ATOM | 1161 | O | MET | A | 148 | 93.502 | 86.433 | 33.902 | 1.00 | 26.32 | A |
| ATOM | 1162 | N | ALA | A | 149 | 93.082 | 87.630 | 35.749 | 1.00 | 21.95 | A |
| ATOM | 1163 | CA | ALA | A | 149 | 93.577 | 86.584 | 36.637 | 1.00 | 26.30 | A |
| ATOM | 1164 | CB | ALA | A | 149 | 93.539 | 87.058 | 38.093 | 1.00 | 17.92 | A |
| ATOM | 1165 | C | ALA | A | 149 | 92.762 | 85.290 | 36.464 | 1.00 | 24.09 | A |
| ATOM | 1166 | O | ALA | A | 149 | 93.336 | 84.239 | 36.228 | 1.00 | 20.02 | A |
| ATOM | 1167 | N | LEU | A | 150 | 91.441 | 85.357 | 36.578 | 1.00 | 23.60 | A |
| ATOM | 1168 | CA | LEU | A | 150 | 90.615 | 84.157 | 36.396 | 1.00 | 21.51 | A |
| ATOM | 1169 | CB | LEU | A | 150 | 89.141 | 84.431 | 36.708 | 1.00 | 21.03 | A |
| ATOM | 1170 | CG | LEU | A | 150 | 88.167 | 83.219 | 36.546 | 1.00 | 31.38 | A |

TABLE 2-continued

| | | | | | | | | | | |
|---|---|---|---|---|---|---|---|---|---|---|
| ATOM | 1171 | CD1 | LEU | A | 150 | 88.557 | 82.048 | 37.474 | 1.00 | 23.78 | A |
| ATOM | 1172 | CD2 | LEU | A | 150 | 86.725 | 83.681 | 36.903 | 1.00 | 28.01 | A |
| ATOM | 1173 | C | LEU | A | 150 | 90.707 | 83.581 | 34.985 | 1.00 | 26.10 | A |
| ATOM | 1174 | O | LEU | A | 150 | 90.700 | 82.351 | 34.794 | 1.00 | 23.93 | A |
| ATOM | 1175 | N | THR | A | 151 | 90.777 | 84.442 | 33.978 | 1.00 | 21.82 | A |
| ATOM | 1176 | CA | THR | A | 151 | 90.895 | 83.927 | 32.622 | 1.00 | 16.71 | A |
| ATOM | 1177 | CB | THR | A | 151 | 90.817 | 85.079 | 31.570 | 1.00 | 24.41 | A |
| ATOM | 1178 | OG1 | THR | A | 151 | 89.512 | 85.680 | 31.646 | 1.00 | 24.76 | A |
| ATOM | 1179 | CG2 | THR | A | 151 | 91.004 | 84.529 | 30.144 | 1.00 | 24.82 | A |
| ATOM | 1180 | C | THR | A | 151 | 92.199 | 83.146 | 32.466 | 1.00 | 22.41 | A |
| ATOM | 1181 | O | THR | A | 151 | 92.214 | 82.096 | 31.853 | 1.00 | 22.92 | A |
| ATOM | 1182 | N | ALA | A | 152 | 93.283 | 83.633 | 33.055 | 1.00 | 26.27 | A |
| ATOM | 1183 | CA | ALA | A | 152 | 94.557 | 82.926 | 32.945 | 1.00 | 19.92 | A |
| ATOM | 1184 | CB | ALA | A | 152 | 95.654 | 83.757 | 33.543 | 1.00 | 15.47 | A |
| ATOM | 1185 | C | ALA | A | 152 | 94.459 | 81.578 | 33.671 | 1.00 | 19.39 | A |
| ATOM | 1186 | O | ALA | A | 152 | 94.882 | 80.567 | 33.133 | 1.00 | 19.38 | A |
| ATOM | 1187 | N | PHE | A | 153 | 93.884 | 81.603 | 34.877 | 1.00 | 17.38 | A |
| ATOM | 1188 | CA | PHE | A | 153 | 93.713 | 80.417 | 35.703 | 1.00 | 14.60 | A |
| ATOM | 1189 | CB | PHE | A | 153 | 92.970 | 80.716 | 37.004 | 1.00 | 17.50 | A |
| ATOM | 1190 | CG | PHE | A | 153 | 92.773 | 79.492 | 37.851 | 1.00 | 22.29 | A |
| ATOM | 1191 | CD1 | PHE | A | 153 | 93.813 | 79.005 | 38.652 | 1.00 | 10.97 | A |
| ATOM | 1192 | CD2 | PHE | A | 153 | 91.551 | 78.828 | 37.855 | 1.00 | 15.16 | A |
| ATOM | 1193 | CE1 | PHE | A | 153 | 93.623 | 77.853 | 39.448 | 1.00 | 20.47 | A |
| ATOM | 1194 | CE2 | PHE | A | 153 | 91.348 | 77.689 | 38.636 | 1.00 | 22.68 | A |
| ATOM | 1195 | CZ | PHE | A | 153 | 92.387 | 77.205 | 39.442 | 1.00 | 21.15 | A |
| ATOM | 1196 | C | PHE | A | 153 | 92.940 | 79.346 | 34.977 | 1.00 | 19.47 | A |
| ATOM | 1197 | O | PHE | A | 153 | 93.360 | 78.219 | 34.971 | 1.00 | 18.15 | A |
| ATOM | 1198 | N | VAL | A | 154 | 91.805 | 79.687 | 34.388 | 1.00 | 17.18 | A |
| ATOM | 1199 | CA | VAL | A | 154 | 91.016 | 78.686 | 33.682 | 1.00 | 14.37 | A |
| ATOM | 1200 | CB | VAL | A | 154 | 89.598 | 79.241 | 33.313 | 1.00 | 17.63 | A |
| ATOM | 1201 | CG1 | VAL | A | 154 | 88.830 | 78.188 | 32.527 | 1.00 | 14.29 | A |
| ATOM | 1202 | CG2 | VAL | A | 154 | 88.835 | 79.585 | 34.588 | 1.00 | 17.52 | A |
| ATOM | 1203 | C | VAL | A | 154 | 91.750 | 78.197 | 32.416 | 1.00 | 19.75 | A |
| ATOM | 1204 | O | VAL | A | 154 | 91.801 | 77.003 | 32.146 | 1.00 | 15.15 | A |
| ATOM | 1205 | N | LEU | A | 155 | 92.336 | 79.109 | 31.652 | 1.00 | 20.48 | A |
| ATOM | 1206 | CA | LEU | A | 155 | 93.093 | 78.710 | 30.457 | 1.00 | 22.98 | A |
| ATOM | 1207 | CB | LEU | A | 155 | 93.729 | 79.960 | 29.791 | 1.00 | 16.47 | A |
| ATOM | 1208 | CG | LEU | A | 155 | 94.688 | 79.745 | 28.623 | 1.00 | 19.59 | A |
| ATOM | 1209 | CD1 | LEU | A | 155 | 94.015 | 78.920 | 27.570 | 1.00 | 17.74 | A |
| ATOM | 1210 | CD2 | LEU | A | 155 | 95.164 | 81.108 | 28.034 | 1.00 | 22.48 | A |
| ATOM | 1211 | C | LEU | A | 155 | 94.200 | 77.680 | 30.800 | 1.00 | 16.38 | A |
| ATOM | 1212 | O | LEU | A | 155 | 94.391 | 76.711 | 30.079 | 1.00 | 21.06 | A |
| ATOM | 1213 | N | ILE | A | 156 | 94.926 | 77.903 | 31.897 | 1.00 | 17.56 | A |
| ATOM | 1214 | CA | ILE | A | 156 | 96.016 | 76.992 | 32.288 | 1.00 | 21.21 | A |
| ATOM | 1215 | CB | ILE | A | 156 | 96.769 | 77.543 | 33.538 | 1.00 | 23.70 | A |
| ATOM | 1216 | CG2 | ILE | A | 156 | 97.704 | 76.490 | 34.155 | 1.00 | 17.82 | A |
| ATOM | 1217 | CG1 | ILE | A | 156 | 97.584 | 78.768 | 33.108 | 1.00 | 20.22 | A |
| ATOM | 1218 | CD1 | ILE | A | 156 | 98.096 | 79.593 | 34.297 | 1.00 | 15.17 | A |
| ATOM | 1219 | C | ILE | A | 156 | 95.392 | 75.608 | 32.555 | 1.00 | 21.00 | A |
| ATOM | 1220 | O | ILE | A | 156 | 95.955 | 74.595 | 32.181 | 1.00 | 18.43 | A |
| ATOM | 1221 | N | SER | A | 157 | 94.222 | 75.577 | 33.187 | 1.00 | 14.32 | A |
| ATOM | 1222 | CA | SER | A | 157 | 93.525 | 74.316 | 33.425 | 1.00 | 22.61 | A |
| ATOM | 1223 | CB | SER | A | 157 | 92.244 | 74.564 | 34.218 | 1.00 | 23.22 | A |
| ATOM | 1224 | OG | SER | A | 157 | 92.563 | 74.830 | 35.582 | 1.00 | 30.07 | A |
| ATOM | 1225 | C | SER | A | 157 | 93.174 | 73.644 | 32.105 | 1.00 | 19.13 | A |
| ATOM | 1226 | O | SER | A | 157 | 93.405 | 72.445 | 31.924 | 1.00 | 23.24 | A |
| ATOM | 1227 | N | LEU | A | 158 | 92.640 | 74.416 | 31.163 | 1.00 | 23.19 | A |
| ATOM | 1228 | CA | LEU | A | 158 | 92.268 | 73.872 | 29.859 | 1.00 | 26.55 | A |
| ATOM | 1229 | CB | LEU | A | 158 | 91.607 | 74.955 | 28.970 | 1.00 | 23.19 | A |
| ATOM | 1230 | CG | LEU | A | 158 | 90.330 | 75.603 | 29.537 | 1.00 | 28.10 | A |
| ATOM | 1231 | CD1 | LEU | A | 158 | 89.618 | 76.320 | 28.444 | 1.00 | 30.58 | A |
| ATOM | 1232 | CD2 | LEU | A | 158 | 89.378 | 74.573 | 30.117 | 1.00 | 26.46 | A |
| ATOM | 1233 | C | LEU | A | 158 | 93.464 | 73.293 | 29.126 | 1.00 | 23.77 | A |
| ATOM | 1234 | O | LEU | A | 158 | 93.342 | 72.294 | 28.417 | 1.00 | 20.25 | A |
| ATOM | 1235 | N | GLN | A | 159 | 94.622 | 73.927 | 29.269 | 1.00 | 20.67 | A |
| ATOM | 1236 | CA | GLN | A | 159 | 95.823 | 73.433 | 28.580 | 1.00 | 19.57 | A |
| ATOM | 1237 | CB | GLN | A | 159 | 96.995 | 74.418 | 28.776 | 1.00 | 20.64 | A |
| ATOM | 1238 | CG | GLN | A | 159 | 96.787 | 75.764 | 28.118 | 1.00 | 25.42 | A |
| ATOM | 1239 | CD | GLN | A | 159 | 97.003 | 75.741 | 26.600 | 1.00 | 26.92 | A |
| ATOM | 1240 | OE1 | GLN | A | 159 | 96.865 | 74.703 | 25.933 | 1.00 | 24.64 | A |
| ATOM | 1241 | NE2 | GLN | A | 159 | 97.341 | 76.899 | 26.049 | 1.00 | 24.27 | A |
| ATOM | 1242 | C | GLN | A | 159 | 96.195 | 72.047 | 29.136 | 1.00 | 25.83 | A |
| ATOM | 1243 | O | GLN | A | 159 | 96.681 | 71.182 | 28.390 | 1.00 | 22.57 | A |
| ATOM | 1244 | N | GLU | A | 160 | 95.963 | 71.833 | 30.433 | 1.00 | 18.37 | A |
| ATOM | 1245 | CA | GLU | A | 160 | 96.275 | 70.533 | 31.010 | 1.00 | 28.44 | A |
| ATOM | 1246 | CB | GLU | A | 160 | 96.124 | 70.505 | 32.527 | 1.00 | 18.70 | A |
| ATOM | 1247 | CG | GLU | A | 160 | 97.204 | 71.226 | 33.289 | 1.00 | 29.07 | A |
| ATOM | 1248 | CD | GLU | A | 160 | 97.071 | 71.010 | 34.792 | 1.00 | 37.12 | A |
| ATOM | 1249 | OE1 | GLU | A | 160 | 96.376 | 70.046 | 35.219 | 1.00 | 29.05 | A |

TABLE 2-continued

| | | | | | | | | | | |
|---|---|---|---|---|---|---|---|---|---|---|
| ATOM | 1250 | OE2 | GLU | A | 160 | 97.673 | 71.806 | 35.539 | 1.00 | 41.97 | A |
| ATOM | 1251 | C | GLU | A | 160 | 95.364 | 69.454 | 30.478 | 1.00 | 29.40 | A |
| ATOM | 1252 | O | GLU | A | 160 | 95.782 | 68.316 | 30.357 | 1.00 | 24.26 | A |
| ATOM | 1253 | N | ALA | A | 161 | 94.110 | 69.796 | 30.177 | 1.00 | 25.80 | A |
| ATOM | 1254 | CA | ALA | A | 161 | 93.182 | 68.775 | 29.705 | 1.00 | 26.76 | A |
| ATOM | 1255 | CB | ALA | A | 161 | 91.827 | 68.987 | 30.370 | 1.00 | 25.94 | A |
| ATOM | 1256 | C | ALA | A | 161 | 93.019 | 68.749 | 28.189 | 1.00 | 29.95 | A |
| ATOM | 1257 | O | ALA | A | 161 | 92.166 | 68.029 | 27.654 | 1.00 | 32.80 | A |
| ATOM | 1258 | N | LYS | A | 162 | 93.848 | 69.514 | 27.492 | 1.00 | 30.99 | A |
| ATOM | 1259 | CA | LYS | A | 162 | 93.741 | 69.628 | 26.043 | 1.00 | 37.27 | A |
| ATOM | 1260 | CB | LYS | A | 162 | 94.762 | 70.671 | 25.553 | 1.00 | 38.61 | A |
| ATOM | 1261 | CG | LYS | A | 162 | 94.792 | 70.892 | 24.048 | 1.00 | 50.32 | A |
| ATOM | 1262 | CD | LYS | A | 162 | 95.668 | 72.093 | 23.628 | 1.00 | 56.78 | A |
| ATOM | 1263 | CE | LYS | A | 162 | 97.171 | 71.809 | 23.618 | 1.00 | 58.73 | A |
| ATOM | 1264 | NZ | LYS | A | 162 | 97.593 | 70.975 | 22.433 | 1.00 | 67.24 | A |
| ATOM | 1265 | C | LYS | A | 162 | 93.885 | 68.321 | 25.254 | 1.00 | 37.81 | A |
| ATOM | 1266 | O | LYS | A | 162 | 93.029 | 67.964 | 24.455 | 1.00 | 33.39 | A |
| ATOM | 1267 | N | ASP | A | 163 | 94.968 | 67.601 | 25.475 | 1.00 | 41.14 | A |
| ATOM | 1268 | CA | ASP | A | 163 | 95.171 | 66.387 | 24.719 | 1.00 | 42.49 | A |
| ATOM | 1269 | CB | ASP | A | 163 | 96.576 | 65.858 | 24.965 | 1.00 | 51.70 | A |
| ATOM | 1270 | CG | ASP | A | 163 | 97.643 | 66.839 | 24.512 | 1.00 | 57.18 | A |
| ATOM | 1271 | OD1 | ASP | A | 163 | 97.366 | 67.598 | 23.557 | 1.00 | 62.80 | A |
| ATOM | 1272 | OD2 | ASP | A | 163 | 98.752 | 66.846 | 25.094 | 1.00 | 64.82 | A |
| ATOM | 1273 | C | ASP | A | 163 | 94.127 | 65.361 | 25.074 | 1.00 | 41.86 | A |
| ATOM | 1274 | O | ASP | A | 163 | 93.582 | 64.687 | 24.214 | 1.00 | 41.54 | A |
| ATOM | 1275 | N | ILE | A | 164 | 93.808 | 65.253 | 26.344 | 1.00 | 37.18 | A |
| ATOM | 1276 | CA | ILE | A | 164 | 92.801 | 64.297 | 26.721 | 1.00 | 37.23 | A |
| ATOM | 1277 | CB | ILE | A | 164 | 92.750 | 64.158 | 28.236 | 1.00 | 43.08 | A |
| ATOM | 1278 | CG2 | ILE | A | 164 | 91.530 | 63.365 | 28.661 | 1.00 | 42.32 | A |
| ATOM | 1279 | CG1 | ILE | A | 164 | 94.054 | 63.514 | 28.705 | 1.00 | 48.60 | A |
| ATOM | 1280 | CD1 | ILE | A | 164 | 94.078 | 63.174 | 30.156 | 1.00 | 56.10 | A |
| ATOM | 1281 | C | ILE | A | 164 | 91.404 | 64.634 | 26.216 | 1.00 | 39.86 | A |
| ATOM | 1282 | O | ILE | A | 164 | 90.656 | 63.748 | 25.830 | 1.00 | 33.04 | A |
| ATOM | 1283 | N | CYS | A | 165 | 91.060 | 65.914 | 26.183 | 1.00 | 32.76 | A |
| ATOM | 1284 | CA | CYS | A | 165 | 89.715 | 66.278 | 25.814 | 1.00 | 34.31 | A |
| ATOM | 1285 | C | CYS | A | 165 | 89.433 | 66.817 | 24.422 | 1.00 | 37.19 | A |
| ATOM | 1286 | O | CYS | A | 165 | 88.287 | 66.818 | 24.011 | 1.00 | 28.15 | A |
| ATOM | 1287 | CB | CYS | A | 165 | 89.180 | 67.278 | 26.839 | 1.00 | 29.46 | A |
| ATOM | 1288 | SG | CYS | A | 165 | 89.010 | 66.566 | 28.503 | 1.00 | 28.08 | A |
| ATOM | 1289 | N | GLU | A | 166 | 90.459 | 67.264 | 23.707 | 1.00 | 45.15 | A |
| ATOM | 1290 | CA | GLU | A | 166 | 90.273 | 67.877 | 22.395 | 1.00 | 51.11 | A |
| ATOM | 1291 | CB | GLU | A | 166 | 91.630 | 68.143 | 21.720 | 1.00 | 59.07 | A |
| ATOM | 1292 | CG | GLU | A | 166 | 92.542 | 66.935 | 21.528 | 1.00 | 66.72 | A |
| ATOM | 1293 | CD | GLU | A | 166 | 93.935 | 67.335 | 21.000 | 1.00 | 71.70 | A |
| ATOM | 1294 | OE1 | GLU | A | 166 | 94.838 | 66.457 | 20.967 | 1.00 | 74.38 | A |
| ATOM | 1295 | OE2 | GLU | A | 166 | 94.123 | 68.526 | 20.619 | 1.00 | 68.32 | A |
| ATOM | 1296 | C | GLU | A | 166 | 89.349 | 67.152 | 21.449 | 1.00 | 50.87 | A |
| ATOM | 1297 | O | GLU | A | 166 | 88.661 | 67.784 | 20.646 | 1.00 | 50.00 | A |
| ATOM | 1298 | N | GLU | A | 167 | 89.314 | 65.833 | 21.559 | 1.00 | 52.19 | A |
| ATOM | 1299 | CA | GLU | A | 167 | 88.448 | 65.027 | 20.718 | 1.00 | 52.32 | A |
| ATOM | 1300 | CB | GLU | A | 167 | 88.840 | 63.559 | 20.838 | 1.00 | 60.45 | A |
| ATOM | 1301 | CG | GLU | A | 167 | 89.074 | 62.885 | 19.504 | 1.00 | 68.41 | A |
| ATOM | 1302 | CD | GLU | A | 167 | 89.979 | 63.713 | 18.605 | 1.00 | 74.42 | A |
| ATOM | 1303 | OE1 | GLU | A | 167 | 91.048 | 64.161 | 19.082 | 1.00 | 77.67 | A |
| ATOM | 1304 | OE2 | GLU | A | 167 | 89.621 | 63.917 | 17.421 | 1.00 | 78.62 | A |
| ATOM | 1305 | C | GLU | A | 167 | 86.963 | 65.177 | 21.059 | 1.00 | 54.06 | A |
| ATOM | 1306 | O | GLU | A | 167 | 86.136 | 65.356 | 20.163 | 1.00 | 52.37 | A |
| ATOM | 1307 | N | GLN | A | 168 | 86.632 | 65.103 | 22.351 | 1.00 | 46.71 | A |
| ATOM | 1308 | CA | GLN | A | 168 | 85.247 | 65.202 | 22.811 | 1.00 | 43.91 | A |
| ATOM | 1309 | CB | GLN | A | 168 | 85.059 | 64.480 | 24.155 | 1.00 | 50.94 | A |
| ATOM | 1310 | CG | GLN | A | 168 | 86.269 | 64.533 | 25.087 | 1.00 | 56.41 | A |
| ATOM | 1311 | CD | GLN | A | 168 | 87.154 | 63.284 | 24.976 | 1.00 | 55.96 | A |
| ATOM | 1312 | OE1 | GLN | A | 168 | 86.830 | 62.226 | 25.526 | 1.00 | 49.92 | A |
| ATOM | 1313 | NE2 | GLN | A | 168 | 88.268 | 63.406 | 24.247 | 1.00 | 57.62 | A |
| ATOM | 1314 | C | GLN | A | 168 | 84.752 | 66.620 | 22.959 | 1.00 | 42.37 | A |
| ATOM | 1315 | O | GLN | A | 168 | 83.547 | 66.856 | 23.073 | 1.00 | 41.71 | A |
| ATOM | 1316 | N | VAL | A | 169 | 85.673 | 67.571 | 22.965 | 1.00 | 33.31 | A |
| ATOM | 1317 | CA | VAL | A | 169 | 85.281 | 68.962 | 23.112 | 1.00 | 35.06 | A |
| ATOM | 1318 | CB | VAL | A | 169 | 85.809 | 69.506 | 24.469 | 1.00 | 27.42 | A |
| ATOM | 1319 | CG1 | VAL | A | 169 | 85.245 | 70.889 | 24.754 | 1.00 | 25.13 | A |
| ATOM | 1320 | CG2 | VAL | A | 169 | 85.402 | 68.540 | 25.573 | 1.00 | 24.56 | A |
| ATOM | 1321 | C | VAL | A | 169 | 85.780 | 69.792 | 21.919 | 1.00 | 34.13 | A |
| ATOM | 1322 | O | VAL | A | 169 | 86.866 | 70.376 | 21.962 | 1.00 | 31.73 | A |
| ATOM | 1323 | N | ASN | A | 170 | 84.971 | 69.841 | 20.857 | 1.00 | 31.12 | A |
| ATOM | 1324 | CA | ASN | A | 170 | 85.367 | 70.554 | 19.646 | 1.00 | 31.56 | A |
| ATOM | 1325 | CB | ASN | A | 170 | 84.377 | 70.283 | 18.503 | 1.00 | 38.49 | A |
| ATOM | 1326 | CG | ASN | A | 170 | 84.352 | 68.798 | 18.058 | 1.00 | 44.51 | A |
| ATOM | 1327 | OD1 | ASN | A | 170 | 83.419 | 68.063 | 18.367 | 1.00 | 50.11 | A |
| ATOM | 1328 | ND2 | ASN | A | 170 | 85.374 | 68.375 | 17.334 | 1.00 | 40.85 | A |

TABLE 2-continued

| ATOM | 1329 | C | ASN | A | 170 | 85.562 | 72.052 | 19.838 | 1.00 | 33.38 | A |
|---|---|---|---|---|---|---|---|---|---|---|---|
| ATOM | 1330 | O | ASN | A | 170 | 86.308 | 72.682 | 19.101 | 1.00 | 32.60 | A |
| ATOM | 1331 | N | SER | A | 171 | 84.931 | 72.641 | 20.843 | 1.00 | 29.65 | A |
| ATOM | 1332 | CA | SER | A | 171 | 85.123 | 74.080 | 21.054 | 1.00 | 27.07 | A |
| ATOM | 1333 | CB | SER | A | 171 | 83.937 | 74.650 | 21.858 | 1.00 | 26.83 | A |
| ATOM | 1334 | OG | SER | A | 171 | 83.675 | 73.861 | 23.020 | 1.00 | 22.03 | A |
| ATOM | 1335 | C | SER | A | 171 | 86.434 | 74.410 | 21.776 | 1.00 | 23.40 | A |
| ATOM | 1336 | O | SER | A | 171 | 86.829 | 75.571 | 21.868 | 1.00 | 25.17 | A |
| ATOM | 1337 | N | LEU | A | 172 | 87.130 | 73.400 | 22.274 | 1.00 | 20.64 | A |
| ATOM | 1338 | CA | LEU | A | 172 | 88.364 | 73.670 | 23.024 | 1.00 | 18.28 | A |
| ATOM | 1339 | CB | LEU | A | 172 | 88.976 | 72.340 | 23.451 | 1.00 | 26.95 | A |
| ATOM | 1340 | CG | LEU | A | 172 | 89.987 | 72.262 | 24.605 | 1.00 | 36.59 | A |
| ATOM | 1341 | CD1 | LEU | A | 172 | 89.724 | 73.283 | 25.714 | 1.00 | 28.04 | A |
| ATOM | 1342 | CD2 | LEU | A | 172 | 89.912 | 70.840 | 25.159 | 1.00 | 30.83 | A |
| ATOM | 1343 | C | LEU | A | 172 | 89.420 | 74.540 | 22.325 | 1.00 | 23.79 | A |
| ATOM | 1344 | O | LEU | A | 172 | 89.867 | 75.551 | 22.863 | 1.00 | 22.52 | A |
| ATOM | 1345 | N | PRO | A | 173 | 89.821 | 74.173 | 21.095 | 1.00 | 28.78 | A |
| ATOM | 1346 | CD | PRO | A | 173 | 89.392 | 73.036 | 20.258 | 1.00 | 26.81 | A |
| ATOM | 1347 | CA | PRO | A | 173 | 90.837 | 74.991 | 20.419 | 1.00 | 28.96 | A |
| ATOM | 1348 | CB | PRO | A | 173 | 91.001 | 74.308 | 19.054 | 1.00 | 28.65 | A |
| ATOM | 1349 | CG | PRO | A | 173 | 90.597 | 72.878 | 19.321 | 1.00 | 33.10 | A |
| ATOM | 1350 | C | PRO | A | 173 | 90.454 | 76.475 | 20.301 | 1.00 | 27.14 | A |
| ATOM | 1351 | O | PRO | A | 173 | 91.259 | 77.366 | 20.599 | 1.00 | 22.88 | A |
| ATOM | 1352 | N | GLY | A | 174 | 89.223 | 76.730 | 19.885 | 1.00 | 24.04 | A |
| ATOM | 1353 | CA | GLY | A | 174 | 88.771 | 78.104 | 19.731 | 1.00 | 24.51 | A |
| ATOM | 1354 | C | GLY | A | 174 | 88.667 | 78.805 | 21.071 | 1.00 | 23.82 | A |
| ATOM | 1355 | O | GLY | A | 174 | 88.943 | 79.985 | 21.172 | 1.00 | 24.00 | A |
| ATOM | 1356 | N | SER | A | 175 | 88.269 | 78.083 | 22.115 | 1.00 | 23.65 | A |
| ATOM | 1357 | CA | SER | A | 175 | 88.167 | 78.706 | 23.462 | 1.00 | 25.41 | A |
| ATOM | 1358 | CB | SER | A | 175 | 87.662 | 77.665 | 24.489 | 1.00 | 21.04 | A |
| ATOM | 1359 | OG | SER | A | 175 | 87.648 | 78.213 | 25.791 | 1.00 | 22.86 | A |
| ATOM | 1360 | C | SER | A | 175 | 89.534 | 79.224 | 23.917 | 1.00 | 23.64 | A |
| ATOM | 1361 | O | SER | A | 175 | 89.691 | 80.347 | 24.440 | 1.00 | 21.39 | A |
| ATOM | 1362 | N | ILE | A | 176 | 90.531 | 78.372 | 23.741 | 1.00 | 24.52 | A |
| ATOM | 1363 | CA | ILE | A | 176 | 91.907 | 78.683 | 24.127 | 1.00 | 20.94 | A |
| ATOM | 1364 | CB | ILE | A | 176 | 92.774 | 77.406 | 23.873 | 1.00 | 19.98 | A |
| ATOM | 1365 | CG2 | ILE | A | 176 | 94.244 | 77.741 | 23.797 | 1.00 | 20.82 | A |
| ATOM | 1366 | CG1 | ILE | A | 176 | 92.449 | 76.370 | 24.970 | 1.00 | 23.34 | A |
| ATOM | 1367 | CD1 | ILE | A | 176 | 93.191 | 75.017 | 24.797 | 1.00 | 23.21 | A |
| ATOM | 1368 | C | ILE | A | 176 | 92.427 | 79.921 | 23.371 | 1.00 | 23.29 | A |
| ATOM | 1369 | O | ILE | A | 176 | 93.011 | 80.845 | 23.953 | 1.00 | 21.00 | A |
| ATOM | 1370 | N | THR | A | 177 | 92.180 | 79.957 | 22.069 | 1.00 | 22.38 | A |
| ATOM | 1371 | CA | THR | A | 177 | 92.622 | 81.096 | 21.280 | 1.00 | 26.70 | A |
| ATOM | 1372 | CB | THR | A | 177 | 92.298 | 80.826 | 19.810 | 1.00 | 30.44 | A |
| ATOM | 1373 | OG1 | THR | A | 177 | 93.142 | 79.754 | 19.352 | 1.00 | 32.66 | A |
| ATOM | 1374 | CG2 | THR | A | 177 | 92.507 | 82.071 | 18.959 | 1.00 | 25.97 | A |
| ATOM | 1375 | C | THR | A | 177 | 91.966 | 82.395 | 21.793 | 1.00 | 28.53 | A |
| ATOM | 1376 | O | THR | A | 177 | 92.635 | 83.437 | 21.992 | 1.00 | 25.08 | A |
| ATOM | 1377 | N | LYS | A | 178 | 90.665 | 82.320 | 22.058 | 1.00 | 24.69 | A |
| ATOM | 1378 | CA | LYS | A | 178 | 89.966 | 83.486 | 22.556 | 1.00 | 22.85 | A |
| ATOM | 1379 | CB | LYS | A | 178 | 88.458 | 83.212 | 22.647 | 1.00 | 33.69 | A |
| ATOM | 1380 | CG | LYS | A | 178 | 87.719 | 83.233 | 21.285 | 1.00 | 37.81 | A |
| ATOM | 1381 | CD | LYS | A | 178 | 86.260 | 82.880 | 21.478 | 1.00 | 45.50 | A |
| ATOM | 1382 | CE | LYS | A | 178 | 85.580 | 82.539 | 20.168 | 1.00 | 55.66 | A |
| ATOM | 1383 | NZ | LYS | A | 178 | 84.321 | 81.738 | 20.375 | 1.00 | 62.92 | A |
| ATOM | 1384 | C | LYS | A | 178 | 90.513 | 83.903 | 23.908 | 1.00 | 27.56 | A |
| ATOM | 1385 | O | LYS | A | 178 | 90.764 | 85.100 | 24.139 | 1.00 | 22.42 | A |
| ATOM | 1386 | N | ALA | A | 179 | 90.708 | 82.945 | 24.818 | 1.00 | 21.82 | A |
| ATOM | 1387 | CA | ALA | A | 179 | 91.232 | 83.327 | 26.117 | 1.00 | 22.17 | A |
| ATOM | 1388 | CB | ALA | A | 179 | 91.326 | 82.107 | 27.056 | 1.00 | 20.58 | A |
| ATOM | 1389 | C | ALA | A | 179 | 92.607 | 83.918 | 25.879 | 1.00 | 23.19 | A |
| ATOM | 1390 | O | ALA | A | 179 | 92.958 | 84.970 | 26.424 | 1.00 | 21.73 | A |
| ATOM | 1391 | N | GLY | A | 180 | 93.392 | 83.244 | 25.046 | 1.00 | 26.28 | A |
| ATOM | 1392 | CA | GLY | A | 180 | 94.732 | 83.741 | 24.790 | 1.00 | 25.77 | A |
| ATOM | 1393 | C | GLY | A | 180 | 94.723 | 85.155 | 24.206 | 1.00 | 29.69 | A |
| ATOM | 1394 | O | GLY | A | 180 | 95.509 | 86.005 | 24.628 | 1.00 | 26.61 | A |
| ATOM | 1395 | N | ASP | A | 181 | 93.869 | 85.403 | 23.215 | 1.00 | 19.22 | A |
| ATOM | 1396 | CA | ASP | A | 181 | 93.776 | 86.745 | 22.600 | 1.00 | 24.71 | A |
| ATOM | 1397 | CB | ASP | A | 181 | 92.670 | 86.781 | 21.544 | 1.00 | 28.40 | A |
| ATOM | 1398 | CG | ASP | A | 181 | 93.045 | 86.061 | 20.266 | 1.00 | 24.26 | A |
| ATOM | 1399 | OD1 | ASP | A | 181 | 94.242 | 85.821 | 20.035 | 1.00 | 26.47 | A |
| ATOM | 1400 | OD2 | ASP | A | 181 | 92.138 | 85.751 | 19.475 | 1.00 | 31.29 | A |
| ATOM | 1401 | C | ASP | A | 181 | 93.465 | 87.814 | 23.635 | 1.00 | 23.38 | A |
| ATOM | 1402 | O | ASP | A | 181 | 94.051 | 88.897 | 23.619 | 1.00 | 24.92 | A |
| ATOM | 1403 | N | PHE | A | 182 | 92.541 | 87.508 | 24.548 | 1.00 | 23.93 | A |
| ATOM | 1404 | CA | PHE | A | 182 | 92.179 | 88.481 | 25.562 | 1.00 | 24.17 | A |
| ATOM | 1405 | CB | PHE | A | 182 | 90.971 | 88.008 | 26.368 | 1.00 | 29.71 | A |
| ATOM | 1406 | CG | PHE | A | 182 | 90.573 | 88.970 | 27.457 | 1.00 | 37.61 | A |
| ATOM | 1407 | CD1 | PHE | A | 182 | 89.777 | 90.074 | 27.174 | 1.00 | 35.83 | A |

TABLE 2-continued

| | | | | | | | | | | |
|---|---|---|---|---|---|---|---|---|---|---|
| ATOM | 1408 | CD2 | PHE | A | 182 | 91.034 | 88.798 | 28.751 | 1.00 | 37.07 | A |
| ATOM | 1409 | CE1 | PHE | A | 182 | 89.447 | 90.989 | 28.165 | 1.00 | 38.94 | A |
| ATOM | 1410 | CE2 | PHE | A | 182 | 90.706 | 89.712 | 29.748 | 1.00 | 42.65 | A |
| ATOM | 1411 | CZ | PHE | A | 182 | 89.915 | 90.806 | 29.456 | 1.00 | 41.10 | A |
| ATOM | 1412 | C | PHE | A | 182 | 93.343 | 88.759 | 26.514 | 1.00 | 29.73 | A |
| ATOM | 1413 | O | PHE | A | 182 | 93.610 | 89.911 | 26.877 | 1.00 | 26.64 | A |
| ATOM | 1414 | N | LEU | A | 183 | 94.041 | 87.710 | 26.933 | 1.00 | 23.11 | A |
| ATOM | 1415 | CA | LEU | A | 183 | 95.163 | 87.923 | 27.847 | 1.00 | 23.03 | A |
| ATOM | 1416 | CB | LEU | A | 183 | 95.794 | 86.587 | 28.302 | 1.00 | 19.13 | A |
| ATOM | 1417 | CG | LEU | A | 183 | 94.927 | 85.684 | 29.181 | 1.00 | 24.04 | A |
| ATOM | 1418 | CD1 | LEU | A | 183 | 95.697 | 84.363 | 29.487 | 1.00 | 23.39 | A |
| ATOM | 1419 | CD2 | LEU | A | 183 | 94.595 | 86.398 | 30.489 | 1.00 | 21.06 | A |
| ATOM | 1420 | C | LEU | A | 183 | 96.237 | 88.742 | 27.140 | 1.00 | 19.58 | A |
| ATOM | 1421 | O | LEU | A | 183 | 96.797 | 89.668 | 27.711 | 1.00 | 23.84 | A |
| ATOM | 1422 | N | GLU | A | 184 | 96.545 | 88.383 | 25.904 | 1.00 | 19.16 | A |
| ATOM | 1423 | CA | GLU | A | 184 | 97.584 | 89.114 | 25.190 | 1.00 | 29.47 | A |
| ATOM | 1424 | CB | GLU | A | 184 | 97.874 | 88.459 | 23.842 | 1.00 | 27.07 | A |
| ATOM | 1425 | CG | GLU | A | 184 | 98.874 | 89.217 | 23.010 | 1.00 | 33.26 | A |
| ATOM | 1426 | CD | GLU | A | 184 | 99.360 | 88.416 | 21.817 | 1.00 | 36.59 | A |
| ATOM | 1427 | OE1 | GLU | A | 184 | 98.869 | 87.295 | 21.569 | 1.00 | 37.18 | A |
| ATOM | 1428 | OE2 | GLU | A | 184 | 100.249 | 88.907 | 21.120 | 1.00 | 40.45 | A |
| ATOM | 1429 | C | GLU | A | 184 | 97.204 | 90.578 | 24.992 | 1.00 | 26.03 | A |
| ATOM | 1430 | O | GLU | A | 184 | 98.004 | 91.471 | 25.273 | 1.00 | 29.51 | A |
| ATOM | 1431 | N | ALA | A | 185 | 95.981 | 90.835 | 24.548 | 1.00 | 28.37 | A |
| ATOM | 1432 | CA | ALA | A | 185 | 95.560 | 92.236 | 24.317 | 1.00 | 32.04 | A |
| ATOM | 1433 | CB | ALA | A | 185 | 94.166 | 92.282 | 23.689 | 1.00 | 31.81 | A |
| ATOM | 1434 | C | ALA | A | 185 | 95.567 | 93.137 | 25.537 | 1.00 | 36.13 | A |
| ATOM | 1435 | O | ALA | A | 185 | 95.706 | 94.353 | 25.401 | 1.00 | 35.39 | A |
| ATOM | 1436 | N | ASN | A | 186 | 95.448 | 92.555 | 26.730 | 1.00 | 32.84 | A |
| ATOM | 1437 | CA | ASN | A | 186 | 95.352 | 93.351 | 27.953 | 1.00 | 29.26 | A |
| ATOM | 1438 | CB | ASN | A | 186 | 94.035 | 93.004 | 28.640 | 1.00 | 27.88 | A |
| ATOM | 1439 | CG | ASN | A | 186 | 92.847 | 93.480 | 27.836 | 1.00 | 33.22 | A |
| ATOM | 1440 | OD1 | ASN | A | 186 | 92.562 | 94.672 | 27.813 | 1.00 | 34.12 | A |
| ATOM | 1441 | ND2 | ASN | A | 186 | 92.175 | 92.566 | 27.143 | 1.00 | 25.25 | A |
| ATOM | 1442 | C | ASN | A | 186 | 96.476 | 93.240 | 28.952 | 1.00 | 27.19 | A |
| ATOM | 1443 | O | ASN | A | 186 | 96.444 | 93.890 | 30.003 | 1.00 | 27.97 | A |
| ATOM | 1444 | N | TYR | A | 187 | 97.472 | 92.433 | 28.610 | 1.00 | 24.51 | A |
| ATOM | 1445 | CA | TYR | A | 187 | 98.612 | 92.176 | 29.486 | 1.00 | 21.48 | A |
| ATOM | 1446 | CB | TYR | A | 187 | 99.634 | 91.255 | 28.785 | 1.00 | 23.19 | A |
| ATOM | 1447 | CG | TYR | A | 187 | 100.651 | 90.604 | 29.729 | 1.00 | 27.39 | A |
| ATOM | 1448 | CD1 | TYR | A | 187 | 100.258 | 89.596 | 30.637 | 1.00 | 24.03 | A |
| ATOM | 1449 | CE1 | TYR | A | 187 | 101.209 | 88.977 | 31.508 | 1.00 | 28.63 | A |
| ATOM | 1450 | CD2 | TYR | A | 187 | 102.004 | 90.982 | 29.712 | 1.00 | 25.92 | A |
| ATOM | 1451 | CE2 | TYR | A | 187 | 102.952 | 90.380 | 30.570 | 1.00 | 28.97 | A |
| ATOM | 1452 | CZ | TYR | A | 187 | 102.551 | 89.379 | 31.465 | 1.00 | 31.32 | A |
| ATOM | 1453 | OH | TYR | A | 187 | 103.498 | 88.788 | 32.293 | 1.00 | 25.25 | A |
| ATOM | 1454 | C | TYR | A | 187 | 99.360 | 93.389 | 29.929 | 1.00 | 29.36 | A |
| ATOM | 1455 | O | TYR | A | 187 | 99.645 | 93.536 | 31.122 | 1.00 | 26.96 | A |
| ATOM | 1456 | N | MET | A | 188 | 99.721 | 94.240 | 28.956 | 1.00 | 25.41 | A |
| ATOM | 1457 | CA | MET | A | 188 | 100.526 | 95.417 | 29.260 | 1.00 | 31.50 | A |
| ATOM | 1458 | CB | MET | A | 188 | 100.794 | 96.215 | 27.981 | 1.00 | 24.85 | A |
| ATOM | 1459 | CG | MET | A | 188 | 101.699 | 95.478 | 27.011 | 1.00 | 26.87 | A |
| ATOM | 1460 | SD | MET | A | 188 | 103.239 | 94.935 | 27.730 | 1.00 | 33.34 | A |
| ATOM | 1461 | CE | MET | A | 188 | 103.886 | 96.512 | 28.315 | 1.00 | 30.68 | A |
| ATOM | 1462 | C | MET | A | 188 | 99.962 | 96.322 | 30.349 | 1.00 | 27.28 | A |
| ATOM | 1463 | O | MET | A | 188 | 100.720 | 96.982 | 31.071 | 1.00 | 26.43 | A |
| ATOM | 1464 | N | ASN | A | 189 | 98.645 | 96.288 | 30.495 | 1.00 | 25.67 | A |
| ATOM | 1465 | CA | ASN | A | 189 | 97.927 | 97.092 | 31.482 | 1.00 | 40.32 | A |
| ATOM | 1466 | CB | ASN | A | 189 | 96.499 | 97.323 | 31.000 | 1.00 | 46.12 | A |
| ATOM | 1467 | CG | ASN | A | 189 | 96.220 | 98.769 | 30.729 | 1.00 | 58.01 | A |
| ATOM | 1468 | OD1 | ASN | A | 189 | 95.564 | 99.113 | 29.728 | 1.00 | 63.96 | A |
| ATOM | 1469 | ND2 | ASN | A | 189 | 96.722 | 99.643 | 31.612 | 1.00 | 54.68 | A |
| ATOM | 1470 | C | ASN | A | 189 | 97.850 | 96.519 | 32.897 | 1.00 | 40.44 | A |
| ATOM | 1471 | O | ASN | A | 189 | 97.220 | 97.109 | 33.770 | 1.00 | 40.07 | A |
| ATOM | 1472 | N | LEU | A | 190 | 98.469 | 95.375 | 33.140 | 1.00 | 37.09 | A |
| ATOM | 1473 | CA | LEU | A | 190 | 98.391 | 94.795 | 34.473 | 1.00 | 32.05 | A |
| ATOM | 1474 | CB | LEU | A | 190 | 98.887 | 93.358 | 34.459 | 1.00 | 27.91 | A |
| ATOM | 1475 | CG | LEU | A | 190 | 98.000 | 92.410 | 33.659 | 1.00 | 25.90 | A |
| ATOM | 1476 | CD1 | LEU | A | 190 | 98.707 | 91.036 | 33.591 | 1.00 | 21.96 | A |
| ATOM | 1477 | CD2 | LEU | A | 190 | 96.619 | 92.343 | 34.315 | 1.00 | 13.68 | A |
| ATOM | 1478 | C | LEU | A | 190 | 99.186 | 95.549 | 35.485 | 1.00 | 32.08 | A |
| ATOM | 1479 | O | LEU | A | 190 | 100.264 | 96.039 | 35.189 | 1.00 | 34.79 | A |
| ATOM | 1480 | N | GLN | A | 191 | 98.653 | 95.630 | 36.696 | 1.00 | 24.96 | A |
| ATOM | 1481 | CA | GLN | A | 191 | 99.359 | 96.299 | 37.771 | 1.00 | 29.96 | A |
| ATOM | 1482 | CB | GLN | A | 191 | 98.443 | 97.330 | 38.429 | 1.00 | 37.43 | A |
| ATOM | 1483 | CG | GLN | A | 191 | 98.000 | 98.434 | 37.486 | 1.00 | 50.78 | A |
| ATOM | 1484 | CD | GLN | A | 191 | 99.178 | 99.289 | 37.084 | 1.00 | 58.93 | A |
| ATOM | 1485 | OE1 | GLN | A | 191 | 99.756 | 99.994 | 37.923 | 1.00 | 65.09 | A |
| ATOM | 1486 | NE2 | GLN | A | 191 | 99.566 | 99.220 | 35.803 | 1.00 | 65.13 | A |

TABLE 2-continued

| ATOM | 1487 | C | GLN | A | 191 | 99.878 | 95.333 | 38.855 | 1.00 | 32.15 | A |
|---|---|---|---|---|---|---|---|---|---|---|---|
| ATOM | 1488 | O | GLN | A | 191 | 100.893 | 95.610 | 39.464 | 1.00 | 28.48 | A |
| ATOM | 1489 | N | ARG | A | 192 | 99.189 | 94.219 | 39.119 | 1.00 | 25.14 | A |
| ATOM | 1490 | CA | ARG | A | 192 | 99.657 | 93.312 | 40.170 | 1.00 | 22.86 | A |
| ATOM | 1491 | CB | ARG | A | 192 | 98.489 | 92.473 | 40.703 | 1.00 | 23.64 | A |
| ATOM | 1492 | CG | ARG | A | 192 | 97.302 | 93.308 | 41.257 | 1.00 | 31.91 | A |
| ATOM | 1493 | CD | ARG | A | 192 | 96.128 | 92.393 | 41.622 | 1.00 | 35.16 | A |
| ATOM | 1494 | NE | ARG | A | 192 | 96.514 | 91.335 | 42.569 | 1.00 | 41.51 | A |
| ATOM | 1495 | CZ | ARG | A | 192 | 95.847 | 90.184 | 42.733 | 1.00 | 44.28 | A |
| ATOM | 1496 | NH1 | ARG | A | 192 | 94.757 | 89.949 | 41.997 | 1.00 | 39.94 | A |
| ATOM | 1497 | NH2 | ARG | A | 192 | 96.255 | 89.280 | 43.641 | 1.00 | 30.46 | A |
| ATOM | 1498 | C | ARG | A | 192 | 100.736 | 92.356 | 39.709 | 1.00 | 19.29 | A |
| ATOM | 1499 | O | ARG | A | 192 | 100.658 | 91.822 | 38.596 | 1.00 | 15.56 | A |
| ATOM | 1500 | N | SER | A | 193 | 101.735 | 92.114 | 40.557 | 1.00 | 20.51 | A |
| ATOM | 1501 | CA | SER | A | 193 | 102.769 | 91.138 | 40.196 | 1.00 | 23.99 | A |
| ATOM | 1502 | CB | SER | A | 193 | 103.853 | 91.066 | 41.250 | 1.00 | 25.82 | A |
| ATOM | 1503 | OG | SER | A | 193 | 104.634 | 92.236 | 41.177 | 1.00 | 29.45 | A |
| ATOM | 1504 | C | SER | A | 193 | 102.123 | 89.754 | 40.041 | 1.00 | 26.36 | A |
| ATOM | 1505 | O | SER | A | 193 | 102.508 | 88.958 | 39.164 | 1.00 | 26.52 | A |
| ATOM | 1506 | N | TYR | A | 194 | 101.123 | 89.479 | 40.877 | 1.00 | 27.26 | A |
| ATOM | 1507 | CA | TYR | A | 194 | 100.429 | 88.201 | 40.790 | 1.00 | 22.13 | A |
| ATOM | 1508 | CB | TYR | A | 194 | 99.303 | 88.108 | 41.823 | 1.00 | 23.41 | A |
| ATOM | 1509 | CG | TYR | A | 194 | 98.539 | 86.783 | 41.755 | 1.00 | 16.74 | A |
| ATOM | 1510 | CD1 | TYR | A | 194 | 99.067 | 85.620 | 42.340 | 1.00 | 19.51 | A |
| ATOM | 1511 | CE1 | TYR | A | 194 | 98.401 | 84.389 | 42.271 | 1.00 | 17.85 | A |
| ATOM | 1512 | CD2 | TYR | A | 194 | 97.312 | 86.692 | 41.087 | 1.00 | 20.75 | A |
| ATOM | 1513 | CE2 | TYR | A | 194 | 96.621 | 85.461 | 41.001 | 1.00 | 25.88 | A |
| ATOM | 1514 | CZ | TYR | A | 194 | 97.181 | 84.312 | 41.603 | 1.00 | 20.62 | A |
| ATOM | 1515 | OH | TYR | A | 194 | 96.522 | 83.107 | 41.540 | 1.00 | 24.87 | A |
| ATOM | 1516 | C | TYR | A | 194 | 99.843 | 87.959 | 39.398 | 1.00 | 23.17 | A |
| ATOM | 1517 | O | TYR | A | 194 | 100.123 | 86.938 | 38.775 | 1.00 | 22.83 | A |
| ATOM | 1518 | N | THR | A | 195 | 99.013 | 88.878 | 38.904 | 1.00 | 18.74 | A |
| ATOM | 1519 | CA | THR | A | 195 | 98.391 | 88.680 | 37.602 | 1.00 | 16.68 | A |
| ATOM | 1520 | CB | THR | A | 195 | 97.427 | 89.817 | 37.264 | 1.00 | 16.43 | A |
| ATOM | 1521 | OG1 | THR | A | 195 | 96.657 | 90.130 | 38.428 | 1.00 | 21.65 | A |
| ATOM | 1522 | CG2 | THR | A | 195 | 96.496 | 89.378 | 36.151 | 1.00 | 22.25 | A |
| ATOM | 1523 | C | THR | A | 195 | 99.437 | 88.593 | 36.498 | 1.00 | 21.37 | A |
| ATOM | 1524 | O | THR | A | 195 | 99.315 | 87.829 | 35.549 | 1.00 | 18.17 | A |
| ATOM | 1525 | N | VAL | A | 196 | 100.506 | 89.359 | 36.647 | 1.00 | 23.63 | A |
| ATOM | 1526 | CA | VAL | A | 196 | 101.531 | 89.334 | 35.639 | 1.00 | 20.64 | A |
| ATOM | 1527 | CB | VAL | A | 196 | 102.620 | 90.409 | 35.959 | 1.00 | 26.84 | A |
| ATOM | 1528 | CG1 | VAL | A | 196 | 103.973 | 90.045 | 35.324 | 1.00 | 25.77 | A |
| ATOM | 1529 | CG2 | VAL | A | 196 | 102.154 | 91.773 | 35.456 | 1.00 | 25.74 | A |
| ATOM | 1530 | C | VAL | A | 196 | 102.147 | 87.933 | 35.583 | 1.00 | 20.37 | A |
| ATOM | 1531 | O | VAL | A | 196 | 102.451 | 87.439 | 34.503 | 1.00 | 19.78 | A |
| ATOM | 1532 | N | ALA | A | 197 | 102.386 | 87.326 | 36.739 | 1.00 | 21.05 | A |
| ATOM | 1533 | CA | ALA | A | 197 | 103.005 | 85.984 | 36.766 | 1.00 | 24.45 | A |
| ATOM | 1534 | CB | ALA | A | 197 | 103.370 | 85.583 | 38.225 | 1.00 | 15.17 | A |
| ATOM | 1535 | C | ALA | A | 197 | 102.056 | 84.951 | 36.162 | 1.00 | 15.00 | A |
| ATOM | 1536 | O | ALA | A | 197 | 102.424 | 84.229 | 35.226 | 1.00 | 20.20 | A |
| ATOM | 1537 | N | ILE | A | 198 | 100.809 | 84.911 | 36.648 | 1.00 | 24.78 | A |
| ATOM | 1538 | CA | ILE | A | 198 | 99.887 | 83.889 | 36.144 | 1.00 | 20.75 | A |
| ATOM | 1539 | CB | ILE | A | 198 | 98.569 | 83.723 | 37.056 | 1.00 | 19.12 | A |
| ATOM | 1540 | CG2 | ILE | A | 198 | 97.602 | 84.931 | 36.915 | 1.00 | 20.52 | A |
| ATOM | 1541 | CG1 | ILE | A | 198 | 97.855 | 82.438 | 36.658 | 1.00 | 19.50 | A |
| ATOM | 1542 | CD1 | ILE | A | 198 | 96.670 | 82.071 | 37.553 | 1.00 | 20.96 | A |
| ATOM | 1543 | C | ILE | A | 198 | 99.545 | 84.052 | 34.674 | 1.00 | 19.83 | A |
| ATOM | 1544 | O | ILE | A | 198 | 99.593 | 83.057 | 33.913 | 1.00 | 21.51 | A |
| ATOM | 1545 | N | ALA | A | 199 | 99.217 | 85.274 | 34.235 | 1.00 | 19.78 | A |
| ATOM | 1546 | CA | ALA | A | 199 | 98.921 | 85.448 | 32.814 | 1.00 | 19.70 | A |
| ATOM | 1547 | CB | ALA | A | 199 | 98.323 | 86.823 | 32.537 | 1.00 | 18.52 | A |
| ATOM | 1548 | C | ALA | A | 199 | 100.226 | 85.268 | 32.049 | 1.00 | 11.15 | A |
| ATOM | 1549 | O | ALA | A | 199 | 100.228 | 84.804 | 30.911 | 1.00 | 17.30 | A |
| ATOM | 1550 | N | GLY | A | 200 | 101.345 | 85.621 | 32.680 | 1.00 | 17.10 | A |
| ATOM | 1551 | CA | GLY | A | 200 | 102.617 | 85.447 | 32.002 | 1.00 | 19.39 | A |
| ATOM | 1552 | C | GLY | A | 200 | 102.800 | 83.976 | 31.647 | 1.00 | 21.92 | A |
| ATOM | 1553 | O | GLY | A | 200 | 103.113 | 83.615 | 30.486 | 1.00 | 19.30 | A |
| ATOM | 1554 | N | TYR | A | 201 | 102.578 | 83.097 | 32.628 | 1.00 | 17.66 | A |
| ATOM | 1555 | CA | TYR | A | 201 | 102.742 | 81.670 | 32.329 | 1.00 | 23.38 | A |
| ATOM | 1556 | CB | TYR | A | 201 | 102.550 | 80.804 | 33.587 | 1.00 | 17.53 | A |
| ATOM | 1557 | CG | TYR | A | 201 | 102.641 | 79.303 | 33.313 | 1.00 | 19.35 | A |
| ATOM | 1558 | CD1 | TYR | A | 201 | 103.714 | 78.768 | 32.608 | 1.00 | 20.15 | A |
| ATOM | 1559 | CE1 | TYR | A | 201 | 103.815 | 77.383 | 32.384 | 1.00 | 25.42 | A |
| ATOM | 1560 | CD2 | TYR | A | 201 | 101.663 | 78.420 | 33.788 | 1.00 | 26.23 | A |
| ATOM | 1561 | CE2 | TYR | A | 201 | 101.749 | 77.037 | 33.573 | 1.00 | 17.93 | A |
| ATOM | 1562 | CZ | TYR | A | 201 | 102.816 | 76.528 | 32.883 | 1.00 | 25.37 | A |
| ATOM | 1563 | OH | TYR | A | 201 | 102.908 | 75.171 | 32.690 | 1.00 | 24.20 | A |
| ATOM | 1564 | C | TYR | A | 201 | 101.740 | 81.238 | 31.242 | 1.00 | 23.90 | A |
| ATOM | 1565 | O | TYR | A | 201 | 102.098 | 80.503 | 30.312 | 1.00 | 18.43 | A |

TABLE 2-continued

| | | | | | | | | | | |
|---|---|---|---|---|---|---|---|---|---|---|
| ATOM | 1566 | N | ALA | A | 202 | 100.490 | 81.698 | 31.349 | 1.00 | 19.10 | A |
| ATOM | 1567 | CA | ALA | A | 202 | 99.484 | 81.306 | 30.367 | 1.00 | 22.19 | A |
| ATOM | 1568 | CB | ALA | A | 202 | 98.132 | 81.940 | 30.715 | 1.00 | 19.48 | A |
| ATOM | 1569 | C | ALA | A | 202 | 99.916 | 81.720 | 28.963 | 1.00 | 23.29 | A |
| ATOM | 1570 | O | ALA | A | 202 | 99.730 | 80.969 | 28.004 | 1.00 | 23.99 | A |
| ATOM | 1571 | N | LEU | A | 203 | 100.487 | 82.919 | 28.832 | 1.00 | 23.24 | A |
| ATOM | 1572 | CA | LEU | A | 203 | 100.929 | 83.371 | 27.510 | 1.00 | 23.06 | A |
| ATOM | 1573 | CB | LEU | A | 203 | 101.178 | 84.894 | 27.514 | 1.00 | 24.75 | A |
| ATOM | 1574 | CG | LEU | A | 203 | 99.907 | 85.744 | 27.664 | 1.00 | 23.34 | A |
| ATOM | 1575 | CD1 | LEU | A | 203 | 100.306 | 87.220 | 27.773 | 1.00 | 27.91 | A |
| ATOM | 1576 | CD2 | LEU | A | 203 | 98.963 | 85.548 | 26.489 | 1.00 | 21.31 | A |
| ATOM | 1577 | C | LEU | A | 203 | 102.182 | 82.611 | 27.060 | 1.00 | 20.01 | A |
| ATOM | 1578 | O | LEU | A | 203 | 102.321 | 82.260 | 25.892 | 1.00 | 22.51 | A |
| ATOM | 1579 | N | ALA | A | 204 | 103.087 | 82.325 | 27.985 | 1.00 | 20.31 | A |
| ATOM | 1580 | CA | ALA | A | 204 | 104.291 | 81.588 | 27.615 | 1.00 | 19.81 | A |
| ATOM | 1581 | CB | ALA | A | 204 | 105.193 | 81.391 | 28.819 | 1.00 | 16.54 | A |
| ATOM | 1582 | C | ALA | A | 204 | 103.893 | 80.248 | 27.035 | 1.00 | 22.33 | A |
| ATOM | 1583 | O | ALA | A | 204 | 104.477 | 79.812 | 26.060 | 1.00 | 23.53 | A |
| ATOM | 1584 | N | GLN | A | 205 | 102.881 | 79.588 | 27.607 | 1.00 | 21.05 | A |
| ATOM | 1585 | CA | GLN | A | 205 | 102.483 | 78.289 | 27.058 | 1.00 | 21.95 | A |
| ATOM | 1586 | CB | GLN | A | 205 | 101.309 | 77.717 | 27.840 | 1.00 | 18.19 | A |
| ATOM | 1587 | CG | GLN | A | 205 | 101.588 | 77.415 | 29.314 | 1.00 | 25.79 | A |
| ATOM | 1588 | CD | GLN | A | 205 | 100.431 | 76.681 | 29.929 | 1.00 | 29.43 | A |
| ATOM | 1589 | OE1 | GLN | A | 205 | 99.299 | 77.200 | 29.967 | 1.00 | 23.15 | A |
| ATOM | 1590 | NE2 | GLN | A | 205 | 100.685 | 75.451 | 30.399 | 1.00 | 23.34 | A |
| ATOM | 1591 | C | GLN | A | 205 | 102.068 | 78.366 | 25.586 | 1.00 | 27.79 | A |
| ATOM | 1592 | O | GLN | A | 205 | 102.165 | 77.392 | 24.847 | 1.00 | 24.19 | A |
| ATOM | 1593 | N | MET | A | 206 | 101.575 | 79.525 | 25.164 | 1.00 | 26.44 | A |
| ATOM | 1594 | CA | MET | A | 206 | 101.117 | 79.661 | 23.789 | 1.00 | 29.37 | A |
| ATOM | 1595 | CB | MET | A | 206 | 99.802 | 80.452 | 23.771 | 1.00 | 26.17 | A |
| ATOM | 1596 | CG | MET | A | 206 | 98.806 | 80.012 | 24.828 | 1.00 | 30.40 | A |
| ATOM | 1597 | SD | MET | A | 206 | 97.200 | 80.847 | 24.718 | 1.00 | 29.96 | A |
| ATOM | 1598 | CE | MET | A | 206 | 97.598 | 82.319 | 25.513 | 1.00 | 41.60 | A |
| ATOM | 1599 | C | MET | A | 206 | 102.138 | 80.349 | 22.889 | 1.00 | 29.92 | A |
| ATOM | 1600 | O | MET | A | 206 | 101.828 | 80.674 | 21.749 | 1.00 | 26.65 | A |
| ATOM | 1601 | N | GLY | A | 207 | 103.345 | 80.586 | 23.394 | 1.00 | 29.43 | A |
| ATOM | 1602 | CA | GLY | A | 207 | 104.352 | 81.278 | 22.593 | 1.00 | 26.83 | A |
| ATOM | 1603 | C | GLY | A | 207 | 104.014 | 82.753 | 22.378 | 1.00 | 34.90 | A |
| ATOM | 1604 | O | GLY | A | 207 | 104.534 | 83.393 | 21.464 | 1.00 | 27.87 | A |
| ATOM | 1605 | N | ARG | A | 208 | 103.171 | 83.313 | 23.244 | 1.00 | 27.86 | A |
| ATOM | 1606 | CA | ARG | A | 208 | 102.784 | 84.698 | 23.107 | 1.00 | 34.19 | A |
| ATOM | 1607 | CB | ARG | A | 208 | 101.256 | 84.788 | 23.147 | 1.00 | 33.23 | A |
| ATOM | 1608 | CG | ARG | A | 208 | 100.654 | 84.008 | 21.992 | 1.00 | 38.52 | A |
| ATOM | 1609 | CD | ARG | A | 208 | 99.191 | 83.574 | 22.162 | 1.00 | 42.22 | A |
| ATOM | 1610 | NE | ARG | A | 208 | 98.288 | 84.690 | 21.974 | 1.00 | 49.84 | A |
| ATOM | 1611 | CZ | ARG | A | 208 | 97.110 | 84.638 | 21.362 | 1.00 | 42.43 | A |
| ATOM | 1612 | NH1 | ARG | A | 208 | 96.641 | 83.509 | 20.856 | 1.00 | 38.92 | A |
| ATOM | 1613 | NH2 | ARG | A | 208 | 96.416 | 85.753 | 21.233 | 1.00 | 48.94 | A |
| ATOM | 1614 | C | ARG | A | 208 | 103.430 | 85.669 | 24.080 | 1.00 | 32.61 | A |
| ATOM | 1615 | O | ARG | A | 208 | 103.113 | 86.839 | 24.056 | 1.00 | 31.15 | A |
| ATOM | 1616 | N | LEU | A | 209 | 104.333 | 85.197 | 24.934 | 1.00 | 26.57 | A |
| ATOM | 1617 | CA | LEU | A | 209 | 104.990 | 86.093 | 25.879 | 1.00 | 31.14 | A |
| ATOM | 1618 | CB | LEU | A | 209 | 105.271 | 85.369 | 27.211 | 1.00 | 22.61 | A |
| ATOM | 1619 | CG | LEU | A | 209 | 105.798 | 86.228 | 28.366 | 1.00 | 35.65 | A |
| ATOM | 1620 | CD1 | LEU | A | 209 | 104.766 | 87.332 | 28.723 | 1.00 | 28.29 | A |
| ATOM | 1621 | CD2 | LEU | A | 209 | 106.083 | 85.364 | 29.589 | 1.00 | 28.03 | A |
| ATOM | 1622 | C | LEU | A | 209 | 106.285 | 86.516 | 25.178 | 1.00 | 32.66 | A |
| ATOM | 1623 | O | LEU | A | 209 | 107.305 | 85.851 | 25.289 | 1.00 | 32.28 | A |
| ATOM | 1624 | N | LYS | A | 210 | 106.212 | 87.611 | 24.426 | 1.00 | 32.19 | A |
| ATOM | 1625 | CA | LYS | A | 210 | 107.337 | 88.134 | 23.658 | 1.00 | 34.10 | A |
| ATOM | 1626 | CB | LYS | A | 210 | 107.118 | 87.884 | 22.169 | 1.00 | 39.67 | A |
| ATOM | 1627 | CG | LYS | A | 210 | 106.844 | 86.472 | 21.772 | 1.00 | 49.14 | A |
| ATOM | 1628 | CD | LYS | A | 210 | 106.174 | 86.418 | 20.399 | 1.00 | 51.11 | A |
| ATOM | 1629 | CE | LYS | A | 210 | 106.928 | 85.462 | 19.474 | 1.00 | 58.79 | A |
| ATOM | 1630 | NZ | LYS | A | 210 | 106.158 | 85.113 | 18.241 | 1.00 | 57.80 | A |
| ATOM | 1631 | C | LYS | A | 210 | 107.421 | 89.644 | 23.793 | 1.00 | 35.59 | A |
| ATOM | 1632 | O | LYS | A | 210 | 106.520 | 90.290 | 24.326 | 1.00 | 30.70 | A |
| ATOM | 1633 | N | GLY | A | 211 | 108.488 | 90.201 | 23.230 | 1.00 | 37.65 | A |
| ATOM | 1634 | CA | GLY | A | 211 | 108.675 | 91.642 | 23.212 | 1.00 | 34.24 | A |
| ATOM | 1635 | C | GLY | A | 211 | 108.350 | 92.423 | 24.453 | 1.00 | 26.73 | A |
| ATOM | 1636 | O | GLY | A | 211 | 108.884 | 92.158 | 25.535 | 1.00 | 31.87 | A |
| ATOM | 1637 | N | PRO | A | 212 | 107.471 | 93.420 | 24.329 | 1.00 | 35.92 | A |
| ATOM | 1638 | CD | PRO | A | 212 | 106.750 | 93.851 | 23.117 | 1.00 | 36.64 | A |
| ATOM | 1639 | CA | PRO | A | 212 | 107.096 | 94.252 | 25.480 | 1.00 | 31.77 | A |
| ATOM | 1640 | CB | PRO | A | 212 | 106.113 | 95.266 | 24.881 | 1.00 | 34.18 | A |
| ATOM | 1641 | CG | PRO | A | 212 | 106.506 | 95.315 | 23.424 | 1.00 | 36.29 | A |
| ATOM | 1642 | C | PRO | A | 212 | 106.456 | 93.397 | 26.585 | 1.00 | 29.56 | A |
| ATOM | 1643 | O | PRO | A | 212 | 106.700 | 93.630 | 27.767 | 1.00 | 27.62 | A |
| ATOM | 1644 | N | LEU | A | 213 | 105.644 | 92.416 | 26.205 | 1.00 | 26.27 | A |

TABLE 2-continued

| | | | | | | | | | | |
|---|---|---|---|---|---|---|---|---|---|---|
| ATOM | 1645 | CA | LEU | A | 213 | 105.036 | 91.569 | 27.232 | 1.00 | 30.09 | A |
| ATOM | 1646 | CB | LEU | A | 213 | 104.048 | 90.590 | 26.613 | 1.00 | 28.37 | A |
| ATOM | 1647 | CG | LEU | A | 213 | 102.726 | 91.280 | 26.223 | 1.00 | 31.49 | A |
| ATOM | 1648 | CD1 | LEU | A | 213 | 102.970 | 92.306 | 25.101 | 1.00 | 29.76 | A |
| ATOM | 1649 | CD2 | LEU | A | 213 | 101.738 | 90.239 | 25.745 | 1.00 | 29.45 | A |
| ATOM | 1650 | C | LEU | A | 213 | 106.112 | 90.830 | 28.032 | 1.00 | 22.05 | A |
| ATOM | 1651 | O | LEU | A | 213 | 106.139 | 90.886 | 29.250 | 1.00 | 25.06 | A |
| ATOM | 1652 | N | LEU | A | 214 | 107.023 | 90.176 | 27.331 | 1.00 | 29.37 | A |
| ATOM | 1653 | CA | LEU | A | 214 | 108.087 | 89.455 | 27.992 | 1.00 | 31.80 | A |
| ATOM | 1654 | CB | LEU | A | 214 | 109.030 | 88.849 | 26.952 | 1.00 | 27.44 | A |
| ATOM | 1655 | CG | LEU | A | 214 | 110.272 | 88.115 | 27.476 | 1.00 | 31.65 | A |
| ATOM | 1656 | CD1 | LEU | A | 214 | 109.889 | 86.976 | 28.445 | 1.00 | 25.93 | A |
| ATOM | 1657 | CD2 | LEU | A | 214 | 111.030 | 87.536 | 26.246 | 1.00 | 25.20 | A |
| ATOM | 1658 | C | LEU | A | 214 | 108.836 | 90.401 | 28.889 | 1.00 | 28.32 | A |
| ATOM | 1659 | O | LEU | A | 214 | 109.110 | 90.091 | 30.049 | 1.00 | 27.69 | A |
| ATOM | 1660 | N | ASN | A | 215 | 109.176 | 91.576 | 28.365 | 1.00 | 33.16 | A |
| ATOM | 1661 | CA | ASN | A | 215 | 109.912 | 92.553 | 29.175 | 1.00 | 30.08 | A |
| ATOM | 1662 | CB | ASN | A | 215 | 110.205 | 93.829 | 28.383 | 1.00 | 37.16 | A |
| ATOM | 1663 | CG | ASN | A | 215 | 110.980 | 94.815 | 29.205 | 1.00 | 39.99 | A |
| ATOM | 1664 | OD1 | ASN | A | 215 | 112.161 | 94.586 | 29.516 | 1.00 | 38.55 | A |
| ATOM | 1665 | ND2 | ASN | A | 215 | 110.311 | 95.895 | 29.629 | 1.00 | 39.72 | A |
| ATOM | 1666 | C | ASN | A | 215 | 109.189 | 92.951 | 30.453 | 1.00 | 26.60 | A |
| ATOM | 1667 | O | ASN | A | 215 | 109.789 | 93.055 | 31.522 | 1.00 | 27.99 | A |
| ATOM | 1668 | N | LYS | A | 216 | 107.891 | 93.204 | 30.346 | 1.00 | 29.96 | A |
| ATOM | 1669 | CA | LYS | A | 216 | 107.116 | 93.562 | 31.536 | 1.00 | 28.98 | A |
| ATOM | 1670 | CB | LYS | A | 216 | 105.669 | 93.842 | 31.124 | 1.00 | 27.44 | A |
| ATOM | 1671 | CG | LYS | A | 216 | 104.773 | 94.180 | 32.297 | 1.00 | 25.28 | A |
| ATOM | 1672 | CD | LYS | A | 216 | 103.384 | 94.434 | 31.799 | 1.00 | 29.65 | A |
| ATOM | 1673 | CE | LYS | A | 216 | 102.375 | 94.667 | 32.940 | 1.00 | 31.45 | A |
| ATOM | 1674 | NZ | LYS | A | 216 | 102.739 | 95.753 | 33.908 | 1.00 | 33.04 | A |
| ATOM | 1675 | C | LYS | A | 216 | 107.177 | 92.385 | 32.529 | 1.00 | 31.98 | A |
| ATOM | 1676 | O | LYS | A | 216 | 107.459 | 92.549 | 33.758 | 1.00 | 23.57 | A |
| ATOM | 1677 | N | PHE | A | 217 | 106.934 | 91.182 | 32.000 | 1.00 | 29.01 | A |
| ATOM | 1678 | CA | PHE | A | 217 | 106.984 | 90.002 | 32.862 | 1.00 | 23.20 | A |
| ATOM | 1679 | CB | PHE | A | 217 | 106.849 | 88.715 | 32.053 | 1.00 | 24.49 | A |
| ATOM | 1680 | CG | PHE | A | 217 | 107.137 | 87.453 | 32.855 | 1.00 | 30.86 | A |
| ATOM | 1681 | CD1 | PHE | A | 217 | 106.184 | 86.923 | 33.729 | 1.00 | 25.74 | A |
| ATOM | 1682 | CD2 | PHE | A | 217 | 108.350 | 86.762 | 32.682 | 1.00 | 33.51 | A |
| ATOM | 1683 | CE1 | PHE | A | 217 | 106.418 | 85.718 | 34.410 | 1.00 | 27.69 | A |
| ATOM | 1684 | CE2 | PHE | A | 217 | 108.598 | 85.553 | 33.359 | 1.00 | 30.90 | A |
| ATOM | 1685 | CZ | PHE | A | 217 | 107.620 | 85.029 | 34.228 | 1.00 | 26.68 | A |
| ATOM | 1686 | C | PHE | A | 217 | 108.277 | 89.949 | 33.655 | 1.00 | 25.85 | A |
| ATOM | 1687 | O | PHE | A | 217 | 108.255 | 89.888 | 34.892 | 1.00 | 26.90 | A |
| ATOM | 1688 | N | LEU | A | 218 | 109.417 | 90.010 | 32.967 | 1.00 | 29.26 | A |
| ATOM | 1689 | CA | LEU | A | 218 | 110.700 | 89.915 | 33.668 | 1.00 | 27.29 | A |
| ATOM | 1690 | CB | LEU | A | 218 | 111.853 | 89.742 | 32.671 | 1.00 | 29.60 | A |
| ATOM | 1691 | CG | LEU | A | 218 | 111.709 | 88.572 | 31.682 | 1.00 | 32.78 | A |
| ATOM | 1692 | CD1 | LEU | A | 218 | 112.729 | 88.696 | 30.537 | 1.00 | 27.26 | A |
| ATOM | 1693 | CD2 | LEU | A | 218 | 111.905 | 87.240 | 32.455 | 1.00 | 24.94 | A |
| ATOM | 1694 | C | LEU | A | 218 | 111.016 | 91.071 | 34.609 | 1.00 | 30.13 | A |
| ATOM | 1695 | O | LEU | A | 218 | 111.452 | 90.857 | 35.751 | 1.00 | 31.21 | A |
| ATOM | 1696 | N | THR | A | 219 | 110.798 | 92.295 | 34.141 | 1.00 | 31.78 | A |
| ATOM | 1697 | CA | THR | A | 219 | 111.097 | 93.480 | 34.958 | 1.00 | 35.74 | A |
| ATOM | 1698 | CB | THR | A | 219 | 111.082 | 94.772 | 34.097 | 1.00 | 33.10 | A |
| ATOM | 1699 | OG1 | THR | A | 219 | 109.778 | 94.981 | 33.536 | 1.00 | 31.70 | A |
| ATOM | 1700 | CG2 | THR | A | 219 | 112.106 | 94.645 | 32.947 | 1.00 | 34.85 | A |
| ATOM | 1701 | C | THR | A | 219 | 110.138 | 93.626 | 36.142 | 1.00 | 30.35 | A |
| ATOM | 1702 | O | THR | A | 219 | 110.431 | 94.334 | 37.101 | 1.00 | 30.89 | A |
| ATOM | 1703 | N | THR | A | 220 | 109.007 | 92.931 | 36.094 | 1.00 | 31.42 | A |
| ATOM | 1704 | CA | THR | A | 220 | 108.081 | 93.014 | 37.216 | 1.00 | 29.70 | A |
| ATOM | 1705 | CB | THR | A | 220 | 106.715 | 92.404 | 36.867 | 1.00 | 33.79 | A |
| ATOM | 1706 | OG1 | THR | A | 220 | 106.091 | 93.206 | 35.862 | 1.00 | 29.37 | A |
| ATOM | 1707 | CG2 | THR | A | 220 | 105.794 | 92.390 | 38.097 | 1.00 | 36.20 | A |
| ATOM | 1708 | C | THR | A | 220 | 108.666 | 92.314 | 38.437 | 1.00 | 30.26 | A |
| ATOM | 1709 | O | THR | A | 220 | 108.320 | 92.622 | 39.579 | 1.00 | 32.43 | A |
| ATOM | 1710 | N | ALA | A | 221 | 109.590 | 91.388 | 38.223 | 1.00 | 30.76 | A |
| ATOM | 1711 | CA | ALA | A | 221 | 110.140 | 90.711 | 39.383 | 1.00 | 33.31 | A |
| ATOM | 1712 | CB | ALA | A | 221 | 111.030 | 89.552 | 38.950 | 1.00 | 29.98 | A |
| ATOM | 1713 | C | ALA | A | 221 | 110.903 | 91.626 | 40.341 | 1.00 | 33.78 | A |
| ATOM | 1714 | O | ALA | A | 221 | 111.664 | 92.480 | 39.932 | 1.00 | 37.00 | A |
| ATOM | 1715 | N | LYS | A | 222 | 110.682 | 91.436 | 41.633 | 1.00 | 35.09 | A |
| ATOM | 1716 | CA | LYS | A | 222 | 111.385 | 92.202 | 42.645 | 1.00 | 35.18 | A |
| ATOM | 1717 | CB | LYS | A | 222 | 110.598 | 92.185 | 43.955 | 1.00 | 43.27 | A |
| ATOM | 1718 | CG | LYS | A | 222 | 111.085 | 93.202 | 44.970 | 1.00 | 51.49 | A |
| ATOM | 1719 | CD | LYS | A | 222 | 110.204 | 93.213 | 46.227 | 1.00 | 60.05 | A |
| ATOM | 1720 | CE | LYS | A | 222 | 110.402 | 94.508 | 47.040 | 1.00 | 63.10 | A |
| ATOM | 1721 | NZ | LYS | A | 222 | 111.855 | 94.791 | 47.290 | 1.00 | 63.82 | A |
| ATOM | 1722 | C | LYS | A | 222 | 112.740 | 91.534 | 42.864 | 1.00 | 39.12 | A |
| ATOM | 1723 | O | LYS | A | 222 | 112.811 | 90.313 | 43.020 | 1.00 | 31.62 | A |

TABLE 2-continued

| | | | | | | | | | | |
|---|---|---|---|---|---|---|---|---|---|---|
| ATOM | 1724 | N | ASP | A | 223 | 113.809 | 92.332 | 42.906 | 1.00 | 35.35 | A |
| ATOM | 1725 | CA | ASP | A | 223 | 115.168 | 91.818 | 43.097 | 1.00 | 33.61 | A |
| ATOM | 1726 | CB | ASP | A | 223 | 115.383 | 91.275 | 44.518 | 1.00 | 42.55 | A |
| ATOM | 1727 | CG | ASP | A | 223 | 115.290 | 92.349 | 45.583 | 1.00 | 50.58 | A |
| ATOM | 1728 | OD1 | ASP | A | 223 | 114.908 | 92.022 | 46.733 | 1.00 | 53.29 | A |
| ATOM | 1729 | OD2 | ASP | A | 223 | 115.609 | 93.518 | 45.282 | 1.00 | 58.47 | A |
| ATOM | 1730 | C | ASP | A | 223 | 115.448 | 90.696 | 42.115 | 1.00 | 31.36 | A |
| ATOM | 1731 | O | ASP | A | 223 | 116.247 | 89.804 | 42.408 | 1.00 | 33.77 | A |
| ATOM | 1732 | N | LYS | A | 224 | 114.786 | 90.737 | 40.962 | 1.00 | 30.77 | A |
| ATOM | 1733 | CA | LYS | A | 224 | 114.964 | 89.706 | 39.940 | 1.00 | 35.01 | A |
| ATOM | 1734 | CB | LYS | A | 224 | 116.370 | 89.807 | 39.382 | 1.00 | 36.58 | A |
| ATOM | 1735 | CG | LYS | A | 224 | 116.683 | 91.208 | 38.878 | 1.00 | 47.96 | A |
| ATOM | 1736 | CD | LYS | A | 224 | 118.037 | 91.262 | 38.207 | 1.00 | 52.39 | A |
| ATOM | 1737 | CE | LYS | A | 224 | 118.284 | 92.622 | 37.573 | 1.00 | 56.76 | A |
| ATOM | 1738 | NZ | LYS | A | 224 | 119.429 | 92.538 | 36.606 | 1.00 | 59.77 | A |
| ATOM | 1739 | C | LYS | A | 224 | 114.720 | 88.268 | 40.446 | 1.00 | 35.05 | A |
| ATOM | 1740 | O | LYS | A | 224 | 115.169 | 87.296 | 39.832 | 1.00 | 31.24 | A |
| ATOM | 1741 | N | ASN | A | 225 | 114.026 | 88.117 | 41.566 | 1.00 | 27.53 | A |
| ATOM | 1742 | CA | ASN | A | 225 | 113.811 | 86.756 | 42.053 | 1.00 | 33.64 | A |
| ATOM | 1743 | CB | ASN | A | 225 | 114.834 | 86.408 | 43.156 | 1.00 | 24.93 | A |
| ATOM | 1744 | CG | ASN | A | 225 | 114.614 | 87.203 | 44.456 | 1.00 | 32.88 | A |
| ATOM | 1745 | OD1 | ASN | A | 225 | 115.462 | 87.178 | 45.355 | 1.00 | 27.17 | A |
| ATOM | 1746 | ND2 | ASN | A | 225 | 113.477 | 87.896 | 44.563 | 1.00 | 23.33 | A |
| ATOM | 1747 | C | ASN | A | 225 | 112.391 | 86.412 | 42.506 | 1.00 | 32.97 | A |
| ATOM | 1748 | O | ASN | A | 225 | 112.114 | 85.247 | 42.781 | 1.00 | 29.39 | A |
| ATOM | 1749 | N | ARG | A | 226 | 111.481 | 87.385 | 42.587 | 1.00 | 27.45 | A |
| ATOM | 1750 | CA | ARG | A | 226 | 110.126 | 87.028 | 43.007 | 1.00 | 24.16 | A |
| ATOM | 1751 | CB | ARG | A | 226 | 110.055 | 86.996 | 44.528 | 1.00 | 29.81 | A |
| ATOM | 1752 | CG | ARG | A | 226 | 110.358 | 88.346 | 45.221 | 1.00 | 29.04 | A |
| ATOM | 1753 | CD | ARG | A | 226 | 110.419 | 88.133 | 46.717 | 1.00 | 29.72 | A |
| ATOM | 1754 | NE | ARG | A | 226 | 110.694 | 89.338 | 47.493 | 1.00 | 36.06 | A |
| ATOM | 1755 | CZ | ARG | A | 226 | 111.862 | 89.992 | 47.530 | 1.00 | 40.98 | A |
| ATOM | 1756 | NH1 | ARG | A | 226 | 112.909 | 89.572 | 46.818 | 1.00 | 42.69 | A |
| ATOM | 1757 | NH2 | ARG | A | 226 | 111.994 | 91.066 | 48.310 | 1.00 | 37.88 | A |
| ATOM | 1758 | C | ARG | A | 226 | 109.069 | 87.973 | 42.477 | 1.00 | 31.57 | A |
| ATOM | 1759 | O | ARG | A | 226 | 109.330 | 89.143 | 42.211 | 1.00 | 25.27 | A |
| ATOM | 1760 | N | TRP | A | 227 | 107.867 | 87.456 | 42.299 | 1.00 | 28.37 | A |
| ATOM | 1761 | CA | TRP | A | 227 | 106.761 | 88.275 | 41.851 | 1.00 | 23.41 | A |
| ATOM | 1762 | CB | TRP | A | 227 | 105.973 | 87.536 | 40.760 | 1.00 | 20.74 | A |
| ATOM | 1763 | CG | TRP | A | 227 | 106.620 | 87.650 | 39.384 | 1.00 | 26.80 | A |
| ATOM | 1764 | CD2 | TRP | A | 227 | 107.850 | 87.041 | 38.950 | 1.00 | 20.68 | A |
| ATOM | 1765 | CE2 | TRP | A | 227 | 108.105 | 87.500 | 37.630 | 1.00 | 22.35 | A |
| ATOM | 1766 | CE3 | TRP | A | 227 | 108.763 | 86.157 | 39.549 | 1.00 | 22.82 | A |
| ATOM | 1767 | CD1 | TRP | A | 227 | 106.189 | 88.430 | 38.330 | 1.00 | 21.29 | A |
| ATOM | 1768 | NE1 | TRP | A | 227 | 107.079 | 88.344 | 37.281 | 1.00 | 28.98 | A |
| ATOM | 1769 | CZ2 | TRP | A | 227 | 109.225 | 87.105 | 36.897 | 1.00 | 24.84 | A |
| ATOM | 1770 | CZ3 | TRP | A | 227 | 109.886 | 85.757 | 38.821 | 1.00 | 22.71 | A |
| ATOM | 1771 | CH2 | TRP | A | 227 | 110.105 | 86.232 | 37.505 | 1.00 | 26.46 | A |
| ATOM | 1772 | C | TRP | A | 227 | 105.918 | 88.521 | 43.097 | 1.00 | 31.42 | A |
| ATOM | 1773 | O | TRP | A | 227 | 105.162 | 87.658 | 43.531 | 1.00 | 30.37 | A |
| ATOM | 1774 | N | GLU | A | 228 | 106.081 | 89.674 | 43.723 | 1.00 | 30.19 | A |
| ATOM | 1775 | CA | GLU | A | 228 | 105.278 | 89.914 | 44.897 | 1.00 | 40.90 | A |
| ATOM | 1776 | CB | GLU | A | 228 | 106.105 | 89.747 | 46.169 | 1.00 | 43.17 | A |
| ATOM | 1777 | CG | GLU | A | 228 | 107.143 | 90.767 | 46.430 | 1.00 | 49.83 | A |
| ATOM | 1778 | CD | GLU | A | 228 | 107.521 | 90.796 | 47.904 | 1.00 | 51.45 | A |
| ATOM | 1779 | OE1 | GLU | A | 228 | 107.955 | 89.753 | 48.428 | 1.00 | 41.85 | A |
| ATOM | 1780 | OE2 | GLU | A | 228 | 107.375 | 91.865 | 48.534 | 1.00 | 56.43 | A |
| ATOM | 1781 | C | GLU | A | 228 | 104.555 | 91.248 | 44.907 | 1.00 | 43.90 | A |
| ATOM | 1782 | O | GLU | A | 228 | 105.015 | 92.225 | 44.320 | 1.00 | 38.10 | A |
| ATOM | 1783 | N | ASP | A | 229 | 103.398 | 91.261 | 45.559 | 1.00 | 45.53 | A |
| ATOM | 1784 | CA | ASP | A | 229 | 102.606 | 92.462 | 45.661 | 1.00 | 49.47 | A |
| ATOM | 1785 | CB | ASP | A | 229 | 101.178 | 92.149 | 45.244 | 1.00 | 48.06 | A |
| ATOM | 1786 | CG | ASP | A | 229 | 101.057 | 91.972 | 43.727 | 1.00 | 50.49 | A |
| ATOM | 1787 | OD1 | ASP | A | 229 | 101.471 | 92.917 | 43.003 | 1.00 | 49.52 | A |
| ATOM | 1788 | OD2 | ASP | A | 229 | 100.573 | 90.910 | 43.263 | 1.00 | 34.83 | A |
| ATOM | 1789 | C | ASP | A | 229 | 102.716 | 92.944 | 47.097 | 1.00 | 56.94 | A |
| ATOM | 1790 | O | ASP | A | 229 | 102.511 | 92.165 | 48.033 | 1.00 | 47.42 | A |
| ATOM | 1791 | N | PRO | A | 230 | 103.104 | 94.229 | 47.290 | 1.00 | 64.41 | A |
| ATOM | 1792 | CD | PRO | A | 230 | 103.414 | 95.217 | 46.238 | 1.00 | 66.97 | A |
| ATOM | 1793 | CA | PRO | A | 230 | 103.261 | 94.830 | 48.625 | 1.00 | 64.83 | A |
| ATOM | 1794 | CB | PRO | A | 230 | 103.783 | 96.239 | 48.322 | 1.00 | 68.61 | A |
| ATOM | 1795 | CG | PRO | A | 230 | 103.206 | 96.530 | 46.968 | 1.00 | 71.34 | A |
| ATOM | 1796 | C | PRO | A | 230 | 101.958 | 94.835 | 49.400 | 1.00 | 61.61 | A |
| ATOM | 1797 | O | PRO | A | 230 | 100.886 | 94.963 | 48.819 | 1.00 | 59.14 | A |
| ATOM | 1798 | N | GLY | A | 231 | 102.066 | 94.671 | 50.713 | 1.00 | 64.01 | A |
| ATOM | 1799 | CA | GLY | A | 231 | 100.884 | 94.647 | 51.552 | 1.00 | 69.86 | A |
| ATOM | 1800 | C | GLY | A | 231 | 100.197 | 93.305 | 51.447 | 1.00 | 70.74 | A |
| ATOM | 1801 | O | GLY | A | 231 | 99.407 | 93.085 | 50.526 | 1.00 | 71.02 | A |
| ATOM | 1802 | N | LYS | A | 232 | 100.487 | 92.408 | 52.388 | 1.00 | 74.07 | A |

TABLE 2-continued

| ATOM | 1803 | CA | LYS | A | 232 | 99.899 | 91.068 | 52.345 | 1.00 | 77.87 | A |
| --- | --- | --- | --- | --- | --- | --- | --- | --- | --- | --- | --- |
| ATOM | 1804 | CB | LYS | A | 232 | 98.369 | 91.170 | 52.297 | 1.00 | 80.70 | A |
| ATOM | 1805 | CG | LYS | A | 232 | 97.722 | 91.539 | 53.624 | 1.00 | 83.42 | A |
| ATOM | 1806 | CD | LYS | A | 232 | 97.830 | 90.372 | 54.609 | 1.00 | 85.26 | A |
| ATOM | 1807 | CE | LYS | A | 232 | 97.028 | 90.622 | 55.884 | 1.00 | 85.21 | A |
| ATOM | 1808 | NZ | LYS | A | 232 | 97.018 | 89.416 | 56.769 | 1.00 | 86.74 | A |
| ATOM | 1809 | C | LYS | A | 232 | 100.443 | 90.345 | 51.087 | 1.00 | 77.00 | A |
| ATOM | 1810 | O | LYS | A | 232 | 99.701 | 89.982 | 50.156 | 1.00 | 76.48 | A |
| ATOM | 1811 | N | GLN | A | 233 | 101.762 | 90.168 | 51.071 | 1.00 | 70.42 | A |
| ATOM | 1812 | CA | GLN | A | 233 | 102.447 | 89.508 | 49.971 | 1.00 | 64.94 | A |
| ATOM | 1813 | CB | GLN | A | 233 | 103.895 | 89.999 | 49.916 | 1.00 | 65.15 | A |
| ATOM | 1814 | CG | GLN | A | 233 | 104.660 | 89.787 | 51.211 | 1.00 | 68.22 | A |
| ATOM | 1815 | CD | GLN | A | 233 | 105.334 | 91.059 | 51.716 | 1.00 | 73.51 | A |
| ATOM | 1816 | OE1 | GLN | A | 233 | 106.256 | 91.581 | 51.087 | 1.00 | 79.17 | A |
| ATOM | 1817 | NE2 | GLN | A | 233 | 104.869 | 91.567 | 52.859 | 1.00 | 73.37 | A |
| ATOM | 1818 | C | GLN | A | 233 | 102.416 | 88.003 | 50.192 | 1.00 | 62.45 | A |
| ATOM | 1819 | O | GLN | A | 233 | 103.423 | 87.332 | 50.007 | 1.00 | 59.36 | A |
| ATOM | 1820 | N | LEU | A | 234 | 101.267 | 87.473 | 50.604 | 1.00 | 59.16 | A |
| ATOM | 1821 | CA | LEU | A | 234 | 101.163 | 86.040 | 50.844 | 1.00 | 57.14 | A |
| ATOM | 1822 | CB | LEU | A | 234 | 100.011 | 85.733 | 51.808 | 1.00 | 58.67 | A |
| ATOM | 1823 | CG | LEU | A | 234 | 98.593 | 86.146 | 51.406 | 1.00 | 59.33 | A |
| ATOM | 1824 | CD1 | LEU | A | 234 | 97.566 | 85.419 | 52.300 | 1.00 | 55.69 | A |
| ATOM | 1825 | CD2 | LEU | A | 234 | 98.455 | 87.680 | 51.521 | 1.00 | 56.83 | A |
| ATOM | 1826 | C | LEU | A | 234 | 101.004 | 85.222 | 49.548 | 1.00 | 56.11 | A |
| ATOM | 1827 | O | LEU | A | 234 | 101.067 | 83.977 | 49.572 | 1.00 | 58.17 | A |
| ATOM | 1828 | N | TYR | A | 235 | 100.835 | 85.906 | 48.415 | 1.00 | 43.77 | A |
| ATOM | 1829 | CA | TYR | A | 235 | 100.694 | 85.205 | 47.142 | 1.00 | 33.72 | A |
| ATOM | 1830 | CB | TYR | A | 235 | 99.701 | 85.954 | 46.262 | 1.00 | 29.90 | A |
| ATOM | 1831 | CG | TYR | A | 235 | 98.416 | 86.253 | 46.982 | 1.00 | 31.05 | A |
| ATOM | 1832 | CD1 | TYR | A | 235 | 97.805 | 87.505 | 46.872 | 1.00 | 32.37 | A |
| ATOM | 1833 | CE1 | TYR | A | 235 | 96.614 | 87.785 | 47.530 | 1.00 | 27.48 | A |
| ATOM | 1834 | CD2 | TYR | A | 235 | 97.799 | 85.273 | 47.779 | 1.00 | 29.78 | A |
| ATOM | 1835 | CE2 | TYR | A | 235 | 96.615 | 85.533 | 48.437 | 1.00 | 27.57 | A |
| ATOM | 1836 | CZ | TYR | A | 235 | 96.026 | 86.789 | 48.303 | 1.00 | 33.50 | A |
| ATOM | 1837 | OH | TYR | A | 235 | 94.822 | 87.009 | 48.889 | 1.00 | 30.21 | A |
| ATOM | 1838 | C | TYR | A | 235 | 102.015 | 85.112 | 46.401 | 1.00 | 31.37 | A |
| ATOM | 1839 | O | TYR | A | 235 | 102.027 | 84.671 | 45.262 | 1.00 | 28.36 | A |
| ATOM | 1840 | N | ASN | A | 236 | 103.130 | 85.519 | 47.023 | 1.00 | 24.27 | A |
| ATOM | 1841 | CA | ASN | A | 236 | 104.399 | 85.505 | 46.292 | 1.00 | 20.44 | A |
| ATOM | 1842 | CB | ASN | A | 236 | 105.472 | 86.335 | 47.017 | 1.00 | 25.88 | A |
| ATOM | 1843 | CG | ASN | A | 236 | 105.651 | 85.944 | 48.484 | 1.00 | 30.25 | A |
| ATOM | 1844 | OD1 | ASN | A | 236 | 104.890 | 85.148 | 49.032 | 1.00 | 39.82 | A |
| ATOM | 1845 | ND2 | ASN | A | 236 | 106.644 | 86.543 | 49.133 | 1.00 | 28.85 | A |
| ATOM | 1846 | C | ASN | A | 236 | 104.955 | 84.137 | 45.960 | 1.00 | 20.82 | A |
| ATOM | 1847 | O | ASN | A | 236 | 105.588 | 83.968 | 44.919 | 1.00 | 20.31 | A |
| ATOM | 1848 | N | VAL | A | 237 | 104.761 | 83.155 | 46.831 | 1.00 | 20.09 | A |
| ATOM | 1849 | CA | VAL | A | 237 | 105.272 | 81.827 | 46.501 | 1.00 | 21.36 | A |
| ATOM | 1850 | CB | VAL | A | 237 | 105.154 | 80.861 | 47.704 | 1.00 | 18.71 | A |
| ATOM | 1851 | CG1 | VAL | A | 237 | 105.601 | 79.471 | 47.312 | 1.00 | 14.08 | A |
| ATOM | 1852 | CG2 | VAL | A | 237 | 106.052 | 81.376 | 48.846 | 1.00 | 27.50 | A |
| ATOM | 1853 | C | VAL | A | 237 | 104.481 | 81.299 | 45.301 | 1.00 | 18.56 | A |
| ATOM | 1854 | O | VAL | A | 237 | 105.063 | 80.794 | 44.343 | 1.00 | 18.22 | A |
| ATOM | 1855 | N | GLU | A | 238 | 103.162 | 81.479 | 45.323 | 1.00 | 17.79 | A |
| ATOM | 1856 | CA | GLU | A | 238 | 102.315 | 80.996 | 44.239 | 1.00 | 16.12 | A |
| ATOM | 1857 | CB | GLU | A | 238 | 100.824 | 81.147 | 44.601 | 1.00 | 17.19 | A |
| ATOM | 1858 | CG | GLU | A | 238 | 99.867 | 80.782 | 43.468 | 1.00 | 14.34 | A |
| ATOM | 1859 | CD | GLU | A | 238 | 98.471 | 81.420 | 43.650 | 1.00 | 11.06 | A |
| ATOM | 1860 | OE1 | GLU | A | 238 | 98.241 | 82.107 | 44.686 | 1.00 | 19.48 | A |
| ATOM | 1861 | OE2 | GLU | A | 238 | 97.621 | 81.200 | 42.783 | 1.00 | 16.80 | A |
| ATOM | 1862 | C | GLU | A | 238 | 102.628 | 81.744 | 42.958 | 1.00 | 20.25 | A |
| ATOM | 1863 | O | GLU | A | 238 | 102.845 | 81.130 | 41.897 | 1.00 | 18.11 | A |
| ATOM | 1864 | N | ALA | A | 239 | 102.684 | 83.071 | 43.036 | 1.00 | 18.43 | A |
| ATOM | 1865 | CA | ALA | A | 239 | 102.975 | 83.867 | 41.835 | 1.00 | 17.27 | A |
| ATOM | 1866 | CB | ALA | A | 239 | 102.988 | 85.340 | 42.221 | 1.00 | 17.99 | A |
| ATOM | 1867 | C | ALA | A | 239 | 104.334 | 83.488 | 41.251 | 1.00 | 16.91 | A |
| ATOM | 1868 | O | ALA | A | 239 | 104.510 | 83.248 | 40.038 | 1.00 | 18.31 | A |
| ATOM | 1869 | N | THR | A | 240 | 105.312 | 83.398 | 42.136 | 1.00 | 12.73 | A |
| ATOM | 1870 | CA | THR | A | 240 | 106.678 | 83.101 | 41.673 | 1.00 | 16.78 | A |
| ATOM | 1871 | CB | THR | A | 240 | 107.675 | 83.337 | 42.835 | 1.00 | 20.26 | A |
| ATOM | 1872 | OG1 | THR | A | 240 | 107.499 | 84.683 | 43.322 | 1.00 | 20.23 | A |
| ATOM | 1873 | CG2 | THR | A | 240 | 109.110 | 83.187 | 42.382 | 1.00 | 15.53 | A |
| ATOM | 1874 | C | THR | A | 240 | 106.790 | 81.686 | 41.087 | 1.00 | 23.59 | A |
| ATOM | 1875 | O | THR | A | 240 | 107.639 | 81.437 | 40.215 | 1.00 | 20.02 | A |
| ATOM | 1876 | N | SER | A | 241 | 105.941 | 80.760 | 41.552 | 1.00 | 15.58 | A |
| ATOM | 1877 | CA | SER | A | 241 | 105.991 | 79.381 | 41.022 | 1.00 | 17.43 | A |
| ATOM | 1878 | CB | SER | A | 241 | 105.162 | 78.441 | 41.906 | 1.00 | 11.67 | A |
| ATOM | 1879 | OG | SER | A | 241 | 105.715 | 78.363 | 43.233 | 1.00 | 15.93 | A |
| ATOM | 1880 | C | SER | A | 241 | 105.438 | 79.442 | 39.595 | 1.00 | 17.10 | A |
| ATOM | 1881 | O | SER | A | 241 | 105.980 | 78.810 | 38.675 | 1.00 | 18.31 | A |

TABLE 2-continued

| ATOM | 1882 | N | TYR | A | 242 | 104.365 | 80.217 | 39.383 | 1.00 | 18.46 | A |
|---|---|---|---|---|---|---|---|---|---|---|---|
| ATOM | 1883 | CA | TYR | A | 242 | 103.846 | 80.367 | 38.013 | 1.00 | 18.91 | A |
| ATOM | 1884 | CB | TYR | A | 242 | 102.622 | 81.307 | 37.942 | 1.00 | 15.98 | A |
| ATOM | 1885 | CG | TYR | A | 242 | 101.263 | 80.652 | 38.192 | 1.00 | 20.69 | A |
| ATOM | 1886 | CD1 | TYR | A | 242 | 100.766 | 79.658 | 37.338 | 1.00 | 13.29 | A |
| ATOM | 1887 | CE1 | TYR | A | 242 | 99.504 | 79.043 | 37.567 | 1.00 | 18.13 | A |
| ATOM | 1888 | CD2 | TYR | A | 242 | 100.486 | 81.030 | 39.286 | 1.00 | 16.91 | A |
| ATOM | 1889 | CE2 | TYR | A | 242 | 99.246 | 80.434 | 39.537 | 1.00 | 11.03 | A |
| ATOM | 1890 | CZ | TYR | A | 242 | 98.759 | 79.444 | 38.669 | 1.00 | 19.17 | A |
| ATOM | 1891 | OH | TYR | A | 242 | 97.505 | 78.916 | 38.898 | 1.00 | 17.62 | A |
| ATOM | 1892 | C | TYR | A | 242 | 104.949 | 81.000 | 37.157 | 1.00 | 23.33 | A |
| ATOM | 1893 | O | TYR | A | 242 | 105.190 | 80.603 | 35.997 | 1.00 | 22.29 | A |
| ATOM | 1894 | N | ALA | A | 243 | 105.613 | 82.004 | 37.717 | 1.00 | 18.34 | A |
| ATOM | 1895 | CA | ALA | A | 243 | 106.634 | 82.697 | 36.929 | 1.00 | 18.89 | A |
| ATOM | 1896 | CB | ALA | A | 243 | 107.164 | 83.901 | 37.694 | 1.00 | 19.57 | A |
| ATOM | 1897 | C | ALA | A | 243 | 107.772 | 81.717 | 36.608 | 1.00 | 21.61 | A |
| ATOM | 1898 | O | ALA | A | 243 | 108.290 | 81.731 | 35.494 | 1.00 | 21.45 | A |
| ATOM | 1899 | N | LEU | A | 244 | 108.145 | 80.861 | 37.565 | 1.00 | 16.89 | A |
| ATOM | 1900 | CA | LEU | A | 244 | 109.239 | 79.899 | 37.309 | 1.00 | 20.89 | A |
| ATOM | 1901 | CB | LEU | A | 244 | 109.588 | 79.103 | 38.587 | 1.00 | 16.59 | A |
| ATOM | 1902 | CG | LEU | A | 244 | 110.578 | 77.933 | 38.379 | 1.00 | 21.10 | A |
| ATOM | 1903 | CD1 | LEU | A | 244 | 111.844 | 78.449 | 37.632 | 1.00 | 20.05 | A |
| ATOM | 1904 | CD2 | LEU | A | 244 | 110.974 | 77.326 | 39.777 | 1.00 | 12.73 | A |
| ATOM | 1905 | C | LEU | A | 244 | 108.813 | 78.947 | 36.182 | 1.00 | 18.67 | A |
| ATOM | 1906 | O | LEU | A | 244 | 109.610 | 78.556 | 35.296 | 1.00 | 19.02 | A |
| ATOM | 1907 | N | LEU | A | 245 | 107.542 | 78.574 | 36.181 | 1.00 | 17.68 | A |
| ATOM | 1908 | CA | LEU | A | 245 | 107.074 | 77.709 | 35.107 | 1.00 | 15.21 | A |
| ATOM | 1909 | CB | LEU | A | 245 | 105.628 | 77.214 | 35.404 | 1.00 | 20.70 | A |
| ATOM | 1910 | CG | LEU | A | 245 | 105.557 | 76.123 | 36.506 | 1.00 | 21.76 | A |
| ATOM | 1911 | CD1 | LEU | A | 245 | 104.108 | 75.956 | 36.996 | 1.00 | 26.34 | A |
| ATOM | 1912 | CD2 | LEU | A | 245 | 106.100 | 74.778 | 35.969 | 1.00 | 16.28 | A |
| ATOM | 1913 | C | LEU | A | 245 | 107.147 | 78.449 | 33.746 | 1.00 | 19.30 | A |
| ATOM | 1914 | O | LEU | A | 245 | 107.449 | 77.831 | 32.717 | 1.00 | 20.79 | A |
| ATOM | 1915 | N | ALA | A | 246 | 106.874 | 79.759 | 33.724 | 1.00 | 18.12 | A |
| ATOM | 1916 | CA | ALA | A | 246 | 106.959 | 80.501 | 32.461 | 1.00 | 18.77 | A |
| ATOM | 1917 | CB | ALA | A | 246 | 106.367 | 81.944 | 32.622 | 1.00 | 16.45 | A |
| ATOM | 1918 | C | ALA | A | 246 | 108.431 | 80.558 | 32.009 | 1.00 | 14.13 | A |
| ATOM | 1919 | O | ALA | A | 246 | 108.738 | 80.352 | 30.823 | 1.00 | 19.75 | A |
| ATOM | 1920 | N | LEU | A | 247 | 109.337 | 80.835 | 32.944 | 1.00 | 15.08 | A |
| ATOM | 1921 | CA | LEU | A | 247 | 110.769 | 80.899 | 32.620 | 1.00 | 18.36 | A |
| ATOM | 1922 | CB | LEU | A | 247 | 111.567 | 81.267 | 33.866 | 1.00 | 19.66 | A |
| ATOM | 1923 | CG | LEU | A | 247 | 111.365 | 82.715 | 34.363 | 1.00 | 20.28 | A |
| ATOM | 1924 | CD1 | LEU | A | 247 | 111.874 | 82.820 | 35.813 | 1.00 | 17.02 | A |
| ATOM | 1925 | CD2 | LEU | A | 247 | 112.098 | 83.725 | 33.441 | 1.00 | 21.44 | A |
| ATOM | 1926 | C | LEU | A | 247 | 111.263 | 79.557 | 32.058 | 1.00 | 23.09 | A |
| ATOM | 1927 | O | LEU | A | 247 | 112.038 | 79.526 | 31.092 | 1.00 | 25.65 | A |
| ATOM | 1928 | N | LEU | A | 248 | 110.796 | 78.447 | 32.624 | 1.00 | 22.19 | A |
| ATOM | 1929 | CA | LEU | A | 248 | 111.239 | 77.124 | 32.123 | 1.00 | 28.05 | A |
| ATOM | 1930 | CB | LEU | A | 248 | 110.815 | 75.977 | 33.081 | 1.00 | 24.02 | A |
| ATOM | 1931 | CG | LEU | A | 248 | 111.577 | 75.998 | 34.437 | 1.00 | 25.05 | A |
| ATOM | 1932 | CD1 | LEU | A | 248 | 110.943 | 75.071 | 35.436 | 1.00 | 24.06 | A |
| ATOM | 1933 | CD2 | LEU | A | 248 | 113.066 | 75.617 | 34.216 | 1.00 | 15.01 | A |
| ATOM | 1934 | C | LEU | A | 248 | 110.657 | 76.914 | 30.745 | 1.00 | 23.21 | A |
| ATOM | 1935 | O | LEU | A | 248 | 111.313 | 76.391 | 29.847 | 1.00 | 25.42 | A |
| ATOM | 1936 | N | GLN | A | 249 | 109.416 | 77.324 | 30.572 | 1.00 | 22.82 | A |
| ATOM | 1937 | CA | GLN | A | 249 | 108.757 | 77.197 | 29.281 | 1.00 | 22.86 | A |
| ATOM | 1938 | CB | GLN | A | 249 | 107.314 | 77.694 | 29.377 | 1.00 | 27.58 | A |
| ATOM | 1939 | CG | GLN | A | 249 | 106.526 | 77.545 | 28.085 | 1.00 | 34.66 | A |
| ATOM | 1940 | CD | GLN | A | 249 | 106.170 | 76.085 | 27.789 | 1.00 | 39.67 | A |
| ATOM | 1941 | OE1 | GLN | A | 249 | 105.459 | 75.434 | 28.554 | 1.00 | 44.37 | A |
| ATOM | 1942 | NE2 | GLN | A | 249 | 106.672 | 75.575 | 26.687 | 1.00 | 37.71 | A |
| ATOM | 1943 | C | GLN | A | 249 | 109.513 | 78.042 | 28.226 | 1.00 | 27.62 | A |
| ATOM | 1944 | O | GLN | A | 249 | 109.623 | 77.655 | 27.079 | 1.00 | 24.60 | A |
| ATOM | 1945 | N | LEU | A | 250 | 110.009 | 79.207 | 28.618 | 1.00 | 32.08 | A |
| ATOM | 1946 | CA | LEU | A | 250 | 110.740 | 80.080 | 27.700 | 1.00 | 30.59 | A |
| ATOM | 1947 | CB | LEU | A | 250 | 110.736 | 81.501 | 28.247 | 1.00 | 28.66 | A |
| ATOM | 1948 | CG | LEU | A | 250 | 109.401 | 82.220 | 28.410 | 1.00 | 30.11 | A |
| ATOM | 1949 | CD1 | LEU | A | 250 | 109.530 | 83.326 | 29.426 | 1.00 | 29.85 | A |
| ATOM | 1950 | CD2 | LEU | A | 250 | 108.960 | 82.728 | 27.062 | 1.00 | 28.49 | A |
| ATOM | 1951 | C | LEU | A | 250 | 112.207 | 79.647 | 27.551 | 1.00 | 36.31 | A |
| ATOM | 1952 | O | LEU | A | 250 | 112.938 | 80.189 | 26.708 | 1.00 | 31.07 | A |
| ATOM | 1953 | N | LYS | A | 251 | 112.627 | 78.682 | 28.373 | 1.00 | 30.98 | A |
| ATOM | 1954 | CA | LYS | A | 251 | 114.016 | 78.226 | 28.410 | 1.00 | 31.57 | A |
| ATOM | 1955 | CB | LYS | A | 251 | 114.420 | 77.554 | 27.098 | 1.00 | 32.85 | A |
| ATOM | 1956 | CG | LYS | A | 251 | 113.715 | 76.232 | 26.890 | 1.00 | 42.53 | A |
| ATOM | 1957 | CD | LYS | A | 251 | 114.060 | 75.631 | 25.555 | 1.00 | 46.71 | A |
| ATOM | 1958 | CE | LYS | A | 251 | 113.233 | 74.376 | 25.314 | 1.00 | 54.63 | A |
| ATOM | 1959 | NZ | LYS | A | 251 | 113.214 | 73.987 | 23.864 | 1.00 | 58.25 | A |
| ATOM | 1960 | C | LYS | A | 251 | 114.943 | 79.412 | 28.712 | 1.00 | 31.12 | A |

TABLE 2-continued

| | | | | | | | | | | |
|---|---|---|---|---|---|---|---|---|---|---|
| ATOM | 1961 | O | LYS | A | 251 | 116.102 | 79.442 | 28.301 | 1.00 | 32.07 | A |
| ATOM | 1962 | N | ASP | A | 252 | 114.438 | 80.376 | 29.470 | 1.00 | 29.36 | A |
| ATOM | 1963 | CA | ASP | A | 252 | 115.239 | 81.521 | 29.830 | 1.00 | 28.62 | A |
| ATOM | 1964 | CB | ASP | A | 252 | 114.346 | 82.738 | 30.091 | 1.00 | 33.61 | A |
| ATOM | 1965 | CG | ASP | A | 252 | 115.150 | 84.017 | 30.237 | 1.00 | 37.36 | A |
| ATOM | 1966 | OD1 | ASP | A | 252 | 116.328 | 83.990 | 29.839 | 1.00 | 49.12 | A |
| ATOM | 1967 | OD2 | ASP | A | 252 | 114.624 | 85.048 | 30.725 | 1.00 | 34.68 | A |
| ATOM | 1968 | C | ASP | A | 252 | 116.097 | 81.183 | 31.046 | 1.00 | 31.99 | A |
| ATOM | 1969 | O | ASP | A | 252 | 115.933 | 81.742 | 32.139 | 1.00 | 30.76 | A |
| ATOM | 1970 | N | PHE | A | 253 | 117.069 | 80.301 | 30.819 | 1.00 | 31.40 | A |
| ATOM | 1971 | CA | PHE | A | 253 | 117.935 | 79.818 | 31.873 | 1.00 | 27.03 | A |
| ATOM | 1972 | CB | PHE | A | 253 | 118.786 | 78.674 | 31.338 | 1.00 | 33.08 | A |
| ATOM | 1973 | CG | PHE | A | 253 | 117.995 | 77.601 | 30.649 | 1.00 | 33.23 | A |
| ATOM | 1974 | CD1 | PHE | A | 253 | 116.815 | 77.109 | 31.205 | 1.00 | 35.86 | A |
| ATOM | 1975 | CD2 | PHE | A | 253 | 118.460 | 77.032 | 29.463 | 1.00 | 34.30 | A |
| ATOM | 1976 | CE1 | PHE | A | 253 | 116.115 | 76.061 | 30.593 | 1.00 | 35.38 | A |
| ATOM | 1977 | CE2 | PHE | A | 253 | 117.762 | 75.987 | 28.853 | 1.00 | 30.02 | A |
| ATOM | 1978 | CZ | PHE | A | 253 | 116.593 | 75.504 | 29.421 | 1.00 | 32.95 | A |
| ATOM | 1979 | C | PHE | A | 253 | 118.823 | 80.800 | 32.619 | 1.00 | 36.01 | A |
| ATOM | 1980 | O | PHE | A | 253 | 119.249 | 80.512 | 33.746 | 1.00 | 32.40 | A |
| ATOM | 1981 | N | ASP | A | 254 | 119.124 | 81.951 | 32.028 | 1.00 | 33.64 | A |
| ATOM | 1982 | CA | ASP | A | 254 | 119.986 | 82.905 | 32.728 | 1.00 | 37.81 | A |
| ATOM | 1983 | CB | ASP | A | 254 | 120.588 | 83.884 | 31.729 | 1.00 | 49.35 | A |
| ATOM | 1984 | CG | ASP | A | 254 | 119.539 | 84.520 | 30.871 | 1.00 | 65.34 | A |
| ATOM | 1985 | OD1 | ASP | A | 254 | 118.936 | 83.793 | 30.046 | 1.00 | 75.38 | A |
| ATOM | 1986 | OD2 | ASP | A | 254 | 119.293 | 85.740 | 31.023 | 1.00 | 75.70 | A |
| ATOM | 1987 | C | ASP | A | 254 | 119.210 | 83.669 | 33.802 | 1.00 | 31.65 | A |
| ATOM | 1988 | O | ASP | A | 254 | 119.791 | 84.196 | 34.752 | 1.00 | 30.63 | A |
| ATOM | 1989 | N | PHE | A | 255 | 117.892 | 83.728 | 33.652 | 1.00 | 28.90 | A |
| ATOM | 1990 | CA | PHE | A | 255 | 117.058 | 84.442 | 34.616 | 1.00 | 29.25 | A |
| ATOM | 1991 | CB | PHE | A | 255 | 115.881 | 85.100 | 33.892 | 1.00 | 28.92 | A |
| ATOM | 1992 | CG | PHE | A | 255 | 115.234 | 86.213 | 34.671 | 1.00 | 38.13 | A |
| ATOM | 1993 | CD1 | PHE | A | 255 | 114.281 | 85.947 | 35.643 | 1.00 | 31.13 | A |
| ATOM | 1994 | CD2 | PHE | A | 255 | 115.596 | 87.546 | 34.432 | 1.00 | 39.51 | A |
| ATOM | 1995 | CE1 | PHE | A | 255 | 113.695 | 86.988 | 36.366 | 1.00 | 38.06 | A |
| ATOM | 1996 | CE2 | PHE | A | 255 | 115.017 | 88.589 | 35.150 | 1.00 | 35.88 | A |
| ATOM | 1997 | CZ | PHE | A | 255 | 114.063 | 88.313 | 36.120 | 1.00 | 39.10 | A |
| ATOM | 1998 | C | PHE | A | 255 | 116.523 | 83.530 | 35.721 | 1.00 | 28.15 | A |
| ATOM | 1999 | O | PHE | A | 255 | 116.078 | 83.996 | 36.767 | 1.00 | 27.42 | A |
| ATOM | 2000 | N | VAL | A | 256 | 116.562 | 82.228 | 35.482 | 1.00 | 24.41 | A |
| ATOM | 2001 | CA | VAL | A | 256 | 116.040 | 81.257 | 36.453 | 1.00 | 21.90 | A |
| ATOM | 2002 | CB | VAL | A | 256 | 116.017 | 79.838 | 35.789 | 1.00 | 26.19 | A |
| ATOM | 2003 | CG1 | VAL | A | 256 | 115.894 | 78.725 | 36.829 | 1.00 | 17.67 | A |
| ATOM | 2004 | CG2 | VAL | A | 256 | 114.827 | 79.770 | 34.812 | 1.00 | 22.75 | A |
| ATOM | 2005 | C | VAL | A | 256 | 116.666 | 81.130 | 37.848 | 1.00 | 22.10 | A |
| ATOM | 2006 | O | VAL | A | 256 | 115.946 | 81.095 | 38.871 | 1.00 | 28.02 | A |
| ATOM | 2007 | N | PRO | A | 257 | 118.007 | 81.124 | 37.931 | 1.00 | 21.20 | A |
| ATOM | 2008 | CD | PRO | A | 257 | 118.995 | 81.442 | 36.886 | 1.00 | 24.71 | A |
| ATOM | 2009 | CA | PRO | A | 257 | 118.667 | 80.963 | 39.234 | 1.00 | 24.35 | A |
| ATOM | 2010 | CB | PRO | A | 257 | 120.169 | 81.097 | 38.899 | 1.00 | 27.97 | A |
| ATOM | 2011 | CG | PRO | A | 257 | 120.234 | 80.711 | 37.411 | 1.00 | 23.95 | A |
| ATOM | 2012 | C | PRO | A | 257 | 118.258 | 81.802 | 40.403 | 1.00 | 24.79 | A |
| ATOM | 2013 | O | PRO | A | 257 | 117.988 | 81.266 | 41.468 | 1.00 | 27.34 | A |
| ATOM | 2014 | N | PRO | A | 258 | 118.189 | 83.134 | 40.250 | 1.00 | 25.57 | A |
| ATOM | 2015 | CD | PRO | A | 258 | 118.491 | 84.076 | 39.165 | 1.00 | 26.97 | A |
| ATOM | 2016 | CA | PRO | A | 258 | 117.785 | 83.828 | 41.487 | 1.00 | 25.28 | A |
| ATOM | 2017 | CB | PRO | A | 258 | 117.840 | 85.322 | 41.103 | 1.00 | 29.92 | A |
| ATOM | 2018 | CG | PRO | A | 258 | 118.862 | 85.363 | 39.944 | 1.00 | 31.32 | A |
| ATOM | 2019 | C | PRO | A | 258 | 116.373 | 83.414 | 41.927 | 1.00 | 25.27 | A |
| ATOM | 2020 | O | PRO | A | 258 | 116.032 | 83.438 | 43.117 | 1.00 | 21.56 | A |
| ATOM | 2021 | N | VAL | A | 259 | 115.552 | 83.013 | 40.963 | 1.00 | 21.83 | A |
| ATOM | 2022 | CA | VAL | A | 259 | 114.175 | 82.658 | 41.291 | 1.00 | 22.97 | A |
| ATOM | 2023 | CB | VAL | A | 259 | 113.339 | 82.571 | 39.988 | 1.00 | 21.99 | A |
| ATOM | 2024 | CG1 | VAL | A | 259 | 111.917 | 82.096 | 40.294 | 1.00 | 17.20 | A |
| ATOM | 2025 | CG2 | VAL | A | 259 | 113.271 | 83.961 | 39.346 | 1.00 | 24.31 | A |
| ATOM | 2026 | C | VAL | A | 259 | 114.069 | 81.358 | 42.085 | 1.00 | 19.11 | A |
| ATOM | 2027 | O | VAL | A | 259 | 113.366 | 81.256 | 43.091 | 1.00 | 22.76 | A |
| ATOM | 2028 | N | VAL | A | 260 | 114.783 | 80.357 | 41.620 | 1.00 | 26.91 | A |
| ATOM | 2029 | CA | VAL | A | 260 | 114.760 | 79.071 | 42.275 | 1.00 | 24.36 | A |
| ATOM | 2030 | CB | VAL | A | 260 | 115.564 | 78.094 | 41.451 | 1.00 | 23.58 | A |
| ATOM | 2031 | CG1 | VAL | A | 260 | 115.723 | 76.787 | 42.189 | 1.00 | 24.55 | A |
| ATOM | 2032 | CG2 | VAL | A | 260 | 114.865 | 77.887 | 40.155 | 1.00 | 21.01 | A |
| ATOM | 2033 | C | VAL | A | 260 | 115.340 | 79.231 | 43.657 | 1.00 | 24.01 | A |
| ATOM | 2034 | O | VAL | A | 260 | 114.815 | 78.721 | 44.651 | 1.00 | 20.85 | A |
| ATOM | 2035 | N | ARG | A | 261 | 116.436 | 79.972 | 43.724 | 1.00 | 24.50 | A |
| ATOM | 2036 | CA | ARG | A | 261 | 117.084 | 80.219 | 45.002 | 1.00 | 19.29 | A |
| ATOM | 2037 | CB | ARG | A | 261 | 118.320 | 81.101 | 44.757 | 1.00 | 26.10 | A |
| ATOM | 2038 | CG | ARG | A | 261 | 119.216 | 81.291 | 45.956 | 1.00 | 42.29 | A |
| ATOM | 2039 | CD | ARG | A | 261 | 120.449 | 82.133 | 45.594 | 1.00 | 48.37 | A |

TABLE 2-continued

| ATOM | 2040 | NE | ARG | A | 261 | 121.239 | 81.474 | 44.553 | 1.00 | 53.77 | A |
| --- | --- | --- | --- | --- | --- | --- | --- | --- | --- | --- | --- |
| ATOM | 2041 | CZ | ARG | A | 261 | 121.406 | 81.910 | 43.301 | 1.00 | 58.06 | A |
| ATOM | 2042 | NH1 | ARG | A | 261 | 120.845 | 83.045 | 42.877 | 1.00 | 55.53 | A |
| ATOM | 2043 | NH2 | ARG | A | 261 | 122.128 | 81.180 | 42.454 | 1.00 | 54.87 | A |
| ATOM | 2044 | C | ARG | A | 261 | 116.114 | 80.883 | 45.999 | 1.00 | 26.55 | A |
| ATOM | 2045 | O | ARG | A | 261 | 116.056 | 80.507 | 47.169 | 1.00 | 25.37 | A |
| ATOM | 2046 | N | TRP | A | 262 | 115.353 | 81.885 | 45.556 | 1.00 | 21.10 | A |
| ATOM | 2047 | CA | TRP | A | 262 | 114.423 | 82.526 | 46.469 | 1.00 | 21.13 | A |
| ATOM | 2048 | CB | TRP | A | 262 | 113.759 | 83.756 | 45.804 | 1.00 | 27.41 | A |
| ATOM | 2049 | CG | TRP | A | 262 | 112.747 | 84.440 | 46.710 | 1.00 | 26.23 | A |
| ATOM | 2050 | CD2 | TRP | A | 262 | 111.344 | 84.176 | 46.770 | 1.00 | 24.38 | A |
| ATOM | 2051 | CE2 | TRP | A | 262 | 110.809 | 84.949 | 47.839 | 1.00 | 22.85 | A |
| ATOM | 2052 | CE3 | TRP | A | 262 | 110.479 | 83.359 | 46.027 | 1.00 | 29.17 | A |
| ATOM | 2053 | CD1 | TRP | A | 262 | 113.008 | 85.351 | 47.715 | 1.00 | 27.15 | A |
| ATOM | 2054 | NE1 | TRP | A | 262 | 111.844 | 85.659 | 48.397 | 1.00 | 25.55 | A |
| ATOM | 2055 | CZ2 | TRP | A | 262 | 109.458 | 84.922 | 48.177 | 1.00 | 22.55 | A |
| ATOM | 2056 | CZ3 | TRP | A | 262 | 109.134 | 83.332 | 46.359 | 1.00 | 22.37 | A |
| ATOM | 2057 | CH2 | TRP | A | 262 | 108.636 | 84.106 | 47.427 | 1.00 | 27.32 | A |
| ATOM | 2058 | C | TRP | A | 262 | 113.345 | 81.504 | 46.891 | 1.00 | 21.59 | A |
| ATOM | 2059 | O | TRP | A | 262 | 113.003 | 81.383 | 48.077 | 1.00 | 21.98 | A |
| ATOM | 2060 | N | LEU | A | 263 | 112.806 | 80.767 | 45.927 | 1.00 | 24.29 | A |
| ATOM | 2061 | CA | LEU | A | 263 | 111.760 | 79.775 | 46.248 | 1.00 | 24.58 | A |
| ATOM | 2062 | CB | LEU | A | 263 | 111.270 | 79.050 | 44.985 | 1.00 | 23.15 | A |
| ATOM | 2063 | CG | LEU | A | 263 | 110.294 | 79.804 | 44.055 | 1.00 | 26.66 | A |
| ATOM | 2064 | CD1 | LEU | A | 263 | 110.179 | 79.064 | 42.702 | 1.00 | 25.63 | A |
| ATOM | 2065 | CD2 | LEU | A | 263 | 108.902 | 79.890 | 44.736 | 1.00 | 19.50 | A |
| ATOM | 2066 | C | LEU | A | 263 | 112.280 | 78.754 | 47.252 | 1.00 | 25.46 | A |
| ATOM | 2067 | O | LEU | A | 263 | 111.589 | 78.396 | 48.213 | 1.00 | 21.54 | A |
| ATOM | 2068 | N | ASN | A | 264 | 113.521 | 78.334 | 47.052 | 1.00 | 27.69 | A |
| ATOM | 2069 | CA | ASN | A | 264 | 114.138 | 77.339 | 47.923 | 1.00 | 26.89 | A |
| ATOM | 2070 | CB | ASN | A | 264 | 115.429 | 76.833 | 47.317 | 1.00 | 30.52 | A |
| ATOM | 2071 | CG | ASN | A | 264 | 115.869 | 75.523 | 47.906 | 1.00 | 37.07 | A |
| ATOM | 2072 | OD1 | ASN | A | 264 | 117.047 | 75.355 | 48.181 | 1.00 | 41.85 | A |
| ATOM | 2073 | ND2 | ASN | A | 264 | 114.936 | 74.576 | 48.093 | 1.00 | 34.54 | A |
| ATOM | 2074 | C | ASN | A | 264 | 114.426 | 77.843 | 49.308 | 1.00 | 31.72 | A |
| ATOM | 2075 | O | ASN | A | 264 | 114.734 | 77.040 | 50.186 | 1.00 | 29.93 | A |
| ATOM | 2076 | N | GLU | A | 265 | 114.368 | 79.161 | 49.518 | 1.00 | 23.33 | A |
| ATOM | 2077 | CA | GLU | A | 265 | 114.583 | 79.677 | 50.868 | 1.00 | 27.89 | A |
| ATOM | 2078 | CB | GLU | A | 265 | 115.256 | 81.057 | 50.817 | 1.00 | 36.54 | A |
| ATOM | 2079 | CG | GLU | A | 265 | 116.666 | 81.031 | 50.220 | 1.00 | 45.81 | A |
| ATOM | 2080 | CD | GLU | A | 265 | 117.203 | 82.426 | 49.890 | 1.00 | 52.24 | A |
| ATOM | 2081 | OE1 | GLU | A | 265 | 116.412 | 83.284 | 49.448 | 1.00 | 55.22 | A |
| ATOM | 2082 | OE2 | GLU | A | 265 | 118.421 | 82.659 | 50.053 | 1.00 | 59.70 | A |
| ATOM | 2083 | C | GLU | A | 265 | 113.240 | 79.794 | 51.617 | 1.00 | 31.76 | A |
| ATOM | 2084 | O | GLU | A | 265 | 113.210 | 80.100 | 52.800 | 1.00 | 31.51 | A |
| ATOM | 2085 | N | GLN | A | 266 | 112.131 | 79.578 | 50.917 | 1.00 | 25.12 | A |
| ATOM | 2086 | CA | GLN | A | 266 | 110.823 | 79.682 | 51.534 | 1.00 | 25.11 | A |
| ATOM | 2087 | CB | GLN | A | 266 | 109.769 | 80.120 | 50.492 | 1.00 | 22.70 | A |
| ATOM | 2088 | CG | GLN | A | 266 | 110.160 | 81.344 | 49.619 | 1.00 | 27.84 | A |
| ATOM | 2089 | CD | GLN | A | 266 | 110.749 | 82.499 | 50.434 | 1.00 | 30.91 | A |
| ATOM | 2090 | OE1 | GLN | A | 266 | 110.138 | 82.961 | 51.386 | 1.00 | 29.87 | A |
| ATOM | 2091 | NE2 | GLN | A | 266 | 111.949 | 82.952 | 50.065 | 1.00 | 23.36 | A |
| ATOM | 2092 | C | GLN | A | 266 | 110.402 | 78.343 | 52.166 | 1.00 | 29.30 | A |
| ATOM | 2093 | O | GLN | A | 266 | 110.826 | 77.247 | 51.730 | 1.00 | 24.87 | A |
| ATOM | 2094 | N | ARG | A | 267 | 109.585 | 78.444 | 53.212 | 1.00 | 15.92 | A |
| ATOM | 2095 | CA | ARG | A | 267 | 109.051 | 77.274 | 53.898 | 1.00 | 25.35 | A |
| ATOM | 2096 | CB | ARG | A | 267 | 108.588 | 77.693 | 55.292 | 1.00 | 33.71 | A |
| ATOM | 2097 | CG | ARG | A | 267 | 107.994 | 76.574 | 56.134 | 1.00 | 51.92 | A |
| ATOM | 2098 | CD | ARG | A | 267 | 107.907 | 76.988 | 57.616 | 1.00 | 62.06 | A |
| ATOM | 2099 | NE | ARG | A | 267 | 106.792 | 76.336 | 58.312 | 1.00 | 68.36 | A |
| ATOM | 2100 | CZ | ARG | A | 267 | 105.511 | 76.589 | 58.055 | 1.00 | 69.62 | A |
| ATOM | 2101 | NH1 | ARG | A | 267 | 105.199 | 77.484 | 57.118 | 1.00 | 71.28 | A |
| ATOM | 2102 | NH2 | ARG | A | 267 | 104.546 | 75.951 | 58.721 | 1.00 | 63.27 | A |
| ATOM | 2103 | C | ARG | A | 267 | 107.868 | 76.833 | 53.031 | 1.00 | 24.21 | A |
| ATOM | 2104 | O | ARG | A | 267 | 106.740 | 76.727 | 53.500 | 1.00 | 21.31 | A |
| ATOM | 2105 | N | TYR | A | 268 | 108.146 | 76.503 | 51.772 | 1.00 | 20.68 | A |
| ATOM | 2106 | CA | TYR | A | 268 | 107.077 | 76.220 | 50.844 | 1.00 | 19.61 | A |
| ATOM | 2107 | CB | TYR | A | 268 | 107.623 | 76.325 | 49.416 | 1.00 | 19.65 | A |
| ATOM | 2108 | CG | TYR | A | 268 | 108.603 | 75.213 | 49.054 | 1.00 | 20.48 | A |
| ATOM | 2109 | CD1 | TYR | A | 268 | 108.141 | 73.919 | 48.758 | 1.00 | 14.04 | A |
| ATOM | 2110 | CE1 | TYR | A | 268 | 109.038 | 72.914 | 48.336 | 1.00 | 17.07 | A |
| ATOM | 2111 | CD2 | TYR | A | 268 | 109.988 | 75.469 | 48.950 | 1.00 | 18.73 | A |
| ATOM | 2112 | CE2 | TYR | A | 268 | 110.896 | 74.462 | 48.562 | 1.00 | 10.52 | A |
| ATOM | 2113 | CZ | TYR | A | 268 | 110.400 | 73.191 | 48.251 | 1.00 | 18.28 | A |
| ATOM | 2114 | OH | TYR | A | 268 | 111.270 | 72.207 | 47.849 | 1.00 | 20.44 | A |
| ATOM | 2115 | C | TYR | A | 268 | 106.320 | 74.921 | 51.058 | 1.00 | 25.67 | A |
| ATOM | 2116 | O | TYR | A | 268 | 105.280 | 74.726 | 50.457 | 1.00 | 20.64 | A |
| ATOM | 2117 | N | TYR | A | 269 | 106.837 | 74.047 | 51.923 | 1.00 | 22.96 | A |
| ATOM | 2118 | CA | TYR | A | 269 | 106.192 | 72.764 | 52.224 | 1.00 | 22.56 | A |

TABLE 2-continued

| | | | | | | | | | | |
|---|---|---|---|---|---|---|---|---|---|---|
| ATOM | 2119 | CB | TYR | A | 269 | 107.284 | 71.749 | 52.550 | 1.00 | 19.40 | A |
| ATOM | 2120 | CG | TYR | A | 269 | 108.279 | 72.324 | 53.538 | 1.00 | 25.20 | A |
| ATOM | 2121 | CD1 | TYR | A | 269 | 108.002 | 72.326 | 54.913 | 1.00 | 21.63 | A |
| ATOM | 2122 | CE1 | TYR | A | 269 | 108.856 | 72.951 | 55.823 | 1.00 | 19.42 | A |
| ATOM | 2123 | CD2 | TYR | A | 269 | 109.452 | 72.970 | 53.098 | 1.00 | 23.97 | A |
| ATOM | 2124 | CE2 | TYR | A | 269 | 110.310 | 73.620 | 54.010 | 1.00 | 18.32 | A |
| ATOM | 2125 | CZ | TYR | A | 269 | 110.002 | 73.600 | 55.359 | 1.00 | 24.42 | A |
| ATOM | 2126 | OH | TYR | A | 269 | 110.809 | 74.232 | 56.269 | 1.00 | 30.40 | A |
| ATOM | 2127 | C | TYR | A | 269 | 105.286 | 72.941 | 53.459 | 1.00 | 19.68 | A |
| ATOM | 2128 | O | TYR | A | 269 | 104.703 | 71.986 | 53.943 | 1.00 | 21.53 | A |
| ATOM | 2129 | N | GLY | A | 270 | 105.176 | 74.170 | 53.948 | 1.00 | 21.67 | A |
| ATOM | 2130 | CA | GLY | A | 270 | 104.406 | 74.456 | 55.146 | 1.00 | 17.59 | A |
| ATOM | 2131 | C | GLY | A | 270 | 102.977 | 73.953 | 55.184 | 1.00 | 25.69 | A |
| ATOM | 2132 | O | GLY | A | 270 | 102.532 | 73.482 | 56.232 | 1.00 | 24.34 | A |
| ATOM | 2133 | N | GLY | A | 271 | 102.266 | 73.984 | 54.057 | 1.00 | 19.73 | A |
| ATOM | 2134 | CA | GLY | A | 271 | 100.868 | 73.577 | 54.104 | 1.00 | 21.41 | A |
| ATOM | 2135 | C | GLY | A | 271 | 100.160 | 74.574 | 55.033 | 1.00 | 26.85 | A |
| ATOM | 2136 | O | GLY | A | 271 | 100.583 | 75.740 | 55.198 | 1.00 | 40.08 | A |
| ATOM | 2137 | N | GLY | A | 272 | 99.091 | 74.158 | 55.662 | 1.00 | 23.80 | A |
| ATOM | 2138 | CA | GLY | A | 272 | 98.437 | 75.085 | 56.568 | 1.00 | 26.88 | A |
| ATOM | 2139 | C | GLY | A | 272 | 97.305 | 75.856 | 55.915 | 1.00 | 23.11 | A |
| ATOM | 2140 | O | GLY | A | 272 | 97.123 | 75.787 | 54.712 | 1.00 | 21.50 | A |
| ATOM | 2141 | N | TYR | A | 273 | 96.567 | 76.618 | 56.710 | 1.00 | 17.15 | A |
| ATOM | 2142 | CA | TYR | A | 273 | 95.425 | 77.353 | 56.196 | 1.00 | 19.83 | A |
| ATOM | 2143 | CB | TYR | A | 273 | 94.836 | 78.198 | 57.313 | 1.00 | 21.62 | A |
| ATOM | 2144 | CG | TYR | A | 273 | 93.616 | 78.988 | 56.897 | 1.00 | 23.29 | A |
| ATOM | 2145 | CD1 | TYR | A | 273 | 92.321 | 78.473 | 57.084 | 1.00 | 20.57 | A |
| ATOM | 2146 | CE1 | TYR | A | 273 | 91.184 | 79.246 | 56.758 | 1.00 | 23.40 | A |
| ATOM | 2147 | CD2 | TYR | A | 273 | 93.759 | 80.281 | 56.359 | 1.00 | 23.31 | A |
| ATOM | 2148 | CE2 | TYR | A | 273 | 92.646 | 81.060 | 56.027 | 1.00 | 22.47 | A |
| ATOM | 2149 | CZ | TYR | A | 273 | 91.371 | 80.532 | 56.235 | 1.00 | 20.88 | A |
| ATOM | 2150 | OH | TYR | A | 273 | 90.314 | 81.304 | 55.896 | 1.00 | 20.65 | A |
| ATOM | 2151 | C | TYR | A | 273 | 95.747 | 78.224 | 54.976 | 1.00 | 23.07 | A |
| ATOM | 2152 | O | TYR | A | 273 | 96.764 | 78.920 | 54.931 | 1.00 | 14.66 | A |
| ATOM | 2153 | N | GLY | A | 274 | 94.891 | 78.150 | 53.966 | 1.00 | 23.18 | A |
| ATOM | 2154 | CA | GLY | A | 274 | 95.092 | 78.955 | 52.768 | 1.00 | 16.12 | A |
| ATOM | 2155 | C | GLY | A | 274 | 96.280 | 78.623 | 51.891 | 1.00 | 25.88 | A |
| ATOM | 2156 | O | GLY | A | 274 | 96.629 | 79.431 | 51.012 | 1.00 | 20.78 | A |
| ATOM | 2157 | N | SER | A | 275 | 96.907 | 77.458 | 52.080 | 1.00 | 14.86 | A |
| ATOM | 2158 | CA | SER | A | 275 | 98.089 | 77.131 | 51.270 | 1.00 | 20.55 | A |
| ATOM | 2159 | CB | SER | A | 275 | 99.074 | 76.297 | 52.077 | 1.00 | 16.52 | A |
| ATOM | 2160 | OG | SER | A | 275 | 98.428 | 75.061 | 52.389 | 1.00 | 21.60 | A |
| ATOM | 2161 | C | SER | A | 275 | 97.806 | 76.335 | 50.005 | 1.00 | 20.94 | A |
| ATOM | 2162 | O | SER | A | 275 | 98.746 | 75.961 | 49.318 | 1.00 | 17.86 | A |
| ATOM | 2163 | N | THR | A | 276 | 96.544 | 76.072 | 49.683 | 1.00 | 18.41 | A |
| ATOM | 2164 | CA | THR | A | 276 | 96.269 | 75.232 | 48.516 | 1.00 | 19.71 | A |
| ATOM | 2165 | CB | THR | A | 276 | 94.730 | 75.059 | 48.238 | 1.00 | 22.45 | A |
| ATOM | 2166 | OG1 | THR | A | 276 | 94.192 | 76.301 | 47.838 | 1.00 | 51.89 | A |
| ATOM | 2167 | CG2 | THR | A | 276 | 93.993 | 74.729 | 49.503 | 1.00 | 5.81 | A |
| ATOM | 2168 | C | THR | A | 276 | 96.967 | 75.607 | 47.228 | 1.00 | 21.51 | A |
| ATOM | 2169 | O | THR | A | 276 | 97.666 | 74.764 | 46.650 | 1.00 | 19.94 | A |
| ATOM | 2170 | N | GLN | A | 277 | 96.823 | 76.850 | 46.754 | 1.00 | 13.97 | A |
| ATOM | 2171 | CA | GLN | A | 277 | 97.463 | 77.189 | 45.485 | 1.00 | 15.27 | A |
| ATOM | 2172 | CB | GLN | A | 277 | 96.942 | 78.540 | 44.964 | 1.00 | 15.99 | A |
| ATOM | 2173 | CG | GLN | A | 277 | 95.421 | 78.529 | 44.563 | 1.00 | 8.40 | A |
| ATOM | 2174 | CD | GLN | A | 277 | 95.100 | 77.321 | 43.742 | 1.00 | 20.22 | A |
| ATOM | 2175 | OE1 | GLN | A | 277 | 95.685 | 77.090 | 42.673 | 1.00 | 16.53 | A |
| ATOM | 2176 | NE2 | GLN | A | 277 | 94.190 | 76.505 | 44.258 | 1.00 | 18.51 | A |
| ATOM | 2177 | C | GLN | A | 277 | 99.007 | 77.220 | 45.567 | 1.00 | 13.58 | A |
| ATOM | 2178 | O | GLN | A | 277 | 99.689 | 76.791 | 44.620 | 1.00 | 15.16 | A |
| ATOM | 2179 | N | ALA | A | 278 | 99.534 | 77.754 | 46.667 | 1.00 | 17.70 | A |
| ATOM | 2180 | CA | ALA | A | 278 | 100.996 | 77.842 | 46.833 | 1.00 | 17.58 | A |
| ATOM | 2181 | CB | ALA | A | 278 | 101.367 | 78.522 | 48.200 | 1.00 | 12.12 | A |
| ATOM | 2182 | C | ALA | A | 278 | 101.539 | 76.426 | 46.798 | 1.00 | 20.92 | A |
| ATOM | 2183 | O | ALA | A | 278 | 102.581 | 76.154 | 46.176 | 1.00 | 19.56 | A |
| ATOM | 2184 | N | THR | A | 279 | 100.821 | 75.524 | 47.477 | 1.00 | 18.75 | A |
| ATOM | 2185 | CA | THR | A | 279 | 101.254 | 74.136 | 47.553 | 1.00 | 15.04 | A |
| ATOM | 2186 | CB | THR | A | 279 | 100.380 | 73.341 | 48.554 | 1.00 | 23.60 | A |
| ATOM | 2187 | OG1 | THR | A | 279 | 100.574 | 73.865 | 49.873 | 1.00 | 16.00 | A |
| ATOM | 2188 | CG2 | THR | A | 279 | 100.755 | 71.832 | 48.531 | 1.00 | 18.05 | A |
| ATOM | 2189 | C | THR | A | 279 | 101.224 | 73.469 | 46.195 | 1.00 | 20.78 | A |
| ATOM | 2190 | O | THR | A | 279 | 102.224 | 72.894 | 45.758 | 1.00 | 14.58 | A |
| ATOM | 2191 | N | PHE | A | 280 | 100.080 | 73.544 | 45.514 | 1.00 | 14.85 | A |
| ATOM | 2192 | CA | PHE | A | 280 | 99.989 | 72.925 | 44.212 | 1.00 | 15.92 | A |
| ATOM | 2193 | CB | PHE | A | 280 | 98.601 | 73.198 | 43.604 | 1.00 | 15.13 | A |
| ATOM | 2194 | CG | PHE | A | 280 | 98.354 | 72.463 | 42.313 | 1.00 | 19.65 | A |
| ATOM | 2195 | CD1 | PHE | A | 280 | 97.543 | 71.341 | 42.284 | 1.00 | 19.12 | A |
| ATOM | 2196 | CD2 | PHE | A | 280 | 98.873 | 72.932 | 41.120 | 1.00 | 17.17 | A |
| ATOM | 2197 | CE1 | PHE | A | 280 | 97.261 | 70.703 | 41.074 | 1.00 | 21.16 | A |

TABLE 2-continued

| ATOM | 2198 | CE2 | PHE | A | 280 | 98.593 | 72.308 | 39.910 | 1.00 | 22.94 | A |
| ATOM | 2199 | CZ | PHE | A | 280 | 97.784 | 71.202 | 39.884 | 1.00 | 22.80 | A |
| ATOM | 2200 | C | PHE | A | 280 | 101.031 | 73.493 | 43.273 | 1.00 | 22.45 | A |
| ATOM | 2201 | O | PHE | A | 280 | 101.706 | 72.768 | 42.534 | 1.00 | 17.39 | A |
| ATOM | 2202 | N | MET | A | 281 | 101.157 | 74.808 | 43.284 | 1.00 | 15.49 | A |
| ATOM | 2203 | CA | MET | A | 281 | 102.061 | 75.445 | 42.339 | 1.00 | 19.30 | A |
| ATOM | 2204 | CB | MET | A | 281 | 101.681 | 76.939 | 42.169 | 1.00 | 16.61 | A |
| ATOM | 2205 | CG | MET | A | 281 | 100.322 | 77.212 | 41.527 | 1.00 | 18.78 | A |
| ATOM | 2206 | SD | MET | A | 281 | 100.020 | 76.356 | 39.946 | 1.00 | 24.71 | A |
| ATOM | 2207 | CE | MET | A | 281 | 101.567 | 76.615 | 39.056 | 1.00 | 22.61 | A |
| ATOM | 2208 | C | MET | A | 281 | 103.576 | 75.321 | 42.559 | 1.00 | 12.99 | A |
| ATOM | 2209 | O | MET | A | 281 | 104.316 | 75.044 | 41.593 | 1.00 | 20.36 | A |
| ATOM | 2210 | N | VAL | A | 282 | 104.036 | 75.481 | 43.800 | 1.00 | 20.60 | A |
| ATOM | 2211 | CA | VAL | A | 282 | 105.475 | 75.395 | 44.084 | 1.00 | 17.17 | A |
| ATOM | 2212 | CB | VAL | A | 282 | 105.795 | 75.806 | 45.562 | 1.00 | 16.00 | A |
| ATOM | 2213 | CG1 | VAL | A | 282 | 105.366 | 74.677 | 46.522 | 1.00 | 16.44 | A |
| ATOM | 2214 | CG2 | VAL | A | 282 | 107.331 | 76.108 | 45.740 | 1.00 | 20.08 | A |
| ATOM | 2215 | C | VAL | A | 282 | 105.974 | 73.961 | 43.790 | 1.00 | 16.69 | A |
| ATOM | 2216 | O | VAL | A | 282 | 107.058 | 73.777 | 43.230 | 1.00 | 16.91 | A |
| ATOM | 2217 | N | PHE | A | 283 | 105.184 | 72.943 | 44.134 | 1.00 | 13.38 | A |
| ATOM | 2218 | CA | PHE | A | 283 | 105.623 | 71.562 | 43.832 | 1.00 | 20.74 | A |
| ATOM | 2219 | CB | PHE | A | 283 | 104.821 | 70.541 | 44.684 | 1.00 | 13.63 | A |
| ATOM | 2220 | CG | PHE | A | 283 | 105.280 | 70.495 | 46.117 | 1.00 | 21.60 | A |
| ATOM | 2221 | CD1 | PHE | A | 283 | 104.633 | 71.260 | 47.107 | 1.00 | 18.08 | A |
| ATOM | 2222 | CD2 | PHE | A | 283 | 106.402 | 69.732 | 46.477 | 1.00 | 17.18 | A |
| ATOM | 2223 | CE1 | PHE | A | 283 | 105.100 | 71.264 | 48.441 | 1.00 | 21.58 | A |
| ATOM | 2224 | CE2 | PHE | A | 283 | 106.873 | 69.736 | 47.809 | 1.00 | 19.10 | A |
| ATOM | 2225 | CZ | PHE | A | 283 | 106.220 | 70.502 | 48.790 | 1.00 | 15.19 | A |
| ATOM | 2226 | C | PHE | A | 283 | 105.559 | 71.274 | 42.329 | 1.00 | 17.88 | A |
| ATOM | 2227 | O | PHE | A | 283 | 106.418 | 70.582 | 41.780 | 1.00 | 17.08 | A |
| ATOM | 2228 | N | GLN | A | 284 | 104.572 | 71.859 | 41.642 | 1.00 | 17.15 | A |
| ATOM | 2229 | CA | GLN | A | 284 | 104.505 | 71.696 | 40.195 | 1.00 | 15.23 | A |
| ATOM | 2230 | CB | GLN | A | 284 | 103.258 | 72.375 | 39.570 | 1.00 | 19.08 | A |
| ATOM | 2231 | CG | GLN | A | 284 | 103.135 | 72.123 | 38.053 | 1.00 | 18.61 | A |
| ATOM | 2232 | CD | GLN | A | 284 | 101.834 | 72.642 | 37.446 | 1.00 | 27.56 | A |
| ATOM | 2233 | OE1 | GLN | A | 284 | 101.215 | 73.561 | 37.957 | 1.00 | 19.72 | A |
| ATOM | 2234 | NE2 | GLN | A | 284 | 101.419 | 72.040 | 36.358 | 1.00 | 28.76 | A |
| ATOM | 2235 | C | GLN | A | 284 | 105.733 | 72.350 | 39.583 | 1.00 | 23.26 | A |
| ATOM | 2236 | O | GLN | A | 284 | 106.403 | 71.749 | 38.721 | 1.00 | 19.38 | A |
| ATOM | 2237 | N | ALA | A | 285 | 106.032 | 73.586 | 40.020 | 1.00 | 20.27 | A |
| ATOM | 2238 | CA | ALA | A | 285 | 107.169 | 74.314 | 39.474 | 1.00 | 22.72 | A |
| ATOM | 2239 | CB | ALA | A | 285 | 107.131 | 75.841 | 39.900 | 1.00 | 13.58 | A |
| ATOM | 2240 | C | ALA | A | 285 | 108.525 | 73.704 | 39.796 | 1.00 | 19.56 | A |
| ATOM | 2241 | O | ALA | A | 285 | 109.342 | 73.571 | 38.891 | 1.00 | 18.63 | A |
| ATOM | 2242 | N | LEU | A | 286 | 108.775 | 73.348 | 41.060 | 1.00 | 17.53 | A |
| ATOM | 2243 | CA | LEU | A | 286 | 110.059 | 72.729 | 41.426 | 1.00 | 22.71 | A |
| ATOM | 2244 | CB | LEU | A | 286 | 110.238 | 72.682 | 42.957 | 1.00 | 20.14 | A |
| ATOM | 2245 | CG | LEU | A | 286 | 110.337 | 74.074 | 43.563 | 1.00 | 26.93 | A |
| ATOM | 2246 | CD1 | LEU | A | 286 | 110.528 | 74.003 | 45.093 | 1.00 | 20.46 | A |
| ATOM | 2247 | CD2 | LEU | A | 286 | 111.470 | 74.793 | 42.896 | 1.00 | 21.22 | A |
| ATOM | 2248 | C | LEU | A | 286 | 110.181 | 71.322 | 40.832 | 1.00 | 18.99 | A |
| ATOM | 2249 | O | LEU | A | 286 | 111.286 | 70.866 | 40.558 | 1.00 | 23.33 | A |
| ATOM | 2250 | N | ALA | A | 287 | 109.058 | 70.631 | 40.629 | 1.00 | 20.11 | A |
| ATOM | 2251 | CA | ALA | A | 287 | 109.135 | 69.321 | 39.980 | 1.00 | 18.27 | A |
| ATOM | 2252 | CB | ALA | A | 287 | 107.786 | 68.606 | 40.005 | 1.00 | 16.55 | A |
| ATOM | 2253 | C | ALA | A | 287 | 109.519 | 69.613 | 38.530 | 1.00 | 25.56 | A |
| ATOM | 2254 | O | ALA | A | 287 | 110.381 | 68.942 | 37.927 | 1.00 | 19.06 | A |
| ATOM | 2255 | N | GLN | A | 288 | 108.907 | 70.634 | 37.935 | 1.00 | 18.68 | A |
| ATOM | 2256 | CA | GLN | A | 288 | 109.249 | 70.877 | 36.536 | 1.00 | 16.52 | A |
| ATOM | 2257 | CB | GLN | A | 288 | 108.392 | 71.977 | 35.894 | 1.00 | 23.21 | A |
| ATOM | 2258 | CG | GLN | A | 288 | 108.681 | 72.106 | 34.390 | 1.00 | 20.99 | A |
| ATOM | 2259 | CD | GLN | A | 288 | 108.188 | 70.889 | 33.579 | 1.00 | 29.85 | A |
| ATOM | 2260 | OE1 | GLN | A | 288 | 108.896 | 70.370 | 32.704 | 1.00 | 29.90 | A |
| ATOM | 2261 | NE2 | GLN | A | 288 | 106.972 | 70.448 | 33.863 | 1.00 | 16.47 | A |
| ATOM | 2262 | C | GLN | A | 288 | 110.719 | 71.258 | 36.345 | 1.00 | 22.79 | A |
| ATOM | 2263 | O | GLN | A | 288 | 111.330 | 70.907 | 35.335 | 1.00 | 16.55 | A |
| ATOM | 2264 | N | TYR | A | 289 | 111.262 | 72.009 | 37.287 | 1.00 | 19.12 | A |
| ATOM | 2265 | CA | TYR | A | 289 | 112.654 | 72.405 | 37.203 | 1.00 | 18.73 | A |
| ATOM | 2266 | CB | TYR | A | 289 | 113.021 | 73.260 | 38.403 | 1.00 | 18.19 | A |
| ATOM | 2267 | CG | TYR | A | 289 | 114.482 | 73.677 | 38.476 | 1.00 | 26.27 | A |
| ATOM | 2268 | CD1 | TYR | A | 289 | 114.898 | 74.932 | 38.001 | 1.00 | 26.70 | A |
| ATOM | 2269 | CE1 | TYR | A | 289 | 116.232 | 75.332 | 38.072 | 1.00 | 25.07 | A |
| ATOM | 2270 | CD2 | TYR | A | 289 | 115.447 | 72.820 | 39.024 | 1.00 | 23.61 | A |
| ATOM | 2271 | CE2 | TYR | A | 289 | 116.796 | 73.199 | 39.098 | 1.00 | 26.68 | A |
| ATOM | 2272 | CZ | TYR | A | 289 | 117.178 | 74.469 | 38.615 | 1.00 | 31.54 | A |
| ATOM | 2273 | OH | TYR | A | 289 | 118.491 | 74.859 | 38.678 | 1.00 | 22.55 | A |
| ATOM | 2274 | C | TYR | A | 289 | 113.541 | 71.142 | 37.207 | 1.00 | 25.66 | A |
| ATOM | 2275 | O | TYR | A | 289 | 114.502 | 71.042 | 36.424 | 1.00 | 21.35 | A |
| ATOM | 2276 | N | GLN | A | 290 | 113.224 | 70.195 | 38.095 | 1.00 | 22.15 | A |

TABLE 2-continued

| | | | | | | | | | | |
|---|---|---|---|---|---|---|---|---|---|---|
| ATOM | 2277 | CA | GLN | A | 290 | 114.013 | 68.974 | 38.200 | 1.00 | 25.92 | A |
| ATOM | 2278 | CB | GLN | A | 290 | 113.751 | 68.295 | 39.535 | 1.00 | 16.82 | A |
| ATOM | 2279 | CG | GLN | A | 290 | 114.234 | 69.185 | 40.698 | 1.00 | 20.11 | A |
| ATOM | 2280 | CD | GLN | A | 290 | 113.869 | 68.620 | 42.062 | 1.00 | 28.81 | A |
| ATOM | 2281 | OE1 | GLN | A | 290 | 114.594 | 67.805 | 42.611 | 1.00 | 23.19 | A |
| ATOM | 2282 | NE2 | GLN | A | 290 | 112.740 | 69.050 | 42.603 | 1.00 | 19.24 | A |
| ATOM | 2283 | C | GLN | A | 290 | 113.792 | 68.037 | 37.053 | 1.00 | 24.56 | A |
| ATOM | 2284 | O | GLN | A | 290 | 114.690 | 67.272 | 36.654 | 1.00 | 22.99 | A |
| ATOM | 2285 | N | LYS | A | 291 | 112.604 | 68.100 | 36.485 | 1.00 | 28.20 | A |
| ATOM | 2286 | CA | LYS | A | 291 | 112.340 | 67.233 | 35.349 | 1.00 | 27.92 | A |
| ATOM | 2287 | CB | LYS | A | 291 | 110.879 | 67.253 | 34.960 | 1.00 | 25.58 | A |
| ATOM | 2288 | CG | LYS | A | 291 | 110.640 | 66.179 | 33.951 | 1.00 | 35.43 | A |
| ATOM | 2289 | CD | LYS | A | 291 | 109.644 | 66.601 | 32.962 | 1.00 | 47.83 | A |
| ATOM | 2290 | CE | LYS | A | 291 | 109.438 | 65.497 | 31.950 | 1.00 | 53.06 | A |
| ATOM | 2291 | NZ | LYS | A | 291 | 108.781 | 64.338 | 32.602 | 1.00 | 54.26 | A |
| ATOM | 2292 | C | LYS | A | 291 | 113.128 | 67.716 | 34.138 | 1.00 | 30.13 | A |
| ATOM | 2293 | O | LYS | A | 291 | 113.543 | 66.915 | 33.313 | 1.00 | 24.65 | A |
| ATOM | 2294 | N | ASP | A | 292 | 113.305 | 69.031 | 34.028 | 1.00 | 21.05 | A |
| ATOM | 2295 | CA | ASP | A | 292 | 114.016 | 69.633 | 32.891 | 1.00 | 25.19 | A |
| ATOM | 2296 | CB | ASP | A | 292 | 113.610 | 71.109 | 32.757 | 1.00 | 23.19 | A |
| ATOM | 2297 | CG | ASP | A | 292 | 112.222 | 71.299 | 32.158 | 1.00 | 33.23 | A |
| ATOM | 2298 | OD1 | ASP | A | 292 | 111.626 | 70.308 | 31.703 | 1.00 | 27.34 | A |
| ATOM | 2299 | OD2 | ASP | A | 292 | 111.737 | 72.452 | 32.131 | 1.00 | 27.83 | A |
| ATOM | 2300 | C | ASP | A | 292 | 115.556 | 69.584 | 33.008 | 1.00 | 23.90 | A |
| ATOM | 2301 | O | ASP | A | 292 | 116.275 | 69.573 | 32.017 | 1.00 | 22.32 | A |
| ATOM | 2302 | N | ALA | A | 293 | 116.034 | 69.604 | 34.236 | 1.00 | 20.48 | A |
| ATOM | 2303 | CA | ALA | A | 293 | 117.451 | 69.602 | 34.558 | 1.00 | 28.06 | A |
| ATOM | 2304 | CB | ALA | A | 293 | 117.602 | 69.472 | 36.065 | 1.00 | 20.35 | A |
| ATOM | 2305 | C | ALA | A | 293 | 118.355 | 68.564 | 33.838 | 1.00 | 29.15 | A |
| ATOM | 2306 | O | ALA | A | 293 | 119.480 | 68.885 | 33.427 | 1.00 | 30.95 | A |
| ATOM | 2307 | N | PRO | A | 294 | 117.913 | 67.302 | 33.732 | 1.00 | 29.07 | A |
| ATOM | 2308 | CD | PRO | A | 294 | 116.811 | 66.630 | 34.437 | 1.00 | 30.66 | A |
| ATOM | 2309 | CA | PRO | A | 294 | 118.777 | 66.331 | 33.051 | 1.00 | 28.43 | A |
| ATOM | 2310 | CB | PRO | A | 294 | 118.013 | 65.019 | 33.196 | 1.00 | 36.12 | A |
| ATOM | 2311 | CG | PRO | A | 294 | 117.307 | 65.185 | 34.516 | 1.00 | 34.80 | A |
| ATOM | 2312 | C | PRO | A | 294 | 119.062 | 66.686 | 31.593 | 1.00 | 34.08 | A |
| ATOM | 2313 | O | PRO | A | 294 | 120.059 | 66.245 | 31.042 | 1.00 | 37.55 | A |
| ATOM | 2314 | N | SER | A | 295 | 118.206 | 67.496 | 30.970 | 1.00 | 31.59 | A |
| ATOM | 2315 | CA | SER | A | 295 | 118.412 | 67.895 | 29.570 | 1.00 | 32.05 | A |
| ATOM | 2316 | CB | SER | A | 295 | 117.053 | 68.031 | 28.827 | 1.00 | 37.77 | A |
| ATOM | 2317 | OG | SER | A | 295 | 116.413 | 66.791 | 28.542 | 1.00 | 38.35 | A |
| ATOM | 2318 | C | SER | A | 295 | 119.141 | 69.246 | 29.412 | 1.00 | 33.12 | A |
| ATOM | 2319 | O | SER | A | 295 | 119.543 | 69.592 | 28.310 | 1.00 | 27.93 | A |
| ATOM | 2320 | N | ASP | A | 296 | 119.310 | 70.014 | 30.490 | 1.00 | 26.80 | A |
| ATOM | 2321 | CA | ASP | A | 296 | 119.913 | 71.328 | 30.352 | 1.00 | 30.74 | A |
| ATOM | 2322 | CB | ASP | A | 296 | 118.782 | 72.415 | 30.256 | 1.00 | 27.90 | A |
| ATOM | 2323 | CG | ASP | A | 296 | 117.839 | 72.252 | 28.986 | 1.00 | 41.52 | A |
| ATOM | 2324 | OD1 | ASP | A | 296 | 118.246 | 72.564 | 27.834 | 1.00 | 38.56 | A |
| ATOM | 2325 | OD2 | ASP | A | 296 | 116.655 | 71.816 | 29.121 | 1.00 | 44.60 | A |
| ATOM | 2326 | C | ASP | A | 296 | 120.862 | 71.604 | 31.525 | 1.00 | 31.76 | A |
| ATOM | 2327 | O | ASP | A | 296 | 120.426 | 71.809 | 32.661 | 1.00 | 31.22 | A |
| ATOM | 2328 | N | HIS | A | 297 | 122.161 | 71.613 | 31.240 | 1.00 | 27.39 | A |
| ATOM | 2329 | CA | HIS | A | 297 | 123.221 | 71.862 | 32.231 | 1.00 | 31.02 | A |
| ATOM | 2330 | CB | HIS | A | 297 | 124.562 | 72.043 | 31.514 | 1.00 | 39.25 | A |
| ATOM | 2331 | CG | HIS | A | 297 | 125.466 | 70.858 | 31.577 | 1.00 | 47.23 | A |
| ATOM | 2332 | CD2 | HIS | A | 297 | 126.818 | 70.762 | 31.501 | 1.00 | 46.79 | A |
| ATOM | 2333 | ND1 | HIS | A | 297 | 125.005 | 69.597 | 31.863 | 1.00 | 48.20 | A |
| ATOM | 2334 | CE1 | HIS | A | 297 | 126.036 | 68.777 | 31.990 | 1.00 | 54.99 | A |
| ATOM | 2335 | NE2 | HIS | A | 297 | 127.146 | 69.462 | 31.778 | 1.00 | 46.54 | A |
| ATOM | 2336 | C | HIS | A | 297 | 122.999 | 73.125 | 33.043 | 1.00 | 27.48 | A |
| ATOM | 2337 | O | HIS | A | 297 | 123.412 | 73.224 | 34.203 | 1.00 | 28.00 | A |
| ATOM | 2338 | N | GLN | A | 298 | 122.396 | 74.117 | 32.401 | 1.00 | 22.60 | A |
| ATOM | 2339 | CA | GLN | A | 298 | 122.174 | 75.396 | 33.046 | 1.00 | 25.08 | A |
| ATOM | 2340 | CB | GLN | A | 298 | 121.569 | 76.409 | 32.065 | 1.00 | 30.41 | A |
| ATOM | 2341 | CG | GLN | A | 298 | 122.332 | 76.669 | 30.783 | 1.00 | 34.42 | A |
| ATOM | 2342 | CD | GLN | A | 298 | 121.872 | 75.791 | 29.603 | 1.00 | 37.26 | A |
| ATOM | 2343 | OE1 | GLN | A | 298 | 121.932 | 76.217 | 28.444 | 1.00 | 36.98 | A |
| ATOM | 2344 | NE2 | GLN | A | 298 | 121.429 | 74.558 | 29.897 | 1.00 | 32.64 | A |
| ATOM | 2345 | C | GLN | A | 298 | 121.276 | 75.302 | 34.280 | 1.00 | 26.28 | A |
| ATOM | 2346 | O | GLN | A | 298 | 121.322 | 76.182 | 35.129 | 1.00 | 23.86 | A |
| ATOM | 2347 | N | GLU | A | 299 | 120.448 | 74.263 | 34.374 | 1.00 | 22.71 | A |
| ATOM | 2348 | CA | GLU | A | 299 | 119.556 | 74.107 | 35.525 | 1.00 | 29.56 | A |
| ATOM | 2349 | CB | GLU | A | 299 | 118.247 | 73.497 | 35.081 | 1.00 | 27.09 | A |
| ATOM | 2350 | CG | GLU | A | 299 | 117.445 | 74.443 | 34.288 | 1.00 | 42.75 | A |
| ATOM | 2351 | CD | GLU | A | 299 | 116.372 | 73.723 | 33.574 | 1.00 | 52.61 | A |
| ATOM | 2352 | OE1 | GLU | A | 299 | 115.342 | 73.415 | 34.208 | 1.00 | 64.24 | A |
| ATOM | 2353 | OE2 | GLU | A | 299 | 116.565 | 73.443 | 32.377 | 1.00 | 59.69 | A |
| ATOM | 2354 | C | GLU | A | 299 | 120.251 | 73.185 | 36.491 | 1.00 | 30.34 | A |
| ATOM | 2355 | O | GLU | A | 299 | 119.841 | 72.042 | 36.706 | 1.00 | 25.19 | A |

TABLE 2-continued

| ATOM | 2356 | N | LEU | A | 300 | 121.289 | 73.724 | 37.099 | 1.00 | 26.72 | A |
|---|---|---|---|---|---|---|---|---|---|---|---|
| ATOM | 2357 | CA | LEU | A | 300 | 122.164 | 72.960 | 37.960 | 1.00 | 26.16 | A |
| ATOM | 2358 | CB | LEU | A | 300 | 123.621 | 73.384 | 37.693 | 1.00 | 24.26 | A |
| ATOM | 2359 | CG | LEU | A | 300 | 124.040 | 74.875 | 37.817 | 1.00 | 23.41 | A |
| ATOM | 2360 | CD1 | LEU | A | 300 | 122.894 | 75.782 | 38.110 | 1.00 | 13.62 | A |
| ATOM | 2361 | CD2 | LEU | A | 300 | 125.064 | 75.023 | 38.845 | 1.00 | 23.86 | A |
| ATOM | 2362 | C | LEU | A | 300 | 121.930 | 73.005 | 39.439 | 1.00 | 31.66 | A |
| ATOM | 2363 | O | LEU | A | 300 | 122.685 | 72.360 | 40.165 | 1.00 | 24.27 | A |
| ATOM | 2364 | N | ASN | A | 301 | 120.899 | 73.717 | 39.895 | 1.00 | 20.86 | A |
| ATOM | 2365 | CA | ASN | A | 301 | 120.674 | 73.844 | 41.335 | 1.00 | 27.51 | A |
| ATOM | 2366 | CB | ASN | A | 301 | 119.685 | 74.974 | 41.629 | 1.00 | 27.49 | A |
| ATOM | 2367 | CG | ASN | A | 301 | 120.338 | 76.367 | 41.606 | 1.00 | 41.50 | A |
| ATOM | 2368 | OD1 | ASN | A | 301 | 121.524 | 76.531 | 41.948 | 1.00 | 42.07 | A |
| ATOM | 2369 | ND2 | ASN | A | 301 | 119.546 | 77.386 | 41.248 | 1.00 | 40.89 | A |
| ATOM | 2370 | C | ASN | A | 301 | 120.139 | 72.561 | 41.946 | 1.00 | 27.36 | A |
| ATOM | 2371 | O | ASN | A | 301 | 119.478 | 71.775 | 41.255 | 1.00 | 20.70 | A |
| ATOM | 2372 | N | LEU | A | 302 | 120.455 | 72.338 | 43.227 | 1.00 | 28.60 | A |
| ATOM | 2373 | CA | LEU | A | 302 | 119.962 | 71.168 | 43.945 | 1.00 | 24.52 | A |
| ATOM | 2374 | CB | LEU | A | 302 | 121.038 | 70.593 | 44.894 | 1.00 | 29.03 | A |
| ATOM | 2375 | CG | LEU | A | 302 | 120.446 | 69.605 | 45.935 | 1.00 | 27.91 | A |
| ATOM | 2376 | CD1 | LEU | A | 302 | 119.494 | 68.711 | 45.254 | 1.00 | 18.13 | A |
| ATOM | 2377 | CD2 | LEU | A | 302 | 121.464 | 68.809 | 46.627 | 1.00 | 28.47 | A |
| ATOM | 2378 | C | LEU | A | 302 | 118.742 | 71.586 | 44.767 | 1.00 | 21.88 | A |
| ATOM | 2379 | O | LEU | A | 302 | 118.888 | 72.203 | 45.817 | 1.00 | 20.14 | A |
| ATOM | 2380 | N | ASP | A | 303 | 117.540 | 71.265 | 44.306 | 1.00 | 18.15 | A |
| ATOM | 2381 | CA | ASP | A | 303 | 116.335 | 71.611 | 45.095 | 1.00 | 29.52 | A |
| ATOM | 2382 | CB | ASP | A | 303 | 115.472 | 72.630 | 44.334 | 1.00 | 25.17 | A |
| ATOM | 2383 | CG | ASP | A | 303 | 115.065 | 72.121 | 42.996 | 1.00 | 37.89 | A |
| ATOM | 2384 | OD1 | ASP | A | 303 | 115.528 | 71.037 | 42.637 | 1.00 | 54.39 | A |
| ATOM | 2385 | OD2 | ASP | A | 303 | 114.298 | 72.780 | 42.279 | 1.00 | 57.27 | A |
| ATOM | 2386 | C | ASP | A | 303 | 115.580 | 70.289 | 45.373 | 1.00 | 22.29 | A |
| ATOM | 2387 | O | ASP | A | 303 | 114.347 | 70.216 | 45.577 | 1.00 | 22.75 | A |
| ATOM | 2388 | N | VAL | A | 304 | 116.382 | 69.240 | 45.425 | 1.00 | 21.19 | A |
| ATOM | 2389 | CA | VAL | A | 304 | 115.925 | 67.870 | 45.624 | 1.00 | 25.10 | A |
| ATOM | 2390 | CB | VAL | A | 304 | 116.935 | 66.930 | 44.914 | 1.00 | 21.32 | A |
| ATOM | 2391 | CG1 | VAL | A | 304 | 118.001 | 66.444 | 45.851 | 1.00 | 13.87 | A |
| ATOM | 2392 | CG2 | VAL | A | 304 | 116.235 | 65.842 | 44.282 | 1.00 | 42.05 | A |
| ATOM | 2393 | C | VAL | A | 304 | 115.770 | 67.499 | 47.102 | 1.00 | 19.73 | A |
| ATOM | 2394 | O | VAL | A | 304 | 116.219 | 68.242 | 47.961 | 1.00 | 19.32 | A |
| ATOM | 2395 | N | SER | A | 305 | 115.136 | 66.360 | 47.402 | 1.00 | 21.55 | A |
| ATOM | 2396 | CA | SER | A | 305 | 114.969 | 65.904 | 48.794 | 1.00 | 24.92 | A |
| ATOM | 2397 | CB | SER | A | 305 | 114.202 | 64.572 | 48.838 | 1.00 | 31.82 | A |
| ATOM | 2398 | OG | SER | A | 305 | 112.797 | 64.716 | 48.530 | 1.00 | 45.40 | A |
| ATOM | 2399 | C | SER | A | 305 | 116.366 | 65.696 | 49.401 | 1.00 | 32.11 | A |
| ATOM | 2400 | O | SER | A | 305 | 117.187 | 64.961 | 48.836 | 1.00 | 19.54 | A |
| ATOM | 2401 | N | LEU | A | 306 | 116.649 | 66.330 | 50.535 | 1.00 | 25.35 | A |
| ATOM | 2402 | CA | LEU | A | 306 | 117.962 | 66.173 | 51.161 | 1.00 | 30.33 | A |
| ATOM | 2403 | CB | LEU | A | 306 | 118.422 | 67.488 | 51.831 | 1.00 | 35.23 | A |
| ATOM | 2404 | CG | LEU | A | 306 | 118.886 | 68.694 | 50.987 | 1.00 | 33.58 | A |
| ATOM | 2405 | CD1 | LEU | A | 306 | 119.870 | 68.352 | 49.838 | 1.00 | 29.73 | A |
| ATOM | 2406 | CD2 | LEU | A | 306 | 117.665 | 69.257 | 50.434 | 1.00 | 39.98 | A |
| ATOM | 2407 | C | LEU | A | 306 | 117.943 | 65.050 | 52.208 | 1.00 | 37.07 | A |
| ATOM | 2408 | O | LEU | A | 306 | 116.874 | 64.515 | 52.547 | 1.00 | 34.41 | A |
| ATOM | 2409 | N | GLN | A | 307 | 119.107 | 64.670 | 52.722 | 1.00 | 37.78 | A |
| ATOM | 2410 | CA | GLN | A | 307 | 119.102 | 63.615 | 53.734 | 1.00 | 47.24 | A |
| ATOM | 2411 | CB | GLN | A | 307 | 120.507 | 63.110 | 54.035 | 1.00 | 52.95 | A |
| ATOM | 2412 | CG | GLN | A | 307 | 120.931 | 61.932 | 53.174 | 1.00 | 64.46 | A |
| ATOM | 2413 | CD | GLN | A | 307 | 121.481 | 62.371 | 51.846 | 1.00 | 70.87 | A |
| ATOM | 2414 | OE1 | GLN | A | 307 | 122.341 | 63.253 | 51.785 | 1.00 | 76.28 | A |
| ATOM | 2415 | NE2 | GLN | A | 307 | 121.001 | 61.755 | 50.767 | 1.00 | 77.08 | A |
| ATOM | 2416 | C | GLN | A | 307 | 118.482 | 64.115 | 55.021 | 1.00 | 42.93 | A |
| ATOM | 2417 | O | GLN | A | 307 | 118.665 | 65.308 | 55.340 | 1.00 | 42.42 | A |
| ATOM | 2418 | OXT | GLN | A | 307 | 117.838 | 63.294 | 55.699 | 1.00 | 44.41 | A |
| ATOM | 2419 | CB | ALA | B | 1 | 64.181 | 107.666 | 4.123 | 1.00 | 39.20 | B |
| ATOM | 2420 | C | ALA | B | 1 | 62.836 | 105.816 | 3.113 | 1.00 | 41.03 | B |
| ATOM | 2421 | O | ALA | B | 1 | 61.659 | 105.713 | 3.477 | 1.00 | 42.08 | B |
| ATOM | 2422 | N | ALA | B | 1 | 62.413 | 108.231 | 2.458 | 1.00 | 40.18 | B |
| ATOM | 2423 | CA | ALA | B | 1 | 63.447 | 107.201 | 2.861 | 1.00 | 43.96 | B |
| ATOM | 2424 | N | ILE | B | 2 | 63.636 | 104.759 | 2.923 | 1.00 | 39.63 | B |
| ATOM | 2425 | CA | ILE | B | 2 | 63.175 | 103.383 | 3.141 | 1.00 | 37.01 | B |
| ATOM | 2426 | CB | ILE | B | 2 | 64.245 | 102.349 | 2.700 | 1.00 | 32.57 | B |
| ATOM | 2427 | CG2 | ILE | B | 2 | 63.775 | 100.936 | 3.064 | 1.00 | 35.80 | B |
| ATOM | 2428 | CG1 | ILE | B | 2 | 64.457 | 102.422 | 1.178 | 1.00 | 34.01 | B |
| ATOM | 2429 | CD1 | ILE | B | 2 | 65.479 | 101.372 | 0.650 | 1.00 | 31.21 | B |
| ATOM | 2430 | C | ILE | B | 2 | 62.831 | 103.151 | 4.633 | 1.00 | 38.27 | B |
| ATOM | 2431 | O | ILE | B | 2 | 63.565 | 103.577 | 5.528 | 1.00 | 32.71 | B |
| ATOM | 2432 | N | SER | B | 3 | 61.714 | 102.486 | 4.897 | 1.00 | 30.65 | B |
| ATOM | 2433 | CA | SER | B | 3 | 61.316 | 102.226 | 6.272 | 1.00 | 26.19 | B |
| ATOM | 2434 | CB | SER | B | 3 | 60.245 | 103.236 | 6.689 | 1.00 | 31.79 | B |

TABLE 2-continued

| | | | | | | | | | | |
|---|---|---|---|---|---|---|---|---|---|---|
| ATOM | 2435 | OG | SER | B | 3 | 59.060 | 103.020 | 5.926 | 1.00 | 27.35 | B |
| ATOM | 2436 | C | SER | B | 3 | 60.744 | 100.826 | 6.435 | 1.00 | 30.38 | B |
| ATOM | 2437 | O | SER | B | 3 | 60.495 | 100.132 | 5.446 | 1.00 | 28.89 | B |
| ATOM | 2438 | N | CYS | B | 4 | 60.559 | 100.410 | 7.690 | 1.00 | 27.89 | B |
| ATOM | 2439 | CA | CYS | B | 4 | 59.941 | 99.127 | 8.003 | 1.00 | 27.29 | B |
| ATOM | 2440 | C | CYS | B | 4 | 58.609 | 99.528 | 8.600 | 1.00 | 26.13 | B |
| ATOM | 2441 | O | CYS | B | 4 | 58.446 | 100.666 | 9.061 | 1.00 | 29.64 | B |
| ATOM | 2442 | CB | CYS | B | 4 | 60.731 | 98.328 | 9.056 | 1.00 | 27.46 | B |
| ATOM | 2443 | SG | CYS | B | 4 | 62.214 | 97.531 | 8.369 | 1.00 | 27.76 | B |
| ATOM | 2444 | N | GLY | B | 5 | 57.648 | 98.622 | 8.561 | 1.00 | 22.65 | B |
| ATOM | 2445 | CA | GLY | B | 5 | 56.366 | 98.916 | 9.155 | 1.00 | 23.57 | B |
| ATOM | 2446 | C | GLY | B | 5 | 56.452 | 98.570 | 10.643 | 1.00 | 24.00 | B |
| ATOM | 2447 | O | GLY | B | 5 | 57.504 | 98.199 | 11.181 | 1.00 | 23.18 | B |
| ATOM | 2448 | N | SER | B | 6 | 55.322 | 98.698 | 11.313 | 1.00 | 21.65 | B |
| ATOM | 2449 | CA | SER | B | 6 | 55.204 | 98.441 | 12.733 | 1.00 | 22.23 | B |
| ATOM | 2450 | CB | SER | B | 6 | 53.722 | 98.511 | 13.098 | 1.00 | 27.49 | B |
| ATOM | 2451 | OG | SER | B | 6 | 53.543 | 98.605 | 14.483 | 1.00 | 33.82 | B |
| ATOM | 2452 | C | SER | B | 6 | 55.785 | 97.062 | 13.091 | 1.00 | 26.45 | B |
| ATOM | 2453 | O | SER | B | 6 | 55.489 | 96.081 | 12.439 | 1.00 | 22.14 | B |
| ATOM | 2454 | N | PRO | B | 7 | 56.639 | 96.980 | 14.122 | 1.00 | 26.74 | B |
| ATOM | 2455 | CD | PRO | B | 7 | 57.230 | 98.026 | 14.973 | 1.00 | 25.89 | B |
| ATOM | 2456 | CA | PRO | B | 7 | 57.191 | 95.661 | 14.468 | 1.00 | 25.01 | B |
| ATOM | 2457 | CB | PRO | B | 7 | 58.175 | 95.984 | 15.592 | 1.00 | 22.52 | B |
| ATOM | 2458 | CG | PRO | B | 7 | 57.589 | 97.228 | 16.232 | 1.00 | 26.49 | B |
| ATOM | 2459 | C | PRO | B | 7 | 56.133 | 94.627 | 14.894 | 1.00 | 27.04 | B |
| ATOM | 2460 | O | PRO | B | 7 | 55.061 | 94.961 | 15.414 | 1.00 | 24.19 | B |
| ATOM | 2461 | N | PRO | B | 8 | 56.439 | 93.345 | 14.700 | 1.00 | 24.37 | B |
| ATOM | 2462 | CD | PRO | B | 8 | 57.540 | 92.754 | 13.936 | 1.00 | 26.75 | B |
| ATOM | 2463 | CA | PRO | B | 8 | 55.431 | 92.366 | 15.099 | 1.00 | 25.28 | B |
| ATOM | 2464 | CB | PRO | B | 8 | 55.974 | 91.048 | 14.538 | 1.00 | 31.15 | B |
| ATOM | 2465 | CG | PRO | B | 8 | 57.401 | 91.314 | 14.245 | 1.00 | 33.33 | B |
| ATOM | 2466 | C | PRO | B | 8 | 55.228 | 92.382 | 16.613 | 1.00 | 30.70 | B |
| ATOM | 2467 | O | PRO | B | 8 | 56.180 | 92.527 | 17.364 | 1.00 | 31.22 | B |
| ATOM | 2468 | N | PRO | B | 9 | 53.971 | 92.314 | 17.074 | 1.00 | 30.39 | B |
| ATOM | 2469 | CD | PRO | B | 9 | 52.724 | 92.280 | 16.275 | 1.00 | 37.82 | B |
| ATOM | 2470 | CA | PRO | B | 9 | 53.686 | 92.322 | 18.518 | 1.00 | 32.22 | B |
| ATOM | 2471 | CB | PRO | B | 9 | 52.155 | 92.415 | 18.589 | 1.00 | 31.66 | B |
| ATOM | 2472 | CG | PRO | B | 9 | 51.705 | 91.731 | 17.265 | 1.00 | 31.37 | B |
| ATOM | 2473 | C | PRO | B | 9 | 54.190 | 91.062 | 19.209 | 1.00 | 26.54 | B |
| ATOM | 2474 | O | PRO | B | 9 | 54.542 | 90.072 | 18.563 | 1.00 | 23.13 | B |
| ATOM | 2475 | N | ILE | B | 10 | 54.214 | 91.111 | 20.526 | 1.00 | 25.96 | B |
| ATOM | 2476 | CA | ILE | B | 10 | 54.651 | 89.969 | 21.302 | 1.00 | 34.36 | B |
| ATOM | 2477 | CB | ILE | B | 10 | 56.150 | 90.068 | 21.770 | 1.00 | 24.92 | B |
| ATOM | 2478 | CG2 | ILE | B | 10 | 56.398 | 91.363 | 22.562 | 1.00 | 24.04 | B |
| ATOM | 2479 | CG1 | ILE | B | 10 | 56.491 | 88.795 | 22.581 | 1.00 | 30.43 | B |
| ATOM | 2480 | CD1 | ILE | B | 10 | 57.991 | 88.536 | 22.813 | 1.00 | 24.83 | B |
| ATOM | 2481 | C | ILE | B | 10 | 53.753 | 89.810 | 22.511 | 1.00 | 33.31 | B |
| ATOM | 2482 | O | ILE | B | 10 | 53.743 | 90.647 | 23.412 | 1.00 | 32.83 | B |
| ATOM | 2483 | N | LEU | B | 11 | 52.992 | 88.724 | 22.525 | 1.00 | 30.71 | B |
| ATOM | 2484 | CA | LEU | B | 11 | 52.108 | 88.483 | 23.659 | 1.00 | 34.63 | B |
| ATOM | 2485 | CB | LEU | B | 11 | 51.217 | 87.277 | 23.365 | 1.00 | 36.50 | B |
| ATOM | 2486 | CG | LEU | B | 11 | 50.279 | 87.435 | 22.161 | 1.00 | 41.37 | B |
| ATOM | 2487 | CD1 | LEU | B | 11 | 49.708 | 86.073 | 21.769 | 1.00 | 42.99 | B |
| ATOM | 2488 | CD2 | LEU | B | 11 | 49.142 | 88.425 | 22.495 | 1.00 | 39.65 | B |
| ATOM | 2489 | C | LEU | B | 11 | 52.912 | 88.247 | 24.946 | 1.00 | 33.29 | B |
| ATOM | 2490 | O | LEU | B | 11 | 53.905 | 87.517 | 24.948 | 1.00 | 28.06 | B |
| ATOM | 2491 | N | ASN | B | 12 | 52.463 | 88.872 | 26.032 | 1.00 | 31.32 | B |
| ATOM | 2492 | CA | ASN | B | 12 | 53.086 | 88.753 | 27.328 | 1.00 | 30.29 | B |
| ATOM | 2493 | CB | ASN | B | 12 | 53.025 | 87.303 | 27.802 | 1.00 | 32.27 | B |
| ATOM | 2494 | CG | ASN | B | 12 | 51.612 | 86.875 | 28.083 | 1.00 | 38.86 | B |
| ATOM | 2495 | OD1 | ASN | B | 12 | 50.917 | 87.526 | 28.864 | 1.00 | 38.55 | B |
| ATOM | 2496 | ND2 | ASN | B | 12 | 51.161 | 85.805 | 27.431 | 1.00 | 34.66 | B |
| ATOM | 2497 | C | ASN | B | 12 | 54.510 | 89.250 | 27.371 | 1.00 | 32.36 | B |
| ATOM | 2498 | O | ASN | B | 12 | 55.277 | 88.858 | 28.239 | 1.00 | 32.55 | B |
| ATOM | 2499 | N | GLY | B | 13 | 54.849 | 90.130 | 26.439 | 1.00 | 28.46 | B |
| ATOM | 2500 | CA | GLY | B | 13 | 56.187 | 90.671 | 26.400 | 1.00 | 28.72 | B |
| ATOM | 2501 | C | GLY | B | 13 | 56.147 | 92.166 | 26.169 | 1.00 | 29.82 | B |
| ATOM | 2502 | O | GLY | B | 13 | 55.075 | 92.780 | 26.153 | 1.00 | 34.03 | B |
| ATOM | 2503 | N | ARG | B | 14 | 57.324 | 92.742 | 25.983 | 1.00 | 28.15 | B |
| ATOM | 2504 | CA | ARG | B | 14 | 57.486 | 94.166 | 25.739 | 1.00 | 31.15 | B |
| ATOM | 2505 | CB | ARG | B | 14 | 58.198 | 94.882 | 26.897 | 1.00 | 34.62 | B |
| ATOM | 2506 | CG | ARG | B | 14 | 57.388 | 95.196 | 28.116 | 1.00 | 41.44 | B |
| ATOM | 2507 | CD | ARG | B | 14 | 58.240 | 95.962 | 29.112 | 1.00 | 42.08 | B |
| ATOM | 2508 | NE | ARG | B | 14 | 57.526 | 96.080 | 30.373 | 1.00 | 49.55 | B |
| ATOM | 2509 | CZ | ARG | B | 14 | 58.023 | 96.595 | 31.487 | 1.00 | 48.40 | B |
| ATOM | 2510 | NH1 | ARG | B | 14 | 59.261 | 97.065 | 31.509 | 1.00 | 40.73 | B |
| ATOM | 2511 | NH2 | ARG | B | 14 | 57.276 | 96.602 | 32.593 | 1.00 | 56.30 | B |
| ATOM | 2512 | C | ARG | B | 14 | 58.409 | 94.342 | 24.567 | 1.00 | 23.56 | B |
| ATOM | 2513 | O | ARG | B | 14 | 59.232 | 93.480 | 24.280 | 1.00 | 23.51 | B |

TABLE 2-continued

| ATOM | 2514 | N | ILE | B | 15 | 58.319 | 95.516 | 23.955 | 1.00 | 27.48 | B |
|---|---|---|---|---|---|---|---|---|---|---|---|
| ATOM | 2515 | CA | ILE | B | 15 | 59.171 | 95.893 | 22.841 | 1.00 | 26.75 | B |
| ATOM | 2516 | CB | ILE | B | 15 | 58.345 | 96.176 | 21.580 | 1.00 | 26.32 | B |
| ATOM | 2517 | CG2 | ILE | B | 15 | 59.250 | 96.815 | 20.497 | 1.00 | 29.30 | B |
| ATOM | 2518 | CG1 | ILE | B | 15 | 57.656 | 94.902 | 21.122 | 1.00 | 30.62 | B |
| ATOM | 2519 | CD1 | ILE | B | 15 | 56.760 | 95.100 | 19.889 | 1.00 | 35.23 | B |
| ATOM | 2520 | C | ILE | B | 15 | 59.767 | 97.212 | 23.279 | 1.00 | 26.59 | B |
| ATOM | 2521 | O | ILE | B | 15 | 59.050 | 98.050 | 23.818 | 1.00 | 30.94 | B |
| ATOM | 2522 | N | SER | B | 16 | 61.055 | 97.409 | 23.036 | 1.00 | 23.15 | B |
| ATOM | 2523 | CA | SER | B | 16 | 61.709 | 98.654 | 23.393 | 1.00 | 32.61 | B |
| ATOM | 2524 | CB | SER | B | 16 | 63.187 | 98.567 | 23.057 | 1.00 | 29.32 | B |
| ATOM | 2525 | OG | SER | B | 16 | 63.359 | 98.151 | 21.717 | 1.00 | 35.31 | B |
| ATOM | 2526 | C | SER | B | 16 | 61.082 | 99.839 | 22.639 | 1.00 | 41.27 | B |
| ATOM | 2527 | O | SER | B | 16 | 60.466 | 99.674 | 21.576 | 1.00 | 36.78 | B |
| ATOM | 2528 | N | TYR | B | 17 | 61.260 | 101.035 | 23.193 | 1.00 | 42.89 | B |
| ATOM | 2529 | CA | TYR | B | 17 | 60.719 | 102.267 | 22.624 | 1.00 | 46.29 | B |
| ATOM | 2530 | CB | TYR | B | 17 | 60.932 | 103.436 | 23.623 | 1.00 | 44.99 | B |
| ATOM | 2531 | CG | TYR | B | 17 | 60.026 | 103.380 | 24.865 | 1.00 | 47.02 | B |
| ATOM | 2532 | CD1 | TYR | B | 17 | 60.510 | 103.694 | 26.151 | 1.00 | 49.03 | B |
| ATOM | 2533 | CE1 | TYR | B | 17 | 59.664 | 103.655 | 27.283 | 1.00 | 48.52 | B |
| ATOM | 2534 | CD2 | TYR | B | 17 | 58.686 | 103.025 | 24.748 | 1.00 | 51.67 | B |
| ATOM | 2535 | CE2 | TYR | B | 17 | 57.833 | 102.974 | 25.861 | 1.00 | 53.32 | B |
| ATOM | 2536 | CZ | TYR | B | 17 | 58.319 | 103.292 | 27.122 | 1.00 | 56.82 | B |
| ATOM | 2537 | OH | TYR | B | 17 | 57.430 | 103.259 | 28.190 | 1.00 | 55.53 | B |
| ATOM | 2538 | C | TYR | B | 17 | 61.397 | 102.551 | 21.285 | 1.00 | 46.15 | B |
| ATOM | 2539 | O | TYR | B | 17 | 62.600 | 102.375 | 21.146 | 1.00 | 50.00 | B |
| ATOM | 2540 | N | TYR | B | 18 | 60.623 | 102.952 | 20.281 | 1.00 | 46.05 | B |
| ATOM | 2541 | CA | TYR | B | 18 | 61.204 | 103.270 | 18.975 | 1.00 | 44.93 | B |
| ATOM | 2542 | CB | TYR | B | 18 | 61.076 | 102.076 | 18.010 | 1.00 | 37.78 | B |
| ATOM | 2543 | CG | TYR | B | 18 | 59.645 | 101.669 | 17.711 | 1.00 | 37.10 | B |
| ATOM | 2544 | CD1 | TYR | B | 18 | 58.890 | 102.343 | 16.750 | 1.00 | 31.24 | B |
| ATOM | 2545 | CE1 | TYR | B | 18 | 57.573 | 101.980 | 16.501 | 1.00 | 34.43 | B |
| ATOM | 2546 | CD2 | TYR | B | 18 | 59.040 | 100.622 | 18.415 | 1.00 | 34.57 | B |
| ATOM | 2547 | CE2 | TYR | B | 18 | 57.730 | 100.255 | 18.184 | 1.00 | 36.06 | B |
| ATOM | 2548 | CZ | TYR | B | 18 | 57.000 | 100.939 | 17.218 | 1.00 | 35.02 | B |
| ATOM | 2549 | OH | TYR | B | 18 | 55.706 | 100.565 | 16.967 | 1.00 | 33.22 | B |
| ATOM | 2550 | C | TYR | B | 18 | 60.524 | 104.514 | 18.375 | 1.00 | 40.62 | B |
| ATOM | 2551 | O | TYR | B | 18 | 59.356 | 104.784 | 18.632 | 1.00 | 40.57 | B |
| ATOM | 2552 | N | SER | B | 19 | 61.280 | 105.260 | 17.586 | 1.00 | 42.39 | B |
| ATOM | 2553 | CA | SER | B | 19 | 60.786 | 106.464 | 16.931 | 1.00 | 49.17 | B |
| ATOM | 2554 | CB | SER | B | 19 | 61.922 | 107.472 | 16.789 | 1.00 | 49.59 | B |
| ATOM | 2555 | OG | SER | B | 19 | 63.070 | 106.843 | 16.237 | 1.00 | 54.17 | B |
| ATOM | 2556 | C | SER | B | 19 | 60.213 | 106.155 | 15.540 | 1.00 | 51.20 | B |
| ATOM | 2557 | O | SER | B | 19 | 60.569 | 105.165 | 14.900 | 1.00 | 42.62 | B |
| ATOM | 2558 | N | THR | B | 20 | 59.347 | 107.041 | 15.073 | 1.00 | 48.91 | B |
| ATOM | 2559 | CA | THR | B | 20 | 58.706 | 106.898 | 13.783 | 1.00 | 49.40 | B |
| ATOM | 2560 | CB | THR | B | 20 | 57.166 | 107.002 | 13.991 | 1.00 | 52.73 | B |
| ATOM | 2561 | OG1 | THR | B | 20 | 56.483 | 106.279 | 12.968 | 1.00 | 60.25 | B |
| ATOM | 2562 | CG2 | THR | B | 20 | 56.714 | 108.456 | 13.943 | 1.00 | 51.71 | B |
| ATOM | 2563 | C | THR | B | 20 | 59.222 | 108.022 | 12.844 | 1.00 | 47.48 | B |
| ATOM | 2564 | O | THR | B | 20 | 59.460 | 109.147 | 13.280 | 1.00 | 50.56 | B |
| ATOM | 2565 | N | PRO | B | 21 | 59.427 | 107.720 | 11.551 | 1.00 | 46.52 | B |
| ATOM | 2566 | CD | PRO | B | 21 | 59.801 | 108.745 | 10.551 | 1.00 | 44.33 | B |
| ATOM | 2567 | CA | PRO | B | 21 | 59.204 | 106.417 | 10.909 | 1.00 | 43.20 | B |
| ATOM | 2568 | CB | PRO | B | 21 | 59.137 | 106.769 | 9.422 | 1.00 | 43.49 | B |
| ATOM | 2569 | CG | PRO | B | 21 | 60.103 | 107.918 | 9.305 | 1.00 | 44.19 | B |
| ATOM | 2570 | C | PRO | B | 21 | 60.342 | 105.456 | 11.248 | 1.00 | 37.71 | B |
| ATOM | 2571 | O | PRO | B | 21 | 61.393 | 105.891 | 11.674 | 1.00 | 38.42 | B |
| ATOM | 2572 | N | THR | B | 22 | 60.123 | 104.155 | 11.067 | 1.00 | 40.00 | B |
| ATOM | 2573 | CA | THR | B | 22 | 61.139 | 103.150 | 11.382 | 1.00 | 37.29 | B |
| ATOM | 2574 | CB | THR | B | 22 | 60.521 | 101.715 | 11.578 | 1.00 | 33.63 | B |
| ATOM | 2575 | OG1 | THR | B | 22 | 59.497 | 101.719 | 12.600 | 1.00 | 36.55 | B |
| ATOM | 2576 | CG2 | THR | B | 22 | 61.626 | 100.734 | 11.963 | 1.00 | 26.59 | B |
| ATOM | 2577 | C | THR | B | 22 | 62.143 | 103.079 | 10.221 | 1.00 | 35.94 | B |
| ATOM | 2578 | O | THR | B | 22 | 61.851 | 102.484 | 9.183 | 1.00 | 33.29 | B |
| ATOM | 2579 | N | ALA | B | 23 | 63.326 | 103.663 | 10.410 | 1.00 | 33.77 | B |
| ATOM | 2580 | CA | ALA | B | 23 | 64.367 | 103.677 | 9.380 | 1.00 | 30.19 | B |
| ATOM | 2581 | CB | ALA | B | 23 | 65.314 | 104.852 | 9.615 | 1.00 | 28.90 | B |
| ATOM | 2582 | C | ALA | B | 23 | 65.192 | 102.399 | 9.300 | 1.00 | 30.98 | B |
| ATOM | 2583 | O | ALA | B | 23 | 65.331 | 101.693 | 10.284 | 1.00 | 23.97 | B |
| ATOM | 2584 | N | VAL | B | 24 | 65.736 | 102.127 | 8.112 | 1.00 | 27.61 | B |
| ATOM | 2585 | CA | VAL | B | 24 | 66.591 | 100.982 | 7.874 | 1.00 | 26.92 | B |
| ATOM | 2586 | CB | VAL | B | 24 | 67.197 | 101.042 | 6.460 | 1.00 | 29.41 | B |
| ATOM | 2587 | CG1 | VAL | B | 24 | 68.357 | 100.043 | 6.326 | 1.00 | 28.58 | B |
| ATOM | 2588 | CG2 | VAL | B | 24 | 66.107 | 100.729 | 5.430 | 1.00 | 26.92 | B |
| ATOM | 2589 | C | VAL | B | 24 | 67.707 | 101.091 | 8.898 | 1.00 | 32.79 | B |
| ATOM | 2590 | O | VAL | B | 24 | 68.266 | 102.166 | 9.077 | 1.00 | 26.10 | B |
| ATOM | 2591 | N | GLY | B | 25 | 68.026 | 100.000 | 9.586 | 1.00 | 28.01 | B |
| ATOM | 2592 | CA | GLY | B | 25 | 69.070 | 100.081 | 10.596 | 1.00 | 31.93 | B |

TABLE 2-continued

| ATOM | 2593 | C | GLY | B | 25 | 68.516 | 100.210 | 12.007 | 1.00 | 34.29 | B |
|------|------|-----|-----|---|----|--------|---------|--------|------|-------|---|
| ATOM | 2594 | O | GLY | B | 25 | 69.251 | 100.080 | 12.966 | 1.00 | 28.44 | B |
| ATOM | 2595 | N | THR | B | 26 | 67.227 | 100.486 | 12.148 | 1.00 | 26.99 | B |
| ATOM | 2596 | CA | THR | B | 26 | 66.650 | 100.568 | 13.474 | 1.00 | 29.37 | B |
| ATOM | 2597 | CB | THR | B | 26 | 65.179 | 100.994 | 13.403 | 1.00 | 30.78 | B |
| ATOM | 2598 | OG1 | THR | B | 26 | 65.111 | 102.295 | 12.808 | 1.00 | 26.87 | B |
| ATOM | 2599 | CG2 | THR | B | 26 | 64.524 | 101.000 | 14.833 | 1.00 | 23.56 | B |
| ATOM | 2600 | C | THR | B | 26 | 66.713 | 99.183 | 14.136 | 1.00 | 32.07 | B |
| ATOM | 2601 | O | THR | B | 26 | 66.462 | 98.171 | 13.473 | 1.00 | 28.44 | B |
| ATOM | 2602 | N | VAL | B | 27 | 67.056 | 99.143 | 15.429 | 1.00 | 28.90 | B |
| ATOM | 2603 | CA | VAL | B | 27 | 67.124 | 97.891 | 16.200 | 1.00 | 29.71 | B |
| ATOM | 2604 | CB | VAL | B | 27 | 68.507 | 97.703 | 16.858 | 1.00 | 36.67 | B |
| ATOM | 2605 | CG1 | VAL | B | 27 | 68.477 | 96.507 | 17.808 | 1.00 | 31.87 | B |
| ATOM | 2606 | CG2 | VAL | B | 27 | 69.554 | 97.478 | 15.793 | 1.00 | 32.00 | B |
| ATOM | 2607 | C | VAL | B | 27 | 66.054 | 97.946 | 17.292 | 1.00 | 26.09 | B |
| ATOM | 2608 | O | VAL | B | 27 | 65.961 | 98.921 | 18.029 | 1.00 | 28.74 | B |
| ATOM | 2609 | N | ILE | B | 28 | 65.230 | 96.913 | 17.349 | 1.00 | 28.74 | B |
| ATOM | 2610 | CA | ILE | B | 28 | 64.126 | 96.780 | 18.294 | 1.00 | 34.25 | B |
| ATOM | 2611 | CB | ILE | B | 28 | 62.802 | 96.400 | 17.552 | 1.00 | 38.10 | B |
| ATOM | 2612 | CG2 | ILE | B | 28 | 61.752 | 95.929 | 18.516 | 1.00 | 49.78 | B |
| ATOM | 2613 | CG1 | ILE | B | 28 | 62.260 | 97.598 | 16.808 | 1.00 | 46.71 | B |
| ATOM | 2614 | CD1 | ILE | B | 28 | 62.252 | 98.826 | 17.612 | 1.00 | 40.93 | B |
| ATOM | 2615 | C | ILE | B | 28 | 64.491 | 95.619 | 19.223 | 1.00 | 38.36 | B |
| ATOM | 2616 | O | ILE | B | 28 | 65.063 | 94.626 | 18.769 | 1.00 | 29.90 | B |
| ATOM | 2617 | N | ARG | B | 29 | 64.134 | 95.724 | 20.503 | 1.00 | 30.42 | B |
| ATOM | 2618 | CA | ARG | B | 29 | 64.470 | 94.673 | 21.458 | 1.00 | 32.43 | B |
| ATOM | 2619 | CB | ARG | B | 29 | 65.468 | 95.242 | 22.461 | 1.00 | 38.54 | B |
| ATOM | 2620 | CG | ARG | B | 29 | 66.234 | 94.231 | 23.273 | 1.00 | 56.74 | B |
| ATOM | 2621 | CD | ARG | B | 29 | 67.479 | 94.939 | 23.821 | 1.00 | 68.43 | B |
| ATOM | 2622 | NE | ARG | B | 29 | 68.210 | 95.573 | 22.722 | 1.00 | 77.31 | B |
| ATOM | 2623 | CZ | ARG | B | 29 | 69.134 | 94.960 | 21.983 | 1.00 | 81.82 | B |
| ATOM | 2624 | NH1 | ARG | B | 29 | 69.454 | 93.693 | 22.237 | 1.00 | 82.00 | B |
| ATOM | 2625 | NH2 | ARG | B | 29 | 69.723 | 95.603 | 20.976 | 1.00 | 82.81 | B |
| ATOM | 2626 | C | ARG | B | 29 | 63.222 | 94.132 | 22.168 | 1.00 | 26.06 | B |
| ATOM | 2627 | O | ARG | B | 29 | 62.432 | 94.884 | 22.704 | 1.00 | 20.11 | B |
| ATOM | 2628 | N | TYR | B | 30 | 63.032 | 92.823 | 22.133 | 1.00 | 22.95 | B |
| ATOM | 2629 | CA | TYR | B | 30 | 61.886 | 92.206 | 22.787 | 1.00 | 31.30 | B |
| ATOM | 2630 | CB | TYR | B | 30 | 61.299 | 91.096 | 21.905 | 1.00 | 28.61 | B |
| ATOM | 2631 | CG | TYR | B | 30 | 60.647 | 91.547 | 20.605 | 1.00 | 29.37 | B |
| ATOM | 2632 | CD1 | TYR | B | 30 | 61.389 | 92.135 | 19.579 | 1.00 | 24.77 | B |
| ATOM | 2633 | CE1 | TYR | B | 30 | 60.781 | 92.553 | 18.387 | 1.00 | 19.11 | B |
| ATOM | 2634 | CD2 | TYR | B | 30 | 59.282 | 91.378 | 20.403 | 1.00 | 29.03 | B |
| ATOM | 2635 | CE2 | TYR | B | 30 | 58.674 | 91.785 | 19.215 | 1.00 | 26.35 | B |
| ATOM | 2636 | CZ | TYR | B | 30 | 59.429 | 92.379 | 18.216 | 1.00 | 23.41 | B |
| ATOM | 2637 | OH | TYR | B | 30 | 58.793 | 92.836 | 17.083 | 1.00 | 26.05 | B |
| ATOM | 2638 | C | TYR | B | 30 | 62.340 | 91.579 | 24.126 | 1.00 | 28.93 | B |
| ATOM | 2639 | O | TYR | B | 30 | 63.497 | 91.168 | 24.283 | 1.00 | 24.49 | B |
| ATOM | 2640 | N | SER | B | 31 | 61.418 | 91.488 | 25.067 | 1.00 | 26.50 | B |
| ATOM | 2641 | CA | SER | B | 31 | 61.697 | 90.903 | 26.369 | 1.00 | 24.95 | B |
| ATOM | 2642 | CB | SER | B | 31 | 62.304 | 91.946 | 27.308 | 1.00 | 21.32 | B |
| ATOM | 2643 | OG | SER | B | 31 | 61.426 | 93.028 | 27.483 | 1.00 | 26.55 | B |
| ATOM | 2644 | C | SER | B | 31 | 60.388 | 90.378 | 26.954 | 1.00 | 29.25 | B |
| ATOM | 2645 | O | SER | B | 31 | 59.287 | 90.780 | 26.529 | 1.00 | 22.45 | B |
| ATOM | 2646 | N | CYS | B | 32 | 60.515 | 89.484 | 27.930 | 1.00 | 27.99 | B |
| ATOM | 2647 | CA | CYS | B | 32 | 59.364 | 88.868 | 28.606 | 1.00 | 32.41 | B |
| ATOM | 2648 | C | CYS | B | 32 | 59.371 | 89.122 | 30.121 | 1.00 | 38.37 | B |
| ATOM | 2649 | O | CYS | B | 32 | 60.431 | 89.311 | 30.719 | 1.00 | 37.82 | B |
| ATOM | 2650 | CB | CYS | B | 32 | 59.371 | 87.347 | 28.400 | 1.00 | 30.70 | B |
| ATOM | 2651 | SG | CYS | B | 32 | 59.450 | 86.770 | 26.677 | 1.00 | 32.11 | B |
| ATOM | 2652 | N | SER | B | 33 | 58.178 | 89.101 | 30.717 | 1.00 | 51.37 | B |
| ATOM | 2653 | CA | SER | B | 33 | 57.995 | 89.265 | 32.163 | 1.00 | 56.15 | B |
| ATOM | 2654 | CB | SER | B | 33 | 56.544 | 89.013 | 32.552 | 1.00 | 60.18 | B |
| ATOM | 2655 | OG | SER | B | 33 | 55.675 | 89.714 | 31.672 | 1.00 | 66.23 | B |
| ATOM | 2656 | C | SER | B | 33 | 58.859 | 88.260 | 32.894 | 1.00 | 57.27 | B |
| ATOM | 2657 | O | SER | B | 33 | 59.535 | 87.427 | 32.274 | 1.00 | 60.30 | B |
| ATOM | 2658 | N | GLY | B | 34 | 58.805 | 88.290 | 34.219 | 1.00 | 53.29 | B |
| ATOM | 2659 | CA | GLY | B | 34 | 59.662 | 87.391 | 34.976 | 1.00 | 47.70 | B |
| ATOM | 2660 | C | GLY | B | 34 | 59.278 | 85.922 | 34.987 | 1.00 | 44.48 | B |
| ATOM | 2661 | O | GLY | B | 34 | 60.129 | 85.033 | 35.135 | 1.00 | 38.34 | B |
| ATOM | 2662 | N | THR | B | 35 | 57.993 | 85.660 | 34.818 | 1.00 | 40.51 | B |
| ATOM | 2663 | CA | THR | B | 35 | 57.524 | 84.290 | 34.860 | 1.00 | 40.76 | B |
| ATOM | 2664 | CB | THR | B | 35 | 56.225 | 84.239 | 35.644 | 1.00 | 41.73 | B |
| ATOM | 2665 | OG1 | THR | B | 35 | 55.258 | 85.077 | 35.014 | 1.00 | 48.51 | B |
| ATOM | 2666 | CG2 | THR | B | 35 | 56.468 | 84.761 | 37.057 | 1.00 | 44.89 | B |
| ATOM | 2667 | C | THR | B | 35 | 57.369 | 83.691 | 33.470 | 1.00 | 39.51 | B |
| ATOM | 2668 | O | THR | B | 35 | 56.786 | 82.613 | 33.286 | 1.00 | 31.97 | B |
| ATOM | 2669 | N | PHE | B | 36 | 57.924 | 84.399 | 32.491 | 1.00 | 35.56 | B |
| ATOM | 2670 | CA | PHE | B | 36 | 57.873 | 83.955 | 31.112 | 1.00 | 31.01 | B |
| ATOM | 2671 | CB | PHE | B | 36 | 57.146 | 84.967 | 30.250 | 1.00 | 33.05 | B |

TABLE 2-continued

| ATOM | 2672 | CG | PHE | B | 36 | 55.673 | 84.918 | 30.396 | 1.00 | 35.23 | B |
|---|---|---|---|---|---|---|---|---|---|---|---|
| ATOM | 2673 | CD1 | PHE | B | 36 | 55.040 | 85.573 | 31.444 | 1.00 | 35.53 | B |
| ATOM | 2674 | CD2 | PHE | B | 36 | 54.909 | 84.204 | 29.483 | 1.00 | 31.53 | B |
| ATOM | 2675 | CE1 | PHE | B | 36 | 53.663 | 85.497 | 31.570 | 1.00 | 37.58 | B |
| ATOM | 2676 | CE2 | PHE | B | 36 | 53.549 | 84.126 | 29.604 | 1.00 | 32.60 | B |
| ATOM | 2677 | CZ | PHE | B | 36 | 52.918 | 84.769 | 30.638 | 1.00 | 32.38 | B |
| ATOM | 2678 | C | PHE | B | 36 | 59.276 | 83.798 | 30.577 | 1.00 | 32.83 | B |
| ATOM | 2679 | O | PHE | B | 36 | 60.212 | 84.347 | 31.125 | 1.00 | 33.40 | B |
| ATOM | 2680 | N | ARG | B | 37 | 59.427 | 83.049 | 29.498 | 1.00 | 30.99 | B |
| ATOM | 2681 | CA | ARG | B | 37 | 60.741 | 82.896 | 28.916 | 1.00 | 29.69 | B |
| ATOM | 2682 | CB | ARG | B | 37 | 61.201 | 81.458 | 29.083 | 1.00 | 30.62 | B |
| ATOM | 2683 | CG | ARG | B | 37 | 61.442 | 81.072 | 30.541 | 1.00 | 35.61 | B |
| ATOM | 2684 | CD | ARG | B | 37 | 62.492 | 81.992 | 31.177 | 1.00 | 39.39 | B |
| ATOM | 2685 | NE | ARG | B | 37 | 62.303 | 82.044 | 32.629 | 1.00 | 49.28 | B |
| ATOM | 2686 | CZ | ARG | B | 37 | 62.847 | 81.168 | 33.451 | 1.00 | 47.41 | B |
| ATOM | 2687 | NH1 | ARG | B | 37 | 63.614 | 80.212 | 32.947 | 1.00 | 53.00 | B |
| ATOM | 2688 | NH2 | ARG | B | 37 | 62.602 | 81.223 | 34.751 | 1.00 | 44.10 | B |
| ATOM | 2689 | C | ARG | B | 37 | 60.713 | 83.280 | 27.439 | 1.00 | 32.05 | B |
| ATOM | 2690 | O | ARG | B | 37 | 59.809 | 82.874 | 26.700 | 1.00 | 25.63 | B |
| ATOM | 2691 | N | LEU | B | 38 | 61.706 | 84.050 | 27.011 | 1.00 | 23.96 | B |
| ATOM | 2692 | CA | LEU | B | 38 | 61.802 | 84.470 | 25.621 | 1.00 | 30.62 | B |
| ATOM | 2693 | CB | LEU | B | 38 | 62.655 | 85.738 | 25.508 | 1.00 | 23.25 | B |
| ATOM | 2694 | CG | LEU | B | 38 | 62.739 | 86.365 | 24.105 | 1.00 | 28.16 | B |
| ATOM | 2695 | CD1 | LEU | B | 38 | 61.376 | 86.948 | 23.659 | 1.00 | 20.01 | B |
| ATOM | 2696 | CD2 | LEU | B | 38 | 63.753 | 87.486 | 24.132 | 1.00 | 32.19 | B |
| ATOM | 2697 | C | LEU | B | 38 | 62.386 | 83.361 | 24.745 | 1.00 | 27.63 | B |
| ATOM | 2698 | O | LEU | B | 38 | 63.447 | 82.793 | 25.036 | 1.00 | 27.98 | B |
| ATOM | 2699 | N | ILE | B | 39 | 61.651 | 83.017 | 23.691 | 1.00 | 30.18 | B |
| ATOM | 2700 | CA | ILE | B | 39 | 62.073 | 81.983 | 22.743 | 1.00 | 27.37 | B |
| ATOM | 2701 | CB | ILE | B | 39 | 60.940 | 80.959 | 22.492 | 1.00 | 30.75 | B |
| ATOM | 2702 | CG2 | ILE | B | 39 | 61.438 | 79.878 | 21.538 | 1.00 | 29.27 | B |
| ATOM | 2703 | CG1 | ILE | B | 39 | 60.455 | 80.359 | 23.822 | 1.00 | 30.90 | B |
| ATOM | 2704 | CD1 | ILE | B | 39 | 61.491 | 79.535 | 24.559 | 1.00 | 26.44 | B |
| ATOM | 2705 | C | ILE | B | 39 | 62.403 | 82.668 | 21.418 | 1.00 | 29.53 | B |
| ATOM | 2706 | O | ILE | B | 39 | 61.510 | 83.256 | 20.797 | 1.00 | 24.87 | B |
| ATOM | 2707 | N | GLY | B | 40 | 63.676 | 82.609 | 20.998 | 1.00 | 21.97 | B |
| ATOM | 2708 | CA | GLY | B | 40 | 64.084 | 83.239 | 19.751 | 1.00 | 23.62 | B |
| ATOM | 2709 | C | GLY | B | 40 | 64.957 | 84.450 | 19.975 | 1.00 | 22.85 | B |
| ATOM | 2710 | O | GLY | B | 40 | 65.065 | 84.921 | 21.104 | 1.00 | 21.42 | B |
| ATOM | 2711 | N | GLU | B | 41 | 65.592 | 84.958 | 18.925 | 1.00 | 27.33 | B |
| ATOM | 2712 | CA | GLU | B | 41 | 66.472 | 86.133 | 19.065 | 1.00 | 29.50 | B |
| ATOM | 2713 | CB | GLU | B | 41 | 67.138 | 86.471 | 17.730 | 1.00 | 33.78 | B |
| ATOM | 2714 | CG | GLU | B | 41 | 68.634 | 86.193 | 17.721 | 1.00 | 52.17 | B |
| ATOM | 2715 | CD | GLU | B | 41 | 69.411 | 87.123 | 18.648 | 1.00 | 57.74 | B |
| ATOM | 2716 | OE1 | GLU | B | 41 | 70.414 | 86.641 | 19.231 | 1.00 | 66.30 | B |
| ATOM | 2717 | OE2 | GLU | B | 41 | 69.034 | 88.326 | 18.791 | 1.00 | 53.76 | B |
| ATOM | 2718 | C | GLU | B | 41 | 65.667 | 87.333 | 19.541 | 1.00 | 30.40 | B |
| ATOM | 2719 | O | GLU | B | 41 | 64.601 | 87.619 | 18.995 | 1.00 | 27.22 | B |
| ATOM | 2720 | N | LYS | B | 42 | 66.197 | 88.049 | 20.528 | 1.00 | 27.86 | B |
| ATOM | 2721 | CA | LYS | B | 42 | 65.538 | 89.215 | 21.135 | 1.00 | 32.03 | B |
| ATOM | 2722 | CB | LYS | B | 42 | 66.171 | 89.495 | 22.504 | 1.00 | 37.19 | B |
| ATOM | 2723 | CG | LYS | B | 42 | 67.610 | 89.990 | 22.379 | 1.00 | 43.78 | B |
| ATOM | 2724 | CD | LYS | B | 42 | 68.196 | 90.536 | 23.674 | 1.00 | 54.68 | B |
| ATOM | 2725 | CE | LYS | B | 42 | 68.055 | 89.538 | 24.812 | 1.00 | 62.51 | B |
| ATOM | 2726 | NZ | LYS | B | 42 | 68.438 | 88.139 | 24.443 | 1.00 | 69.20 | B |
| ATOM | 2727 | C | LYS | B | 42 | 65.586 | 90.530 | 20.331 | 1.00 | 32.32 | B |
| ATOM | 2728 | O | LYS | B | 42 | 64.771 | 91.432 | 20.555 | 1.00 | 27.61 | B |
| ATOM | 2729 | N | SER | B | 43 | 66.547 | 90.680 | 19.422 | 1.00 | 28.99 | B |
| ATOM | 2730 | CA | SER | B | 43 | 66.611 | 91.946 | 18.672 | 1.00 | 33.61 | B |
| ATOM | 2731 | CB | SER | B | 43 | 68.012 | 92.565 | 18.722 | 1.00 | 29.97 | B |
| ATOM | 2732 | OG | SER | B | 43 | 68.478 | 92.606 | 20.047 | 1.00 | 47.21 | B |
| ATOM | 2733 | C | SER | B | 43 | 66.273 | 91.770 | 17.224 | 1.00 | 28.57 | B |
| ATOM | 2734 | O | SER | B | 43 | 66.765 | 90.841 | 16.588 | 1.00 | 32.11 | B |
| ATOM | 2735 | N | LEU | B | 44 | 65.443 | 92.661 | 16.697 | 1.00 | 26.09 | B |
| ATOM | 2736 | CA | LEU | B | 44 | 65.127 | 92.607 | 15.280 | 1.00 | 25.34 | B |
| ATOM | 2737 | CB | LEU | B | 44 | 63.620 | 92.609 | 14.987 | 1.00 | 21.75 | B |
| ATOM | 2738 | CG | LEU | B | 44 | 62.608 | 91.642 | 15.593 | 1.00 | 33.26 | B |
| ATOM | 2739 | CD1 | LEU | B | 44 | 61.455 | 91.487 | 14.626 | 1.00 | 24.66 | B |
| ATOM | 2740 | CD2 | LEU | B | 44 | 63.227 | 90.293 | 15.976 | 1.00 | 19.72 | B |
| ATOM | 2741 | C | LEU | B | 44 | 65.738 | 93.863 | 14.694 | 1.00 | 27.39 | B |
| ATOM | 2742 | O | LEU | B | 44 | 65.759 | 94.919 | 15.334 | 1.00 | 29.07 | B |
| ATOM | 2743 | N | LEU | B | 45 | 66.201 | 93.740 | 13.456 | 1.00 | 26.79 | B |
| ATOM | 2744 | CA | LEU | B | 45 | 66.854 | 94.812 | 12.727 | 1.00 | 26.17 | B |
| ATOM | 2745 | CB | LEU | B | 45 | 68.202 | 94.303 | 12.213 | 1.00 | 25.36 | B |
| ATOM | 2746 | CG | LEU | B | 45 | 69.343 | 95.281 | 11.950 | 1.00 | 35.90 | B |
| ATOM | 2747 | CD1 | LEU | B | 45 | 70.263 | 94.668 | 10.905 | 1.00 | 31.78 | B |
| ATOM | 2748 | CD2 | LEU | B | 45 | 68.853 | 96.627 | 11.519 | 1.00 | 39.62 | B |
| ATOM | 2749 | C | LEU | B | 45 | 66.016 | 95.198 | 11.516 | 1.00 | 25.11 | B |
| ATOM | 2750 | O | LEU | B | 45 | 65.568 | 94.320 | 10.761 | 1.00 | 20.94 | B |

TABLE 2-continued

| ATOM | 2751 | N | CYS | B | 46 | 65.803 | 96.487 | 11.298 | 1.00 | 24.85 | B |
|---|---|---|---|---|---|---|---|---|---|---|---|
| ATOM | 2752 | CA | CYS | B | 46 | 65.057 | 96.887 | 10.097 | 1.00 | 22.87 | B |
| ATOM | 2753 | C | CYS | B | 46 | 66.106 | 96.897 | 8.976 | 1.00 | 29.24 | B |
| ATOM | 2754 | O | CYS | B | 46 | 67.099 | 97.601 | 9.051 | 1.00 | 28.50 | B |
| ATOM | 2755 | CB | CYS | B | 46 | 64.446 | 98.284 | 10.251 | 1.00 | 26.50 | B |
| ATOM | 2756 | SG | CYS | B | 46 | 63.677 | 98.900 | 8.705 | 1.00 | 27.31 | B |
| ATOM | 2757 | N | ILE | B | 47 | 65.877 | 96.106 | 7.943 | 1.00 | 24.65 | B |
| ATOM | 2758 | CA | ILE | B | 47 | 66.817 | 95.991 | 6.842 | 1.00 | 28.64 | B |
| ATOM | 2759 | CB | ILE | B | 47 | 67.412 | 94.572 | 6.871 | 1.00 | 30.17 | B |
| ATOM | 2760 | CG2 | ILE | B | 47 | 68.114 | 94.258 | 5.601 | 1.00 | 42.28 | B |
| ATOM | 2761 | CG1 | ILE | B | 47 | 68.341 | 94.458 | 8.070 | 1.00 | 40.16 | B |
| ATOM | 2762 | CD1 | ILE | B | 47 | 69.121 | 93.190 | 8.107 | 1.00 | 53.27 | B |
| ATOM | 2763 | C | ILE | B | 47 | 66.098 | 96.188 | 5.504 | 1.00 | 28.32 | B |
| ATOM | 2764 | O | ILE | B | 47 | 64.874 | 96.332 | 5.466 | 1.00 | 24.72 | B |
| ATOM | 2765 | N | THR | B | 48 | 66.853 | 96.238 | 4.413 | 1.00 | 24.30 | B |
| ATOM | 2766 | CA | THR | B | 48 | 66.236 | 96.267 | 3.091 | 1.00 | 27.24 | B |
| ATOM | 2767 | CB | THR | B | 48 | 66.215 | 97.672 | 2.405 | 1.00 | 31.04 | B |
| ATOM | 2768 | OG1 | THR | B | 48 | 65.632 | 97.534 | 1.090 | 1.00 | 26.58 | B |
| ATOM | 2769 | CG2 | THR | B | 48 | 67.627 | 98.250 | 2.271 | 1.00 | 23.59 | B |
| ATOM | 2770 | C | THR | B | 48 | 67.048 | 95.280 | 2.254 | 1.00 | 26.55 | B |
| ATOM | 2771 | O | THR | B | 48 | 68.276 | 95.371 | 2.173 | 1.00 | 27.30 | B |
| ATOM | 2772 | N | LYS | B | 49 | 66.370 | 94.295 | 1.688 | 1.00 | 24.39 | B |
| ATOM | 2773 | CA | LYS | B | 49 | 67.031 | 93.309 | 0.837 | 1.00 | 25.65 | B |
| ATOM | 2774 | CB | LYS | B | 49 | 66.323 | 91.943 | 0.940 | 1.00 | 27.44 | B |
| ATOM | 2775 | CG | LYS | B | 49 | 66.358 | 91.351 | 2.368 | 1.00 | 36.21 | B |
| ATOM | 2776 | CD | LYS | B | 49 | 67.171 | 90.103 | 2.479 | 1.00 | 40.52 | B |
| ATOM | 2777 | CE | LYS | B | 49 | 68.570 | 90.294 | 2.025 | 1.00 | 41.63 | B |
| ATOM | 2778 | NZ | LYS | B | 49 | 69.314 | 89.069 | 2.403 | 1.00 | 46.47 | B |
| ATOM | 2779 | C | LYS | B | 49 | 67.041 | 93.752 | −0.632 | 1.00 | 33.01 | B |
| ATOM | 2780 | O | LYS | B | 49 | 67.987 | 93.450 | −1.353 | 1.00 | 28.70 | B |
| ATOM | 2781 | N | ASP | B | 50 | 65.994 | 94.451 | −1.083 | 1.00 | 26.02 | B |
| ATOM | 2782 | CA | ASP | B | 50 | 65.933 | 94.859 | −2.495 | 1.00 | 29.77 | B |
| ATOM | 2783 | CB | ASP | B | 50 | 64.575 | 94.503 | −3.108 | 1.00 | 28.99 | B |
| ATOM | 2784 | CG | ASP | B | 50 | 63.439 | 95.221 | −2.440 | 1.00 | 26.54 | B |
| ATOM | 2785 | OD1 | ASP | B | 50 | 63.720 | 96.043 | −1.562 | 1.00 | 25.74 | B |
| ATOM | 2786 | OD2 | ASP | B | 50 | 62.262 | 94.969 | −2.779 | 1.00 | 32.42 | B |
| ATOM | 2787 | C | ASP | B | 50 | 66.200 | 96.327 | −2.744 | 1.00 | 30.62 | B |
| ATOM | 2788 | O | ASP | B | 50 | 66.037 | 96.794 | −3.858 | 1.00 | 24.13 | B |
| ATOM | 2789 | N | LYS | B | 51 | 66.610 | 97.050 | −1.709 | 1.00 | 27.94 | B |
| ATOM | 2790 | CA | LYS | B | 51 | 66.889 | 98.473 | −1.824 | 1.00 | 31.18 | B |
| ATOM | 2791 | CB | LYS | B | 51 | 68.014 | 98.742 | −2.819 | 1.00 | 34.46 | B |
| ATOM | 2792 | CG | LYS | B | 51 | 69.381 | 98.355 | −2.297 | 1.00 | 41.85 | B |
| ATOM | 2793 | CD | LYS | B | 51 | 70.447 | 98.960 | −3.175 | 1.00 | 49.97 | B |
| ATOM | 2794 | CE | LYS | B | 51 | 71.826 | 98.869 | −2.564 | 1.00 | 59.90 | B |
| ATOM | 2795 | NZ | LYS | B | 51 | 72.754 | 99.713 | −3.366 | 1.00 | 67.70 | B |
| ATOM | 2796 | C | LYS | B | 51 | 65.666 | 99.305 | −2.186 | 1.00 | 30.87 | B |
| ATOM | 2797 | O | LYS | B | 51 | 65.786 | 100.430 | −2.634 | 1.00 | 28.68 | B |
| ATOM | 2798 | N | VAL | B | 52 | 64.483 | 98.748 | −1.992 | 1.00 | 26.95 | B |
| ATOM | 2799 | CA | VAL | B | 52 | 63.263 | 99.501 | −2.231 | 1.00 | 26.37 | B |
| ATOM | 2800 | CB | VAL | B | 52 | 62.456 | 98.945 | −3.402 | 1.00 | 27.69 | B |
| ATOM | 2801 | CG1 | VAL | B | 52 | 61.123 | 99.695 | −3.511 | 1.00 | 32.70 | B |
| ATOM | 2802 | CG2 | VAL | B | 52 | 63.236 | 99.113 | −4.679 | 1.00 | 32.13 | B |
| ATOM | 2803 | C | VAL | B | 52 | 62.375 | 99.437 | −1.000 | 1.00 | 30.79 | B |
| ATOM | 2804 | O | VAL | B | 52 | 61.949 | 100.461 | −0.491 | 1.00 | 26.76 | B |
| ATOM | 2805 | N | ASP | B | 53 | 62.102 | 98.232 | −0.512 | 1.00 | 26.86 | B |
| ATOM | 2806 | CA | ASP | B | 53 | 61.210 | 98.074 | 0.642 | 1.00 | 26.94 | B |
| ATOM | 2807 | CB | ASP | B | 53 | 60.156 | 96.999 | 0.318 | 1.00 | 42.02 | B |
| ATOM | 2808 | CG | ASP | B | 53 | 59.285 | 97.356 | −0.871 | 1.00 | 53.53 | B |
| ATOM | 2809 | OD1 | ASP | B | 53 | 58.878 | 98.540 | −0.943 | 1.00 | 63.13 | B |
| ATOM | 2810 | OD2 | ASP | B | 53 | 58.964 | 96.476 | −1.727 | 1.00 | 64.13 | B |
| ATOM | 2811 | C | ASP | B | 53 | 62.006 | 97.651 | 1.888 | 1.00 | 25.00 | B |
| ATOM | 2812 | O | ASP | B | 53 | 63.063 | 97.038 | 1.773 | 1.00 | 22.23 | B |
| ATOM | 2813 | N | GLY | B | 54 | 61.490 | 97.959 | 3.072 | 1.00 | 20.64 | B |
| ATOM | 2814 | CA | GLY | B | 54 | 62.170 | 97.578 | 4.293 | 1.00 | 24.10 | B |
| ATOM | 2815 | C | GLY | B | 54 | 61.441 | 96.397 | 4.919 | 1.00 | 25.17 | B |
| ATOM | 2816 | O | GLY | B | 54 | 60.237 | 96.266 | 4.728 | 1.00 | 25.23 | B |
| ATOM | 2817 | N | THR | B | 55 | 62.169 | 95.517 | 5.605 | 1.00 | 23.87 | B |
| ATOM | 2818 | CA | THR | B | 55 | 61.589 | 94.373 | 6.318 | 1.00 | 20.36 | B |
| ATOM | 2819 | CB | THR | B | 55 | 61.679 | 93.051 | 5.518 | 1.00 | 27.74 | B |
| ATOM | 2820 | OG1 | THR | B | 55 | 61.052 | 92.004 | 6.267 | 1.00 | 24.11 | B |
| ATOM | 2821 | CG2 | THR | B | 55 | 63.151 | 92.669 | 5.212 | 1.00 | 21.92 | B |
| ATOM | 2822 | C | THR | B | 55 | 62.371 | 94.156 | 7.600 | 1.00 | 22.54 | B |
| ATOM | 2823 | O | THR | B | 55 | 63.535 | 94.526 | 7.675 | 1.00 | 24.57 | B |
| ATOM | 2824 | N | TRP | B | 56 | 61.743 | 93.589 | 8.624 | 1.00 | 23.11 | B |
| ATOM | 2825 | CA | TRP | B | 56 | 62.513 | 93.285 | 9.827 | 1.00 | 25.54 | B |
| ATOM | 2826 | CB | TRP | B | 56 | 61.580 | 92.954 | 10.988 | 1.00 | 23.18 | B |
| ATOM | 2827 | CG | TRP | B | 56 | 60.874 | 94.202 | 11.420 | 1.00 | 19.51 | B |
| ATOM | 2828 | CD2 | TRP | B | 56 | 61.456 | 95.282 | 12.147 | 1.00 | 21.91 | B |
| ATOM | 2829 | CE2 | TRP | B | 56 | 60.473 | 96.302 | 12.247 | 1.00 | 26.89 | B |

TABLE 2-continued

| | | | | | | | | | | |
|---|---|---|---|---|---|---|---|---|---|---|
| ATOM | 2830 | CE3 | TRP | B | 56 | 62.722 | 95.491 | 12.729 | 1.00 | 25.30 | B |
| ATOM | 2831 | CD1 | TRP | B | 56 | 59.595 | 94.578 | 11.119 | 1.00 | 21.93 | B |
| ATOM | 2832 | NE1 | TRP | B | 56 | 59.343 | 95.849 | 11.617 | 1.00 | 21.49 | B |
| ATOM | 2833 | CZ2 | TRP | B | 56 | 60.713 | 97.521 | 12.895 | 1.00 | 26.71 | B |
| ATOM | 2834 | CZ3 | TRP | B | 56 | 62.963 | 96.706 | 13.380 | 1.00 | 29.35 | B |
| ATOM | 2835 | CH2 | TRP | B | 56 | 61.957 | 97.706 | 13.451 | 1.00 | 28.96 | B |
| ATOM | 2836 | C | TRP | B | 56 | 63.335 | 92.075 | 9.384 | 1.00 | 28.11 | B |
| ATOM | 2837 | O | TRP | B | 56 | 62.882 | 91.296 | 8.535 | 1.00 | 23.54 | B |
| ATOM | 2838 | N | ASP | B | 57 | 64.535 | 91.909 | 9.926 | 1.00 | 20.44 | B |
| ATOM | 2839 | CA | ASP | B | 57 | 65.401 | 90.812 | 9.470 | 1.00 | 25.81 | B |
| ATOM | 2840 | CB | ASP | B | 57 | 66.885 | 91.113 | 9.761 | 1.00 | 30.15 | B |
| ATOM | 2841 | CG | ASP | B | 57 | 67.234 | 91.045 | 11.255 | 1.00 | 35.84 | B |
| ATOM | 2842 | OD1 | ASP | B | 57 | 66.319 | 91.161 | 12.102 | 1.00 | 23.31 | B |
| ATOM | 2843 | OD2 | ASP | B | 57 | 68.443 | 90.889 | 11.581 | 1.00 | 41.06 | B |
| ATOM | 2844 | C | ASP | B | 57 | 65.058 | 89.433 | 9.963 | 1.00 | 26.11 | B |
| ATOM | 2845 | O | ASP | B | 57 | 65.634 | 88.455 | 9.486 | 1.00 | 28.90 | B |
| ATOM | 2846 | N | LYS | B | 58 | 64.114 | 89.336 | 10.896 | 1.00 | 29.91 | B |
| ATOM | 2847 | CA | LYS | B | 58 | 63.687 | 88.032 | 11.411 | 1.00 | 27.97 | B |
| ATOM | 2848 | CB | LYS | B | 58 | 64.697 | 87.491 | 12.443 | 1.00 | 30.61 | B |
| ATOM | 2849 | CG | LYS | B | 58 | 64.884 | 88.378 | 13.650 | 1.00 | 38.23 | B |
| ATOM | 2850 | CD | LYS | B | 58 | 65.966 | 87.831 | 14.618 | 1.00 | 41.02 | B |
| ATOM | 2851 | CE | LYS | B | 58 | 67.406 | 88.063 | 14.115 | 1.00 | 37.73 | B |
| ATOM | 2852 | NZ | LYS | B | 58 | 67.830 | 89.511 | 14.119 | 1.00 | 29.19 | B |
| ATOM | 2853 | C | LYS | B | 58 | 62.319 | 88.105 | 12.045 | 1.00 | 22.71 | B |
| ATOM | 2854 | O | LYS | B | 58 | 61.795 | 89.188 | 12.311 | 1.00 | 26.33 | B |
| ATOM | 2855 | N | PRO | B | 59 | 61.700 | 86.947 | 12.292 | 1.00 | 25.99 | B |
| ATOM | 2856 | CD | PRO | B | 59 | 62.084 | 85.584 | 11.885 | 1.00 | 24.09 | B |
| ATOM | 2857 | CA | PRO | B | 59 | 60.367 | 86.972 | 12.919 | 1.00 | 22.11 | B |
| ATOM | 2858 | CB | PRO | B | 59 | 59.902 | 85.515 | 12.845 | 1.00 | 26.86 | B |
| ATOM | 2859 | CG | PRO | B | 59 | 60.730 | 84.913 | 11.746 | 1.00 | 29.91 | B |
| ATOM | 2860 | C | PRO | B | 59 | 60.509 | 87.419 | 14.369 | 1.00 | 30.21 | B |
| ATOM | 2861 | O | PRO | B | 59 | 61.593 | 87.307 | 14.968 | 1.00 | 28.15 | B |
| ATOM | 2862 | N | ALA | B | 60 | 59.433 | 87.924 | 14.951 | 1.00 | 25.43 | B |
| ATOM | 2863 | CA | ALA | B | 60 | 59.516 | 88.330 | 16.339 | 1.00 | 26.37 | B |
| ATOM | 2864 | CB | ALA | B | 60 | 58.260 | 89.089 | 16.742 | 1.00 | 26.63 | B |
| ATOM | 2865 | C | ALA | B | 60 | 59.644 | 87.085 | 17.223 | 1.00 | 21.91 | B |
| ATOM | 2866 | O | ALA | B | 60 | 59.104 | 86.068 | 16.914 | 1.00 | 22.47 | B |
| ATOM | 2867 | N | PRO | B | 61 | 60.358 | 87.173 | 18.350 | 1.00 | 23.37 | B |
| ATOM | 2868 | CD | PRO | B | 61 | 61.134 | 88.320 | 18.870 | 1.00 | 22.24 | B |
| ATOM | 2869 | CA | PRO | B | 61 | 60.476 | 86.007 | 19.227 | 1.00 | 19.99 | B |
| ATOM | 2870 | CB | PRO | B | 61 | 61.650 | 86.386 | 20.130 | 1.00 | 21.18 | B |
| ATOM | 2871 | CG | PRO | B | 61 | 61.458 | 87.876 | 20.314 | 1.00 | 22.73 | B |
| ATOM | 2872 | C | PRO | B | 61 | 59.151 | 85.933 | 20.024 | 1.00 | 27.42 | B |
| ATOM | 2873 | O | PRO | B | 61 | 58.314 | 86.831 | 19.903 | 1.00 | 27.48 | B |
| ATOM | 2874 | N | LYS | B | 62 | 58.960 | 84.893 | 20.834 | 1.00 | 21.73 | B |
| ATOM | 2875 | CA | LYS | B | 62 | 57.737 | 84.770 | 21.648 | 1.00 | 26.90 | B |
| ATOM | 2876 | CB | LYS | B | 62 | 56.880 | 83.576 | 21.187 | 1.00 | 32.90 | B |
| ATOM | 2877 | CG | LYS | B | 62 | 56.318 | 83.743 | 19.779 | 1.00 | 39.12 | B |
| ATOM | 2878 | CD | LYS | B | 62 | 55.638 | 82.502 | 19.258 | 1.00 | 48.29 | B |
| ATOM | 2879 | CE | LYS | B | 62 | 55.142 | 82.741 | 17.828 | 1.00 | 54.55 | B |
| ATOM | 2880 | NZ | LYS | B | 62 | 54.620 | 81.478 | 17.213 | 1.00 | 59.87 | B |
| ATOM | 2881 | C | LYS | B | 62 | 58.050 | 84.601 | 23.133 | 1.00 | 30.68 | B |
| ATOM | 2882 | O | LYS | B | 62 | 59.190 | 84.287 | 23.528 | 1.00 | 24.62 | B |
| ATOM | 2883 | N | CYS | B | 63 | 57.039 | 84.843 | 23.958 | 1.00 | 25.15 | B |
| ATOM | 2884 | CA | CYS | B | 63 | 57.171 | 84.675 | 25.405 | 1.00 | 27.27 | B |
| ATOM | 2885 | C | CYS | B | 63 | 56.314 | 83.481 | 25.792 | 1.00 | 30.43 | B |
| ATOM | 2886 | O | CYS | B | 63 | 55.111 | 83.454 | 25.515 | 1.00 | 30.82 | B |
| ATOM | 2887 | CB | CYS | B | 63 | 56.646 | 85.903 | 26.149 | 1.00 | 25.60 | B |
| ATOM | 2888 | SG | CYS | B | 63 | 57.682 | 87.384 | 25.922 | 1.00 | 31.81 | B |
| ATOM | 2889 | N | GLU | B | 64 | 56.934 | 82.486 | 26.414 | 1.00 | 29.14 | B |
| ATOM | 2890 | CA | GLU | B | 64 | 56.220 | 81.297 | 26.871 | 1.00 | 27.87 | B |
| ATOM | 2891 | CB | GLU | B | 64 | 56.938 | 80.043 | 26.393 | 1.00 | 22.54 | B |
| ATOM | 2892 | CG | GLU | B | 64 | 56.839 | 79.836 | 24.884 | 1.00 | 30.23 | B |
| ATOM | 2893 | CD | GLU | B | 64 | 57.354 | 78.472 | 24.471 | 1.00 | 25.42 | B |
| ATOM | 2894 | OE1 | GLU | B | 64 | 58.146 | 77.879 | 25.221 | 1.00 | 28.63 | B |
| ATOM | 2895 | OE2 | GLU | B | 64 | 56.993 | 77.994 | 23.396 | 1.00 | 24.45 | B |
| ATOM | 2896 | C | GLU | B | 64 | 56.172 | 81.301 | 28.394 | 1.00 | 27.43 | B |
| ATOM | 2897 | O | GLU | B | 64 | 57.189 | 81.564 | 29.036 | 1.00 | 28.45 | B |
| ATOM | 2898 | N | TYR | B | 65 | 55.003 | 81.039 | 28.981 | 1.00 | 30.82 | B |
| ATOM | 2899 | CA | TYR | B | 65 | 54.898 | 81.016 | 30.449 | 1.00 | 26.71 | B |
| ATOM | 2900 | CB | TYR | B | 65 | 53.474 | 80.638 | 30.881 | 1.00 | 24.67 | B |
| ATOM | 2901 | CG | TYR | B | 65 | 53.222 | 80.754 | 32.382 | 1.00 | 30.61 | B |
| ATOM | 2902 | CD1 | TYR | B | 65 | 53.558 | 81.915 | 33.078 | 1.00 | 37.93 | B |
| ATOM | 2903 | CE1 | TYR | B | 65 | 53.369 | 82.013 | 34.464 | 1.00 | 37.10 | B |
| ATOM | 2904 | CD2 | TYR | B | 65 | 52.681 | 79.689 | 33.102 | 1.00 | 29.91 | B |
| ATOM | 2905 | CE2 | TYR | B | 65 | 52.481 | 79.765 | 34.477 | 1.00 | 32.04 | B |
| ATOM | 2906 | CZ | TYR | B | 65 | 52.829 | 80.927 | 35.149 | 1.00 | 38.91 | B |
| ATOM | 2907 | OH | TYR | B | 65 | 52.653 | 81.014 | 36.510 | 1.00 | 40.82 | B |
| ATOM | 2908 | C | TYR | B | 65 | 55.931 | 79.969 | 30.908 | 1.00 | 26.37 | B |

TABLE 2-continued

| ATOM | 2909 | O | TYR | B | 65 | 56.022 | 78.891 | 30.339 | 1.00 | 27.39 | B |
|---|---|---|---|---|---|---|---|---|---|---|---|
| ATOM | 2910 | N | PHE | B | 66 | 56.722 | 80.290 | 31.924 | 1.00 | 30.93 | B |
| ATOM | 2911 | CA | PHE | B | 66 | 57.770 | 79.381 | 32.362 | 1.00 | 29.14 | B |
| ATOM | 2912 | CB | PHE | B | 66 | 58.611 | 80.060 | 33.455 | 1.00 | 27.56 | B |
| ATOM | 2913 | CG | PHE | B | 66 | 59.743 | 79.210 | 33.998 | 1.00 | 28.67 | B |
| ATOM | 2914 | CD1 | PHE | B | 66 | 60.632 | 78.559 | 33.139 | 1.00 | 33.68 | B |
| ATOM | 2915 | CD2 | PHE | B | 66 | 59.907 | 79.055 | 35.371 | 1.00 | 30.48 | B |
| ATOM | 2916 | CE1 | PHE | B | 66 | 61.669 | 77.763 | 33.648 | 1.00 | 35.23 | B |
| ATOM | 2917 | CE2 | PHE | B | 66 | 60.931 | 78.267 | 35.895 | 1.00 | 26.93 | B |
| ATOM | 2918 | CZ | PHE | B | 66 | 61.816 | 77.618 | 35.041 | 1.00 | 31.25 | B |
| ATOM | 2919 | C | PHE | B | 66 | 57.283 | 78.013 | 32.844 | 1.00 | 32.09 | B |
| ATOM | 2920 | O | PHE | B | 66 | 56.382 | 77.924 | 33.671 | 1.00 | 31.84 | B |
| ATOM | 2921 | N | ASN | B | 67 | 57.882 | 76.956 | 32.312 | 1.00 | 28.91 | B |
| ATOM | 2922 | CA | ASN | B | 67 | 57.553 | 75.591 | 32.727 | 1.00 | 31.14 | B |
| ATOM | 2923 | CB | ASN | B | 67 | 57.124 | 74.763 | 31.524 | 1.00 | 32.40 | B |
| ATOM | 2924 | CG | ASN | B | 67 | 56.635 | 73.368 | 31.903 | 1.00 | 37.56 | B |
| ATOM | 2925 | OD1 | ASN | B | 67 | 57.193 | 72.701 | 32.784 | 1.00 | 33.77 | B |
| ATOM | 2926 | ND2 | ASN | B | 67 | 55.589 | 72.914 | 31.218 | 1.00 | 40.31 | B |
| ATOM | 2927 | C | ASN | B | 67 | 58.844 | 75.009 | 33.318 | 1.00 | 30.31 | B |
| ATOM | 2928 | O | ASN | B | 67 | 59.719 | 74.551 | 32.577 | 1.00 | 26.39 | B |
| ATOM | 2929 | N | LYS | B | 68 | 58.960 | 75.038 | 34.644 | 1.00 | 28.27 | B |
| ATOM | 2930 | CA | LYS | B | 68 | 60.148 | 74.535 | 35.329 | 1.00 | 29.00 | B |
| ATOM | 2931 | CB | LYS | B | 68 | 60.041 | 74.792 | 36.843 | 1.00 | 35.08 | B |
| ATOM | 2932 | CG | LYS | B | 68 | 58.984 | 73.906 | 37.518 | 1.00 | 41.56 | B |
| ATOM | 2933 | CD | LYS | B | 68 | 59.179 | 73.778 | 39.031 | 1.00 | 52.33 | B |
| ATOM | 2934 | CE | LYS | B | 68 | 58.907 | 75.077 | 39.764 | 1.00 | 54.82 | B |
| ATOM | 2935 | NZ | LYS | B | 68 | 58.896 | 74.891 | 41.250 | 1.00 | 58.88 | B |
| ATOM | 2936 | C | LYS | B | 68 | 60.398 | 73.039 | 35.087 | 1.00 | 32.74 | B |
| ATOM | 2937 | O | LYS | B | 68 | 61.507 | 72.556 | 35.318 | 1.00 | 32.92 | B |
| ATOM | 2938 | N | TYR | B | 69 | 59.389 | 72.305 | 34.611 | 1.00 | 33.19 | B |
| ATOM | 2939 | CA | TYR | B | 69 | 59.559 | 70.867 | 34.354 | 1.00 | 25.62 | B |
| ATOM | 2940 | CB | TYR | B | 69 | 58.259 | 70.096 | 34.687 | 1.00 | 30.97 | B |
| ATOM | 2941 | CG | TYR | B | 69 | 57.801 | 70.349 | 36.107 | 1.00 | 30.82 | B |
| ATOM | 2942 | CD1 | TYR | B | 69 | 56.774 | 71.266 | 36.378 | 1.00 | 28.48 | B |
| ATOM | 2943 | CE1 | TYR | B | 69 | 56.444 | 71.623 | 37.697 | 1.00 | 31.73 | B |
| ATOM | 2944 | CD2 | TYR | B | 69 | 58.486 | 69.776 | 37.192 | 1.00 | 31.64 | B |
| ATOM | 2945 | CE2 | TYR | B | 69 | 58.174 | 70.118 | 38.507 | 1.00 | 38.99 | B |
| ATOM | 2946 | CZ | TYR | B | 69 | 57.153 | 71.053 | 38.756 | 1.00 | 39.94 | B |
| ATOM | 2947 | OH | TYR | B | 69 | 56.901 | 71.467 | 40.048 | 1.00 | 41.68 | B |
| ATOM | 2948 | C | TYR | B | 69 | 60.029 | 70.516 | 32.955 | 1.00 | 31.61 | B |
| ATOM | 2949 | O | TYR | B | 69 | 60.549 | 69.414 | 32.722 | 1.00 | 31.53 | B |
| ATOM | 2950 | N | SER | B | 70 | 59.889 | 71.447 | 32.017 | 1.00 | 29.13 | B |
| ATOM | 2951 | CA | SER | B | 70 | 60.328 | 71.162 | 30.649 | 1.00 | 31.79 | B |
| ATOM | 2952 | CB | SER | B | 70 | 59.926 | 72.310 | 29.708 | 1.00 | 27.84 | B |
| ATOM | 2953 | OG | SER | B | 70 | 58.524 | 72.534 | 29.725 | 1.00 | 38.42 | B |
| ATOM | 2954 | C | SER | B | 70 | 61.849 | 70.949 | 30.544 | 1.00 | 34.24 | B |
| ATOM | 2955 | O | SER | B | 70 | 62.624 | 71.534 | 31.296 | 1.00 | 31.38 | B |
| ATOM | 2956 | N | SER | B | 71 | 62.261 | 70.097 | 29.613 | 1.00 | 33.64 | B |
| ATOM | 2957 | CA | SER | B | 71 | 63.676 | 69.832 | 29.351 | 1.00 | 36.09 | B |
| ATOM | 2958 | CB | SER | B | 71 | 64.265 | 68.809 | 30.324 | 1.00 | 39.34 | B |
| ATOM | 2959 | OG | SER | B | 71 | 63.823 | 67.519 | 30.007 | 1.00 | 41.01 | B |
| ATOM | 2960 | C | SER | B | 71 | 63.790 | 69.308 | 27.907 | 1.00 | 41.17 | B |
| ATOM | 2961 | O | SER | B | 71 | 62.959 | 68.520 | 27.432 | 1.00 | 41.90 | B |
| ATOM | 2962 | N | CYS | B | 72 | 64.805 | 69.766 | 27.195 | 1.00 | 32.35 | B |
| ATOM | 2963 | CA | CYS | B | 72 | 64.970 | 69.351 | 25.816 | 1.00 | 36.35 | B |
| ATOM | 2964 | C | CYS | B | 72 | 66.139 | 68.393 | 25.722 | 1.00 | 36.24 | B |
| ATOM | 2965 | O | CYS | B | 72 | 67.089 | 68.472 | 26.503 | 1.00 | 34.41 | B |
| ATOM | 2966 | CB | CYS | B | 72 | 65.205 | 70.586 | 24.920 | 1.00 | 26.09 | B |
| ATOM | 2967 | SG | CYS | B | 72 | 63.836 | 71.795 | 24.962 | 1.00 | 32.64 | B |
| ATOM | 2968 | N | PRO | B | 73 | 66.069 | 67.453 | 24.779 | 1.00 | 35.65 | B |
| ATOM | 2969 | CD | PRO | B | 73 | 64.958 | 67.148 | 23.867 | 1.00 | 38.10 | B |
| ATOM | 2970 | CA | PRO | B | 73 | 67.157 | 66.494 | 24.617 | 1.00 | 35.61 | B |
| ATOM | 2971 | CB | PRO | B | 73 | 66.567 | 65.461 | 23.661 | 1.00 | 35.75 | B |
| ATOM | 2972 | CG | PRO | B | 73 | 65.662 | 66.314 | 22.806 | 1.00 | 40.23 | B |
| ATOM | 2973 | C | PRO | B | 73 | 68.355 | 67.203 | 24.011 | 1.00 | 37.18 | B |
| ATOM | 2974 | O | PRO | B | 73 | 68.225 | 68.277 | 23.427 | 1.00 | 31.86 | B |
| ATOM | 2975 | N | GLU | B | 74 | 69.521 | 66.595 | 24.151 | 1.00 | 30.08 | B |
| ATOM | 2976 | CA | GLU | B | 74 | 70.726 | 67.168 | 23.594 | 1.00 | 36.66 | B |
| ATOM | 2977 | CB | GLU | B | 74 | 71.904 | 66.221 | 23.830 | 1.00 | 40.69 | B |
| ATOM | 2978 | CG | GLU | B | 74 | 73.123 | 66.500 | 22.972 | 1.00 | 55.61 | B |
| ATOM | 2979 | CD | GLU | B | 74 | 74.357 | 66.847 | 23.791 | 1.00 | 65.33 | B |
| ATOM | 2980 | OE1 | GLU | B | 74 | 75.476 | 66.535 | 23.311 | 1.00 | 68.86 | B |
| ATOM | 2981 | OE2 | GLU | B | 74 | 74.214 | 67.432 | 24.899 | 1.00 | 67.56 | B |
| ATOM | 2982 | C | GLU | B | 74 | 70.526 | 67.411 | 22.099 | 1.00 | 31.83 | B |
| ATOM | 2983 | O | GLU | B | 74 | 70.179 | 66.517 | 21.347 | 1.00 | 34.92 | B |
| ATOM | 2984 | N | PRO | B | 75 | 70.743 | 68.639 | 21.648 | 1.00 | 29.85 | B |
| ATOM | 2985 | CD | PRO | B | 75 | 71.019 | 69.851 | 22.431 | 1.00 | 29.21 | B |
| ATOM | 2986 | CA | PRO | B | 75 | 70.573 | 68.944 | 20.227 | 1.00 | 31.16 | B |
| ATOM | 2987 | CB | PRO | B | 75 | 70.349 | 70.441 | 20.235 | 1.00 | 30.77 | B |

TABLE 2-continued

| ATOM | 2988 | CG | PRO | B | 75 | 71.310 | 70.872 | 21.362 | 1.00 | 28.27 | B |
|---|---|---|---|---|---|---|---|---|---|---|---|
| ATOM | 2989 | C | PRO | B | 75 | 71.855 | 68.552 | 19.507 | 1.00 | 37.41 | B |
| ATOM | 2990 | O | PRO | B | 75 | 72.949 | 68.998 | 19.877 | 1.00 | 35.98 | B |
| ATOM | 2991 | N | ILE | B | 76 | 71.728 | 67.726 | 18.474 | 1.00 | 37.41 | B |
| ATOM | 2992 | CA | ILE | B | 76 | 72.904 | 67.277 | 17.757 | 1.00 | 41.40 | B |
| ATOM | 2993 | CB | ILE | B | 76 | 73.069 | 65.755 | 17.912 | 1.00 | 47.80 | B |
| ATOM | 2994 | CG2 | ILE | B | 76 | 74.385 | 65.302 | 17.272 | 1.00 | 48.99 | B |
| ATOM | 2995 | CG1 | ILE | B | 76 | 73.078 | 65.396 | 19.404 | 1.00 | 48.44 | B |
| ATOM | 2996 | CD1 | ILE | B | 76 | 72.926 | 63.918 | 19.671 | 1.00 | 55.08 | B |
| ATOM | 2997 | C | ILE | B | 76 | 72.874 | 67.654 | 16.294 | 1.00 | 38.62 | B |
| ATOM | 2998 | O | ILE | B | 76 | 71.874 | 67.480 | 15.625 | 1.00 | 39.69 | B |
| ATOM | 2999 | N | VAL | B | 77 | 73.984 | 68.195 | 15.813 | 1.00 | 36.89 | B |
| ATOM | 3000 | CA | VAL | B | 77 | 74.107 | 68.610 | 14.433 | 1.00 | 38.30 | B |
| ATOM | 3001 | CB | VAL | B | 77 | 74.290 | 70.119 | 14.331 | 1.00 | 39.19 | B |
| ATOM | 3002 | CG1 | VAL | B | 77 | 74.483 | 70.519 | 12.871 | 1.00 | 39.16 | B |
| ATOM | 3003 | CG2 | VAL | B | 77 | 73.081 | 70.826 | 14.946 | 1.00 | 40.99 | B |
| ATOM | 3004 | C | VAL | B | 77 | 75.307 | 67.939 | 13.761 | 1.00 | 40.36 | B |
| ATOM | 3005 | O | VAL | B | 77 | 76.457 | 68.351 | 13.948 | 1.00 | 41.17 | B |
| ATOM | 3006 | N | PRO | B | 78 | 75.057 | 66.893 | 12.966 | 1.00 | 40.75 | B |
| ATOM | 3007 | CD | PRO | B | 78 | 73.785 | 66.267 | 12.590 | 1.00 | 37.39 | B |
| ATOM | 3008 | CA | PRO | B | 78 | 76.183 | 66.228 | 12.303 | 1.00 | 40.96 | B |
| ATOM | 3009 | CB | PRO | B | 78 | 75.506 | 65.195 | 11.412 | 1.00 | 41.91 | B |
| ATOM | 3010 | CG | PRO | B | 78 | 74.119 | 65.745 | 11.229 | 1.00 | 45.49 | B |
| ATOM | 3011 | C | PRO | B | 78 | 76.997 | 67.232 | 11.525 | 1.00 | 37.80 | B |
| ATOM | 3012 | O | PRO | B | 78 | 76.447 | 68.140 | 10.913 | 1.00 | 37.38 | B |
| ATOM | 3013 | N | GLY | B | 79 | 78.312 | 67.083 | 11.590 | 1.00 | 32.94 | B |
| ATOM | 3014 | CA | GLY | B | 79 | 79.186 | 68.002 | 10.900 | 1.00 | 36.40 | B |
| ATOM | 3015 | C | GLY | B | 79 | 79.427 | 69.261 | 11.712 | 1.00 | 34.31 | B |
| ATOM | 3016 | O | GLY | B | 79 | 80.209 | 70.109 | 11.304 | 1.00 | 42.13 | B |
| ATOM | 3017 | N | GLY | B | 80 | 78.760 | 69.404 | 12.855 | 1.00 | 36.96 | B |
| ATOM | 3018 | CA | GLY | B | 80 | 78.960 | 70.608 | 13.664 | 1.00 | 39.25 | B |
| ATOM | 3019 | C | GLY | B | 80 | 79.072 | 70.348 | 15.164 | 1.00 | 35.08 | B |
| ATOM | 3020 | O | GLY | B | 80 | 78.994 | 69.202 | 15.609 | 1.00 | 40.28 | B |
| ATOM | 3021 | N | TYR | B | 81 | 79.225 | 71.410 | 15.953 | 1.00 | 37.65 | B |
| ATOM | 3022 | CA | TYR | B | 81 | 79.345 | 71.271 | 17.408 | 1.00 | 33.04 | B |
| ATOM | 3023 | CB | TYR | B | 81 | 80.800 | 71.019 | 17.799 | 1.00 | 29.39 | B |
| ATOM | 3024 | CG | TYR | B | 81 | 81.745 | 72.112 | 17.331 | 1.00 | 31.26 | B |
| ATOM | 3025 | CD1 | TYR | B | 81 | 82.169 | 73.116 | 18.199 | 1.00 | 28.35 | B |
| ATOM | 3026 | CE1 | TYR | B | 81 | 82.992 | 74.143 | 17.766 | 1.00 | 28.17 | B |
| ATOM | 3027 | CD2 | TYR | B | 81 | 82.181 | 72.163 | 16.004 | 1.00 | 28.62 | B |
| ATOM | 3028 | CE2 | TYR | B | 81 | 83.006 | 73.188 | 15.559 | 1.00 | 31.47 | B |
| ATOM | 3029 | CZ | TYR | B | 81 | 83.401 | 74.174 | 16.449 | 1.00 | 30.40 | B |
| ATOM | 3030 | OH | TYR | B | 81 | 84.172 | 75.207 | 16.012 | 1.00 | 32.87 | B |
| ATOM | 3031 | C | TYR | B | 81 | 78.847 | 72.536 | 18.095 | 1.00 | 33.96 | B |
| ATOM | 3032 | O | TYR | B | 81 | 78.696 | 73.581 | 17.454 | 1.00 | 30.79 | B |
| ATOM | 3033 | N | LYS | B | 82 | 78.600 | 72.431 | 19.398 | 1.00 | 23.56 | B |
| ATOM | 3034 | CA | LYS | B | 82 | 78.114 | 73.557 | 20.195 | 1.00 | 29.94 | B |
| ATOM | 3035 | CB | LYS | B | 82 | 77.348 | 73.034 | 21.428 | 1.00 | 25.29 | B |
| ATOM | 3036 | CG | LYS | B | 82 | 76.140 | 72.144 | 21.057 | 1.00 | 27.67 | B |
| ATOM | 3037 | CD | LYS | B | 82 | 75.335 | 71.652 | 22.266 | 1.00 | 33.47 | B |
| ATOM | 3038 | CE | LYS | B | 82 | 76.215 | 71.041 | 23.365 | 1.00 | 44.83 | B |
| ATOM | 3039 | NZ | LYS | B | 82 | 77.091 | 69.944 | 22.837 | 1.00 | 45.24 | B |
| ATOM | 3040 | C | LYS | B | 82 | 79.205 | 74.526 | 20.629 | 1.00 | 29.85 | B |
| ATOM | 3041 | O | LYS | B | 82 | 80.270 | 74.110 | 21.099 | 1.00 | 31.44 | B |
| ATOM | 3042 | N | ILE | B | 83 | 78.980 | 75.822 | 20.428 | 1.00 | 25.93 | B |
| ATOM | 3043 | CA | ILE | B | 83 | 79.959 | 76.795 | 20.887 | 1.00 | 21.30 | B |
| ATOM | 3044 | CB | ILE | B | 83 | 80.449 | 77.771 | 19.800 | 1.00 | 29.03 | B |
| ATOM | 3045 | CG2 | ILE | B | 83 | 81.296 | 77.004 | 18.799 | 1.00 | 23.68 | B |
| ATOM | 3046 | CG1 | ILE | B | 83 | 79.278 | 78.514 | 19.155 | 1.00 | 24.89 | B |
| ATOM | 3047 | CD1 | ILE | B | 83 | 79.722 | 79.571 | 18.148 | 1.00 | 27.44 | B |
| ATOM | 3048 | C | ILE | B | 83 | 79.362 | 77.581 | 22.027 | 1.00 | 26.62 | B |
| ATOM | 3049 | O | ILE | B | 83 | 80.038 | 78.408 | 22.636 | 1.00 | 32.15 | B |
| ATOM | 3050 | N | ARG | B | 84 | 78.092 | 77.330 | 22.324 | 1.00 | 24.60 | B |
| ATOM | 3051 | CA | ARG | B | 84 | 77.471 | 77.981 | 23.469 | 1.00 | 25.74 | B |
| ATOM | 3052 | CB | ARG | B | 84 | 77.047 | 79.396 | 23.131 | 1.00 | 34.80 | B |
| ATOM | 3053 | CG | ARG | B | 84 | 76.583 | 80.160 | 24.348 | 1.00 | 45.89 | B |
| ATOM | 3054 | CD | ARG | B | 84 | 76.518 | 81.629 | 24.027 | 1.00 | 56.25 | B |
| ATOM | 3055 | NE | ARG | B | 84 | 77.801 | 82.302 | 24.217 | 1.00 | 62.31 | B |
| ATOM | 3056 | CZ | ARG | B | 84 | 78.276 | 82.707 | 25.397 | 1.00 | 64.61 | B |
| ATOM | 3057 | NH1 | ARG | B | 84 | 77.581 | 82.496 | 26.512 | 1.00 | 65.21 | B |
| ATOM | 3058 | NH2 | ARG | B | 84 | 79.421 | 83.386 | 25.454 | 1.00 | 61.85 | B |
| ATOM | 3059 | C | ARG | B | 84 | 76.278 | 77.199 | 23.984 | 1.00 | 27.61 | B |
| ATOM | 3060 | O | ARG | B | 84 | 75.487 | 76.687 | 23.189 | 1.00 | 24.27 | B |
| ATOM | 3061 | N | GLY | B | 85 | 76.166 | 77.105 | 25.314 | 1.00 | 25.11 | B |
| ATOM | 3062 | CA | GLY | B | 85 | 75.074 | 76.374 | 25.959 | 1.00 | 23.64 | B |
| ATOM | 3063 | C | GLY | B | 85 | 75.394 | 74.877 | 26.115 | 1.00 | 32.13 | B |
| ATOM | 3064 | O | GLY | B | 85 | 75.961 | 74.257 | 25.200 | 1.00 | 25.66 | B |
| ATOM | 3065 | N | SER | B | 86 | 75.094 | 74.293 | 27.281 | 1.00 | 24.97 | B |
| ATOM | 3066 | CA | SER | B | 86 | 75.347 | 72.859 | 27.473 | 1.00 | 34.32 | B |

TABLE 2-continued

| | | | | | | | | | | |
|---|---|---|---|---|---|---|---|---|---|---|
| ATOM | 3067 | CB | SER | B | 86 | 76.755 | 72.588 | 28.034 | 1.00 | 31.54 | B |
| ATOM | 3068 | OG | SER | B | 86 | 76.964 | 73.322 | 29.223 | 1.00 | 42.05 | B |
| ATOM | 3069 | C | SER | B | 86 | 74.315 | 72.304 | 28.415 | 1.00 | 27.65 | B |
| ATOM | 3070 | O | SER | B | 86 | 73.536 | 73.064 | 28.979 | 1.00 | 24.75 | B |
| ATOM | 3071 | N | THR | B | 87 | 74.294 | 70.982 | 28.573 | 1.00 | 27.03 | B |
| ATOM | 3072 | CA | THR | B | 87 | 73.325 | 70.314 | 29.454 | 1.00 | 29.87 | B |
| ATOM | 3073 | CB | THR | B | 87 | 73.532 | 68.806 | 29.450 | 1.00 | 34.20 | B |
| ATOM | 3074 | OG1 | THR | B | 87 | 73.876 | 68.395 | 28.125 | 1.00 | 54.47 | B |
| ATOM | 3075 | CG2 | THR | B | 87 | 72.263 | 68.107 | 29.856 | 1.00 | 36.26 | B |
| ATOM | 3076 | C | THR | B | 87 | 73.420 | 70.767 | 30.903 | 1.00 | 30.09 | B |
| ATOM | 3077 | O | THR | B | 87 | 74.501 | 71.113 | 31.381 | 1.00 | 30.94 | B |
| ATOM | 3078 | N | PRO | B | 88 | 72.293 | 70.771 | 31.626 | 1.00 | 26.03 | B |
| ATOM | 3079 | CD | PRO | B | 88 | 72.370 | 71.088 | 33.060 | 1.00 | 30.64 | B |
| ATOM | 3080 | CA | PRO | B | 88 | 70.921 | 70.406 | 31.240 | 1.00 | 33.13 | B |
| ATOM | 3081 | CB | PRO | B | 88 | 70.225 | 70.211 | 32.585 | 1.00 | 28.86 | B |
| ATOM | 3082 | CG | PRO | B | 88 | 70.903 | 71.248 | 33.440 | 1.00 | 31.91 | B |
| ATOM | 3083 | C | PRO | B | 88 | 70.228 | 71.482 | 30.388 | 1.00 | 31.83 | B |
| ATOM | 3084 | O | PRO | B | 88 | 70.495 | 72.668 | 30.535 | 1.00 | 29.33 | B |
| ATOM | 3085 | N | TYR | B | 89 | 69.340 | 71.059 | 29.503 | 1.00 | 27.84 | B |
| ATOM | 3086 | CA | TYR | B | 89 | 68.613 | 71.990 | 28.641 | 1.00 | 29.55 | B |
| ATOM | 3087 | CB | TYR | B | 89 | 68.553 | 71.414 | 27.239 | 1.00 | 27.73 | B |
| ATOM | 3088 | CG | TYR | B | 89 | 69.938 | 71.078 | 26.722 | 1.00 | 29.87 | B |
| ATOM | 3089 | CD1 | TYR | B | 89 | 70.326 | 69.759 | 26.501 | 1.00 | 33.12 | B |
| ATOM | 3090 | CE1 | TYR | B | 89 | 71.605 | 69.456 | 26.036 | 1.00 | 26.70 | B |
| ATOM | 3091 | CD2 | TYR | B | 89 | 70.865 | 72.086 | 26.467 | 1.00 | 32.19 | B |
| ATOM | 3092 | CE2 | TYR | B | 89 | 72.134 | 71.795 | 26.007 | 1.00 | 28.60 | B |
| ATOM | 3093 | CZ | TYR | B | 89 | 72.492 | 70.482 | 25.802 | 1.00 | 27.81 | B |
| ATOM | 3094 | OH | TYR | B | 89 | 73.770 | 70.211 | 25.415 | 1.00 | 32.86 | B |
| ATOM | 3095 | C | TYR | B | 89 | 67.212 | 72.242 | 29.176 | 1.00 | 25.88 | B |
| ATOM | 3096 | O | TYR | B | 89 | 66.333 | 71.400 | 29.025 | 1.00 | 25.96 | B |
| ATOM | 3097 | N | ARG | B | 90 | 67.015 | 73.405 | 29.790 | 1.00 | 25.05 | B |
| ATOM | 3098 | CA | ARG | B | 90 | 65.732 | 73.778 | 30.386 | 1.00 | 21.94 | B |
| ATOM | 3099 | CB | ARG | B | 90 | 65.950 | 74.306 | 31.802 | 1.00 | 25.43 | B |
| ATOM | 3100 | CG | ARG | B | 90 | 66.836 | 73.368 | 32.650 | 1.00 | 35.30 | B |
| ATOM | 3101 | CD | ARG | B | 90 | 66.308 | 71.933 | 32.684 | 1.00 | 30.92 | B |
| ATOM | 3102 | NE | ARG | B | 90 | 65.162 | 71.857 | 33.578 | 1.00 | 38.77 | B |
| ATOM | 3103 | CZ | ARG | B | 90 | 64.577 | 70.721 | 33.950 | 1.00 | 43.50 | B |
| ATOM | 3104 | NH1 | ARG | B | 90 | 65.038 | 69.562 | 33.500 | 1.00 | 42.19 | B |
| ATOM | 3105 | NH2 | ARG | B | 90 | 63.529 | 70.750 | 34.771 | 1.00 | 39.16 | B |
| ATOM | 3106 | C | ARG | B | 90 | 65.001 | 74.823 | 29.580 | 1.00 | 26.84 | B |
| ATOM | 3107 | O | ARG | B | 90 | 65.540 | 75.372 | 28.606 | 1.00 | 21.63 | B |
| ATOM | 3108 | N | HIS | B | 91 | 63.767 | 75.095 | 29.999 | 1.00 | 24.57 | B |
| ATOM | 3109 | CA | HIS | B | 91 | 62.903 | 76.057 | 29.318 | 1.00 | 28.69 | B |
| ATOM | 3110 | CB | HIS | B | 91 | 61.570 | 76.143 | 30.062 | 1.00 | 26.54 | B |
| ATOM | 3111 | CG | HIS | B | 91 | 60.516 | 76.909 | 29.326 | 1.00 | 34.66 | B |
| ATOM | 3112 | CD2 | HIS | B | 91 | 59.414 | 77.563 | 29.770 | 1.00 | 26.97 | B |
| ATOM | 3113 | ND1 | HIS | B | 91 | 60.513 | 77.035 | 27.952 | 1.00 | 29.34 | B |
| ATOM | 3114 | CE1 | HIS | B | 91 | 59.457 | 77.735 | 27.582 | 1.00 | 27.63 | B |
| ATOM | 3115 | NE2 | HIS | B | 91 | 58.775 | 78.066 | 28.666 | 1.00 | 34.45 | B |
| ATOM | 3116 | C | HIS | B | 91 | 63.546 | 77.445 | 29.177 | 1.00 | 30.22 | B |
| ATOM | 3117 | O | HIS | B | 91 | 63.937 | 78.069 | 30.161 | 1.00 | 23.98 | B |
| ATOM | 3118 | N | GLY | B | 92 | 63.663 | 77.915 | 27.941 | 1.00 | 26.25 | B |
| ATOM | 3119 | CA | GLY | B | 92 | 64.260 | 79.209 | 27.702 | 1.00 | 20.48 | B |
| ATOM | 3120 | C | GLY | B | 92 | 65.752 | 79.118 | 27.458 | 1.00 | 24.40 | B |
| ATOM | 3121 | O | GLY | B | 92 | 66.310 | 80.102 | 27.019 | 1.00 | 24.34 | B |
| ATOM | 3122 | N | ASP | B | 93 | 66.407 | 77.974 | 27.724 | 1.00 | 20.35 | B |
| ATOM | 3123 | CA | ASP | B | 93 | 67.857 | 77.884 | 27.472 | 1.00 | 19.73 | B |
| ATOM | 3124 | CB | ASP | B | 93 | 68.487 | 76.575 | 27.992 | 1.00 | 23.61 | B |
| ATOM | 3125 | CG | ASP | B | 93 | 68.579 | 76.504 | 29.504 | 1.00 | 20.60 | B |
| ATOM | 3126 | OD1 | ASP | B | 93 | 68.336 | 77.522 | 30.167 | 1.00 | 23.89 | B |
| ATOM | 3127 | OD2 | ASP | B | 93 | 68.884 | 75.401 | 30.020 | 1.00 | 25.06 | B |
| ATOM | 3128 | C | ASP | B | 93 | 68.138 | 77.911 | 25.981 | 1.00 | 25.02 | B |
| ATOM | 3129 | O | ASP | B | 93 | 67.362 | 77.415 | 25.170 | 1.00 | 24.06 | B |
| ATOM | 3130 | N | SER | B | 94 | 69.298 | 78.422 | 25.625 | 1.00 | 21.77 | B |
| ATOM | 3131 | CA | SER | B | 94 | 69.641 | 78.511 | 24.229 | 1.00 | 27.05 | B |
| ATOM | 3132 | CB | SER | B | 94 | 69.779 | 79.972 | 23.834 | 1.00 | 28.57 | B |
| ATOM | 3133 | OG | SER | B | 94 | 70.417 | 80.035 | 22.587 | 1.00 | 38.84 | B |
| ATOM | 3134 | C | SER | B | 94 | 70.935 | 77.815 | 23.908 | 1.00 | 25.71 | B |
| ATOM | 3135 | O | SER | B | 94 | 71.833 | 77.727 | 24.753 | 1.00 | 26.52 | B |
| ATOM | 3136 | N | VAL | B | 95 | 71.051 | 77.331 | 22.678 | 1.00 | 27.36 | B |
| ATOM | 3137 | CA | VAL | B | 95 | 72.291 | 76.689 | 22.245 | 1.00 | 26.56 | B |
| ATOM | 3138 | CB | VAL | B | 95 | 72.096 | 75.178 | 22.088 | 1.00 | 26.82 | B |
| ATOM | 3139 | CG1 | VAL | B | 95 | 73.282 | 74.581 | 21.344 | 1.00 | 34.06 | B |
| ATOM | 3140 | CG2 | VAL | B | 95 | 71.908 | 74.549 | 23.460 | 1.00 | 30.69 | B |
| ATOM | 3141 | C | VAL | B | 95 | 72.729 | 77.273 | 20.908 | 1.00 | 30.07 | B |
| ATOM | 3142 | O | VAL | B | 95 | 71.903 | 77.496 | 20.019 | 1.00 | 26.03 | B |
| ATOM | 3143 | N | THR | B | 96 | 74.026 | 77.526 | 20.758 | 1.00 | 27.23 | B |
| ATOM | 3144 | CA | THR | B | 96 | 74.540 | 78.058 | 19.503 | 1.00 | 23.14 | B |
| ATOM | 3145 | CB | THR | B | 96 | 75.242 | 79.419 | 19.687 | 1.00 | 32.77 | B |

TABLE 2-continued

| | | | | | | | | | | |
|---|---|---|---|---|---|---|---|---|---|---|
| ATOM | 3146 | OG1 | THR | B | 96 | 74.292 | 80.383 | 20.163 | 1.00 | 26.94 | B |
| ATOM | 3147 | CG2 | THR | B | 96 | 75.845 | 79.896 | 18.329 | 1.00 | 26.13 | B |
| ATOM | 3148 | C | THR | B | 96 | 75.550 | 77.071 | 18.915 | 1.00 | 33.62 | B |
| ATOM | 3149 | O | THR | B | 96 | 76.445 | 76.614 | 19.618 | 1.00 | 26.19 | B |
| ATOM | 3150 | N | PHE | B | 97 | 75.381 | 76.732 | 17.638 | 1.00 | 28.29 | B |
| ATOM | 3151 | CA | PHE | B | 97 | 76.249 | 75.788 | 16.922 | 1.00 | 27.82 | B |
| ATOM | 3152 | CB | PHE | B | 97 | 75.409 | 74.849 | 16.039 | 1.00 | 27.23 | B |
| ATOM | 3153 | CG | PHE | B | 97 | 74.598 | 73.858 | 16.796 | 1.00 | 30.99 | B |
| ATOM | 3154 | CD1 | PHE | B | 97 | 73.325 | 74.183 | 17.257 | 1.00 | 28.10 | B |
| ATOM | 3155 | CD2 | PHE | B | 97 | 75.149 | 72.633 | 17.153 | 1.00 | 24.15 | B |
| ATOM | 3156 | CE1 | PHE | B | 97 | 72.608 | 73.310 | 18.081 | 1.00 | 29.54 | B |
| ATOM | 3157 | CE2 | PHE | B | 97 | 74.434 | 71.756 | 17.975 | 1.00 | 26.96 | B |
| ATOM | 3158 | CZ | PHE | B | 97 | 73.155 | 72.101 | 18.444 | 1.00 | 28.76 | B |
| ATOM | 3159 | C | PHE | B | 97 | 77.247 | 76.479 | 15.980 | 1.00 | 33.87 | B |
| ATOM | 3160 | O | PHE | B | 97 | 77.088 | 77.663 | 15.628 | 1.00 | 30.90 | B |
| ATOM | 3161 | N | ALA | B | 98 | 78.274 | 75.725 | 15.582 | 1.00 | 33.98 | B |
| ATOM | 3162 | CA | ALA | B | 98 | 79.266 | 76.152 | 14.574 | 1.00 | 34.14 | B |
| ATOM | 3163 | CB | ALA | B | 98 | 80.551 | 76.651 | 15.211 | 1.00 | 38.55 | B |
| ATOM | 3164 | C | ALA | B | 98 | 79.544 | 74.880 | 13.785 | 1.00 | 36.15 | B |
| ATOM | 3165 | O | ALA | B | 98 | 79.370 | 73.775 | 14.312 | 1.00 | 35.98 | B |
| ATOM | 3166 | N | CYS | B | 99 | 79.953 | 75.018 | 12.527 | 1.00 | 38.50 | B |
| ATOM | 3167 | CA | CYS | B | 99 | 80.266 | 73.843 | 11.711 | 1.00 | 39.15 | B |
| ATOM | 3168 | C | CYS | B | 99 | 81.747 | 73.512 | 11.779 | 1.00 | 36.00 | B |
| ATOM | 3169 | O | CYS | B | 99 | 82.573 | 74.408 | 11.865 | 1.00 | 32.17 | B |
| ATOM | 3170 | CB | CYS | B | 99 | 79.901 | 74.086 | 10.251 | 1.00 | 42.12 | B |
| ATOM | 3171 | SG | CYS | B | 99 | 78.108 | 74.162 | 9.949 | 1.00 | 40.52 | B |
| ATOM | 3172 | N | LYS | B | 100 | 82.089 | 72.229 | 11.749 | 1.00 | 35.70 | B |
| ATOM | 3173 | CA | LYS | B | 100 | 83.498 | 71.842 | 11.770 | 1.00 | 40.35 | B |
| ATOM | 3174 | CB | LYS | B | 100 | 83.632 | 70.319 | 11.848 | 1.00 | 43.13 | B |
| ATOM | 3175 | CG | LYS | B | 100 | 83.185 | 69.707 | 13.148 | 1.00 | 38.59 | B |
| ATOM | 3176 | CD | LYS | B | 100 | 82.771 | 68.263 | 12.966 | 1.00 | 44.87 | B |
| ATOM | 3177 | CE | LYS | B | 100 | 82.689 | 67.562 | 14.314 | 1.00 | 48.06 | B |
| ATOM | 3178 | NZ | LYS | B | 100 | 82.353 | 66.122 | 14.196 | 1.00 | 53.59 | B |
| ATOM | 3179 | C | LYS | B | 100 | 84.190 | 72.329 | 10.482 | 1.00 | 45.56 | B |
| ATOM | 3180 | O | LYS | B | 100 | 83.532 | 72.770 | 9.525 | 1.00 | 42.57 | B |
| ATOM | 3181 | N | THR | B | 101 | 85.519 | 72.239 | 10.456 | 1.00 | 47.39 | B |
| ATOM | 3182 | CA | THR | B | 101 | 86.286 | 72.651 | 9.282 | 1.00 | 48.55 | B |
| ATOM | 3183 | CB | THR | B | 101 | 87.794 | 72.408 | 9.497 | 1.00 | 48.03 | B |
| ATOM | 3184 | OG1 | THR | B | 101 | 88.281 | 73.285 | 10.521 | 1.00 | 47.14 | B |
| ATOM | 3185 | CG2 | THR | B | 101 | 88.557 | 72.683 | 8.212 | 1.00 | 51.80 | B |
| ATOM | 3186 | C | THR | B | 101 | 85.816 | 71.876 | 8.042 | 1.00 | 47.72 | B |
| ATOM | 3187 | O | THR | B | 101 | 85.523 | 70.681 | 8.127 | 1.00 | 43.56 | B |
| ATOM | 3188 | N | ASN | B | 102 | 85.747 | 72.555 | 6.901 | 1.00 | 47.11 | B |
| ATOM | 3189 | CA | ASN | B | 102 | 85.294 | 71.943 | 5.647 | 1.00 | 48.36 | B |
| ATOM | 3190 | CB | ASN | B | 102 | 85.961 | 70.594 | 5.375 | 1.00 | 53.67 | B |
| ATOM | 3191 | CG | ASN | B | 102 | 87.461 | 70.703 | 5.219 | 1.00 | 58.65 | B |
| ATOM | 3192 | OD1 | ASN | B | 102 | 87.980 | 71.763 | 4.856 | 1.00 | 59.24 | B |
| ATOM | 3193 | ND2 | ASN | B | 102 | 88.171 | 69.599 | 5.484 | 1.00 | 61.19 | B |
| ATOM | 3194 | C | ASN | B | 102 | 83.797 | 71.728 | 5.632 | 1.00 | 49.36 | B |
| ATOM | 3195 | O | ASN | B | 102 | 83.284 | 70.965 | 4.814 | 1.00 | 51.85 | B |
| ATOM | 3196 | N | PHE | B | 103 | 83.097 | 72.378 | 6.555 | 1.00 | 48.85 | B |
| ATOM | 3197 | CA | PHE | B | 103 | 81.641 | 72.294 | 6.617 | 1.00 | 44.54 | B |
| ATOM | 3198 | CB | PHE | B | 103 | 81.179 | 71.539 | 7.855 | 1.00 | 44.01 | B |
| ATOM | 3199 | CG | PHE | B | 103 | 81.335 | 70.067 | 7.740 | 1.00 | 45.42 | B |
| ATOM | 3200 | CD1 | PHE | B | 103 | 82.554 | 69.461 | 8.037 | 1.00 | 47.36 | B |
| ATOM | 3201 | CD2 | PHE | B | 103 | 80.270 | 69.274 | 7.323 | 1.00 | 44.68 | B |
| ATOM | 3202 | CE1 | PHE | B | 103 | 82.715 | 68.064 | 7.921 | 1.00 | 44.91 | B |
| ATOM | 3203 | CE2 | PHE | B | 103 | 80.413 | 67.883 | 7.202 | 1.00 | 46.13 | B |
| ATOM | 3204 | CZ | PHE | B | 103 | 81.638 | 67.276 | 7.503 | 1.00 | 44.51 | B |
| ATOM | 3205 | C | PHE | B | 103 | 81.103 | 73.700 | 6.663 | 1.00 | 43.79 | B |
| ATOM | 3206 | O | PHE | B | 103 | 81.736 | 74.577 | 7.239 | 1.00 | 41.42 | B |
| ATOM | 3207 | N | SER | B | 104 | 79.939 | 73.908 | 6.052 | 1.00 | 46.45 | B |
| ATOM | 3208 | CA | SER | B | 104 | 79.306 | 75.216 | 6.007 | 1.00 | 47.47 | B |
| ATOM | 3209 | CB | SER | B | 104 | 79.176 | 75.706 | 4.570 | 1.00 | 53.61 | B |
| ATOM | 3210 | OG | SER | B | 104 | 77.886 | 75.379 | 4.057 | 1.00 | 61.85 | B |
| ATOM | 3211 | C | SER | B | 104 | 77.921 | 75.051 | 6.596 | 1.00 | 46.27 | B |
| ATOM | 3212 | O | SER | B | 104 | 77.285 | 74.007 | 6.425 | 1.00 | 46.36 | B |
| ATOM | 3213 | N | MET | B | 105 | 77.435 | 76.089 | 7.269 | 1.00 | 47.80 | B |
| ATOM | 3214 | CA | MET | B | 105 | 76.129 | 75.998 | 7.913 | 1.00 | 50.16 | B |
| ATOM | 3215 | CB | MET | B | 105 | 76.114 | 76.848 | 9.184 | 1.00 | 42.24 | B |
| ATOM | 3216 | CG | MET | B | 105 | 74.783 | 76.829 | 9.931 | 1.00 | 39.50 | B |
| ATOM | 3217 | SD | MET | B | 105 | 74.951 | 77.585 | 11.559 | 1.00 | 31.98 | B |
| ATOM | 3218 | CE | MET | B | 105 | 76.153 | 76.456 | 12.300 | 1.00 | 32.14 | B |
| ATOM | 3219 | C | MET | B | 105 | 74.948 | 76.398 | 7.046 | 1.00 | 52.75 | B |
| ATOM | 3220 | O | MET | B | 105 | 75.066 | 77.234 | 6.147 | 1.00 | 52.67 | B |
| ATOM | 3221 | N | ASN | B | 106 | 73.807 | 75.787 | 7.343 | 1.00 | 57.15 | B |
| ATOM | 3222 | CA | ASN | B | 106 | 72.560 | 76.072 | 6.664 | 1.00 | 56.25 | B |
| ATOM | 3223 | CB | ASN | B | 106 | 72.186 | 74.950 | 5.722 | 1.00 | 63.78 | B |
| ATOM | 3224 | CG | ASN | B | 106 | 72.678 | 75.210 | 4.332 | 1.00 | 72.25 | B |

TABLE 2-continued

| ATOM | 3225 | OD1 | ASN | B | 106 | 72.787 | 76.372 | 3.916 | 1.00 | 78.63 | B |
|---|---|---|---|---|---|---|---|---|---|---|---|
| ATOM | 3226 | ND2 | ASN | B | 106 | 72.995 | 74.141 | 3.597 | 1.00 | 74.20 | B |
| ATOM | 3227 | C | ASN | B | 106 | 71.504 | 76.200 | 7.727 | 1.00 | 54.17 | B |
| ATOM | 3228 | O | ASN | B | 106 | 71.303 | 75.277 | 8.508 | 1.00 | 56.24 | B |
| ATOM | 3229 | N | GLY | B | 107 | 70.833 | 77.342 | 7.762 | 1.00 | 50.67 | B |
| ATOM | 3230 | CA | GLY | B | 107 | 69.805 | 77.552 | 8.763 | 1.00 | 44.02 | B |
| ATOM | 3231 | C | GLY | B | 107 | 70.334 | 78.414 | 9.886 | 1.00 | 42.66 | B |
| ATOM | 3232 | O | GLY | B | 107 | 71.478 | 78.864 | 9.854 | 1.00 | 41.68 | B |
| ATOM | 3233 | N | ASN | B | 108 | 69.500 | 78.646 | 10.889 | 1.00 | 46.24 | B |
| ATOM | 3234 | CA | ASN | B | 108 | 69.878 | 79.464 | 12.032 | 1.00 | 47.08 | B |
| ATOM | 3235 | CB | ASN | B | 108 | 68.613 | 79.910 | 12.751 | 1.00 | 55.35 | B |
| ATOM | 3236 | CG | ASN | B | 108 | 67.793 | 80.851 | 11.903 | 1.00 | 63.30 | B |
| ATOM | 3237 | OD1 | ASN | B | 108 | 68.164 | 82.013 | 11.722 | 1.00 | 67.44 | B |
| ATOM | 3238 | ND2 | ASN | B | 108 | 66.691 | 80.352 | 11.346 | 1.00 | 68.11 | B |
| ATOM | 3239 | C | ASN | B | 108 | 70.808 | 78.723 | 12.981 | 1.00 | 39.04 | B |
| ATOM | 3240 | O | ASN | B | 108 | 70.560 | 77.577 | 13.347 | 1.00 | 33.47 | B |
| ATOM | 3241 | N | LYS | B | 109 | 71.858 | 79.406 | 13.402 | 1.00 | 34.53 | B |
| ATOM | 3242 | CA | LYS | B | 109 | 72.859 | 78.806 | 14.280 | 1.00 | 35.55 | B |
| ATOM | 3243 | CB | LYS | B | 109 | 74.138 | 79.632 | 14.217 | 1.00 | 35.53 | B |
| ATOM | 3244 | CG | LYS | B | 109 | 73.909 | 81.037 | 14.698 | 1.00 | 37.21 | B |
| ATOM | 3245 | CD | LYS | B | 109 | 75.176 | 81.691 | 15.171 | 1.00 | 43.67 | B |
| ATOM | 3246 | CE | LYS | B | 109 | 74.913 | 83.141 | 15.501 | 1.00 | 53.84 | B |
| ATOM | 3247 | NZ | LYS | B | 109 | 76.079 | 83.848 | 16.124 | 1.00 | 67.33 | B |
| ATOM | 3248 | C | LYS | B | 109 | 72.456 | 78.639 | 15.753 | 1.00 | 33.59 | B |
| ATOM | 3249 | O | LYS | B | 109 | 73.116 | 77.900 | 16.490 | 1.00 | 32.99 | B |
| ATOM | 3250 | N | SER | B | 110 | 71.409 | 79.337 | 16.198 | 1.00 | 29.02 | B |
| ATOM | 3251 | CA | SER | B | 110 | 70.972 | 79.239 | 17.597 | 1.00 | 31.62 | B |
| ATOM | 3252 | CB | SER | B | 110 | 71.068 | 80.588 | 18.298 | 1.00 | 28.39 | B |
| ATOM | 3253 | OG | SER | B | 110 | 72.395 | 81.073 | 18.276 | 1.00 | 35.28 | B |
| ATOM | 3254 | C | SER | B | 110 | 69.547 | 78.730 | 17.734 | 1.00 | 33.04 | B |
| ATOM | 3255 | O | SER | B | 110 | 68.665 | 79.049 | 16.935 | 1.00 | 28.18 | B |
| ATOM | 3256 | N | VAL | B | 111 | 69.336 | 77.927 | 18.761 | 1.00 | 32.94 | B |
| ATOM | 3257 | CA | VAL | B | 111 | 68.028 | 77.360 | 19.032 | 1.00 | 28.12 | B |
| ATOM | 3258 | CB | VAL | B | 111 | 67.998 | 75.911 | 18.507 | 1.00 | 34.53 | B |
| ATOM | 3259 | CG1 | VAL | B | 111 | 69.117 | 75.074 | 19.143 | 1.00 | 27.59 | B |
| ATOM | 3260 | CG2 | VAL | B | 111 | 66.694 | 75.304 | 18.785 | 1.00 | 41.47 | B |
| ATOM | 3261 | C | VAL | B | 111 | 67.729 | 77.488 | 20.539 | 1.00 | 26.65 | B |
| ATOM | 3262 | O | VAL | B | 111 | 68.631 | 77.621 | 21.359 | 1.00 | 27.71 | B |
| ATOM | 3263 | N | TRP | B | 112 | 66.447 | 77.496 | 20.866 | 1.00 | 26.33 | B |
| ATOM | 3264 | CA | TRP | B | 112 | 65.932 | 77.654 | 22.205 | 1.00 | 21.46 | B |
| ATOM | 3265 | CB | TRP | B | 112 | 65.023 | 78.895 | 22.287 | 1.00 | 27.43 | B |
| ATOM | 3266 | CG | TRP | B | 112 | 65.772 | 80.142 | 22.392 | 1.00 | 28.72 | B |
| ATOM | 3267 | CD2 | TRP | B | 112 | 66.455 | 80.818 | 21.323 | 1.00 | 27.13 | B |
| ATOM | 3268 | CE2 | TRP | B | 112 | 67.130 | 81.922 | 21.894 | 1.00 | 23.65 | B |
| ATOM | 3269 | CE3 | TRP | B | 112 | 66.560 | 80.595 | 19.944 | 1.00 | 27.06 | B |
| ATOM | 3270 | CD1 | TRP | B | 112 | 66.053 | 80.849 | 23.542 | 1.00 | 29.24 | B |
| ATOM | 3271 | NE1 | TRP | B | 112 | 66.875 | 81.916 | 23.242 | 1.00 | 22.18 | B |
| ATOM | 3272 | CZ2 | TRP | B | 112 | 67.896 | 82.804 | 21.132 | 1.00 | 24.55 | B |
| ATOM | 3273 | CZ3 | TRP | B | 112 | 67.328 | 81.476 | 19.179 | 1.00 | 32.51 | B |
| ATOM | 3274 | CH2 | TRP | B | 112 | 67.985 | 82.570 | 19.782 | 1.00 | 28.74 | B |
| ATOM | 3275 | C | TRP | B | 112 | 65.113 | 76.462 | 22.622 | 1.00 | 24.09 | B |
| ATOM | 3276 | O | TRP | B | 112 | 64.348 | 75.924 | 21.826 | 1.00 | 23.03 | B |
| ATOM | 3277 | N | CYS | B | 113 | 65.257 | 76.065 | 23.886 | 1.00 | 16.00 | B |
| ATOM | 3278 | CA | CYS | B | 113 | 64.507 | 74.942 | 24.421 | 1.00 | 22.66 | B |
| ATOM | 3279 | C | CYS | B | 113 | 63.090 | 75.442 | 24.775 | 1.00 | 27.37 | B |
| ATOM | 3280 | O | CYS | B | 113 | 62.892 | 76.248 | 25.702 | 1.00 | 23.71 | B |
| ATOM | 3281 | CB | CYS | B | 113 | 65.230 | 74.386 | 25.636 | 1.00 | 24.38 | B |
| ATOM | 3282 | SG | CYS | B | 113 | 64.295 | 73.084 | 26.474 | 1.00 | 25.70 | B |
| ATOM | 3283 | N | GLN | B | 114 | 62.105 | 74.973 | 24.014 | 1.00 | 22.77 | B |
| ATOM | 3284 | CA | GLN | B | 114 | 60.704 | 75.406 | 24.190 | 1.00 | 27.53 | B |
| ATOM | 3285 | CB | GLN | B | 114 | 59.993 | 75.312 | 22.852 | 1.00 | 23.87 | B |
| ATOM | 3286 | CG | GLN | B | 114 | 60.669 | 76.101 | 21.776 | 1.00 | 25.80 | B |
| ATOM | 3287 | CD | GLN | B | 114 | 59.934 | 75.957 | 20.455 | 1.00 | 34.33 | B |
| ATOM | 3288 | OE1 | GLN | B | 114 | 59.540 | 74.850 | 20.084 | 1.00 | 40.82 | B |
| ATOM | 3289 | NE2 | GLN | B | 114 | 59.749 | 77.062 | 19.744 | 1.00 | 28.51 | B |
| ATOM | 3290 | C | GLN | B | 114 | 59.918 | 74.632 | 25.242 | 1.00 | 24.17 | B |
| ATOM | 3291 | O | GLN | B | 114 | 60.324 | 73.557 | 25.638 | 1.00 | 24.70 | B |
| ATOM | 3292 | N | ALA | B | 115 | 58.806 | 75.187 | 25.704 | 1.00 | 28.17 | B |
| ATOM | 3293 | CA | ALA | B | 115 | 57.984 | 74.520 | 26.720 | 1.00 | 32.79 | B |
| ATOM | 3294 | CB | ALA | B | 115 | 56.769 | 75.392 | 27.068 | 1.00 | 30.00 | B |
| ATOM | 3295 | C | ALA | B | 115 | 57.523 | 73.107 | 26.316 | 1.00 | 34.03 | B |
| ATOM | 3296 | O | ALA | B | 115 | 57.338 | 72.237 | 27.170 | 1.00 | 33.21 | B |
| ATOM | 3297 | N | ASN | B | 116 | 57.343 | 72.881 | 25.020 | 1.00 | 36.70 | B |
| ATOM | 3298 | CA | ASN | B | 116 | 56.913 | 71.573 | 24.526 | 1.00 | 38.02 | B |
| ATOM | 3299 | CB | ASN | B | 116 | 56.230 | 71.728 | 23.168 | 1.00 | 34.90 | B |
| ATOM | 3300 | CG | ASN | B | 116 | 57.198 | 72.144 | 22.087 | 1.00 | 33.42 | B |
| ATOM | 3301 | OD1 | ASN | B | 116 | 58.359 | 72.454 | 22.364 | 1.00 | 28.93 | B |
| ATOM | 3302 | ND2 | ASN | B | 116 | 56.728 | 72.167 | 20.853 | 1.00 | 30.98 | B |
| ATOM | 3303 | C | ASN | B | 116 | 58.104 | 70.608 | 24.392 | 1.00 | 34.77 | B |

TABLE 2-continued

| | | | | | | | | | | |
|---|---|---|---|---|---|---|---|---|---|---|
| ATOM | 3304 | O | ASN | B | 116 | 58.017 | 69.612 | 23.695 | 1.00 | 37.59 | B |
| ATOM | 3305 | N | ASN | B | 117 | 59.219 | 70.937 | 25.044 | 1.00 | 36.92 | B |
| ATOM | 3306 | CA | ASN | B | 117 | 60.425 | 70.094 | 25.072 | 1.00 | 31.01 | B |
| ATOM | 3307 | CB | ASN | B | 117 | 60.095 | 68.728 | 25.699 | 1.00 | 35.95 | B |
| ATOM | 3308 | CG | ASN | B | 117 | 59.327 | 68.855 | 27.022 | 1.00 | 41.69 | B |
| ATOM | 3309 | OD1 | ASN | B | 117 | 58.165 | 68.448 | 27.116 | 1.00 | 48.82 | B |
| ATOM | 3310 | ND2 | ASN | B | 117 | 59.966 | 69.428 | 28.041 | 1.00 | 38.48 | B |
| ATOM | 3311 | C | ASN | B | 117 | 61.155 | 69.913 | 23.753 | 1.00 | 35.04 | B |
| ATOM | 3312 | O | ASN | B | 117 | 61.989 | 69.010 | 23.584 | 1.00 | 30.97 | B |
| ATOM | 3313 | N | MET | B | 118 | 60.877 | 70.804 | 22.814 | 1.00 | 32.90 | B |
| ATOM | 3314 | CA | MET | B | 118 | 61.544 | 70.747 | 21.539 | 1.00 | 30.69 | B |
| ATOM | 3315 | CB | MET | B | 118 | 60.533 | 70.486 | 20.426 | 1.00 | 39.19 | B |
| ATOM | 3316 | CG | MET | B | 118 | 60.143 | 69.004 | 20.284 | 1.00 | 45.35 | B |
| ATOM | 3317 | SD | MET | B | 118 | 58.844 | 68.904 | 19.065 | 1.00 | 61.98 | B |
| ATOM | 3318 | CE | MET | B | 118 | 57.379 | 68.930 | 20.152 | 1.00 | 59.12 | B |
| ATOM | 3319 | C | MET | B | 118 | 62.299 | 72.033 | 21.290 | 1.00 | 32.74 | B |
| ATOM | 3320 | O | MET | B | 118 | 61.958 | 73.093 | 21.820 | 1.00 | 31.41 | B |
| ATOM | 3321 | N | TRP | B | 119 | 63.322 | 71.913 | 20.460 | 1.00 | 30.27 | B |
| ATOM | 3322 | CA | TRP | B | 119 | 64.197 | 73.007 | 20.122 | 1.00 | 32.04 | B |
| ATOM | 3323 | CB | TRP | B | 119 | 65.519 | 72.477 | 19.556 | 1.00 | 29.45 | B |
| ATOM | 3324 | CG | TRP | B | 119 | 66.377 | 71.888 | 20.618 | 1.00 | 34.08 | B |
| ATOM | 3325 | CD2 | TRP | B | 119 | 67.091 | 72.613 | 21.638 | 1.00 | 29.55 | B |
| ATOM | 3326 | CE2 | TRP | B | 119 | 67.641 | 71.653 | 22.514 | 1.00 | 32.16 | B |
| ATOM | 3327 | CE3 | TRP | B | 119 | 67.309 | 73.974 | 21.891 | 1.00 | 27.61 | B |
| ATOM | 3328 | CD1 | TRP | B | 119 | 66.533 | 70.563 | 20.907 | 1.00 | 27.66 | B |
| ATOM | 3329 | NE1 | TRP | B | 119 | 67.287 | 70.419 | 22.045 | 1.00 | 29.97 | B |
| ATOM | 3330 | CZ2 | TRP | B | 119 | 68.401 | 72.018 | 23.634 | 1.00 | 33.69 | B |
| ATOM | 3331 | CZ3 | TRP | B | 119 | 68.067 | 74.333 | 23.002 | 1.00 | 28.67 | B |
| ATOM | 3332 | CH2 | TRP | B | 119 | 68.603 | 73.356 | 23.860 | 1.00 | 29.17 | B |
| ATOM | 3333 | C | TRP | B | 119 | 63.672 | 74.059 | 19.188 | 1.00 | 35.37 | B |
| ATOM | 3334 | O | TRP | B | 119 | 62.946 | 73.750 | 18.264 | 1.00 | 34.01 | B |
| ATOM | 3335 | N | GLY | B | 120 | 64.129 | 75.279 | 19.507 | 1.00 | 44.82 | B |
| ATOM | 3336 | CA | GLY | B | 120 | 63.928 | 76.577 | 18.868 | 1.00 | 40.39 | B |
| ATOM | 3337 | C | GLY | B | 120 | 62.736 | 76.818 | 18.037 | 1.00 | 45.27 | B |
| ATOM | 3338 | O | GLY | B | 120 | 61.922 | 75.920 | 17.884 | 1.00 | 54.52 | B |
| ATOM | 3339 | N | PRO | B | 121 | 62.570 | 78.049 | 17.525 | 1.00 | 39.72 | B |
| ATOM | 3340 | CD | PRO | B | 121 | 63.331 | 79.268 | 17.805 | 1.00 | 34.64 | B |
| ATOM | 3341 | CA | PRO | B | 121 | 61.411 | 78.339 | 16.678 | 1.00 | 40.69 | B |
| ATOM | 3342 | CB | PRO | B | 121 | 61.355 | 79.869 | 16.674 | 1.00 | 33.54 | B |
| ATOM | 3343 | CG | PRO | B | 121 | 62.781 | 80.221 | 16.775 | 1.00 | 38.11 | B |
| ATOM | 3344 | C | PRO | B | 121 | 61.717 | 77.733 | 15.294 | 1.00 | 38.17 | B |
| ATOM | 3345 | O | PRO | B | 121 | 60.817 | 77.305 | 14.591 | 1.00 | 40.16 | B |
| ATOM | 3346 | N | THR | B | 122 | 62.994 | 77.693 | 14.930 | 1.00 | 33.84 | B |
| ATOM | 3347 | CA | THR | B | 122 | 63.424 | 77.113 | 13.660 | 1.00 | 38.91 | B |
| ATOM | 3348 | CB | THR | B | 122 | 64.548 | 77.939 | 12.988 | 1.00 | 42.26 | B |
| ATOM | 3349 | OG1 | THR | B | 122 | 65.803 | 77.671 | 13.634 | 1.00 | 39.47 | B |
| ATOM | 3350 | CG2 | THR | B | 122 | 64.259 | 79.431 | 13.106 | 1.00 | 40.58 | B |
| ATOM | 3351 | C | THR | B | 122 | 63.968 | 75.708 | 13.874 | 1.00 | 40.61 | B |
| ATOM | 3352 | O | THR | B | 122 | 64.163 | 75.266 | 14.999 | 1.00 | 43.52 | B |
| ATOM | 3353 | N | ARG | B | 123 | 64.220 | 75.005 | 12.784 | 1.00 | 42.70 | B |
| ATOM | 3354 | CA | ARG | B | 123 | 64.762 | 73.656 | 12.870 | 1.00 | 46.43 | B |
| ATOM | 3355 | CB | ARG | B | 123 | 64.505 | 72.912 | 11.549 | 1.00 | 48.19 | B |
| ATOM | 3356 | CG | ARG | B | 123 | 64.849 | 71.433 | 11.600 | 1.00 | 63.34 | B |
| ATOM | 3357 | CD | ARG | B | 123 | 64.109 | 70.638 | 10.517 | 1.00 | 71.72 | B |
| ATOM | 3358 | NE | ARG | B | 123 | 62.664 | 70.564 | 10.762 | 1.00 | 75.72 | B |
| ATOM | 3359 | CZ | ARG | B | 123 | 61.734 | 70.934 | 9.881 | 1.00 | 77.53 | B |
| ATOM | 3360 | NH1 | ARG | B | 123 | 62.096 | 71.410 | 8.690 | 1.00 | 78.13 | B |
| ATOM | 3361 | NH2 | ARG | B | 123 | 60.444 | 70.820 | 10.184 | 1.00 | 75.29 | B |
| ATOM | 3362 | C | ARG | B | 123 | 66.270 | 73.774 | 13.141 | 1.00 | 36.14 | B |
| ATOM | 3363 | O | ARG | B | 123 | 66.861 | 74.816 | 12.880 | 1.00 | 34.06 | B |
| ATOM | 3364 | N | LEU | B | 124 | 66.888 | 72.714 | 13.659 | 1.00 | 36.62 | B |
| ATOM | 3365 | CA | LEU | B | 124 | 68.326 | 72.743 | 13.939 | 1.00 | 35.68 | B |
| ATOM | 3366 | CB | LEU | B | 124 | 68.818 | 71.410 | 14.509 | 1.00 | 37.22 | B |
| ATOM | 3367 | CG | LEU | B | 124 | 68.399 | 71.019 | 15.933 | 1.00 | 38.68 | B |
| ATOM | 3368 | CD1 | LEU | B | 124 | 69.008 | 69.670 | 16.342 | 1.00 | 37.12 | B |
| ATOM | 3369 | CD2 | LEU | B | 124 | 68.860 | 72.097 | 16.874 | 1.00 | 34.15 | B |
| ATOM | 3370 | C | LEU | B | 124 | 69.081 | 73.029 | 12.656 | 1.00 | 37.07 | B |
| ATOM | 3371 | O | LEU | B | 124 | 68.701 | 72.584 | 11.583 | 1.00 | 35.87 | B |
| ATOM | 3372 | N | PRO | B | 125 | 70.168 | 73.787 | 12.750 | 1.00 | 40.36 | B |
| ATOM | 3373 | CD | PRO | B | 125 | 70.832 | 74.306 | 13.962 | 1.00 | 38.05 | B |
| ATOM | 3374 | CA | PRO | B | 125 | 70.933 | 74.085 | 11.538 | 1.00 | 35.47 | B |
| ATOM | 3375 | CB | PRO | B | 125 | 71.993 | 75.069 | 12.029 | 1.00 | 35.51 | B |
| ATOM | 3376 | CG | PRO | B | 125 | 72.224 | 74.641 | 13.460 | 1.00 | 35.57 | B |
| ATOM | 3377 | C | PRO | B | 125 | 71.535 | 72.794 | 11.002 | 1.00 | 40.45 | B |
| ATOM | 3378 | O | PRO | B | 125 | 71.432 | 71.739 | 11.640 | 1.00 | 33.92 | B |
| ATOM | 3379 | N | THR | B | 126 | 72.131 | 72.867 | 9.814 | 1.00 | 41.58 | B |
| ATOM | 3380 | CA | THR | B | 126 | 72.765 | 71.704 | 9.217 | 1.00 | 41.03 | B |
| ATOM | 3381 | CB | THR | B | 126 | 71.929 | 71.137 | 8.006 | 1.00 | 42.99 | B |
| ATOM | 3382 | OG1 | THR | B | 126 | 71.625 | 72.182 | 7.075 | 1.00 | 45.10 | B |

TABLE 2-continued

| ATOM | 3383 | CG2 | THR | B | 126 | 70.628 | 70.529 | 8.503 | 1.00 | 40.83 | B |
|---|---|---|---|---|---|---|---|---|---|---|---|
| ATOM | 3384 | C | THR | B | 126 | 74.157 | 72.116 | 8.777 | 1.00 | 41.16 | B |
| ATOM | 3385 | O | THR | B | 126 | 74.415 | 73.299 | 8.544 | 1.00 | 40.35 | B |
| ATOM | 3386 | N | CYS | B | 127 | 75.074 | 71.158 | 8.716 | 1.00 | 42.86 | B |
| ATOM | 3387 | CA | CYS | B | 127 | 76.433 | 71.468 | 8.279 | 1.00 | 48.44 | B |
| ATOM | 3388 | C | CYS | B | 127 | 76.774 | 70.561 | 7.098 | 1.00 | 53.76 | B |
| ATOM | 3389 | O | CYS | B | 127 | 76.711 | 69.336 | 7.219 | 1.00 | 55.59 | B |
| ATOM | 3390 | CB | CYS | B | 127 | 77.440 | 71.249 | 9.422 | 1.00 | 49.29 | B |
| ATOM | 3391 | SG | CYS | B | 127 | 77.365 | 72.471 | 10.779 | 1.00 | 41.21 | B |
| ATOM | 3392 | N | VAL | B | 128 | 77.117 | 71.159 | 5.960 | 1.00 | 52.99 | B |
| ATOM | 3393 | CA | VAL | B | 128 | 77.466 | 70.386 | 4.764 | 1.00 | 58.11 | B |
| ATOM | 3394 | CB | VAL | B | 128 | 76.479 | 70.674 | 3.612 | 1.00 | 60.17 | B |
| ATOM | 3395 | CG1 | VAL | B | 128 | 76.356 | 72.179 | 3.395 | 1.00 | 59.61 | B |
| ATOM | 3396 | CG2 | VAL | B | 128 | 76.974 | 70.005 | 2.322 | 1.00 | 62.78 | B |
| ATOM | 3397 | C | VAL | B | 128 | 78.881 | 70.738 | 4.290 | 1.00 | 55.96 | B |
| ATOM | 3398 | O | VAL | B | 128 | 79.307 | 71.875 | 4.427 | 1.00 | 56.76 | B |
| ATOM | 3399 | N | SER | B | 129 | 79.604 | 69.763 | 3.747 | 1.00 | 58.88 | B |
| ATOM | 3400 | CA | SER | B | 129 | 80.976 | 69.974 | 3.241 | 1.00 | 63.04 | B |
| ATOM | 3401 | CB | SER | B | 129 | 81.489 | 68.685 | 2.616 | 1.00 | 64.42 | B |
| ATOM | 3402 | OG | SER | B | 129 | 80.566 | 68.249 | 1.633 | 1.00 | 74.77 | B |
| ATOM | 3403 | C | SER | B | 129 | 81.061 | 71.092 | 2.194 | 1.00 | 60.01 | B |
| ATOM | 3404 | O | SER | B | 129 | 82.054 | 71.856 | 2.166 | 1.00 | 59.63 | B |
| ATOM | 3405 | OXT | SER | B | 129 | 80.121 | 71.165 | 1.381 | 1.00 | 61.43 | B |
| END | | | | | | | | | | | |

TABLE 3

| ATOM | 2419 | CB | ALA | B | 1 | 64.181 | 107.666 | 4.123 | 1.00 | 39.20 | B |
|---|---|---|---|---|---|---|---|---|---|---|---|
| ATOM | 2420 | C | ALA | B | 1 | 62.836 | 105.816 | 3.113 | 1.00 | 41.03 | B |
| ATOM | 2421 | O | ALA | B | 1 | 61.659 | 105.713 | 3.477 | 1.00 | 42.08 | B |
| ATOM | 2422 | N | ALA | B | 1 | 62.413 | 108.231 | 2.458 | 1.00 | 40.18 | B |
| ATOM | 2423 | CA | ALA | B | 1 | 63.447 | 107.201 | 2.861 | 1.00 | 43.96 | B |
| ATOM | 2424 | N | ILE | B | 2 | 63.636 | 104.759 | 2.923 | 1.00 | 39.63 | B |
| ATOM | 2425 | CA | ILE | B | 2 | 63.175 | 103.383 | 3.141 | 1.00 | 37.01 | B |
| ATOM | 2426 | CB | ILE | B | 2 | 64.245 | 102.349 | 2.700 | 1.00 | 32.57 | B |
| ATOM | 2427 | CG2 | ILE | B | 2 | 63.775 | 100.936 | 3.064 | 1.00 | 35.80 | B |
| ATOM | 2428 | CG1 | ILE | B | 2 | 64.457 | 102.422 | 1.178 | 1.00 | 34.01 | B |
| ATOM | 2429 | CD1 | ILE | B | 2 | 65.479 | 101.372 | 0.650 | 1.00 | 31.21 | B |
| ATOM | 2430 | C | ILE | B | 2 | 62.831 | 103.151 | 4.633 | 1.00 | 38.27 | B |
| ATOM | 2431 | O | ILE | B | 2 | 63.565 | 103.577 | 5.528 | 1.00 | 32.71 | B |
| ATOM | 2432 | N | SER | B | 3 | 61.714 | 102.486 | 4.897 | 1.00 | 30.65 | B |
| ATOM | 2433 | CA | SER | B | 3 | 61.316 | 102.226 | 6.272 | 1.00 | 26.19 | B |
| ATOM | 2434 | CB | SER | B | 3 | 60.245 | 103.236 | 6.689 | 1.00 | 31.79 | B |
| ATOM | 2435 | OG | SER | B | 3 | 59.060 | 103.020 | 5.926 | 1.00 | 27.35 | B |
| ATOM | 2436 | C | SER | B | 3 | 60.744 | 100.826 | 6.435 | 1.00 | 30.38 | B |
| ATOM | 2437 | O | SER | B | 3 | 60.495 | 100.132 | 5.446 | 1.00 | 28.89 | B |
| ATOM | 2438 | N | CYS | B | 4 | 60.559 | 100.410 | 7.690 | 1.00 | 27.89 | B |
| ATOM | 2439 | CA | CYS | B | 4 | 59.941 | 99.127 | 8.003 | 1.00 | 27.29 | B |
| ATOM | 2440 | C | CYS | B | 4 | 58.609 | 99.528 | 8.600 | 1.00 | 26.13 | B |
| ATOM | 2441 | O | CYS | B | 4 | 58.446 | 100.666 | 9.061 | 1.00 | 29.64 | B |
| ATOM | 2442 | CB | CYS | B | 4 | 60.731 | 98.328 | 9.056 | 1.00 | 27.46 | B |
| ATOM | 2443 | SG | CYS | B | 4 | 62.214 | 97.531 | 8.369 | 1.00 | 27.76 | B |
| ATOM | 2444 | N | GLY | B | 5 | 57.648 | 98.622 | 8.561 | 1.00 | 22.65 | B |
| ATOM | 2445 | CA | GLY | B | 5 | 56.366 | 98.916 | 9.155 | 1.00 | 23.57 | B |
| ATOM | 2446 | C | GLY | B | 5 | 56.452 | 98.570 | 10.643 | 1.00 | 24.00 | B |
| ATOM | 2447 | O | GLY | B | 5 | 57.504 | 98.199 | 11.181 | 1.00 | 23.18 | B |
| ATOM | 2448 | N | SER | B | 6 | 55.322 | 98.698 | 11.313 | 1.00 | 21.65 | B |
| ATOM | 2449 | CA | SER | B | 6 | 55.204 | 98.441 | 12.733 | 1.00 | 22.23 | B |
| ATOM | 2450 | CB | SER | B | 6 | 53.722 | 98.511 | 13.098 | 1.00 | 27.49 | B |
| ATOM | 2451 | OG | SER | B | 6 | 53.543 | 98.605 | 14.483 | 1.00 | 33.82 | B |
| ATOM | 2452 | C | SER | B | 6 | 55.785 | 97.062 | 13.091 | 1.00 | 26.45 | B |
| ATOM | 2453 | O | SER | B | 6 | 55.489 | 96.081 | 12.439 | 1.00 | 22.14 | B |
| ATOM | 2454 | N | PRO | B | 7 | 56.639 | 96.980 | 14.122 | 1.00 | 26.74 | B |
| ATOM | 2455 | CD | PRO | B | 7 | 57.230 | 98.026 | 14.973 | 1.00 | 25.89 | B |
| ATOM | 2456 | CA | PRO | B | 7 | 57.191 | 95.661 | 14.468 | 1.00 | 25.01 | B |
| ATOM | 2457 | CB | PRO | B | 7 | 58.175 | 95.984 | 15.592 | 1.00 | 22.52 | B |
| ATOM | 2458 | CG | PRO | B | 7 | 57.589 | 97.228 | 16.232 | 1.00 | 26.49 | B |
| ATOM | 2459 | C | PRO | B | 7 | 56.133 | 94.627 | 14.894 | 1.00 | 27.04 | B |
| ATOM | 2460 | O | PRO | B | 7 | 55.061 | 94.961 | 15.414 | 1.00 | 24.19 | B |
| ATOM | 2461 | N | PRO | B | 8 | 56.439 | 93.345 | 14.700 | 1.00 | 24.37 | B |
| ATOM | 2462 | CD | PRO | B | 8 | 57.540 | 92.754 | 13.936 | 1.00 | 26.75 | B |
| ATOM | 2463 | CA | PRO | B | 8 | 55.431 | 92.366 | 15.099 | 1.00 | 25.28 | B |
| ATOM | 2464 | CB | PRO | B | 8 | 55.974 | 91.048 | 14.538 | 1.00 | 31.15 | B |
| ATOM | 2465 | CG | PRO | B | 8 | 57.401 | 91.314 | 14.245 | 1.00 | 33.33 | B |
| ATOM | 2466 | C | PRO | B | 8 | 55.228 | 92.382 | 16.613 | 1.00 | 30.70 | B |
| ATOM | 2467 | O | PRO | B | 8 | 56.180 | 92.527 | 17.364 | 1.00 | 31.22 | B |

TABLE 3-continued

| | | | | | | | | | | |
|---|---|---|---|---|---|---|---|---|---|---|
| ATOM | 2468 | N | PRO | B | 9 | 53.971 | 92.314 | 17.074 | 1.00 | 30.39 B |
| ATOM | 2469 | CD | PRO | B | 9 | 52.724 | 92.280 | 16.275 | 1.00 | 37.82 B |
| ATOM | 2470 | CA | PRO | B | 9 | 53.686 | 92.322 | 18.518 | 1.00 | 32.22 B |
| ATOM | 2471 | CB | PRO | B | 9 | 52.155 | 92.415 | 18.589 | 1.00 | 31.66 B |
| ATOM | 2472 | CG | PRO | B | 9 | 51.705 | 91.731 | 17.265 | 1.00 | 31.37 B |
| ATOM | 2473 | C | PRO | B | 9 | 54.190 | 91.062 | 19.209 | 1.00 | 26.54 B |
| ATOM | 2474 | O | PRO | B | 9 | 54.542 | 90.072 | 18.563 | 1.00 | 23.13 B |
| ATOM | 2475 | N | ILE | B | 10 | 54.214 | 91.111 | 20.526 | 1.00 | 25.96 B |
| ATOM | 2476 | CA | ILE | B | 10 | 54.651 | 89.969 | 21.302 | 1.00 | 34.36 B |
| ATOM | 2477 | CB | ILE | B | 10 | 56.150 | 90.068 | 21.770 | 1.00 | 24.92 B |
| ATOM | 2478 | CG2 | ILE | B | 10 | 56.398 | 91.363 | 22.562 | 1.00 | 24.04 B |
| ATOM | 2479 | CG1 | ILE | B | 10 | 56.491 | 88.795 | 22.581 | 1.00 | 30.43 B |
| ATOM | 2480 | CD1 | ILE | B | 10 | 57.991 | 88.536 | 22.813 | 1.00 | 24.83 B |
| ATOM | 2481 | C | ILE | B | 10 | 53.753 | 89.810 | 22.511 | 1.00 | 33.31 B |
| ATOM | 2482 | O | ILE | B | 10 | 53.743 | 90.647 | 23.412 | 1.00 | 32.83 B |
| ATOM | 2483 | N | LEU | B | 11 | 52.992 | 88.724 | 22.525 | 1.00 | 30.71 B |
| ATOM | 2484 | CA | LEU | B | 11 | 52.108 | 88.483 | 23.659 | 1.00 | 34.63 B |
| ATOM | 2485 | CB | LEU | B | 11 | 51.217 | 87.277 | 23.365 | 1.00 | 36.50 B |
| ATOM | 2486 | CG | LEU | B | 11 | 50.279 | 87.435 | 22.161 | 1.00 | 41.37 B |
| ATOM | 2487 | CD1 | LEU | B | 11 | 49.708 | 86.073 | 21.769 | 1.00 | 42.99 B |
| ATOM | 2488 | CD2 | LEU | B | 11 | 49.142 | 88.425 | 22.495 | 1.00 | 39.65 B |
| ATOM | 2489 | C | LEU | B | 11 | 52.912 | 88.247 | 24.946 | 1.00 | 33.29 B |
| ATOM | 2490 | O | LEU | B | 11 | 53.905 | 87.517 | 24.948 | 1.00 | 28.06 B |
| ATOM | 2491 | N | ASN | B | 12 | 52.463 | 88.872 | 26.032 | 1.00 | 31.32 B |
| ATOM | 2492 | CA | ASN | B | 12 | 53.086 | 88.753 | 27.328 | 1.00 | 30.29 B |
| ATOM | 2493 | CB | ASN | B | 12 | 53.025 | 87.303 | 27.802 | 1.00 | 32.27 B |
| ATOM | 2494 | CG | ASN | B | 12 | 51.612 | 86.875 | 28.083 | 1.00 | 38.86 B |
| ATOM | 2495 | OD1 | ASN | B | 12 | 50.917 | 87.526 | 28.864 | 1.00 | 38.55 B |
| ATOM | 2496 | ND2 | ASN | B | 12 | 51.161 | 85.805 | 27.431 | 1.00 | 34.66 B |
| ATOM | 2497 | C | ASN | B | 12 | 54.510 | 89.250 | 27.371 | 1.00 | 32.36 B |
| ATOM | 2498 | O | ASN | B | 12 | 55.277 | 88.858 | 28.239 | 1.00 | 32.55 B |
| ATOM | 2499 | N | GLY | B | 13 | 54.849 | 90.130 | 26.439 | 1.00 | 28.46 B |
| ATOM | 2500 | CA | GLY | B | 13 | 56.187 | 90.671 | 26.400 | 1.00 | 28.72 B |
| ATOM | 2501 | C | GLY | B | 13 | 56.147 | 92.166 | 26.169 | 1.00 | 29.82 B |
| ATOM | 2502 | O | GLY | B | 13 | 55.075 | 92.780 | 26.153 | 1.00 | 34.03 B |
| ATOM | 2503 | N | ARG | B | 14 | 57.324 | 92.742 | 25.983 | 1.00 | 28.15 B |
| ATOM | 2504 | CA | ARG | B | 14 | 57.486 | 94.166 | 25.739 | 1.00 | 31.15 B |
| ATOM | 2505 | CB | ARG | B | 14 | 58.198 | 94.882 | 26.897 | 1.00 | 34.62 B |
| ATOM | 2506 | CG | ARG | B | 14 | 57.388 | 95.196 | 28.116 | 1.00 | 41.44 B |
| ATOM | 2507 | CD | ARG | B | 14 | 58.240 | 95.962 | 29.112 | 1.00 | 42.08 B |
| ATOM | 2508 | NE | ARG | B | 14 | 57.526 | 96.080 | 30.373 | 1.00 | 49.55 B |
| ATOM | 2509 | CZ | ARG | B | 14 | 58.023 | 96.595 | 31.487 | 1.00 | 48.40 B |
| ATOM | 2510 | NH1 | ARG | B | 14 | 59.261 | 97.065 | 31.509 | 1.00 | 40.73 B |
| ATOM | 2511 | NH2 | ARG | B | 14 | 57.276 | 96.602 | 32.593 | 1.00 | 56.30 B |
| ATOM | 2512 | C | ARG | B | 14 | 58.409 | 94.342 | 24.567 | 1.00 | 23.56 B |
| ATOM | 2513 | O | ARG | B | 14 | 59.232 | 93.480 | 24.280 | 1.00 | 23.51 B |
| ATOM | 2514 | N | ILE | B | 15 | 58.319 | 95.516 | 23.955 | 1.00 | 27.48 B |
| ATOM | 2515 | CA | ILE | B | 15 | 59.171 | 95.893 | 22.841 | 1.00 | 26.75 B |
| ATOM | 2516 | CB | ILE | B | 15 | 58.345 | 96.176 | 21.580 | 1.00 | 26.32 B |
| ATOM | 2517 | CG2 | ILE | B | 15 | 59.250 | 96.815 | 20.497 | 1.00 | 29.30 B |
| ATOM | 2518 | CG1 | ILE | B | 15 | 57.656 | 94.902 | 21.122 | 1.00 | 30.62 B |
| ATOM | 2519 | CD1 | ILE | B | 15 | 56.760 | 95.100 | 19.889 | 1.00 | 35.23 B |
| ATOM | 2520 | C | ILE | B | 15 | 59.767 | 97.212 | 23.279 | 1.00 | 26.59 B |
| ATOM | 2521 | O | ILE | B | 15 | 59.050 | 98.050 | 23.818 | 1.00 | 30.94 B |
| ATOM | 2522 | N | SER | B | 16 | 61.055 | 97.409 | 23.036 | 1.00 | 23.15 B |
| ATOM | 2523 | CA | SER | B | 16 | 61.709 | 98.654 | 23.393 | 1.00 | 32.61 B |
| ATOM | 2524 | CB | SER | B | 16 | 63.187 | 98.567 | 23.057 | 1.00 | 29.32 B |
| ATOM | 2525 | OG | SER | B | 16 | 63.359 | 98.151 | 21.717 | 1.00 | 35.31 B |
| ATOM | 2526 | C | SER | B | 16 | 61.082 | 99.839 | 22.639 | 1.00 | 41.27 B |
| ATOM | 2527 | O | SER | B | 16 | 60.466 | 99.674 | 21.576 | 1.00 | 36.78 B |
| ATOM | 2528 | N | TYR | B | 17 | 61.260 | 101.035 | 23.193 | 1.00 | 42.89 B |
| ATOM | 2529 | CA | TYR | B | 17 | 60.719 | 102.267 | 22.624 | 1.00 | 46.29 B |
| ATOM | 2530 | CB | TYR | B | 17 | 60.932 | 103.436 | 23.623 | 1.00 | 44.99 B |
| ATOM | 2531 | CG | TYR | B | 17 | 60.026 | 103.380 | 24.865 | 1.00 | 47.02 B |
| ATOM | 2532 | CD1 | TYR | B | 17 | 60.510 | 103.694 | 26.151 | 1.00 | 49.03 B |
| ATOM | 2533 | CE1 | TYR | B | 17 | 59.664 | 103.655 | 27.283 | 1.00 | 48.52 B |
| ATOM | 2534 | CD2 | TYR | B | 17 | 58.686 | 103.025 | 24.748 | 1.00 | 51.67 B |
| ATOM | 2535 | CE2 | TYR | B | 17 | 57.833 | 102.974 | 25.861 | 1.00 | 53.32 B |
| ATOM | 2536 | CZ | TYR | B | 17 | 58.319 | 103.292 | 27.122 | 1.00 | 56.82 B |
| ATOM | 2537 | OH | TYR | B | 17 | 57.430 | 103.259 | 28.190 | 1.00 | 55.53 B |
| ATOM | 2538 | C | TYR | B | 17 | 61.397 | 102.551 | 21.285 | 1.00 | 46.15 B |
| ATOM | 2539 | O | TYR | B | 17 | 62.600 | 102.375 | 21.146 | 1.00 | 50.00 B |
| ATOM | 2540 | N | TYR | B | 18 | 60.623 | 102.952 | 20.281 | 1.00 | 46.05 B |
| ATOM | 2541 | CA | TYR | B | 18 | 61.204 | 103.270 | 18.975 | 1.00 | 44.93 B |
| ATOM | 2542 | CB | TYR | B | 18 | 61.076 | 102.076 | 18.010 | 1.00 | 37.78 B |
| ATOM | 2543 | CG | TYR | B | 18 | 59.645 | 101.669 | 17.711 | 1.00 | 37.10 B |
| ATOM | 2544 | CD1 | TYR | B | 18 | 58.890 | 102.343 | 16.750 | 1.00 | 31.24 B |
| ATOM | 2545 | CE1 | TYR | B | 18 | 57.573 | 101.980 | 16.501 | 1.00 | 34.43 B |
| ATOM | 2546 | CD2 | TYR | B | 18 | 59.040 | 100.622 | 18.415 | 1.00 | 34.57 B |

TABLE 3-continued

| | | | | | | | | | | |
|---|---|---|---|---|---|---|---|---|---|---|
| ATOM | 2547 | CE2 | TYR | B | 18 | 57.730 | 100.255 | 18.184 | 1.00 | 36.06 B |
| ATOM | 2548 | CZ | TYR | B | 18 | 57.000 | 100.939 | 17.218 | 1.00 | 35.02 B |
| ATOM | 2549 | OH | TYR | B | 18 | 55.706 | 100.565 | 16.967 | 1.00 | 33.22 B |
| ATOM | 2550 | C | TYR | B | 18 | 60.524 | 104.514 | 18.375 | 1.00 | 40.62 B |
| ATOM | 2551 | O | TYR | B | 18 | 59.356 | 104.784 | 18.632 | 1.00 | 40.57 B |
| ATOM | 2552 | N | SER | B | 19 | 61.280 | 105.260 | 17.586 | 1.00 | 42.39 B |
| ATOM | 2553 | CA | SER | B | 19 | 60.786 | 106.464 | 16.931 | 1.00 | 49.17 B |
| ATOM | 2554 | CB | SER | B | 19 | 61.922 | 107.472 | 16.789 | 1.00 | 49.59 B |
| ATOM | 2555 | OG | SER | B | 19 | 63.070 | 106.843 | 16.237 | 1.00 | 54.17 B |
| ATOM | 2556 | C | SER | B | 19 | 60.213 | 106.155 | 15.540 | 1.00 | 51.20 B |
| ATOM | 2557 | O | SER | B | 19 | 60.569 | 105.165 | 14.900 | 1.00 | 42.62 B |
| ATOM | 2558 | N | THR | B | 20 | 59.347 | 107.041 | 15.073 | 1.00 | 48.91 B |
| ATOM | 2559 | CA | THR | B | 20 | 58.706 | 106.898 | 13.783 | 1.00 | 49.40 B |
| ATOM | 2560 | CB | THR | B | 20 | 57.166 | 107.002 | 13.991 | 1.00 | 52.73 B |
| ATOM | 2561 | OG1 | THR | B | 20 | 56.483 | 106.279 | 12.968 | 1.00 | 60.25 B |
| ATOM | 2562 | CG2 | THR | B | 20 | 56.714 | 108.456 | 13.943 | 1.00 | 51.71 B |
| ATOM | 2563 | C | THR | B | 20 | 59.222 | 108.022 | 12.844 | 1.00 | 47.48 B |
| ATOM | 2564 | O | THR | B | 20 | 59.460 | 109.147 | 13.280 | 1.00 | 50.56 B |
| ATOM | 2565 | N | PRO | B | 21 | 59.427 | 107.720 | 11.551 | 1.00 | 46.52 B |
| ATOM | 2566 | CD | PRO | B | 21 | 59.801 | 108.745 | 10.551 | 1.00 | 44.33 B |
| ATOM | 2567 | CA | PRO | B | 21 | 59.204 | 106.417 | 10.909 | 1.00 | 43.20 B |
| ATOM | 2568 | CB | PRO | B | 21 | 59.137 | 106.769 | 9.422 | 1.00 | 43.49 B |
| ATOM | 2569 | CG | PRO | B | 21 | 60.103 | 107.918 | 9.305 | 1.00 | 44.19 B |
| ATOM | 2570 | C | PRO | B | 21 | 60.342 | 105.456 | 11.248 | 1.00 | 37.71 B |
| ATOM | 2571 | O | PRO | B | 21 | 61.393 | 105.891 | 11.674 | 1.00 | 38.42 B |
| ATOM | 2572 | N | THR | B | 22 | 60.123 | 104.155 | 11.067 | 1.00 | 40.00 B |
| ATOM | 2573 | CA | THR | B | 22 | 61.139 | 103.150 | 11.382 | 1.00 | 37.29 B |
| ATOM | 2574 | CB | THR | B | 22 | 60.521 | 101.715 | 11.578 | 1.00 | 33.63 B |
| ATOM | 2575 | OG1 | THR | B | 22 | 59.497 | 101.719 | 12.600 | 1.00 | 36.55 B |
| ATOM | 2576 | CG2 | THR | B | 22 | 61.626 | 100.734 | 11.963 | 1.00 | 26.59 B |
| ATOM | 2577 | C | THR | B | 22 | 62.143 | 103.079 | 10.221 | 1.00 | 35.94 B |
| ATOM | 2578 | O | THR | B | 22 | 61.851 | 102.484 | 9.183 | 1.00 | 33.29 B |
| ATOM | 2579 | N | ALA | B | 23 | 63.326 | 103.663 | 10.410 | 1.00 | 33.77 B |
| ATOM | 2580 | CA | ALA | B | 23 | 64.367 | 103.677 | 9.380 | 1.00 | 30.19 B |
| ATOM | 2581 | CB | ALA | B | 23 | 65.314 | 104.852 | 9.615 | 1.00 | 28.90 B |
| ATOM | 2582 | C | ALA | B | 23 | 65.192 | 102.399 | 9.300 | 1.00 | 30.98 B |
| ATOM | 2583 | O | ALA | B | 23 | 65.331 | 101.693 | 10.284 | 1.00 | 23.97 B |
| ATOM | 2584 | N | VAL | B | 24 | 65.736 | 102.127 | 8.112 | 1.00 | 27.61 B |
| ATOM | 2585 | CA | VAL | B | 24 | 66.591 | 100.982 | 7.874 | 1.00 | 26.92 B |
| ATOM | 2586 | CB | VAL | B | 24 | 67.197 | 101.042 | 6.460 | 1.00 | 29.41 B |
| ATOM | 2587 | CG1 | VAL | B | 24 | 68.357 | 100.043 | 6.326 | 1.00 | 28.58 B |
| ATOM | 2588 | CG2 | VAL | B | 24 | 66.107 | 100.729 | 5.430 | 1.00 | 26.92 B |
| ATOM | 2589 | C | VAL | B | 24 | 67.707 | 101.091 | 8.898 | 1.00 | 32.79 B |
| ATOM | 2590 | O | VAL | B | 24 | 68.266 | 102.166 | 9.077 | 1.00 | 26.10 B |
| ATOM | 2591 | N | GLY | B | 25 | 68.026 | 100.000 | 9.586 | 1.00 | 28.01 B |
| ATOM | 2592 | CA | GLY | B | 25 | 69.070 | 100.081 | 10.596 | 1.00 | 31.93 B |
| ATOM | 2593 | C | GLY | B | 25 | 68.516 | 100.210 | 12.007 | 1.00 | 34.29 B |
| ATOM | 2594 | O | GLY | B | 25 | 69.251 | 100.080 | 12.966 | 1.00 | 28.44 B |
| ATOM | 2595 | N | THR | B | 26 | 67.227 | 100.486 | 12.148 | 1.00 | 26.99 B |
| ATOM | 2596 | CA | THR | B | 26 | 66.650 | 100.568 | 13.474 | 1.00 | 29.37 B |
| ATOM | 2597 | CB | THR | B | 26 | 65.179 | 100.994 | 13.403 | 1.00 | 30.78 B |
| ATOM | 2598 | OG1 | THR | B | 26 | 65.111 | 102.295 | 12.808 | 1.00 | 26.87 B |
| ATOM | 2599 | CG2 | THR | B | 26 | 64.524 | 101.000 | 14.833 | 1.00 | 23.56 B |
| ATOM | 2600 | C | THR | B | 26 | 66.713 | 99.183 | 14.136 | 1.00 | 32.07 B |
| ATOM | 2601 | O | THR | B | 26 | 66.462 | 98.171 | 13.473 | 1.00 | 28.44 B |
| ATOM | 2602 | N | VAL | B | 27 | 67.056 | 99.143 | 15.429 | 1.00 | 28.90 B |
| ATOM | 2603 | CA | VAL | B | 27 | 67.124 | 97.891 | 16.200 | 1.00 | 29.71 B |
| ATOM | 2604 | CB | VAL | B | 27 | 68.507 | 97.703 | 16.858 | 1.00 | 36.67 B |
| ATOM | 2605 | CG1 | VAL | B | 27 | 68.477 | 96.507 | 17.808 | 1.00 | 31.87 B |
| ATOM | 2606 | CG2 | VAL | B | 27 | 69.554 | 97.478 | 15.793 | 1.00 | 32.00 B |
| ATOM | 2607 | C | VAL | B | 27 | 66.054 | 97.946 | 17.292 | 1.00 | 26.09 B |
| ATOM | 2608 | O | VAL | B | 27 | 65.961 | 98.921 | 18.029 | 1.00 | 28.74 B |
| ATOM | 2609 | N | ILE | B | 28 | 65.230 | 96.913 | 17.349 | 1.00 | 28.74 B |
| ATOM | 2610 | CA | ILE | B | 28 | 64.126 | 96.780 | 18.294 | 1.00 | 34.25 B |
| ATOM | 2611 | CB | ILE | B | 28 | 62.802 | 96.400 | 17.552 | 1.00 | 38.10 B |
| ATOM | 2612 | CG2 | ILE | B | 28 | 61.752 | 95.929 | 18.516 | 1.00 | 49.78 B |
| ATOM | 2613 | CG1 | ILE | B | 28 | 62.260 | 97.598 | 16.808 | 1.00 | 46.71 B |
| ATOM | 2614 | CD1 | ILE | B | 28 | 62.252 | 98.826 | 17.612 | 1.00 | 40.93 B |
| ATOM | 2615 | C | ILE | B | 28 | 64.491 | 95.619 | 19.223 | 1.00 | 38.36 B |
| ATOM | 2616 | O | ILE | B | 28 | 65.063 | 94.626 | 18.769 | 1.00 | 29.90 B |
| ATOM | 2617 | N | ARG | B | 29 | 64.134 | 95.724 | 20.503 | 1.00 | 30.42 B |
| ATOM | 2618 | CA | ARG | B | 29 | 64.470 | 94.673 | 21.458 | 1.00 | 32.43 B |
| ATOM | 2619 | CB | ARG | B | 29 | 65.468 | 95.242 | 22.461 | 1.00 | 38.54 B |
| ATOM | 2620 | CG | ARG | B | 29 | 66.234 | 94.231 | 23.273 | 1.00 | 56.74 B |
| ATOM | 2621 | CD | ARG | B | 29 | 67.479 | 94.939 | 23.821 | 1.00 | 68.43 B |
| ATOM | 2622 | NE | ARG | B | 29 | 68.210 | 95.573 | 22.722 | 1.00 | 77.31 B |
| ATOM | 2623 | CZ | ARG | B | 29 | 69.134 | 94.960 | 21.983 | 1.00 | 81.82 B |
| ATOM | 2624 | NH1 | ARG | B | 29 | 69.454 | 93.693 | 22.237 | 1.00 | 82.00 B |
| ATOM | 2625 | NH2 | ARG | B | 29 | 69.723 | 95.603 | 20.976 | 1.00 | 82.81 B |

TABLE 3-continued

| | | | | | | | | | |
|---|---|---|---|---|---|---|---|---|---|
| ATOM | 2626 | C | ARG | B | 29 | 63.222 | 94.132 | 22.168 | 1.00 | 26.06 B |
| ATOM | 2627 | O | ARG | B | 29 | 62.432 | 94.884 | 22.704 | 1.00 | 20.11 B |
| ATOM | 2628 | N | TYR | B | 30 | 63.032 | 92.823 | 22.133 | 1.00 | 22.95 B |
| ATOM | 2629 | CA | TYR | B | 30 | 61.886 | 92.206 | 22.787 | 1.00 | 31.30 B |
| ATOM | 2630 | CB | TYR | B | 30 | 61.299 | 91.096 | 21.905 | 1.00 | 28.61 B |
| ATOM | 2631 | CG | TYR | B | 30 | 60.647 | 91.547 | 20.605 | 1.00 | 29.37 B |
| ATOM | 2632 | CD1 | TYR | B | 30 | 61.389 | 92.135 | 19.579 | 1.00 | 24.77 B |
| ATOM | 2633 | CE1 | TYR | B | 30 | 60.781 | 92.553 | 18.387 | 1.00 | 19.11 B |
| ATOM | 2634 | CD2 | TYR | B | 30 | 59.282 | 91.378 | 20.403 | 1.00 | 29.03 B |
| ATOM | 2635 | CE2 | TYR | B | 30 | 58.674 | 91.785 | 19.215 | 1.00 | 26.35 B |
| ATOM | 2636 | CZ | TYR | B | 30 | 59.429 | 92.379 | 18.216 | 1.00 | 23.41 B |
| ATOM | 2637 | OH | TYR | B | 30 | 58.793 | 92.836 | 17.083 | 1.00 | 26.05 B |
| ATOM | 2638 | C | TYR | B | 30 | 62.340 | 91.579 | 24.126 | 1.00 | 28.93 B |
| ATOM | 2639 | O | TYR | B | 30 | 63.497 | 91.168 | 24.283 | 1.00 | 24.49 B |
| ATOM | 2640 | N | SER | B | 31 | 61.418 | 91.488 | 25.067 | 1.00 | 26.50 B |
| ATOM | 2641 | CA | SER | B | 31 | 61.697 | 90.903 | 26.369 | 1.00 | 24.95 B |
| ATOM | 2642 | CB | SER | B | 31 | 62.304 | 91.946 | 27.308 | 1.00 | 21.32 B |
| ATOM | 2643 | OG | SER | B | 31 | 61.426 | 93.028 | 27.483 | 1.00 | 26.55 B |
| ATOM | 2644 | C | SER | B | 31 | 60.388 | 90.378 | 26.954 | 1.00 | 29.25 B |
| ATOM | 2645 | O | SER | B | 31 | 59.287 | 90.780 | 26.529 | 1.00 | 22.45 B |
| ATOM | 2646 | N | CYS | B | 32 | 60.515 | 89.484 | 27.930 | 1.00 | 27.99 B |
| ATOM | 2647 | CA | CYS | B | 32 | 59.364 | 88.868 | 28.606 | 1.00 | 32.41 B |
| ATOM | 2648 | C | CYS | B | 32 | 59.371 | 89.122 | 30.121 | 1.00 | 38.37 B |
| ATOM | 2649 | O | CYS | B | 32 | 60.431 | 89.311 | 30.719 | 1.00 | 37.82 B |
| ATOM | 2650 | CB | CYS | B | 32 | 59.371 | 87.347 | 28.400 | 1.00 | 30.70 B |
| ATOM | 2651 | SG | CYS | B | 32 | 59.450 | 86.770 | 26.677 | 1.00 | 32.11 B |
| ATOM | 2652 | N | SER | B | 33 | 58.178 | 89.101 | 30.717 | 1.00 | 51.37 B |
| ATOM | 2653 | CA | SER | B | 33 | 57.995 | 89.265 | 32.163 | 1.00 | 56.15 B |
| ATOM | 2654 | CB | SER | B | 33 | 56.544 | 89.013 | 32.552 | 1.00 | 60.18 B |
| ATOM | 2655 | OG | SER | B | 33 | 55.675 | 89.714 | 31.672 | 1.00 | 66.23 B |
| ATOM | 2656 | C | SER | B | 33 | 58.859 | 88.260 | 32.894 | 1.00 | 57.27 B |
| ATOM | 2657 | O | SER | B | 33 | 59.535 | 87.427 | 32.274 | 1.00 | 60.30 B |
| ATOM | 2658 | N | GLY | B | 34 | 58.805 | 88.290 | 34.219 | 1.00 | 53.29 B |
| ATOM | 2659 | CA | GLY | B | 34 | 59.662 | 87.391 | 34.976 | 1.00 | 47.70 B |
| ATOM | 2660 | C | GLY | B | 34 | 59.278 | 85.922 | 34.987 | 1.00 | 44.48 B |
| ATOM | 2661 | O | GLY | B | 34 | 60.129 | 85.033 | 35.135 | 1.00 | 38.34 B |
| ATOM | 2662 | N | THR | B | 35 | 57.993 | 85.660 | 34.818 | 1.00 | 40.51 B |
| ATOM | 2663 | CA | THR | B | 35 | 57.524 | 84.290 | 34.860 | 1.00 | 40.76 B |
| ATOM | 2664 | CB | THR | B | 35 | 56.225 | 84.239 | 35.644 | 1.00 | 41.73 B |
| ATOM | 2665 | OG1 | THR | B | 35 | 55.258 | 85.077 | 35.014 | 1.00 | 48.51 B |
| ATOM | 2666 | CG2 | THR | B | 35 | 56.468 | 84.761 | 37.057 | 1.00 | 44.89 B |
| ATOM | 2667 | C | THR | B | 35 | 57.369 | 83.691 | 33.470 | 1.00 | 39.51 B |
| ATOM | 2668 | O | THR | B | 35 | 56.786 | 82.613 | 33.286 | 1.00 | 31.97 B |
| ATOM | 2669 | N | PHE | B | 36 | 57.924 | 84.399 | 32.491 | 1.00 | 35.56 B |
| ATOM | 2670 | CA | PHE | B | 36 | 57.873 | 83.955 | 31.112 | 1.00 | 31.01 B |
| ATOM | 2671 | CB | PHE | B | 36 | 57.146 | 84.967 | 30.250 | 1.00 | 33.05 B |
| ATOM | 2672 | CG | PHE | B | 36 | 55.673 | 84.918 | 30.396 | 1.00 | 35.23 B |
| ATOM | 2673 | CD1 | PHE | B | 36 | 55.040 | 85.573 | 31.444 | 1.00 | 35.53 B |
| ATOM | 2674 | CD2 | PHE | B | 36 | 54.909 | 84.204 | 29.483 | 1.00 | 31.53 B |
| ATOM | 2675 | CE1 | PHE | B | 36 | 53.663 | 85.497 | 31.570 | 1.00 | 37.58 B |
| ATOM | 2676 | CE2 | PHE | B | 36 | 53.549 | 84.126 | 29.604 | 1.00 | 32.60 B |
| ATOM | 2677 | CZ | PHE | B | 36 | 52.918 | 84.769 | 30.638 | 1.00 | 32.38 B |
| ATOM | 2678 | C | PHE | B | 36 | 59.276 | 83.798 | 30.577 | 1.00 | 32.83 B |
| ATOM | 2679 | O | PHE | B | 36 | 60.212 | 84.347 | 31.125 | 1.00 | 33.40 B |
| ATOM | 2680 | N | ARG | B | 37 | 59.427 | 83.049 | 29.498 | 1.00 | 30.99 B |
| ATOM | 2681 | CA | ARG | B | 37 | 60.741 | 82.896 | 28.916 | 1.00 | 29.69 B |
| ATOM | 2682 | CB | ARG | B | 37 | 61.201 | 81.458 | 29.083 | 1.00 | 30.62 B |
| ATOM | 2683 | CG | ARG | B | 37 | 61.442 | 81.072 | 30.541 | 1.00 | 35.61 B |
| ATOM | 2684 | CD | ARG | B | 37 | 62.492 | 81.992 | 31.177 | 1.00 | 39.39 B |
| ATOM | 2685 | NE | ARG | B | 37 | 62.303 | 82.044 | 32.629 | 1.00 | 49.28 B |
| ATOM | 2686 | CZ | ARG | B | 37 | 62.847 | 81.168 | 33.451 | 1.00 | 47.41 B |
| ATOM | 2687 | NH1 | ARG | B | 37 | 63.614 | 80.212 | 32.947 | 1.00 | 53.00 B |
| ATOM | 2688 | NH2 | AEG | B | 37 | 62.602 | 81.223 | 34.751 | 1.00 | 44.10 B |
| ATOM | 2689 | C | ARG | B | 37 | 60.713 | 83.280 | 27.439 | 1.00 | 32.05 B |
| ATOM | 2690 | O | ARG | B | 37 | 59.809 | 82.874 | 26.700 | 1.00 | 25.63 B |
| ATOM | 2691 | N | LEU | B | 38 | 61.706 | 84.050 | 27.011 | 1.00 | 23.96 B |
| ATOM | 2692 | CA | LEU | B | 38 | 61.802 | 84.470 | 25.621 | 1.00 | 30.62 B |
| ATOM | 2693 | CB | LEU | B | 38 | 62.655 | 85.738 | 25.508 | 1.00 | 23.25 B |
| ATOM | 2694 | CG | LEU | B | 38 | 62.739 | 86.365 | 24.105 | 1.00 | 28.16 B |
| ATOM | 2695 | CD1 | LEU | B | 38 | 61.376 | 86.948 | 23.659 | 1.00 | 20.01 B |
| ATOM | 2696 | CD2 | LEU | B | 38 | 63.753 | 87.486 | 24.132 | 1.00 | 32.19 B |
| ATOM | 2697 | C | LEU | B | 38 | 62.386 | 83.361 | 24.745 | 1.00 | 27.63 B |
| ATOM | 2698 | O | LEU | B | 38 | 63.447 | 82.793 | 25.036 | 1.00 | 27.98 B |
| ATOM | 2699 | N | ILE | B | 39 | 61.651 | 83.017 | 23.691 | 1.00 | 30.18 B |
| ATOM | 2700 | CA | ILE | B | 39 | 62.073 | 81.983 | 22.743 | 1.00 | 27.37 B |
| ATOM | 2701 | CB | ILE | B | 39 | 60.940 | 80.959 | 22.492 | 1.00 | 30.75 B |
| ATOM | 2702 | CG2 | ILE | B | 39 | 61.438 | 79.878 | 21.538 | 1.00 | 29.27 B |
| ATOM | 2703 | CG1 | ILE | B | 39 | 60.455 | 80.359 | 23.822 | 1.00 | 30.90 B |
| ATOM | 2704 | CD1 | ILE | B | 39 | 61.491 | 79.535 | 24.559 | 1.00 | 26.44 B |

TABLE 3-continued

| ATOM | 2705 | C | ILE | B | 39 | 62.403 | 82.668 | 21.418 | 1.00 | 29.53 | B |
|---|---|---|---|---|---|---|---|---|---|---|---|
| ATOM | 2706 | O | ILE | B | 39 | 61.510 | 83.256 | 20.797 | 1.00 | 24.87 | B |
| ATOM | 2707 | N | GLY | B | 40 | 63.676 | 82.609 | 20.998 | 1.00 | 21.97 | B |
| ATOM | 2708 | CA | GLY | B | 40 | 64.084 | 83.239 | 19.751 | 1.00 | 23.62 | B |
| ATOM | 2709 | C | GLY | B | 40 | 64.957 | 84.450 | 19.975 | 1.00 | 22.85 | B |
| ATOM | 2710 | O | GLY | B | 40 | 65.065 | 84.921 | 21.104 | 1.00 | 21.42 | B |
| ATOM | 2711 | N | GLU | B | 41 | 65.592 | 84.958 | 18.925 | 1.00 | 27.33 | B |
| ATOM | 2712 | CA | GLU | B | 41 | 66.472 | 86.133 | 19.065 | 1.00 | 29.50 | B |
| ATOM | 2713 | CB | GLU | B | 41 | 67.138 | 86.471 | 17.730 | 1.00 | 33.78 | B |
| ATOM | 2714 | CG | GLU | B | 41 | 68.634 | 86.193 | 17.721 | 1.00 | 52.17 | B |
| ATOM | 2715 | CD | GLU | B | 41 | 69.411 | 87.123 | 18.648 | 1.00 | 57.74 | B |
| ATOM | 2716 | OE1 | GLU | B | 41 | 70.414 | 86.641 | 19.231 | 1.00 | 66.30 | B |
| ATOM | 2717 | OE2 | GLU | B | 41 | 69.034 | 88.326 | 18.791 | 1.00 | 53.76 | B |
| ATOM | 2718 | C | GLU | B | 41 | 65.667 | 87.333 | 19.541 | 1.00 | 30.40 | B |
| ATOM | 2719 | O | GLU | B | 41 | 64.601 | 87.619 | 18.995 | 1.00 | 27.22 | B |
| ATOM | 2720 | N | LYS | B | 42 | 66.197 | 88.049 | 20.528 | 1.00 | 27.86 | B |
| ATOM | 2721 | CA | LYS | B | 42 | 65.538 | 89.215 | 21.135 | 1.00 | 32.03 | B |
| ATOM | 2722 | CB | LYS | B | 42 | 66.171 | 89.495 | 22.504 | 1.00 | 37.19 | B |
| ATOM | 2723 | CG | LYS | B | 42 | 67.610 | 89.990 | 22.379 | 1.00 | 43.78 | B |
| ATOM | 2724 | CD | LYS | B | 42 | 68.196 | 90.536 | 23.674 | 1.00 | 54.68 | B |
| ATOM | 2725 | CE | LYS | B | 42 | 68.055 | 89.538 | 24.812 | 1.00 | 62.51 | B |
| ATOM | 2726 | NZ | LYS | B | 42 | 68.438 | 88.139 | 24.443 | 1.00 | 69.20 | B |
| ATOM | 2727 | C | LYS | B | 42 | 65.586 | 90.530 | 20.331 | 1.00 | 32.32 | B |
| ATOM | 2728 | O | LYS | B | 42 | 64.771 | 91.432 | 20.555 | 1.00 | 27.61 | B |
| ATOM | 2729 | N | SER | B | 43 | 66.547 | 90.680 | 19.422 | 1.00 | 28.99 | B |
| ATOM | 2730 | CA | SER | B | 43 | 66.611 | 91.946 | 18.672 | 1.00 | 33.61 | B |
| ATOM | 2731 | CB | SER | B | 43 | 68.012 | 92.565 | 18.722 | 1.00 | 29.97 | B |
| ATOM | 2732 | OG | SER | B | 43 | 68.478 | 92.606 | 20.047 | 1.00 | 47.21 | B |
| ATOM | 2733 | C | SER | B | 43 | 66.273 | 91.770 | 17.224 | 1.00 | 28.57 | B |
| ATOM | 2734 | O | SER | B | 43 | 66.765 | 90.841 | 16.588 | 1.00 | 32.11 | B |
| ATOM | 2735 | N | LEU | B | 44 | 65.443 | 92.661 | 16.697 | 1.00 | 26.09 | B |
| ATOM | 2736 | CA | LEU | B | 44 | 65.127 | 92.607 | 15.280 | 1.00 | 25.34 | B |
| ATOM | 2737 | CB | LEU | B | 44 | 63.620 | 92.609 | 14.987 | 1.00 | 21.75 | B |
| ATOM | 2738 | CG | LEU | B | 44 | 62.608 | 91.642 | 15.593 | 1.00 | 33.26 | B |
| ATOM | 2739 | CD1 | LEU | B | 44 | 61.455 | 91.487 | 14.626 | 1.00 | 24.66 | B |
| ATOM | 2740 | CD2 | LEU | B | 44 | 63.227 | 90.293 | 15.976 | 1.00 | 19.72 | B |
| ATOM | 2741 | C | LEU | B | 44 | 65.738 | 93.863 | 14.694 | 1.00 | 27.39 | B |
| ATOM | 2742 | O | LEU | B | 44 | 65.759 | 94.919 | 15.334 | 1.00 | 29.07 | B |
| ATOM | 2743 | N | LEU | B | 45 | 66.201 | 93.740 | 13.456 | 1.00 | 26.79 | B |
| ATOM | 2744 | CA | LEU | B | 45 | 66.854 | 94.812 | 12.727 | 1.00 | 26.17 | B |
| ATOM | 2745 | CB | LEU | B | 45 | 68.202 | 94.303 | 12.213 | 1.00 | 25.36 | B |
| ATOM | 2746 | CG | LEU | B | 45 | 69.343 | 95.281 | 11.950 | 1.00 | 35.90 | B |
| ATOM | 2747 | CD1 | LEU | B | 45 | 70.263 | 94.668 | 10.905 | 1.00 | 31.78 | B |
| ATOM | 2748 | CD2 | LEU | B | 45 | 68.853 | 96.627 | 11.519 | 1.00 | 39.62 | B |
| ATOM | 2749 | C | LEU | B | 45 | 66.016 | 95.198 | 11.516 | 1.00 | 25.11 | B |
| ATOM | 2750 | O | LEU | B | 45 | 65.568 | 94.320 | 10.761 | 1.00 | 20.94 | B |
| ATOM | 2751 | N | CYS | B | 46 | 65.803 | 96.487 | 11.298 | 1.00 | 24.85 | B |
| ATOM | 2752 | CA | CYS | B | 46 | 65.057 | 96.887 | 10.097 | 1.00 | 22.87 | B |
| ATOM | 2753 | C | CYS | B | 46 | 66.106 | 96.897 | 8.976 | 1.00 | 29.24 | B |
| ATOM | 2754 | O | CYS | B | 46 | 67.099 | 97.601 | 9.051 | 1.00 | 28.50 | B |
| ATOM | 2755 | CB | CYS | B | 46 | 64.446 | 98.284 | 10.251 | 1.00 | 26.50 | B |
| ATOM | 2756 | SG | CYS | B | 46 | 63.677 | 98.900 | 8.705 | 1.00 | 27.31 | B |
| ATOM | 2757 | N | ILE | B | 47 | 65.877 | 96.106 | 7.943 | 1.00 | 24.65 | B |
| ATOM | 2758 | CA | ILE | B | 47 | 66.817 | 95.991 | 6.842 | 1.00 | 28.64 | B |
| ATOM | 2759 | CB | ILE | B | 47 | 67.412 | 94.572 | 6.871 | 1.00 | 30.17 | B |
| ATOM | 2760 | CG2 | ILE | B | 47 | 68.114 | 94.258 | 5.601 | 1.00 | 42.28 | B |
| ATOM | 2761 | CG1 | ILE | B | 47 | 68.341 | 94.458 | 8.070 | 1.00 | 40.16 | B |
| ATOM | 2762 | CD1 | ILE | B | 47 | 69.121 | 93.190 | 8.107 | 1.00 | 53.27 | B |
| ATOM | 2763 | C | ILE | B | 47 | 66.098 | 96.188 | 5.504 | 1.00 | 28.32 | B |
| ATOM | 2764 | O | ILE | B | 47 | 64.874 | 96.332 | 5.466 | 1.00 | 24.72 | B |
| ATOM | 2765 | N | THR | B | 48 | 66.853 | 96.238 | 4.413 | 1.00 | 24.30 | B |
| ATOM | 2766 | CA | THR | B | 48 | 66.236 | 96.267 | 3.091 | 1.00 | 27.24 | B |
| ATOM | 2767 | CB | THR | B | 48 | 66.215 | 97.672 | 2.405 | 1.00 | 31.04 | B |
| ATOM | 2768 | OG1 | THR | B | 48 | 65.632 | 97.534 | 1.090 | 1.00 | 26.58 | B |
| ATOM | 2769 | CG2 | THR | B | 48 | 67.627 | 98.250 | 2.271 | 1.00 | 23.59 | B |
| ATOM | 2770 | C | THR | B | 48 | 67.048 | 95.280 | 2.254 | 1.00 | 26.55 | B |
| ATOM | 2771 | O | THR | B | 48 | 68.276 | 95.371 | 2.173 | 1.00 | 27.30 | B |
| ATOM | 2772 | N | LYS | B | 49 | 66.370 | 94.295 | 1.688 | 1.00 | 24.39 | B |
| ATOM | 2773 | CA | LYS | B | 49 | 67.031 | 93.309 | 0.837 | 1.00 | 25.65 | B |
| ATOM | 2774 | CB | LYS | B | 49 | 66.323 | 91.943 | 0.940 | 1.00 | 27.44 | B |
| ATOM | 2775 | CG | LYS | B | 49 | 66.358 | 91.351 | 2.368 | 1.00 | 36.21 | B |
| ATOM | 2776 | CD | LYS | B | 49 | 67.171 | 90.103 | 2.479 | 1.00 | 40.52 | B |
| ATOM | 2777 | CE | LYS | B | 49 | 68.570 | 90.294 | 2.025 | 1.00 | 41.63 | B |
| ATOM | 2778 | NZ | LYS | B | 49 | 69.314 | 89.069 | 2.403 | 1.00 | 46.47 | B |
| ATOM | 2779 | C | LYS | B | 49 | 67.041 | 93.752 | −0.632 | 1.00 | 33.01 | B |
| ATOM | 2780 | O | LYS | B | 49 | 67.987 | 93.450 | −1.353 | 1.00 | 28.70 | B |
| ATOM | 2781 | N | ASP | B | 50 | 65.994 | 94.451 | −1.083 | 1.00 | 26.02 | B |
| ATOM | 2782 | CA | ASP | B | 50 | 65.933 | 94.859 | −2.495 | 1.00 | 29.77 | B |
| ATOM | 2783 | CB | ASP | B | 50 | 64.575 | 94.503 | −3.108 | 1.00 | 28.99 | B |

TABLE 3-continued

| ATOM | 2784 | CG  | ASP | B | 50 | 63.439 | 95.221  | −2.440 | 1.00 | 26.54 | B |
| ATOM | 2785 | OD1 | ASP | B | 50 | 63.720 | 96.043  | −1.562 | 1.00 | 25.74 | B |
| ATOM | 2786 | OD2 | ASP | B | 50 | 62.262 | 94.969  | −2.779 | 1.00 | 32.42 | B |
| ATOM | 2787 | C   | ASP | B | 50 | 66.200 | 96.327  | −2.744 | 1.00 | 30.62 | B |
| ATOM | 2788 | O   | ASP | B | 50 | 66.037 | 96.794  | −3.858 | 1.00 | 24.13 | B |
| ATOM | 2789 | N   | LYS | B | 51 | 66.610 | 97.050  | −1.709 | 1.00 | 27.94 | B |
| ATOM | 2790 | CA  | LYS | B | 51 | 66.889 | 98.473  | −1.824 | 1.00 | 31.18 | B |
| ATOM | 2791 | CB  | LYS | B | 51 | 68.014 | 98.742  | −2.819 | 1.00 | 34.46 | B |
| ATOM | 2792 | CG  | LYS | B | 51 | 69.381 | 98.355  | −2.297 | 1.00 | 41.85 | B |
| ATOM | 2793 | CD  | LYS | B | 51 | 70.447 | 98.960  | −3.175 | 1.00 | 49.97 | B |
| ATOM | 2794 | CE  | LYS | B | 51 | 71.826 | 98.869  | −2.564 | 1.00 | 59.90 | B |
| ATOM | 2795 | NZ  | LYS | B | 51 | 72.754 | 99.713  | −3.366 | 1.00 | 67.70 | B |
| ATOM | 2796 | C   | LYS | B | 51 | 65.666 | 99.305  | −2.186 | 1.00 | 30.87 | B |
| ATOM | 2797 | O   | LYS | B | 51 | 65.786 | 100.430 | −2.634 | 1.00 | 28.68 | B |
| ATOM | 2798 | N   | VAL | B | 52 | 64.483 | 98.748  | −1.992 | 1.00 | 26.95 | B |
| ATOM | 2799 | CA  | VAL | B | 52 | 63.263 | 99.501  | −2.231 | 1.00 | 26.37 | B |
| ATOM | 2800 | CB  | VAL | B | 52 | 62.456 | 98.945  | −3.402 | 1.00 | 27.69 | B |
| ATOM | 2801 | CG1 | VAL | B | 52 | 61.123 | 99.695  | −3.511 | 1.00 | 32.70 | B |
| ATOM | 2802 | CG2 | VAL | B | 52 | 63.236 | 99.113  | −4.679 | 1.00 | 32.13 | B |
| ATOM | 2803 | C   | VAL | B | 52 | 62.375 | 99.437  | −1.000 | 1.00 | 30.79 | B |
| ATOM | 2804 | O   | VAL | B | 52 | 61.949 | 100.461 | −0.491 | 1.00 | 26.76 | B |
| ATOM | 2805 | N   | ASP | B | 53 | 62.102 | 98.232  | −0.512 | 1.00 | 26.86 | B |
| ATOM | 2806 | CA  | ASP | B | 53 | 61.210 | 98.074  | 0.642  | 1.00 | 26.94 | B |
| ATOM | 2807 | CB  | ASP | B | 53 | 60.156 | 96.999  | 0.318  | 1.00 | 42.02 | B |
| ATOM | 2808 | CG  | ASP | B | 53 | 59.285 | 97.356  | −0.871 | 1.00 | 53.53 | B |
| ATOM | 2809 | OD1 | ASP | B | 53 | 58.878 | 98.540  | −0.943 | 1.00 | 63.13 | B |
| ATOM | 2810 | OD2 | ASP | B | 53 | 58.964 | 96.476  | −1.727 | 1.00 | 64.13 | B |
| ATOM | 2811 | C   | ASP | B | 53 | 62.006 | 97.651  | 1.888  | 1.00 | 25.00 | B |
| ATOM | 2812 | O   | ASP | B | 53 | 63.063 | 97.038  | 1.773  | 1.00 | 22.23 | B |
| ATOM | 2813 | N   | GLY | B | 54 | 61.490 | 97.959  | 3.072  | 1.00 | 20.64 | B |
| ATOM | 2814 | CA  | GLY | B | 54 | 62.170 | 97.578  | 4.293  | 1.00 | 24.10 | B |
| ATOM | 2815 | C   | GLY | B | 54 | 61.441 | 96.397  | 4.919  | 1.00 | 25.17 | B |
| ATOM | 2816 | O   | GLY | B | 54 | 60.237 | 96.266  | 4.728  | 1.00 | 25.23 | B |
| ATOM | 2817 | N   | THR | B | 55 | 62.169 | 95.517  | 5.605  | 1.00 | 23.87 | B |
| ATOM | 2818 | CA  | THR | B | 55 | 61.589 | 94.373  | 6.318  | 1.00 | 20.36 | B |
| ATOM | 2819 | CB  | THR | B | 55 | 61.679 | 93.051  | 5.518  | 1.00 | 27.74 | B |
| ATOM | 2820 | OG1 | THR | B | 55 | 61.052 | 92.004  | 6.267  | 1.00 | 24.11 | B |
| ATOM | 2821 | CG2 | THR | B | 55 | 63.151 | 92.669  | 5.212  | 1.00 | 21.92 | B |
| ATOM | 2822 | C   | THR | B | 55 | 62.371 | 94.156  | 7.600  | 1.00 | 22.54 | B |
| ATOM | 2823 | O   | THR | B | 55 | 63.535 | 94.526  | 7.675  | 1.00 | 24.57 | B |
| ATOM | 2824 | N   | TRP | B | 56 | 61.743 | 93.589  | 8.624  | 1.00 | 23.11 | B |
| ATOM | 2825 | CA  | TRP | B | 56 | 62.513 | 93.285  | 9.827  | 1.00 | 25.54 | B |
| ATOM | 2826 | CB  | TRP | B | 56 | 61.580 | 92.954  | 10.988 | 1.00 | 23.18 | B |
| ATOM | 2827 | CG  | TRP | B | 56 | 60.874 | 94.202  | 11.420 | 1.00 | 19.51 | B |
| ATOM | 2828 | CD2 | TRP | B | 56 | 61.456 | 95.282  | 12.147 | 1.00 | 21.91 | B |
| ATOM | 2829 | CE2 | TRP | B | 56 | 60.473 | 96.302  | 12.247 | 1.00 | 26.89 | B |
| ATOM | 2830 | CE3 | TRP | B | 56 | 62.722 | 95.491  | 12.729 | 1.00 | 25.30 | B |
| ATOM | 2831 | CD1 | TRP | B | 56 | 59.595 | 94.578  | 11.119 | 1.00 | 21.93 | B |
| ATOM | 2832 | NE1 | TRP | B | 56 | 59.343 | 95.849  | 11.617 | 1.00 | 21.49 | B |
| ATOM | 2833 | CZ2 | TRP | B | 56 | 60.713 | 97.521  | 12.895 | 1.00 | 26.71 | B |
| ATOM | 2834 | CZ3 | TRP | B | 56 | 62.963 | 96.706  | 13.380 | 1.00 | 29.35 | B |
| ATOM | 2835 | CH2 | TRP | B | 56 | 61.957 | 97.706  | 13.451 | 1.00 | 28.96 | B |
| ATOM | 2836 | C   | TRP | B | 56 | 63.335 | 92.075  | 9.384  | 1.00 | 28.11 | B |
| ATOM | 2837 | O   | TRP | B | 56 | 62.882 | 91.296  | 8.535  | 1.00 | 23.54 | B |
| ATOM | 2838 | N   | ASP | B | 57 | 64.535 | 91.909  | 9.926  | 1.00 | 20.44 | B |
| ATOM | 2839 | CA  | ASP | B | 57 | 65.401 | 90.812  | 9.470  | 1.00 | 25.81 | B |
| ATOM | 2840 | CB  | ASP | B | 57 | 66.885 | 91.113  | 9.761  | 1.00 | 30.15 | B |
| ATOM | 2841 | CG  | ASP | B | 57 | 67.234 | 91.045  | 11.255 | 1.00 | 35.84 | B |
| ATOM | 2842 | OD1 | ASP | B | 57 | 66.319 | 91.161  | 12.102 | 1.00 | 23.31 | B |
| ATOM | 2843 | OD2 | ASP | B | 57 | 68.443 | 90.889  | 11.581 | 1.00 | 41.06 | B |
| ATOM | 2844 | C   | ASP | B | 57 | 65.058 | 89.433  | 9.963  | 1.00 | 26.11 | B |
| ATOM | 2845 | O   | ASP | B | 57 | 65.634 | 88.455  | 9.486  | 1.00 | 28.90 | B |
| ATOM | 2846 | N   | LYS | B | 58 | 64.114 | 89.336  | 10.896 | 1.00 | 29.91 | B |
| ATOM | 2847 | CA  | LYS | B | 58 | 63.687 | 88.032  | 11.411 | 1.00 | 27.97 | B |
| ATOM | 2848 | CB  | LYS | B | 58 | 64.697 | 87.491  | 12.443 | 1.00 | 30.61 | B |
| ATOM | 2849 | CG  | LYS | B | 58 | 64.884 | 88.378  | 13.650 | 1.00 | 38.23 | B |
| ATOM | 2850 | CD  | LYS | B | 58 | 65.966 | 87.831  | 14.618 | 1.00 | 41.02 | B |
| ATOM | 2851 | CE  | LYS | B | 58 | 67.406 | 88.063  | 14.115 | 1.00 | 37.73 | B |
| ATOM | 2852 | NZ  | LYS | B | 58 | 67.830 | 89.511  | 14.119 | 1.00 | 29.19 | B |
| ATOM | 2853 | C   | LYS | B | 58 | 62.319 | 88.105  | 12.045 | 1.00 | 22.71 | B |
| ATOM | 2854 | O   | LYS | B | 58 | 61.795 | 89.188  | 12.311 | 1.00 | 26.33 | B |
| ATOM | 2855 | N   | PRO | B | 59 | 61.700 | 86.947  | 12.292 | 1.00 | 25.99 | B |
| ATOM | 2856 | CD  | PRO | B | 59 | 62.084 | 85.584  | 11.885 | 1.00 | 24.09 | B |
| ATOM | 2857 | CA  | PRO | B | 59 | 60.367 | 86.972  | 12.919 | 1.00 | 22.11 | B |
| ATOM | 2858 | CB  | PRO | B | 59 | 59.902 | 85.515  | 12.845 | 1.00 | 26.86 | B |
| ATOM | 2859 | CG  | PRO | B | 59 | 60.730 | 84.913  | 11.746 | 1.00 | 29.91 | B |
| ATOM | 2860 | C   | PRO | B | 59 | 60.509 | 87.419  | 14.369 | 1.00 | 30.21 | B |
| ATOM | 2861 | O   | PRO | B | 59 | 61.593 | 87.307  | 14.968 | 1.00 | 28.15 | B |
| ATOM | 2862 | N   | ALA | B | 60 | 59.433 | 87.924  | 14.951 | 1.00 | 25.43 | B |

TABLE 3-continued

| | | | | | | | | | | |
|---|---|---|---|---|---|---|---|---|---|---|
| ATOM | 2863 | CA | ALA | B | 60 | 59.516 | 88.330 | 16.339 | 1.00 | 26.37 B |
| ATOM | 2864 | CB | ALA | B | 60 | 58.260 | 89.089 | 16.742 | 1.00 | 26.63 B |
| ATOM | 2865 | C | ALA | B | 60 | 59.644 | 87.085 | 17.223 | 1.00 | 21.91 B |
| ATOM | 2866 | O | ALA | B | 60 | 59.104 | 86.068 | 16.914 | 1.00 | 22.47 B |
| ATOM | 2867 | N | PRO | B | 61 | 60.358 | 87.173 | 18.350 | 1.00 | 23.37 B |
| ATOM | 2868 | CD | PRO | B | 61 | 61.134 | 88.320 | 18.870 | 1.00 | 22.24 B |
| ATOM | 2869 | CA | PRO | B | 61 | 60.476 | 86.007 | 19.227 | 1.00 | 19.99 B |
| ATOM | 2870 | CB | PRO | B | 61 | 61.650 | 86.386 | 20.130 | 1.00 | 21.18 B |
| ATOM | 2871 | CG | PRO | B | 61 | 61.458 | 87.876 | 20.314 | 1.00 | 22.73 B |
| ATOM | 2872 | C | PRO | B | 61 | 59.151 | 85.933 | 20.024 | 1.00 | 27.42 B |
| ATOM | 2873 | O | PRO | B | 61 | 58.314 | 86.831 | 19.903 | 1.00 | 27.48 B |
| ATOM | 2874 | N | LYS | B | 62 | 58.960 | 84.893 | 20.834 | 1.00 | 21.73 B |
| ATOM | 2875 | CA | LYS | B | 62 | 57.737 | 84.770 | 21.648 | 1.00 | 26.90 B |
| ATOM | 2876 | CB | LYS | B | 62 | 56.880 | 83.576 | 21.187 | 1.00 | 32.90 B |
| ATOM | 2877 | CG | LYS | B | 62 | 56.318 | 83.743 | 19.779 | 1.00 | 39.12 B |
| ATOM | 2878 | CD | LYS | B | 62 | 55.638 | 82.502 | 19.258 | 1.00 | 48.29 B |
| ATOM | 2879 | CE | LYS | B | 62 | 55.142 | 82.741 | 17.828 | 1.00 | 54.55 B |
| ATOM | 2880 | NZ | LYS | B | 62 | 54.620 | 81.478 | 17.213 | 1.00 | 59.87 B |
| ATOM | 2881 | C | LYS | B | 62 | 58.050 | 84.601 | 23.133 | 1.00 | 30.68 B |
| ATOM | 2882 | O | LYS | B | 62 | 59.190 | 84.287 | 23.528 | 1.00 | 24.62 B |
| ATOM | 2883 | N | CYS | B | 63 | 57.039 | 84.843 | 23.958 | 1.00 | 25.15 B |
| ATOM | 2884 | CA | CYS | B | 63 | 57.171 | 84.675 | 25.405 | 1.00 | 27.27 B |
| ATOM | 2885 | C | CYS | B | 63 | 56.314 | 83.481 | 25.792 | 1.00 | 30.43 B |
| ATOM | 2886 | O | CYS | B | 63 | 55.111 | 83.454 | 25.515 | 1.00 | 30.82 B |
| ATOM | 2887 | CB | CYS | B | 63 | 56.646 | 85.903 | 26.149 | 1.00 | 25.60 B |
| ATOM | 2888 | SG | CYS | B | 63 | 57.682 | 87.384 | 25.922 | 1.00 | 31.81 B |
| ATOM | 2889 | N | GLU | B | 64 | 56.934 | 82.486 | 26.414 | 1.00 | 29.14 B |
| ATOM | 2890 | CA | GLU | B | 64 | 56.220 | 81.297 | 26.871 | 1.00 | 27.87 B |
| ATOM | 2891 | CB | GLU | B | 64 | 56.938 | 80.043 | 26.393 | 1.00 | 22.54 B |
| ATOM | 2892 | CG | GLU | B | 64 | 56.839 | 79.836 | 24.884 | 1.00 | 30.23 B |
| ATOM | 2893 | CD | GLU | B | 64 | 57.354 | 78.472 | 24.471 | 1.00 | 25.42 B |
| ATOM | 2894 | OE1 | GLU | B | 64 | 58.146 | 77.879 | 25.221 | 1.00 | 28.63 B |
| ATOM | 2895 | OE2 | GLU | B | 64 | 56.993 | 77.994 | 23.396 | 1.00 | 24.45 B |
| ATOM | 2896 | C | GLU | B | 64 | 56.172 | 81.301 | 28.394 | 1.00 | 27.43 B |
| ATOM | 2897 | O | GLU | B | 64 | 57.189 | 81.564 | 29.036 | 1.00 | 28.45 B |
| ATOM | 2898 | N | TYR | B | 65 | 55.003 | 81.039 | 28.981 | 1.00 | 30.82 B |
| ATOM | 2899 | CA | TYR | B | 65 | 54.898 | 81.016 | 30.449 | 1.00 | 26.71 B |
| ATOM | 2900 | CB | TYR | B | 65 | 53.474 | 80.638 | 30.881 | 1.00 | 24.67 B |
| ATOM | 2901 | CG | TYR | B | 65 | 53.222 | 80.754 | 32.382 | 1.00 | 30.61 B |
| ATOM | 2902 | CD1 | TYR | B | 65 | 53.558 | 81.915 | 33.078 | 1.00 | 37.93 B |
| ATOM | 2903 | CE1 | TYR | B | 65 | 53.369 | 82.013 | 34.464 | 1.00 | 37.10 B |
| ATOM | 2904 | CD2 | TYR | B | 65 | 52.681 | 79.689 | 33.102 | 1.00 | 29.91 B |
| ATOM | 2905 | CE2 | TYR | B | 65 | 52.481 | 79.765 | 34.477 | 1.00 | 32.04 B |
| ATOM | 2906 | CZ | TYR | B | 65 | 52.829 | 80.927 | 35.149 | 1.00 | 38.91 B |
| ATOM | 2907 | OH | TYR | B | 65 | 52.653 | 81.014 | 36.510 | 1.00 | 40.82 B |
| ATOM | 2908 | C | TYR | B | 65 | 55.931 | 79.969 | 30.908 | 1.00 | 26.37 B |
| ATOM | 2909 | O | TYR | B | 65 | 56.022 | 78.891 | 30.339 | 1.00 | 27.39 B |
| ATOM | 2910 | N | PHE | B | 66 | 56.722 | 80.290 | 31.924 | 1.00 | 30.93 B |
| ATOM | 2911 | CA | PHE | B | 66 | 57.770 | 79.381 | 32.362 | 1.00 | 29.14 B |
| ATOM | 2912 | CB | PHE | B | 66 | 58.611 | 80.060 | 33.455 | 1.00 | 27.56 B |
| ATOM | 2913 | CG | PHE | B | 66 | 59.743 | 79.210 | 33.998 | 1.00 | 28.67 B |
| ATOM | 2914 | CD1 | PHE | B | 66 | 60.632 | 78.559 | 33.139 | 1.00 | 33.68 B |
| ATOM | 2915 | CD2 | PHE | B | 66 | 59.907 | 79.055 | 35.371 | 1.00 | 30.48 B |
| ATOM | 2916 | CE1 | PHE | B | 66 | 61.669 | 77.763 | 33.648 | 1.00 | 35.23 B |
| ATOM | 2917 | CE2 | PHE | B | 66 | 60.931 | 78.267 | 35.895 | 1.00 | 26.93 B |
| ATOM | 2918 | CZ | PHE | B | 66 | 61.816 | 77.618 | 35.041 | 1.00 | 31.25 B |
| ATOM | 2919 | C | PHE | B | 66 | 57.283 | 78.013 | 32.844 | 1.00 | 32.09 B |
| ATOM | 2920 | O | PHE | B | 66 | 56.382 | 77.924 | 33.671 | 1.00 | 31.84 B |
| ATOM | 2921 | N | ASN | B | 67 | 57.882 | 76.956 | 32.312 | 1.00 | 28.91 B |
| ATOM | 2922 | CA | ASN | B | 67 | 57.553 | 75.591 | 32.727 | 1.00 | 31.14 B |
| ATOM | 2923 | CB | ASN | B | 67 | 57.124 | 74.763 | 31.524 | 1.00 | 32.40 B |
| ATOM | 2924 | CG | ASN | B | 67 | 56.635 | 73.368 | 31.903 | 1.00 | 37.56 B |
| ATOM | 2925 | OD1 | ASN | B | 67 | 57.193 | 72.701 | 32.784 | 1.00 | 33.77 B |
| ATOM | 2926 | ND2 | ASN | B | 67 | 55.589 | 72.914 | 31.218 | 1.00 | 40.31 B |
| ATOM | 2927 | C | ASN | B | 67 | 58.844 | 75.009 | 33.318 | 1.00 | 30.31 B |
| ATOM | 2928 | O | ASN | B | 67 | 59.719 | 74.551 | 32.577 | 1.00 | 26.39 B |
| ATOM | 2929 | N | LYS | B | 68 | 58.960 | 75.038 | 34.644 | 1.00 | 28.27 B |
| ATOM | 2930 | CA | LYS | B | 68 | 60.148 | 74.535 | 35.329 | 1.00 | 29.00 B |
| ATOM | 2931 | CB | LYS | B | 68 | 60.041 | 74.792 | 36.843 | 1.00 | 35.08 B |
| ATOM | 2932 | CG | LYS | B | 68 | 58.984 | 73.906 | 37.518 | 1.00 | 41.56 B |
| ATOM | 2933 | CD | LYS | B | 68 | 59.179 | 73.778 | 39.031 | 1.00 | 52.33 B |
| ATOM | 2934 | CE | LYS | B | 68 | 58.907 | 75.077 | 39.764 | 1.00 | 54.82 B |
| ATOM | 2935 | NZ | LYS | B | 68 | 58.896 | 74.891 | 41.250 | 1.00 | 58.88 B |
| ATOM | 2936 | C | LYS | B | 68 | 60.398 | 73.039 | 35.087 | 1.00 | 32.74 B |
| ATOM | 2937 | O | LYS | B | 68 | 61.507 | 72.556 | 35.318 | 1.00 | 32.92 B |
| ATOM | 2938 | N | TYR | B | 69 | 59.389 | 72.305 | 34.611 | 1.00 | 33.19 B |
| ATOM | 2939 | CA | TYR | B | 69 | 59.559 | 70.867 | 34.354 | 1.00 | 25.62 B |
| ATOM | 2940 | CB | TYR | B | 69 | 58.259 | 70.096 | 34.687 | 1.00 | 30.97 B |
| ATOM | 2941 | CG | TYR | B | 69 | 57.801 | 70.349 | 36.107 | 1.00 | 30.82 B |

TABLE 3-continued

| | | | | | | | | | | |
|---|---|---|---|---|---|---|---|---|---|---|
| ATOM | 2942 | CD1 | TYR | B | 69 | 56.774 | 71.266 | 36.378 | 1.00 | 28.48 B |
| ATOM | 2943 | CE1 | TYR | B | 69 | 56.444 | 71.623 | 37.697 | 1.00 | 31.73 B |
| ATOM | 2944 | CD2 | TYR | B | 69 | 58.486 | 69.776 | 37.192 | 1.00 | 31.64 B |
| ATOM | 2945 | CE2 | TYR | B | 69 | 58.174 | 70.118 | 38.507 | 1.00 | 38.99 B |
| ATOM | 2946 | CZ | TYR | B | 69 | 57.153 | 71.053 | 38.756 | 1.00 | 39.94 B |
| ATOM | 2947 | OH | TYR | B | 69 | 56.901 | 71.467 | 40.048 | 1.00 | 41.68 B |
| ATOM | 2948 | C | TYR | B | 69 | 60.029 | 70.516 | 32.955 | 1.00 | 31.61 B |
| ATOM | 2949 | O | TYR | B | 69 | 60.549 | 69.414 | 32.722 | 1.00 | 31.53 B |
| ATOM | 2950 | N | SER | B | 70 | 59.889 | 71.447 | 32.017 | 1.00 | 29.13 B |
| ATOM | 2951 | CA | SER | B | 70 | 60.328 | 71.162 | 30.649 | 1.00 | 31.79 B |
| ATOM | 2952 | CB | SER | B | 70 | 59.926 | 72.310 | 29.708 | 1.00 | 27.84 B |
| ATOM | 2953 | OG | SER | B | 70 | 58.524 | 72.534 | 29.725 | 1.00 | 38.42 B |
| ATOM | 2954 | C | SER | B | 70 | 61.849 | 70.949 | 30.544 | 1.00 | 34.24 B |
| ATOM | 2955 | O | SER | B | 70 | 62.624 | 71.534 | 31.296 | 1.00 | 31.38 B |
| ATOM | 2956 | N | SER | B | 71 | 62.261 | 70.097 | 29.613 | 1.00 | 33.64 B |
| ATOM | 2957 | CA | SER | B | 71 | 63.676 | 69.832 | 29.351 | 1.00 | 36.09 B |
| ATOM | 2958 | CB | SER | B | 71 | 64.265 | 68.809 | 30.324 | 1.00 | 39.34 B |
| ATOM | 2959 | OG | SER | B | 71 | 63.823 | 67.519 | 30.007 | 1.00 | 41.01 B |
| ATOM | 2960 | C | SER | B | 71 | 63.790 | 69.308 | 27.907 | 1.00 | 41.17 B |
| ATOM | 2961 | O | SER | B | 71 | 62.959 | 68.520 | 27.432 | 1.00 | 41.90 B |
| ATOM | 2962 | N | CYS | B | 72 | 64.805 | 69.766 | 27.195 | 1.00 | 32.35 B |
| ATOM | 2963 | CA | CYS | B | 72 | 64.970 | 69.351 | 25.816 | 1.00 | 36.35 B |
| ATOM | 2964 | C | CYS | B | 72 | 66.139 | 68.393 | 25.722 | 1.00 | 36.24 B |
| ATOM | 2965 | O | CYS | B | 72 | 67.089 | 68.472 | 26.503 | 1.00 | 34.41 B |
| ATOM | 2966 | CB | CYS | B | 72 | 65.205 | 70.586 | 24.920 | 1.00 | 26.09 B |
| ATOM | 2967 | SG | CYS | B | 72 | 63.836 | 71.795 | 24.962 | 1.00 | 32.64 B |
| ATOM | 2968 | N | PRO | B | 73 | 66.069 | 67.453 | 24.779 | 1.00 | 35.65 B |
| ATOM | 2969 | CD | PRO | B | 73 | 64.958 | 67.148 | 23.867 | 1.00 | 38.10 B |
| ATOM | 2970 | CA | PRO | B | 73 | 67.157 | 66.494 | 24.617 | 1.00 | 35.61 B |
| ATOM | 2971 | CB | PRO | B | 73 | 66.567 | 65.461 | 23.661 | 1.00 | 35.75 B |
| ATOM | 2972 | CG | PRO | B | 73 | 65.662 | 66.314 | 22.806 | 1.00 | 40.23 B |
| ATOM | 2973 | C | PRO | B | 73 | 68.355 | 67.203 | 24.011 | 1.00 | 37.18 B |
| ATOM | 2974 | O | PRO | B | 73 | 68.225 | 68.277 | 23.427 | 1.00 | 31.86 B |
| ATOM | 2975 | N | GLU | B | 74 | 69.521 | 66.595 | 24.151 | 1.00 | 30.08 B |
| ATOM | 2976 | CA | GLU | B | 74 | 70.726 | 67.168 | 23.594 | 1.00 | 36.66 B |
| ATOM | 2977 | CB | GLU | B | 74 | 71.904 | 66.221 | 23.830 | 1.00 | 40.69 B |
| ATOM | 2978 | CG | GLU | B | 74 | 73.123 | 66.500 | 22.972 | 1.00 | 55.61 B |
| ATOM | 2979 | CD | GLU | B | 74 | 74.357 | 66.847 | 23.791 | 1.00 | 65.33 B |
| ATOM | 2980 | OE1 | GLU | B | 74 | 75.476 | 66.535 | 23.311 | 1.00 | 68.86 B |
| ATOM | 2981 | OE2 | GLU | B | 74 | 74.214 | 67.432 | 24.899 | 1.00 | 67.56 B |
| ATOM | 2982 | C | GLU | B | 74 | 70.526 | 67.411 | 22.099 | 1.00 | 31.83 B |
| ATOM | 2983 | O | GLU | B | 74 | 70.179 | 66.517 | 21.347 | 1.00 | 34.92 B |
| ATOM | 2984 | N | PRO | B | 75 | 70.743 | 68.639 | 21.648 | 1.00 | 29.85 B |
| ATOM | 2985 | CD | PRO | B | 75 | 71.019 | 69.851 | 22.431 | 1.00 | 29.21 B |
| ATOM | 2986 | CA | PRO | B | 75 | 70.573 | 68.944 | 20.227 | 1.00 | 31.16 B |
| ATOM | 2987 | CB | PRO | B | 75 | 70.349 | 70.441 | 20.235 | 1.00 | 30.77 B |
| ATOM | 2988 | CG | PRO | B | 75 | 71.310 | 70.872 | 21.362 | 1.00 | 28.27 B |
| ATOM | 2989 | C | PRO | B | 75 | 71.855 | 68.552 | 19.507 | 1.00 | 37.41 B |
| ATOM | 2990 | O | PRO | B | 75 | 72.949 | 68.998 | 19.877 | 1.00 | 35.98 B |
| ATOM | 2991 | N | ILE | B | 76 | 71.728 | 67.726 | 18.474 | 1.00 | 37.41 B |
| ATOM | 2992 | CA | ILE | B | 76 | 72.904 | 67.277 | 17.757 | 1.00 | 41.40 B |
| ATOM | 2993 | CB | ILE | B | 76 | 73.069 | 65.755 | 17.912 | 1.00 | 47.80 B |
| ATOM | 2994 | CG2 | ILE | B | 76 | 74.385 | 65.302 | 17.272 | 1.00 | 48.99 B |
| ATOM | 2995 | CG1 | ILE | B | 76 | 73.078 | 65.396 | 19.404 | 1.00 | 48.44 B |
| ATOM | 2996 | CD1 | ILE | B | 76 | 72.926 | 63.918 | 19.671 | 1.00 | 55.08 B |
| ATOM | 2997 | C | ILE | B | 76 | 72.874 | 67.654 | 16.294 | 1.00 | 38.62 B |
| ATOM | 2998 | O | ILE | B | 76 | 71.874 | 67.480 | 15.625 | 1.00 | 39.69 B |
| ATOM | 2999 | N | VAL | B | 77 | 73.984 | 68.195 | 15.813 | 1.00 | 36.89 B |
| ATOM | 3000 | CA | VAL | B | 77 | 74.107 | 68.610 | 14.433 | 1.00 | 38.30 B |
| ATOM | 3001 | CB | VAL | B | 77 | 74.290 | 70.119 | 14.331 | 1.00 | 39.19 B |
| ATOM | 3002 | CG1 | VAL | B | 77 | 74.483 | 70.519 | 12.871 | 1.00 | 39.16 B |
| ATOM | 3003 | CG2 | VAL | B | 77 | 73.081 | 70.826 | 14.946 | 1.00 | 40.99 B |
| ATOM | 3004 | C | VAL | B | 77 | 75.307 | 67.939 | 13.761 | 1.00 | 40.36 B |
| ATOM | 3005 | O | VAL | B | 77 | 76.457 | 68.351 | 13.948 | 1.00 | 41.17 B |
| ATOM | 3006 | N | PRO | B | 78 | 75.057 | 66.893 | 12.966 | 1.00 | 40.75 B |
| ATOM | 3007 | CD | PRO | B | 78 | 73.785 | 66.267 | 12.590 | 1.00 | 37.39 B |
| ATOM | 3008 | CA | PRO | B | 78 | 76.183 | 66.228 | 12.303 | 1.00 | 40.96 B |
| ATOM | 3009 | CB | PRO | B | 78 | 75.506 | 65.195 | 11.412 | 1.00 | 41.91 B |
| ATOM | 3010 | CG | PRO | B | 78 | 74.119 | 65.745 | 11.229 | 1.00 | 45.49 B |
| ATOM | 3011 | C | PRO | B | 78 | 76.997 | 67.232 | 11.525 | 1.00 | 37.80 B |
| ATOM | 3012 | O | PRO | B | 78 | 76.447 | 68.140 | 10.913 | 1.00 | 37.38 B |
| ATOM | 3013 | N | GLY | B | 79 | 78.312 | 67.083 | 11.590 | 1.00 | 32.94 B |
| ATOM | 3014 | CA | GLY | B | 79 | 79.186 | 68.002 | 10.900 | 1.00 | 36.40 B |
| ATOM | 3015 | C | GLY | B | 79 | 79.427 | 69.261 | 11.712 | 1.00 | 34.31 B |
| ATOM | 3016 | O | GLY | B | 79 | 80.209 | 70.109 | 11.304 | 1.00 | 42.13 B |
| ATOM | 3017 | N | GLY | B | 80 | 78.760 | 69.404 | 12.855 | 1.00 | 36.96 B |
| ATOM | 3018 | CA | GLY | B | 80 | 78.960 | 70.608 | 13.664 | 1.00 | 39.25 B |
| ATOM | 3019 | C | GLY | B | 80 | 79.072 | 70.348 | 15.164 | 1.00 | 35.08 B |
| ATOM | 3020 | O | GLY | B | 80 | 78.994 | 69.202 | 15.609 | 1.00 | 40.28 B |

TABLE 3-continued

| ATOM | 3021 | N | TYR | B | 81 | 79.225 | 71.410 | 15.953 | 1.00 | 37.65 | B |
|---|---|---|---|---|---|---|---|---|---|---|---|
| ATOM | 3022 | CA | TYR | B | 81 | 79.345 | 71.271 | 17.408 | 1.00 | 33.04 | B |
| ATOM | 3023 | CB | TYR | B | 81 | 80.800 | 71.019 | 17.799 | 1.00 | 29.39 | B |
| ATOM | 3024 | CG | TYR | B | 81 | 81.745 | 72.112 | 17.331 | 1.00 | 31.26 | B |
| ATOM | 3025 | CD1 | TYR | B | 81 | 82.169 | 73.116 | 18.199 | 1.00 | 28.35 | B |
| ATOM | 3026 | CE1 | TYR | B | 81 | 82.992 | 74.143 | 17.766 | 1.00 | 28.17 | B |
| ATOM | 3027 | CD2 | TYR | B | 81 | 82.181 | 72.163 | 16.004 | 1.00 | 28.62 | B |
| ATOM | 3028 | CE2 | TYR | B | 81 | 83.006 | 73.188 | 15.559 | 1.00 | 31.47 | B |
| ATOM | 3029 | CZ | TYR | B | 81 | 83.401 | 74.174 | 16.449 | 1.00 | 30.40 | B |
| ATOM | 3030 | OH | TYR | B | 81 | 84.172 | 75.207 | 16.012 | 1.00 | 32.87 | B |
| ATOM | 3031 | C | TYR | B | 81 | 78.847 | 72.536 | 18.095 | 1.00 | 33.96 | B |
| ATOM | 3032 | O | TYR | B | 81 | 78.696 | 73.581 | 17.454 | 1.00 | 30.79 | B |
| ATOM | 3033 | N | LYS | B | 82 | 78.600 | 72.431 | 19.398 | 1.00 | 23.56 | B |
| ATOM | 3034 | CA | LYS | B | 82 | 78.114 | 73.557 | 20.195 | 1.00 | 29.94 | B |
| ATOM | 3035 | CB | LYS | B | 82 | 77.348 | 73.034 | 21.428 | 1.00 | 25.29 | B |
| ATOM | 3036 | CG | LYS | B | 82 | 76.140 | 72.144 | 21.057 | 1.00 | 27.67 | B |
| ATOM | 3037 | CD | LYS | B | 82 | 75.335 | 71.652 | 22.266 | 1.00 | 33.47 | B |
| ATOM | 3038 | CE | LYS | B | 82 | 76.215 | 71.041 | 23.365 | 1.00 | 44.83 | B |
| ATOM | 3039 | NZ | LYS | B | 82 | 77.091 | 69.944 | 22.837 | 1.00 | 45.24 | B |
| ATOM | 3040 | C | LYS | B | 82 | 79.205 | 74.526 | 20.629 | 1.00 | 29.85 | B |
| ATOM | 3041 | O | LYS | B | 82 | 80.270 | 74.110 | 21.099 | 1.00 | 31.44 | B |
| ATOM | 3042 | N | ILE | B | 83 | 78.980 | 75.822 | 20.428 | 1.00 | 25.93 | B |
| ATOM | 3043 | CA | ILE | B | 83 | 79.959 | 76.795 | 20.887 | 1.00 | 21.30 | B |
| ATOM | 3044 | CB | ILE | B | 83 | 80.449 | 77.771 | 19.800 | 1.00 | 29.03 | B |
| ATOM | 3045 | CG2 | ILE | B | 83 | 81.296 | 77.004 | 18.799 | 1.00 | 23.68 | B |
| ATOM | 3046 | CG1 | ILE | B | 83 | 79.278 | 78.514 | 19.155 | 1.00 | 24.89 | B |
| ATOM | 3047 | CD1 | ILE | B | 83 | 79.722 | 79.571 | 18.148 | 1.00 | 27.44 | B |
| ATOM | 3048 | C | ILE | B | 83 | 79.362 | 77.581 | 22.027 | 1.00 | 26.62 | B |
| ATOM | 3049 | O | ILE | B | 83 | 80.038 | 78.408 | 22.636 | 1.00 | 32.15 | B |
| ATOM | 3050 | N | ARG | B | 84 | 78.092 | 77.330 | 22.324 | 1.00 | 24.60 | B |
| ATOM | 3051 | CA | ARG | B | 84 | 77.471 | 77.981 | 23.469 | 1.00 | 25.74 | B |
| ATOM | 3052 | CB | ARG | B | 84 | 77.047 | 79.396 | 23.131 | 1.00 | 34.80 | B |
| ATOM | 3053 | CG | ARG | B | 84 | 76.583 | 80.160 | 24.348 | 1.00 | 45.89 | B |
| ATOM | 3054 | CD | ARG | B | 84 | 76.518 | 81.629 | 24.027 | 1.00 | 56.25 | B |
| ATOM | 3055 | NE | ARG | B | 84 | 77.801 | 82.302 | 24.217 | 1.00 | 62.31 | B |
| ATOM | 3056 | CZ | ARG | B | 84 | 78.276 | 82.707 | 25.397 | 1.00 | 64.61 | B |
| ATOM | 3057 | NH1 | ARG | B | 84 | 77.581 | 82.496 | 26.512 | 1.00 | 65.21 | B |
| ATOM | 3058 | NH2 | ARG | B | 84 | 79.421 | 83.386 | 25.454 | 1.00 | 61.85 | B |
| ATOM | 3059 | C | ARG | B | 84 | 76.278 | 77.199 | 23.984 | 1.00 | 27.61 | B |
| ATOM | 3060 | O | ARG | B | 84 | 75.487 | 76.687 | 23.189 | 1.00 | 24.27 | B |
| ATOM | 3061 | N | GLY | B | 85 | 76.166 | 77.105 | 25.314 | 1.00 | 25.11 | B |
| ATOM | 3062 | CA | GLY | B | 85 | 75.074 | 76.374 | 25.959 | 1.00 | 23.64 | B |
| ATOM | 3063 | C | GLY | B | 85 | 75.394 | 74.877 | 26.115 | 1.00 | 32.13 | B |
| ATOM | 3064 | O | GLY | B | 85 | 75.961 | 74.257 | 25.200 | 1.00 | 25.66 | B |
| ATOM | 3065 | N | SER | B | 86 | 75.094 | 74.293 | 27.281 | 1.00 | 24.97 | B |
| ATOM | 3066 | CA | SER | B | 86 | 75.347 | 72.859 | 27.473 | 1.00 | 34.32 | B |
| ATOM | 3067 | CB | SER | B | 86 | 76.755 | 72.588 | 28.034 | 1.00 | 31.54 | B |
| ATOM | 3068 | OG | SER | B | 86 | 76.964 | 73.322 | 29.223 | 1.00 | 42.05 | B |
| ATOM | 3069 | C | SER | B | 86 | 74.315 | 72.304 | 28.415 | 1.00 | 27.65 | B |
| ATOM | 3070 | O | SER | B | 86 | 73.536 | 73.064 | 28.979 | 1.00 | 24.75 | B |
| ATOM | 3071 | N | THR | B | 87 | 74.294 | 70.982 | 28.573 | 1.00 | 27.03 | B |
| ATOM | 3072 | CA | THR | B | 87 | 73.325 | 70.314 | 29.454 | 1.00 | 29.87 | B |
| ATOM | 3073 | CB | THR | B | 87 | 73.532 | 68.806 | 29.450 | 1.00 | 34.20 | B |
| ATOM | 3074 | OG1 | THR | B | 87 | 73.876 | 68.395 | 28.125 | 1.00 | 54.47 | B |
| ATOM | 3075 | CG2 | THR | B | 87 | 72.263 | 68.107 | 29.856 | 1.00 | 36.26 | B |
| ATOM | 3076 | C | THR | B | 87 | 73.420 | 70.767 | 30.903 | 1.00 | 30.09 | B |
| ATOM | 3077 | O | THR | B | 87 | 74.501 | 71.113 | 31.381 | 1.00 | 30.94 | B |
| ATOM | 3078 | N | PRO | B | 88 | 72.293 | 70.771 | 31.626 | 1.00 | 26.03 | B |
| ATOM | 3079 | CD | PRO | B | 88 | 72.370 | 71.088 | 33.060 | 1.00 | 30.64 | B |
| ATOM | 3080 | CA | PRO | B | 88 | 70.921 | 70.406 | 31.240 | 1.00 | 33.13 | B |
| ATOM | 3081 | CB | PRO | B | 88 | 70.225 | 70.211 | 32.585 | 1.00 | 28.86 | B |
| ATOM | 3082 | CG | PRO | B | 88 | 70.903 | 71.248 | 33.440 | 1.00 | 31.91 | B |
| ATOM | 3083 | C | PRO | B | 88 | 70.228 | 71.482 | 30.388 | 1.00 | 31.83 | B |
| ATOM | 3084 | O | PRO | B | 88 | 70.495 | 72.668 | 30.535 | 1.00 | 29.33 | B |
| ATOM | 3085 | N | TYR | B | 89 | 69.340 | 71.059 | 29.503 | 1.00 | 27.84 | B |
| ATOM | 3086 | CA | TYR | B | 89 | 68.613 | 71.990 | 28.641 | 1.00 | 29.55 | B |
| ATOM | 3087 | CB | TYR | B | 89 | 68.553 | 71.414 | 27.239 | 1.00 | 27.73 | B |
| ATOM | 3088 | CG | TYR | B | 89 | 69.938 | 71.078 | 26.722 | 1.00 | 29.87 | B |
| ATOM | 3089 | CD1 | TYR | B | 89 | 70.326 | 69.759 | 26.501 | 1.00 | 33.12 | B |
| ATOM | 3090 | CE1 | TYR | B | 89 | 71.605 | 69.456 | 26.036 | 1.00 | 26.70 | B |
| ATOM | 3091 | CD2 | TYR | B | 89 | 70.865 | 72.086 | 26.467 | 1.00 | 32.19 | B |
| ATOM | 3092 | CE2 | TYR | B | 89 | 72.134 | 71.795 | 26.007 | 1.00 | 28.60 | B |
| ATOM | 3093 | CZ | TYR | B | 89 | 72.492 | 70.482 | 25.802 | 1.00 | 27.81 | B |
| ATOM | 3094 | OH | TYR | B | 89 | 73.770 | 70.211 | 25.415 | 1.00 | 32.86 | B |
| ATOM | 3095 | C | TYR | B | 89 | 67.212 | 72.242 | 29.176 | 1.00 | 25.88 | B |
| ATOM | 3096 | O | TYR | B | 89 | 66.333 | 71.400 | 29.025 | 1.00 | 25.96 | B |
| ATOM | 3097 | N | ARG | B | 90 | 67.015 | 73.405 | 29.790 | 1.00 | 25.05 | B |
| ATOM | 3098 | CA | ARG | B | 90 | 65.732 | 73.778 | 30.386 | 1.00 | 21.94 | B |
| ATOM | 3099 | CB | ARG | B | 90 | 65.950 | 74.306 | 31.802 | 1.00 | 25.43 | B |

TABLE 3-continued

| | | | | | | | | | | |
|---|---|---|---|---|---|---|---|---|---|---|
| ATOM | 3100 | CG | ARG | B | 90 | 66.836 | 73.368 | 32.650 | 1.00 | 35.30 B |
| ATOM | 3101 | CD | ARG | B | 90 | 66.308 | 71.933 | 32.684 | 1.00 | 30.92 B |
| ATOM | 3102 | NE | ARG | B | 90 | 65.162 | 71.857 | 33.578 | 1.00 | 38.77 B |
| ATOM | 3103 | CZ | ARG | B | 90 | 64.577 | 70.721 | 33.950 | 1.00 | 43.50 B |
| ATOM | 3104 | NH1 | ARG | B | 90 | 65.038 | 69.562 | 33.500 | 1.00 | 42.19 B |
| ATOM | 3105 | NH2 | ARG | B | 90 | 63.529 | 70.750 | 34.771 | 1.00 | 39.16 B |
| ATOM | 3106 | C | ARG | B | 90 | 65.001 | 74.823 | 29.580 | 1.00 | 26.84 B |
| ATOM | 3107 | O | ARG | B | 90 | 65.540 | 75.372 | 28.606 | 1.00 | 21.63 B |
| ATOM | 3108 | N | HIS | B | 91 | 63.767 | 75.095 | 29.999 | 1.00 | 24.57 B |
| ATOM | 3109 | CA | HIS | B | 91 | 62.903 | 76.057 | 29.318 | 1.00 | 28.69 B |
| ATOM | 3110 | CB | HIS | B | 91 | 61.570 | 76.143 | 30.062 | 1.00 | 26.54 B |
| ATOM | 3111 | CG | HIS | B | 91 | 60.516 | 76.909 | 29.326 | 1.00 | 34.66 B |
| ATOM | 3112 | CD2 | HIS | B | 91 | 59.414 | 77.563 | 29.770 | 1.00 | 26.97 B |
| ATOM | 3113 | ND1 | HIS | B | 91 | 60.513 | 77.035 | 27.952 | 1.00 | 29.34 B |
| ATOM | 3114 | CE1 | HIS | B | 91 | 59.457 | 77.735 | 27.582 | 1.00 | 27.63 B |
| ATOM | 3115 | NE2 | HIS | B | 91 | 58.775 | 78.066 | 28.666 | 1.00 | 34.45 B |
| ATOM | 3116 | C | HIS | B | 91 | 63.546 | 77.445 | 29.177 | 1.00 | 30.22 B |
| ATOM | 3117 | O | HIS | B | 91 | 63.937 | 78.069 | 30.161 | 1.00 | 23.98 B |
| ATOM | 3118 | N | GLY | B | 92 | 63.663 | 77.915 | 27.941 | 1.00 | 26.25 B |
| ATOM | 3119 | CA | GLY | B | 92 | 64.260 | 79.209 | 27.702 | 1.00 | 20.48 B |
| ATOM | 3120 | C | GLY | B | 92 | 65.752 | 79.118 | 27.458 | 1.00 | 24.40 B |
| ATOM | 3121 | O | GLY | B | 92 | 66.310 | 80.102 | 27.019 | 1.00 | 24.34 B |
| ATOM | 3122 | N | ASP | B | 93 | 66.407 | 77.974 | 27.724 | 1.00 | 20.35 B |
| ATOM | 3123 | CA | ASP | B | 93 | 67.857 | 77.884 | 27.472 | 1.00 | 19.73 B |
| ATOM | 3124 | CB | ASP | B | 93 | 68.487 | 76.575 | 27.992 | 1.00 | 23.61 B |
| ATOM | 3125 | CG | ASP | B | 93 | 68.579 | 76.504 | 29.504 | 1.00 | 20.60 B |
| ATOM | 3126 | OD1 | ASP | B | 93 | 68.336 | 77.522 | 30.167 | 1.00 | 23.89 B |
| ATOM | 3127 | OD2 | ASP | B | 93 | 68.884 | 75.401 | 30.020 | 1.00 | 25.06 B |
| ATOM | 3128 | C | ASP | B | 93 | 68.138 | 77.911 | 25.981 | 1.00 | 25.02 B |
| ATOM | 3129 | O | ASP | B | 93 | 67.362 | 77.415 | 25.170 | 1.00 | 24.06 B |
| ATOM | 3130 | N | SER | B | 94 | 69.298 | 78.422 | 25.625 | 1.00 | 21.77 B |
| ATOM | 3131 | CA | SER | B | 94 | 69.641 | 78.511 | 24.229 | 1.00 | 27.05 B |
| ATOM | 3132 | CB | SER | B | 94 | 69.779 | 79.972 | 23.834 | 1.00 | 28.57 B |
| ATOM | 3133 | OG | SER | B | 94 | 70.417 | 80.035 | 22.587 | 1.00 | 38.84 B |
| ATOM | 3134 | C | SER | B | 94 | 70.935 | 77.815 | 23.908 | 1.00 | 25.71 B |
| ATOM | 3135 | O | SER | B | 94 | 71.833 | 77.727 | 24.753 | 1.00 | 26.52 B |
| ATOM | 3136 | N | VAL | B | 95 | 71.051 | 77.331 | 22.678 | 1.00 | 27.36 B |
| ATOM | 3137 | CA | VAL | B | 95 | 72.291 | 76.689 | 22.245 | 1.00 | 26.56 B |
| ATOM | 3138 | CB | VAL | B | 95 | 72.096 | 75.178 | 22.088 | 1.00 | 26.82 B |
| ATOM | 3139 | CG1 | VAL | B | 95 | 73.282 | 74.581 | 21.344 | 1.00 | 34.06 B |
| ATOM | 3140 | CG2 | VAL | B | 95 | 71.908 | 74.549 | 23.460 | 1.00 | 30.69 B |
| ATOM | 3141 | C | VAL | B | 95 | 72.729 | 77.273 | 20.908 | 1.00 | 30.07 B |
| ATOM | 3142 | O | VAL | B | 95 | 71.903 | 77.496 | 20.019 | 1.00 | 26.03 B |
| ATOM | 3143 | N | THR | B | 96 | 74.026 | 77.526 | 20.758 | 1.00 | 27.23 B |
| ATOM | 3144 | CA | THR | B | 96 | 74.540 | 78.058 | 19.503 | 1.00 | 23.14 B |
| ATOM | 3145 | CB | THR | B | 96 | 75.242 | 79.419 | 19.687 | 1.00 | 32.77 B |
| ATOM | 3146 | OG1 | THR | B | 96 | 74.292 | 80.383 | 20.163 | 1.00 | 26.94 B |
| ATOM | 3147 | CG2 | THR | B | 96 | 75.845 | 79.896 | 18.329 | 1.00 | 26.13 B |
| ATOM | 3148 | C | THR | B | 96 | 75.550 | 77.071 | 18.915 | 1.00 | 33.62 B |
| ATOM | 3149 | O | THR | B | 96 | 76.445 | 76.614 | 19.618 | 1.00 | 26.19 B |
| ATOM | 3150 | N | PHE | B | 97 | 75.381 | 76.732 | 17.638 | 1.00 | 28.29 B |
| ATOM | 3151 | CA | PHE | B | 97 | 76.249 | 75.788 | 16.922 | 1.00 | 27.82 B |
| ATOM | 3152 | CB | PHE | B | 97 | 75.409 | 74.849 | 16.039 | 1.00 | 27.23 B |
| ATOM | 3153 | CG | PHE | B | 97 | 74.598 | 73.858 | 16.796 | 1.00 | 30.99 B |
| ATOM | 3154 | CD1 | PHE | B | 97 | 73.325 | 74.183 | 17.257 | 1.00 | 28.10 B |
| ATOM | 3155 | CD2 | PHE | B | 97 | 75.149 | 72.633 | 17.153 | 1.00 | 24.15 B |
| ATOM | 3156 | CE1 | PHE | B | 97 | 72.608 | 73.310 | 18.081 | 1.00 | 29.54 B |
| ATOM | 3157 | CE2 | PHE | B | 97 | 74.434 | 71.756 | 17.975 | 1.00 | 26.96 B |
| ATOM | 3158 | CZ | PHE | B | 97 | 73.155 | 72.101 | 18.444 | 1.00 | 28.76 B |
| ATOM | 3159 | C | PHE | B | 97 | 77.247 | 76.479 | 15.980 | 1.00 | 33.87 B |
| ATOM | 3160 | O | PHE | B | 97 | 77.088 | 77.663 | 15.628 | 1.00 | 30.90 B |
| ATOM | 3161 | N | ALA | B | 98 | 78.274 | 75.725 | 15.582 | 1.00 | 33.98 B |
| ATOM | 3162 | CA | ALA | B | 98 | 79.266 | 76.152 | 14.574 | 1.00 | 34.14 B |
| ATOM | 3163 | CB | ALA | B | 98 | 80.551 | 76.651 | 15.211 | 1.00 | 38.55 B |
| ATOM | 3164 | C | ALA | B | 98 | 79.544 | 74.880 | 13.785 | 1.00 | 36.15 B |
| ATOM | 3165 | O | ALA | B | 98 | 79.370 | 73.775 | 14.312 | 1.00 | 35.98 B |
| ATOM | 3166 | N | CYS | B | 99 | 79.953 | 75.018 | 12.527 | 1.00 | 38.50 B |
| ATOM | 3167 | CA | CYS | B | 99 | 80.266 | 73.843 | 11.711 | 1.00 | 39.15 B |
| ATOM | 3168 | C | CYS | B | 99 | 81.747 | 73.512 | 11.779 | 1.00 | 36.00 B |
| ATOM | 3169 | O | CYS | B | 99 | 82.573 | 74.408 | 11.865 | 1.00 | 32.17 B |
| ATOM | 3170 | CB | CYS | B | 99 | 79.901 | 74.086 | 10.251 | 1.00 | 42.12 B |
| ATOM | 3171 | SG | CYS | B | 99 | 78.108 | 74.162 | 9.949 | 1.00 | 40.52 B |
| ATOM | 3172 | N | LYS | B | 100 | 82.089 | 72.229 | 11.749 | 1.00 | 35.70 B |
| ATOM | 3173 | CA | LYS | B | 100 | 83.498 | 71.842 | 11.770 | 1.00 | 40.35 B |
| ATOM | 3174 | CB | LYS | B | 100 | 83.632 | 70.319 | 11.848 | 1.00 | 43.13 B |
| ATOM | 3175 | CG | LYS | B | 100 | 83.185 | 69.707 | 13.148 | 1.00 | 38.59 B |
| ATOM | 3176 | CD | LYS | B | 100 | 82.771 | 68.263 | 12.966 | 1.00 | 44.87 B |
| ATOM | 3177 | CE | LYS | B | 100 | 82.689 | 67.562 | 14.314 | 1.00 | 48.06 B |
| ATOM | 3178 | NZ | LYS | B | 100 | 82.353 | 66.122 | 14.196 | 1.00 | 53.59 B |

TABLE 3-continued

| ATOM | 3179 | C | LYS | B | 100 | 84.190 | 72.329 | 10.482 | 1.00 | 45.56 | B |
|---|---|---|---|---|---|---|---|---|---|---|---|
| ATOM | 3180 | O | LYS | B | 100 | 83.532 | 72.770 | 9.525 | 1.00 | 42.57 | B |
| ATOM | 3181 | N | THR | B | 101 | 85.519 | 72.239 | 10.456 | 1.00 | 47.39 | B |
| ATOM | 3182 | CA | THR | B | 101 | 86.286 | 72.651 | 9.282 | 1.00 | 48.55 | B |
| ATOM | 3183 | CB | THR | B | 101 | 87.794 | 72.408 | 9.497 | 1.00 | 48.03 | B |
| ATOM | 3184 | OG1 | THR | B | 101 | 88.281 | 73.285 | 10.521 | 1.00 | 47.14 | B |
| ATOM | 3185 | CG2 | THR | B | 101 | 88.557 | 72.683 | 8.212 | 1.00 | 51.80 | B |
| ATOM | 3186 | C | THR | B | 101 | 85.816 | 71.876 | 8.042 | 1.00 | 47.72 | B |
| ATOM | 3187 | O | THR | B | 101 | 85.523 | 70.681 | 8.127 | 1.00 | 43.56 | B |
| ATOM | 3188 | N | ASN | B | 102 | 85.747 | 72.555 | 6.901 | 1.00 | 47.11 | B |
| ATOM | 3189 | CA | ASN | B | 102 | 85.294 | 71.943 | 5.647 | 1.00 | 48.36 | B |
| ATOM | 3190 | CB | ASN | B | 102 | 85.961 | 70.594 | 5.375 | 1.00 | 53.67 | B |
| ATOM | 3191 | CG | ASN | B | 102 | 87.461 | 70.703 | 5.219 | 1.00 | 58.65 | B |
| ATOM | 3192 | OD1 | ASN | B | 102 | 87.980 | 71.763 | 4.856 | 1.00 | 59.24 | B |
| ATOM | 3193 | ND2 | ASN | B | 102 | 88.171 | 69.599 | 5.484 | 1.00 | 61.19 | B |
| ATOM | 3194 | C | ASN | B | 102 | 83.797 | 71.728 | 5.632 | 1.00 | 49.36 | B |
| ATOM | 3195 | O | ASN | B | 102 | 83.284 | 70.965 | 4.814 | 1.00 | 51.85 | B |
| ATOM | 3196 | N | PHE | B | 103 | 83.097 | 72.378 | 6.555 | 1.00 | 48.85 | B |
| ATOM | 3197 | CA | PHE | B | 103 | 81.641 | 72.294 | 6.617 | 1.00 | 44.54 | B |
| ATOM | 3198 | CB | PHE | B | 103 | 81.179 | 71.539 | 7.855 | 1.00 | 44.01 | B |
| ATOM | 3199 | CG | PHE | B | 103 | 81.335 | 70.067 | 7.740 | 1.00 | 45.42 | B |
| ATOM | 3200 | CD1 | PHE | B | 103 | 82.554 | 69.461 | 8.037 | 1.00 | 47.36 | B |
| ATOM | 3201 | CD2 | PHE | B | 103 | 80.270 | 69.274 | 7.323 | 1.00 | 44.68 | B |
| ATOM | 3202 | CE1 | PHE | B | 103 | 82.715 | 68.064 | 7.921 | 1.00 | 44.91 | B |
| ATOM | 3203 | CE2 | PHE | B | 103 | 80.413 | 67.883 | 7.202 | 1.00 | 46.13 | B |
| ATOM | 3204 | CZ | PHE | B | 103 | 81.638 | 67.276 | 7.503 | 1.00 | 44.51 | B |
| ATOM | 3205 | C | PHE | B | 103 | 81.103 | 73.700 | 6.663 | 1.00 | 43.79 | B |
| ATOM | 3206 | O | PHE | B | 103 | 81.736 | 74.577 | 7.239 | 1.00 | 41.42 | B |
| ATOM | 3207 | N | SER | B | 104 | 79.939 | 73.908 | 6.052 | 1.00 | 46.45 | B |
| ATOM | 3208 | CA | SER | B | 104 | 79.306 | 75.216 | 6.007 | 1.00 | 47.47 | B |
| ATOM | 3209 | CB | SER | B | 104 | 79.176 | 75.706 | 4.570 | 1.00 | 53.61 | B |
| ATOM | 3210 | OG | SER | B | 104 | 77.886 | 75.379 | 4.057 | 1.00 | 61.85 | B |
| ATOM | 3211 | C | SER | B | 104 | 77.921 | 75.051 | 6.596 | 1.00 | 46.27 | B |
| ATOM | 3212 | O | SER | B | 104 | 77.285 | 74.007 | 6.425 | 1.00 | 46.36 | B |
| ATOM | 3213 | N | MET | B | 105 | 77.435 | 76.089 | 7.269 | 1.00 | 47.80 | B |
| ATOM | 3214 | CA | MET | B | 105 | 76.129 | 75.998 | 7.913 | 1.00 | 50.16 | B |
| ATOM | 3215 | CB | MET | B | 105 | 76.114 | 76.848 | 9.184 | 1.00 | 42.24 | B |
| ATOM | 3216 | CG | MET | B | 105 | 74.783 | 76.829 | 9.931 | 1.00 | 39.50 | B |
| ATOM | 3217 | SD | MET | B | 105 | 74.951 | 77.585 | 11.559 | 1.00 | 31.98 | B |
| ATOM | 3218 | CE | MET | B | 105 | 76.153 | 76.456 | 12.300 | 1.00 | 32.14 | B |
| ATOM | 3219 | C | MET | B | 105 | 74.948 | 76.398 | 7.046 | 1.00 | 52.75 | B |
| ATOM | 3220 | O | MET | B | 105 | 75.066 | 77.234 | 6.147 | 1.00 | 52.67 | B |
| ATOM | 3221 | N | ASN | B | 106 | 73.807 | 75.787 | 7.343 | 1.00 | 57.15 | B |
| ATOM | 3222 | CA | ASN | B | 106 | 72.560 | 76.072 | 6.664 | 1.00 | 56.25 | B |
| ATOM | 3223 | CB | ASN | B | 106 | 72.186 | 74.950 | 5.722 | 1.00 | 63.78 | B |
| ATOM | 3224 | CG | ASN | B | 106 | 72.678 | 75.210 | 4.332 | 1.00 | 72.25 | B |
| ATOM | 3225 | OD1 | ASN | B | 106 | 72.787 | 76.372 | 3.916 | 1.00 | 78.63 | B |
| ATOM | 3226 | ND2 | ASN | B | 106 | 72.995 | 74.141 | 3.597 | 1.00 | 74.20 | B |
| ATOM | 3227 | C | ASN | B | 106 | 71.504 | 76.200 | 7.727 | 1.00 | 54.17 | B |
| ATOM | 3228 | O | ASN | B | 106 | 71.303 | 75.277 | 8.508 | 1.00 | 56.24 | B |
| ATOM | 3229 | N | GLY | B | 107 | 70.833 | 77.342 | 7.762 | 1.00 | 50.67 | B |
| ATOM | 3230 | CA | GLY | B | 107 | 69.805 | 77.552 | 8.763 | 1.00 | 44.02 | B |
| ATOM | 3231 | C | GLY | B | 107 | 70.334 | 78.414 | 9.886 | 1.00 | 42.66 | B |
| ATOM | 3232 | O | GLY | B | 107 | 71.478 | 78.864 | 9.854 | 1.00 | 41.68 | B |
| ATOM | 3233 | N | ASN | B | 108 | 69.500 | 78.646 | 10.889 | 1.00 | 46.24 | B |
| ATOM | 3234 | CA | ASN | B | 108 | 69.878 | 79.464 | 12.032 | 1.00 | 47.08 | B |
| ATOM | 3235 | CB | ASN | B | 108 | 68.613 | 79.910 | 12.751 | 1.00 | 55.35 | B |
| ATOM | 3236 | CG | ASN | B | 108 | 67.793 | 80.851 | 11.903 | 1.00 | 63.30 | B |
| ATOM | 3237 | OD1 | ASN | B | 108 | 68.164 | 82.013 | 11.722 | 1.00 | 67.44 | B |
| ATOM | 3238 | ND2 | ASN | B | 108 | 66.691 | 80.352 | 11.346 | 1.00 | 68.11 | B |
| ATOM | 3239 | C | ASN | B | 108 | 70.808 | 78.723 | 12.981 | 1.00 | 39.04 | B |
| ATOM | 3240 | O | ASN | B | 108 | 70.560 | 77.577 | 13.347 | 1.00 | 33.47 | B |
| ATOM | 3241 | N | LYS | B | 109 | 71.858 | 79.406 | 13.402 | 1.00 | 34.53 | B |
| ATOM | 3242 | CA | LYS | B | 109 | 72.859 | 78.806 | 14.280 | 1.00 | 35.55 | B |
| ATOM | 3243 | CB | LYS | B | 109 | 74.138 | 79.632 | 14.217 | 1.00 | 35.53 | B |
| ATOM | 3244 | CG | LYS | B | 109 | 73.909 | 81.037 | 14.698 | 1.00 | 37.21 | B |
| ATOM | 3245 | CD | LYS | B | 109 | 75.176 | 81.691 | 15.171 | 1.00 | 43.67 | B |
| ATOM | 3246 | CE | LYS | B | 109 | 74.913 | 83.141 | 15.501 | 1.00 | 53.84 | B |
| ATOM | 3247 | NZ | LYS | B | 109 | 76.079 | 83.848 | 16.124 | 1.00 | 67.33 | B |
| ATOM | 3248 | C | LYS | B | 109 | 72.456 | 78.639 | 15.753 | 1.00 | 33.59 | B |
| ATOM | 3249 | O | LYS | B | 109 | 73.116 | 77.900 | 16.490 | 1.00 | 32.99 | B |
| ATOM | 3250 | N | SER | B | 110 | 71.409 | 79.337 | 16.198 | 1.00 | 29.02 | B |
| ATOM | 3251 | CA | SER | B | 110 | 70.972 | 79.239 | 17.597 | 1.00 | 31.62 | B |
| ATOM | 3252 | CB | SER | B | 110 | 71.068 | 80.588 | 18.298 | 1.00 | 28.39 | B |
| ATOM | 3253 | OG | SER | B | 110 | 72.395 | 81.073 | 18.276 | 1.00 | 35.28 | B |
| ATOM | 3254 | C | SER | B | 110 | 69.547 | 78.730 | 17.734 | 1.00 | 33.04 | B |
| ATOM | 3255 | O | SER | B | 110 | 68.665 | 79.049 | 16.935 | 1.00 | 28.18 | B |
| ATOM | 3256 | N | VAL | B | 111 | 69.336 | 77.927 | 18.761 | 1.00 | 32.94 | B |
| ATOM | 3257 | CA | VAL | B | 111 | 68.028 | 77.360 | 19.032 | 1.00 | 28.12 | B |

TABLE 3-continued

| | | | | | | | | | | |
|---|---|---|---|---|---|---|---|---|---|---|
| ATOM | 3258 | CB | VAL | B | 111 | 67.998 | 75.911 | 18.507 | 1.00 | 34.53 B |
| ATOM | 3259 | CG1 | VAL | B | 111 | 69.117 | 75.074 | 19.143 | 1.00 | 27.59 B |
| ATOM | 3260 | CG2 | VAL | B | 111 | 66.694 | 75.304 | 18.785 | 1.00 | 41.47 B |
| ATOM | 3261 | C | VAL | B | 111 | 67.729 | 77.488 | 20.539 | 1.00 | 26.65 B |
| ATOM | 3262 | O | VAL | B | 111 | 68.631 | 77.621 | 21.359 | 1.00 | 27.71 B |
| ATOM | 3263 | N | TRP | B | 112 | 66.447 | 77.496 | 20.866 | 1.00 | 26.33 B |
| ATOM | 3264 | CA | TRP | B | 112 | 65.932 | 77.654 | 22.205 | 1.00 | 21.46 B |
| ATOM | 3265 | CB | TRP | B | 112 | 65.023 | 78.895 | 22.287 | 1.00 | 27.43 B |
| ATOM | 3266 | CG | TRP | B | 112 | 65.772 | 80.142 | 22.392 | 1.00 | 28.72 B |
| ATOM | 3267 | CD2 | TRP | B | 112 | 66.455 | 80.818 | 21.323 | 1.00 | 27.13 B |
| ATOM | 3268 | CE2 | TRP | B | 112 | 67.130 | 81.922 | 21.894 | 1.00 | 23.65 B |
| ATOM | 3269 | CE3 | TRP | B | 112 | 66.560 | 80.595 | 19.944 | 1.00 | 27.06 B |
| ATOM | 3270 | CD1 | TRP | B | 112 | 66.053 | 80.849 | 23.542 | 1.00 | 29.24 B |
| ATOM | 3271 | NE1 | TRP | B | 112 | 66.875 | 81.916 | 23.242 | 1.00 | 22.18 B |
| ATOM | 3272 | CZ2 | TRP | B | 112 | 67.896 | 82.804 | 21.132 | 1.00 | 24.55 B |
| ATOM | 3273 | CZ3 | TRP | B | 112 | 67.328 | 81.476 | 19.179 | 1.00 | 32.51 B |
| ATOM | 3274 | CH2 | TRP | B | 112 | 67.985 | 82.570 | 19.782 | 1.00 | 28.74 B |
| ATOM | 3275 | C | TRP | B | 112 | 65.113 | 76.462 | 22.622 | 1.00 | 24.09 B |
| ATOM | 3276 | O | TRP | B | 112 | 64.348 | 75.924 | 21.826 | 1.00 | 23.03 B |
| ATOM | 3277 | N | CYS | B | 113 | 65.257 | 76.065 | 23.886 | 1.00 | 16.00 B |
| ATOM | 3278 | CA | CYS | B | 113 | 64.507 | 74.942 | 24.421 | 1.00 | 22.66 B |
| ATOM | 3279 | C | CYS | B | 113 | 63.090 | 75.442 | 24.775 | 1.00 | 27.37 B |
| ATOM | 3280 | O | CYS | B | 113 | 62.892 | 76.248 | 25.702 | 1.00 | 23.71 B |
| ATOM | 3281 | CB | CYS | B | 113 | 65.230 | 74.386 | 25.636 | 1.00 | 24.38 B |
| ATOM | 3282 | SG | CYS | B | 113 | 64.295 | 73.084 | 26.474 | 1.00 | 25.70 B |
| ATOM | 3283 | N | GLN | B | 114 | 62.105 | 74.973 | 24.014 | 1.00 | 22.77 B |
| ATOM | 3284 | CA | GLN | B | 114 | 60.704 | 75.406 | 24.190 | 1.00 | 27.53 B |
| ATOM | 3285 | CB | GLN | B | 114 | 59.993 | 75.312 | 22.852 | 1.00 | 23.87 B |
| ATOM | 3286 | CG | GLN | B | 114 | 60.669 | 76.101 | 21.776 | 1.00 | 25.80 B |
| ATOM | 3287 | CD | GLN | B | 114 | 59.934 | 75.957 | 20.455 | 1.00 | 34.33 B |
| ATOM | 3288 | OE1 | GLN | B | 114 | 59.540 | 74.850 | 20.084 | 1.00 | 40.82 B |
| ATOM | 3289 | NE2 | GLN | B | 114 | 59.749 | 77.062 | 19.744 | 1.00 | 28.51 B |
| ATOM | 3290 | C | GLN | B | 114 | 59.918 | 74.632 | 25.242 | 1.00 | 24.17 B |
| ATOM | 3291 | O | GLN | B | 114 | 60.324 | 73.557 | 25.638 | 1.00 | 24.70 B |
| ATOM | 3292 | N | ALA | B | 115 | 58.806 | 75.187 | 25.704 | 1.00 | 28.17 B |
| ATOM | 3293 | CA | ALA | B | 115 | 57.984 | 74.520 | 26.720 | 1.00 | 32.79 B |
| ATOM | 3294 | CB | ALA | B | 115 | 56.769 | 75.392 | 27.068 | 1.00 | 30.00 B |
| ATOM | 3295 | C | ALA | B | 115 | 57.523 | 73.107 | 26.316 | 1.00 | 34.03 B |
| ATOM | 3296 | O | ALA | B | 115 | 57.338 | 72.237 | 27.170 | 1.00 | 33.21 B |
| ATOM | 3297 | N | ASN | B | 116 | 57.343 | 72.881 | 25.020 | 1.00 | 36.70 B |
| ATOM | 3298 | CA | ASN | B | 116 | 56.913 | 71.573 | 24.526 | 1.00 | 38.02 B |
| ATOM | 3299 | CB | ASN | B | 116 | 56.230 | 71.728 | 23.168 | 1.00 | 34.90 B |
| ATOM | 3300 | CG | ASN | B | 116 | 57.198 | 72.144 | 22.087 | 1.00 | 33.42 B |
| ATOM | 3301 | OD1 | ASN | B | 116 | 58.359 | 72.454 | 22.364 | 1.00 | 28.93 B |
| ATOM | 3302 | ND2 | ASN | B | 116 | 56.728 | 72.167 | 20.853 | 1.00 | 30.98 B |
| ATOM | 3303 | C | ASN | B | 116 | 58.104 | 70.608 | 24.392 | 1.00 | 34.77 B |
| ATOM | 3304 | O | ASN | B | 116 | 58.017 | 69.612 | 23.695 | 1.00 | 37.59 B |
| ATOM | 3305 | N | ASN | B | 117 | 59.219 | 70.937 | 25.044 | 1.00 | 36.92 B |
| ATOM | 3306 | CA | ASN | B | 117 | 60.425 | 70.094 | 25.072 | 1.00 | 31.01 B |
| ATOM | 3307 | CB | ASN | B | 117 | 60.095 | 68.728 | 25.699 | 1.00 | 35.95 B |
| ATOM | 3308 | CG | ASN | B | 117 | 59.327 | 68.855 | 27.022 | 1.00 | 41.69 B |
| ATOM | 3309 | OD1 | ASN | B | 117 | 58.165 | 68.448 | 27.116 | 1.00 | 48.82 B |
| ATOM | 3310 | ND2 | ASN | B | 117 | 59.966 | 69.428 | 28.041 | 1.00 | 38.48 B |
| ATOM | 3311 | C | ASN | B | 117 | 61.155 | 69.913 | 23.753 | 1.00 | 35.04 B |
| ATOM | 3312 | O | ASN | B | 117 | 61.989 | 69.010 | 23.584 | 1.00 | 30.97 B |
| ATOM | 3313 | N | MET | B | 118 | 60.877 | 70.804 | 22.814 | 1.00 | 32.90 B |
| ATOM | 3314 | CA | MET | B | 118 | 61.544 | 70.747 | 21.539 | 1.00 | 30.69 B |
| ATOM | 3315 | CB | MET | B | 118 | 60.533 | 70.486 | 20.426 | 1.00 | 39.19 B |
| ATOM | 3316 | CG | MET | B | 118 | 60.143 | 69.004 | 20.284 | 1.00 | 45.35 B |
| ATOM | 3317 | SD | MET | B | 118 | 58.844 | 68.904 | 19.065 | 1.00 | 61.98 B |
| ATOM | 3318 | CE | MET | B | 118 | 57.379 | 68.930 | 20.152 | 1.00 | 59.12 B |
| ATOM | 3319 | C | MET | B | 118 | 62.299 | 72.033 | 21.290 | 1.00 | 32.74 B |
| ATOM | 3320 | O | MET | B | 118 | 61.958 | 73.093 | 21.820 | 1.00 | 31.41 B |
| ATOM | 3321 | N | TRP | B | 119 | 63.322 | 71.913 | 20.460 | 1.00 | 30.27 B |
| ATOM | 3322 | CA | TRP | B | 119 | 64.197 | 73.007 | 20.122 | 1.00 | 32.04 B |
| ATOM | 3323 | CB | TRP | B | 119 | 65.519 | 72.477 | 19.556 | 1.00 | 29.45 B |
| ATOM | 3324 | CG | TRP | B | 119 | 66.377 | 71.888 | 20.618 | 1.00 | 34.08 B |
| ATOM | 3325 | CD2 | TRP | B | 119 | 67.091 | 72.613 | 21.638 | 1.00 | 29.55 B |
| ATOM | 3326 | CE2 | TRP | B | 119 | 67.641 | 71.653 | 22.514 | 1.00 | 32.16 B |
| ATOM | 3327 | CE3 | TRP | B | 119 | 67.309 | 73.974 | 21.891 | 1.00 | 27.61 B |
| ATOM | 3328 | CD1 | TRP | B | 119 | 66.533 | 70.563 | 20.907 | 1.00 | 27.66 B |
| ATOM | 3329 | NE1 | TRP | B | 119 | 67.287 | 70.419 | 22.045 | 1.00 | 29.97 B |
| ATOM | 3330 | CZ2 | TRP | B | 119 | 68.401 | 72.018 | 23.634 | 1.00 | 33.69 B |
| ATOM | 3331 | CZ3 | TRP | B | 119 | 68.067 | 74.333 | 23.002 | 1.00 | 28.67 B |
| ATOM | 3332 | CH2 | TRP | B | 119 | 68.603 | 73.356 | 23.860 | 1.00 | 29.17 B |
| ATOM | 3333 | C | TRP | B | 119 | 63.672 | 74.059 | 19.188 | 1.00 | 35.37 B |
| ATOM | 3334 | O | TRP | B | 119 | 62.946 | 73.750 | 18.264 | 1.00 | 34.01 B |
| ATOM | 3335 | N | GLY | B | 120 | 64.129 | 75.279 | 19.507 | 1.00 | 44.82 B |
| ATOM | 3336 | CA | GLY | B | 120 | 63.928 | 76.577 | 18.868 | 1.00 | 40.39 B |

TABLE 3-continued

| ATOM | 3337 | C | GLY | B | 120 | 62.736 | 76.818 | 18.037 | 1.00 | 45.27 | B |
|---|---|---|---|---|---|---|---|---|---|---|---|
| ATOM | 3338 | O | GLY | B | 120 | 61.922 | 75.920 | 17.884 | 1.00 | 54.52 | B |
| ATOM | 3339 | N | PRO | B | 121 | 62.570 | 78.049 | 17.525 | 1.00 | 39.72 | B |
| ATOM | 3340 | CD | PRO | B | 121 | 63.331 | 79.268 | 17.805 | 1.00 | 34.64 | B |
| ATOM | 3341 | CA | PRO | B | 121 | 61.411 | 78.339 | 16.678 | 1.00 | 40.69 | B |
| ATOM | 3342 | CB | PRO | B | 121 | 61.355 | 79.869 | 16.674 | 1.00 | 33.54 | B |
| ATOM | 3343 | CG | PRO | B | 121 | 62.781 | 80.221 | 16.775 | 1.00 | 38.11 | B |
| ATOM | 3344 | C | PRO | B | 121 | 61.717 | 77.733 | 15.294 | 1.00 | 38.17 | B |
| ATOM | 3345 | O | PRO | B | 121 | 60.817 | 77.305 | 14.591 | 1.00 | 40.16 | B |
| ATOM | 3346 | N | THR | B | 122 | 62.994 | 77.693 | 14.930 | 1.00 | 33.84 | B |
| ATOM | 3347 | CA | THR | B | 122 | 63.424 | 77.113 | 13.660 | 1.00 | 38.91 | B |
| ATOM | 3348 | CB | THR | B | 122 | 64.548 | 77.939 | 12.988 | 1.00 | 42.26 | B |
| ATOM | 3349 | OG1 | THR | B | 122 | 65.803 | 77.671 | 13.634 | 1.00 | 39.47 | B |
| ATOM | 3350 | CG2 | THR | B | 122 | 64.259 | 79.431 | 13.106 | 1.00 | 40.58 | B |
| ATOM | 3351 | C | THR | B | 122 | 63.968 | 75.708 | 13.874 | 1.00 | 40.61 | B |
| ATOM | 3352 | O | THR | B | 122 | 64.163 | 75.266 | 14.999 | 1.00 | 43.52 | B |
| ATOM | 3353 | N | ARG | B | 123 | 64.220 | 75.005 | 12.784 | 1.00 | 42.70 | B |
| ATOM | 3354 | CA | ARG | B | 123 | 64.762 | 73.656 | 12.870 | 1.00 | 46.43 | B |
| ATOM | 3355 | CB | ARG | B | 123 | 64.505 | 72.912 | 11.549 | 1.00 | 48.19 | B |
| ATOM | 3356 | CG | ARG | B | 123 | 64.849 | 71.433 | 11.600 | 1.00 | 63.34 | B |
| ATOM | 3357 | CD | ARG | B | 123 | 64.109 | 70.638 | 10.517 | 1.00 | 71.72 | B |
| ATOM | 3358 | NE | ARG | B | 123 | 62.664 | 70.564 | 10.762 | 1.00 | 75.72 | B |
| ATOM | 3359 | CZ | ARG | B | 123 | 61.734 | 70.934 | 9.881 | 1.00 | 77.53 | B |
| ATOM | 3360 | NH1 | ARG | B | 123 | 62.096 | 71.410 | 8.690 | 1.00 | 78.13 | B |
| ATOM | 3361 | NH2 | ARG | B | 123 | 60.444 | 70.820 | 10.184 | 1.00 | 75.29 | B |
| ATOM | 3362 | C | ARG | B | 123 | 66.270 | 73.774 | 13.141 | 1.00 | 36.14 | B |
| ATOM | 3363 | O | ARG | B | 123 | 66.861 | 74.816 | 12.880 | 1.00 | 34.06 | B |
| ATOM | 3364 | N | LEU | B | 124 | 66.888 | 72.714 | 13.659 | 1.00 | 36.62 | B |
| ATOM | 3365 | CA | LEU | B | 124 | 68.326 | 72.743 | 13.939 | 1.00 | 35.68 | B |
| ATOM | 3366 | CB | LEU | B | 124 | 68.818 | 71.410 | 14.509 | 1.00 | 37.22 | B |
| ATOM | 3367 | CG | LEU | B | 124 | 68.399 | 71.019 | 15.933 | 1.00 | 38.68 | B |
| ATOM | 3368 | CD1 | LEU | B | 124 | 69.008 | 69.670 | 16.342 | 1.00 | 37.12 | B |
| ATOM | 3369 | CD2 | LEU | B | 124 | 68.860 | 72.097 | 16.874 | 1.00 | 34.15 | B |
| ATOM | 3370 | C | LEU | B | 124 | 69.081 | 73.029 | 12.656 | 1.00 | 37.07 | B |
| ATOM | 3371 | O | LEU | B | 124 | 68.701 | 72.584 | 11.583 | 1.00 | 35.87 | B |
| ATOM | 3372 | N | PRO | B | 125 | 70.168 | 73.787 | 12.750 | 1.00 | 40.36 | B |
| ATOM | 3373 | CD | PRO | B | 125 | 70.832 | 74.306 | 13.962 | 1.00 | 38.05 | B |
| ATOM | 3374 | CA | PRO | B | 125 | 70.933 | 74.085 | 11.538 | 1.00 | 35.47 | B |
| ATOM | 3375 | CB | PRO | B | 125 | 71.993 | 75.069 | 12.029 | 1.00 | 35.51 | B |
| ATOM | 3376 | CG | PRO | B | 125 | 72.224 | 74.641 | 13.460 | 1.00 | 35.57 | B |
| ATOM | 3377 | C | PRO | B | 125 | 71.535 | 72.794 | 11.002 | 1.00 | 40.45 | B |
| ATOM | 3378 | O | PRO | B | 125 | 71.432 | 71.739 | 11.640 | 1.00 | 33.92 | B |
| ATOM | 3379 | N | THR | B | 126 | 72.131 | 72.867 | 9.814 | 1.00 | 41.58 | B |
| ATOM | 3380 | CA | THR | B | 126 | 72.765 | 71.704 | 9.217 | 1.00 | 41.03 | B |
| ATOM | 3381 | CB | THR | B | 126 | 71.929 | 71.137 | 8.006 | 1.00 | 42.99 | B |
| ATOM | 3382 | OG1 | THR | B | 126 | 71.625 | 72.182 | 7.075 | 1.00 | 45.10 | B |
| ATOM | 3383 | CG2 | THR | B | 126 | 70.628 | 70.529 | 8.503 | 1.00 | 40.83 | B |
| ATOM | 3384 | C | THR | B | 126 | 74.157 | 72.116 | 8.777 | 1.00 | 41.16 | B |
| ATOM | 3385 | O | THR | B | 126 | 74.415 | 73.299 | 8.544 | 1.00 | 40.35 | B |
| ATOM | 3386 | N | CYS | B | 127 | 75.074 | 71.158 | 8.716 | 1.00 | 42.86 | B |
| ATOM | 3387 | CA | CYS | B | 127 | 76.433 | 71.468 | 8.279 | 1.00 | 48.44 | B |
| ATOM | 3388 | C | CYS | B | 127 | 76.774 | 70.561 | 7.098 | 1.00 | 53.76 | B |
| ATOM | 3389 | O | CYS | B | 127 | 76.711 | 69.336 | 7.219 | 1.00 | 55.59 | B |
| ATOM | 3390 | CB | CYS | B | 127 | 77.440 | 71.249 | 9.422 | 1.00 | 49.29 | B |
| ATOM | 3391 | SG | CYS | B | 127 | 77.365 | 72.471 | 10.779 | 1.00 | 41.21 | B |
| ATOM | 3392 | N | VAL | B | 128 | 77.117 | 71.159 | 5.960 | 1.00 | 52.99 | B |
| ATOM | 3393 | CA | VAL | B | 128 | 77.466 | 70.386 | 4.764 | 1.00 | 58.11 | B |
| ATOM | 3394 | CB | VAL | B | 128 | 76.479 | 70.674 | 3.612 | 1.00 | 60.17 | B |
| ATOM | 3395 | CG1 | VAL | B | 128 | 76.356 | 72.179 | 3.395 | 1.00 | 59.61 | B |
| ATOM | 3396 | CG2 | VAL | B | 128 | 76.974 | 70.005 | 2.322 | 1.00 | 62.78 | B |
| ATOM | 3397 | C | VAL | B | 128 | 78.881 | 70.738 | 4.290 | 1.00 | 55.96 | B |
| ATOM | 3398 | O | VAL | B | 128 | 79.307 | 71.875 | 4.427 | 1.00 | 56.76 | B |
| ATOM | 3399 | N | SER | B | 129 | 79.604 | 69.763 | 3.747 | 1.00 | 58.88 | B |
| ATOM | 3400 | CA | SER | B | 129 | 80.976 | 69.974 | 3.241 | 1.00 | 63.04 | B |
| ATOM | 3401 | CB | SER | B | 129 | 81.489 | 68.685 | 2.616 | 1.00 | 64.42 | B |
| ATOM | 3402 | OG | SER | B | 129 | 80.566 | 68.249 | 1.633 | 1.00 | 74.77 | B |
| ATOM | 3403 | C | SER | B | 129 | 81.061 | 71.092 | 2.194 | 1.00 | 60.01 | B |
| ATOM | 3404 | O | SER | B | 129 | 82.054 | 71.856 | 2.166 | 1.00 | 59.63 | B |
| ATOM | 3405 | OXT | SER | B | 129 | 80.121 | 71.165 | 1.381 | 1.00 | 61.43 | B |
| ATOM | 3406 | CB | ALA | C | 1 | 51.630 | 81.929 | 2.879 | 1.00 | 35.79 | C |
| ATOM | 3407 | C | ALA | C | 1 | 50.853 | 84.288 | 2.366 | 1.00 | 35.46 | C |
| ATOM | 3408 | O | ALA | C | 1 | 50.053 | 85.212 | 2.282 | 1.00 | 40.99 | C |
| ATOM | 3409 | N | ALA | C | 1 | 49.558 | 82.473 | 1.552 | 1.00 | 39.80 | C |
| ATOM | 3410 | CA | ALA | C | 1 | 50.392 | 82.883 | 2.708 | 1.00 | 38.04 | C |
| ATOM | 3411 | N | ILE | C | 2 | 52.138 | 84.436 | 2.113 | 1.00 | 25.56 | C |
| ATOM | 3412 | CA | ILE | C | 2 | 52.684 | 85.736 | 1.810 | 1.00 | 32.00 | C |
| ATOM | 3413 | CB | ILE | C | 2 | 53.982 | 85.933 | 2.591 | 1.00 | 24.33 | C |
| ATOM | 3414 | CG2 | ILE | C | 2 | 54.794 | 87.063 | 1.974 | 1.00 | 24.84 | C |
| ATOM | 3415 | CG1 | ILE | C | 2 | 53.647 | 86.140 | 4.085 | 1.00 | 31.72 | C |

TABLE 3-continued

| ATOM | 3416 | CD1 | ILE | C | 2 | 54.875 | 86.286 | 5.004 | 1.00 | 28.23 | C |
|---|---|---|---|---|---|---|---|---|---|---|---|
| ATOM | 3417 | C | ILE | C | 2 | 52.955 | 85.930 | 0.331 | 1.00 | 29.98 | C |
| ATOM | 3418 | O | ILE | C | 2 | 53.280 | 84.966 | −0.364 | 1.00 | 24.28 | C |
| ATOM | 3419 | N | SER | C | 3 | 52.816 | 87.164 | −0.156 | 1.00 | 25.13 | C |
| ATOM | 3420 | CA | SER | C | 3 | 53.130 | 87.453 | −1.564 | 1.00 | 24.56 | C |
| ATOM | 3421 | CB | SER | C | 3 | 51.848 | 87.773 | −2.360 | 1.00 | 23.32 | C |
| ATOM | 3422 | OG | SER | C | 3 | 51.206 | 88.949 | −1.866 | 1.00 | 28.18 | C |
| ATOM | 3423 | C | SER | C | 3 | 54.111 | 88.630 | −1.651 | 1.00 | 28.79 | C |
| ATOM | 3424 | O | SER | C | 3 | 54.240 | 89.413 | −0.703 | 1.00 | 25.00 | C |
| ATOM | 3425 | N | CYS | C | 4 | 54.834 | 88.720 | −2.766 | 1.00 | 24.82 | C |
| ATOM | 3426 | CA | CYS | C | 4 | 55.760 | 89.824 | −3.003 | 1.00 | 23.87 | C |
| ATOM | 3427 | C | CYS | C | 4 | 55.114 | 90.751 | −4.020 | 1.00 | 26.63 | C |
| ATOM | 3428 | O | CYS | C | 4 | 54.488 | 90.277 | −4.974 | 1.00 | 24.86 | C |
| ATOM | 3429 | CB | CYS | C | 4 | 57.075 | 89.341 | −3.595 | 1.00 | 26.41 | C |
| ATOM | 3430 | SG | CYS | C | 4 | 58.182 | 88.516 | −2.412 | 1.00 | 26.19 | C |
| ATOM | 3431 | N | GLY | C | 5 | 55.270 | 92.056 | −3.843 | 1.00 | 25.01 | C |
| ATOM | 3432 | CA | GLY | C | 5 | 54.697 | 93.002 | −4.800 | 1.00 | 23.78 | C |
| ATOM | 3433 | C | GLY | C | 5 | 55.467 | 93.100 | −6.115 | 1.00 | 33.19 | C |
| ATOM | 3434 | O | GLY | C | 5 | 56.444 | 92.346 | −6.350 | 1.00 | 24.73 | C |
| ATOM | 3435 | N | SER | C | 6 | 55.020 | 94.068 | −6.975 | 1.00 | 24.24 | C |
| ATOM | 3436 | CA | SER | C | 6 | 55.654 | 94.257 | −8.285 | 1.00 | 31.29 | C |
| ATOM | 3437 | CB | SER | C | 6 | 54.994 | 95.528 | −8.834 | 1.00 | 28.12 | C |
| ATOM | 3438 | OG | SER | C | 6 | 53.739 | 95.485 | −9.097 | 1.00 | 30.57 | C |
| ATOM | 3439 | C | SER | C | 6 | 57.187 | 94.422 | −8.106 | 1.00 | 28.51 | C |
| ATOM | 3440 | O | SER | C | 6 | 57.681 | 95.162 | −7.262 | 1.00 | 27.78 | C |
| ATOM | 3441 | N | PRO | C | 7 | 57.921 | 93.562 | −8.849 | 1.00 | 24.89 | C |
| ATOM | 3442 | CD | PRO | C | 7 | 57.432 | 92.669 | −9.919 | 1.00 | 29.34 | C |
| ATOM | 3443 | CA | PRO | C | 7 | 59.391 | 93.554 | −8.765 | 1.00 | 29.21 | C |
| ATOM | 3444 | CB | PRO | C | 7 | 59.778 | 92.308 | −9.570 | 1.00 | 30.50 | C |
| ATOM | 3445 | CG | PRO | C | 7 | 58.721 | 92.286 | −10.660 | 1.00 | 34.19 | C |
| ATOM | 3446 | C | PRO | C | 7 | 60.066 | 94.829 | −9.286 | 1.00 | 25.82 | C |
| ATOM | 3447 | O | PRO | C | 7 | 59.490 | 95.586 | −10.054 | 1.00 | 30.82 | C |
| ATOM | 3448 | N | PRO | C | 8 | 61.312 | 95.071 | −8.879 | 1.00 | 25.55 | C |
| ATOM | 3449 | CD | PRO | C | 8 | 62.239 | 94.221 | −8.107 | 1.00 | 22.99 | C |
| ATOM | 3450 | CA | PRO | C | 8 | 61.972 | 96.293 | −9.360 | 1.00 | 27.11 | C |
| ATOM | 3451 | CB | PRO | C | 8 | 63.315 | 96.292 | −8.613 | 1.00 | 23.33 | C |
| ATOM | 3452 | CG | PRO | C | 8 | 63.116 | 95.255 | −7.464 | 1.00 | 30.29 | C |
| ATOM | 3453 | C | PRO | C | 8 | 62.162 | 96.260 | −10.877 | 1.00 | 27.57 | C |
| ATOM | 3454 | O | PRO | C | 8 | 62.478 | 95.206 | −11.457 | 1.00 | 27.35 | C |
| ATOM | 3455 | N | PRO | C | 9 | 61.945 | 97.401 | −11.552 | 1.00 | 28.23 | C |
| ATOM | 3456 | CD | PRO | C | 9 | 61.527 | 98.718 | −11.049 | 1.00 | 30.53 | C |
| ATOM | 3457 | CA | PRO | C | 9 | 62.116 | 97.415 | −13.009 | 1.00 | 29.41 | C |
| ATOM | 3458 | CB | PRO | C | 9 | 61.430 | 98.714 | −13.417 | 1.00 | 30.12 | C |
| ATOM | 3459 | CG | PRO | C | 9 | 61.742 | 99.607 | −12.272 | 1.00 | 31.67 | C |
| ATOM | 3460 | C | PRO | C | 9 | 63.607 | 97.389 | −13.404 | 1.00 | 37.14 | C |
| ATOM | 3461 | O | PRO | C | 9 | 64.487 | 97.661 | −12.572 | 1.00 | 30.31 | C |
| ATOM | 3462 | N | ILE | C | 10 | 63.883 | 97.070 | −14.669 | 1.00 | 30.28 | C |
| ATOM | 3463 | CA | ILE | C | 10 | 65.252 | 97.015 | −15.166 | 1.00 | 29.72 | C |
| ATOM | 3464 | CB | ILE | C | 10 | 65.704 | 95.533 | −15.351 | 1.00 | 30.40 | C |
| ATOM | 3465 | CG2 | ILE | C | 10 | 64.708 | 94.766 | −16.273 | 1.00 | 30.23 | C |
| ATOM | 3466 | CG1 | ILE | C | 10 | 67.121 | 95.474 | −15.931 | 1.00 | 28.32 | C |
| ATOM | 3467 | CD1 | ILE | C | 10 | 67.729 | 94.058 | −15.907 | 1.00 | 27.53 | C |
| ATOM | 3468 | C | ILE | C | 10 | 65.380 | 97.792 | −16.488 | 1.00 | 36.89 | C |
| ATOM | 3469 | O | ILE | C | 10 | 64.732 | 97.472 | −17.491 | 1.00 | 34.25 | C |
| ATOM | 3470 | N | LEU | C | 11 | 66.219 | 98.822 | −16.483 | 1.00 | 38.68 | C |
| ATOM | 3471 | CA | LEU | C | 11 | 66.436 | 99.629 | −17.678 | 1.00 | 36.69 | C |
| ATOM | 3472 | CB | LEU | C | 11 | 67.269 | 100.846 | −17.320 | 1.00 | 40.95 | C |
| ATOM | 3473 | CG | LEU | C | 11 | 66.804 | 102.189 | −17.855 | 1.00 | 45.07 | C |
| ATOM | 3474 | CD1 | LEU | C | 11 | 65.484 | 102.575 | −17.199 | 1.00 | 43.54 | C |
| ATOM | 3475 | CD2 | LEU | C | 11 | 67.875 | 103.215 | −17.565 | 1.00 | 43.98 | C |
| ATOM | 3476 | C | LEU | C | 11 | 67.176 | 98.837 | −18.758 | 1.00 | 39.52 | C |
| ATOM | 3477 | O | LEU | C | 11 | 68.193 | 98.204 | −18.475 | 1.00 | 37.78 | C |
| ATOM | 3478 | N | ASN | C | 12 | 66.680 | 98.899 | −19.988 | 1.00 | 30.25 | C |
| ATOM | 3479 | CA | ASN | C | 12 | 67.284 | 98.227 | −21.121 | 1.00 | 28.03 | C |
| ATOM | 3480 | CB | ASN | C | 12 | 68.705 | 98.746 | −21.351 | 1.00 | 38.34 | C |
| ATOM | 3481 | CG | ASN | C | 12 | 68.739 | 100.231 | −21.653 | 1.00 | 42.68 | C |
| ATOM | 3482 | OD1 | ASN | C | 12 | 69.139 | 101.036 | −20.813 | 1.00 | 47.15 | C |
| ATOM | 3483 | ND2 | ASN | C | 12 | 68.318 | 100.596 | −22.859 | 1.00 | 44.31 | C |
| ATOM | 3484 | C | ASN | C | 12 | 67.294 | 96.721 | −20.910 | 1.00 | 36.66 | C |
| ATOM | 3485 | O | ASN | C | 12 | 68.253 | 96.075 | −21.417 | 1.00 | 38.52 | C |
| ATOM | 3486 | N | GLY | C | 13 | 66.330 | 96.216 | −20.179 | 1.00 | 37.43 | C |
| ATOM | 3487 | CA | GLY | C | 13 | 66.219 | 94.783 | −19.993 | 1.00 | 37.37 | C |
| ATOM | 3488 | C | GLY | C | 13 | 64.776 | 94.380 | −19.800 | 1.00 | 34.87 | C |
| ATOM | 3489 | O | GLY | C | 13 | 63.859 | 95.180 | −19.928 | 1.00 | 37.34 | C |
| ATOM | 3490 | N | ARG | C | 14 | 64.557 | 93.119 | −19.493 | 1.00 | 35.59 | C |
| ATOM | 3491 | CA | ARG | C | 14 | 63.201 | 92.681 | −19.259 | 1.00 | 36.84 | C |
| ATOM | 3492 | CB | ARG | C | 14 | 62.562 | 92.191 | −20.558 | 1.00 | 41.62 | C |
| ATOM | 3493 | CG | ARG | C | 14 | 63.338 | 91.087 | −21.221 | 1.00 | 51.45 | C |
| ATOM | 3494 | CD | ARG | C | 14 | 63.739 | 91.505 | −22.634 | 1.00 | 65.10 | C |

TABLE 3-continued

| ATOM | 3495 | NE | ARG | C | 14 | 64.692 | 92.626 | −22.649 | 1.00 | 73.47 | C |
|------|------|-----|-----|---|----|--------|--------|---------|------|-------|---|
| ATOM | 3496 | CZ | ARG | C | 14 | 64.669 | 93.630 | −23.528 | 1.00 | 76.84 | C |
| ATOM | 3497 | NH1 | ARG | C | 14 | 63.736 | 93.667 | −24.477 | 1.00 | 76.76 | C |
| ATOM | 3498 | NH2 | ARG | C | 14 | 65.576 | 94.600 | −23.457 | 1.00 | 76.89 | C |
| ATOM | 3499 | C | ARG | C | 14 | 63.179 | 91.573 | −18.224 | 1.00 | 34.90 | C |
| ATOM | 3500 | O | ARG | C | 14 | 64.211 | 90.974 | −17.875 | 1.00 | 30.74 | C |
| ATOM | 3501 | N | ILE | C | 15 | 61.985 | 91.308 | −17.725 | 1.00 | 32.52 | C |
| ATOM | 3502 | CA | ILE | C | 15 | 61.809 | 90.274 | −16.740 | 1.00 | 35.90 | C |
| ATOM | 3503 | CB | ILE | C | 15 | 61.048 | 90.814 | −15.525 | 1.00 | 31.54 | C |
| ATOM | 3504 | CG2 | ILE | C | 15 | 60.749 | 89.677 | −14.553 | 1.00 | 25.41 | C |
| ATOM | 3505 | CG1 | ILE | C | 15 | 61.862 | 91.952 | −14.893 | 1.00 | 30.46 | C |
| ATOM | 3506 | CD1 | ILE | C | 15 | 61.086 | 92.836 | −13.959 | 1.00 | 28.46 | C |
| ATOM | 3507 | C | ILE | C | 15 | 61.013 | 89.156 | −17.357 | 1.00 | 39.71 | C |
| ATOM | 3508 | O | ILE | C | 15 | 60.004 | 89.403 | −18.022 | 1.00 | 39.51 | C |
| ATOM | 3509 | N | SER | C | 16 | 61.469 | 87.932 | −17.136 | 1.00 | 39.22 | C |
| ATOM | 3510 | CA | SER | C | 16 | 60.762 | 86.750 | −17.623 | 1.00 | 50.26 | C |
| ATOM | 3511 | CB | SER | C | 16 | 61.410 | 85.472 | −17.077 | 1.00 | 53.90 | C |
| ATOM | 3512 | OG | SER | C | 16 | 61.213 | 85.384 | −15.655 | 1.00 | 59.12 | C |
| ATOM | 3513 | C | SER | C | 16 | 59.326 | 86.801 | −17.091 | 1.00 | 50.15 | C |
| ATOM | 3514 | O | SER | C | 16 | 59.097 | 87.096 | −15.911 | 1.00 | 46.35 | C |
| ATOM | 3515 | N | TYR | C | 17 | 58.377 | 86.475 | −17.961 | 1.00 | 54.91 | C |
| ATOM | 3516 | CA | TYR | C | 17 | 56.951 | 86.453 | −17.629 | 1.00 | 50.96 | C |
| ATOM | 3517 | CB | TYR | C | 17 | 56.154 | 85.806 | −18.765 | 1.00 | 56.78 | C |
| ATOM | 3518 | CG | TYR | C | 17 | 54.665 | 86.055 | −18.678 | 1.00 | 58.05 | C |
| ATOM | 3519 | CD1 | TYR | C | 17 | 54.109 | 87.224 | −19.209 | 1.00 | 59.99 | C |
| ATOM | 3520 | CE1 | TYR | C | 17 | 52.751 | 87.509 | −19.071 | 1.00 | 61.22 | C |
| ATOM | 3521 | CD2 | TYR | C | 17 | 53.822 | 85.163 | −18.004 | 1.00 | 55.94 | C |
| ATOM | 3522 | CE2 | TYR | C | 17 | 52.457 | 85.438 | −17.854 | 1.00 | 58.29 | C |
| ATOM | 3523 | CZ | TYR | C | 17 | 51.926 | 86.620 | −18.395 | 1.00 | 61.48 | C |
| ATOM | 3524 | OH | TYR | C | 17 | 50.577 | 86.917 | −18.272 | 1.00 | 63.66 | C |
| ATOM | 3525 | C | TYR | C | 17 | 56.708 | 85.652 | −16.360 | 1.00 | 49.21 | C |
| ATOM | 3526 | O | TYR | C | 17 | 57.228 | 84.555 | −16.189 | 1.00 | 51.47 | C |
| ATOM | 3527 | N | TYR | C | 18 | 55.921 | 86.212 | −15.459 | 1.00 | 49.68 | C |
| ATOM | 3528 | CA | TYR | C | 18 | 55.600 | 85.528 | −14.218 | 1.00 | 46.63 | C |
| ATOM | 3529 | CB | TYR | C | 18 | 56.361 | 86.154 | −13.033 | 1.00 | 42.78 | C |
| ATOM | 3530 | CG | TYR | C | 18 | 56.242 | 87.663 | −12.969 | 1.00 | 35.46 | C |
| ATOM | 3531 | CD1 | TYR | C | 18 | 57.129 | 88.488 | −13.678 | 1.00 | 36.33 | C |
| ATOM | 3532 | CE1 | TYR | C | 18 | 56.996 | 89.880 | −13.663 | 1.00 | 33.08 | C |
| ATOM | 3533 | CD2 | TYR | C | 18 | 55.220 | 88.270 | −12.243 | 1.00 | 29.58 | C |
| ATOM | 3534 | CE2 | TYR | C | 18 | 55.083 | 89.665 | −12.218 | 1.00 | 29.35 | C |
| ATOM | 3535 | CZ | TYR | C | 18 | 55.968 | 90.465 | −12.921 | 1.00 | 27.89 | C |
| ATOM | 3536 | OH | TYR | C | 18 | 55.863 | 91.850 | −12.860 | 1.00 | 32.49 | C |
| ATOM | 3537 | C | TYR | C | 18 | 54.100 | 85.695 | −14.022 | 1.00 | 43.03 | C |
| ATOM | 3538 | O | TYR | C | 18 | 53.496 | 86.659 | −14.513 | 1.00 | 41.84 | C |
| ATOM | 3539 | N | SER | C | 19 | 53.496 | 84.758 | −13.314 | 1.00 | 44.03 | C |
| ATOM | 3540 | CA | SER | C | 19 | 52.067 | 84.849 | −13.068 | 1.00 | 49.05 | C |
| ATOM | 3541 | CB | SER | C | 19 | 51.430 | 83.455 | −13.036 | 1.00 | 48.59 | C |
| ATOM | 3542 | OG | SER | C | 19 | 52.115 | 82.585 | −12.147 | 1.00 | 50.14 | C |
| ATOM | 3543 | C | SER | C | 19 | 51.823 | 85.584 | −11.749 | 1.00 | 50.35 | C |
| ATOM | 3544 | O | SER | C | 19 | 52.661 | 85.567 | −10.839 | 1.00 | 46.39 | C |
| ATOM | 3545 | N | THR | C | 20 | 50.607 | 86.109 | −11.537 | 1.00 | 52.04 | C |
| ATOM | 3546 | CA | THR | C | 20 | 50.099 | 86.975 | −10.488 | 1.00 | 53.58 | C |
| ATOM | 3547 | CB | THR | C | 20 | 49.571 | 88.293 | −11.054 | 1.00 | 55.84 | C |
| ATOM | 3548 | OG1 | THR | C | 20 | 48.476 | 88.030 | −11.940 | 1.00 | 60.69 | C |
| ATOM | 3549 | CG2 | THR | C | 20 | 50.671 | 89.029 | −11.802 | 1.00 | 52.60 | C |
| ATOM | 3550 | C | THR | C | 20 | 49.003 | 86.277 | −9.703 | 1.00 | 56.21 | C |
| ATOM | 3551 | O | THR | C | 20 | 48.037 | 85.783 | −10.339 | 1.00 | 59.04 | C |
| ATOM | 3552 | N | PRO | C | 21 | 49.034 | 86.244 | −8.386 | 1.00 | 47.82 | C |
| ATOM | 3553 | CD | PRO | C | 21 | 48.004 | 85.901 | −7.826 | 1.00 | 47.40 | C |
| ATOM | 3554 | CA | PRO | C | 21 | 50.027 | 86.916 | −7.519 | 1.00 | 42.99 | C |
| ATOM | 3555 | CB | PRO | C | 21 | 49.335 | 86.932 | −6.151 | 1.00 | 43.36 | C |
| ATOM | 3556 | CG | PRO | C | 21 | 48.022 | 86.266 | −6.380 | 1.00 | 47.21 | C |
| ATOM | 3557 | C | PRO | C | 21 | 51.356 | 86.153 | −7.464 | 1.00 | 39.76 | C |
| ATOM | 3558 | O | PRO | C | 21 | 51.481 | 85.058 | −8.071 | 1.00 | 37.13 | C |
| ATOM | 3559 | N | ILE | C | 22 | 52.324 | 86.813 | −6.805 | 1.00 | 33.73 | C |
| ATOM | 3560 | CA | ILE | C | 22 | 53.646 | 86.216 | −6.676 | 1.00 | 31.36 | C |
| ATOM | 3561 | CB | ILE | C | 22 | 54.766 | 87.216 | −6.985 | 1.00 | 33.33 | C |
| ATOM | 3562 | CG2 | ILE | C | 22 | 56.125 | 86.572 | −6.755 | 1.00 | 33.08 | C |
| ATOM | 3563 | CG1 | ILE | C | 22 | 54.641 | 87.724 | −8.423 | 1.00 | 24.06 | C |
| ATOM | 3564 | CD1 | ILE | C | 22 | 55.565 | 88.876 | −8.747 | 1.00 | 24.35 | C |
| ATOM | 3565 | C | ILE | C | 22 | 53.824 | 85.628 | −5.269 | 1.00 | 34.54 | C |
| ATOM | 3566 | O | ILE | C | 22 | 53.977 | 86.348 | −4.285 | 1.00 | 28.13 | C |
| ATOM | 3567 | N | ALA | C | 23 | 53.864 | 84.299 | −5.155 | 1.00 | 28.78 | C |
| ATOM | 3568 | CA | ALA | C | 23 | 54.048 | 83.695 | −3.836 | 1.00 | 30.59 | C |
| ATOM | 3569 | CB | ALA | C | 23 | 53.437 | 82.316 | −3.834 | 1.00 | 31.70 | C |
| ATOM | 3570 | C | ALA | C | 23 | 55.517 | 83.599 | −3.412 | 1.00 | 30.12 | C |
| ATOM | 3571 | O | ALA | C | 23 | 56.399 | 83.517 | −4.266 | 1.00 | 25.80 | C |
| ATOM | 3572 | N | VAL | C | 24 | 55.784 | 83.613 | −2.102 | 1.00 | 32.21 | C |
| ATOM | 3573 | CA | VAL | C | 24 | 57.165 | 83.456 | −1.625 | 1.00 | 30.00 | C |

TABLE 3-continued

| ATOM | 3574 | CB | VAL | C | 24 | 57.272 | 83.290 | −0.087 | 1.00 | 35.52 | C |
| --- | --- | --- | --- | --- | --- | --- | --- | --- | --- | --- | --- |
| ATOM | 3575 | CG1 | VAL | C | 24 | 56.808 | 84.568 | 0.597 | 1.00 | 35.78 | C |
| ATOM | 3576 | CG2 | VAL | C | 24 | 56.459 | 82.108 | 0.378 | 1.00 | 39.11 | C |
| ATOM | 3577 | C | VAL | C | 24 | 57.673 | 82.175 | −2.253 | 1.00 | 31.34 | C |
| ATOM | 3578 | O | VAL | C | 24 | 56.918 | 81.231 | −2.413 | 1.00 | 28.53 | C |
| ATOM | 3579 | N | GLY | C | 25 | 58.947 | 82.128 | −2.603 | 1.00 | 30.39 | C |
| ATOM | 3580 | CA | GLY | C | 25 | 59.456 | 80.936 | −3.249 | 1.00 | 32.92 | C |
| ATOM | 3581 | C | GLY | C | 25 | 59.526 | 81.119 | −4.764 | 1.00 | 34.28 | C |
| ATOM | 3582 | O | GLY | C | 25 | 60.245 | 80.389 | −5.443 | 1.00 | 37.66 | C |
| ATOM | 3583 | N | THR | C | 26 | 58.785 | 82.086 | −5.296 | 1.00 | 25.38 | C |
| ATOM | 3584 | CA | THR | C | 26 | 58.791 | 82.337 | −6.735 | 1.00 | 33.97 | C |
| ATOM | 3585 | CB | THR | C | 26 | 57.652 | 83.304 | −7.169 | 1.00 | 27.23 | C |
| ATOM | 3586 | OG1 | THR | C | 26 | 56.390 | 82.761 | −6.784 | 1.00 | 35.09 | C |
| ATOM | 3587 | CG2 | THR | C | 26 | 57.650 | 83.514 | −8.696 | 1.00 | 27.35 | C |
| ATOM | 3588 | C | THR | C | 26 | 60.113 | 82.985 | −7.132 | 1.00 | 35.06 | C |
| ATOM | 3589 | O | THR | C | 26 | 60.614 | 83.888 | −6.441 | 1.00 | 32.34 | C |
| ATOM | 3590 | N | VAL | C | 27 | 60.662 | 82.523 | −8.246 | 1.00 | 27.52 | C |
| ATOM | 3591 | CA | VAL | C | 27 | 61.914 | 83.046 | −8.795 | 1.00 | 30.48 | C |
| ATOM | 3592 | CB | VAL | C | 27 | 62.901 | 81.912 | −9.116 | 1.00 | 35.60 | C |
| ATOM | 3593 | CG1 | VAL | C | 27 | 64.064 | 82.451 | −9.936 | 1.00 | 34.59 | C |
| ATOM | 3594 | CG2 | VAL | C | 27 | 63.398 | 81.269 | −7.830 | 1.00 | 34.12 | C |
| ATOM | 3595 | C | VAL | C | 27 | 61.632 | 83.751 | −10.114 | 1.00 | 32.83 | C |
| ATOM | 3596 | O | VAL | C | 27 | 60.908 | 83.216 | −10.953 | 1.00 | 31.75 | C |
| ATOM | 3597 | N | ILE | C | 28 | 62.168 | 84.956 | −10.310 | 1.00 | 31.95 | C |
| ATOM | 3598 | CA | ILE | C | 28 | 61.967 | 85.628 | −11.600 | 1.00 | 25.76 | C |
| ATOM | 3599 | CB | ILE | C | 28 | 61.234 | 86.962 | −11.482 | 1.00 | 25.19 | C |
| ATOM | 3600 | CG2 | ILE | C | 28 | 59.782 | 86.710 | −11.057 | 1.00 | 27.07 | C |
| ATOM | 3601 | CG1 | ILE | C | 28 | 61.981 | 87.915 | −10.530 | 1.00 | 20.91 | C |
| ATOM | 3602 | CD1 | ILE | C | 28 | 61.363 | 89.345 | −10.512 | 1.00 | 24.89 | C |
| ATOM | 3603 | C | ILE | C | 28 | 63.341 | 85.870 | −12.187 | 1.00 | 29.97 | C |
| ATOM | 3604 | O | ILE | C | 28 | 64.341 | 85.934 | −11.450 | 1.00 | 24.78 | C |
| ATOM | 3605 | N | ARG | C | 29 | 63.394 | 86.015 | −13.505 | 1.00 | 31.68 | C |
| ATOM | 3606 | CA | ARG | C | 29 | 64.673 | 86.191 | −14.185 | 1.00 | 33.25 | C |
| ATOM | 3607 | CB | ARG | C | 29 | 64.962 | 84.984 | −15.093 | 1.00 | 43.21 | C |
| ATOM | 3608 | CG | ARG | C | 29 | 65.539 | 83.751 | −14.395 | 1.00 | 55.79 | C |
| ATOM | 3609 | CD | ARG | C | 29 | 64.795 | 82.458 | −14.794 | 1.00 | 63.30 | C |
| ATOM | 3610 | NE | ARG | C | 29 | 63.873 | 82.000 | −13.745 | 1.00 | 66.73 | C |
| ATOM | 3611 | CZ | ARG | C | 29 | 62.570 | 81.762 | −13.917 | 1.00 | 68.37 | C |
| ATOM | 3612 | NH1 | ARG | C | 29 | 62.003 | 81.935 | −15.119 | 1.00 | 66.91 | C |
| ATOM | 3613 | NH2 | ARG | C | 29 | 61.831 | 81.353 | −12.883 | 1.00 | 61.65 | C |
| ATOM | 3614 | C | ARG | C | 29 | 64.794 | 87.444 | −15.020 | 1.00 | 30.28 | C |
| ATOM | 3615 | O | ARG | C | 29 | 63.956 | 87.732 | −15.872 | 1.00 | 29.65 | C |
| ATOM | 3616 | N | TYR | C | 30 | 65.867 | 88.181 | −14.778 | 1.00 | 32.96 | C |
| ATOM | 3617 | CA | TYR | C | 30 | 66.159 | 89.400 | −15.527 | 1.00 | 31.51 | C |
| ATOM | 3618 | CB | TYR | C | 30 | 66.759 | 90.437 | −14.590 | 1.00 | 27.74 | C |
| ATOM | 3619 | CG | TYR | C | 30 | 65.773 | 91.001 | −13.617 | 1.00 | 23.76 | C |
| ATOM | 3620 | CD1 | TYR | C | 30 | 65.257 | 90.224 | −12.571 | 1.00 | 28.24 | C |
| ATOM | 3621 | CE1 | TYR | C | 30 | 64.350 | 90.773 | −11.631 | 1.00 | 28.16 | C |
| ATOM | 3622 | CD2 | TYR | C | 30 | 65.360 | 92.327 | −13.718 | 1.00 | 27.82 | C |
| ATOM | 3623 | CE2 | TYR | C | 30 | 64.456 | 92.879 | −12.793 | 1.00 | 28.53 | C |
| ATOM | 3624 | CZ | TYR | C | 30 | 63.971 | 92.097 | −11.758 | 1.00 | 22.02 | C |
| ATOM | 3625 | OH | TYR | C | 30 | 63.160 | 92.703 | −10.848 | 1.00 | 24.79 | C |
| ATOM | 3626 | C | TYR | C | 30 | 67.161 | 89.133 | −16.641 | 1.00 | 25.91 | C |
| ATOM | 3627 | O | TYR | C | 30 | 68.007 | 88.254 | −16.520 | 1.00 | 26.19 | C |
| ATOM | 3628 | N | SER | C | 31 | 67.065 | 89.883 | −17.731 | 1.00 | 28.15 | C |
| ATOM | 3629 | CA | SER | C | 31 | 68.027 | 89.740 | −18.811 | 1.00 | 28.99 | C |
| ATOM | 3630 | CB | SER | C | 31 | 67.611 | 88.643 | −19.795 | 1.00 | 25.70 | C |
| ATOM | 3631 | OG | SER | C | 31 | 66.381 | 88.981 | −20.380 | 1.00 | 32.21 | C |
| ATOM | 3632 | C | SER | C | 31 | 68.124 | 91.082 | −19.518 | 1.00 | 30.27 | C |
| ATOM | 3633 | O | SER | C | 31 | 67.213 | 91.910 | −19.437 | 1.00 | 31.27 | C |
| ATOM | 3634 | N | CYS | C | 32 | 69.238 | 91.304 | −20.192 | 1.00 | 27.74 | C |
| ATOM | 3635 | CA | CYS | C | 32 | 69.457 | 92.558 | −20.890 | 1.00 | 32.43 | C |
| ATOM | 3636 | C | CYS | C | 32 | 69.378 | 92.286 | −22.369 | 1.00 | 36.47 | C |
| ATOM | 3637 | O | CYS | C | 32 | 69.611 | 91.146 | −22.819 | 1.00 | 33.53 | C |
| ATOM | 3638 | CB | CYS | C | 32 | 70.840 | 93.110 | −20.530 | 1.00 | 30.11 | C |
| ATOM | 3639 | SG | CYS | C | 32 | 70.999 | 93.505 | −18.757 | 1.00 | 30.29 | C |
| ATOM | 3640 | N | SER | C | 33 | 68.922 | 93.383 | −23.026 | 1.00 | 41.81 | C |
| ATOM | 3641 | CA | SER | C | 33 | 69.024 | 93.272 | −24.485 | 1.00 | 48.46 | C |
| ATOM | 3642 | CB | SER | C | 33 | 68.136 | 94.544 | −24.975 | 1.00 | 51.34 | C |
| ATOM | 3643 | OG | SER | C | 33 | 68.752 | 95.734 | −24.524 | 1.00 | 57.23 | C |
| ATOM | 3644 | C | SER | C | 33 | 70.449 | 92.848 | −24.842 | 1.00 | 54.01 | C |
| ATOM | 3645 | O | SER | C | 33 | 71.347 | 92.852 | −23.989 | 1.00 | 61.22 | C |
| ATOM | 3646 | N | GLY | C | 34 | 70.633 | 92.487 | −26.096 | 1.00 | 55.17 | C |
| ATOM | 3647 | CA | GLY | C | 34 | 71.928 | 91.989 | −26.558 | 1.00 | 49.56 | C |
| ATOM | 3648 | C | GLY | C | 34 | 73.161 | 92.877 | −26.748 | 1.00 | 47.38 | C |
| ATOM | 3649 | O | GLY | C | 34 | 74.279 | 92.377 | −26.942 | 1.00 | 46.07 | C |
| ATOM | 3650 | N | THR | C | 35 | 72.832 | 94.184 | −26.690 | 1.00 | 41.74 | C |
| ATOM | 3651 | CA | THR | C | 35 | 73.932 | 95.134 | −26.777 | 1.00 | 46.36 | C |
| ATOM | 3652 | CB | THR | C | 35 | 73.603 | 96.329 | −27.720 | 1.00 | 51.23 | C |

TABLE 3-continued

| ATOM | 3653 | OG1 | THR | C | 35 | 72.301 | 96.848 | −27.419 | 1.00 | 57.47 | C |
|---|---|---|---|---|---|---|---|---|---|---|---|
| ATOM | 3654 | CG2 | THR | C | 35 | 73.641 | 95.881 | −29.190 | 1.00 | 54.03 | C |
| ATOM | 3655 | C | THR | C | 35 | 74.305 | 95.658 | −25.383 | 1.00 | 43.55 | C |
| ATOM | 3656 | O | THR | C | 35 | 75.001 | 96.655 | −25.258 | 1.00 | 40.41 | C |
| ATOM | 3657 | N | PHE | C | 36 | 73.840 | 94.969 | −24.342 | 1.00 | 34.64 | C |
| ATOM | 3658 | CA | PHE | C | 36 | 74.133 | 95.342 | −22.965 | 1.00 | 31.17 | C |
| ATOM | 3659 | CB | PHE | C | 36 | 72.888 | 95.857 | −22.253 | 1.00 | 30.28 | C |
| ATOM | 3660 | CG | PHE | C | 36 | 72.414 | 97.176 | −22.750 | 1.00 | 32.70 | C |
| ATOM | 3661 | CD1 | PHE | C | 36 | 71.692 | 97.266 | −23.944 | 1.00 | 36.40 | C |
| ATOM | 3662 | CD2 | PHE | C | 36 | 72.729 | 98.343 | −22.054 | 1.00 | 33.13 | C |
| ATOM | 3663 | CE1 | PHE | C | 36 | 71.301 | 98.500 | −24.427 | 1.00 | 37.59 | C |
| ATOM | 3664 | CE2 | PHE | C | 36 | 72.345 | 99.588 | −22.528 | 1.00 | 32.44 | C |
| ATOM | 3665 | CZ | PHE | C | 36 | 71.629 | 99.673 | −23.718 | 1.00 | 38.52 | C |
| ATOM | 3666 | C | PHE | C | 36 | 74.612 | 94.107 | −22.239 | 1.00 | 34.05 | C |
| ATOM | 3667 | O | PHE | C | 36 | 74.432 | 93.001 | −22.727 | 1.00 | 31.93 | C |
| ATOM | 3668 | N | ARG | C | 37 | 75.236 | 94.292 | −21.079 | 1.00 | 28.78 | C |
| ATOM | 3669 | CA | ARG | C | 37 | 75.703 | 93.167 | −20.295 | 1.00 | 27.36 | C |
| ATOM | 3670 | CB | ARG | C | 37 | 77.233 | 93.140 | −20.235 | 1.00 | 27.49 | C |
| ATOM | 3671 | CG | ARG | C | 37 | 77.871 | 92.816 | −21.587 | 1.00 | 21.08 | C |
| ATOM | 3672 | CD | ARG | C | 37 | 77.403 | 91.440 | −22.049 | 1.00 | 27.97 | C |
| ATOM | 3673 | NE | ARG | C | 37 | 78.050 | 91.042 | −23.301 | 1.00 | 35.17 | C |
| ATOM | 3674 | CZ | ARG | C | 37 | 77.641 | 91.427 | −24.503 | 1.00 | 36.96 | C |
| ATOM | 3675 | NH1 | ARG | C | 37 | 76.572 | 92.213 | −24.620 | 1.00 | 32.52 | C |
| ATOM | 3676 | NH2 | ARG | C | 37 | 78.308 | 91.039 | −25.581 | 1.00 | 37.15 | C |
| ATOM | 3677 | C | ARG | C | 37 | 75.091 | 93.309 | −18.913 | 1.00 | 29.60 | C |
| ATOM | 3678 | O | ARG | C | 37 | 75.060 | 94.400 | −18.336 | 1.00 | 25.97 | C |
| ATOM | 3679 | N | LEU | C | 38 | 74.614 | 92.193 | −18.383 | 1.00 | 25.39 | C |
| ATOM | 3680 | CA | LEU | C | 38 | 73.952 | 92.202 | −17.083 | 1.00 | 27.27 | C |
| ATOM | 3681 | CB | LEU | C | 38 | 73.038 | 90.984 | −16.980 | 1.00 | 27.65 | C |
| ATOM | 3682 | CG | LEU | C | 38 | 72.221 | 90.971 | −15.692 | 1.00 | 35.28 | C |
| ATOM | 3683 | CD1 | LEU | C | 38 | 70.799 | 91.354 | −16.019 | 1.00 | 33.06 | C |
| ATOM | 3684 | CD2 | LEU | C | 38 | 72.278 | 89.589 | −15.051 | 1.00 | 40.58 | C |
| ATOM | 3685 | C | LEU | C | 38 | 74.951 | 92.203 | −15.926 | 1.00 | 24.03 | C |
| ATOM | 3686 | O | LEU | C | 38 | 75.851 | 91.376 | −15.892 | 1.00 | 27.79 | C |
| ATOM | 3687 | N | ILE | C | 39 | 74.794 | 93.146 | −15.001 | 1.00 | 25.30 | C |
| ATOM | 3688 | CA | ILE | C | 39 | 75.654 | 93.264 | −13.819 | 1.00 | 26.06 | C |
| ATOM | 3689 | CB | ILE | C | 39 | 76.255 | 94.707 | −13.686 | 1.00 | 31.18 | C |
| ATOM | 3690 | CG2 | ILE | C | 39 | 77.130 | 94.813 | −12.455 | 1.00 | 28.29 | C |
| ATOM | 3691 | CG1 | ILE | C | 39 | 77.057 | 95.071 | −14.955 | 1.00 | 37.49 | C |
| ATOM | 3692 | CD1 | ILE | C | 39 | 78.059 | 94.022 | −15.415 | 1.00 | 46.78 | C |
| ATOM | 3693 | C | ILE | C | 39 | 74.787 | 92.979 | −12.590 | 1.00 | 27.54 | C |
| ATOM | 3694 | O | ILE | C | 39 | 73.807 | 93.683 | −12.327 | 1.00 | 21.11 | C |
| ATOM | 3695 | N | GLY | C | 40 | 75.140 | 91.950 | −11.829 | 1.00 | 28.46 | C |
| ATOM | 3696 | CA | GLY | C | 40 | 74.351 | 91.619 | −10.654 | 1.00 | 28.45 | C |
| ATOM | 3697 | C | GLY | C | 40 | 73.691 | 90.275 | −10.901 | 1.00 | 31.11 | C |
| ATOM | 3698 | O | GLY | C | 40 | 73.762 | 89.752 | −12.008 | 1.00 | 27.47 | C |
| ATOM | 3699 | N | GLU | C | 41 | 73.057 | 89.713 | −9.876 | 1.00 | 32.89 | C |
| ATOM | 3700 | CA | GLU | C | 41 | 72.395 | 88.411 | −9.994 | 1.00 | 37.70 | C |
| ATOM | 3701 | CB | GLU | C | 41 | 72.006 | 87.900 | −8.597 | 1.00 | 35.85 | C |
| ATOM | 3702 | CG | GLU | C | 41 | 71.217 | 86.601 | −8.624 | 1.00 | 47.53 | C |
| ATOM | 3703 | CD | GLU | C | 41 | 71.983 | 85.447 | −9.235 | 1.00 | 48.84 | C |
| ATOM | 3704 | OE1 | GLU | C | 41 | 71.419 | 84.733 | −10.088 | 1.00 | 44.21 | C |
| ATOM | 3705 | OE2 | GLU | C | 41 | 73.153 | 85.252 | −8.842 | 1.00 | 56.76 | C |
| ATOM | 3706 | C | GLU | C | 41 | 71.161 | 88.510 | −10.893 | 1.00 | 32.10 | C |
| ATOM | 3707 | O | GLU | C | 41 | 70.336 | 89.404 | −10.718 | 1.00 | 31.37 | C |
| ATOM | 3708 | N | LYS | C | 42 | 71.033 | 87.604 | −11.857 | 1.00 | 33.31 | C |
| ATOM | 3709 | CA | LYS | C | 42 | 69.879 | 87.647 | −12.760 | 1.00 | 33.67 | C |
| ATOM | 3710 | CB | LYS | C | 42 | 70.207 | 86.955 | −14.069 | 1.00 | 33.01 | C |
| ATOM | 3711 | CG | LYS | C | 42 | 70.550 | 85.515 | −13.891 | 1.00 | 39.88 | C |
| ATOM | 3712 | CD | LYS | C | 42 | 70.862 | 84.895 | −15.238 | 1.00 | 43.23 | C |
| ATOM | 3713 | CE | LYS | C | 42 | 71.922 | 83.820 | −15.105 | 1.00 | 48.14 | C |
| ATOM | 3714 | NZ | LYS | C | 42 | 71.648 | 82.872 | −13.965 | 1.00 | 52.44 | C |
| ATOM | 3715 | C | LYS | C | 42 | 68.591 | 87.038 | −12.185 | 1.00 | 34.36 | C |
| ATOM | 3716 | O | LYS | C | 42 | 67.509 | 87.306 | −12.687 | 1.00 | 37.69 | C |
| ATOM | 3717 | N | SER | C | 43 | 68.685 | 86.265 | −11.117 | 1.00 | 25.52 | C |
| ATOM | 3718 | CA | SER | C | 43 | 67.472 | 85.664 | −10.565 | 1.00 | 31.67 | C |
| ATOM | 3719 | CB | SER | C | 43 | 67.668 | 84.155 | −10.331 | 1.00 | 28.31 | C |
| ATOM | 3720 | OG | SER | C | 43 | 67.869 | 83.464 | −11.537 | 1.00 | 39.90 | C |
| ATOM | 3721 | C | SER | C | 43 | 67.099 | 86.274 | −9.233 | 1.00 | 29.32 | C |
| ATOM | 3722 | O | SER | C | 43 | 67.945 | 86.318 | −8.342 | 1.00 | 31.30 | C |
| ATOM | 3723 | N | LEU | C | 44 | 65.853 | 86.735 | −9.087 | 1.00 | 27.40 | C |
| ATOM | 3724 | CA | LEU | C | 44 | 65.393 | 87.267 | −7.808 | 1.00 | 28.37 | C |
| ATOM | 3725 | CB | LEU | C | 44 | 64.744 | 88.638 | −7.931 | 1.00 | 27.60 | C |
| ATOM | 3726 | CG | LEU | C | 44 | 65.498 | 89.876 | −8.393 | 1.00 | 38.75 | C |
| ATOM | 3727 | CD1 | LEU | C | 44 | 64.700 | 91.149 | −7.896 | 1.00 | 26.06 | C |
| ATOM | 3728 | CD2 | LEU | C | 44 | 66.913 | 89.846 | −7.907 | 1.00 | 39.16 | C |
| ATOM | 3729 | C | LEU | C | 44 | 64.352 | 86.315 | −7.218 | 1.00 | 29.49 | C |
| ATOM | 3730 | O | LEU | C | 44 | 63.469 | 85.796 | −7.914 | 1.00 | 35.15 | C |
| ATOM | 3731 | N | LEU | C | 45 | 64.434 | 86.137 | −5.919 | 1.00 | 25.55 | C |

TABLE 3-continued

| | | | | | | | | | | |
|---|---|---|---|---|---|---|---|---|---|---|
| ATOM | 3732 | CA | LEU | C | 45 | 63.560 | 85.222 | −5.230 | 1.00 | 28.43 C |
| ATOM | 3733 | CB | LEU | C | 45 | 64.412 | 84.210 | −4.469 | 1.00 | 28.67 C |
| ATOM | 3734 | CG | LEU | C | 45 | 63.709 | 83.269 | −3.493 | 1.00 | 30.62 C |
| ATOM | 3735 | CD1 | LEU | C | 45 | 62.896 | 82.195 | −4.244 | 1.00 | 32.56 C |
| ATOM | 3736 | CD2 | LEU | C | 45 | 64.798 | 82.623 | −2.649 | 1.00 | 31.55 C |
| ATOM | 3737 | C | LEU | C | 45 | 62.664 | 85.961 | −4.263 | 1.00 | 28.71 C |
| ATOM | 3738 | O | LEU | C | 45 | 63.094 | 86.894 | −3.558 | 1.00 | 21.68 C |
| ATOM | 3739 | N | CYS | C | 46 | 61.410 | 85.547 | −4.238 | 1.00 | 25.91 C |
| ATOM | 3740 | CA | CYS | C | 46 | 60.455 | 86.152 | −3.343 | 1.00 | 26.90 C |
| ATOM | 3741 | C | CYS | C | 46 | 60.610 | 85.392 | −2.032 | 1.00 | 30.25 C |
| ATOM | 3742 | O | CYS | C | 46 | 60.448 | 84.173 | −1.980 | 1.00 | 28.51 C |
| ATOM | 3743 | CB | CYS | C | 46 | 59.021 | 86.026 | −3.908 | 1.00 | 28.02 C |
| ATOM | 3744 | SG | CYS | C | 46 | 57.741 | 86.546 | −2.696 | 1.00 | 28.63 C |
| ATOM | 3745 | N | ILE | C | 47 | 60.925 | 86.115 | −0.971 | 1.00 | 21.11 C |
| ATOM | 3746 | CA | ILE | C | 47 | 61.120 | 85.484 | 0.314 | 1.00 | 24.65 C |
| ATOM | 3747 | CB | ILE | C | 47 | 62.619 | 85.501 | 0.722 | 1.00 | 32.62 C |
| ATOM | 3748 | CG2 | ILE | C | 47 | 63.505 | 84.878 | −0.358 | 1.00 | 27.06 C |
| ATOM | 3749 | CG1 | ILE | C | 47 | 63.050 | 86.958 | 0.959 | 1.00 | 25.64 C |
| ATOM | 3750 | CD1 | ILE | C | 47 | 64.429 | 87.119 | 1.592 | 1.00 | 32.03 C |
| ATOM | 3751 | C | ILE | C | 47 | 60.431 | 86.274 | 1.421 | 1.00 | 31.05 C |
| ATOM | 3752 | O | ILE | C | 47 | 59.931 | 87.399 | 1.226 | 1.00 | 22.58 C |
| ATOM | 3753 | N | THR | C | 48 | 60.421 | 85.669 | 2.596 | 1.00 | 27.58 C |
| ATOM | 3754 | CA | THR | C | 48 | 59.964 | 86.388 | 3.764 | 1.00 | 27.51 C |
| ATOM | 3755 | CB | THR | C | 48 | 58.584 | 85.987 | 4.273 | 1.00 | 28.85 C |
| ATOM | 3756 | OG1 | THR | C | 48 | 58.303 | 86.778 | 5.426 | 1.00 | 25.48 C |
| ATOM | 3757 | CG2 | THR | C | 48 | 58.490 | 84.526 | 4.619 | 1.00 | 26.50 C |
| ATOM | 3758 | C | THR | C | 48 | 61.001 | 86.164 | 4.839 | 1.00 | 29.22 C |
| ATOM | 3759 | O | THR | C | 48 | 61.455 | 85.049 | 5.060 | 1.00 | 29.40 C |
| ATOM | 3760 | N | LYS | C | 49 | 61.445 | 87.243 | 5.463 | 1.00 | 27.29 C |
| ATOM | 3761 | CA | LYS | C | 49 | 62.425 | 87.112 | 6.522 | 1.00 | 31.22 C |
| ATOM | 3762 | CB | LYS | C | 49 | 63.478 | 88.220 | 6.427 | 1.00 | 26.53 C |
| ATOM | 3763 | CG | LYS | C | 49 | 64.229 | 88.239 | 5.134 | 1.00 | 35.41 C |
| ATOM | 3764 | CD | LYS | C | 49 | 65.703 | 88.351 | 5.346 | 1.00 | 40.12 C |
| ATOM | 3765 | CE | LYS | C | 49 | 66.262 | 87.134 | 6.055 | 1.00 | 42.32 C |
| ATOM | 3766 | NZ | LYS | C | 49 | 67.729 | 87.262 | 6.166 | 1.00 | 46.64 C |
| ATOM | 3767 | C | LYS | C | 49 | 61.745 | 87.219 | 7.877 | 1.00 | 33.53 C |
| ATOM | 3768 | O | LYS | C | 49 | 62.249 | 86.692 | 8.856 | 1.00 | 30.36 C |
| ATOM | 3769 | N | ASP | C | 50 | 60.596 | 87.896 | 7.952 | 1.00 | 25.34 C |
| ATOM | 3770 | CA | ASP | C | 50 | 59.978 | 88.083 | 9.253 | 1.00 | 26.98 C |
| ATOM | 3771 | CB | ASP | C | 50 | 59.961 | 89.579 | 9.597 | 1.00 | 25.16 C |
| ATOM | 3772 | CG | ASP | C | 50 | 59.154 | 90.397 | 8.607 | 1.00 | 27.41 C |
| ATOM | 3773 | OD1 | ASP | C | 50 | 58.459 | 89.768 | 7.749 | 1.00 | 22.49 C |
| ATOM | 3774 | OD2 | ASP | C | 50 | 59.207 | 91.664 | 8.693 | 1.00 | 26.37 C |
| ATOM | 3775 | C | ASP | C | 50 | 58.598 | 87.492 | 9.365 | 1.00 | 25.28 C |
| ATOM | 3776 | O | ASP | C | 50 | 57.883 | 87.770 | 10.321 | 1.00 | 24.69 C |
| ATOM | 3777 | N | LYS | C | 51 | 58.247 | 86.664 | 8.386 | 1.00 | 26.19 C |
| ATOM | 3778 | CA | LYS | C | 51 | 56.948 | 86.006 | 8.319 | 1.00 | 23.97 C |
| ATOM | 3779 | CB | LYS | C | 51 | 56.717 | 85.091 | 9.526 | 1.00 | 31.09 C |
| ATOM | 3780 | CG | LYS | C | 51 | 57.749 | 84.021 | 9.749 | 1.00 | 32.84 C |
| ATOM | 3781 | CD | LYS | C | 51 | 57.625 | 82.919 | 8.769 | 1.00 | 44.41 C |
| ATOM | 3782 | CE | LYS | C | 51 | 58.505 | 81.752 | 9.179 | 1.00 | 52.55 C |
| ATOM | 3783 | NZ | LYS | C | 51 | 58.266 | 81.397 | 10.605 | 1.00 | 51.40 C |
| ATOM | 3784 | C | LYS | C | 51 | 55.791 | 86.996 | 8.241 | 1.00 | 25.78 C |
| ATOM | 3785 | O | LYS | C | 51 | 54.660 | 86.628 | 8.510 | 1.00 | 25.03 C |
| ATOM | 3786 | N | VAL | C | 52 | 56.048 | 88.252 | 7.896 | 1.00 | 25.78 C |
| ATOM | 3787 | CA | VAL | C | 52 | 54.937 | 89.195 | 7.758 | 1.00 | 23.31 C |
| ATOM | 3788 | CB | VAL | C | 52 | 54.976 | 90.286 | 8.894 | 1.00 | 30.82 C |
| ATOM | 3789 | CG1 | VAL | C | 52 | 53.786 | 91.197 | 8.802 | 1.00 | 27.39 C |
| ATOM | 3790 | CG2 | VAL | C | 52 | 54.946 | 89.611 | 10.264 | 1.00 | 33.79 C |
| ATOM | 3791 | C | VAL | C | 52 | 55.085 | 89.832 | 6.376 | 1.00 | 29.16 C |
| ATOM | 3792 | O | VAL | C | 52 | 54.193 | 89.764 | 5.537 | 1.00 | 25.28 C |
| ATOM | 3793 | N | ASP | C | 53 | 56.248 | 90.433 | 6.146 | 1.00 | 31.64 C |
| ATOM | 3794 | CA | ASP | C | 53 | 56.575 | 91.099 | 4.892 | 1.00 | 27.94 C |
| ATOM | 3795 | CB | ASP | C | 53 | 57.647 | 92.167 | 5.150 | 1.00 | 28.37 C |
| ATOM | 3796 | CG | ASP | C | 53 | 57.189 | 93.235 | 6.132 | 1.00 | 30.66 C |
| ATOM | 3797 | OD1 | ASP | C | 53 | 56.323 | 94.069 | 5.744 | 1.00 | 20.78 C |
| ATOM | 3798 | OD2 | ASP | C | 53 | 57.700 | 93.245 | 7.287 | 1.00 | 27.56 C |
| ATOM | 3799 | C | ASP | C | 53 | 57.112 | 90.126 | 3.837 | 1.00 | 23.86 C |
| ATOM | 3800 | O | ASP | C | 53 | 57.862 | 89.212 | 4.164 | 1.00 | 24.61 C |
| ATOM | 3801 | N | GLY | C | 54 | 56.735 | 90.327 | 2.573 | 1.00 | 26.63 C |
| ATOM | 3802 | CA | GLY | C | 54 | 57.253 | 89.489 | 1.476 | 1.00 | 20.87 C |
| ATOM | 3803 | C | GLY | C | 54 | 58.190 | 90.420 | 0.730 | 1.00 | 25.47 C |
| ATOM | 3804 | O | GLY | C | 54 | 57.814 | 91.563 | 0.435 | 1.00 | 19.97 C |
| ATOM | 3805 | N | THR | C | 55 | 59.422 | 89.999 | 0.459 | 1.00 | 22.42 C |
| ATOM | 3806 | CA | THR | C | 55 | 60.345 | 90.907 | −0.247 | 1.00 | 21.92 C |
| ATOM | 3807 | CB | THR | C | 55 | 61.326 | 91.591 | 0.760 | 1.00 | 24.17 C |
| ATOM | 3808 | OG1 | THR | C | 55 | 61.999 | 92.669 | 0.106 | 1.00 | 24.68 C |
| ATOM | 3809 | CG2 | THR | C | 55 | 62.401 | 90.597 | 1.251 | 1.00 | 24.06 C |
| ATOM | 3810 | C | THR | C | 55 | 61.184 | 90.153 | −1.284 | 1.00 | 22.33 C |

TABLE 3-continued

| | | | | | | | | | |
|---|---|---|---|---|---|---|---|---|---|
| ATOM | 3811 | O | THR | C | 55 | 61.298 | 88.929 | −1.209 | 1.00 | 24.76 C |
| ATOM | 3812 | N | TRP | C | 56 | 61.767 | 90.882 | −2.230 | 1.00 | 22.04 C |
| ATOM | 3813 | CA | TRP | C | 56 | 62.637 | 90.281 | −3.226 | 1.00 | 21.23 C |
| ATOM | 3814 | CB | TRP | C | 56 | 62.689 | 91.142 | −4.506 | 1.00 | 28.51 C |
| ATOM | 3815 | CG | TRP | C | 56 | 61.377 | 91.081 | −5.223 | 1.00 | 25.63 C |
| ATOM | 3816 | CD2 | TRP | C | 56 | 60.853 | 89.962 | −5.970 | 1.00 | 26.11 C |
| ATOM | 3817 | CE2 | TRP | C | 56 | 59.512 | 90.266 | −6.287 | 1.00 | 23.40 C |
| ATOM | 3818 | CE3 | TRP | C | 56 | 61.384 | 88.723 | −6.383 | 1.00 | 25.94 C |
| ATOM | 3819 | CD1 | TRP | C | 56 | 60.374 | 91.988 | −5.141 | 1.00 | 23.59 C |
| ATOM | 3820 | NE1 | TRP | C | 56 | 59.249 | 91.513 | −5.771 | 1.00 | 25.69 C |
| ATOM | 3821 | CZ2 | TRP | C | 56 | 58.679 | 89.384 | −7.003 | 1.00 | 24.25 C |
| ATOM | 3822 | CZ3 | TRP | C | 56 | 60.555 | 87.832 | −7.095 | 1.00 | 26.08 C |
| ATOM | 3823 | CH2 | TRP | C | 56 | 59.209 | 88.177 | −7.398 | 1.00 | 29.68 C |
| ATOM | 3824 | C | TRP | C | 56 | 63.994 | 90.185 | −2.504 | 1.00 | 22.58 C |
| ATOM | 3825 | O | TRP | C | 56 | 64.379 | 91.119 | −1.805 | 1.00 | 23.17 C |
| ATOM | 3826 | N | ASP | C | 57 | 64.698 | 89.064 | −2.660 | 1.00 | 24.44 C |
| ATOM | 3827 | CA | ASP | C | 57 | 65.949 | 88.838 | −1.931 | 1.00 | 26.43 C |
| ATOM | 3828 | CB | ASP | C | 57 | 66.293 | 87.334 | −1.894 | 1.00 | 26.66 C |
| ATOM | 3829 | CG | ASP | C | 57 | 66.722 | 86.762 | −3.256 | 1.00 | 31.79 C |
| ATOM | 3830 | OD1 | ASP | C | 57 | 67.168 | 85.599 | −3.268 | 1.00 | 36.29 C |
| ATOM | 3831 | OD2 | ASP | C | 57 | 66.613 | 87.435 | −4.298 | 1.00 | 30.66 C |
| ATOM | 3832 | C | ASP | C | 57 | 67.173 | 89.647 | −2.317 | 1.00 | 29.20 C |
| ATOM | 3833 | O | ASP | C | 57 | 68.161 | 89.651 | −1.589 | 1.00 | 32.18 C |
| ATOM | 3834 | N | LYS | C | 58 | 67.084 | 90.363 | −3.428 | 1.00 | 31.78 C |
| ATOM | 3835 | CA | LYS | C | 58 | 68.180 | 91.182 | −3.928 | 1.00 | 31.51 C |
| ATOM | 3836 | CB | LYS | C | 58 | 69.081 | 90.366 | −4.866 | 1.00 | 37.98 C |
| ATOM | 3837 | CG | LYS | C | 58 | 70.061 | 89.452 | −4.166 | 1.00 | 49.29 C |
| ATOM | 3838 | CD | LYS | C | 58 | 69.648 | 87.987 | −4.237 | 1.00 | 58.25 C |
| ATOM | 3839 | CE | LYS | C | 58 | 69.569 | 87.484 | −5.686 | 1.00 | 55.39 C |
| ATOM | 3840 | NZ | LYS | C | 58 | 68.893 | 86.136 | −5.803 | 1.00 | 46.73 C |
| ATOM | 3841 | C | LYS | C | 58 | 67.614 | 92.311 | −4.741 | 1.00 | 29.28 C |
| ATOM | 3842 | O | LYS | C | 58 | 66.442 | 92.301 | −5.106 | 1.00 | 29.16 C |
| ATOM | 3843 | N | PRO | C | 59 | 68.429 | 93.340 | −4.958 | 1.00 | 32.29 C |
| ATOM | 3844 | CD | PRO | C | 59 | 69.835 | 93.582 | −4.659 | 1.00 | 26.68 C |
| ATOM | 3845 | CA | PRO | C | 59 | 67.912 | 94.387 | −5.841 | 1.00 | 24.28 C |
| ATOM | 3846 | CB | PRO | C | 59 | 68.919 | 95.530 | −5.673 | 1.00 | 28.93 C |
| ATOM | 3847 | CG | PRO | C | 59 | 70.198 | 94.856 | −5.368 | 1.00 | 30.90 C |
| ATOM | 3848 | C | PRO | C | 59 | 67.949 | 93.982 | −7.321 | 1.00 | 29.24 C |
| ATOM | 3849 | O | PRO | C | 59 | 68.694 | 93.012 | −7.627 | 1.00 | 23.42 C |
| ATOM | 3850 | N | ALA | C | 60 | 67.208 | 94.594 | −8.172 | 1.00 | 28.57 C |
| ATOM | 3851 | CA | ALA | C | 60 | 67.247 | 94.196 | −9.570 | 1.00 | 31.26 C |
| ATOM | 3852 | CB | ALA | C | 60 | 66.284 | 95.039 | −10.363 | 1.00 | 24.31 C |
| ATOM | 3853 | C | ALA | C | 60 | 68.674 | 94.376 | −10.126 | 1.00 | 32.02 C |
| ATOM | 3854 | O | ALA | C | 60 | 69.403 | 95.259 | −9.700 | 1.00 | 29.35 C |
| ATOM | 3855 | N | PRO | C | 61 | 69.101 | 93.498 | −11.046 | 1.00 | 29.11 C |
| ATOM | 3856 | CD | PRO | C | 61 | 68.453 | 92.245 | −11.466 | 1.00 | 26.65 C |
| ATOM | 3857 | CA | PRO | C | 61 | 70.449 | 93.643 | −11.625 | 1.00 | 26.17 C |
| ATOM | 3858 | CB | PRO | C | 61 | 70.690 | 92.296 | −12.307 | 1.00 | 28.95 C |
| ATOM | 3859 | CG | PRO | C | 61 | 69.280 | 91.838 | −12.676 | 1.00 | 27.22 C |
| ATOM | 3860 | C | PRO | C | 61 | 70.327 | 94.812 | −12.632 | 1.00 | 26.90 C |
| ATOM | 3861 | O | PRO | C | 61 | 69.221 | 95.303 | −12.859 | 1.00 | 22.51 C |
| ATOM | 3862 | N | LYS | C | 62 | 71.430 | 95.280 | −13.208 | 1.00 | 21.80 C |
| ATOM | 3863 | CA | LYS | C | 62 | 71.379 | 96.409 | −14.158 | 1.00 | 24.26 C |
| ATOM | 3864 | CB | LYS | C | 62 | 72.173 | 97.615 | −13.637 | 1.00 | 26.24 C |
| ATOM | 3865 | CG | LYS | C | 62 | 71.776 | 98.107 | −12.246 | 1.00 | 39.00 C |
| ATOM | 3866 | CD | LYS | C | 62 | 71.465 | 99.585 | −12.222 | 1.00 | 41.85 C |
| ATOM | 3867 | CE | LYS | C | 62 | 71.357 | 100.084 | −10.800 | 1.00 | 46.78 C |
| ATOM | 3868 | NZ | LYS | C | 62 | 72.692 | 100.117 | −10.118 | 1.00 | 55.22 C |
| ATOM | 3869 | C | LYS | C | 62 | 71.955 | 96.043 | −15.507 | 1.00 | 21.61 C |
| ATOM | 3870 | O | LYS | C | 62 | 72.735 | 95.097 | −15.607 | 1.00 | 25.68 C |
| ATOM | 3871 | N | CYS | C | 63 | 71.585 | 96.790 | −16.549 | 1.00 | 27.02 C |
| ATOM | 3872 | CA | CYS | C | 63 | 72.113 | 96.526 | −17.903 | 1.00 | 27.02 C |
| ATOM | 3873 | C | CYS | C | 63 | 73.118 | 97.601 | −18.302 | 1.00 | 30.37 C |
| ATOM | 3874 | O | CYS | C | 63 | 72.751 | 98.758 | −18.416 | 1.00 | 32.00 C |
| ATOM | 3875 | CB | CYS | C | 63 | 70.989 | 96.504 | −18.932 | 1.00 | 28.91 C |
| ATOM | 3876 | SG | CYS | C | 63 | 69.851 | 95.146 | −18.602 | 1.00 | 29.20 C |
| ATOM | 3877 | N | GLU | C | 64 | 74.376 | 97.213 | −18.514 | 1.00 | 23.24 C |
| ATOM | 3878 | CA | GLU | C | 64 | 75.417 | 98.167 | −18.890 | 1.00 | 30.86 C |
| ATOM | 3879 | CB | GLU | C | 64 | 76.707 | 97.873 | −18.098 | 1.00 | 31.31 C |
| ATOM | 3880 | CG | GLU | C | 64 | 77.231 | 99.028 | −17.228 | 1.00 | 39.58 C |
| ATOM | 3881 | CD | GLU | C | 64 | 78.383 | 98.616 | −16.287 | 1.00 | 40.40 C |
| ATOM | 3882 | OE1 | GLU | C | 64 | 79.134 | 97.679 | −16.620 | 1.00 | 26.79 C |
| ATOM | 3883 | OE2 | GLU | C | 64 | 78.543 | 99.238 | −15.208 | 1.00 | 48.25 C |
| ATOM | 3884 | C | GLU | C | 64 | 75.703 | 98.035 | −20.380 | 1.00 | 25.87 C |
| ATOM | 3885 | O | GLU | C | 64 | 75.849 | 96.923 | −20.882 | 1.00 | 19.45 C |
| ATOM | 3886 | N | TYR | C | 65 | 75.782 | 99.155 | −21.093 | 1.00 | 25.32 C |
| ATOM | 3887 | CA | TYR | C | 65 | 76.106 | 99.110 | −22.530 | 1.00 | 31.90 C |
| ATOM | 3888 | CB | TYR | C | 65 | 76.325 | 100.536 | −23.061 | 1.00 | 36.00 C |
| ATOM | 3889 | CG | TYR | C | 65 | 76.254 | 100.650 | −24.570 | 1.00 | 42.53 C |

TABLE 3-continued

| ATOM | 3890 | CD1 | TYR | C | 65 | 75.041 | 100.470 | -25.238 | 1.00 | 42.78 | C |
| --- | --- | --- | --- | --- | --- | --- | --- | --- | --- | --- | --- |
| ATOM | 3891 | CE1 | TYR | C | 65 | 74.951 | 100.568 | -26.621 | 1.00 | 40.68 | C |
| ATOM | 3892 | CD2 | TYR | C | 65 | 77.396 | 100.937 | -25.331 | 1.00 | 48.40 | C |
| ATOM | 3893 | CE2 | TYR | C | 65 | 77.321 | 101.040 | -26.729 | 1.00 | 48.66 | C |
| ATOM | 3894 | CZ | TYR | C | 65 | 76.086 | 100.848 | -27.366 | 1.00 | 48.38 | C |
| ATOM | 3895 | OH | TYR | C | 65 | 75.998 | 100.897 | -28.750 | 1.00 | 49.96 | C |
| ATOM | 3896 | C | TYR | C | 65 | 77.407 | 98.304 | -22.704 | 1.00 | 26.60 | C |
| ATOM | 3897 | O | TYR | C | 65 | 78.410 | 98.634 | -22.101 | 1.00 | 27.68 | C |
| ATOM | 3898 | N | PHE | C | 66 | 77.404 | 97.279 | -23.541 | 1.00 | 24.63 | C |
| ATOM | 3899 | CA | PHE | C | 66 | 78.583 | 96.428 | -23.736 | 1.00 | 25.64 | C |
| ATOM | 3900 | CB | PHE | C | 66 | 78.250 | 95.339 | -24.776 | 1.00 | 30.86 | C |
| ATOM | 3901 | CG | PHE | C | 66 | 79.408 | 94.427 | -25.130 | 1.00 | 30.23 | C |
| ATOM | 3902 | CD1 | PHE | C | 66 | 80.137 | 93.775 | -24.143 | 1.00 | 25.24 | C |
| ATOM | 3903 | CD2 | PHE | C | 66 | 79.753 | 94.208 | -26.481 | 1.00 | 33.99 | C |
| ATOM | 3904 | CE1 | PHE | C | 66 | 81.206 | 92.899 | -24.478 | 1.00 | 28.31 | C |
| ATOM | 3905 | CE2 | PHE | C | 66 | 80.822 | 93.329 | -26.838 | 1.00 | 29.10 | C |
| ATOM | 3906 | CZ | PHE | C | 66 | 81.550 | 92.672 | -25.826 | 1.00 | 27.94 | C |
| ATOM | 3907 | C | PHE | C | 66 | 79.896 | 97.121 | -24.133 | 1.00 | 32.19 | C |
| ATOM | 3908 | O | PHE | C | 66 | 79.931 | 97.955 | -25.044 | 1.00 | 29.06 | C |
| ATOM | 3909 | N | ASN | C | 67 | 80.977 | 96.766 | -23.440 | 1.00 | 25.19 | C |
| ATOM | 3910 | CA | ASN | C | 67 | 82.297 | 97.296 | -23.754 | 1.00 | 27.44 | C |
| ATOM | 3911 | CB | ASN | C | 67 | 82.845 | 98.203 | -22.639 | 1.00 | 28.12 | C |
| ATOM | 3912 | CG | ASN | C | 67 | 84.126 | 98.921 | -23.066 | 1.00 | 33.33 | C |
| ATOM | 3913 | OD1 | ASN | C | 67 | 84.904 | 98.390 | -23.870 | 1.00 | 27.62 | C |
| ATOM | 3914 | ND2 | ASN | C | 67 | 84.356 | 100.126 | -22.528 | 1.00 | 28.36 | C |
| ATOM | 3915 | C | ASN | C | 67 | 83.245 | 96.106 | -23.942 | 1.00 | 30.05 | C |
| ATOM | 3916 | O | ASN | C | 67 | 83.706 | 95.489 | -22.967 | 1.00 | 18.34 | C |
| ATOM | 3917 | N | LYS | C | 68 | 83.565 | 95.816 | -25.199 | 1.00 | 24.67 | C |
| ATOM | 3918 | CA | LYS | C | 68 | 84.428 | 94.686 | -25.511 | 1.00 | 29.80 | C |
| ATOM | 3919 | CB | LYS | C | 68 | 84.491 | 94.441 | -27.024 | 1.00 | 29.48 | C |
| ATOM | 3920 | CG | LYS | C | 68 | 85.095 | 95.574 | -27.875 | 1.00 | 39.59 | C |
| ATOM | 3921 | CD | LYS | C | 68 | 85.233 | 95.076 | -29.326 | 1.00 | 45.75 | C |
| ATOM | 3922 | CE | LYS | C | 68 | 85.993 | 96.016 | -30.254 | 1.00 | 52.45 | C |
| ATOM | 3923 | NZ | LYS | C | 68 | 85.111 | 96.916 | -31.073 | 1.00 | 56.09 | C |
| ATOM | 3924 | C | LYS | C | 68 | 85.821 | 94.831 | -24.995 | 1.00 | 32.29 | C |
| ATOM | 3925 | O | LYS | C | 68 | 86.541 | 93.833 | -24.921 | 1.00 | 27.75 | C |
| ATOM | 3926 | N | TYR | C | 69 | 86.237 | 96.059 | -24.663 | 1.00 | 25.84 | C |
| ATOM | 3927 | CA | TYR | C | 69 | 87.599 | 96.229 | -24.153 | 1.00 | 24.63 | C |
| ATOM | 3928 | CB | TYR | C | 69 | 88.147 | 97.625 | -24.434 | 1.00 | 27.26 | C |
| ATOM | 3929 | CG | TYR | C | 69 | 88.161 | 97.948 | -25.876 | 1.00 | 31.88 | C |
| ATOM | 3930 | CD1 | TYR | C | 69 | 87.105 | 98.635 | -26.441 | 1.00 | 25.30 | C |
| ATOM | 3931 | CE1 | TYR | C | 69 | 87.067 | 98.885 | -27.791 | 1.00 | 33.19 | C |
| ATOM | 3932 | CD2 | TYR | C | 69 | 89.213 | 97.503 | -26.708 | 1.00 | 32.15 | C |
| ATOM | 3933 | CE2 | TYR | C | 69 | 89.186 | 97.749 | -28.079 | 1.00 | 32.52 | C |
| ATOM | 3934 | CZ | TYR | C | 69 | 88.095 | 98.453 | -28.614 | 1.00 | 34.98 | C |
| ATOM | 3935 | OH | TYR | C | 69 | 88.031 | 98.764 | -29.952 | 1.00 | 32.72 | C |
| ATOM | 3936 | C | TYR | C | 69 | 87.687 | 95.997 | -22.673 | 1.00 | 30.28 | C |
| ATOM | 3937 | O | TYR | C | 69 | 88.777 | 95.781 | -22.158 | 1.00 | 28.03 | C |
| ATOM | 3938 | N | SER | C | 70 | 86.565 | 96.050 | -21.967 | 1.00 | 29.29 | C |
| ATOM | 3939 | CA | SER | C | 70 | 86.597 | 95.868 | -20.505 | 1.00 | 23.26 | C |
| ATOM | 3940 | CB | SER | C | 70 | 85.204 | 96.061 | -19.871 | 1.00 | 25.19 | C |
| ATOM | 3941 | OG | SER | C | 70 | 84.518 | 97.144 | -20.277 | 1.00 | 30.67 | C |
| ATOM | 3942 | C | SER | C | 70 | 87.175 | 94.504 | -20.128 | 1.00 | 29.31 | C |
| ATOM | 3943 | O | SER | C | 70 | 86.714 | 93.455 | -20.641 | 1.00 | 33.25 | C |
| ATOM | 3944 | N | SER | C | 71 | 88.113 | 94.596 | -19.092 | 1.00 | 34.01 | C |
| ATOM | 3945 | CA | SER | C | 71 | 88.825 | 93.422 | -18.570 | 1.00 | 33.07 | C |
| ATOM | 3946 | CB | SER | C | 71 | 90.139 | 93.197 | -19.334 | 1.00 | 37.09 | C |
| ATOM | 3947 | OG | SER | C | 71 | 90.774 | 91.992 | -18.919 | 1.00 | 38.97 | C |
| ATOM | 3948 | C | SER | C | 71 | 89.145 | 93.621 | -17.099 | 1.00 | 31.37 | C |
| ATOM | 3949 | O | SER | C | 71 | 89.965 | 94.464 | -16.748 | 1.00 | 31.95 | C |
| ATOM | 3950 | N | CYS | C | 72 | 88.518 | 92.836 | -16.230 | 1.00 | 32.50 | C |
| ATOM | 3951 | CA | CYS | C | 72 | 88.760 | 92.984 | -14.803 | 1.00 | 31.24 | C |
| ATOM | 3952 | C | CYS | C | 72 | 89.899 | 92.131 | -14.294 | 1.00 | 32.97 | C |
| ATOM | 3953 | O | CYS | C | 72 | 90.062 | 90.989 | -14.695 | 1.00 | 37.51 | C |
| ATOM | 3954 | CB | CYS | C | 72 | 87.479 | 92.670 | -14.032 | 1.00 | 31.14 | C |
| ATOM | 3955 | SG | CYS | C | 72 | 86.104 | 93.792 | -14.488 | 1.00 | 35.33 | C |
| ATOM | 3956 | N | PRO | C | 73 | 90.723 | 92.681 | -13.401 | 1.00 | 31.28 | C |
| ATOM | 3957 | CD | PRO | C | 73 | 90.688 | 94.015 | -12.785 | 1.00 | 34.25 | C |
| ATOM | 3958 | CA | PRO | C | 73 | 91.836 | 91.900 | -12.875 | 1.00 | 37.83 | C |
| ATOM | 3959 | CB | PRO | C | 73 | 92.700 | 92.953 | -12.199 | 1.00 | 39.00 | C |
| ATOM | 3960 | CG | PRO | C | 73 | 91.667 | 93.862 | -11.635 | 1.00 | 36.58 | C |
| ATOM | 3961 | C | PRO | C | 73 | 91.325 | 90.889 | -11.872 | 1.00 | 40.84 | C |
| ATOM | 3962 | O | PRO | C | 73 | 90.265 | 91.088 | -11.284 | 1.00 | 40.57 | C |
| ATOM | 3963 | N | GLU | C | 74 | 92.185 | 89.834 | -11.599 | 1.00 | 44.75 | C |
| ATOM | 3964 | CA | GLU | C | 74 | 91.750 | 88.788 | -10.731 | 1.00 | 50.06 | C |
| ATOM | 3965 | CB | GLU | C | 74 | 92.854 | 87.743 | -10.680 | 1.00 | 55.68 | C |
| ATOM | 3966 | CG | GLU | C | 74 | 93.109 | 86.845 | -9.771 | 1.00 | 64.35 | C |
| ATOM | 3967 | CD | GLU | C | 74 | 92.171 | 85.710 | -10.135 | 1.00 | 67.16 | C |
| ATOM | 3968 | OE1 | GLU | C | 74 | 92.147 | 85.315 | -11.320 | 1.00 | 67.98 | C |

TABLE 3-continued

| | | | | | | | | | | |
|---|---|---|---|---|---|---|---|---|---|---|
| ATOM | 3969 | OE2 | GLU | C | 74 | 91.459 | 85.216 | −9.236 | 1.00 | 69.43 C |
| ATOM | 3970 | C | GLU | C | 74 | 91.482 | 89.377 | −9.347 | 1.00 | 45.69 C |
| ATOM | 3971 | O | GLU | C | 74 | 92.282 | 90.168 | −8.832 | 1.00 | 43.16 C |
| ATOM | 3972 | N | PRO | C | 75 | 90.195 | 89.176 | −8.898 | 1.00 | 45.27 C |
| ATOM | 3973 | CD | PRO | C | 75 | 89.118 | 88.373 | −9.504 | 1.00 | 46.99 C |
| ATOM | 3974 | CA | PRO | C | 75 | 89.789 | 89.765 | −7.622 | 1.00 | 46.84 C |
| ATOM | 3975 | CB | PRO | C | 75 | 88.278 | 89.575 | −7.643 | 1.00 | 45.59 C |
| ATOM | 3976 | CG | PRO | C | 75 | 88.129 | 88.251 | −8.380 | 1.00 | 43.10 C |
| ATOM | 3977 | C | PRO | C | 75 | 90.484 | 88.987 | −6.471 | 1.00 | 46.31 C |
| ATOM | 3978 | O | PRO | C | 75 | 90.622 | 87.764 | −6.533 | 1.00 | 43.58 C |
| ATOM | 3979 | N | ILE | C | 76 | 90.967 | 89.682 | −5.452 | 1.00 | 44.06 C |
| ATOM | 3980 | CA | ILE | C | 76 | 91.585 | 88.961 | −4.346 | 1.00 | 49.43 C |
| ATOM | 3981 | CB | ILE | C | 76 | 93.091 | 89.252 | −4.220 | 1.00 | 50.66 C |
| ATOM | 3982 | CG2 | ILE | C | 76 | 93.648 | 88.589 | −2.960 | 1.00 | 51.02 C |
| ATOM | 3983 | CG1 | ILE | C | 76 | 93.829 | 88.692 | −5.433 | 1.00 | 53.97 C |
| ATOM | 3984 | CD1 | ILE | C | 76 | 95.327 | 88.938 | −5.393 | 1.00 | 58.58 C |
| ATOM | 3985 | C | ILE | C | 76 | 90.910 | 89.320 | −3.041 | 1.00 | 47.39 C |
| ATOM | 3986 | O | ILE | C | 76 | 90.663 | 90.496 | −2.770 | 1.00 | 45.77 C |
| ATOM | 3987 | N | VAL | C | 77 | 90.596 | 88.303 | −2.240 | 1.00 | 47.49 C |
| ATOM | 3988 | CA | VAL | C | 77 | 89.933 | 88.516 | −0.949 | 1.00 | 47.30 C |
| ATOM | 3989 | CB | VAL | C | 77 | 88.466 | 87.930 | −0.945 | 1.00 | 46.81 C |
| ATOM | 3990 | CG1 | VAL | C | 77 | 87.848 | 88.039 | 0.474 | 1.00 | 43.39 C |
| ATOM | 3991 | CG2 | VAL | C | 77 | 87.604 | 88.654 | −1.986 | 1.00 | 42.04 C |
| ATOM | 3992 | C | VAL | C | 77 | 90.725 | 87.855 | 0.188 | 1.00 | 47.58 C |
| ATOM | 3993 | O | VAL | C | 77 | 90.823 | 86.620 | 0.263 | 1.00 | 45.09 C |
| ATOM | 3994 | N | PRO | C | 78 | 91.301 | 88.669 | 1.086 | 1.00 | 44.97 C |
| ATOM | 3995 | CD | PRO | C | 78 | 91.365 | 90.140 | 1.032 | 1.00 | 45.60 C |
| ATOM | 3996 | CA | PRO | C | 78 | 92.078 | 88.143 | 2.221 | 1.00 | 44.08 C |
| ATOM | 3997 | CB | PRO | C | 78 | 92.461 | 89.407 | 2.989 | 1.00 | 45.76 C |
| ATOM | 3998 | CG | PRO | C | 78 | 92.593 | 90.447 | 1.892 | 1.00 | 46.75 C |
| ATOM | 3999 | C | PRO | C | 78 | 91.208 | 87.217 | 3.065 | 1.00 | 43.84 C |
| ATOM | 4000 | O | PRO | C | 78 | 90.088 | 87.568 | 3.403 | 1.00 | 43.30 C |
| ATOM | 4001 | N | GLY | C | 79 | 91.705 | 86.035 | 3.395 | 1.00 | 44.86 C |
| ATOM | 4002 | CA | GLY | C | 79 | 90.913 | 85.126 | 4.204 | 1.00 | 43.45 C |
| ATOM | 4003 | C | GLY | C | 79 | 89.868 | 84.402 | 3.379 | 1.00 | 45.18 C |
| ATOM | 4004 | O | GLY | C | 79 | 89.025 | 83.667 | 3.914 | 1.00 | 43.18 C |
| ATOM | 4005 | N | GLY | C | 80 | 89.922 | 84.605 | 2.067 | 1.00 | 41.25 C |
| ATOM | 4006 | CA | GLY | C | 80 | 88.970 | 83.946 | 1.185 | 1.00 | 39.64 C |
| ATOM | 4007 | C | GLY | C | 80 | 89.622 | 83.287 | −0.022 | 1.00 | 44.23 C |
| ATOM | 4008 | O | GLY | C | 80 | 90.827 | 83.420 | −0.269 | 1.00 | 40.56 C |
| ATOM | 4009 | N | TYR | C | 81 | 88.829 | 82.545 | −0.779 | 1.00 | 42.62 C |
| ATOM | 4010 | CA | TYR | C | 81 | 89.343 | 81.905 | −1.973 | 1.00 | 46.24 C |
| ATOM | 4011 | CB | TYR | C | 81 | 89.908 | 80.496 | −1.655 | 1.00 | 44.92 C |
| ATOM | 4012 | CG | TYR | C | 81 | 88.934 | 79.522 | −1.020 | 1.00 | 46.64 C |
| ATOM | 4013 | CD1 | TYR | C | 81 | 88.405 | 78.463 | −1.754 | 1.00 | 48.03 C |
| ATOM | 4014 | CE1 | TYR | C | 81 | 87.438 | 77.618 | −1.221 | 1.00 | 48.43 C |
| ATOM | 4015 | CD2 | TYR | C | 81 | 88.478 | 79.709 | 0.281 | 1.00 | 47.96 C |
| ATOM | 4016 | CE2 | TYR | C | 81 | 87.503 | 78.871 | 0.826 | 1.00 | 50.43 C |
| ATOM | 4017 | CZ | TYR | C | 81 | 86.980 | 77.827 | 0.062 | 1.00 | 51.08 C |
| ATOM | 4018 | OH | TYR | C | 81 | 85.948 | 77.038 | 0.550 | 1.00 | 54.25 C |
| ATOM | 4019 | C | TYR | C | 81 | 88.233 | 81.854 | −3.028 | 1.00 | 50.13 C |
| ATOM | 4020 | O | TYR | C | 81 | 87.039 | 81.840 | −2.711 | 1.00 | 46.05 C |
| ATOM | 4021 | N | LYS | C | 82 | 88.643 | 81.853 | −4.289 | 1.00 | 50.32 C |
| ATOM | 4022 | CA | LYS | C | 82 | 87.697 | 81.828 | −5.380 | 1.00 | 53.74 C |
| ATOM | 4023 | CB | LYS | C | 82 | 88.393 | 82.238 | −6.681 | 1.00 | 53.51 C |
| ATOM | 4024 | CG | LYS | C | 82 | 87.466 | 82.280 | −7.884 | 1.00 | 54.66 C |
| ATOM | 4025 | CD | LYS | C | 82 | 88.182 | 82.779 | −9.126 | 1.00 | 52.50 C |
| ATOM | 4026 | CE | LYS | C | 82 | 89.254 | 81.803 | −9.563 | 1.00 | 53.91 C |
| ATOM | 4027 | NZ | LYS | C | 82 | 90.030 | 82.321 | −10.718 | 1.00 | 52.48 C |
| ATOM | 4028 | C | LYS | C | 82 | 87.089 | 80.447 | −5.528 | 1.00 | 54.39 C |
| ATOM | 4029 | O | LYS | C | 82 | 87.782 | 79.435 | −5.429 | 1.00 | 54.15 C |
| ATOM | 4030 | N | ILE | C | 83 | 85.783 | 80.412 | −5.740 | 1.00 | 53.36 C |
| ATOM | 4031 | CA | ILE | C | 83 | 85.083 | 79.157 | −5.935 | 1.00 | 56.28 C |
| ATOM | 4032 | CB | ILE | C | 83 | 83.815 | 79.085 | −5.070 | 1.00 | 57.52 C |
| ATOM | 4033 | CG2 | ILE | C | 83 | 82.803 | 78.186 | −5.698 | 1.00 | 58.38 C |
| ATOM | 4034 | CG1 | ILE | C | 83 | 84.162 | 78.510 | −3.702 | 1.00 | 59.41 C |
| ATOM | 4035 | CD1 | ILE | C | 83 | 85.312 | 79.203 | −3.034 | 1.00 | 64.54 C |
| ATOM | 4036 | C | ILE | C | 83 | 84.698 | 79.018 | −7.408 | 1.00 | 60.57 C |
| ATOM | 4037 | O | ILE | C | 83 | 84.790 | 77.926 | −7.969 | 1.00 | 61.13 C |
| ATOM | 4038 | N | ARG | C | 84 | 84.274 | 80.125 | −8.025 | 1.00 | 58.19 C |
| ATOM | 4039 | CA | ARG | C | 84 | 83.859 | 80.134 | −9.432 | 1.00 | 55.53 C |
| ATOM | 4040 | CB | ARG | C | 84 | 82.340 | 80.259 | −9.557 | 1.00 | 59.40 C |
| ATOM | 4041 | CG | ARG | C | 84 | 81.555 | 79.123 | −8.937 | 1.00 | 66.78 C |
| ATOM | 4042 | CD | ARG | C | 84 | 80.080 | 79.471 | −8.783 | 1.00 | 70.71 C |
| ATOM | 4043 | NE | ARG | C | 84 | 79.338 | 78.353 | −8.204 | 1.00 | 78.82 C |
| ATOM | 4044 | CZ | ARG | C | 84 | 78.041 | 78.384 | −7.902 | 1.00 | 82.83 C |
| ATOM | 4045 | NH1 | ARG | C | 84 | 77.331 | 79.487 | −8.124 | 1.00 | 84.17 C |
| ATOM | 4046 | NH2 | ARG | C | 84 | 77.454 | 77.308 | −7.378 | 1.00 | 84.81 C |
| ATOM | 4047 | C | ARG | C | 84 | 84.475 | 81.305 | −10.156 | 1.00 | 54.25 C |

TABLE 3-continued

| | | | | | | | | | |
|---|---|---|---|---|---|---|---|---|---|
| ATOM | 4048 | O | ARG | C | 84 | 84.812 | 82.313 | −9.543 | 1.00 | 52.78 | C |
| ATOM | 4049 | N | GLY | C | 85 | 84.612 | 81.164 | −11.468 | 1.00 | 51.61 | C |
| ATOM | 4050 | CA | GLY | C | 85 | 85.166 | 82.234 | −12.265 | 1.00 | 52.64 | C |
| ATOM | 4051 | C | GLY | C | 85 | 86.542 | 81.935 | −12.801 | 1.00 | 52.39 | C |
| ATOM | 4052 | O | GLY | C | 85 | 87.400 | 81.412 | −12.093 | 1.00 | 53.26 | C |
| ATOM | 4053 | N | SER | C | 86 | 86.768 | 82.264 | −14.063 | 1.00 | 56.65 | C |
| ATOM | 4054 | CA | SER | C | 86 | 88.074 | 82.013 | −14.636 | 1.00 | 60.26 | C |
| ATOM | 4055 | CB | SER | C | 86 | 88.078 | 80.685 | −15.393 | 1.00 | 63.40 | C |
| ATOM | 4056 | OG | SER | C | 86 | 89.410 | 80.222 | −15.570 | 1.00 | 73.69 | C |
| ATOM | 4057 | C | SER | C | 86 | 88.482 | 83.126 | −15.567 | 1.00 | 56.75 | C |
| ATOM | 4058 | O | SER | C | 86 | 87.650 | 83.698 | −16.257 | 1.00 | 55.15 | C |
| ATOM | 4059 | N | THR | C | 87 | 89.775 | 83.428 | −15.565 | 1.00 | 58.49 | C |
| ATOM | 4060 | CA | THR | C | 87 | 90.343 | 84.457 | −16.417 | 1.00 | 57.84 | C |
| ATOM | 4061 | CB | THR | C | 87 | 91.816 | 84.711 | −16.006 | 1.00 | 62.33 | C |
| ATOM | 4062 | OG1 | THR | C | 87 | 91.873 | 85.892 | −15.197 | 1.00 | 69.91 | C |
| ATOM | 4063 | CG2 | THR | C | 87 | 92.724 | 84.863 | −17.215 | 1.00 | 64.96 | C |
| ATOM | 4064 | C | THR | C | 87 | 90.257 | 84.034 | −17.886 | 1.00 | 55.75 | C |
| ATOM | 4065 | O | THR | C | 87 | 90.241 | 82.842 | −18.198 | 1.00 | 56.65 | C |
| ATOM | 4066 | N | PRO | C | 88 | 90.134 | 85.007 | −18.805 | 1.00 | 52.96 | C |
| ATOM | 4067 | CD | PRO | C | 88 | 90.192 | 84.766 | −20.259 | 1.00 | 53.18 | C |
| ATOM | 4068 | CA | PRO | C | 88 | 90.069 | 86.442 | −18.533 | 1.00 | 52.06 | C |
| ATOM | 4069 | CB | PRO | C | 88 | 90.533 | 87.060 | −19.849 | 1.00 | 50.34 | C |
| ATOM | 4070 | CG | PRO | C | 88 | 89.909 | 86.162 | −20.842 | 1.00 | 52.45 | C |
| ATOM | 4071 | C | PRO | C | 88 | 88.630 | 86.844 | −18.183 | 1.00 | 47.83 | C |
| ATOM | 4072 | O | PRO | C | 88 | 87.666 | 86.219 | −18.628 | 1.00 | 43.02 | C |
| ATOM | 4073 | N | TYR | C | 89 | 88.502 | 87.903 | −17.398 | 1.00 | 40.94 | C |
| ATOM | 4074 | CA | TYR | C | 89 | 87.204 | 88.376 | −16.977 | 1.00 | 40.87 | C |
| ATOM | 4075 | CB | TYR | C | 89 | 87.276 | 88.839 | −15.516 | 1.00 | 41.58 | C |
| ATOM | 4076 | CG | TYR | C | 89 | 87.666 | 87.730 | −14.570 | 1.00 | 47.21 | C |
| ATOM | 4077 | CD1 | TYR | C | 89 | 88.886 | 87.759 | −13.879 | 1.00 | 48.57 | C |
| ATOM | 4078 | CE1 | TYR | C | 89 | 89.260 | 86.711 | −13.043 | 1.00 | 52.12 | C |
| ATOM | 4079 | CD2 | TYR | C | 89 | 86.835 | 86.625 | −14.397 | 1.00 | 47.83 | C |
| ATOM | 4080 | CE2 | TYR | C | 89 | 87.203 | 85.573 | −13.567 | 1.00 | 52.56 | C |
| ATOM | 4081 | CZ | TYR | C | 89 | 88.409 | 85.618 | −12.892 | 1.00 | 52.86 | C |
| ATOM | 4082 | OH | TYR | C | 89 | 88.734 | 84.568 | −12.059 | 1.00 | 55.18 | C |
| ATOM | 4083 | C | TYR | C | 89 | 86.775 | 89.516 | −17.874 | 1.00 | 37.75 | C |
| ATOM | 4084 | O | TYR | C | 89 | 87.368 | 90.582 | −17.837 | 1.00 | 35.86 | C |
| ATOM | 4085 | N | ARG | C | 90 | 85.742 | 89.282 | −18.677 | 1.00 | 36.76 | C |
| ATOM | 4086 | CA | ARG | C | 90 | 85.227 | 90.291 | −19.591 | 1.00 | 31.74 | C |
| ATOM | 4087 | CB | ARG | C | 90 | 84.956 | 89.672 | −20.957 | 1.00 | 39.30 | C |
| ATOM | 4088 | CG | ARG | C | 90 | 86.211 | 89.526 | −21.808 | 1.00 | 51.87 | C |
| ATOM | 4089 | CD | ARG | C | 90 | 86.620 | 88.085 | −21.981 | 1.00 | 60.63 | C |
| ATOM | 4090 | NE | ARG | C | 90 | 87.619 | 87.933 | −23.048 | 1.00 | 68.24 | C |
| ATOM | 4091 | CZ | ARG | C | 90 | 88.091 | 86.767 | −23.501 | 1.00 | 68.54 | C |
| ATOM | 4092 | NH1 | ARG | C | 90 | 87.673 | 85.604 | −22.993 | 1.00 | 64.59 | C |
| ATOM | 4093 | NH2 | ARG | C | 90 | 88.987 | 86.767 | −24.479 | 1.00 | 70.32 | C |
| ATOM | 4094 | C | ARG | C | 90 | 83.959 | 90.915 | −19.048 | 1.00 | 31.15 | C |
| ATOM | 4095 | O | ARG | C | 90 | 83.414 | 90.456 | −18.040 | 1.00 | 24.92 | C |
| ATOM | 4096 | N | HIS | C | 91 | 83.483 | 91.955 | −19.725 | 1.00 | 23.82 | C |
| ATOM | 4097 | CA | HIS | C | 91 | 82.285 | 92.674 | −19.301 | 1.00 | 23.05 | C |
| ATOM | 4098 | CB | HIS | C | 91 | 81.872 | 93.640 | −20.406 | 1.00 | 26.29 | C |
| ATOM | 4099 | CG | HIS | C | 91 | 80.849 | 94.665 | −19.998 | 1.00 | 23.49 | C |
| ATOM | 4100 | CD2 | HIS | C | 91 | 80.142 | 95.553 | −20.744 | 1.00 | 20.45 | C |
| ATOM | 4101 | ND1 | HIS | C | 91 | 80.515 | 94.920 | −18.685 | 1.00 | 28.99 | C |
| ATOM | 4102 | CE1 | HIS | C | 91 | 79.651 | 95.923 | −18.637 | 1.00 | 19.30 | C |
| ATOM | 4103 | NE2 | HIS | C | 91 | 79.412 | 96.325 | −19.873 | 1.00 | 28.70 | C |
| ATOM | 4104 | C | HIS | C | 91 | 81.142 | 91.717 | −19.003 | 1.00 | 24.93 | C |
| ATOM | 4105 | O | HIS | C | 91 | 80.771 | 90.926 | −19.862 | 1.00 | 22.92 | C |
| ATOM | 4106 | N | GLY | C | 92 | 80.575 | 91.808 | −17.801 | 1.00 | 25.08 | C |
| ATOM | 4107 | CA | GLY | C | 92 | 79.459 | 90.949 | −17.435 | 1.00 | 25.83 | C |
| ATOM | 4108 | C | GLY | C | 92 | 79.834 | 89.612 | −16.803 | 1.00 | 26.66 | C |
| ATOM | 4109 | O | GLY | C | 92 | 78.964 | 88.947 | −16.233 | 1.00 | 30.96 | C |
| ATOM | 4110 | N | ASP | C | 93 | 81.098 | 89.203 | −16.913 | 1.00 | 24.69 | C |
| ATOM | 4111 | CA | ASP | C | 93 | 81.558 | 87.940 | −16.311 | 1.00 | 28.03 | C |
| ATOM | 4112 | CB | ASP | C | 93 | 83.001 | 87.609 | −16.749 | 1.00 | 26.26 | C |
| ATOM | 4113 | CG | ASP | C | 93 | 83.101 | 87.123 | −18.214 | 1.00 | 33.28 | C |
| ATOM | 4114 | OD1 | ASP | C | 93 | 84.243 | 86.973 | −18.725 | 1.00 | 35.30 | C |
| ATOM | 4115 | OD2 | ASP | C | 93 | 82.056 | 86.885 | −18.859 | 1.00 | 33.91 | C |
| ATOM | 4116 | C | ASP | C | 93 | 81.535 | 88.080 | −14.791 | 1.00 | 32.16 | C |
| ATOM | 4117 | O | ASP | C | 93 | 81.641 | 89.197 | −14.254 | 1.00 | 32.11 | C |
| ATOM | 4118 | N | SER | C | 94 | 81.400 | 86.966 | −14.082 | 1.00 | 27.90 | C |
| ATOM | 4119 | CA | SER | C | 94 | 81.395 | 87.050 | −12.632 | 1.00 | 37.96 | C |
| ATOM | 4120 | CB | SER | C | 94 | 79.983 | 86.889 | −12.104 | 1.00 | 35.76 | C |
| ATOM | 4121 | OG | SER | C | 94 | 79.577 | 85.556 | −12.314 | 1.00 | 39.23 | C |
| ATOM | 4122 | C | SER | C | 94 | 82.287 | 85.986 | −11.997 | 1.00 | 38.51 | C |
| ATOM | 4123 | O | SER | C | 94 | 82.713 | 85.038 | −12.655 | 1.00 | 36.22 | C |
| ATOM | 4124 | N | VAL | C | 95 | 82.550 | 86.154 | −10.706 | 1.00 | 38.03 | C |
| ATOM | 4125 | CA | VAL | C | 95 | 83.373 | 85.221 | −9.943 | 1.00 | 42.81 | C |
| ATOM | 4126 | CB | VAL | C | 95 | 84.825 | 85.728 | −9.743 | 1.00 | 41.37 | C |

TABLE 3-continued

| ATOM | 4127 | CG1 | VAL | C | 95 | 85.454 | 86.006 | −11.073 | 1.00 | 46.63 | C |
|---|---|---|---|---|---|---|---|---|---|---|---|
| ATOM | 4128 | CG2 | VAL | C | 95 | 84.840 | 86.980 | −8.916 | 1.00 | 36.92 | C |
| ATOM | 4129 | C | VAL | C | 95 | 82.724 | 85.111 | −8.587 | 1.00 | 43.66 | C |
| ATOM | 4130 | O | VAL | C | 95 | 82.023 | 86.024 | −8.155 | 1.00 | 43.47 | C |
| ATOM | 4131 | N | THR | C | 96 | 82.939 | 83.988 | −7.918 | 1.00 | 45.64 | C |
| ATOM | 4132 | CA | THR | C | 96 | 82.356 | 83.806 | −6.599 | 1.00 | 46.87 | C |
| ATOM | 4133 | CB | THR | C | 96 | 81.258 | 82.736 | −6.600 | 1.00 | 46.87 | C |
| ATOM | 4134 | OG1 | THR | C | 96 | 80.233 | 83.101 | −7.531 | 1.00 | 40.12 | C |
| ATOM | 4135 | CG2 | THR | C | 96 | 80.635 | 82.635 | −5.208 | 1.00 | 50.66 | C |
| ATOM | 4136 | C | THR | C | 96 | 83.432 | 83.403 | −5.612 | 1.00 | 43.20 | C |
| ATOM | 4137 | O | THR | C | 96 | 84.363 | 82.686 | −5.962 | 1.00 | 41.73 | C |
| ATOM | 4138 | N | PHE | C | 97 | 83.302 | 83.886 | −4.387 | 1.00 | 39.07 | C |
| ATOM | 4139 | CA | PHE | C | 97 | 84.267 | 83.578 | −3.349 | 1.00 | 43.95 | C |
| ATOM | 4140 | CB | PHE | C | 97 | 84.898 | 84.854 | −2.810 | 1.00 | 45.41 | C |
| ATOM | 4141 | CG | PHE | C | 97 | 85.850 | 85.519 | −3.750 | 1.00 | 46.14 | C |
| ATOM | 4142 | CD1 | PHE | C | 97 | 85.422 | 86.543 | −4.594 | 1.00 | 42.85 | C |
| ATOM | 4143 | CD2 | PHE | C | 97 | 87.195 | 85.162 | −3.749 | 1.00 | 45.67 | C |
| ATOM | 4144 | CE1 | PHE | C | 97 | 86.320 | 87.194 | −5.406 | 1.00 | 39.79 | C |
| ATOM | 4145 | CE2 | PHE | C | 97 | 88.101 | 85.812 | −4.562 | 1.00 | 42.72 | C |
| ATOM | 4146 | CZ | PHE | C | 97 | 87.663 | 86.829 | −5.390 | 1.00 | 41.65 | C |
| ATOM | 4147 | C | PHE | C | 97 | 83.646 | 82.859 | −2.158 | 1.00 | 46.38 | C |
| ATOM | 4148 | O | PHE | C | 97 | 82.421 | 82.804 | −1.988 | 1.00 | 39.27 | C |
| ATOM | 4149 | N | ALA | C | 98 | 84.530 | 82.332 | −1.318 | 1.00 | 48.32 | C |
| ATOM | 4150 | CA | ALA | C | 98 | 84.155 | 81.664 | −0.076 | 1.00 | 46.94 | C |
| ATOM | 4151 | CB | ALA | C | 98 | 84.112 | 80.158 | −0.277 | 1.00 | 46.22 | C |
| ATOM | 4152 | C | ALA | C | 98 | 85.254 | 82.038 | 0.929 | 1.00 | 46.65 | C |
| ATOM | 4153 | O | ALA | C | 98 | 86.394 | 82.293 | 0.536 | 1.00 | 44.10 | C |
| ATOM | 4154 | N | CYS | C | 99 | 84.914 | 82.103 | 2.212 | 1.00 | 46.08 | C |
| ATOM | 4155 | CA | CYS | C | 99 | 85.917 | 82.423 | 3.209 | 1.00 | 47.08 | C |
| ATOM | 4156 | C | CYS | C | 99 | 86.590 | 81.156 | 3.711 | 1.00 | 46.05 | C |
| ATOM | 4157 | O | CYS | C | 99 | 85.963 | 80.096 | 3.760 | 1.00 | 43.34 | C |
| ATOM | 4158 | CB | CYS | C | 99 | 85.289 | 83.168 | 4.375 | 1.00 | 44.52 | C |
| ATOM | 4159 | SG | CYS | C | 99 | 84.727 | 84.800 | 3.844 | 1.00 | 44.83 | C |
| ATOM | 4160 | N | LYS | C | 100 | 87.874 | 81.273 | 4.056 | 1.00 | 47.36 | C |
| ATOM | 4161 | CA | LYS | C | 100 | 88.645 | 80.147 | 4.574 | 1.00 | 48.81 | C |
| ATOM | 4162 | CB | LYS | C | 100 | 90.135 | 80.489 | 4.594 | 1.00 | 49.39 | C |
| ATOM | 4163 | CG | LYS | C | 100 | 90.750 | 80.658 | 3.219 | 1.00 | 54.21 | C |
| ATOM | 4164 | CD | LYS | C | 100 | 92.190 | 81.114 | 3.317 | 1.00 | 54.87 | C |
| ATOM | 4165 | CE | LYS | C | 100 | 92.806 | 81.267 | 1.942 | 1.00 | 57.13 | C |
| ATOM | 4166 | NZ | LYS | C | 100 | 94.197 | 81.768 | 2.053 | 1.00 | 60.72 | C |
| ATOM | 4167 | C | LYS | C | 100 | 88.165 | 79.861 | 5.997 | 1.00 | 49.95 | C |
| ATOM | 4168 | O | LYS | C | 100 | 87.495 | 80.705 | 6.619 | 1.00 | 48.69 | C |
| ATOM | 4169 | N | THR | C | 101 | 88.786 | 78.765 | 6.373 | 1.00 | 51.22 | C |
| ATOM | 4170 | CA | THR | C | 101 | 88.580 | 78.229 | 7.709 | 1.00 | 55.29 | C |
| ATOM | 4171 | CB | THR | C | 101 | 89.528 | 77.069 | 8.012 | 1.00 | 57.10 | C |
| ATOM | 4172 | OG1 | THR | C | 101 | 89.306 | 76.008 | 7.077 | 1.00 | 64.35 | C |
| ATOM | 4173 | CG2 | THR | C | 101 | 89.308 | 76.559 | 9.429 | 1.00 | 57.34 | C |
| ATOM | 4174 | C | THR | C | 101 | 88.780 | 79.304 | 8.764 | 1.00 | 49.93 | C |
| ATOM | 4175 | O | THR | C | 101 | 89.894 | 79.947 | 8.793 | 1.00 | 47.27 | C |
| ATOM | 4176 | N | ASN | C | 102 | 88.004 | 79.652 | 9.763 | 1.00 | 46.86 | C |
| ATOM | 4177 | CA | ASN | C | 102 | 88.149 | 80.670 | 10.780 | 1.00 | 48.18 | C |
| ATOM | 4178 | CB | ASN | C | 102 | 89.557 | 80.629 | 11.363 | 1.00 | 46.95 | C |
| ATOM | 4179 | CG | ASN | C | 102 | 89.845 | 79.289 | 12.014 | 1.00 | 48.40 | C |
| ATOM | 4180 | OD1 | ASN | C | 102 | 88.985 | 78.720 | 12.693 | 1.00 | 41.35 | C |
| ATOM | 4181 | ND2 | ASN | C | 102 | 91.051 | 78.775 | 11.810 | 1.00 | 49.40 | C |
| ATOM | 4182 | C | ASN | C | 102 | 87.761 | 82.030 | 10.236 | 1.00 | 49.20 | C |
| ATOM | 4183 | O | ASN | C | 102 | 88.252 | 83.052 | 10.922 | 1.00 | 46.49 | C |
| ATOM | 4184 | N | PHE | C | 103 | 87.220 | 82.295 | 9.176 | 1.00 | 48.20 | C |
| ATOM | 4185 | CA | PHE | C | 103 | 86.584 | 83.570 | 8.755 | 1.00 | 49.30 | C |
| ATOM | 4186 | CB | PHE | C | 103 | 87.390 | 84.074 | 7.554 | 1.00 | 46.94 | C |
| ATOM | 4187 | CG | PHE | C | 103 | 88.859 | 84.187 | 7.814 | 1.00 | 45.01 | C |
| ATOM | 4188 | CD1 | PHE | C | 103 | 89.671 | 83.059 | 7.792 | 1.00 | 48.38 | C |
| ATOM | 4189 | CD2 | PHE | C | 103 | 89.437 | 85.421 | 8.082 | 1.00 | 48.98 | C |
| ATOM | 4190 | CE1 | PHE | C | 103 | 91.045 | 83.157 | 8.034 | 1.00 | 48.94 | C |
| ATOM | 4191 | CE2 | PHE | C | 103 | 90.810 | 85.533 | 8.328 | 1.00 | 48.39 | C |
| ATOM | 4192 | CZ | PHE | C | 103 | 91.616 | 84.400 | 8.302 | 1.00 | 46.82 | C |
| ATOM | 4193 | C | PHE | C | 103 | 85.097 | 83.521 | 8.378 | 1.00 | 50.21 | C |
| ATOM | 4194 | O | PHE | C | 103 | 84.570 | 82.478 | 7.968 | 1.00 | 49.82 | C |
| ATOM | 4195 | N | SER | C | 104 | 84.414 | 84.647 | 8.565 | 1.00 | 48.66 | C |
| ATOM | 4196 | CA | SER | C | 104 | 83.012 | 84.745 | 8.214 | 1.00 | 45.33 | C |
| ATOM | 4197 | CB | SER | C | 104 | 82.165 | 85.191 | 9.417 | 1.00 | 46.37 | C |
| ATOM | 4198 | OG | SER | C | 104 | 82.048 | 86.605 | 9.522 | 1.00 | 57.43 | C |
| ATOM | 4199 | C | SER | C | 104 | 82.984 | 85.792 | 7.108 | 1.00 | 41.51 | C |
| ATOM | 4200 | O | SER | C | 104 | 83.757 | 86.736 | 7.130 | 1.00 | 38.53 | C |
| ATOM | 4201 | N | MET | C | 105 | 82.114 | 85.616 | 6.129 | 1.00 | 41.72 | C |
| ATOM | 4202 | CA | MET | C | 105 | 82.036 | 86.573 | 5.038 | 1.00 | 43.60 | C |
| ATOM | 4203 | CB | MET | C | 105 | 81.601 | 85.872 | 3.748 | 1.00 | 44.67 | C |
| ATOM | 4204 | CG | MET | C | 105 | 81.330 | 86.830 | 2.579 | 1.00 | 40.80 | C |
| ATOM | 4205 | SD | MET | C | 105 | 80.914 | 85.922 | 1.118 | 1.00 | 45.07 | C |

TABLE 3-continued

| | | | | | | | | | | |
|---|---|---|---|---|---|---|---|---|---|---|
| ATOM | 4206 | CE | MET | C | 105 | 82.489 | 85.186 | 0.675 | 1.00 | 39.55 C |
| ATOM | 4207 | C | MET | C | 105 | 81.077 | 87.722 | 5.308 | 1.00 | 46.26 C |
| ATOM | 4208 | O | MET | C | 105 | 79.972 | 87.519 | 5.816 | 1.00 | 44.17 C |
| ATOM | 4209 | N | ASN | C | 106 | 81.518 | 88.927 | 4.963 | 1.00 | 47.38 C |
| ATOM | 4210 | CA | ASN | C | 106 | 80.707 | 90.137 | 5.078 | 1.00 | 49.51 C |
| ATOM | 4211 | CB | ASN | C | 106 | 81.391 | 91.160 | 5.984 | 1.00 | 56.07 C |
| ATOM | 4212 | CG | ASN | C | 106 | 80.769 | 92.539 | 5.879 | 1.00 | 63.53 C |
| ATOM | 4213 | OD1 | ASN | C | 106 | 80.925 | 93.233 | 4.867 | 1.00 | 66.72 C |
| ATOM | 4214 | ND2 | ASN | C | 106 | 80.048 | 92.943 | 6.921 | 1.00 | 68.89 C |
| ATOM | 4215 | C | ASN | C | 106 | 80.572 | 90.688 | 3.645 | 1.00 | 49.28 C |
| ATOM | 4216 | O | ASN | C | 106 | 81.566 | 91.073 | 3.015 | 1.00 | 46.49 C |
| ATOM | 4217 | N | GLY | C | 107 | 79.344 | 90.700 | 3.130 | 1.00 | 50.96 C |
| ATOM | 4218 | CA | GLY | C | 107 | 79.102 | 91.178 | 1.776 | 1.00 | 47.29 C |
| ATOM | 4219 | C | GLY | C | 107 | 78.620 | 90.074 | 0.846 | 1.00 | 46.96 C |
| ATOM | 4220 | O | GLY | C | 107 | 78.421 | 88.940 | 1.275 | 1.00 | 48.97 C |
| ATOM | 4221 | N | ASN | C | 108 | 78.439 | 90.398 | −0.434 | 1.00 | 50.83 C |
| ATOM | 4222 | CA | ASN | C | 108 | 77.974 | 89.429 | −1.426 | 1.00 | 49.00 C |
| ATOM | 4223 | CB | ASN | C | 108 | 77.392 | 90.148 | −2.635 | 1.00 | 56.26 C |
| ATOM | 4224 | CG | ASN | C | 108 | 76.392 | 91.180 | −2.247 | 1.00 | 61.63 C |
| ATOM | 4225 | OD1 | ASN | C | 108 | 76.703 | 92.371 | −2.168 | 1.00 | 67.56 C |
| ATOM | 4226 | ND2 | ASN | C | 108 | 75.176 | 90.735 | −1.977 | 1.00 | 62.48 C |
| ATOM | 4227 | C | ASN | C | 108 | 79.125 | 88.561 | −1.887 | 1.00 | 46.12 C |
| ATOM | 4228 | O | ASN | C | 108 | 80.217 | 89.064 | −2.155 | 1.00 | 42.01 C |
| ATOM | 4229 | N | LYS | C | 109 | 78.858 | 87.266 | −2.016 | 1.00 | 38.69 C |
| ATOM | 4230 | CA | LYS | C | 109 | 79.874 | 86.310 | −2.407 | 1.00 | 41.12 C |
| ATOM | 4231 | CB | LYS | C | 109 | 79.444 | 84.897 | −2.023 | 1.00 | 44.04 C |
| ATOM | 4232 | CG | LYS | C | 109 | 78.255 | 84.360 | −2.804 | 1.00 | 45.47 C |
| ATOM | 4233 | CD | LYS | C | 109 | 77.585 | 83.222 | −2.019 | 1.00 | 51.74 C |
| ATOM | 4234 | CE | LYS | C | 109 | 76.584 | 82.453 | −2.865 | 1.00 | 59.58 C |
| ATOM | 4235 | NZ | LYS | C | 109 | 77.262 | 81.664 | −3.956 | 1.00 | 64.18 C |
| ATOM | 4236 | C | LYS | C | 109 | 80.199 | 86.324 | −3.874 | 1.00 | 40.75 C |
| ATOM | 4237 | O | LYS | C | 109 | 81.189 | 85.714 | −4.307 | 1.00 | 41.19 C |
| ATOM | 4238 | N | SER | C | 110 | 79.358 | 86.988 | −4.655 | 1.00 | 38.36 C |
| ATOM | 4239 | CA | SER | C | 110 | 79.578 | 87.024 | −6.101 | 1.00 | 36.23 C |
| ATOM | 4240 | CB | SER | C | 110 | 78.437 | 86.305 | −6.834 | 1.00 | 39.46 C |
| ATOM | 4241 | OG | SER | C | 110 | 78.481 | 84.918 | −6.579 | 1.00 | 36.52 C |
| ATOM | 4242 | C | SER | C | 110 | 79.635 | 88.421 | −6.581 | 1.00 | 29.42 C |
| ATOM | 4243 | O | SER | C | 110 | 78.876 | 89.247 | −6.098 | 1.00 | 28.55 C |
| ATOM | 4244 | N | VAL | C | 111 | 80.560 | 88.692 | −7.499 | 1.00 | 30.69 C |
| ATOM | 4245 | CA | VAL | C | 111 | 80.678 | 90.017 | −8.105 | 1.00 | 29.50 C |
| ATOM | 4246 | CB | VAL | C | 111 | 81.934 | 90.782 | −7.652 | 1.00 | 33.90 C |
| ATOM | 4247 | CG1 | VAL | C | 111 | 81.666 | 91.463 | −6.325 | 1.00 | 32.11 C |
| ATOM | 4248 | CG2 | VAL | C | 111 | 83.135 | 89.825 | −7.579 | 1.00 | 26.88 C |
| ATOM | 4249 | C | VAL | C | 111 | 80.718 | 89.916 | −9.632 | 1.00 | 29.99 C |
| ATOM | 4250 | O | VAL | C | 111 | 80.996 | 88.853 | −10.194 | 1.00 | 27.74 C |
| ATOM | 4251 | N | TRP | C | 112 | 80.448 | 91.034 | −10.299 | 1.00 | 25.72 C |
| ATOM | 4252 | CA | TRP | C | 112 | 80.437 | 91.062 | −11.756 | 1.00 | 25.20 C |
| ATOM | 4253 | CB | TRP | C | 112 | 79.020 | 91.411 | −12.237 | 1.00 | 26.69 C |
| ATOM | 4254 | CG | TRP | C | 112 | 78.107 | 90.226 | −12.146 | 1.00 | 33.34 C |
| ATOM | 4255 | CD2 | TRP | C | 112 | 77.481 | 89.706 | −10.957 | 1.00 | 30.54 C |
| ATOM | 4256 | CE2 | TRP | C | 112 | 76.820 | 88.505 | −11.322 | 1.00 | 33.04 C |
| ATOM | 4257 | CE3 | TRP | C | 112 | 77.421 | 90.133 | −9.622 | 1.00 | 31.04 C |
| ATOM | 4258 | CD1 | TRP | C | 112 | 77.799 | 89.338 | −13.158 | 1.00 | 37.78 C |
| ATOM | 4259 | NE1 | TRP | C | 112 | 77.029 | 88.309 | −12.665 | 1.00 | 35.55 C |
| ATOM | 4260 | CZ2 | TRP | C | 112 | 76.110 | 87.729 | −10.397 | 1.00 | 27.67 C |
| ATOM | 4261 | CZ3 | TRP | C | 112 | 76.713 | 89.357 | −8.696 | 1.00 | 30.48 C |
| ATOM | 4262 | CH2 | TRP | C | 112 | 76.067 | 88.168 | −9.092 | 1.00 | 26.73 C |
| ATOM | 4263 | C | TRP | C | 112 | 81.456 | 92.052 | −12.307 | 1.00 | 27.63 C |
| ATOM | 4264 | O | TRP | C | 112 | 81.719 | 93.091 | −11.701 | 1.00 | 22.47 C |
| ATOM | 4265 | N | CYS | C | 113 | 82.042 | 91.719 | −13.455 | 1.00 | 26.10 C |
| ATOM | 4266 | CA | CYS | C | 113 | 83.025 | 92.593 | −14.083 | 1.00 | 25.33 C |
| ATOM | 4267 | C | CYS | C | 113 | 82.313 | 93.725 | −14.830 | 1.00 | 30.04 C |
| ATOM | 4268 | O | CYS | C | 113 | 81.611 | 93.488 | −15.824 | 1.00 | 28.98 C |
| ATOM | 4269 | CB | CYS | C | 113 | 83.897 | 91.780 | −15.029 | 1.00 | 26.64 C |
| ATOM | 4270 | SG | CYS | C | 113 | 85.096 | 92.793 | −15.958 | 1.00 | 29.69 C |
| ATOM | 4271 | N | GLN | C | 114 | 82.478 | 94.951 | −14.336 | 1.00 | 22.99 C |
| ATOM | 4272 | CA | GLN | C | 114 | 81.842 | 96.127 | −14.927 | 1.00 | 25.16 C |
| ATOM | 4273 | CB | GLN | C | 114 | 81.597 | 97.177 | −13.835 | 1.00 | 28.73 C |
| ATOM | 4274 | CG | GLN | C | 114 | 80.857 | 96.602 | −12.630 | 1.00 | 36.89 C |
| ATOM | 4275 | CD | GLN | C | 114 | 80.727 | 97.569 | −11.457 | 1.00 | 42.08 C |
| ATOM | 4276 | OE1 | GLN | C | 114 | 79.802 | 98.365 | −11.382 | 1.00 | 49.79 C |
| ATOM | 4277 | NE2 | GLN | C | 114 | 81.665 | 97.493 | −10.539 | 1.00 | 49.11 C |
| ATOM | 4278 | C | GLN | C | 114 | 82.630 | 96.739 | −16.092 | 1.00 | 31.28 C |
| ATOM | 4279 | O | GLN | C | 114 | 83.827 | 96.444 | −16.284 | 1.00 | 27.34 C |
| ATOM | 4280 | N | ALA | C | 115 | 81.956 | 97.594 | −16.865 | 1.00 | 25.85 C |
| ATOM | 4281 | CA | ALA | C | 115 | 82.564 | 98.246 | −18.031 | 1.00 | 28.40 C |
| ATOM | 4282 | CB | ALA | C | 115 | 81.577 | 99.211 | −18.667 | 1.00 | 20.65 C |
| ATOM | 4283 | C | ALA | C | 115 | 83.844 | 98.990 | −17.651 | 1.00 | 28.38 C |
| ATOM | 4284 | O | ALA | C | 115 | 84.797 | 99.004 | −18.432 | 1.00 | 23.27 C |

TABLE 3-continued

| | | | | | | | | | | |
|---|---|---|---|---|---|---|---|---|---|---|
| ATOM | 4285 | N | ASN | C | 116 | 83.873 | 99.587 | −16.456 | 1.00 | 23.81 C |
| ATOM | 4286 | CA | ASN | C | 116 | 85.060 | 100.327 | −16.002 | 1.00 | 28.02 C |
| ATOM | 4287 | CB | ASN | C | 116 | 84.663 | 101.425 | −14.993 | 1.00 | 28.32 C |
| ATOM | 4288 | CG | ASN | C | 116 | 83.983 | 100.858 | −13.746 | 1.00 | 27.71 C |
| ATOM | 4289 | OD1 | ASN | C | 116 | 84.129 | 99.674 | −13.436 | 1.00 | 24.66 C |
| ATOM | 4290 | ND2 | ASN | C | 116 | 83.247 | 101.707 | −13.020 | 1.00 | 23.76 C |
| ATOM | 4291 | C | ASN | C | 116 | 86.139 | 99.447 | −15.378 | 1.00 | 27.65 C |
| ATOM | 4292 | O | ASN | C | 116 | 87.027 | 99.957 | −14.695 | 1.00 | 31.18 C |
| ATOM | 4293 | N | ASN | C | 117 | 86.060 | 98.132 | −15.593 | 1.00 | 27.61 C |
| ATOM | 4294 | CA | ASN | C | 117 | 87.030 | 97.189 | −15.048 | 1.00 | 29.18 C |
| ATOM | 4295 | CB | ASN | C | 117 | 88.475 | 97.578 | −15.449 | 1.00 | 27.03 C |
| ATOM | 4296 | CG | ASN | C | 117 | 88.724 | 97.389 | −16.951 | 1.00 | 30.01 C |
| ATOM | 4297 | OD1 | ASN | C | 117 | 87.901 | 96.793 | −17.638 | 1.00 | 27.30 C |
| ATOM | 4298 | ND2 | ASN | C | 117 | 89.853 | 97.883 | −17.455 | 1.00 | 29.00 C |
| ATOM | 4299 | C | ASN | C | 117 | 86.958 | 96.986 | −13.543 | 1.00 | 31.56 C |
| ATOM | 4300 | O | ASN | C | 117 | 87.748 | 96.230 | −12.994 | 1.00 | 31.15 C |
| ATOM | 4301 | N | MET | C | 118 | 86.035 | 97.652 | −12.860 | 1.00 | 33.87 C |
| ATOM | 4302 | CA | MET | C | 118 | 85.918 | 97.430 | −11.421 | 1.00 | 38.31 C |
| ATOM | 4303 | CB | MET | C | 118 | 85.431 | 98.700 | −10.723 | 1.00 | 43.16 C |
| ATOM | 4304 | CG | MET | C | 118 | 86.446 | 99.857 | −10.744 | 1.00 | 53.52 C |
| ATOM | 4305 | SD | MET | C | 118 | 85.763 | 101.385 | −10.037 | 1.00 | 58.36 C |
| ATOM | 4306 | CE | MET | C | 118 | 86.038 | 101.027 | −8.271 | 1.00 | 63.17 C |
| ATOM | 4307 | C | MET | C | 118 | 84.937 | 96.281 | −11.182 | 1.00 | 41.22 C |
| ATOM | 4308 | O | MET | C | 118 | 84.034 | 96.039 | −12.001 | 1.00 | 39.23 C |
| ATOM | 4309 | N | TRP | C | 119 | 85.108 | 95.588 | −10.058 | 1.00 | 39.36 C |
| ATOM | 4310 | CA | TRP | C | 119 | 84.276 | 94.458 | −9.706 | 1.00 | 34.52 C |
| ATOM | 4311 | CB | TRP | C | 119 | 85.044 | 93.494 | −8.830 | 1.00 | 37.83 C |
| ATOM | 4312 | CG | TRP | C | 119 | 85.916 | 92.608 | −9.625 | 1.00 | 34.11 C |
| ATOM | 4313 | CD2 | TRP | C | 119 | 85.497 | 91.515 | −10.449 | 1.00 | 33.34 C |
| ATOM | 4314 | CE2 | TRP | C | 119 | 86.652 | 90.975 | −11.053 | 1.00 | 32.21 C |
| ATOM | 4315 | CE3 | TRP | C | 119 | 84.250 | 90.935 | −10.741 | 1.00 | 29.94 C |
| ATOM | 4316 | CD1 | TRP | C | 119 | 87.264 | 92.691 | −9.755 | 1.00 | 31.13 C |
| ATOM | 4317 | NE1 | TRP | C | 119 | 87.721 | 91.715 | −10.608 | 1.00 | 36.90 C |
| ATOM | 4318 | CZ2 | TRP | C | 119 | 86.610 | 89.897 | −11.919 | 1.00 | 29.11 C |
| ATOM | 4319 | CZ3 | TRP | C | 119 | 84.206 | 89.869 | −11.594 | 1.00 | 31.88 C |
| ATOM | 4320 | CH2 | TRP | C | 119 | 85.384 | 89.352 | −12.181 | 1.00 | 32.92 C |
| ATOM | 4321 | C | TRP | C | 119 | 82.930 | 94.725 | −9.066 | 1.00 | 45.62 C |
| ATOM | 4322 | O | TRP | C | 119 | 82.742 | 95.703 | −8.345 | 1.00 | 44.53 C |
| ATOM | 4323 | N | GLY | C | 120 | 82.022 | 93.799 | −9.399 | 1.00 | 52.00 C |
| ATOM | 4324 | CA | GLY | C | 120 | 80.621 | 93.709 | −8.986 | 1.00 | 49.90 C |
| ATOM | 4325 | C | GLY | C | 120 | 79.864 | 94.960 | −8.669 | 1.00 | 50.22 C |
| ATOM | 4326 | O | GLY | C | 120 | 80.454 | 96.037 | −8.703 | 1.00 | 53.01 C |
| ATOM | 4327 | N | PRO | C | 121 | 78.546 | 94.853 | −8.388 | 1.00 | 42.28 C |
| ATOM | 4328 | CD | PRO | C | 121 | 77.760 | 93.635 | −8.569 | 1.00 | 46.84 C |
| ATOM | 4329 | CA | PRO | C | 121 | 77.673 | 95.988 | −8.042 | 1.00 | 46.16 C |
| ATOM | 4330 | CB | PRO | C | 121 | 76.263 | 95.395 | −8.040 | 1.00 | 42.57 C |
| ATOM | 4331 | CG | PRO | C | 121 | 76.380 | 94.189 | −8.846 | 1.00 | 45.38 C |
| ATOM | 4332 | C | PRO | C | 121 | 78.054 | 96.442 | −6.637 | 1.00 | 48.97 C |
| ATOM | 4333 | O | PRO | C | 121 | 78.066 | 97.631 | −6.340 | 1.00 | 49.57 C |
| ATOM | 4334 | N | THR | C | 122 | 78.361 | 95.485 | −5.766 | 1.00 | 45.65 C |
| ATOM | 4335 | CA | THR | C | 122 | 78.735 | 95.807 | −4.388 | 1.00 | 48.81 C |
| ATOM | 4336 | CB | THR | C | 122 | 78.209 | 94.712 | −3.397 | 1.00 | 52.30 C |
| ATOM | 4337 | OG1 | THR | C | 122 | 76.777 | 94.615 | −3.488 | 1.00 | 54.63 C |
| ATOM | 4338 | CG2 | THR | C | 122 | 78.563 | 95.064 | −1.953 | 1.00 | 54.73 C |
| ATOM | 4339 | C | THR | C | 122 | 80.264 | 95.881 | −4.287 | 1.00 | 51.31 C |
| ATOM | 4340 | O | THR | C | 122 | 80.964 | 95.769 | −5.277 | 1.00 | 49.95 C |
| ATOM | 4341 | N | ARG | C | 123 | 80.792 | 96.106 | −3.094 | 1.00 | 56.40 C |
| ATOM | 4342 | CA | ARG | C | 123 | 82.233 | 96.099 | −2.936 | 1.00 | 54.17 C |
| ATOM | 4343 | CB | ARG | C | 123 | 82.628 | 96.777 | −1.621 | 1.00 | 62.98 C |
| ATOM | 4344 | CG | ARG | C | 123 | 82.258 | 98.275 | −1.561 | 1.00 | 73.33 C |
| ATOM | 4345 | CD | ARG | C | 123 | 82.868 | 98.987 | −0.336 | 1.00 | 77.96 C |
| ATOM | 4346 | NE | ARG | C | 123 | 83.483 | 100.279 | −0.674 | 1.00 | 80.89 C |
| ATOM | 4347 | CZ | ARG | C | 123 | 84.558 | 100.439 | −1.458 | 1.00 | 80.79 C |
| ATOM | 4348 | NH1 | ARG | C | 123 | 85.166 | 99.392 | −2.007 | 1.00 | 79.18 C |
| ATOM | 4349 | NH2 | ARG | C | 123 | 85.035 | 101.656 | −1.696 | 1.00 | 81.16 C |
| ATOM | 4350 | C | ARG | C | 123 | 82.566 | 94.608 | −2.890 | 1.00 | 52.07 C |
| ATOM | 4351 | O | ARG | C | 123 | 81.687 | 93.780 | −2.609 | 1.00 | 51.24 C |
| ATOM | 4352 | N | LEU | C | 124 | 83.801 | 94.245 | −3.210 | 1.00 | 46.24 C |
| ATOM | 4353 | CA | LEU | C | 124 | 84.175 | 92.836 | −3.137 | 1.00 | 43.03 C |
| ATOM | 4354 | CB | LEU | C | 124 | 85.682 | 92.655 | −3.342 | 1.00 | 38.28 C |
| ATOM | 4355 | CG | LEU | C | 124 | 86.181 | 92.386 | −4.766 | 1.00 | 39.78 C |
| ATOM | 4356 | CD1 | LEU | C | 124 | 87.714 | 92.314 | −4.721 | 1.00 | 41.84 C |
| ATOM | 4357 | CD2 | LEU | C | 124 | 85.591 | 91.090 | −5.304 | 0.00 | 41.07 C |
| ATOM | 4358 | C | LEU | C | 124 | 83.785 | 92.371 | −1.738 | 1.00 | 35.52 C |
| ATOM | 4359 | O | LEU | C | 124 | 83.740 | 93.175 | −0.807 | 1.00 | 32.32 C |
| ATOM | 4360 | N | PRO | C | 125 | 83.473 | 91.080 | −1.574 | 1.00 | 31.53 C |
| ATOM | 4361 | CD | PRO | C | 125 | 83.668 | 89.969 | −2.523 | 1.00 | 35.48 C |
| ATOM | 4362 | CA | PRO | C | 125 | 83.093 | 90.568 | −0.255 | 1.00 | 36.74 C |
| ATOM | 4363 | CB | PRO | C | 125 | 82.663 | 89.127 | −0.554 | 1.00 | 32.42 C |

TABLE 3-continued

| ATOM | 4364 | CG | PRO | C | 125 | 83.629 | 88.741 | −1.610 | 1.00 | 33.06 | C |
| --- | --- | --- | --- | --- | --- | --- | --- | --- | --- | --- | --- |
| ATOM | 4365 | C | PRO | C | 125 | 84.328 | 90.593 | 0.623 | 1.00 | 36.97 | C |
| ATOM | 4366 | O | PRO | C | 125 | 85.438 | 90.594 | 0.117 | 1.00 | 34.38 | C |
| ATOM | 4367 | N | THR | C | 126 | 84.130 | 90.571 | 1.930 | 1.00 | 41.39 | C |
| ATOM | 4368 | CA | THR | C | 126 | 85.239 | 90.584 | 2.857 | 1.00 | 44.67 | C |
| ATOM | 4369 | CB | THR | C | 126 | 85.171 | 91.881 | 3.691 | 1.00 | 49.35 | C |
| ATOM | 4370 | OG1 | THR | C | 126 | 86.470 | 92.211 | 4.174 | 1.00 | 58.86 | C |
| ATOM | 4371 | CG2 | THR | C | 126 | 84.227 | 91.731 | 4.855 | 1.00 | 46.39 | C |
| ATOM | 4372 | C | THR | C | 126 | 85.179 | 89.343 | 3.765 | 1.00 | 43.43 | C |
| ATOM | 4373 | O | THR | C | 126 | 84.101 | 88.820 | 4.068 | 1.00 | 41.61 | C |
| ATOM | 4374 | N | CYS | C | 127 | 86.333 | 88.832 | 4.164 | 1.00 | 46.42 | C |
| ATOM | 4375 | CA | CYS | C | 127 | 86.348 | 87.679 | 5.068 | 1.00 | 46.58 | C |
| ATOM | 4376 | C | CYS | C | 127 | 86.997 | 88.162 | 6.361 | 1.00 | 47.12 | C |
| ATOM | 4377 | O | CYS | C | 127 | 88.182 | 88.490 | 6.384 | 1.00 | 44.98 | C |
| ATOM | 4378 | CB | CYS | C | 127 | 87.153 | 86.515 | 4.485 | 1.00 | 41.09 | C |
| ATOM | 4379 | SG | CYS | C | 127 | 86.397 | 85.641 | 3.072 | 1.00 | 36.94 | C |
| ATOM | 4380 | N | VAL | C | 128 | 86.202 | 88.224 | 7.422 | 1.00 | 47.64 | C |
| ATOM | 4381 | CA | VAL | C | 128 | 86.671 | 88.675 | 8.725 | 1.00 | 50.09 | C |
| ATOM | 4382 | CB | VAL | C | 128 | 85.674 | 89.670 | 9.349 | 1.00 | 53.76 | C |
| ATOM | 4383 | CG1 | VAL | C | 128 | 84.322 | 88.993 | 9.553 | 1.00 | 56.55 | C |
| ATOM | 4384 | CG2 | VAL | C | 128 | 86.211 | 90.180 | 10.678 | 1.00 | 55.81 | C |
| ATOM | 4385 | C | VAL | C | 128 | 86.860 | 87.494 | 9.696 | 1.00 | 50.97 | C |
| ATOM | 4386 | O | VAL | C | 128 | 86.117 | 86.494 | 9.653 | 1.00 | 47.21 | C |
| ATOM | 4387 | N | SER | C | 129 | 87.860 | 87.611 | 10.563 | 1.00 | 44.79 | C |
| ATOM | 4388 | CA | SER | C | 129 | 88.146 | 86.561 | 11.534 | 1.00 | 41.23 | C |
| ATOM | 4389 | CB | SER | C | 129 | 89.373 | 86.901 | 12.370 | 1.00 | 36.76 | C |
| ATOM | 4390 | OG | SER | C | 129 | 89.483 | 85.955 | 13.423 | 1.00 | 38.45 | C |
| ATOM | 4391 | C | SER | C | 129 | 87.020 | 86.289 | 12.506 | 1.00 | 42.12 | C |
| ATOM | 4392 | O | SER | C | 129 | 86.396 | 87.214 | 13.030 | 1.00 | 38.42 | C |
| ATOM | 4393 | N | VAL | C | 130 | 86.783 | 85.004 | 12.747 | 1.00 | 42.88 | C |
| ATOM | 4394 | CA | VAL | C | 130 | 85.786 | 84.566 | 13.712 | 1.00 | 48.17 | C |
| ATOM | 4395 | CB | VAL | C | 130 | 85.679 | 83.028 | 13.724 | 1.00 | 49.37 | C |
| ATOM | 4396 | CG1 | VAL | C | 130 | 85.006 | 82.570 | 15.003 | 1.00 | 55.87 | C |
| ATOM | 4397 | CG2 | VAL | C | 130 | 84.879 | 82.558 | 12.510 | 1.00 | 47.26 | C |
| ATOM | 4398 | C | VAL | C | 130 | 86.191 | 85.042 | 15.124 | 1.00 | 47.25 | C |
| ATOM | 4399 | O | VAL | C | 130 | 85.334 | 85.271 | 15.976 | 1.00 | 49.24 | C |
| ATOM | 4400 | N | PHE | C | 131 | 87.495 | 85.202 | 15.360 | 1.00 | 42.64 | C |
| ATOM | 4401 | CA | PHE | C | 131 | 87.979 | 85.639 | 16.665 | 1.00 | 43.25 | C |
| ATOM | 4402 | CB | PHE | C | 131 | 89.429 | 85.174 | 16.873 | 1.00 | 37.67 | C |
| ATOM | 4403 | CG | PHE | C | 131 | 89.608 | 83.691 | 16.666 | 1.00 | 36.56 | C |
| ATOM | 4404 | CD1 | PHE | C | 131 | 90.324 | 83.218 | 15.589 | 1.00 | 30.51 | C |
| ATOM | 4405 | CD2 | PHE | C | 131 | 88.927 | 82.770 | 17.461 | 1.00 | 32.59 | C |
| ATOM | 4406 | CE1 | PHE | C | 131 | 90.357 | 81.848 | 15.278 | 1.00 | 32.11 | C |
| ATOM | 4407 | CE2 | PHE | C | 131 | 88.955 | 81.399 | 17.157 | 1.00 | 37.78 | C |
| ATOM | 4408 | CZ | PHE | C | 131 | 89.674 | 80.938 | 16.055 | 1.00 | 33.91 | C |
| ATOM | 4409 | C | PHE | C | 131 | 87.849 | 87.146 | 16.797 | 1.00 | 45.03 | C |
| ATOM | 4410 | O | PHE | C | 131 | 88.533 | 87.896 | 16.104 | 1.00 | 43.08 | C |
| ATOM | 4411 | N | PRO | C | 132 | 86.980 | 87.606 | 17.719 | 1.00 | 49.31 | C |
| ATOM | 4412 | CD | PRO | C | 132 | 86.384 | 86.810 | 18.806 | 1.00 | 48.64 | C |
| ATOM | 4413 | CA | PRO | C | 132 | 86.730 | 89.029 | 17.954 | 1.00 | 51.76 | C |
| ATOM | 4414 | CB | PRO | C | 132 | 85.882 | 89.026 | 19.227 | 1.00 | 51.00 | C |
| ATOM | 4415 | CG | PRO | C | 132 | 86.345 | 87.802 | 19.927 | 1.00 | 49.99 | C |
| ATOM | 4416 | C | PRO | C | 132 | 87.948 | 89.921 | 18.054 | 1.00 | 54.56 | C |
| ATOM | 4417 | O | PRO | C | 132 | 88.018 | 90.941 | 17.371 | 1.00 | 59.16 | C |
| ATOM | 4418 | N | LEU | C | 133 | 88.913 | 89.558 | 18.887 | 1.00 | 53.87 | C |
| ATOM | 4419 | CA | LEU | C | 133 | 90.089 | 90.396 | 18.991 | 1.00 | 56.98 | C |
| ATOM | 4420 | CB | LEU | C | 133 | 90.854 | 90.093 | 20.274 | 1.00 | 53.54 | C |
| ATOM | 4421 | CG | LEU | C | 133 | 89.997 | 90.162 | 21.538 | 1.00 | 52.81 | C |
| ATOM | 4422 | CD1 | LEU | C | 133 | 90.901 | 90.183 | 22.748 | 1.00 | 53.95 | C |
| ATOM | 4423 | CD2 | LEU | C | 133 | 89.142 | 91.398 | 21.540 | 1.00 | 53.34 | C |
| ATOM | 4424 | C | LEU | C | 133 | 90.958 | 90.156 | 17.772 | 1.00 | 58.59 | C |
| ATOM | 4425 | O | LEU | C | 133 | 92.106 | 90.579 | 17.726 | 1.00 | 54.07 | C |
| ATOM | 4426 | N | GLU | C | 134 | 91.054 | 89.741 | 16.857 | 1.00 | 60.78 | C |
| ATOM | 4427 | CA | GLU | C | 134 | 91.010 | 89.158 | 15.522 | 1.00 | 70.26 | C |
| ATOM | 4428 | CB | GLU | C | 134 | 91.448 | 90.184 | 14.475 | 1.00 | 72.39 | C |
| ATOM | 4429 | CG | GLU | C | 134 | 90.575 | 91.428 | 14.421 | 1.00 | 75.60 | C |
| ATOM | 4430 | CD | GLU | C | 134 | 89.133 | 91.113 | 14.077 | 1.00 | 78.38 | C |
| ATOM | 4431 | OE1 | GLU | C | 134 | 88.819 | 89.923 | 13.866 | 1.00 | 80.20 | C |
| ATOM | 4432 | OE2 | GLU | C | 134 | 88.317 | 92.057 | 14.018 | 1.00 | 80.22 | C |
| ATOM | 4433 | C | GLU | C | 134 | 91.879 | 87.908 | 15.438 | 1.00 | 71.86 | C |
| ATOM | 4434 | O | GLU | C | 134 | 92.143 | 87.521 | 16.835 | 1.00 | 73.34 | C |
| ATOM | 4435 | OXT | GLU | C | 134 | 92.658 | 87.662 | 14.702 | 1.00 | 76.05 | C |
| ATOM | 4436 | C1 | NAG | D | 1 | 91.022 | 77.190 | 13.373 | 1.00 | 39.02 | D |
| ATOM | 4437 | O1 | NAG | D | 1 | 90.217 | 76.061 | 13.510 | 1.00 | 53.38 | D |
| ATOM | 4438 | C2 | NAG | D | 1 | 92.379 | 76.764 | 12.861 | 1.00 | 36.79 | D |
| ATOM | 4439 | N2 | NAG | D | 1 | 92.264 | 76.234 | 11.516 | 1.00 | 39.67 | D |
| ATOM | 4440 | C7 | NAG | D | 1 | 92.851 | 76.904 | 10.527 | 1.00 | 40.49 | D |
| ATOM | 4441 | O7 | NAG | D | 1 | 93.458 | 77.963 | 10.726 | 1.00 | 46.19 | D |
| ATOM | 4442 | C8 | NAG | D | 1 | 92.771 | 76.338 | 9.115 | 1.00 | 36.88 | D |

TABLE 3-continued

| ATOM | 4443 | C3 | NAG | D | 1 | 92.972 | 75.726 | 13.816 | 1.00 | 35.88 | D |
|------|------|----|-----|---|---|--------|--------|--------|------|-------|---|
| ATOM | 4444 | O3 | NAG | D | 1 | 94.293 | 75.444 | 13.394 | 1.00 | 40.30 | D |
| ATOM | 4445 | C4 | NAG | D | 1 | 92.986 | 76.292 | 15.264 | 1.00 | 37.37 | D |
| ATOM | 4446 | O4 | NAG | D | 1 | 93.308 | 75.255 | 16.169 | 1.00 | 36.52 | D |
| ATOM | 4447 | C5 | NAG | D | 1 | 91.610 | 76.877 | 15.659 | 1.00 | 38.38 | D |
| ATOM | 4448 | O5 | NAG | D | 1 | 91.167 | 77.818 | 14.663 | 1.00 | 39.81 | D |
| ATOM | 4449 | C6 | NAG | D | 1 | 91.599 | 77.601 | 16.994 | 1.00 | 34.64 | D |
| ATOM | 4450 | O6 | NAG | D | 1 | 92.510 | 78.695 | 16.984 | 1.00 | 35.80 | D |
| ATOM | 4451 | C1 | NAG | E | 1 | 90.580 | 70.350 | 4.612  | 1.00 | 80.29 | E |
| ATOM | 4452 | O1 | NAG | E | 1 | 90.608 | 71.734 | 4.755  | 1.00 | 82.28 | E |
| ATOM | 4453 | C2 | NAG | E | 1 | 91.606 | 69.705 | 5.560  | 1.00 | 79.89 | E |
| ATOM | 4454 | N2 | NAG | E | 1 | 91.383 | 70.221 | 6.901  | 1.00 | 79.48 | E |
| ATOM | 4455 | C7 | NAG | E | 1 | 90.709 | 69.507 | 7.799  | 1.00 | 79.52 | E |
| ATOM | 4456 | O7 | NAG | E | 1 | 89.865 | 68.652 | 7.495  | 1.00 | 78.01 | E |
| ATOM | 4457 | C8 | NAG | E | 1 | 91.027 | 69.791 | 9.263  | 1.00 | 77.64 | E |
| ATOM | 4458 | C3 | NAG | E | 1 | 93.061 | 70.018 | 5.141  | 1.00 | 79.82 | E |
| ATOM | 4459 | O3 | NAG | E | 1 | 93.945 | 69.116 | 5.805  | 1.00 | 80.58 | E |
| ATOM | 4460 | C4 | NAG | E | 1 | 93.291 | 69.924 | 3.618  | 1.00 | 80.30 | E |
| ATOM | 4461 | O4 | NAG | E | 1 | 94.526 | 70.547 | 3.285  | 1.00 | 80.30 | E |
| ATOM | 4462 | C5 | NAG | E | 1 | 92.148 | 70.607 | 2.853  | 1.00 | 80.10 | E |
| ATOM | 4463 | O5 | NAG | E | 1 | 90.884 | 70.035 | 3.252  | 1.00 | 79.60 | E |
| ATOM | 4464 | C6 | NAG | E | 1 | 92.253 | 70.476 | 1.341  | 1.00 | 80.36 | E |
| ATOM | 4465 | O6 | NAG | E | 1 | 91.044 | 70.874 | 0.705  | 1.00 | 78.94 | E |
| END  |      |    |     |   |   |        |        |        |      |       |   |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method of structure-based identification of candidate compounds for binding to complement receptor type 2 (CR2) proteins or to a complex of CR2 and its ligand, comprising:

a. providing a three dimensional structure of a CR2 short consensus repeat (SCR) 1-2 region selected from the group consisting of:

i. a structure defined by atomic coordinates of a three dimensional structure of a crystalline CR2 SCR1-2 region in complex with C3d;

ii. a structure defined by atomic coordinates selected from the group consisting of:

(1) atomic coordinates represented in a table selected from the group consisting of Table 2 (CR2-C3d) and Table 3 (CR2 only); and, (2) atomic coordinates that define a three dimensional structure, wherein at least 50% of said structure has an average root-mean-square deviation (RMSD) from backbone atoms in secondary structure elements in at least one domain of a three dimensional structure represented by said atomic coordinates of (1) of equal to or less than about 1.0 Å; and iii. a structure defined by atomic coordinates derived from CR2 protein molecules arranged in a crystalline manner in a space group R32 so as to form a unit cell of dimensions a=b=170.5 Å, c173.8 Å;

b. identifying a candidate compound for binding to said CR2 SCR 1-2 region by performing structure based drug design with said structure of (a);

c. synthesizing said candidate compound identified in step (b); and d. selecting candidate compounds from step (c) that bind to CR2.

2. The method of claim 1, wherein said step of selecting comprises selecting candidate compounds that bind to and activate CR2.

3. The method of claim 1, wherein said method further comprises:

e. selecting candidate compounds that inhibit the binding of CR2 to its ligand.

4. The method of claim 3, wherein said step (e) of selecting comprises:

i. contacting said candidate compound synthesized in step (c) with CR2 or a fragment thereof and a CR2 ligand or a fragment thereof under conditions in which a CR2-CR2 ligand complex can form in the absence of said candidate compound; and ii. measuring the binding affinity of said CR2 or fragment thereof to said CR2 ligand or fragment thereof; wherein a candidate inhibitor compound is selected as a compound that inhibits the binding of CR2 to its ligand when there is a decrease in the binding affinity of said CR2 or fragment thereof for said CR2 ligand or fragment thereof, as compared to in the absence of said candidate inhibitor compound.

5. The method of claim 3, wherein said ligand is selected from the group consisting of C3d, CD23, and Epstein Barr Virus (EBV) gp350/220, or CR2-binding fragments thereof.

6. The method of claim 3, wherein said ligand is a gp350/220 viral membrane protein from EBV or a CR2-binding fragment thereof.

7. The method of claim 3, wherein said CR2 protein or fragment thereof comprises an amino acid sequence selected from the group consisting of SEQ ID NO:4 and SEQ ID NO:6.

8. The method of claim 1, wherein said method further comprises:
   e. selecting candidate compounds that stabilizes a complex of CR2 with its ligand.

9. The method of claim 8, wherein step (e) of selecting comprises:
   i. contacting said candidate compound synthesized in step (c) with a CR2-CR2 ligand complex, wherein said CR2-CR2 ligand complex comprises CR2 or a fragment thereof and a CR2 ligand, or a fragment thereof;
   ii. measuring the stability of said CR2-CR2 ligand complex of (i), wherein a,candidate stabilizer compound is selected as a compound that stabilizes the CR2-CR2 ligand complex when there is an increase in the stability of the said complex as compared to in the absence of said candidate stabilizer compound.

10. The method of claim 8, wherein said ligand is selected from the group consisting of C3d and CD23.

11. The method of claim 8, wherein said CR2 protein or fragment thereof comprises an amino acid sequence selected from the group consisting of SEQ ID NO:4 and SEQ ID NO:6.

12. The method of claim 1, wherein said step of identifying comprises identifying candidate compounds for binding to the SCR2 domain of said CR2.

13. The method of claim 1, wherein said step of identifying comprises identifying candidate compounds for binding to the interface between the SCR1 and SCR2 domains of CR2.

14. The method of claim 1, wherein said step of identifying comprises identifying candidate compounds for binding to the dimer interface between two CR2 proteins.

15. The method of claim 1, wherein said step of identifying comprises identifying candidate compounds for binding to the interface between CR2 and C3d, C3, a CR2-binding fragment of C3 containing C3d, or a fragment thereof.

16. The method of claim 1, wherein said step of identifying comprises identifying candidate compounds for binding to the B strand and the B-C loop of CR2 SCR2 comprising the segment: G79-G80-Y81-K82-I83-R84-G85-S86-T87-P88-Y89.

17. The method of claim 1, wherein said step of identifying comprises identifying candidate compounds for binding to a site on the B strand of CR2 SCR2 comprising position K100.

18. The method of claim 1, wherein said step of identifying comprises identifying candidate compounds for binding to a segment of CR2 SCR2 comprising V130-F131-P132-L133.

19. The method of claim 1, wherein said step of identifying comprises identifying candidate compounds for binding to a segment of CR2 SCR2 comprising the fragment T101-N102-F103.

20. The method of claim 1, wherein said step of identifying comprises identifying candidate compounds for binding to the loop between helix 2-3 of C3d comprising the segment Q68-P69-S70-S71.

21. The method of claim 1, wherein said step of identifying comprises identifying candidate compounds for binding to Helix 5 of C3d comprising the segment S104-Q105-V106-L107-C108-G109-A110-V111-K112-W113-L114-I115-L116-E117-K118-Q119-K120-P121-D122.

22. The method of claim 1, wherein said step of identifying comprises identifying candidate compounds for binding to Helix 7of C3d comprising the segment N170-S171-L172-P173-G174-S175-I176-T177-K178-A179-G180-D181-F182-L183-E184-A185.

23. The method of claim 1, wherein said step of identifying comprises identifying candidate compounds for binding to amino acid residues at positions 84 and 86 of an amino acid sequence selected from the group consisting of SEQ ID NO:4 and SEQ ID NO:6.

24. The method of claim 1, wherein said step of identifying comprises directed drug design.

25. The method of claim 1, wherein said step of identifying comprises random drug design.

26. The method of claim 1, wherein said step of identifying comprises grid-based drug design.

27. The method of claim 1, wherein said step of identifying comprises computational screening of one or more databases of chemical compounds.

* * * * *

SEQUENCE LISTING

```
<160> NUMBER OF SEQ ID NOS: 9
<210> SEQ ID NO 1
<211> LENGTH: 1033
<212> TYPE: PRT
<213> ORGANISM: Homo sapiens

<400> SEQUENCE: 1

Met Gly Ala Ala Gly Leu Leu Gly Val Phe Leu Ala Leu Val Ala Pro
1               5                   10                  15

Gly Val Leu Gly Ile Ser Cys Gly Ser Pro Pro Ile Leu Asn Gly
            20                  25                  30

Arg Ile Ser Tyr Tyr Ser Thr Pro Ile Ala Val Gly Thr Val Ile Arg
            35                  40                  45

Tyr Ser Cys Ser Gly Thr Phe Arg Leu Ile Gly Glu Lys Ser Leu Leu
        50                  55                  60

Cys Ile Thr Lys Asp Lys Val Asp Gly Thr Trp Asp Lys Pro Ala Pro
65                  70                  75                  80

Lys Cys Glu Tyr Phe Asn Lys Tyr Ser Ser Cys Pro Glu Pro Ile Val
                85                  90                  95

Pro Gly Gly Tyr Lys Ile Arg Gly Ser Thr Pro Tyr Arg His Gly Asp
            100                 105                 110

Ser Val Thr Phe Ala Cys Lys Thr Asn Phe Ser Met Asn Gly Asn Lys
            115                 120                 125

Ser Val Trp Cys Gln Ala Asn Asn Met Trp Gly Pro Thr Arg Leu Pro
        130                 135                 140

Thr Cys Val Ser Val Phe Pro Leu Glu Cys Pro Ala Leu Pro Met Ile
145                 150                 155                 160

His Asn Gly His His Thr Ser Glu Asn Val Gly Ser Ile Ala Pro Gly
                165                 170                 175
```

-continued

```
Leu Ser Val Thr Tyr Ser Cys Glu Ser Gly Tyr Leu Val Gly Glu
            180                 185                 190

Lys Ile Ile Asn Cys Leu Ser Ser Gly Lys Trp Ser Ala Val Pro Pro
        195                 200                 205

Thr Cys Glu Glu Ala Arg Cys Lys Ser Leu Gly Arg Phe Pro Asn Gly
    210                 215                 220

Lys Val Lys Glu Pro Pro Ile Leu Arg Val Gly Val Thr Ala Asn Phe
225                 230                 235                 240

Phe Cys Asp Glu Gly Tyr Arg Leu Gln Gly Pro Pro Ser Ser Arg Cys
                245                 250                 255

Val Ile Ala Gly Gln Gly Val Ala Trp Thr Lys Met Pro Val Cys Glu
            260                 265                 270

Glu Ile Phe Cys Pro Ser Pro Pro Ile Leu Asn Gly Arg His Ile
        275                 280                 285

Gly Asn Ser Leu Ala Asn Val Ser Tyr Gly Ser Ile Val Thr Tyr Thr
    290                 295                 300

Cys Asp Pro Asp Pro Glu Glu Gly Val Asn Phe Ile Leu Ile Gly Glu
305                 310                 315                 320

Ser Thr Leu Arg Cys Thr Val Asp Ser Gln Lys Thr Gly Thr Trp Ser
                325                 330                 335

Gly Pro Ala Pro Arg Cys Glu Leu Ser Thr Ser Ala Val Gln Cys Pro
            340                 345                 350

His Pro Gln Ile Leu Arg Gly Arg Met Val Ser Gly Gln Lys Asp Arg
        355                 360                 365

Tyr Thr Tyr Asn Asp Thr Val Ile Phe Ala Cys Met Phe Gly Phe Thr
    370                 375                 380

Leu Lys Gly Ser Lys Gln Ile Arg Cys Asn Ala Gln Gly Thr Trp Glu
385                 390                 395                 400

Pro Ser Ala Pro Val Cys Glu Lys Glu Cys Gln Ala Pro Pro Asn Ile
                405                 410                 415

Leu Asn Gly Gln Lys Glu Asp Arg His Met Val Arg Phe Asp Pro Gly
            420                 425                 430

Thr Ser Ile Lys Tyr Ser Cys Asn Pro Gly Tyr Val Leu Val Gly Glu
        435                 440                 445

Glu Ser Ile Gln Cys Thr Ser Glu Gly Val Trp Thr Pro Pro Val Pro
    450                 455                 460

Gln Cys Lys Val Ala Ala Cys Glu Ala Thr Gly Arg Gln Leu Leu Thr
465                 470                 475                 480

Lys Pro Gln His Gln Phe Val Arg Pro Asp Val Asn Ser Ser Cys Gly
                485                 490                 495

Glu Gly Tyr Lys Leu Ser Gly Ser Val Tyr Gln Glu Cys Gln Gly Thr
            500                 505                 510

Ile Pro Trp Phe Met Glu Ile Arg Leu Cys Lys Glu Ile Thr Cys Pro
        515                 520                 525

Pro Pro Pro Val Ile Tyr Asn Gly Ala His Thr Gly Ser Ser Leu Glu
    530                 535                 540

Asp Phe Pro Tyr Gly Thr Thr Val Thr Tyr Thr Cys Asn Pro Gly Pro
545                 550                 555                 560

Glu Arg Gly Val Glu Phe Ser Leu Ile Gly Glu Ser Thr Ile Arg Cys
                565                 570                 575

Thr Ser Asn Asp Gln Glu Arg Gly Thr Trp Ser Gly Pro Ala Pro Leu
            580                 585                 590

Cys Lys Leu Ser Leu Leu Ala Val Gln Cys Ser His Val His Ile Ala
```

-continued

```
              595                 600                 605
Asn Gly Tyr Lys Ile Ser Gly Lys Glu Ala Pro Tyr Phe Tyr Asn Asp
            610                 615                 620

Thr Val Thr Phe Lys Cys Tyr Ser Gly Phe Thr Leu Lys Gly Ser Ser
625                 630                 635                 640

Gln Ile Arg Cys Lys Ala Asp Asn Thr Trp Asp Pro Glu Ile Pro Val
                645                 650                 655

Cys Glu Lys Glu Thr Cys Gln His Val Arg Gln Ser Leu Gln Glu Leu
                660                 665                 670

Pro Ala Gly Ser Arg Val Glu Leu Val Asn Thr Ser Cys Gln Asp Gly
                675                 680                 685

Tyr Gln Leu Thr Gly His Ala Tyr Gln Met Cys Gln Asp Ala Glu Asn
            690                 695                 700

Gly Ile Trp Phe Lys Lys Ile Pro Leu Cys Lys Val Ile His Cys His
705                 710                 715                 720

Pro Pro Pro Val Ile Val Asn Gly Lys His Thr Gly Met Met Ala Glu
                725                 730                 735

Asn Phe Leu Tyr Gly Asn Glu Val Ser Tyr Glu Cys Asp Gln Gly Phe
                740                 745                 750

Tyr Leu Leu Gly Glu Lys Lys Leu Gln Cys Arg Ser Asp Ser Lys Gly
                755                 760                 765

His Gly Ser Trp Ser Gly Pro Ser Pro Gln Cys Leu Arg Ser Pro Pro
                770                 775                 780

Val Thr Arg Cys Pro Asn Pro Glu Val Lys His Gly Tyr Lys Leu Asn
785                 790                 795                 800

Lys Thr His Ser Ala Tyr Ser His Asn Asp Ile Val Tyr Val Asp Cys
                805                 810                 815

Asn Pro Gly Phe Ile Met Asn Gly Ser Arg Val Ile Arg Cys His Thr
                820                 825                 830

Asp Asn Thr Trp Val Pro Gly Val Pro Thr Cys Met Lys Lys Ala Phe
                835                 840                 845

Ile Gly Cys Pro Pro Pro Lys Thr Pro Asn Gly Asn His Thr Gly
850                 855                 860

Gly Asn Ile Ala Arg Phe Ser Pro Gly Met Ser Ile Leu Tyr Ser Cys
865                 870                 875                 880

Asp Gln Gly Tyr Leu Leu Val Gly Glu Ala Leu Leu Leu Cys Thr His
                885                 890                 895

Glu Gly Thr Trp Ser Gln Pro Ala Pro His Cys Lys Glu Val Asn Cys
                900                 905                 910

Ser Ser Pro Ala Asp Met Asp Gly Ile Gln Lys Gly Leu Glu Pro Arg
                915                 920                 925

Lys Met Tyr Gln Tyr Gly Ala Val Val Thr Leu Glu Cys Glu Asp Gly
                930                 935                 940

Tyr Met Leu Glu Gly Ser Pro Gln Ser Gln Cys Gln Ser Asp His Gln
945                 950                 955                 960

Trp Asn Pro Pro Leu Ala Val Cys Arg Ser Arg Ser Leu Ala Pro Val
                965                 970                 975

Leu Cys Gly Ile Ala Ala Gly Leu Ile Leu Leu Thr Phe Leu Ile Val
                980                 985                 990

Ile Thr Leu Tyr Val Ile Ser  His Arg Glu Arg Asn Tyr Tyr Thr
                995                 1000                1005

Asp Thr  Ser Gln Lys Glu Ala  Phe His Leu Glu Ala  Arg Glu Val
     1010                1015                1020
```

```
Tyr Ser  Val Asp Pro Tyr Asn  Pro Ala Ser
    1025                1030
```

<210> SEQ ID NO 2
<211> LENGTH: 60
<212> TYPE: PRT
<213> ORGANISM: Homo sapiens
<400> SEQUENCE: 2

```
Cys Gly Ser Pro Pro Ile Leu Asn Gly Arg Ile Ser Tyr Tyr Ser
1               5                   10                  15

Thr Pro Ile Ala Val Gly Thr Val Ile Arg Tyr Ser Cys Ser Gly Thr
            20                  25                  30

Phe Arg Leu Ile Gly Glu Lys Ser Leu Leu Cys Ile Thr Lys Asp Lys
            35                  40                  45

Val Asp Gly Thr Trp Asp Lys Pro Ala Pro Lys Cys
        50                  55                  60
```

<210> SEQ ID NO 3
<211> LENGTH: 56
<212> TYPE: PRT
<213> ORGANISM: Homo sapiens
<400> SEQUENCE: 3

```
Cys Pro Glu Pro Ile Val Pro Gly Gly Tyr Lys Ile Arg Gly Ser Thr
1               5                   10                  15

Pro Tyr Arg His Gly Asp Ser Val Thr Phe Ala Cys Lys Thr Asn Phe
            20                  25                  30

Ser Met Asn Gly Asn Lys Ser Val Trp Cys Gln Ala Asn Asn Met Trp
            35                  40                  45

Gly Pro Thr Arg Leu Pro Thr Cys
        50                  55
```

<210> SEQ ID NO 4
<211> LENGTH: 134
<212> TYPE: PRT
<213> ORGANISM: Homo sapiens
<400> SEQUENCE: 4

```
Gly Ile Ser Cys Gly Ser Pro Pro Ile Leu Asn Gly Arg Ile Ser
1               5                   10                  15

Tyr Tyr Ser Thr Pro Ile Ala Val Gly Thr Val Ile Arg Tyr Ser Cys
            20                  25                  30

Ser Gly Thr Phe Arg Leu Ile Gly Glu Lys Ser Leu Leu Cys Ile Thr
            35                  40                  45

Lys Asp Lys Val Asp Gly Thr Trp Asp Lys Pro Ala Pro Lys Cys Glu
        50                  55                  60

Tyr Phe Asn Lys Tyr Ser Ser Cys Pro Glu Pro Ile Val Pro Gly Gly
65                  70                  75                  80

Tyr Lys Ile Arg Gly Ser Thr Pro Tyr Arg His Gly Asp Ser Val Thr
            85                  90                  95

Phe Ala Cys Lys Thr Asn Phe Ser Met Asn Gly Asn Lys Ser Val Trp
            100                 105                 110

Cys Gln Ala Asn Asn Met Trp Gly Pro Thr Arg Leu Pro Thr Cys Val
            115                 120                 125

Ser Val Phe Pro Leu Glu
    130
```

```
<210> SEQ ID NO 5
<211> LENGTH: 1025
<212> TYPE: PRT
<213> ORGANISM: Mus musculus

<400> SEQUENCE: 5

Met Leu Thr Trp Phe Leu Phe Tyr Phe Ser Glu Ile Ser Cys Asp Pro
1               5                   10                  15

Pro Pro Glu Val Lys Asn Ala Arg Lys Pro Tyr Tyr Ser Leu Pro Ile
            20                  25                  30

Val Pro Gly Thr Val Leu Arg Tyr Thr Cys Ser Pro Ser Tyr Arg Leu
        35                  40                  45

Ile Gly Glu Lys Ala Ile Phe Cys Ile Ser Glu Asn Gln Val His Ala
    50                  55                  60

Thr Trp Asp Lys Ala Pro Pro Ile Cys Glu Ser Val Asn Lys Thr Ile
65                  70                  75                  80

Ser Cys Ser Asp Pro Ile Val Pro Gly Gly Phe Met Asn Lys Gly Ser
                85                  90                  95

Lys Ala Pro Phe Arg His Gly Asp Ser Val Thr Phe Thr Cys Lys Ala
            100                 105                 110

Asn Phe Thr Met Lys Gly Ser Lys Thr Val Trp Cys Gln Ala Asn Glu
        115                 120                 125

Met Trp Gly Pro Thr Ala Leu Pro Val Cys Glu Ser Asp Phe Pro Leu
    130                 135                 140

Glu Cys Pro Ser Leu Pro Thr Ile His Asn Gly His His Thr Gly Gln
145                 150                 155                 160

His Val Asp Gln Phe Val Ala Gly Leu Ser Val Thr Tyr Ser Cys Glu
                165                 170                 175

Pro Gly Tyr Leu Leu Thr Gly Lys Lys Thr Ile Lys Cys Leu Ser Ser
            180                 185                 190

Gly Asp Trp Asp Gly Val Ile Pro Thr Cys Lys Glu Ala Gln Cys Glu
        195                 200                 205

His Pro Gly Lys Phe Pro Asn Gly Gln Val Lys Glu Pro Leu Ser Leu
    210                 215                 220

Gln Val Gly Thr Thr Val Tyr Phe Ser Cys Asn Glu Gly Tyr Gln Leu
225                 230                 235                 240

Gln Gly Gln Pro Ser Ser Gln Cys Val Ile Val Glu Gln Lys Ala Ile
                245                 250                 255

Trp Thr Lys Lys Pro Val Cys Lys Glu Ile Leu Cys Pro Pro Pro Pro
            260                 265                 270

Pro Val Arg Asn Gly Ser His Thr Gly Ser Phe Ser Glu Asn Val Pro
        275                 280                 285

Tyr Gly Ser Thr Val Thr Tyr Thr Cys Asp Pro Ser Pro Glu Lys Gly
    290                 295                 300

Val Ser Phe Thr Leu Ile Gly Glu Lys Thr Ile Asn Cys Thr Thr Gly
305                 310                 315                 320

Ser Gln Lys Thr Gly Ile Trp Ser Gly Pro Ala Pro Tyr Cys Val Leu
                325                 330                 335

Ser Thr Ser Ala Val Leu Cys Leu Gln Pro Lys Ile Lys Arg Gly Gln
            340                 345                 350

Ile Leu Ser Ile Leu Lys Asp Ser Tyr Ser Tyr Asn Asp Thr Val Ala
        355                 360                 365

Phe Ser Cys Glu Pro Gly Phe Thr Leu Lys Gly Asn Arg Ser Ile Arg
    370                 375                 380
```

-continued

```
Cys Asn Ala His Gly Thr Trp Glu Pro Pro Val Pro Val Cys Glu Lys
385                 390                 395                 400

Gly Cys Gln Ala Pro Pro Lys Ile Ile Asn Gly Gln Lys Glu Asp Ser
            405                 410                 415

Tyr Leu Leu Asn Phe Asp Pro Gly Thr Ser Ile Arg Tyr Ser Cys Asp
                420                 425                 430

Pro Gly Tyr Leu Leu Val Gly Glu Asp Thr Ile His Cys Thr Pro Glu
        435                 440                 445

Gly Lys Trp Thr Pro Ile Thr Pro Gln Cys Thr Val Ala Glu Cys Lys
    450                 455                 460

Pro Val Gly Pro His Leu Phe Lys Arg Pro Gln Asn Gln Phe Ile Arg
465                 470                 475                 480

Thr Ala Val Asn Ser Cys Asp Glu Gly Phe Gln Leu Ser Glu Ser
                485                 490                 495

Ala Tyr Gln Leu Cys Gln Gly Thr Ile Pro Trp Phe Ile Glu Ile Arg
            500                 505                 510

Leu Cys Lys Glu Ile Thr Cys Pro Pro Pro Val Ile His Asn Gly
                515                 520                 525

Thr His Thr Trp Ser Ser Glu Asp Val Pro Tyr Gly Thr Val Val
    530                 535                 540

Thr Tyr Met Cys Tyr Pro Gly Pro Glu Glu Gly Val Lys Phe Lys Leu
545                 550                 555                 560

Ile Gly Glu Gln Thr Ile His Cys Thr Ser Asp Ser Arg Gly Arg Gly
                565                 570                 575

Ser Trp Ser Ser Pro Ala Pro Leu Cys Lys Leu Ser Leu Pro Ala Val
            580                 585                 590

Gln Cys Thr Asp Val His Val Glu Asn Gly Val Lys Leu Thr Asp Asn
        595                 600                 605

Lys Ala Pro Tyr Phe Tyr Asn Asp Ser Val Met Phe Lys Cys Asp Asp
    610                 615                 620

Gly Tyr Ile Leu Ser Gly Ser Ser Gln Ile Arg Cys Lys Ala Asn Asn
625                 630                 635                 640

Thr Trp Asp Pro Glu Lys Pro Leu Cys Lys Lys Glu Gly Cys Glu Pro
                645                 650                 655

Met Arg Val His Gly Leu Pro Asp Asp Ser His Ile Lys Leu Val Lys
            660                 665                 670

Arg Thr Cys Gln Asn Gly Tyr Gln Leu Thr Gly Tyr Thr Tyr Glu Lys
        675                 680                 685

Cys Gln Asn Ala Glu Asn Gly Thr Trp Phe Lys Lys Ile Glu Val Cys
    690                 695                 700

Thr Val Ile Leu Cys Gln Pro Pro Lys Ile Ala Asn Gly Gly His
705                 710                 715                 720

Thr Gly Met Met Ala Lys His Phe Leu Tyr Gly Asn Glu Val Ser Tyr
                725                 730                 735

Glu Cys Asp Glu Gly Phe Tyr Leu Leu Gly Glu Lys Ser Leu Gln Cys
            740                 745                 750

Val Asn Asp Ser Lys Gly His Gly Ser Trp Ser Gly Pro Pro Pro Gln
        755                 760                 765

Cys Leu Gln Ser Ser Pro Leu Thr His Cys Pro Asp Pro Glu Val Lys
    770                 775                 780

His Gly Tyr Lys Leu Asn Lys Thr His Ser Ala Phe Ser His Asn Asp
785                 790                 795                 800
```

-continued

```
Ile Val His Phe Val Cys Asn Gln Gly Phe Ile Met Asn Gly Ser His
            805                 810                 815

Leu Ile Arg Cys His Thr Asn Asn Thr Trp Leu Pro Gly Val Pro Thr
            820                 825                 830

Cys Ile Arg Lys Ala Ser Leu Gly Cys Gln Ser Pro Ser Thr Ile Pro
            835                 840                 845

Asn Gly Asn His Thr Gly Gly Ser Ile Ala Arg Phe Pro Pro Gly Met
850                 855                 860

Ser Val Met Tyr Ser Cys Tyr Gln Gly Phe Leu Met Ala Gly Glu Ala
865                 870                 875                 880

Arg Leu Ile Cys Thr His Glu Gly Thr Trp Ser Gln Pro Pro Pro Phe
            885                 890                 895

Cys Lys Glu Val Asn Cys Ser Phe Pro Glu Asp Thr Asn Gly Ile Gln
            900                 905                 910

Lys Gly Phe Gln Pro Gly Lys Thr Tyr Arg Phe Gly Ala Thr Val Thr
            915                 920                 925

Leu Glu Cys Glu Asp Gly Tyr Thr Leu Glu Gly Ser Pro Gln Ser Gln
        930                 935                 940

Cys Gln Asp Asp Ser Gln Trp Asn Pro Leu Ala Leu Cys Lys Tyr
945                 950                 955                 960

Arg Arg Trp Ser Thr Ile Pro Leu Ile Cys Gly Ile Ser Val Gly Ser
            965                 970                 975

Ala Leu Ile Ile Leu Met Ser Val Gly Phe Cys Met Ile Leu Lys His
            980                 985                 990

Arg Glu Ser Asn Tyr Tyr Thr Lys  Thr Arg Pro Lys Glu  Gly Ala Leu
        995                 1000                1005

His Leu  Glu Thr Arg Glu Val  Tyr Ser Ile Asp Pro  Tyr Asn Pro
    1010                1015                1020

Ala Ser
    1025

<210> SEQ ID NO 6
<211> LENGTH: 135
<212> TYPE: PRT
<213> ORGANISM: Mus musculus

<400> SEQUENCE: 6

Glu Ile Ser Cys Asp Pro Pro Glu Val Lys Asn Ala Arg Lys Pro
1               5                   10                  15

Tyr Tyr Ser Leu Pro Ile Val Pro Gly Thr Val Leu Arg Tyr Thr Cys
            20                  25                  30

Ser Pro Ser Tyr Arg Leu Ile Gly Glu Lys Ala Ile Phe Cys Ile Ser
        35                  40                  45

Glu Asn Gln Val His Ala Thr Trp Asp Lys Ala Pro Ile Cys Glu
50                  55                  60

Ser Val Asn Lys Thr Ile Ser Cys Ser Asp Pro Ile Val Pro Gly Gly
65                  70                  75                  80

Phe Met Asn Lys Gly Ser Lys Ala Pro Phe Arg His Gly Asp Ser Val
            85                  90                  95

Thr Phe Thr Cys Lys Ala Asn Phe Thr Met Lys Gly Ser Lys Thr Val
            100                 105                 110

Trp Cys Gln Ala Asn Glu Met Trp Gly Pro Thr Ala Leu Pro Val Cys
            115                 120                 125

Glu Ser Asp Phe Pro Leu Glu
        130                 135
```

```
<210> SEQ ID NO 7
<211> LENGTH: 310
<212> TYPE: PRT
<213> ORGANISM: Homo sapiens

<400> SEQUENCE: 7

Met Leu Asp Ala Glu Arg Leu Lys His Leu Ile Val Thr Pro Ser Gly
1               5                   10                  15

Ala Gly Glu Gln Asn Met Ile Gly Met Thr Pro Thr Val Ile Ala Val
            20                  25                  30

His Tyr Leu Asp Glu Thr Glu Gln Trp Glu Lys Phe Gly Leu Glu Lys
        35                  40                  45

Arg Gln Gly Ala Leu Glu Leu Ile Lys Lys Gly Tyr Thr Gln Gln Leu
    50                  55                  60

Ala Phe Arg Gln Pro Ser Ser Ala Phe Ala Ala Phe Val Lys Arg Ala
65                  70                  75                  80

Pro Ser Thr Trp Leu Thr Ala Tyr Val Val Lys Val Phe Ser Leu Ala
                85                  90                  95

Val Asn Leu Ile Ala Ile Asp Ser Gln Val Leu Cys Gly Ala Val Lys
            100                 105                 110

Trp Leu Ile Leu Glu Lys Gln Lys Pro Asp Gly Val Phe Gln Glu Asp
        115                 120                 125

Ala Pro Val Ile His Gln Glu Met Ile Gly Gly Leu Arg Asn Asn Asn
    130                 135                 140

Glu Lys Asp Met Ala Leu Thr Ala Phe Val Leu Ile Ser Leu Gln Glu
145                 150                 155                 160

Ala Lys Asp Ile Cys Glu Glu Gln Val Asn Ser Leu Pro Gly Ser Ile
                165                 170                 175

Thr Lys Ala Gly Asp Phe Leu Glu Ala Asn Tyr Met Asn Leu Gln Arg
            180                 185                 190

Ser Tyr Thr Val Ala Ile Ala Gly Tyr Ala Leu Ala Gln Met Gly Arg
        195                 200                 205

Leu Lys Gly Pro Leu Leu Asn Lys Phe Leu Thr Thr Ala Lys Asp Lys
    210                 215                 220

Asn Arg Trp Glu Asp Pro Gly Lys Gln Leu Tyr Asn Val Glu Ala Thr
225                 230                 235                 240

Ser Tyr Ala Leu Leu Ala Leu Leu Gln Leu Lys Asp Phe Asp Phe Val
                245                 250                 255

Pro Pro Val Val Arg Trp Leu Asn Glu Gln Arg Tyr Tyr Gly Gly Gly
            260                 265                 270

Tyr Gly Ser Thr Gln Ala Thr Phe Met Val Phe Gln Ala Leu Ala Gln
        275                 280                 285

Tyr Gln Lys Asp Ala Pro Asp His Gln Glu Leu Asn Leu Asp Val Ser
    290                 295                 300

Leu Gln Leu Pro Ser Arg
305                 310

<210> SEQ ID NO 8
<211> LENGTH: 310
<212> TYPE: PRT
<213> ORGANISM: Homo sapiens

<400> SEQUENCE: 8

Met Leu Asp Ala Glu Arg Leu Lys His Leu Ile Val Thr Pro Ser Gly
1               5                   10                  15
```

```
Ala Gly Glu Gln Asn Met Ile Gly Met Thr Pro Thr Val Ile Ala Val
            20                  25                  30

His Tyr Leu Asp Glu Thr Glu Gln Trp Glu Lys Phe Gly Leu Glu Lys
            35                  40                  45

Arg Gln Gly Ala Leu Glu Leu Ile Lys Lys Gly Tyr Thr Gln Gln Leu
        50                  55                  60

Ala Phe Arg Gln Pro Ser Ser Ala Phe Ala Ala Phe Val Lys Arg Ala
65                  70                  75                  80

Pro Ser Thr Trp Leu Thr Ala Tyr Val Val Lys Val Phe Ser Leu Ala
                85                  90                  95

Val Asn Leu Ile Ala Ile Asp Ser Gln Val Leu Cys Gly Ala Val Lys
            100                 105                 110

Trp Leu Ile Leu Glu Lys Gln Lys Pro Asp Gly Val Phe Gln Glu Asp
            115                 120                 125

Ala Pro Val Ile His Gln Glu Met Ile Gly Gly Leu Arg Asn Asn Asn
130                 135                 140

Glu Lys Asp Met Ala Leu Thr Ala Phe Val Leu Ile Ser Leu Gln Glu
145                 150                 155                 160

Ala Lys Asp Ile Cys Glu Glu Gln Val Arg Ser Leu Pro Gly Ser Ile
                165                 170                 175

Thr Lys Ala Gly Asp Phe Leu Glu Ala Asn Tyr Met Asn Leu Gln Arg
            180                 185                 190

Ser Tyr Thr Val Ala Ile Ala Gly Tyr Ala Leu Ala Gln Met Gly Arg
                195                 200                 205

Leu Lys Gly Pro Leu Leu Asn Lys Phe Leu Thr Thr Ala Lys Asp Lys
        210                 215                 220

Asn Arg Trp Glu Asp Pro Gly Lys Gln Leu Tyr Asn Val Glu Ala Thr
225                 230                 235                 240

Ser Tyr Ala Leu Leu Ala Leu Leu Gln Leu Lys Asp Phe Asp Phe Val
                245                 250                 255

Pro Pro Val Val Arg Trp Leu Asn Glu Gln Arg Tyr Tyr Gly Gly Gly
            260                 265                 270

Tyr Gly Ser Thr Gln Ala Thr Phe Met Val Phe Gln Ala Leu Ala Gln
        275                 280                 285

Tyr Gln Lys Asp Ala Pro Asp His Gln Glu Leu Asn Leu Asp Val Ser
        290                 295                 300

Leu Gln Leu Pro Ser Arg
305                 310

<210> SEQ ID NO 9
<211> LENGTH: 310
<212> TYPE: PRT
<213> ORGANISM: Homo sapiens

<400> SEQUENCE: 9

Met Leu Asp Ala Glu Arg Leu Lys His Leu Ile Val Thr Pro Ser Gly
1               5                   10                  15

Ala Gly Glu Gln Asn Met Ile Gly Met Thr Pro Thr Val Ile Ala Val
            20                  25                  30

His Tyr Leu Asp Glu Thr Glu Gln Trp Glu Lys Phe Gly Leu Glu Lys
            35                  40                  45

Arg Gln Gly Ala Leu Glu Leu Ile Lys Lys Gly Tyr Thr Gln Gln Leu
        50                  55                  60

Ala Phe Arg Gln Pro Ser Ser Ala Phe Ala Ala Phe Val Lys Arg Ala
```

-continued

```
65                  70                  75                  80
Pro Ser Thr Trp Leu Thr Ala Tyr Val Val Lys Val Phe Ser Leu Ala
                85                  90                  95
Val Asn Leu Ile Ala Ile Asp Ser Gln Val Leu Cys Gly Ala Val Lys
                100                 105                 110
Trp Leu Arg Arg Glu Lys Gln Lys Pro Asp Gly Val Phe Gln Glu Asp
                115                 120                 125
Ala Pro Val Ile His Gln Glu Met Ile Gly Gly Leu Arg Asn Asn Asn
                130                 135                 140
Glu Lys Asp Met Ala Leu Thr Ala Phe Val Leu Ile Ser Leu Gln Glu
145                 150                 155                 160
Ala Lys Asp Ile Cys Glu Glu Gln Val Ala Ser Leu Pro Gly Ser Ile
                165                 170                 175
Thr Lys Ala Gly Asp Phe Leu Glu Ala Asn Tyr Met Asn Leu Gln Arg
                180                 185                 190
Ser Tyr Thr Val Ala Ile Ala Gly Tyr Ala Leu Ala Gln Met Gly Arg
                195                 200                 205
Leu Lys Gly Pro Leu Leu Asn Lys Phe Leu Thr Thr Ala Lys Asp Lys
210                 215                 220
Asn Arg Trp Glu Asp Pro Gly Lys Gln Leu Tyr Asn Val Glu Ala Thr
225                 230                 235                 240
Ser Tyr Ala Leu Leu Ala Leu Leu Gln Leu Lys Asp Phe Asp Phe Val
                245                 250                 255
Pro Pro Val Val Arg Trp Leu Asn Glu Gln Arg Tyr Tyr Gly Gly Gly
                260                 265                 270
Tyr Gly Ser Thr Gln Ala Thr Phe Met Val Phe Gln Ala Leu Ala Gln
                275                 280                 285
Tyr Gln Lys Asp Ala Pro Asp His Gln Glu Leu Asn Leu Asp Val Ser
                290                 295                 300
Leu Gln Leu Pro Ser Arg
305                 310
```